United States Patent
Anderson et al.

(10) Patent No.: US 11,873,295 B2
(45) Date of Patent: Jan. 16, 2024

(54) ALLOSTERIC CHROMENONE INHIBITORS OF PHOSPHOINOSITIDE 3-KINASE (PI3K) FOR THE TREATMENT OF DISEASE

(71) Applicant: Petra Pharma Corporation, New York, NY (US)

(72) Inventors: Erin Danielle Anderson, Arvada, CO (US); Sean Douglas Aronow, Boulder, CO (US); Nicholas A. Boyles, Hillsboro, OR (US); Surendra Dawadi, Longmont, CO (US); Eugene R. Hickey, Danbury, CT (US); Thomas Combs Irvin, Erie, CO (US); Edward A. Kesicki, New York, NY (US); Gabrielle R. Kolakowski, Durango, CO (US); Jennifer Lynn Knight, Jersey City, NJ (US); Manoj Kumar, Broomfield, CO (US); Katelyn Frances Long, Lafayette, CO (US); Christopher Glenn Mayne, Boulder, CO (US); Alfredo Picado, Superior, CO (US); Gerit Maria Pototschnig, San Diego, CA (US); Michael Brian Welch, Westminster, CO (US); Tien Widjaja, Lafayette, CO (US); Xiaohong Chen, Broomfield, CO (US); Nathan Edward Wright, San Diego, CA (US); Hua-Yu Wang, Chula Vista, CA (US)

(73) Assignee: PETRA PHARMA CORPORATION, New York, NY (US)

( * ) Notice: Subject to any disclaimer, the term of this patent is extended or adjusted under 35 U.S.C. 154(b) by 0 days.

(21) Appl. No.: 17/734,705

(22) Filed: May 2, 2022

(65) Prior Publication Data

US 2023/0017140 A1 Jan. 19, 2023

Related U.S. Application Data

(60) Provisional application No. 63/253,232, filed on Oct. 7, 2021, provisional application No. 63/250,530, filed on Sep. 30, 2021, provisional application No. 63/227,526, filed on Jul. 30, 2021, provisional application No. 63/183,355, filed on May 3, 2021.

(51) Int. Cl.
| | |
|---|---|
| C07D 405/10 | (2006.01) |
| A61P 35/00 | (2006.01) |
| C07D 311/30 | (2006.01) |
| C07D 405/12 | (2006.01) |
| C07D 407/04 | (2006.01) |
| C07D 413/10 | (2006.01) |
| C07D 417/12 | (2006.01) |

(52) U.S. Cl.
CPC ............ *C07D 405/10* (2013.01); *A61P 35/00* (2018.01); *C07D 311/30* (2013.01); *C07D 405/12* (2013.01); *C07D 407/04* (2013.01); *C07D 413/10* (2013.01); *C07D 417/12* (2013.01)

(58) Field of Classification Search
CPC .. C07D 405/10; C07D 405/12; C07D 407/04; C07D 413/10; C07D 417/12; A61K 31/352; A61K 31/4155; A61K 31/4433; A61K 31/506
See application file for complete search history.

(56) References Cited

U.S. PATENT DOCUMENTS 7,598,377 B2   10/2009 Jackson et al.
7,872,011 B2   1/2011 Jackson et al.
(Continued)

FOREIGN PATENT DOCUMENTS

CN   108299365 A   7/2018
EP   0223744 A2   5/1987
(Continued)

OTHER PUBLICATIONS

Fry, Review: Phosphoinositide 3-kinase signaling in breast cancer: how big a role might it play?, Breast Cancer Res 2001, 3:304-312.*
(Continued)

*Primary Examiner* — Deepak R Rao
(74) *Attorney, Agent, or Firm* — Joseph M Pletcher

(57) ABSTRACT

The disclosure relates to compounds of Formula (I) as allosteric chromenone inhibitors of phosphoinositide 3-kinase (PI3K) useful in the treatment of diseases or disorders associated with PI3K modulation, Formula (I):

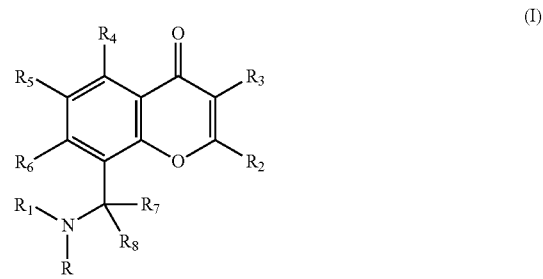

or pharmaceutically acceptable salts thereof wherein R, $R_1$, $R_2$, $R_3$, $R_4$, $R_5$, $R_6$, $R_7$, and $R_8$, are as defined herein. The disclosure also relates to methods of making and using compounds of Formula (I) or pharmaceutically acceptable salts thereof.

125 Claims, No Drawings

(56) References Cited

U.S. PATENT DOCUMENTS

| | | | |
|---|---|---|---|
| 8,399,460 | B2 | 3/2013 | Barlaam et al. |
| 8,513,221 | B2 * | 8/2013 | Liang .................. A61P 9/00 514/118 |
| 2007/0015802 | A1 | 1/2007 | Lal et al. |
| 2011/0098271 | A1 | 4/2011 | Barlaam et al. |

FOREIGN PATENT DOCUMENTS

| | | | |
|---|---|---|---|
| EP | 0341104 | A2 | 11/1989 |
| WO | 90/06921 | A1 | 6/1990 |
| WO | 01/53266 | A1 | 7/2001 |
| WO | 2004/004632 | A2 | 1/2004 |
| WO | 2004/016607 | A1 | 2/2004 |
| WO | 2009/093972 | A1 | 7/2009 |
| WO | 2010/037127 | A1 | 4/2010 |
| WO | 2010/037129 | A1 | 4/2010 |
| WO | 2011/051704 | A1 | 5/2011 |
| WO | 2017/156520 | A1 | 9/2017 |
| WO | 2021/202964 | A1 | 10/2021 |
| WO | 2021/226677 | A1 | 11/2021 |
| WO | 2022/164812 | A1 | 8/2022 |
| WO | 2022/235575 | A1 | 11/2022 |
| WO | 2022/251482 | A1 | 12/2022 |
| WO | 2023/056407 | A1 | 4/2023 |
| WO | 2023/060262 | A1 | 4/2023 |
| WO | 2023/078401 | A1 | 5/2023 |
| WO | 2023/081209 | A1 | 5/2023 |
| WO | 2023/104111 | A1 | 6/2023 |

OTHER PUBLICATIONS

Simone, Oncology: Introduction, Cecil Textbook of Medicine, 20th Edition, vol. 1, pp. 1004-101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Acute Leukemia, Merck Manual (Online Edition) 6 pages, pp. 1-6 (2013).*
Copending U.S. Appl. No. 17/221,209, filed Apr. 2, 2021.
Copending U.S. Appl. No. 17/734,745, filed May 2, 2022.
Copending U.S. Appl. No. 17/825,680, filed May 26, 2022.
Copending U.S. Appl. No. 17/936,973, filed Sep. 30, 2022.
Barlaam et al., Journal of Medical Chemistry, vol. 58, No. 2, Jan. 22, 2015, pp. 943-962.
Barlaam et al., Biorganic & Medicinal Chemistry Letters, vol. 26, No. 9, Mar. 11, 2016, pp. 2318-2323.
Fitzgerald et al., Annals of Oncology, v30, Supplement 5, Oct. 1, 2019, p. v110.
Gaestel et al., Current Medicinal Chemistry, vol. 14, No. 21, Sep. 1, 2007, pp. 2214-2234.
Giordanetto et al., Bioorganic & Medicinal Chemistry Letters vol. 24, Issue 16, Aug. 15, 2014, pp. 3936-3943.
Golub et al., Science (Oct. 15, 1999), Vo. 286, 531-537.
Hon et al., Oncogene (2012) 31, 3655-3666, published online Nov. 28, 2011.
Klippel, A. et al. Preclinical characterization of LOXO-783 (LOX-22783), a highly potent, mutant selective and brain-penetrant allosteric PI3Kα H1047R inhibitor. Presented at: 2021 AACR-NCI-EORTC Virtual International Conference on Molecular Targets and Cancer Therapeutics, On: Oct. 7, 2021.
Lala et al., Cancer and Metastasis Reviews (Mar. 1998), 17(1), 91-106.
Li et al., Am J Clin Exp Urol 2014; 2(3):188-198; Epub 02 Oct. 2, 2014.
Written Opinion for PCT/US2022/027304 (dated Jul. 4, 2022).
International Search Report for PCT/US2022/027304 (dated Jul. 4, 2022).
Copending U.S. Appl. No. 18/309,226, filed Apr. 28, 2023.
Miller et al. Identification of allosteric binding sites for PI3Kα oncogenic mutant specific inhibitor design. Bioorg Med Chem. Feb. 15, 2017; 25(4):1481-1486.

* cited by examiner

ALLOSTERIC CHROMENONE INHIBITORS OF PHOSPHOINOSITIDE 3-KINASE (PI3K) FOR THE TREATMENT OF DISEASE

FIELD

The present invention is directed to allosteric chromenone inhibitors of phosphoinositide 3-kinase (PI3K) useful in the treatment of diseases, or disorders associated with PI3K modulation. The invention is directed toward compounds, and compositions which inhibit PI3K, methods of (or uses for) treating a disease, or disorder associated with PI3K (e.g., CLOVES syndrome (congenital lipomatous overgrowth, vascular malformations, epidermal naevi, scoliosis/skeletal and spinal syndrome), PIK3CA-related overgrowth syndrome (PROS), breast cancer, brain cancer, prostate cancer, endometrial cancer, gastric cancer, leukemia, lymphoma, sarcoma, colorectal cancer, lung cancer, ovarian cancer, skin cancer, or head and neck cancer), and using, or methods of using, PI3K inhibitors in combination with one or more additional cancer therapies.

BACKGROUND

The activity of cells can be regulated by external signals that stimulate, or inhibit intracellular events. The process by which stimulatory, or inhibitory signals are transmitted into, and within a cell to elicit an intracellular response is referred to as signal transduction. Over the past decades, cascades of signal transduction events have been elucidated, and found to play a central role in a variety of biological responses. Defects in various components of signal transduction pathways have been found to account for a vast number of diseases, including numerous forms of cancer, inflammatory disorders, metabolic disorders, vascular, and neuronal diseases (Gaestel et al. *Current Medicinal Chemistry* (2007) 14:2214-2234).

Kinases represent a class of important signaling molecules. Kinases can generally be classified into protein kinases, lipid kinases, and certain kinases exhibiting dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids, and lipid-derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in, or associated with cell membranes. Examples of such enzymes include phosphoinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique, and conserved family of intracellular lipid kinases that phosphorylate the 3'-OH group on phosphatidylinositols, or phosphoinositides. The PI3K family comprises 15 kinases with distinct substrate specificities, expression patterns, and modes of regulation (Katso et al., Annu Rev Cell Dev Biol. 2001; 17:615-75). The class I PI3Ks (p110α, p110β, p110δ, and p110γ) are typically activated by tyrosine kinases, or G-protein coupled receptors to generate PIP3, which engages downstream effectors such as those in the pathways of Akt/PDK1, mTOR, the Tec family kinases, and the Rho family GTPases. The class II, and III PI3Ks play a key role in intracellular trafficking through the synthesis of PI(3)P, and PI(3,4)P$_2$.

The PI3K isoforms have been implicated, for example, in a variety of human cancers, and disorders. Mutations in the gene coding for PI3K isoforms, or mutations which lead to upregulation of a PI3K isoform are believed to occur in many human cancers. Mutations in the gene coding for a PI3K isoform are point mutations clustered within several hotspots in helical, and kinase domains. Because of the high rate of PI3K mutations, targeting of this pathway may provide valuable therapeutic opportunities.

Genetic alterations in genes in PI3K signaling are believed to be involved in a range of cancers such as endometrial cancer, breast cancer, esophageal squamous-cell cancer, cervical squamous-cell carcinoma, cervical adenocarcinoma, colorectal adenocarcinoma, bladder urothelial carcinoma, glioblastoma, ovarian cancer, non-small-cell lung cancer, esophagogastric cancer, nerve-sheath tumor, head and neck squamous-cell carcinoma, melanoma, esophagogastric adenocarcinoma, soft-tissue sarcoma, prostate cancer, fibrolamellar carcinoma, hepatocellular carcinoma, diffuse glioma, colorectal cancer, pancreatic cancer, cholangiocarcinoma, B-cell lymphoma, mesothelioma, adrenocortical carcinoma, renal non-clear-cell carcinoma, renal clear-cell carcinoma, germ-cell carcinoma, thymic tumor, pheochromocytoma, miscellaneous neuroepithelial tumor, thyroid cancer, leukemia, and encapsulated glioma (Goncalves M D, Hopkins B D, Cantley L C. Phosphatidylinositol 3-Kinase, Growth Disorders, and Cancer. N Engl J Med. 2018 Nov. 22; 379(21):2052-2062).

The alpha (α) isoform of PI3K has been implicated, for example, in a variety of human cancers. Angiogenesis has been shown to selectively require the a isoform of PI3K in the control of endothelial cell migration. (Graupera et al, Nature 2008; 453; 662-6). Mutations in the gene coding for PI3Kα, or mutations which lead to upregulation of PI3Kα are believed to occur in many human cancers such as lung, stomach, endometrial, ovarian, bladder, breast, colon, brain, prostate, and skin cancers. Mutations in the gene coding for PI3Kα are point mutations clustered within several hotspots in helical, and kinase domains, such as E542K, E545K, and H1047R. Many of these mutations have been shown to be oncogenic gain-of-function mutations. Because of the high rate of PI3Kα mutations, targeting of this pathway may provide valuable therapeutic opportunities. While other PI3K isoforms such as PI3Kδ, or PI3Kγ are expressed primarily in hematopoietic cells, PI3Kα, along with PI3Kβ, is expressed constitutively.

Mutated PI3Kα has been implicated in brain metastases in HR+/HER2− metastatic breast cancers. Development of brain-penetrant PI3Kα inhibitors may provide improved therapeutic benefit over current PI3Kα inhibitors. (Fitzgerald et al., Association between PIK3CA mutation status and development of brain metastases in HR+/HER2− metastatic breast cancer. Ann Oncol 30:v110, 2019 (suppl 5)).

Due to the central role of PI3Kα in regulating organismal glucose homeostasis, PI3K inhibition in patients often gives rise to hyperglycemia and/or hyperinsulinemia (Busaidy N L, et al, Management of metabolic effects associated with anticancer agents targeting the PI3K-Akt-mTOR pathway. J Clin Oncol 2012; 30:2919-28). High levels of circulating insulin could potentially be mitogenic and/or antiapoptotic for cancer cells, and thus negate the antiproliferative effects of PI3K inhibitors (Blouin M-J, et al, Abstract 4615: the hyperinsulinemia caused by PI3K inhibitors attenuates their antineoplastic efficacy, but can be minimized by co-administration of metformin. Cancer Res 2013; 73:4615).

In the setting of cancer with mutated PI3Kα, one way to overcome the problem of compensatory production of insulin and/or glucose upon systemic PI3Kα inhibition would be to develop inhibitors with enhanced selectivity for mutant PI3Kα over wild-type PI3Kα. This would create an increased window for drug dosing to selectively inhibit the pathologic signaling of mutant PI3Kα in the cancer cells without affecting the wild-type PI3Kα in the host tissues that control systemic metabolism (Okkenhaug K, Graupera M, Vanhaesebroeck B. Targeting PI3K in Cancer: Impact on Tumor Cells, Their Protective Stroma, Angiogenesis, and Immunotherapy. Cancer Discov. 2016 October; 6(10):1090-1105), thus limiting toxicities, and permitting higher doses, and more complete inhibition of the drug target (Ariella B. Hanker, et al, Challenges for the clinical development of PI3K inhibitors: Strategies to improve their impact in solid tumors. Cancer Discov. 2019 April; 9(4): 482-491).

Currently PI3Kα inhibitors are nearly equipotent to wild-type, and mutant PI3Kα. Mutant selective inhibitors have been elusive due to the PI3Kα mutations location far from the active site. As such, inhibitors which target a second, peripheral binding pocket near a known mutation (e.g., H1047R) may provide a route to selective PI3Kα inhibition. Thus, targeting a mutated, peripheral binding pocket of PI3Kα, provides a valuable therapeutic target for drug development.

As such, kinases, for example lipid kinases such as PI3Ks, are prime targets for drug development. The present invention provides a new class of kinase inhibitors.

SUMMARY

In one aspect, the present invention relates to compounds of Formula (I):

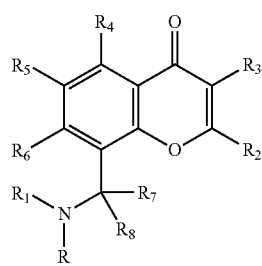

(I)

or pharmaceutically acceptable salts thereof, wherein:
R is —H or $C_1$-$C_3$ alkyl;

$R_1$ is a group of the formula:

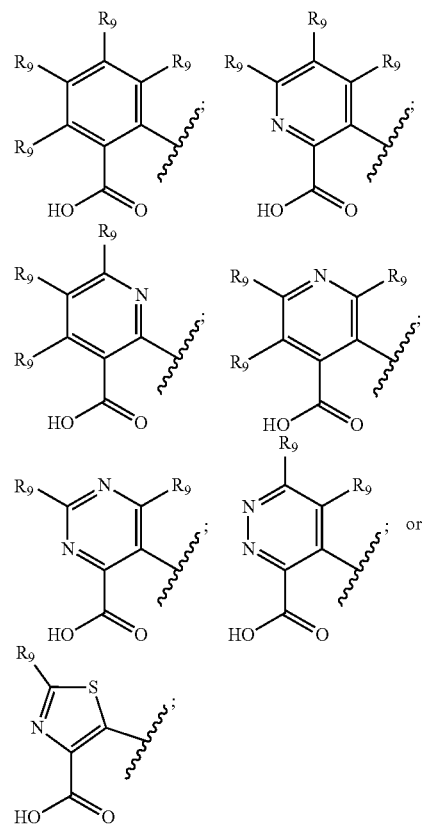

$R_2$ is a group of the formula:

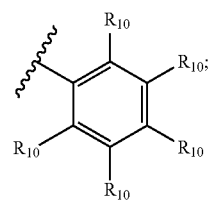

$R_3$ is —H, halogen, —CN, —N(H)($C_1$-$C_3$ alkyl), —N($C_1$-$C_3$ alkyl)$_2$, —N(H)(CH$_2$CH$_2$CO$_2$H), —C(O)$C_1$-$C_3$ alkyl, $C_1$-$C_6$ alkyl, $C_1$-$C_6$ haloalkyl, $C_1$-$C_6$ hydroxyalkyl, $C_3$-$C_5$ cycloalkyl, an optionally substituted heterocycle of 3 to 5 ring atoms containing 1, 2, or 3 ring heteroatoms independently selected from N, O, or S, or an optionally substituted heteroaryl of 5 or 6 ring atoms containing 1, 2, or 3 ring heteroatoms independently selected from N, O, or S; wherein the optionally substituted heterocycle or heteroaryl is each optionally substituted with one to three substituents each independently selected from halogen, $C_1$-$C_3$ alkyl, or $C_1$-$C_3$ haloalkyl;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, —CN, $C_1$-$C_6$ alkyl, $C_1$-$C_6$ haloalkyl, $C_1$-$C_6$ alkoxy, or $C_3$-$C_5$ cycloalkyl;

each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —C(O)O$C_1$-$C_3$ alkyl, —CON$R_{11}R_{11}$, —$NR_{11}R_{11}$, —$NR_{11}$—CO$_2R_{11}$, —OH, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, $C_1$-$C_3$ alkoxy, or —CON$R_{11}R_{11}$; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{11}$, —$NR_{11}R_{11}$, —OH or —CN; and each $R_{11}$ is independently —H or $C_1$-$C_3$ alkyl.

In another aspect, the present invention provides a pharmaceutical composition comprising a compound of Formula (I), (II), or (III), or a pharmaceutically acceptable salt thereof, and a pharmaceutically acceptable diluent, or carrier.

In another aspect, the present invention provides a method of modulating PI3K (e.g., PI3Kα) activity (e.g., in vitro, or in vivo), comprising contacting a cell with a therapeutically effective amount of a compound of Formula (I), (II), or (III), or a pharmaceutically acceptable salt thereof.

In some aspects, the present invention provides a method of treating, or preventing a disease, or disorder disclosed herein in a subject in need thereof, comprising administering to the subject a therapeutically effective amount of a compound of Formula (I), (II), or (III), or a pharmaceutically acceptable salt thereof.

In some aspects, the present invention provides a method of treating, or preventing a disease, or disorder disclosed herein in a subject in need thereof, comprising administering to the subject a therapeutically effective amount of a pharmaceutical composition of a compound of Formula (I), (II), or (III), or a pharmaceutically acceptable salt thereof.

In some aspects, the present invention provides a method of treating a disease, or disorder disclosed herein in a subject in need thereof, comprising administering to the subject a therapeutically effective amount of a compound of Formula (I), (II), or (III), or a pharmaceutically acceptable salt thereof.

In some aspects, the present invention provides a method of treating a disease, or disorder disclosed herein in a subject in need thereof, comprising administering to the subject a therapeutically effective amount of a pharmaceutical composition of a compound of Formula (I), (II), or (III), or a pharmaceutically acceptable salt thereof.

In another aspect, the present invention provides a compound of Formula (I), (II), or (III), or a pharmaceutically acceptable salt thereof for use in therapy.

In another aspect, the present invention provides a compound of Formula (I), (II), or (III), or a pharmaceutically acceptable salt thereof for use in modulating PI3K (e.g., PI3Kα) activity (e.g., in vitro, or in vivo).

In another aspect, the present invention provides a compound of Formula (I), (II), or (III), or a pharmaceutically acceptable salt thereof, for use in selective inhibition for mutant PI3Kα over wild-type PI3Kα.

In another aspect, the present invention provides a compound of Formula (I), (II), or (III), or a pharmaceutically acceptable salt thereof, for use in treating, or preventing a disease, or disorder disclosed herein.

In another aspect, the present invention provides a compound of Formula (I), (II), or (III), or a pharmaceutically acceptable salt thereof, for use in treating a disease, or disorder disclosed herein.

In another aspect, the present invention provides use of a compound of Formula (I), (II), or (III), or a pharmaceutically acceptable salt thereof, in the manufacture of a medicament for modulating PI3K (e.g., PI3Kα) activity (e.g., in vitro, or in vivo).

In another aspect, the present invention provides use of a compound of Formula (I), (II), or (III), or a pharmaceutically acceptable salt thereof, in the manufacture of a medicament for treating, or preventing a disease, or disorder disclosed herein.

In another aspect, the present invention provides use of a compound of Formula (I), (II), or (III), or a pharmaceutically acceptable salt thereof, in the manufacture of a medicament for treating a disease, or disorder disclosed herein.

In another aspect, the present invention provides a method of preparing a compound of Formula (I), (II), or (III), or a pharmaceutically acceptable salt thereof.

In another aspect, the present invention provides a method of preparing a compound, comprising one, or more steps described herein.

In another aspect, the present invention provides a compound obtainable by, or obtained by, a method for preparing a compound as described herein (e.g., a method comprising one, or more steps described in the Schemes).

In another aspect, the present invention provides an intermediate as described herein, being suitable for use in a method for preparing a compound as described herein (e.g., the intermediate is selected from the intermediates described in the Examples).

Other features, and advantages of the invention will be apparent from the following detailed description, and claims.

DETAILED DESCRIPTION

The present invention provides methods of treating, preventing, or ameliorating a disease, or disorder, (or uses in the treatment, prevention, or amelioration of a disease, or disorder), in which PI3K plays a role by administering to a patient in need thereof a therapeutically effective amount of a PI3K inhibitor of the present invention. The methods (or uses) of the present invention can be used in the treatment of a variety of PI3K-dependent diseases, and disorders.

In some embodiments, the disease, or disorder is a cancer (e.g., breast cancer, brain cancers, prostate cancer, endometrial cancer, gastric cancer, leukemia, lymphoma, sarcoma, colorectal cancer, lung cancer, ovarian cancer, skin cancer, or head and neck cancer). In some embodiments, the disease, or disorder associated with PI3K includes, but is not limited to, CLOVES syndrome (congenital lipomatous overgrowth, vascular malformations, epidermal naevi, scoliosis/skeletal and spinal syndrome), PIK3CA-related overgrowth syndrome (PROS), endometrial cancer, breast cancer, esophageal squamous-cell cancer, cervical squamous-cell carcinoma, cervical adenocarcinoma, colorectal adenocarcinoma, bladder urothelial carcinoma, glioblastoma, ovarian cancer, non-small-cell lung cancer, esophagogastric cancer, nerve-sheath tumor, head and neck squamous-cell carcinoma, melanoma, esophagogastric adenocarcinoma, soft-tissue sarcoma, prostate cancer, fibrolamellar carcinoma, hepatocellular carcinoma, diffuse glioma, colorectal cancer, pancreatic cancer, cholangiocarcinoma, B-cell lymphoma, mesothelioma, adrenocortical carcinoma, renal non-clear-cell carcinoma, renal clear-cell carcinoma, germ-cell carcinoma, thymic tumor, pheochromocytoma, miscellaneous neuroepithelial tumor, thyroid cancer, leukemia, and encapsulated glioma.

The details of the invention are set forth in the accompanying description below. Although methods, and materials similar, or equivalent to those described herein can be used in the practice, or testing of the present disclosure, illustrative methods, and materials are now described. Other features, objects, and advantages of the invention will be apparent from the description, and from the claims. In the specification, and the appended claims, the singular forms also include the plural unless the context clearly dictates otherwise. Unless defined otherwise, all technical, and scientific terms used herein have the same meaning as commonly understood by one of ordinary skill in the art to which this invention belongs. All patents, and publications cited in this specification are incorporated herein by reference in their entireties.

Definitions

The articles "a", and "an" refer to one, or more than one (i.e., to at least one) of the grammatical object of the article. By way of example, "an element" means one element, or more than one element.

The term "and/or" means either "and", or "or" unless indicated otherwise.

The term "administer", "administering", or "administration" refers to either directly administering a disclosed compound, or pharmaceutically acceptable salt of the disclosed compound, or a composition to a subject.

The term "alkenyl" refers to a straight, or branched chain unsaturated hydrocarbon containing 2-12 carbon atoms. The "alkenyl" group contains at least one double bond in the chain. The double bond of an alkenyl group can be unconjugated, or conjugated to another unsaturated group. Examples of alkenyl groups include ethenyl, propenyl, n-butenyl, iso-butenyl, pentenyl, or hexenyl.

The term "alkoxy" refers to a straight, or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

The term "alkyl" refers to a straight, or branched chain saturated hydrocarbon containing 1-12 carbon atoms, preferably 1-6 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, iso-pentyl, neopentyl, and isohexyl.

The term "alkynyl" refers to a straight, or branched chain unsaturated hydrocarbon containing 2-12 carbon atoms. The "alkynyl" group contains at least one triple bond in the chain. Examples of alkynyl groups include ethynyl, propargyl, n-butynyl, iso-butynyl, pentynyl, or hexynyl.

The term "aromatic" means a planar ring having 4n+2 electrons in a conjugated system. As used herein, "conjugated system" means a system of connected p-orbitals with delocalized electrons, and the system may include lone electron pairs.

The term "aryl" unless otherwise specifically defined refers to cyclic, aromatic hydrocarbon groups that have 1 to 3 aromatic rings, including monocyclic, or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). Furthermore, when containing two fused rings the aryl groups herein defined may have one, or more saturated, or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, and tetrahydrobenzoannulenyl.

The term "carrier" encompasses carriers, excipients, and diluents, and means a material, composition, or vehicle, such as a liquid, or solid filler, diluent, excipient, solvent, or encapsulating material, involved in carrying, or transporting a pharmaceutical agent from one organ, or portion of the body, to another organ, or portion of the body of a subject.

The term "cyano" means a substituent having a carbon atom joined to a nitrogen atom by a triple bond, i.e., C≡N.

The term "cycloalkyl" means mono, or polycyclic saturated carbon rings containing 3-18 carbon atoms, preferably 3-10 carbon atoms. Examples of cycloalkyl groups include, without limitation, cyclopropyl, cyclobutyl, cyclopentyl, cyclohexyl, cycloheptanyl, cyclooctanyl, norbornyl, norborenyl, bicyclo[2.2.2]octanyl, and bicyclo[2.2.2]octenyl.

The term "disorder" means, and is used interchangeably with, the terms disease, condition, or illness, unless otherwise indicated.

The term "haloalkoxy" refers to an alkoxy group, as defined herein, which is substituted with one, or more halogen. Examples of haloalkoxy groups include, but are not limited to, trifluoromethoxy, difluoromethoxy, pentafluoroethoxy, and trichloromethoxy.

The term "haloalkyl" refers to an alkyl group, as defined herein, which is substituted with one, or more halogen. Examples of haloalkyl groups include, but are not limited to, trifluoromethyl, difluoromethyl, pentafluoroethyl, and trichloromethyl.

The term "halogen" or "halo" refers to fluorine, chlorine, bromine, or iodine.

The term "heteroaryl" unless otherwise specifically defined means a monovalent monocyclic, or a polycyclic aromatic radical of 5 to 24 ring atoms, preferably 5 to 10 ring atoms, containing one, or more ring heteroatoms selected from N, O, S, P, or B, preferably 1, 2, 3, or 4 ring heteroatoms selected from N, O, or S, the remaining ring atoms being C. A polycyclic aromatic radical includes two, or more fused rings, and may further include two, or more spiro-fused rings, e.g., bicyclic, tricyclic, tetracyclic, and the like. Unless otherwise specifically defined, "fused" means two rings sharing two ring atoms. Unless otherwise specifically defined, "spiro-fused" means two rings sharing one ring atom. Heteroaryl as herein defined also means a bicyclic heteroaromatic group wherein the heteroatom is selected from N, O, S, P, or B, preferably N, O, or S. Heteroaryl as herein defined also means a tricyclic heteroaromatic group containing one, or more ring heteroatoms selected from N, O, S, P, or B, preferably N, O, or S. Heteroaryl as herein defined also means a tetracyclic heteroaromatic group containing one, or more ring heteroatoms selected from N, O, S, P, or B, preferably N, O, or S. Examples of heteroaromatic groups include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolinyl, indolinonyl, dihydrobenzothiophenyl, dihydrobenzofuranyl, benzofuranyl, chromanyl, thiochromanyl, tetrahydroquinolinyl, dihydrobenzothiazinyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, and 3H-indolyl. Furthermore, when containing two, or more fused rings, the heteroaryl groups defined herein may have one, or more saturated, or partially unsaturated ring fused with one, or more fully unsaturated aromatic ring. In heteroaryl ring systems containing more than two fused rings, a saturated, or partially unsaturated ring may further be fused with a saturated, or partially unsaturated ring described herein. Furthermore, when containing three, or more fused rings, the heteroaryl groups defined herein may have one, or more saturated, or partially unsaturated ring spiro-fused. Any saturated, or partially unsaturated ring described herein is optionally substituted with one, or more oxo. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizinyl, pyrazolo[1,5-a]pyrimidin-7(4H)-onyl, 3,4-dihydropyrazino[1,2-a]indol-1(2H)-onyl, benzo[c][1,2]oxaborol-1(3H)-olyl, 6,6a,7,8-tetrahydro-9H-pyrido[2,3-b]pyrrolo[1,2-d][1,4]oxazin-9-onyl, and 6a',7'-dihydro-6'H,9'H-spiro[cyclopropane-1,8'-pyrido[2,3-b]pyrrolo[1,2-d][1,4]oxazin]-9'-onyl.

The term "heterocyclyl", "heterocycle", or "heterocycloalkyl" means mono, or polycyclic rings containing 3-24 atoms, preferably 3-10 atoms, which include carbon, and one, or more heteroatoms selected from N, O, S, P, or B, preferably 1, 2, 3, or 4 heteroatoms selected from N, O, and S, and wherein the rings are not aromatic. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" refers to an alkyl group, as defined herein, which is substituted with a hydroxy group.

The term "isomers" refers to compounds that have the same molecular formula but differ in the nature or sequence of bonding of their atoms or the arrangement of their atoms in space. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomers or as a mixture thereof. A mixture containing equal proportions of the enantiomers is called a "racemic mixture".

The term "modulate", "modulation", or "modulating" refers to a biological activity of a compound, or substrate that inhibits and/or activates PI3K.

The term "patient", or "subject" is a mammal, e.g., a human, mouse, rat, guinea pig, dog, cat, horse, cow, pig, or non-human primate, such as a monkey, chimpanzee, baboon, or rhesus. Preferably, the mammal is human.

The term "therapeutically effective amount" when used in connection with a compound refers to the amount or dose of the compound which upon single or multiple dose administration to the patient, provides the desired effect in the patient under diagnosis or treatment. An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The term "treating" with regard to a subject, includes restraining, slowing, stopping, or reversing the progression or severity of an existing symptom or disorder.

Compounds of the Present Invention

In one aspect, the present invention provides compounds of Formula (I), or pharmaceutically acceptable salts thereof:

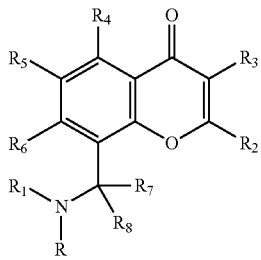

wherein R, R$_1$, R$_2$, R$_3$, R$_4$, R$_5$, R$_6$, R$_7$, and R$_8$, are as defined in the Summary for Formula (I).

In a further aspect, compounds of Formula (I) wherein R$_8$ is H have Formula (II), or pharmaceutically acceptable salts thereof:

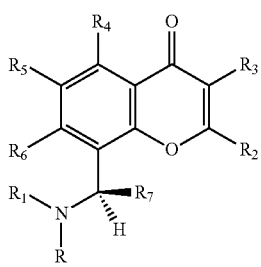

wherein R, R$_1$, R$_2$, R$_3$, R$_4$, R$_5$, R$_6$, and R$_7$, are as defined in the Summary for Formula (I).

In a compound of Formula (I), or pharmaceutically acceptable salts thereof,

R is —H or C$_1$-C$_3$ alkyl;
R$_1$ is a group of the formula:

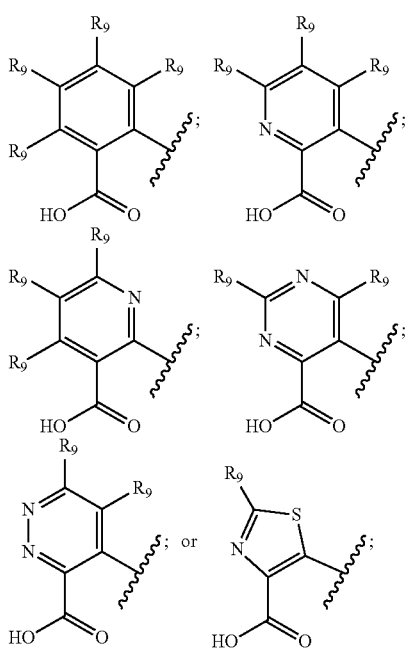

R$_2$ is a group of the formula:

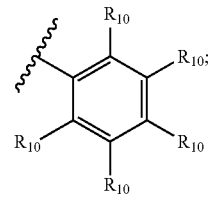

R$_3$ is —H, halogen, —CN, C$_1$-C$_6$ alkyl, C$_1$-C$_6$ haloalkyl, C$_3$-C$_5$ cycloalkyl, a heterocycle of 3 to 5 ring atoms containing 1, 2, or 3 ring heteroatoms independently selected from N, O, or S, or a heteroaryl of 5 ring atoms containing 1, 2, or 3 ring heteroatoms independently selected from N, O, or S;

each of R$_4$, R$_5$ and R$_6$ is independently —H, halogen, C$_1$-C$_6$ alkyl or C$_1$-C$_6$ haloalkyl;

R$_7$ is —CN, C$_1$-C$_6$ alkyl or C$_1$-C$_6$ haloalkyl;
R$_8$ is —H or C$_1$-C$_6$ alkyl;

each R$_9$ is independently —H, halogen, C$_1$-C$_6$ alkyl, C$_1$-C$_6$ haloalkyl, C$_1$-C$_6$ alkoxy, or C$_3$-C$_5$ cycloalkyl;

each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_2$-C$_6$ alkenyl, an optionally substituted C$_2$-C$_6$ alkynyl, an optionally substituted C$_3$-C$_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyrazole, isoxazole, isothiazole, imidazole, oxazole, or thiazole; wherein the optionally substituted C$_1$-C$_6$ alkyl, C$_2$-C$_6$ alkenyl, or C$_2$-C$_6$ alkynyl is each optionally substituted with a —CN, —OH, oxetanyl, or C$_1$-C$_3$ alkoxy; the optionally substituted C$_3$-C$_5$ cycloalkyl, phenyl, 1,3-benzodioxole, 2,3-dihydro-1,4-benzodioxine, heterocycle or heteroaryl is each optionally substituted with one to three substituents each independently selected from halogen, C$_1$-C$_3$ alkyl, C$_1$-C$_3$ haloalkyl, C$_1$-C$_3$ alkoxy, C$_1$-C$_3$ haloalkoxy, —SO$_2$R$_{11}$, —NR$_{11}$R$_{11}$, —OH or —CN; and each R$_{11}$ is independently —H or C$_1$-C$_3$ alkyl In a compound of Formula (I), or pharmaceutically acceptable salts thereof, R is —H or C$_1$-C$_3$ alkyl;
R$_1$ is a group of the formula:

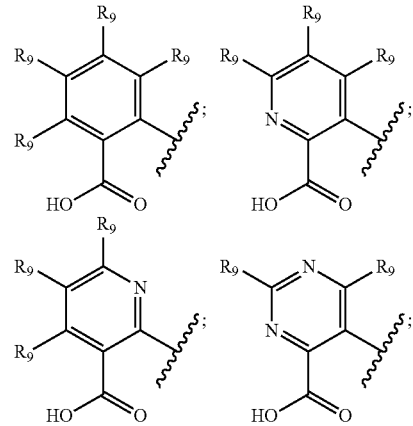

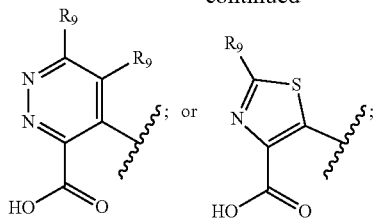

R₂ is a group of the formula:

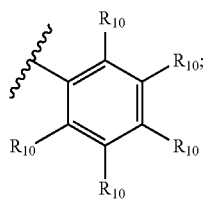

R₃ is —H, —CN, $C_1$-$C_6$ alkyl or $C_1$-$C_6$ haloalkyl;

each of R₄, R₅ and R₆ is independently —H, halogen, $C_1$-$C_6$ alkyl or $C_1$-$C_6$ haloalkyl;

R₇ is —CN, $C_1$-$C_6$ alkyl or $C_1$-$C_6$ haloalkyl;

R₈ is —H or $C_1$-$C_6$ alkyl;

each R₉ is independently —H, halogen, $C_1$-$C_6$ alkyl, $C_1$-$C_6$ haloalkyl, $C_1$-$C_6$ alkoxy, or $C_3$-$C_5$ cycloalkyl;

each R₁₀ is independently —H, —CN, halogen, $C_1$-$C_6$ haloalkyl, $C_1$-$C_6$ alkoxy, $C_1$-$C_6$ haloalkoxy, —SO₂R₁₁, —CONR₁₁R₁₁, —NR₁₁R₁₁, —NR₁₁—CO₂R₁₁, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR₁₁R₁₁, —OH or —CN; and each R₁₁ is independently —H or $C_1$-$C_3$ alkyl In a compound of Formula (I), or pharmaceutically acceptable salts thereof, R is —H or $C_1$-$C_3$ alkyl;

R₁ is a group of the formula:

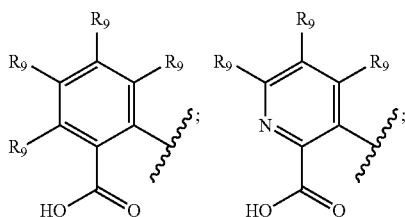

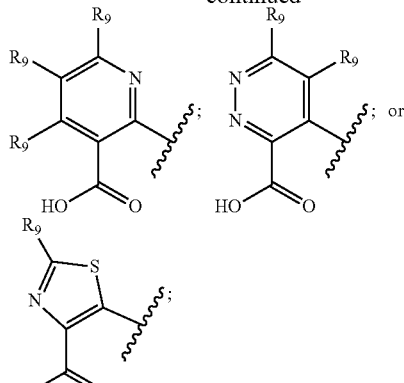

R₂ is a group of the formula:

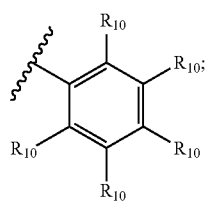

R₃ is —H, —CN, $C_1$-$C_6$ alkyl or $C_1$-$C_6$ haloalkyl;

each of R₄, R₅ and R₆ is independently —H, halogen, $C_1$-$C_6$ alkyl or $C_1$-$C_6$ haloalkyl;

R₇ is —CN, $C_1$-$C_6$ alkyl or $C_1$-$C_6$ haloalkyl;

R₈ is —H or $C_1$-$C_6$ alkyl;

each R₉ is independently —H, halogen, $C_1$-$C_6$ alkyl, $C_1$-$C_6$ haloalkyl, $C_1$-$C_6$ alkoxy, or $C_3$-$C_5$ cycloalkyl;

each R₁₀ is independently —H, —CN, halogen, $C_1$-$C_6$ haloalkyl, $C_1$-$C_6$ alkoxy, $C_1$-$C_6$ haloalkoxy, —SO₂R₁₁, —CONR₁₁R₁₁, —NR₁₁R₁₁, —NR₁₁—CO₂R₁₁, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR₁₁R₁₁, —OH or —CN; and each R₁₁ is independently —H or $C_1$-$C_3$ alkyl.

In a compound of Formula (I), or (II), or pharmaceutically acceptable salts thereof, R₂ is a group of the formula:

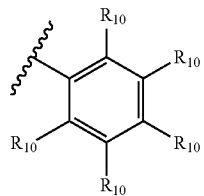

wherein each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{11}$, —$NR_{11}R_{11}$, —OH or —CN.

In a compound of Formula (I), or (II), or pharmaceutically acceptable salts thereof, $R_2$ is a group of the formula:

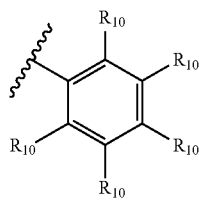

wherein each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and each $R_{11}$ is independently —H or $C_1$-$C_3$ alkyl.

In yet a further compound of Formula (I), or (II), or pharmaceutically acceptable salts thereof, $R_2$ is a group of the formula:

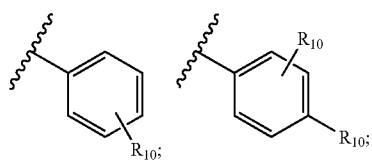

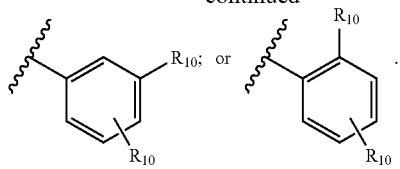

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_2$ is a group of the formula:

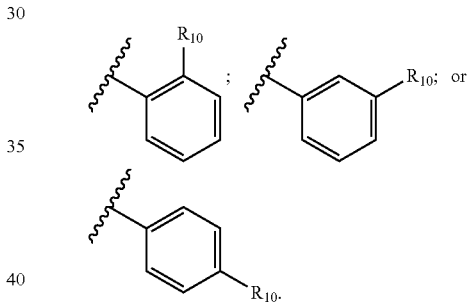

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, each $R_{10}$ is independently —H, —CN, halogen, $C_1$-$C_6$ haloalkyl, $C_1$-$C_6$ alkoxy, —$SO_2R_{11}$, —$CONR_{11}R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, or an optionally substituted heteroaryl selected from selected from pyrazole, isoxazole, isothiazole, imidazole, oxazole, or thiazole;

wherein the optionally substituted C₁-C₆ alkyl is optionally substituted with a —CN, —OH, or C₁-C₃ alkoxy; and the optionally substituted C₃-C₅ cycloalkyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR₁₁R₁₁, —OH or —CN.

In yet a further compound of Formula (I), or (II), or pharmaceutically acceptable salts thereof, each R₁₀ is independently —H, —CN, halogen, $C_1$-$C_6$ haloalkyl, $C_1$-$C_6$ alkoxy, —SO₂R₁₁, —C(O)OC₁-C₃ alkyl, —CONR₁₁R₁₁, a $C_1$-$C_6$ alkyl optionally substituted with —CN or —CONR₁₁R₁₁ (preferably each R₁₁ is $C_1$-$C_3$ alkyl), a $C_3$ cycloalkyl optionally substituted with $C_1$-$C_3$ alkyl or —CN, an optionally substituted heterocycle selected from pyrrolidine, an optionally substituted phenyl (preferably an optionally substituted phenyl substituted by a —CN), or an optionally substituted heteroaryl selected from pyrazole or oxazole.

In yet a further compound of Formula (I), or (II), or pharmaceutically acceptable salts thereof, each R₁₀ is independently —H, —CN, halogen, $C_1$-$C_6$ haloalkyl, $C_1$-$C_6$ alkoxy, —SO₂R₁₁, —CONR₁₁R₁₁, a $C_1$-$C_6$ alkyl optionally substituted with —CN, a $C_3$ cycloalkyl optionally substituted with $C_1$-$C_3$ alkyl or —CN, an optionally substituted heterocycle selected from pyrrolidine, or an optionally substituted heteroaryl selected from pyrazole or oxazole.

In yet a further compound of Formula (I), or (II), or pharmaceutically acceptable salts thereof, each R₁₀ is independently

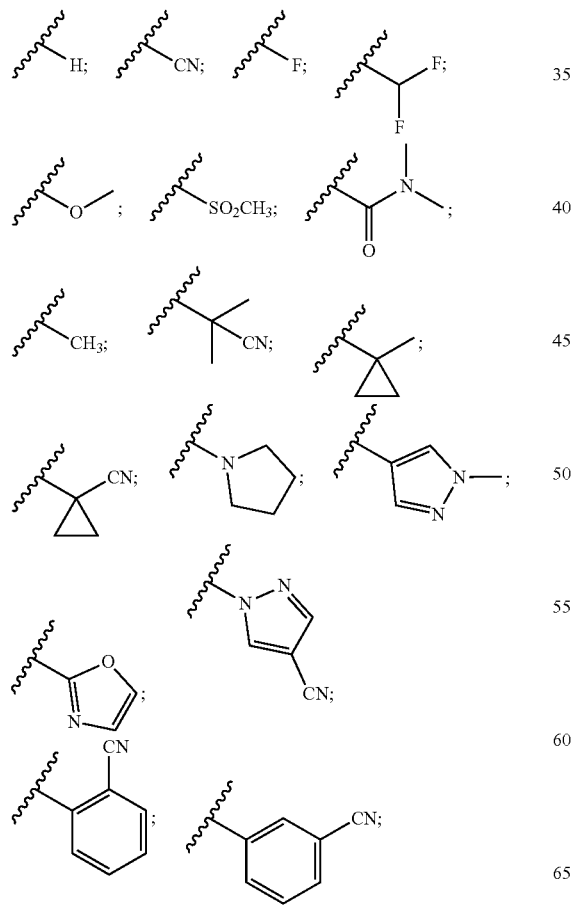

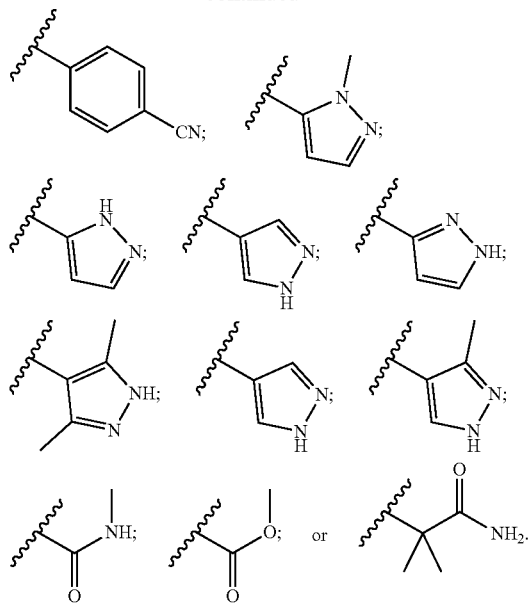

In yet a further compound of Formula (I), or (II), or pharmaceutically acceptable salts thereof, each R₁₀ is independently

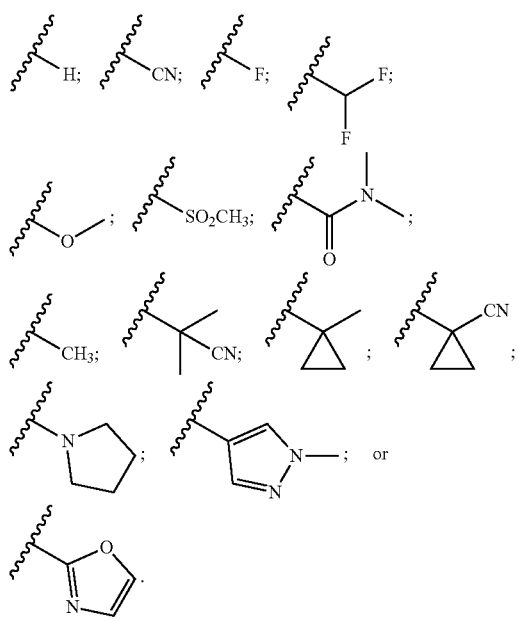

In yet a further compound of Formula (I), or (II), or pharmaceutically acceptable salts thereof, R₂ is a group of the formula:

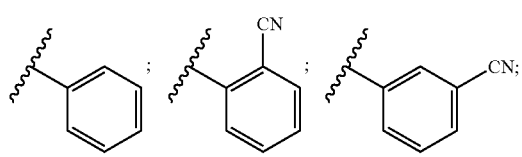

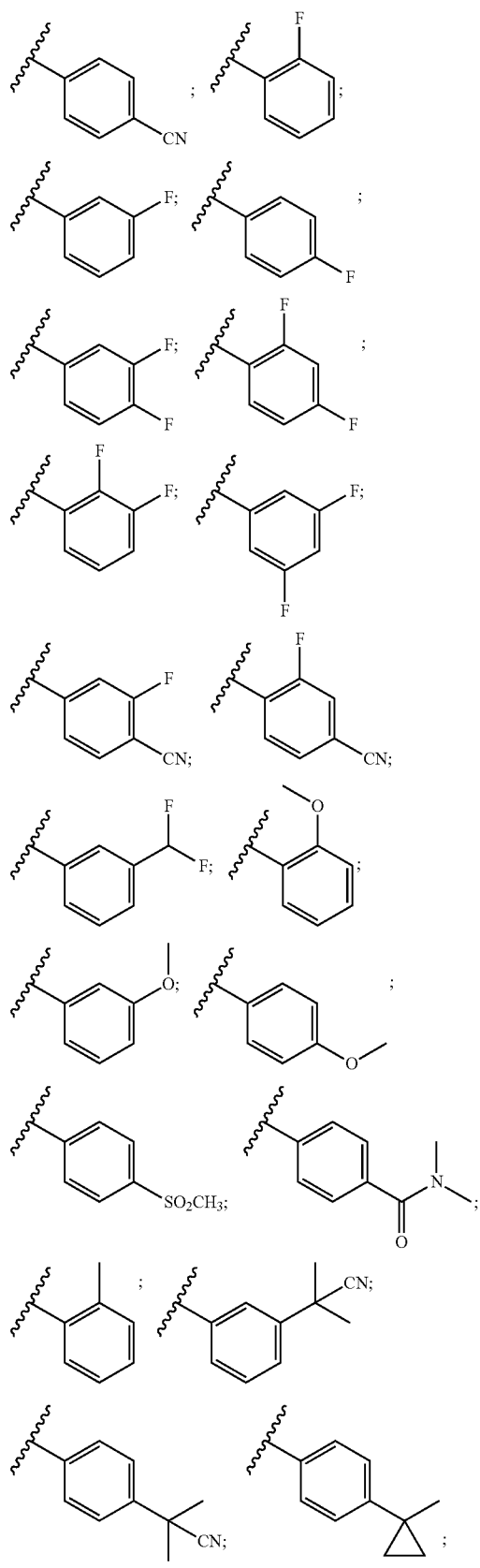
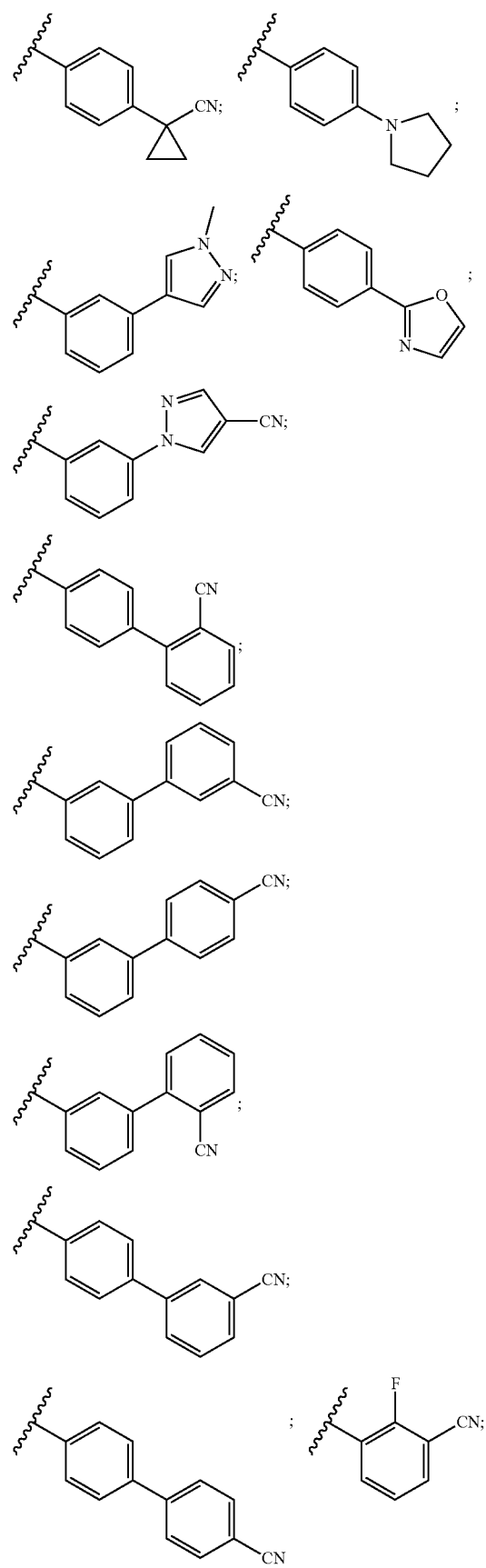

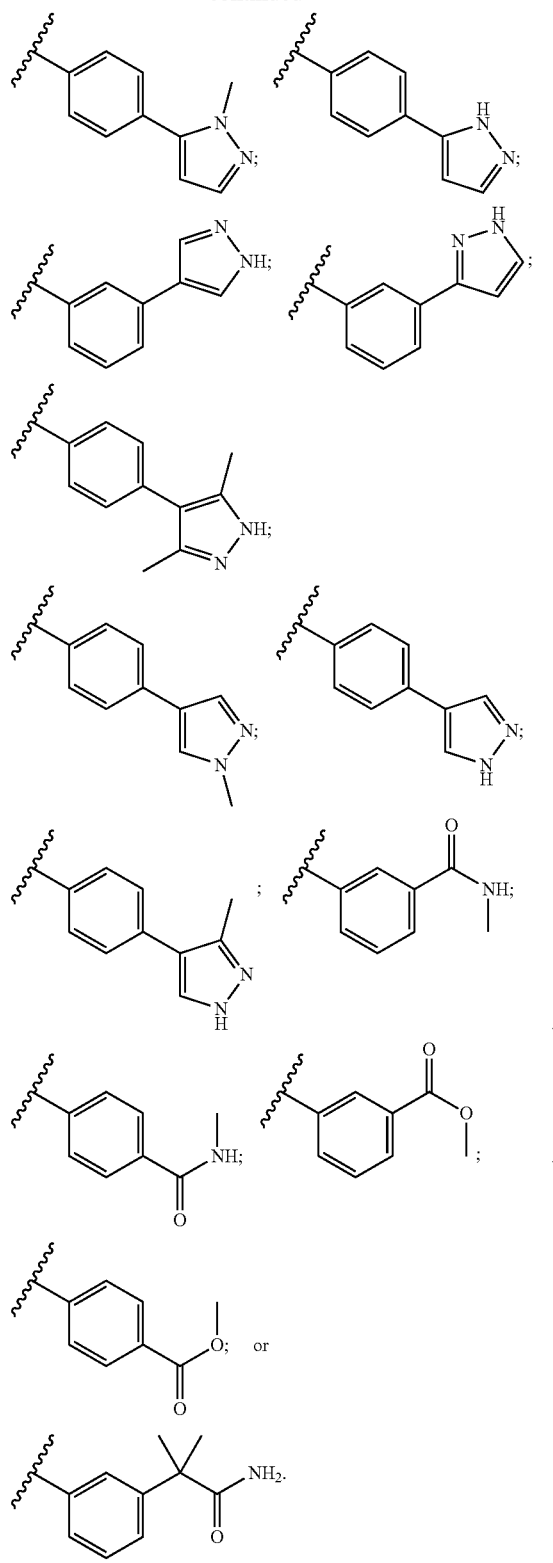
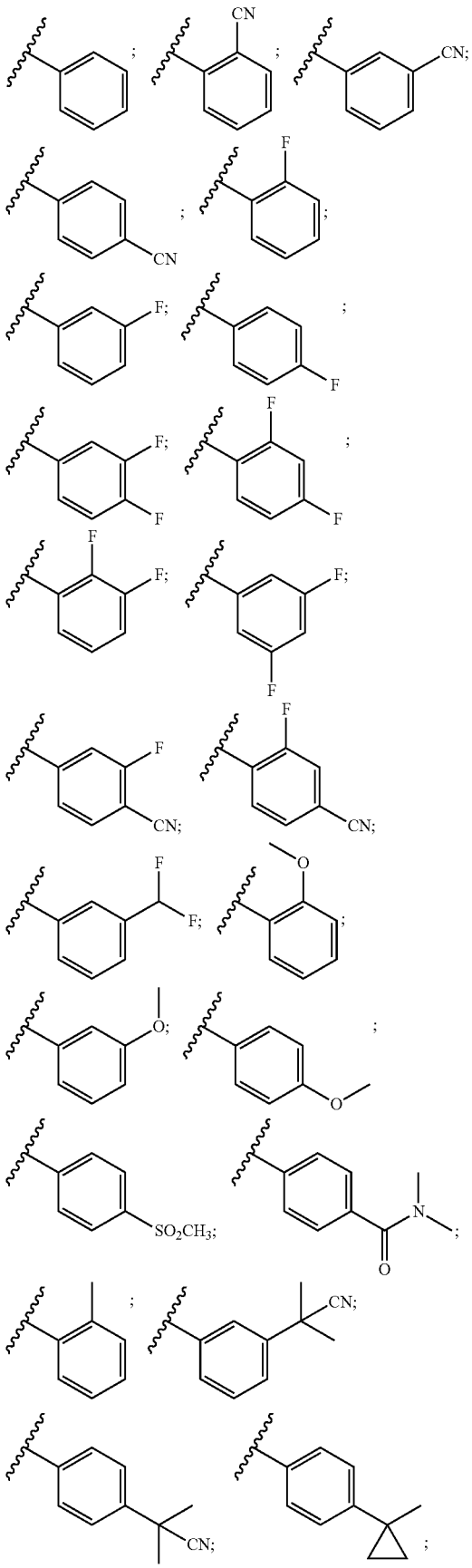
In yet a further compound of Formula (I), or (II), or pharmaceutically acceptable salts thereof, R₂ is a group of the formula:

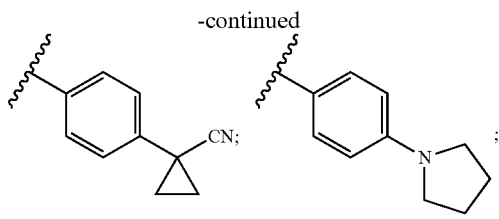

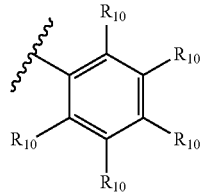

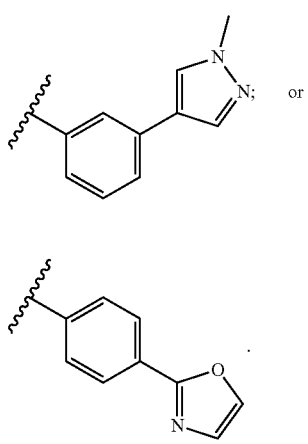

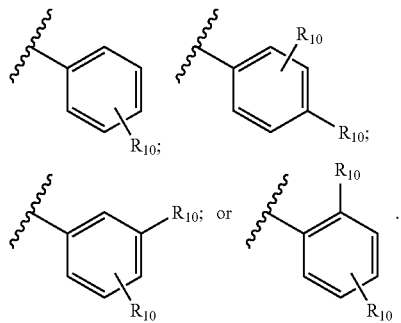

wherein each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN; and each $R_{11}$ is independently —H or $C_1$-$C_3$ alkyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), and $R_2$ is a group of the formula:

In yet a further compound of Formula (I), or (II), or pharmaceutically acceptable salts thereof, $R_3$ is —H, halogen, —CN, —N(H)(CH$_2$CH$_2$CO$_2$H), —C(O)C$_1$-C$_3$ alkyl, $C_1$-$C_6$ alkyl, $C_1$-$C_6$ haloalkyl, oxetane, isoxazole, or pyridine (preferably 3-pyridine). In yet a further compound of Formula (I), or (II), or pharmaceutically acceptable salts thereof, $R_3$ is —H, halogen, —CN, $C_1$-$C_6$ alkyl, $C_1$-$C_6$ haloalkyl, $C_3$-$C_5$ cycloalkyl, a heterocycle of 3 to 5 ring atoms containing 1, 2, or 3 ring heteroatoms independently selected from N, O, or S, or a heteroaryl of 5 ring atoms containing 1, 2, or 3 ring heteroatoms independently selected from N, O, or S. In yet a further compound of Formula (I), or (II), or pharmaceutically acceptable salts thereof, $R_3$ is —H, halogen, —CN, $C_1$-$C_6$ alkyl, $C_1$-$C_6$ haloalkyl, oxetane, or isoxazole. In yet a further compound of Formula (I), or (II), or pharmaceutically acceptable salts thereof, $R_3$ is —H, —CN, $C_1$-$C_6$ alkyl, or $C_1$-$C_6$ haloalkyl. In yet a further compound of Formula (I), or (II), or pharmaceutically acceptable salts thereof, $R_3$ is —H, —CN, $C_1$-$C_3$ alkyl or $C_1$-$C_3$ haloalkyl (preferably $R_3$ is —H, —CN, or $C_1$-$C_3$ alkyl); most preferably $R_3$ is —H, or methyl.

In yet a further compound of Formula (I), or (II), or pharmaceutically acceptable salts thereof, $R_4$ is H or halogen, preferably $R_4$ is H.

In yet a further compound of Formula (I), or (II), or pharmaceutically acceptable salts thereof, $R_5$ is —H, halogen, $C_1$-$C_6$ alkyl, or $C_1$-$C_6$ haloalkyl; preferably $R_5$ is —H, halogen, $C_1$-$C_3$ alkyl or $C_1$-$C_3$ haloalkyl; more preferably $R_5$ is —H, halogen, methyl, or trifluoromethyl.

In yet a further compound of Formula (I), or (II), or pharmaceutically acceptable salts thereof, $R_6$ is —H, or halogen.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), and $R_2$ is a group of the formula:

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_3$ is —H, methyl or trifluoromethyl (preferably $R_3$ is —H, or methyl), and $R_2$ is a group of the formula:

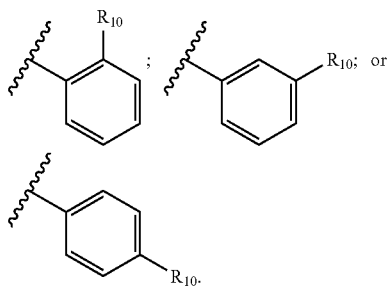

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In a compound of Formula (I), or (II), or pharmaceutically acceptable salts thereof, $R_4$ is —H or halogen (preferably $R_4$ is —H), and $R_2$ is a group of the formula:

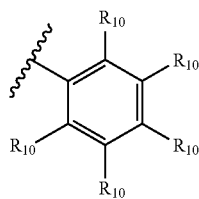

wherein each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and each $R_{11}$ is independently —H or $C_1$-$C_3$ alkyl.

In yet a further compound of Formula (I), or (II), or pharmaceutically acceptable salts thereof, $R_4$ is —H or halogen (preferably $R_4$ is —H), and $R_2$ is a group of the formula:

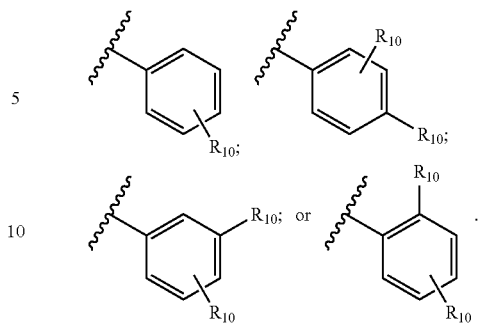

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_4$ is —H or halogen (preferably $R_4$ is —H), and $R_2$ is a group of the formula:

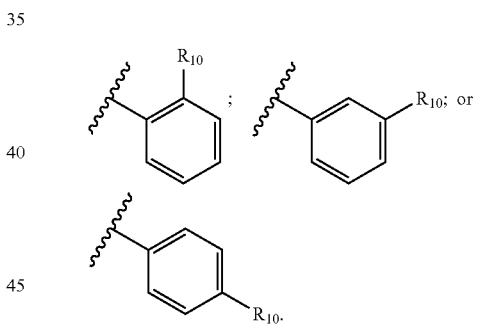

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_5$ is —H, halogen, $C_1$-$C_6$ alkyl, or $C_1$-$C_6$ haloalkyl, and $R_2$ is a group of the formula:

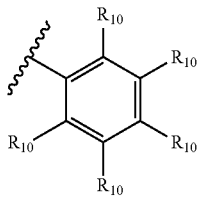

wherein each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and each $R_{11}$ is independently —H or $C_1$-$C_3$ alkyl.

In yet a further compound of Formula (I), or (II), or pharmaceutically acceptable salts thereof, $R_5$ is —H, halogen, $C_1$-$C_3$ alkyl or $C_1$-$C_3$ haloalkyl, and $R_2$ is a group of the formula:

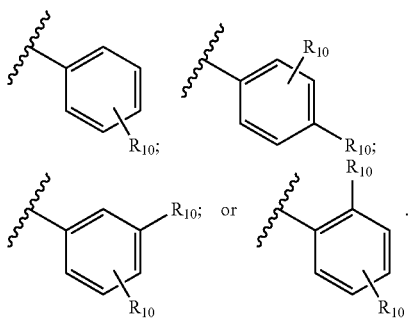

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_5$ is —H, halogen, methyl, or trifluoromethyl, and $R_2$ is a group of the formula:

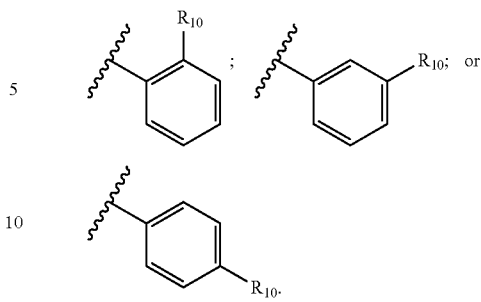

In yet a further compound of Formula (I), or (II), or pharmaceutically acceptable salts thereof, $R_6$ is —H, or halogen, and $R_2$ is a group of the formula:

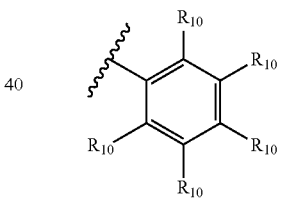

wherein each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and each $R_{11}$ is independently —H or $C_1$-$C_3$ alkyl.

In yet a further compound of Formula (I), or (II), or pharmaceutically acceptable salts thereof, $R_6$ is —H, or halogen, and $R_2$ is a group of the formula:

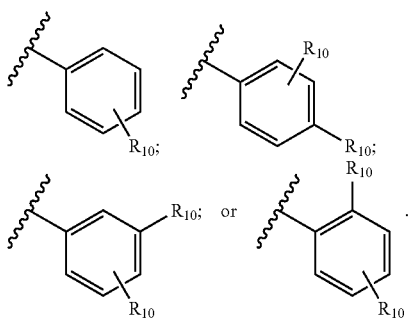

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_6$ is —H, or halogen, and $R_2$ is a group of the formula:

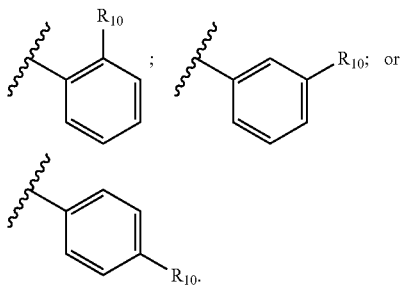

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, and $R_4$ is H or halogen; more preferably $R_3$ is —H, —CN, or $C_1$-$C_3$ alkyl, and $R_4$ is H; most preferably $R_3$ is —H, or methyl, and $R_4$ is H.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), and $R_5$ is —H, halogen, $C_1$-$C_3$ alkyl or $C_1$-$C_3$ haloalkyl; more preferably $R_3$ is —H, or methyl, and $R_5$ is —H, halogen, methyl, or trifluoromethyl.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), and $R_6$ is —H, or halogen; more preferably $R_3$ is —H, or methyl, and $R_6$ is —H, or halogen.

In yet a further compound of Formula (I), or (II), or pharmaceutically acceptable salts thereof, $R_4$ is —H or halogen (preferably $R_4$ is —H), and $R_5$ is —H, halogen, $C_1$-$C_3$ alkyl or $C_1$-$C_3$ haloalkyl; preferably $R_5$ is —H, halogen, methyl, or trifluoromethyl.

In yet a further compound of Formula (I), or (II), or pharmaceutically acceptable salts thereof, $R_4$ is —H or halogen (preferably $R_4$ is —H) and $R_6$ is —H, or halogen.

In yet a further compound of Formula (I), or (II), or pharmaceutically acceptable salts thereof, $R_5$ is —H, halogen, $C_1$-$C_3$ alkyl or $C_1$-$C_3$ haloalkyl, and $R_6$ is —H, or halogen; preferably $R_5$ is —H, halogen, methyl, or trifluoromethyl, and $R_6$ is H.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), $R_4$ is —H or halogen (preferably $R_4$ is —H), and $R_2$ is a group of the formula:

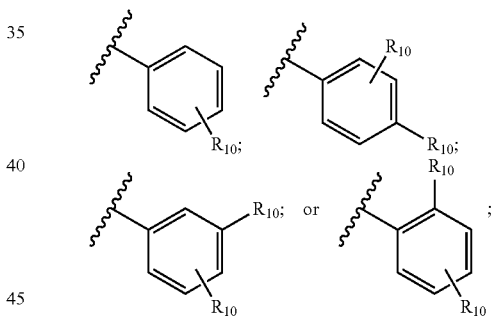

preferably $R_3$ is —H, or methyl, $R_4$ is —H, and $R_2$ is a group of the formula:

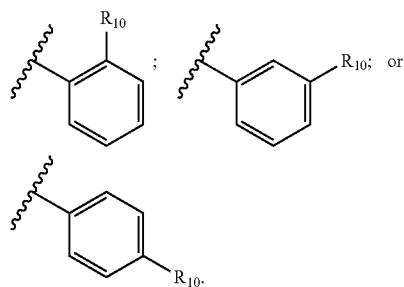

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), $R_5$ is —H, halogen, $C_1$-$C_6$ alkyl, or $C_1$-$C_6$ haloalkyl, and $R_2$ is a group of the formula:

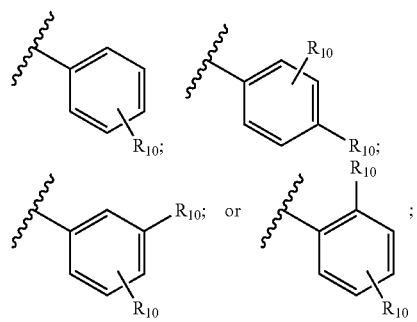

more preferably $R_3$ is —H, or methyl, $R_5$ is —H, halogen, methyl, or trifluoromethyl, and $R_2$ is a group of the formula:

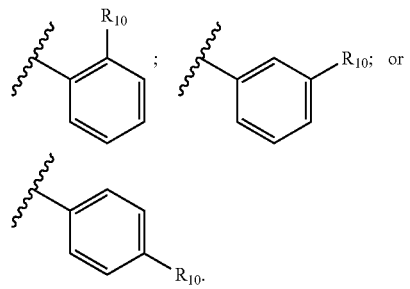

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), $R_6$ is —H, or halogen, and $R_2$ is a group of the formula:

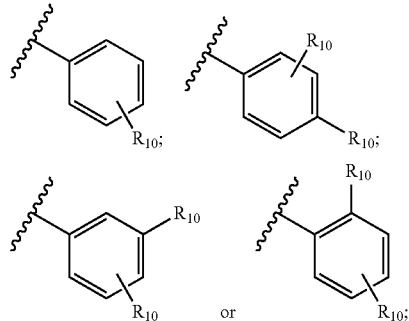

more preferably $R_3$ is —H, or methyl, $R_6$ is —H, and $R_2$ is a group of the formula:

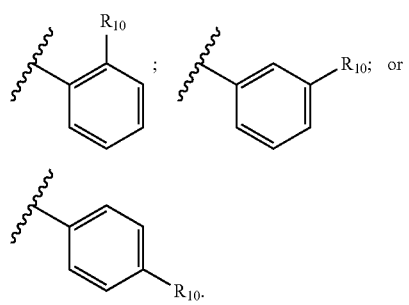

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_4$ is —H or halogen (preferably $R_4$ is —H), $R_5$ is —H, halogen, $C_1$-$C_3$ alkyl or $C_1$-$C_3$ haloalkyl, and $R_2$ is a group of the formula:

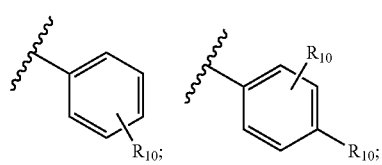

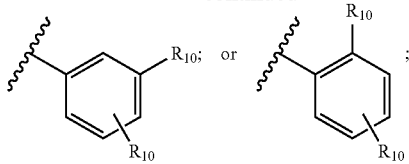

more preferably $R_5$ is —H, halogen, methyl, or trifluoromethyl, and $R_2$ is a group of the formula:

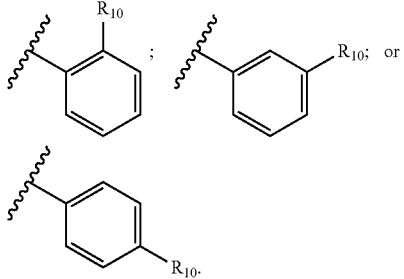

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In a compound of Formula (I), or (II), or pharmaceutically acceptable salts thereof, $R_4$ is —H or halogen (preferably $R_4$ is —H), $R_6$ is —H, or halogen, and $R_2$ is a group of the formula:

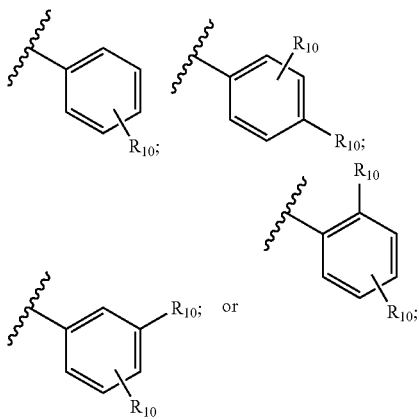

more preferably $R_4$ and $R_6$ are each —H, and $R_2$ is a group of the formula:

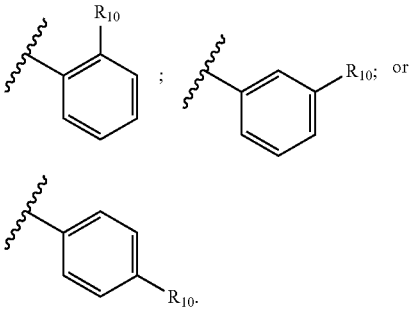

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_6$ is —H, or halogen, and $R_2$ is a group of the formula:

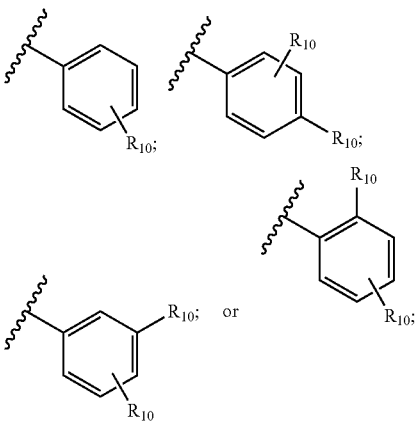

preferably $R_5$ is —H, halogen, methyl, or trifluoromethyl, $R_6$ is —H, and $R_2$ is a group of the formula:

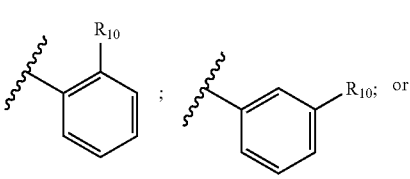

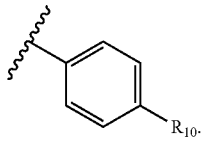

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), and $R_5$ is —H, halogen, $C_1$-$C_3$ alkyl or $C_1$-$C_3$ haloalkyl; more preferably $R_3$ is —H, or methyl, $R_4$ is —H, and $R_5$ is —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), and $R_6$ is —H, or halogen; more preferably $R_3$ is —H, or methyl, and $R_4$ and $R_6$ are each H.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_5$ is —H, halogen, $C_1$-$C_3$ alkyl or $C_1$-$C_3$ haloalkyl, $R_6$ is —H, or halogen; more preferably $R_3$ is —H, or methyl, $R_5$ is —H, halogen, methyl, or trifluoromethyl, and $R_6$ is H.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_4$ is —H or halogen (preferably $R_4$ is —H), and $R_6$ is —H, or halogen; more preferably $R_5$ is —H, halogen, methyl, or trifluoromethyl, and $R_4$ and $R_6$ are each H.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_5$ is —H, halogen, $C_1$-$C_6$ alkyl, $C_1$-$C_6$ haloalkyl, or $C_1$-$C_6$ alkoxy, and $R_2$ is a group of the formula:

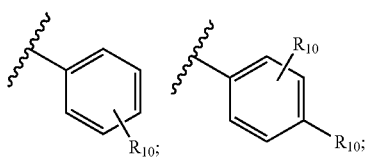

more preferably $R_3$ is —H, or methyl, $R_4$ is —H, $R_5$ is —H, halogen, methyl, or trifluoromethyl, and $R_2$ is a group of the formula:

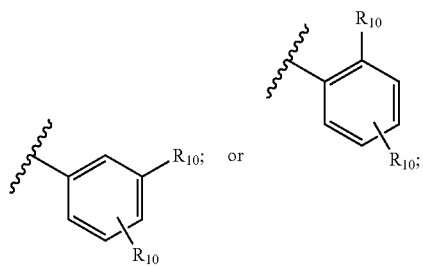

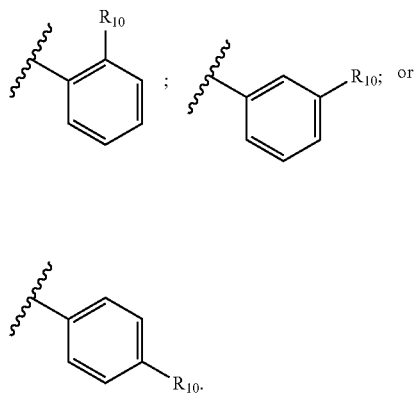

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, and $R_2$ is a group of the formula:

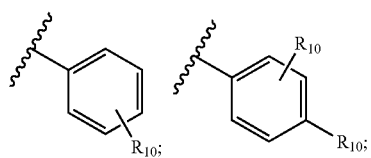

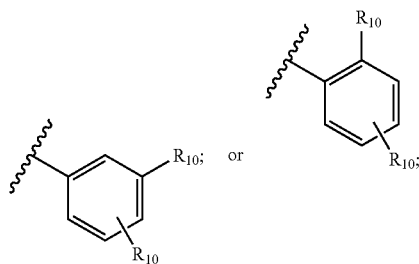

more preferably $R_3$ is —H, or methyl, $R_4$ and $R_6$ are each —H, and $R_2$ is a group of the formula:

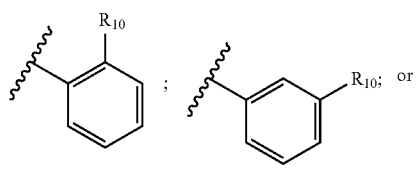

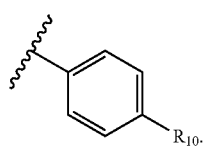

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_5$ is —H, halogen, $C_1$-$C_6$ alkyl, or $C_1$-$C_6$ haloalkyl, $R_6$ is —H, or halogen, and $R_2$ is a group of the formula:

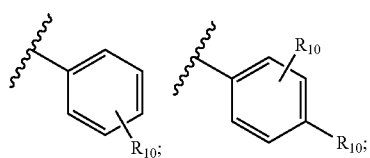

more preferably $R_3$ is —H, or methyl, $R_5$ is —H, halogen, methyl, or trifluoromethyl, $R_6$ is —H, and $R_2$ is a group of the formula:

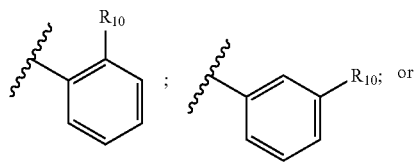

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_4$ is —H or halogen (preferably $R_4$ is —H), $R_6$ is —H, or halogen, and $R_2$ is a group of the formula:

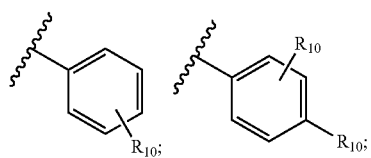

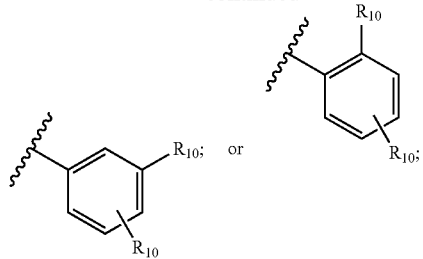

more preferably $R_5$ is —H, halogen, methyl, or trifluoromethyl, $R_4$ is —H, $R_6$ is —H, or halogen, and $R_2$ is a group of the formula:

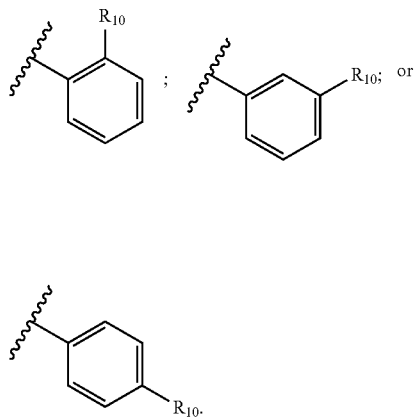

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, and $R_5$ is —H, halogen, $C_1$-$C_3$ alkyl or $C_1$-$C_3$ haloalkyl; more preferably $R_3$ is —H, or methyl, $R_4$ and $R_6$ are each —H, and $R_5$ is —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, $R_5$ is —H, halogen, $C_1$-$C_3$ alkyl or $C_1$-$C_3$ haloalkyl, and $R_2$ is a group of the formula:

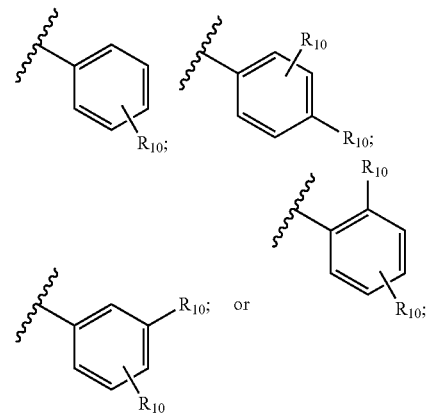

more preferably $R_3$ is —H, or methyl, $R_4$ is —H, $R_6$ is —H, or halogen, $R_5$ is —H, halogen, methyl, or trifluoromethyl, and $R_2$ is a group of the formula:

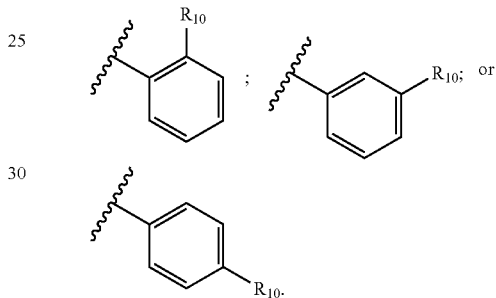

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, R is —H.

In yet a further compound of Formula (I), or (II), or pharmaceutically acceptable salts thereof, $R_7$ is —CN, $C_1$-$C_6$ alkyl, or $C_1$-$C_6$ haloalkyl; preferably $R_7$ is —CN, $C_1$-$C_3$ alkyl or $C_1$-$C_3$ haloalkyl; more preferably $R_7$ is —CN, methyl or trifluoromethyl.

In yet a further compound of Formula (I), or (II), or pharmaceutically acceptable salts thereof, $R_8$ is —H.

In yet a further compound of Formula (I), or (II), or pharmaceutically acceptable salts thereof, $R_7$ is —CN, $C_1$-$C_3$ alkyl or $C_1$-$C_3$ haloalkyl, and R is —H. In yet a further compound of Formula (I), or (II), or pharmaceutically acceptable salts thereof, $R_7$ is $C_1$-$C_3$ alkyl (preferably methyl), and R is —H.

In yet a further compound of Formula (I), or (II), or pharmaceutically acceptable salts thereof, $R_8$ and R are each —H.

In yet a further compound of Formula (I), or (II), or pharmaceutically acceptable salts thereof, $R_7$ is —CN, $C_1$-$C_3$ alkyl or $C_1$-$C_3$ haloalkyl, and $R_8$ is H. In yet a further compound of Formula (I), or (II), or pharmaceutically acceptable salts thereof, $R_7$ is $C_1$-$C_3$ alkyl (preferably methyl), and $R_8$ is H.

In yet a further compound of Formula (I), or (II), or pharmaceutically acceptable salts thereof, $R_7$ is —CN, $C_1$-$C_3$ alkyl or $C_1$-$C_3$ haloalkyl, and $R_8$ and R are each —H. In yet a further compound of Formula (I), or (II), or pharmaceutically acceptable salts thereof, $R_7$ is $C_1$-$C_3$ alkyl (preferably methyl), and $R_8$ and R are each —H.

In yet a further compound of Formula (I), or (II), or pharmaceutically acceptable salts thereof, $R_7$ is —CN, $C_1$-$C_3$ alkyl or $C_1$-$C_3$ haloalkyl, $R_8$ is —H, R is —H, and $R_2$ is a group of the formula:

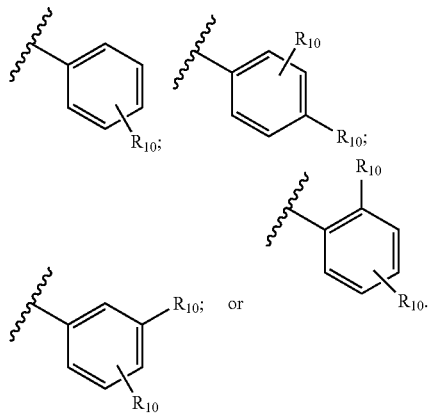

In yet a further compound of Formula (I), or (II), or pharmaceutically acceptable salts thereof, $R_7$ is $C_1$-$C_3$ alkyl (preferably methyl), $R_8$ is —H, R is —H, and $R_2$ is a group of the formula:

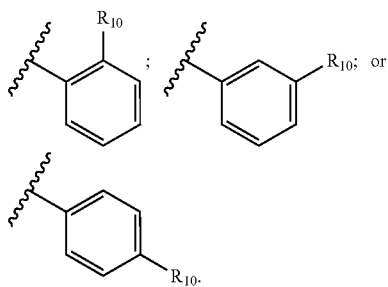

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_7$ is —CN, $C_1$-$C_3$ alkyl or $C_1$-$C_3$ haloalkyl, and $R_8$ and R are each —H. In yet a further compound of Formula (I), or (II), or pharmaceutically acceptable salts thereof, $R_3$ is —H, or methyl, $R_7$ is $C_1$-$C_3$ alkyl (preferably methyl), and $R_8$ and R are each —H.

In yet a further compound of Formula (I), or (II), or pharmaceutically acceptable salts thereof, $R_7$ is —CN, $C_1$-$C_3$ alkyl or $C_1$-$C_3$ haloalkyl, and $R_4$, $R_5$ and R are each —H. In yet a further compound of Formula (I), or (II), or pharmaceutically acceptable salts thereof, $R_7$ is $C_1$-$C_3$ alkyl (preferably methyl), and $R_4$, $R_5$ and R are each —H.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_7$ is —CN, methyl or trifluoromethyl, and $R_8$ and R are each —H. In yet a further compound of Formula (I), or (II), or pharmaceutically acceptable salts thereof, $R_5$ is —H, halogen, methyl, or trifluoromethyl, $R_7$ is methyl, and $R_8$ and R are each —H.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, $R_5$ is —H, halogen, $C_1$-$C_6$ alkyl, or $C_1$-$C_6$ haloalkyl, $R_7$ is —CN, methyl or trifluoromethyl, $R_8$ is —H, R is —H, and $R_2$ is a group of the formula:

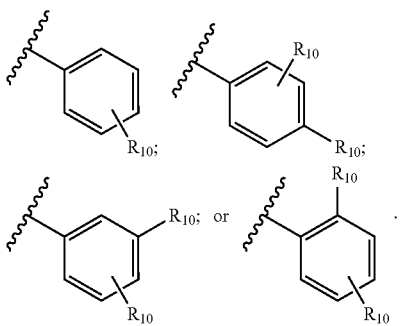

more preferably $R_3$ is —H, or methyl, $R_4$ is —H, $R_6$ is —H, or halogen, $R_5$ is —H, halogen, methyl, or trifluoromethyl, $R_7$ is methyl, $R_8$ is —H, R is —H, and $R_2$ is a group of the formula:

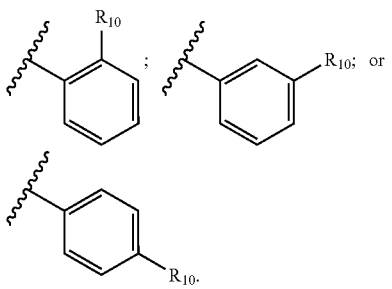

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_1$ is a group of the formula:

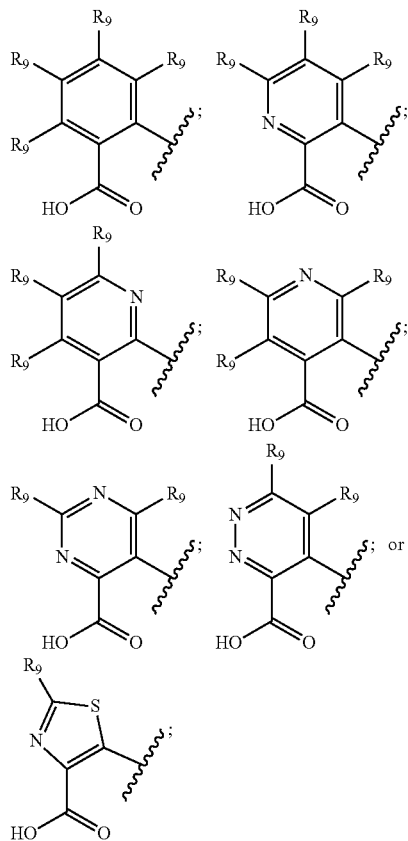

wherein each $R_9$ is independently —H, halogen, —CN, $C_1$-$C_3$ alkyl, $C_1$-$C_3$ haloalkyl, $C_1$-$C_3$ alkoxy, or $C_3$-$C_5$ cycloalkyl; preferably each $R_9$ is independently —H, halogen, —CN, methyl, trifluoromethyl, methoxy, or cyclopropyl.

In yet a further compound of Formula (I), or (II), or pharmaceutically acceptable salts thereof, $R_1$ is a group of the formula:

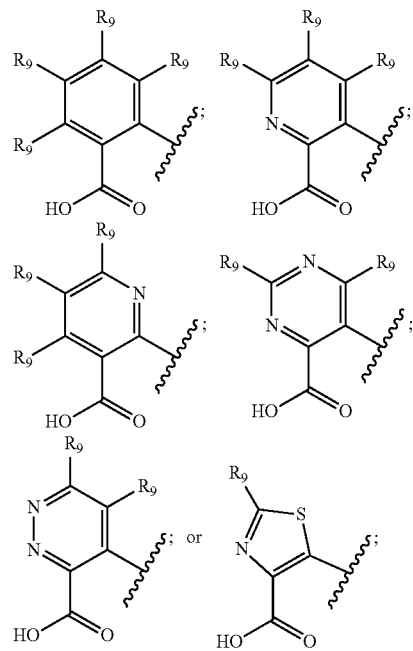

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl; preferably each $R_9$ is independently —H, halogen, $C_1$-$C_3$ alkyl, $C_1$-$C_3$ haloalkyl, $C_1$-$C_3$ alkoxy, or $C_3$-$C_5$ cycloalkyl; more preferably each $R_9$ is independently —H, halogen, methyl, trifluoromethyl, methoxy, or cyclopropyl.

In yet a further compound of Formula (I), or (II), or pharmaceutically acceptable salts thereof, $R_1$ is a group of the formula:

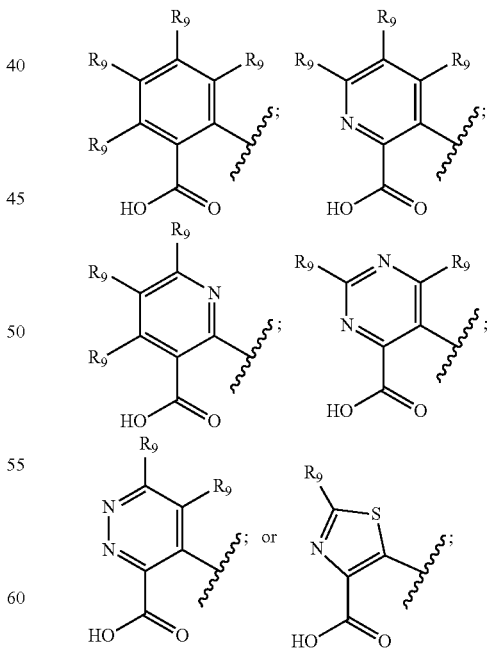

wherein each $R_9$ is independently —H, halogen, $C_1$-$C_3$ alkyl, $C_1$-$C_3$ haloalkyl, or $C_3$-$C_5$ cycloalkyl; preferably each $R_9$ is independently —H, halogen, methyl, trifluoromethyl, or cyclopropyl.

In yet a further compound of Formula (I), or (II), or pharmaceutically acceptable salts thereof, $R_1$ is a group of the formula:

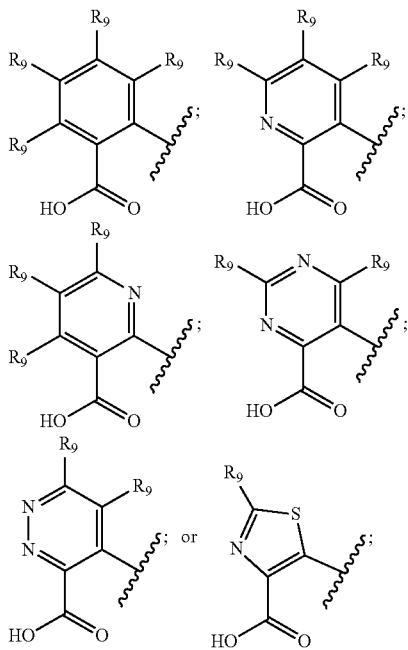

wherein each $R_9$ is independently —H, halogen, $C_1$-$C_3$ alkyl or $C_1$-$C_3$ haloalkyl; preferably each $R_9$ is independently —H, halogen, methyl or trifluoromethyl.

In yet a further compound of Formula (I), or (II), or pharmaceutically acceptable salts thereof, $R_1$ is a group of the formula:

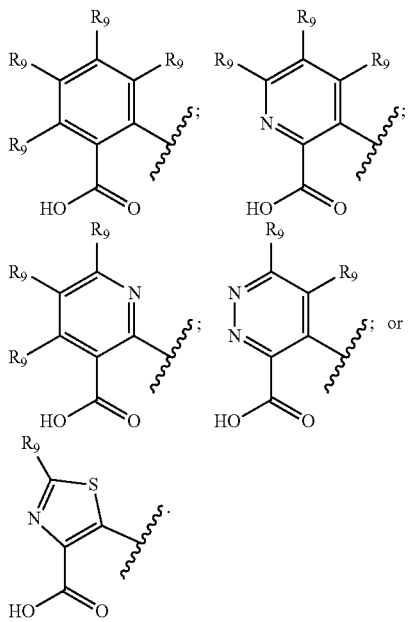

In yet a further compound of Formula (I), or (II), or pharmaceutically acceptable salts thereof, $R_1$ is a group of the formula:

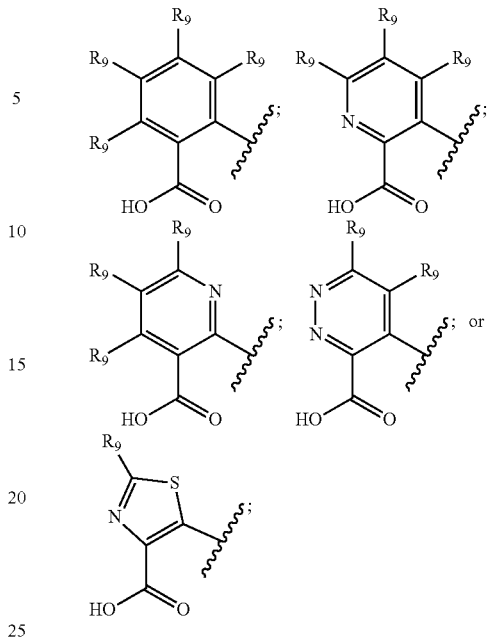

wherein each $R_9$ is independently —H, halogen, $C_1$-$C_3$ alkyl or $C_1$-$C_3$ haloalkyl; preferably each $R_9$ is independently —H, halogen, methyl or trifluoromethyl.

In yet a further compound of Formula (I), or (II), or pharmaceutically acceptable salts thereof, $R_1$ is a group of the formula:

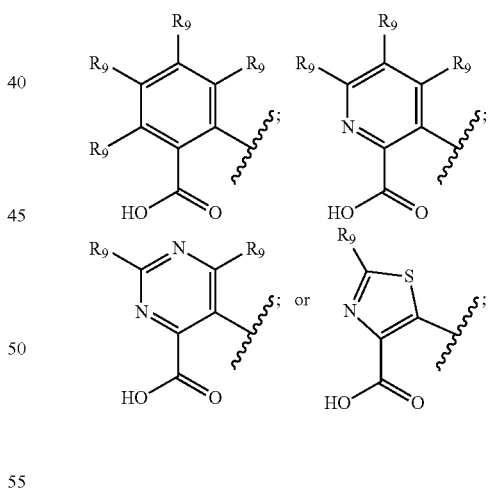

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl. Preferably each $R_9$ is independently —H, halogen, $C_1$-$C_3$ alkyl, $C_1$-$C_3$ haloalkyl, or $C_3$-$C_5$ cycloalkyl. More preferably each $R_9$ is independently —H, halogen, methyl, trifluoromethyl, or cyclopropyl.

In yet a further compound of Formula (I), or (II), or pharmaceutically acceptable salts thereof, $R_1$ is a group of the formula:

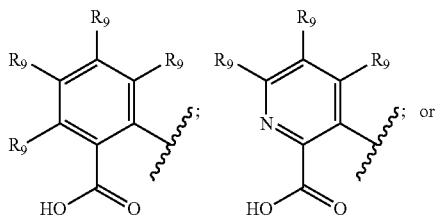

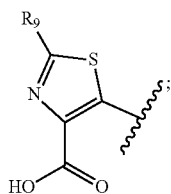

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl. Preferably each $R_9$ is independently —H, halogen, $C_1$-$C_3$ alkyl or $C_1$-$C_3$ haloalkyl. More preferably each $R_9$ is independently —H, halogen, methyl or trifluoromethyl.

In yet a further compound of Formula (I), or (II), or pharmaceutically acceptable salts thereof, $R_1$ is a group of the formula

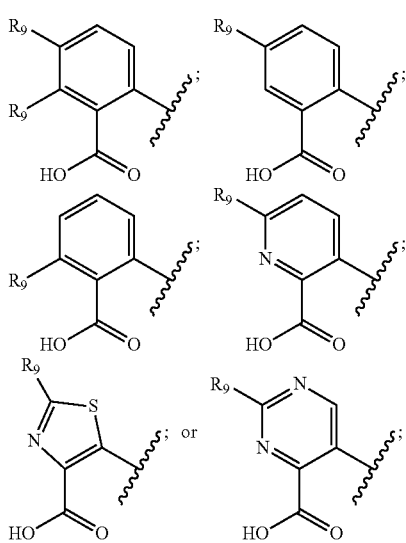

wherein each $R_9$ is independently —H, halogen, —CN, $C_1$-$C_6$ alkyl, $C_1$-$C_6$ haloalkyl, $C_1$-$C_6$ alkoxy, or $C_3$-$C_5$ cycloalkyl; preferably each $R_9$ is independently —H, halogen, —CN, $C_1$-$C_3$ alkyl, $C_1$-$C_3$ haloalkyl, $C_1$-$C_3$ alkoxy, or $C_3$-$C_5$ cycloalkyl; more preferably each $R_9$ is independently —H, halogen, —CN, methyl, trifluoromethyl, methoxy, or cyclopropyl.

In yet a further compound of Formula (I), or (II), or pharmaceutically acceptable salts thereof, $R_1$ is a group of the formula

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl; preferably each $R_9$ is independently —H, halogen, $C_1$-$C_3$ alkyl, $C_1$-$C_3$ haloalkyl, $C_1$-$C_3$ alkoxy, or $C_3$-$C_5$ cycloalkyl; more preferably each $R_9$ is independently —H, halogen, methyl, trifluoromethyl, methoxy, or cyclopropyl.

In yet a further compound of Formula (I), or (II), or pharmaceutically acceptable salts thereof, $R_1$ is a group of the formula:

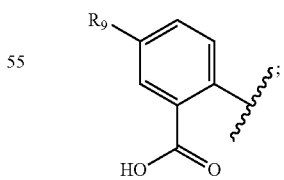

wherein each $R_9$ is independently —H, halogen, —CN, $C_1$-$C_3$ alkyl, $C_1$-$C_3$ haloalkyl or $C_1$-$C_3$ alkoxy. Preferably each $R_9$ is independently —H, halogen, $C_1$-$C_3$ alkyl or $C_1$-$C_3$ haloalkyl. More preferably each $R_9$ is independently —H, halogen, methyl or trifluoromethyl.

In yet a further compound of Formula (I), or (II), or pharmaceutically acceptable salts thereof, $R_1$ is a group of the formula:

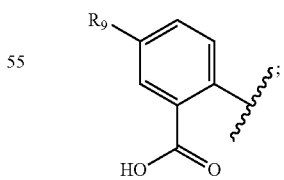

wherein $R_9$ is —H, halogen, —CN, $C_1$-$C_3$ haloalkyl, or $C_1$-$C_3$ alkoxy. Preferably $R_9$ is —H, halogen, or $C_1$-$C_3$ haloalkyl. More preferably $R_9$ is —H, or trifluoromethyl.

In yet a further compound of Formula (I), or (II), or pharmaceutically acceptable salts thereof, $R_1$ is a group of the formula:

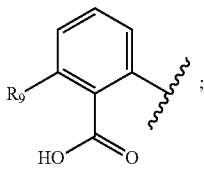

wherein $R_9$ is —H, halogen, —CN, $C_1$-$C_3$ haloalkyl, or $C_1$-$C_3$ alkoxy. Preferably $R_9$ is —H, halogen, or $C_1$-$C_3$ haloalkyl. More preferably $R_9$ is —H, or halogen. Even more preferably, $R_9$ is —H, or fluoro.

In yet a further compound of Formula (I), or (II), or pharmaceutically acceptable salts thereof, $R_1$ is a group of the formula:

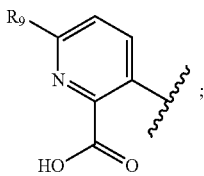

wherein $R_9$ is —H, halogen, —CN, $C_1$-$C_3$ alkyl, $C_1$-$C_3$ haloalkyl, $C_1$-$C_3$ alkoxy, or $C_3$-$C_5$ cycloalkyl. Preferably $R_9$ is —H, halogen, $C_1$-$C_3$ alkyl, $C_1$-$C_3$ haloalkyl, or $C_3$-$C_5$ cycloalkyl. More preferably $R_9$ is independently —H, halogen, methyl, trifluoromethyl, or cyclopropyl.

In yet a further compound of Formula (I), or (II), or pharmaceutically acceptable salts thereof, $R_1$ is a group of the formula:

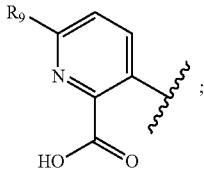

wherein $R_9$ is —H, halogen, or $C_1$-$C_3$ haloalkyl. Preferably $R_9$ is independently halogen or trifluoromethyl. More preferably $R_9$ is chloro or trifluoromethyl.

In yet a further compound of Formula (I), or (II), or pharmaceutically acceptable salts thereof, $R_1$ is a group of the formula:

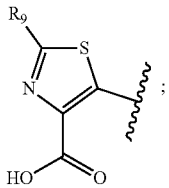

wherein $R_9$ is —H, halogen, —CN, $C_1$-$C_6$ alkyl, $C_1$-$C_6$ haloalkyl or $C_1$-$C_6$ alkoxy. Preferably $R_9$ is —H, halogen, $C_1$-$C_6$ alkyl or $C_1$-$C_6$ haloalkyl. More preferably $R_9$ is —H, halogen, $C_1$-$C_3$ alkyl or $C_1$-$C_3$ haloalkyl.

In yet a further compound of Formula (I), or (II), or pharmaceutically acceptable salts thereof, $R_1$ is a group of the formula:

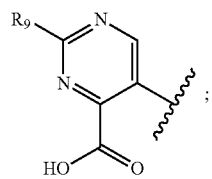

wherein $R_9$ is —H, halogen, —CN, $C_1$-$C_3$ alkyl, $C_1$-$C_3$ haloalkyl, $C_1$-$C_3$ alkoxy, or $C_3$-$C_5$ cycloalkyl. Preferably $R_9$ is —H, halogen, $C_1$-$C_3$ alkyl, $C_1$-$C_3$ haloalkyl, or $C_3$-$C_5$ cycloalkyl. More preferably $R_9$ is —H, halogen, methyl, trifluoromethyl, or cyclopropyl.

In yet a further compound of Formula (I), or (II), or pharmaceutically acceptable salts thereof, $R_1$ is a group of the formula:

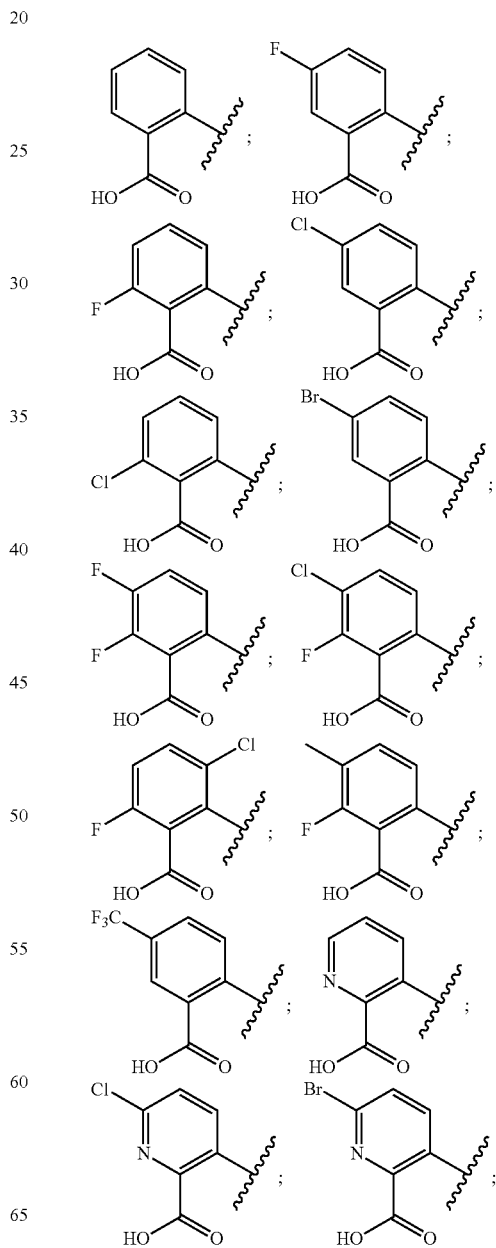

-continued

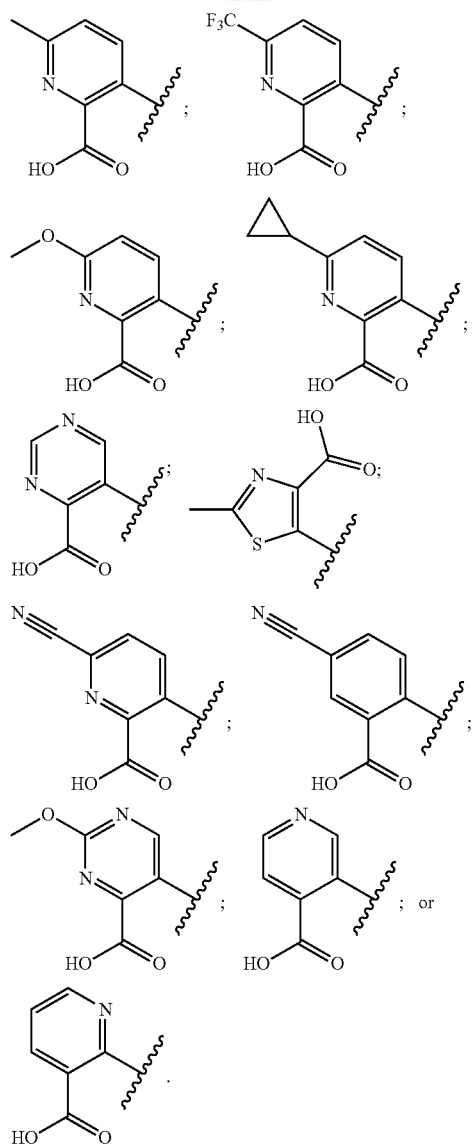

In yet a further compound of Formula (I), or (II), or pharmaceutically acceptable salts thereof, $R_1$ is a group of the formula:

-continued

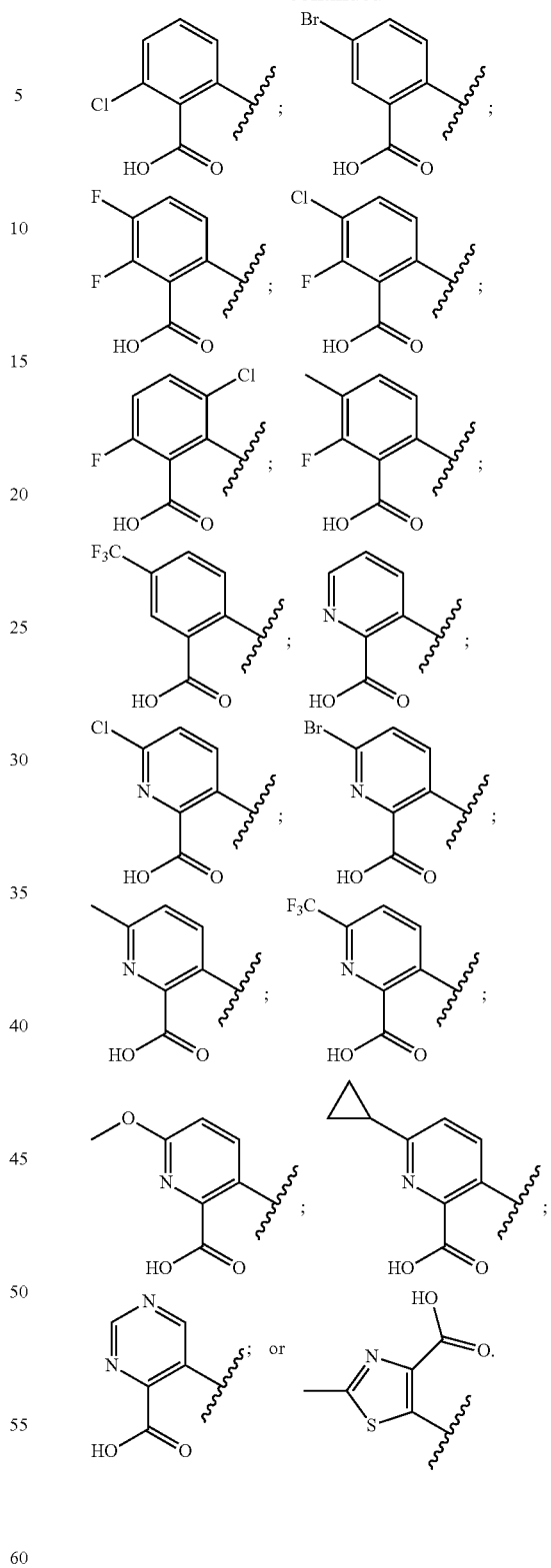

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_6$ is —H, or halogen, $R_5$ is —H, halogen, $C_1$-$C_3$ alkyl or $C_1$-$C_3$ haloalkyl, and $R_1$ is a group of the formula:

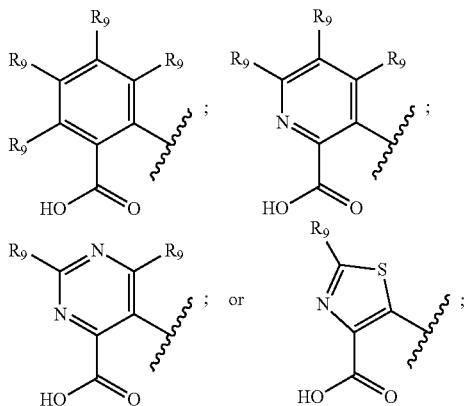

wherein each $R_9$ is independently —H, halogen, $C_1$-$C_3$ alkyl, $C_1$-$C_3$ haloalkyl, or $C_3$-$C_5$ cycloalkyl. More preferably each $R_9$ is independently —H, halogen, methyl, trifluoromethyl, or cyclopropyl. Preferably $R_3$ is —H, methyl, or trifluoromethyl, $R_4$ is —H, or halogen, $R_6$ is —H, or halogen, R is —H, halogen, methyl, or trifluoromethyl, and each $R_9$ is independently —H, halogen, methyl, trifluoromethyl, or cyclopropyl.

In yet a further compound of Formula (I), or (II), or pharmaceutically acceptable salts thereof, $R_3$ is —H, —CN, or $C_1$-$C_3$ alkyl, $R_4$ is —H, $R_6$ is —H, or halogen, $R_5$ is —H, halogen, $C_1$-$C_3$ alkyl or $C_1$-$C_3$ haloalkyl, and $R_1$ is a group of the formula:

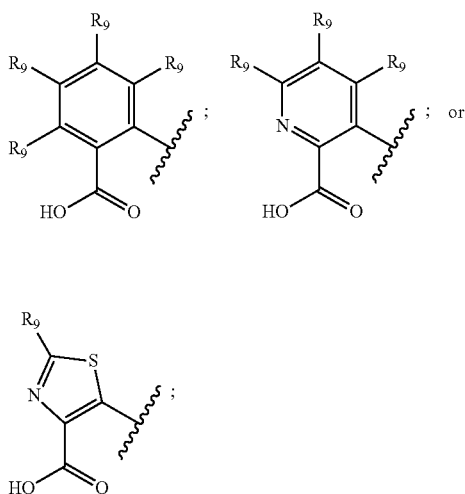

wherein each $R_9$ is independently —H, halogen, $C_1$-$C_3$ alkyl or $C_1$-$C_3$ haloalkyl. Preferably $R_3$ is —H, or methyl, $R_4$ is —H, $R_6$ is —H, or halogen, $R_5$ is —H, halogen, methyl, or trifluoromethyl, and each $R_9$ is independently —H, halogen, methyl, or trifluoromethyl.

In yet a further compound of Formula (I), or (II), or pharmaceutically acceptable salts thereof, $R_7$ is —CN, methyl or trifluoromethyl, $R_8$ and R are each —H, and $R_1$ is a group of the formula:

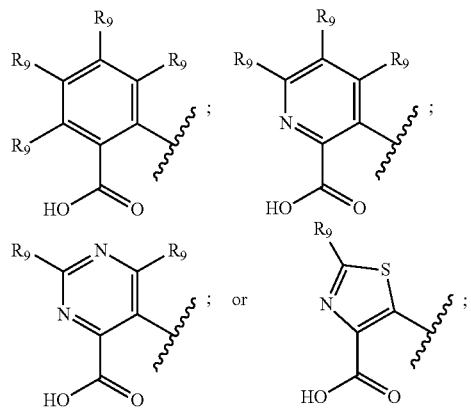

wherein each $R_9$ is independently —H, halogen, $C_1$-$C_3$ alkyl, $C_1$-$C_3$ haloalkyl, or $C_3$-$C_5$ cycloalkyl; more preferably $R_7$ is methyl, $R_8$ and R are each —H, and each $R_9$ is independently —H, halogen, methyl, trifluoromethyl, or cyclopropyl.

In yet a further compound of Formula (I), or (II), or pharmaceutically acceptable salts thereof, $R_7$ is —CN, methyl or trifluoromethyl, $R_8$ and R are each —H, and $R_1$ is a group of the formula:

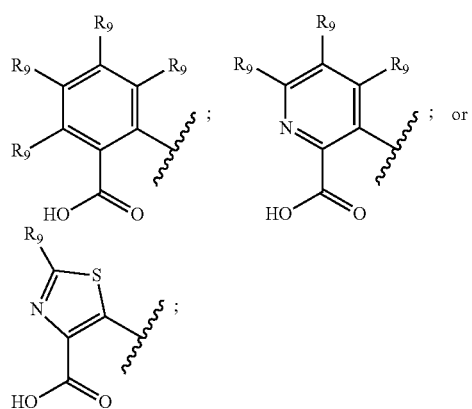

wherein each $R_9$ is independently —H, halogen, $C_1$-$C_3$ alkyl or $C_1$-$C_3$ haloalkyl; more preferably $R_7$ is methyl, $R_8$ and R are each —H, and each $R_9$ is independently —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

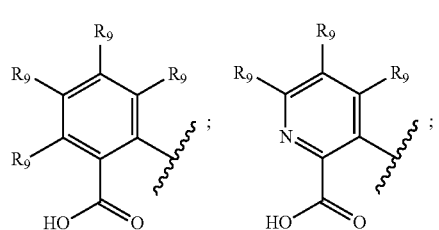

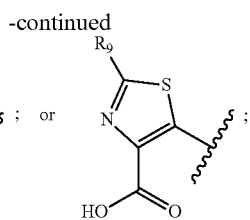

wherein each $R_9$ is independently —H, halogen, $C_1$-$C_3$ alkyl, $C_1$-$C_3$ haloalkyl, or $C_3$-$C_5$ cycloalkyl; more preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and each $R_9$ is independently —H, halogen, methyl, trifluoromethyl, or cyclopropyl.

In yet a further compound of Formula (I), or (II), or pharmaceutically acceptable salts thereof, $R_3$ is —H, —CN, or $C_1$-$C_3$ alkyl, $R_4$, $R_5$ and R are each —H, $R_8$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

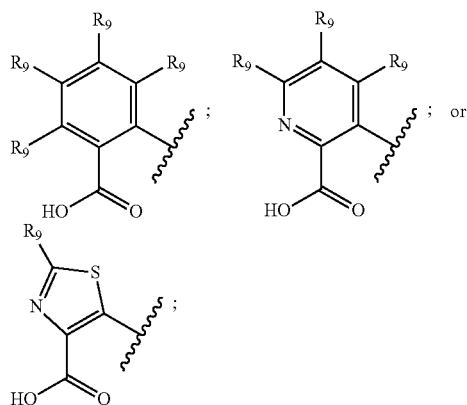

wherein each $R_9$ is independently —H, halogen, $C_1$-$C_3$ alkyl or $C_1$-$C_3$ haloalkyl; more preferably $R_3$ is —H, or methyl, $R_4$, $R_6$, $R_8$ and R are each —H, $R_5$ is —H, halogen, methyl, or trifluoromethyl, $R_7$ is methyl, and each $R_9$ is independently —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

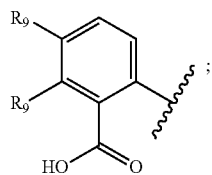

wherein each $R_9$ is independently —H, halogen, $C_1$-$C_3$ alkyl or $C_1$-$C_3$ haloalkyl; preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and each $R_9$ is independently —H, halogen, methyl or trifluoromethyl.

In yet a further compound of Formula (I), or (II), or pharmaceutically acceptable salts thereof, $R_3$ is —H, —CN, or $C_1$-$C_3$ alkyl, $R_4$, $R_5$ and R are each —H, $R_8$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

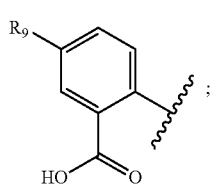

wherein $R_9$ is —H, halogen, or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is —H, or trifluoromethyl.

In yet a further compound of Formula (I), or (II), or pharmaceutically acceptable salts thereof, $R_3$ is —H, —CN, or $C_1$-$C_3$ alkyl, $R_4$, $R_5$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

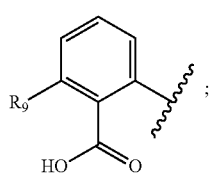

wherein $R_9$ is —H, halogen, or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is —H, or halogen, more preferably $R_9$ is —H, or fluoro.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

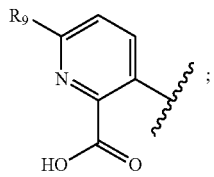

wherein $R_9$ is —H, halogen, $C_1$-$C_3$ alkyl, $C_1$-$C_3$ haloalkyl, or $C_3$-$C_5$ cycloalkyl; preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and $R_9$ is —H, halogen, methyl, trifluoromethyl, or cyclopropyl.

In yet a further compound of Formula (I), or (II), or pharmaceutically acceptable salts thereof, $R_3$ is —H, —CN, or $C_1$-$C_3$ alkyl, $R_4$, $R_5$ and R are each —H, $R_8$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

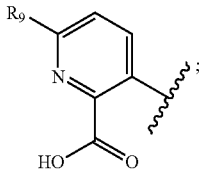

wherein $R_9$ is —H, halogen, or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is independently halogen or trifluoromethyl.

In yet a further compound of Formula (I), or (II), or pharmaceutically acceptable salts thereof, $R_3$ is —H, —CN, or $C_1$-$C_3$ alkyl, $R_4$, $R_5$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

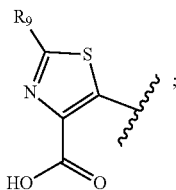

wherein $R_9$ is —H, halogen, $C_1$-$C_3$ alkyl or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is —H, halogen, $C_1$-$C_3$ alkyl or $C_1$-$C_3$ haloalkyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

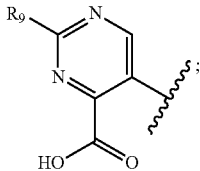

wherein $R_9$ is —H, halogen, $C_1$-$C_3$ alkyl, $C_1$-$C_3$ haloalkyl, or $C_3$-$C_5$ cycloalkyl; preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and $R_9$ is —H, halogen, methyl, trifluoromethyl, or cyclopropyl.

In yet a further compound of Formula (I), or (II), or pharmaceutically acceptable salts thereof, $R_1$ is a group of the formula:

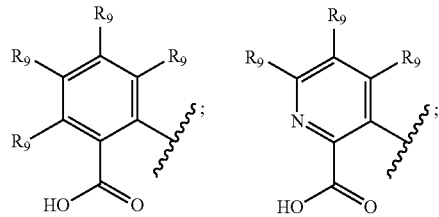

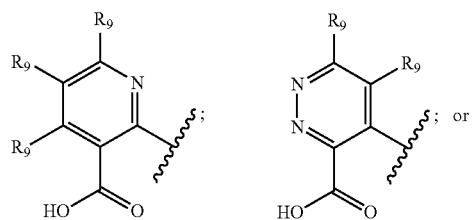

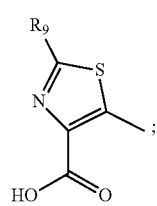

wherein each $R_9$ is independently —H, halogen, $C_1$-$C_3$ alkyl or $C_1$-$C_3$ haloalkyl, and $R_2$ is a group of the formula:

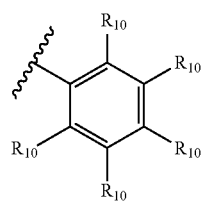

wherein each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN; and each $R_{11}$ is independently —H or $C_1$-$C_3$ alkyl.

In yet a further compound of Formula (I), or (II), or pharmaceutically acceptable salts thereof, $R_1$ is a group of the formula:

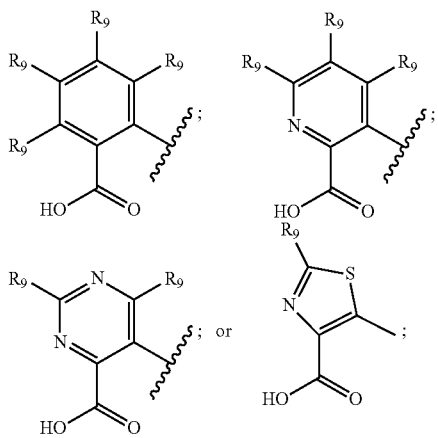 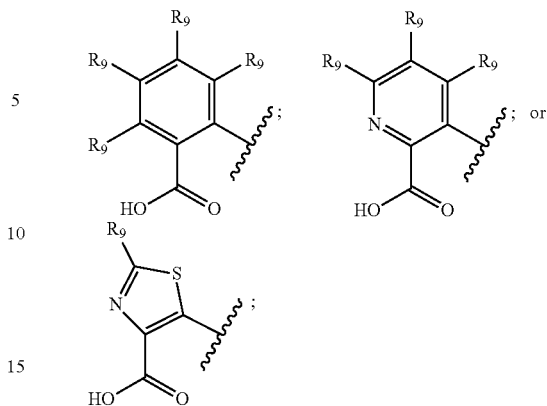

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl, and $R_2$ is a group of the formula:

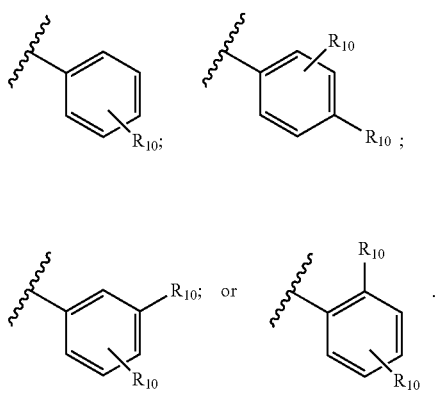 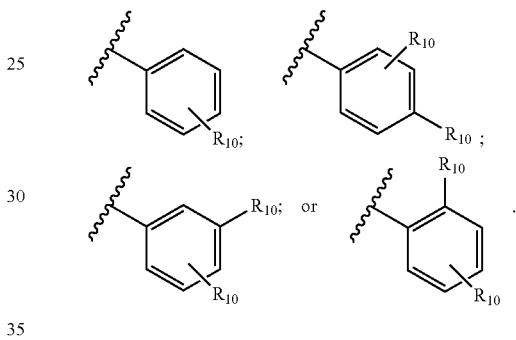

Preferably each $R_9$ is independently —H, halogen, $C_1$-$C_3$ alkyl, $C_1$-$C_3$ haloalkyl, or $C_3$-$C_5$ cycloalkyl. Most preferably each $R_9$ is independently —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl, and $R_2$ is a group of the formula:

Preferably each $R_9$ is independently —H, halogen, $C_1$-$C_3$ alkyl or $C_1$-$C_3$ haloalkyl. Most preferably each $R_9$ is independently —H, halogen, methyl, or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

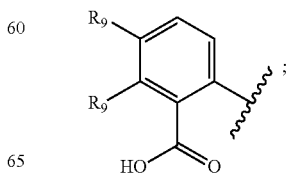

wherein each $R_9$ is independently —H, halogen, $C_1$-$C_3$ alkyl or $C_1$-$C_3$ haloalkyl, and $R_2$ is a group of the formula:

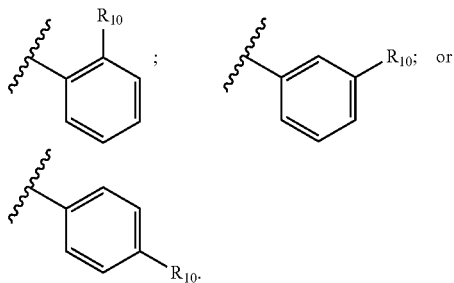

Preferably each $R_9$ is independently —H, halogen, methyl or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

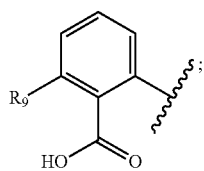

wherein $R_9$ is —H, halogen, or $C_1$-$C_3$ haloalkyl, and $R_2$ is a group of the formula:

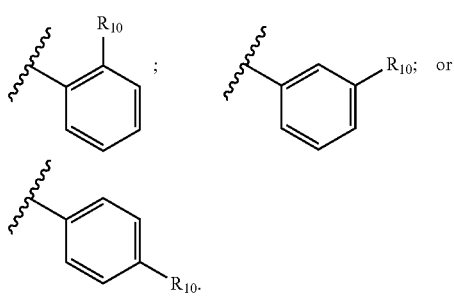

Preferably $R_9$ is —H, or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

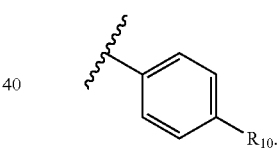

wherein $R_9$ is —H, halogen, or $C_1$-$C_3$ haloalkyl, and $R_2$ is a group of the formula:

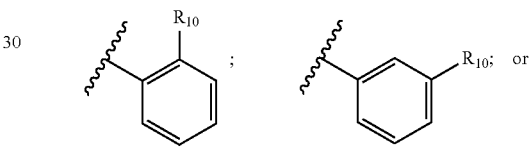

Preferably $R_9$ is —H, or halogen. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

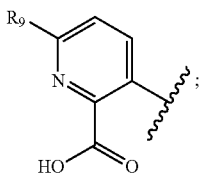

wherein $R_9$ is —H, halogen, $C_1$-$C_3$ alkyl, $C_1$-$C_3$ haloalkyl, or $C_3$-$C_5$ cycloalkyl, and $R_2$ is a group of the formula:

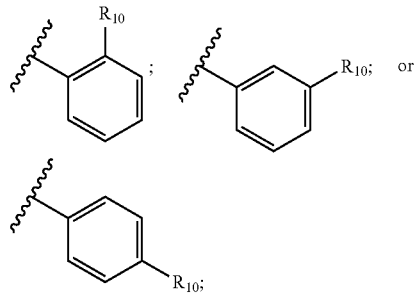

preferably $R_9$ is —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

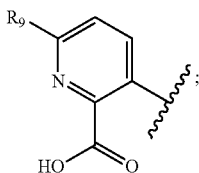

wherein $R_9$ is halogen, or $C_1$-$C_3$ haloalkyl, and $R_2$ is a group of the formula:

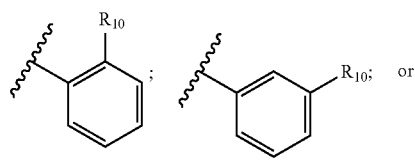

preferably $R_9$ is halogen or trifluoromethyl. More preferably $R_9$ is chloro or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

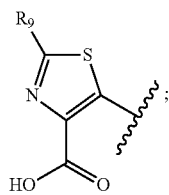

wherein $R_9$ is —H, halogen, $C_1$-$C_3$ alkyl or $C_1$-$C_3$ haloalkyl, and $R_2$ is a group of the formula:

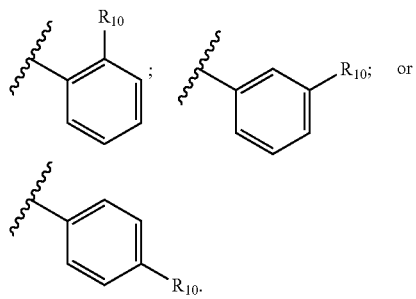

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl

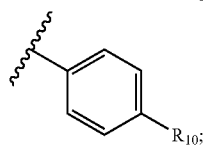

is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_1$ is a group of the formula:

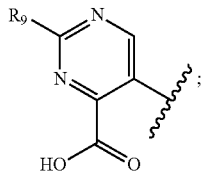

wherein $R_9$ is —H, halogen, $C_1$-$C_3$ alkyl, $C_1$-$C_3$ haloalkyl, or $C_3$-$C_5$ cycloalkyl, and $R_2$ is a group of the formula:

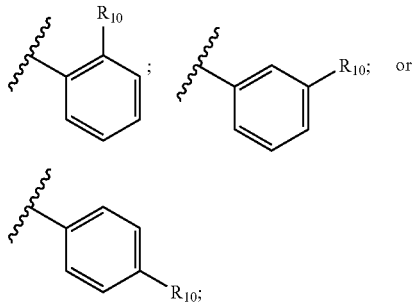

preferably $R_9$ is —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_2$ is a group of the formula:

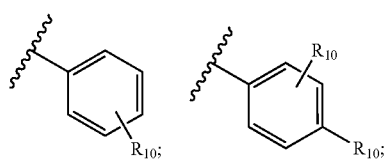

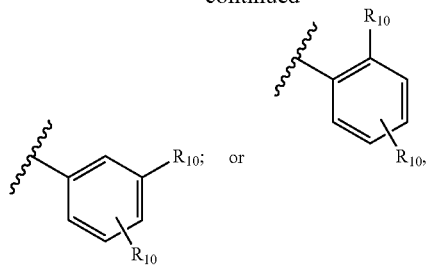

$R_3$ is —H, —CN, $C_1$-$C_3$ alkyl, or $C_1$-$C_3$ haloalkyl, $R_4$ is —H, or halogen, $R_6$ is —H, or halogen, $R_5$ is —H, halogen, $C_1$-$C_3$ alkyl or $C_1$-$C_3$ haloalkyl, and $R_1$ is a group of the formula:

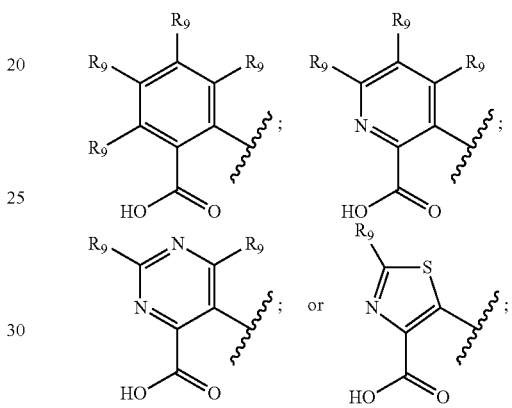

wherein each $R_9$ is independently —H, halogen, $C_1$-$C_3$ alkyl, $C_1$-$C_3$ haloalkyl, or $C_3$-$C_5$ cycloalkyl. Preferably $R_3$ is —H, methyl, or trifluoromethyl, $R_4$ is —H, or halogen, $R_6$ is —H, or halogen, $R_5$ is —H, halogen, methyl, or trifluoromethyl, and each $R_9$ is independently —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_2$ is a group of the formula:

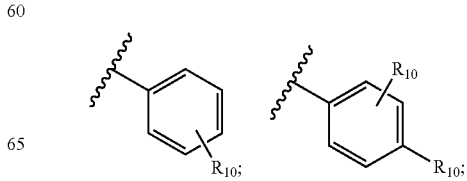

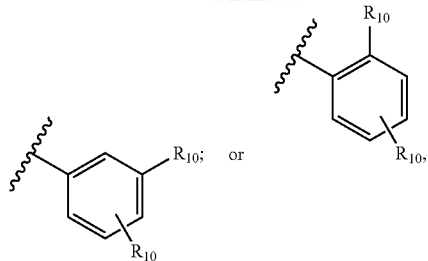

$R_3$ is —H, —CN, or $C_1$-$C_3$ alkyl, $R_4$ is —H, $R_6$ is —H, or halogen, $R_5$ is —H, halogen, $C_1$-$C_3$ alkyl or $C_1$-$C_3$ haloalkyl, and $R_1$ is a group of the formula:

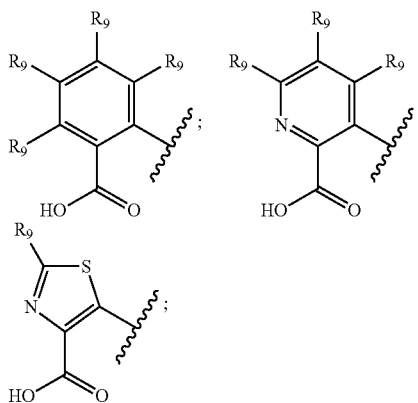

wherein each $R_9$ is independently —H, halogen, or $C_1$-$C_3$ haloalkyl. Preferably $R_3$ is —H, or methyl, $R_4$ and $R_6$ are each —H, $R_5$ is —H, halogen, methyl, or trifluoromethyl, and each $R_9$ is independently —H, halogen, methyl, or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_2$ is a group of the formula:

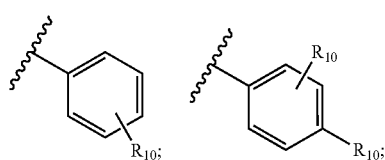

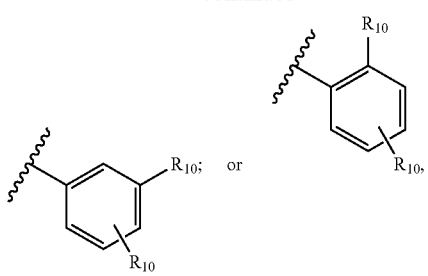

$R_7$ is —CN, methyl or trifluoromethyl, $R_8$ and R are each —H, and $R_1$ is a group of the formula:

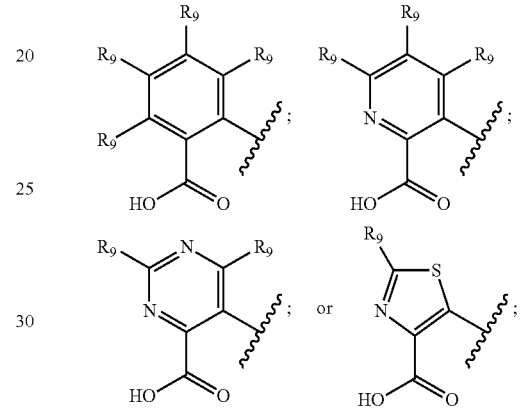

wherein each $R_9$ is independently —H, halogen, methyl, $C_1$-$C_3$ haloalkyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_2$ is a group of the formula:

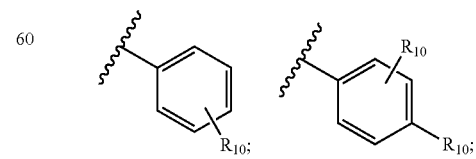

-continued

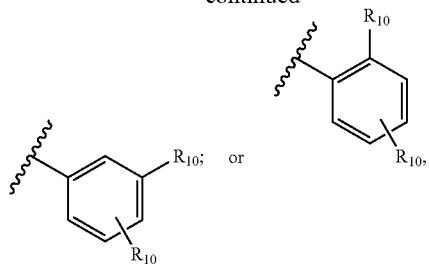

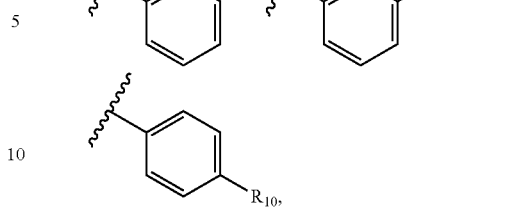

$R_7$ is —CN, methyl or trifluoromethyl, $R_8$ and R are each —H, and $R_1$ is a group of the formula:

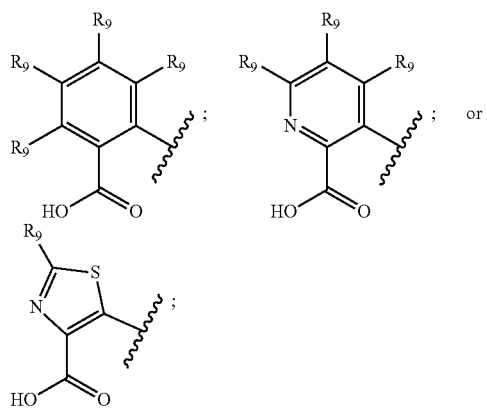

wherein each $R_9$ is independently —H, halogen, methyl, or $C_1$-$C_3$ haloalkyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

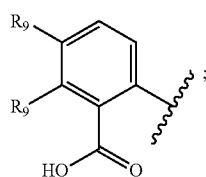

wherein each $R_9$ is independently —H, halogen, methyl or trifluoromethyl, $R_2$ is a group of the formula:

$R_7$ is $C_1$-$C_3$ alkyl (preferably methyl), and $R_8$ and R are each —H. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

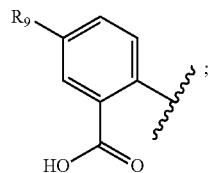

wherein $R_9$ is —H, halogen, or trifluoromethyl, (preferably $R_9$ is —H, or trifluoromethyl), $R_2$ is a group of the formula:

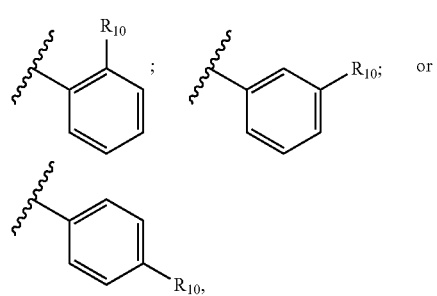

$R_7$ is $C_1$-$C_3$ alkyl (preferably methyl), and $R_8$ and R are each —H. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_1$ is a group of the formula:

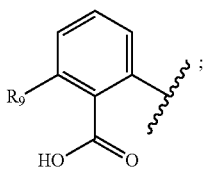

wherein $R_9$ is —H, halogen, or $C_1$-$C_3$ haloalkyl (preferably $R_9$ is —H, or halogen), $R_2$ is a group of the formula:

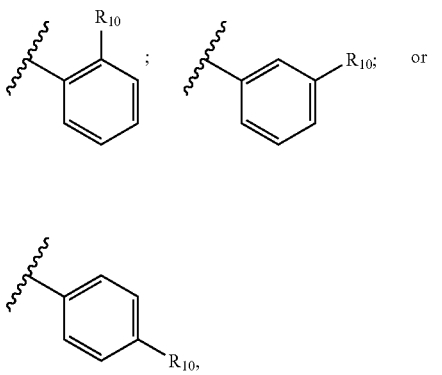

$R_7$ is $C_1$-$C_3$ alkyl (preferably methyl), and $R_8$ and R are each —H. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_1$ is a group of the formula:

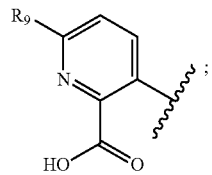

wherein $R_9$ is —H, halogen, methyl, trifluoromethyl, or cyclopropyl, $R_2$ is a group of the formula:

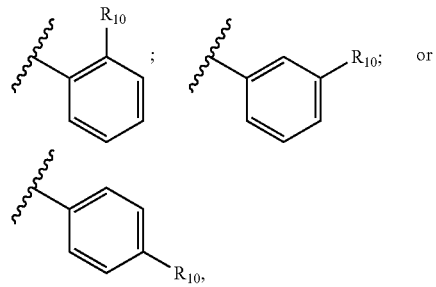

$R_7$ is $C_1$-$C_3$ alkyl (preferably methyl), and $R_8$ and R are each —H. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_1$ is a group of the formula:

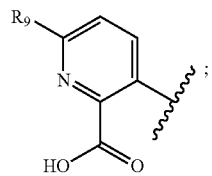

wherein $R_9$ is —H, halogen, or trifluoromethyl (preferably $R_9$ is halogen or trifluoromethyl), $R_2$ is a group of the formula:

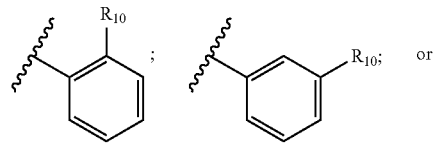

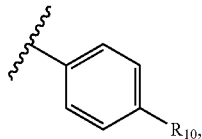

$R_7$ is $C_1$-$C_3$ alkyl (preferably methyl), and $R_8$ and R are each —H. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

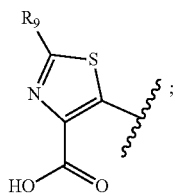

wherein $R_9$ is —H, halogen, $C_1$-$C_3$ alkyl or $C_1$-$C_3$ haloalkyl, $R_2$ is a group of the formula:

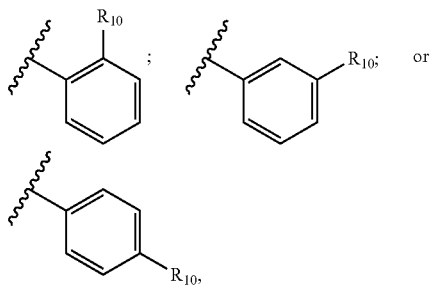

$R_7$ is $C_1$-$C_3$ alkyl (preferably methyl), and $R_8$ and R are each —H. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

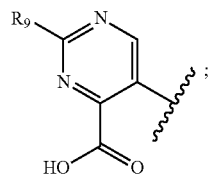

wherein $R_9$ is —H, halogen, $C_1$-$C_3$ alkyl, $C_1$-$C_3$ haloalkyl, or $C_3$-$C_5$ cycloalkyl, $R_2$ is a group of the formula:

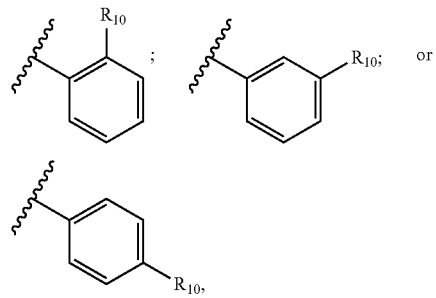

$R_7$ is $C_1$-$C_3$ alkyl (preferably methyl), and $R_8$ and R are each —H. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_2$ is a group of the formula:

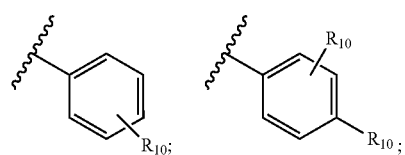

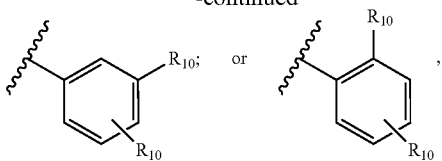

$R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is H, or halogen, $R_7$ is —CN, methyl or trifluoromethyl, and $R_1$ is a group of the formula:

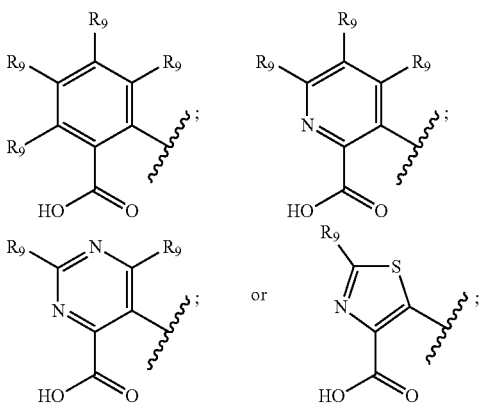

wherein each $R_9$ is independently —H, halogen, methyl, $C_1$-$C_3$ haloalkyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_2$ is a group of the formula:

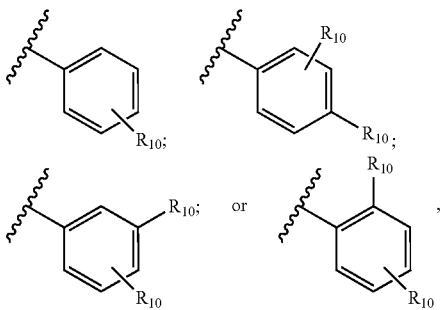

$R_3$ is —H, —CN, or $C_1$-$C_3$ alkyl, $R_4$, $R_5$ and R are each —H, $R_5$ is —H, halogen, $C_1$-$C_3$ alkyl or $C_1$-$C_3$ haloalkyl, $R_6$ is —H or halogen, $R_7$ is —CN, methyl or trifluoromethyl, and $R_1$ is a group of the formula:

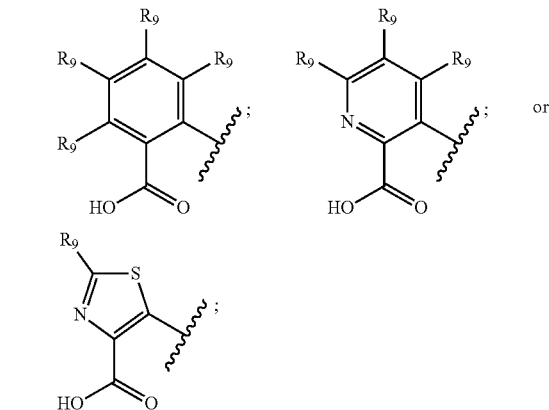

wherein each $R_9$ is independently —H, halogen, methyl, or $C_1$-$C_3$ haloalkyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_1$ is a group of the formula:

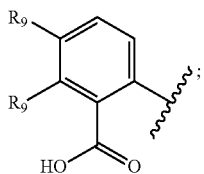

wherein each $R_9$ is independently —H, halogen, methyl or trifluoromethyl, $R_2$ is a group of the formula:

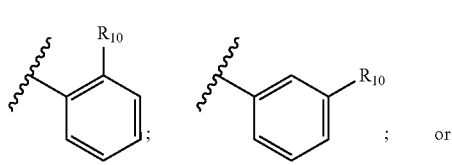

-continued

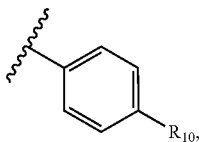

R$_3$ is —H, methyl, or trifluoromethyl, R$_4$ is —H, or halogen, R$_8$ and R are each —H, R$_5$ is —H, halogen, methyl or trifluoromethyl, R$_6$ is —H, or halogen, and R$_7$ is C$_1$-C$_3$ alkyl (preferably methyl). Preferably, each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_3$-C$_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted C$_1$-C$_6$ alkyl is optionally substituted with a —CN, —OH, or C$_1$-C$_3$ alkoxy; the optionally substituted C$_3$-C$_5$ cycloalkyl, phenyl, heterocycle or heteroaryl is each optionally substituted with one to three substituents each independently selected from halogen, C$_1$-C$_3$ alkyl, C$_1$-C$_3$ haloalkyl, C$_1$-C$_3$ alkoxy, C$_1$-C$_3$ haloalkoxy, —NR$_{11}$R$_{11}$, —OH or —CN.

In yet a further compound of Formula (I), or (II), or pharmaceutically acceptable salts thereof, R$_1$ is a group of the formula:

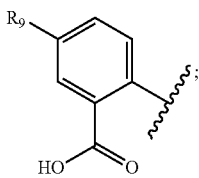

wherein R$_9$ is —H, halogen, or trifluoromethyl, (preferably R$_9$ is —H, or trifluoromethyl), R$_2$ is a group of the formula:

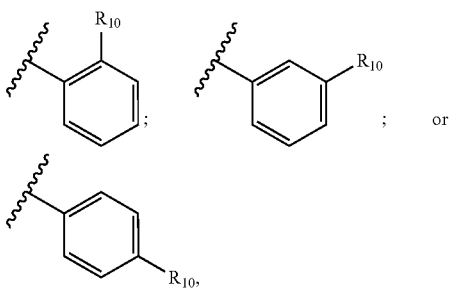

R$_3$ is —H, or methyl, R$_4$, R$_5$ and R are each —H, R$_5$ is —H, halogen, methyl, or trifluoromethyl, R$_6$ is —H or halogen, and R$_7$ is C$_1$-C$_3$ alkyl (preferably methyl). Preferably, each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_3$-C$_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted C$_1$-C$_6$ alkyl is optionally substituted with a —CN, —OH, or C$_1$-C$_3$ alkoxy; the optionally substituted C$_3$-C$_5$ cycloalkyl, phenyl, heterocycle or heteroaryl is each optionally substituted with one to three substituents each independently selected from halogen, C$_1$-C$_3$ alkyl, C$_1$-C$_3$ haloalkyl, C$_1$-C$_3$ alkoxy, C$_1$-C$_3$ haloalkoxy, —NR$_{11}$R$_{11}$, —OH or —CN.

In yet a further compound of Formula (I), or (II), or pharmaceutically acceptable salts thereof, R$_1$ is a group of the formula:

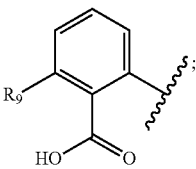

wherein R$_9$ is —H, halogen, or C$_1$-C$_3$ haloalkyl (preferably R$_9$ is —H, or halogen), R$_2$ is a group of the formula:

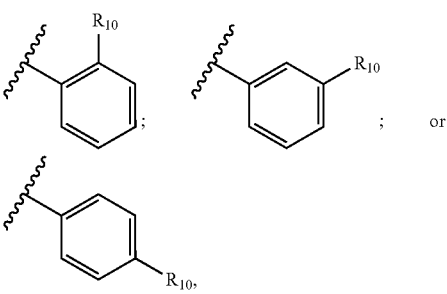

R$_3$ is —H, or methyl, R$_4$, R$_5$ and R are each —H, R$_5$ is —H, halogen, methyl, or trifluoromethyl, R$_6$ is —H or halogen, and R$_7$ is C$_1$-C$_3$ alkyl (preferably methyl). Preferably, each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_3$-C$_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted C$_1$-C$_6$ alkyl is optionally substituted with a —CN, —OH, or C$_1$-C$_3$ alkoxy; the optionally substituted C$_3$-C$_5$ cycloalkyl, phenyl, heterocycle or heteroaryl is each optionally substituted with one to three substituents each independently selected from halogen, C$_1$-C$_3$ alkyl, C$_1$-C$_3$ haloalkyl, C$_1$-C$_3$ alkoxy, C$_1$-C$_3$ haloalkoxy, —NR$_{11}$R$_{11}$, —OH or —CN.

In yet a further compound of Formula (I), or (II), or pharmaceutically acceptable salts thereof, R$_1$ is a group of the formula:

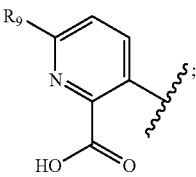

wherein $R_9$ is independently —H, halogen, methyl, trifluoromethyl, or cyclopropyl, $R_2$ is a group of the formula:

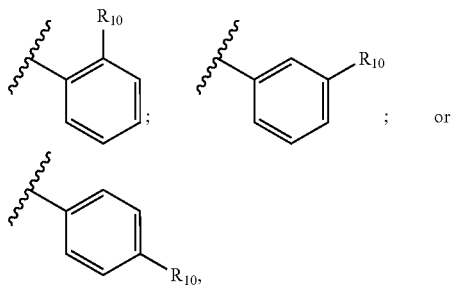

$R_3$ is —H, methyl, or trifluoromethyl, $R_4$ is —H, or halogen, $R_8$ and R are each —H, $R_5$ is —H, halogen, methyl or trifluoromethyl, $R_6$ is —H, or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

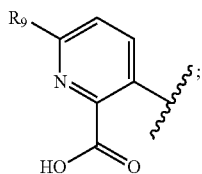

wherein $R_9$ is —H, halogen, or trifluoromethyl, (preferably $R_9$ is halogen or trifluoromethyl), $R_2$ is a group of the formula:

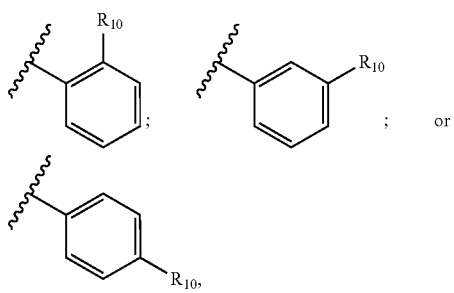

$R_3$ is —H, or methyl, $R_4$, $R_5$ and R are each —H, $R_5$ is —H, halogen, methyl, or trifluoromethyl, $R_6$ is —H or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (I), or (II), or pharmaceutically acceptable salts thereof, $R_1$ is a group of the formula:

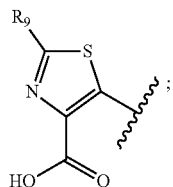

wherein $R_9$ is —H, halogen, $C_1$-$C_3$ alkyl or $C_1$-$C_3$ haloalkyl, $R_2$ is a group of the formula:

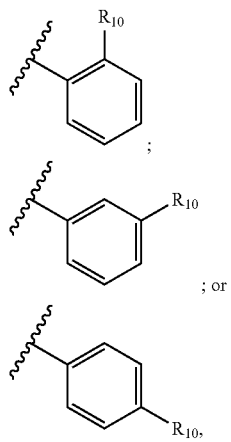

$R_3$ is —H, or methyl, $R_4$, $R_5$ and R are each —H, $R_5$ is —H, halogen, methyl, or trifluoromethyl, $R_6$ is —H or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), or (II), or pharmaceutically acceptable salts thereof, $R_1$ is a group of the formula:

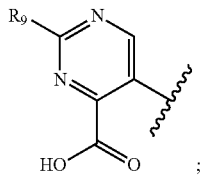

wherein $R_9$ is —H, halogen, methyl, trifluoromethyl, or cyclopropyl, $R_2$ is a group of the formula:

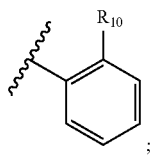

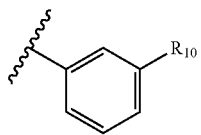; or

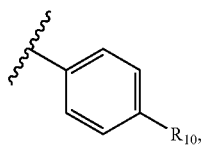

$R_3$ is —H, methyl, or trifluoromethyl, $R_4$ is —H, or halogen, $R_8$ and R are each —H, $R_5$ is —H, halogen, methyl or trifluoromethyl, $R_6$ is —H, or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In a further aspect, compounds of Formula (I) or (II) have Formula (III), or pharmaceutically acceptable salts thereof:

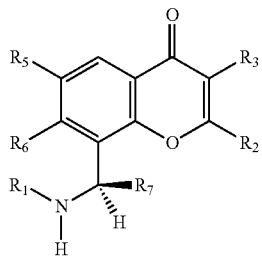

wherein $R_1$, $R_2$, $R_3$, $R_5$, $R_6$, and $R_7$ are as defined in the Summary for Formula (I) above.

In a compound of Formula (III), or pharmaceutically acceptable salts thereof, $R_2$ is a group of the formula:

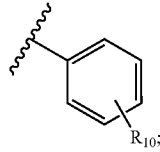

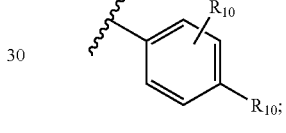

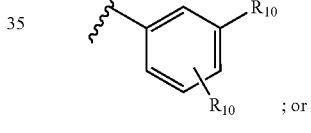; or

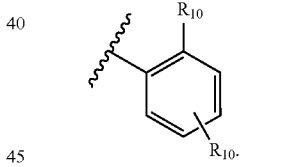

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_2$ is a group of the formula:

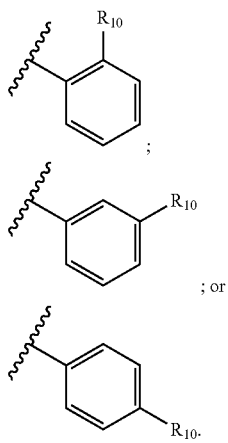

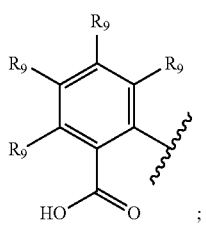

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_3$ is —H, —CN, $C_1$-$C_3$ alkyl, $C_1$-$C_3$ haloalkyl; preferably $R_3$ is —H, —CN, or $C_1$-$C_3$ alkyl; most preferably $R_3$ is —H, or methyl.

In yet a further compound of Formula (III), or pharmaceutically acceptable salts thereof, $R_5$ is —H, halogen, $C_1$-$C_6$ alkyl, or $C_1$-$C_6$ haloalkyl; preferably $R_5$ is —H, halogen, $C_1$-$C_3$ alkyl or $C_1$-$C_3$ haloalkyl; more preferably $R_5$ is —H, halogen, methyl, or trifluoromethyl.

In yet a further compound of Formula (III), or pharmaceutically acceptable salts thereof, $R_6$ is —H or halogen; preferably $R_6$ is —H.

In yet a further compound of Formula (III), or pharmaceutically acceptable salts thereof, $R_7$ is —CN, $C_1$-$C_6$ alkyl, or $C_1$-$C_6$ haloalkyl; preferably $R_7$ is —CN, $C_1$-$C_3$ alkyl or $C_1$-$C_3$ haloalkyl; more preferably $R_7$ is —CN, methyl or trifluoromethyl.

In yet a further compound of Formula (III), or pharmaceutically acceptable salts thereof, $R_1$ is a group of the formula:

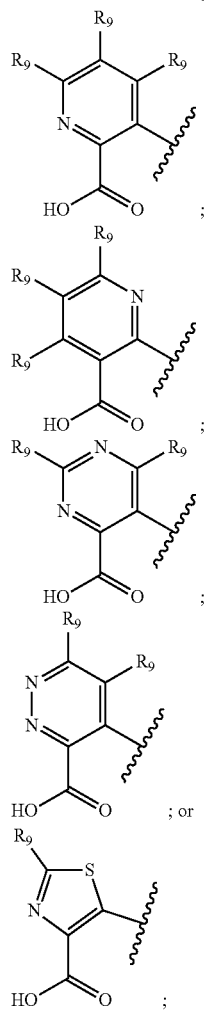

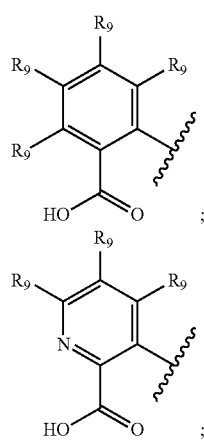

wherein each $R_9$ is independently —H, halogen, $C_1$-$C_3$ alkyl, $C_1$-$C_3$ haloalkyl, or $C_3$-$C_5$ cycloalkyl; preferably each $R_9$ is independently —H, halogen, methyl, trifluoromethyl, or cyclopropyl.

In yet a further compound of Formula (III), or pharmaceutically acceptable salts thereof, $R_1$ is a group of the formula:

-continued

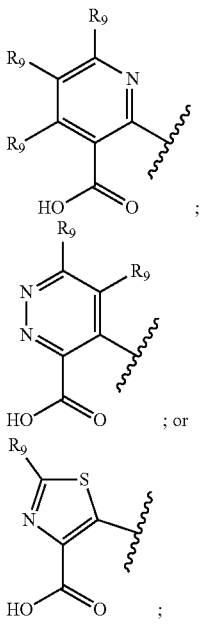

wherein each $R_9$ is independently —H, halogen, $C_1$-$C_3$ alkyl or $C_1$-$C_3$ haloalkyl; preferably each $R_9$ is independently —H, halogen, methyl, or trifluoromethyl.

In yet a further compound of Formula (III), or pharmaceutically acceptable salts thereof, $R_1$ is a group of the formula:

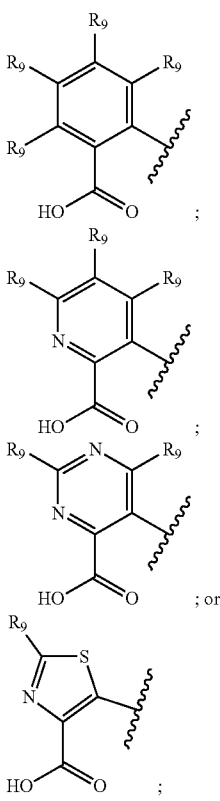

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl. Preferably each $R_9$ is independently —H, halogen, $C_1$-$C_3$ alkyl, $C_1$-$C_3$ haloalkyl, or $C_3$-$C_5$ cycloalkyl. More preferably each $R_9$ is independently —H, halogen, methyl, trifluoromethyl, or cyclopropyl.

In yet a further compound of Formula (III), or pharmaceutically acceptable salts thereof, $R_1$ is a group of the formula:

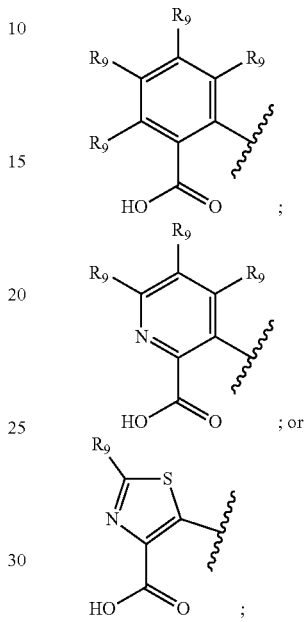

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl. Preferably each $R_9$ is independently —H, halogen, $C_1$-$C_3$ alkyl or $C_1$-$C_3$ haloalkyl. More preferably each $R_9$ is independently —H, halogen, methyl, or trifluoromethyl.

In yet a further compound of Formula (III), or pharmaceutically acceptable salts thereof, $R_1$ is a group of the formula:

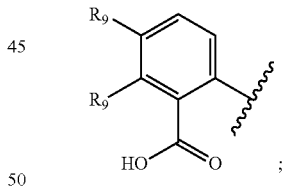

wherein each $R_9$ is independently —H, halogen, $C_1$-$C_3$ alkyl or $C_1$-$C_3$ haloalkyl. Preferably each $R_9$ is independently —H, halogen, methyl or trifluoromethyl.

In yet a further compound of Formula (III), or pharmaceutically acceptable salts thereof, $R_1$ is a group of the formula:

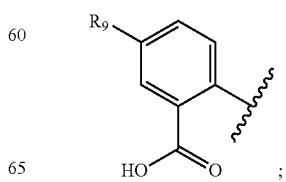

wherein R$_9$ is —H, halogen, or C$_1$-C$_3$ haloalkyl. Preferably R$_9$ is —H, or trifluoromethyl.

In yet a further compound of Formula (III), or pharmaceutically acceptable salts thereof, R$_1$ is a group of the formula:

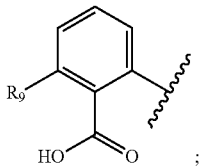

;

wherein R$_9$ is —H, halogen, or C$_1$-C$_3$ haloalkyl. Preferably R$_9$ is —H, or halogen. More preferably, R$_9$ is —H, or fluoro.

In yet a further compound of Formula (III), or pharmaceutically acceptable salts thereof, R$_1$ is a group of the formula:

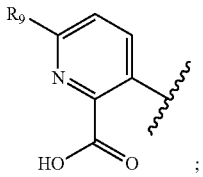

;

wherein R$_9$ is —H, halogen, C$_1$-C$_3$ alkyl, C$_1$-C$_3$ haloalkyl, or C$_3$-C$_5$ cycloalkyl. Preferably R$_9$ is —H, halogen, methyl, trifluoromethyl, or cyclopropyl.

In yet a further compound of Formula (III), or pharmaceutically acceptable salts thereof, R$_1$ is a group of the formula:

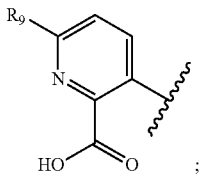

;

wherein R$_9$ is —H, halogen, or C$_1$-C$_3$ haloalkyl. Preferably R$_9$ is halogen or trifluoromethyl. More preferably R$_9$ is chloro or trifluoromethyl.

In yet a further compound of Formula (III), or pharmaceutically acceptable salts thereof, R$_1$ is a group of the formula:

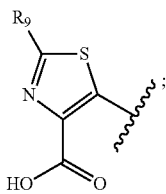

;

wherein R$_9$ is —H, halogen, C$_1$-C$_3$ alkyl or C$_1$-C$_3$ haloalkyl. Preferably R$_9$ is —H, methyl, or trifluoromethyl.

In yet a further compound of Formula (III), or pharmaceutically acceptable salts thereof, R$_1$ is a group of the formula:

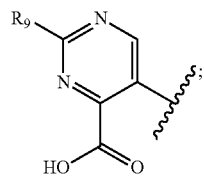

;

wherein R$_9$ is —H, halogen, C$_1$-C$_3$ alkyl, C$_1$-C$_3$ haloalkyl, or C$_3$-C$_5$ cycloalkyl. Preferably R$_9$ is —H, halogen, methyl, trifluoromethyl, or cyclopropyl.

In yet a further compound of Formula (III), or pharmaceutically acceptable salts thereof, each R$_9$ is independently H, halogen, C$_1$-C$_3$ alkyl, C$_1$-C$_3$ haloalkyl, or C$_3$-C$_5$ cycloalkyl.

In yet a further compound of Formula (III), or pharmaceutically acceptable salts thereof, R$_1$ is a group of the formula:

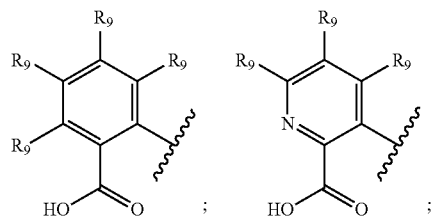

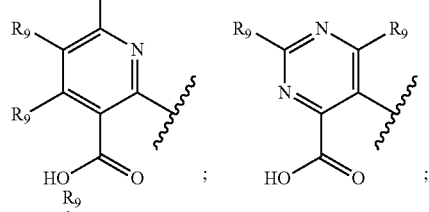

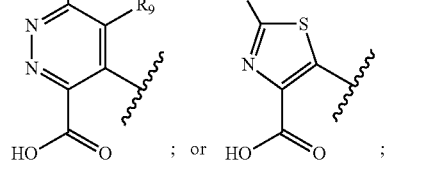

; or

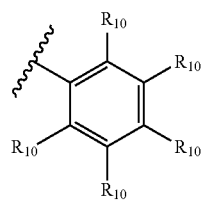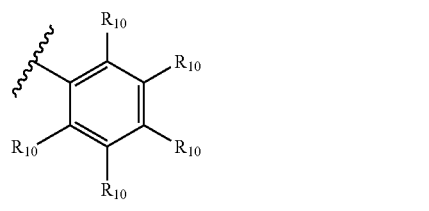

;

wherein each R$_9$ is independently —H, halogen, C$_1$-C$_3$ alkyl, C$_1$-C$_3$ haloalkyl, or C$_3$-C$_5$ cycloalkyl, and R$_2$ is a group of the formula:

wherein each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_3$-C$_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and each $R_{11}$ is independently —H or $C_1$-$C_3$ alkyl.

In yet a further compound of Formula (III), or pharmaceutically acceptable salts thereof, $R_1$ is a group of the formula:

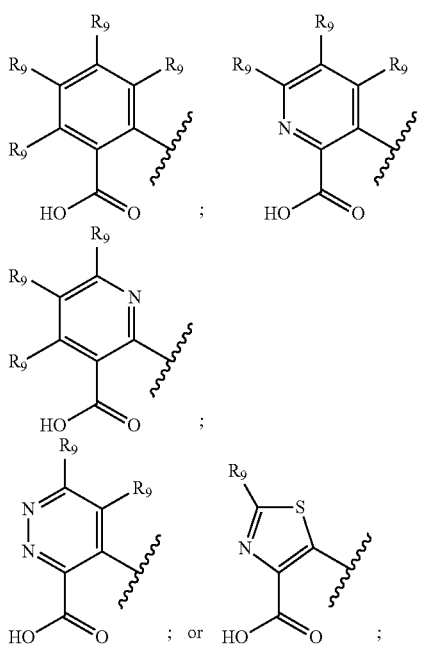

wherein each $R_9$ is independently —H, halogen, $C_1$-$C_3$ alkyl or $C_1$-$C_3$ haloalkyl, and $R_2$ is a group of the formula:

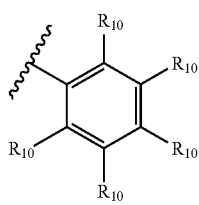

wherein each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and each $R_{11}$ is independently —H or $C_1$-$C_3$ alkyl.

In yet a further compound of Formula (III), or pharmaceutically acceptable salts thereof, $R_1$ is a group of the formula:

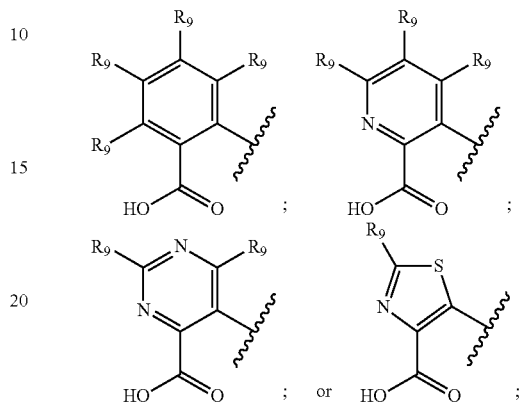

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl, and $R_2$ is a group of the formula:

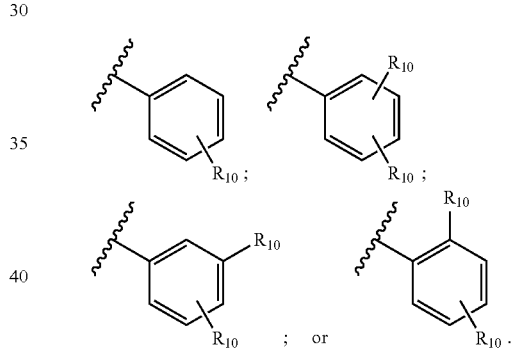

Preferably each $R_9$ is independently —H, halogen, $C_1$-$C_3$ alkyl, $C_1$-$C_3$ haloalkyl, or $C_3$-$C_5$ cycloalkyl. Most preferably each $R_9$ is independently —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

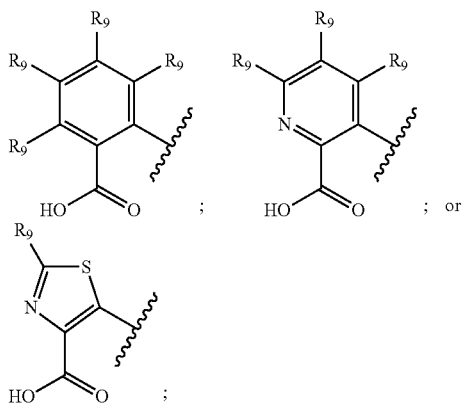

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl, and $R_2$ is a group of the formula:

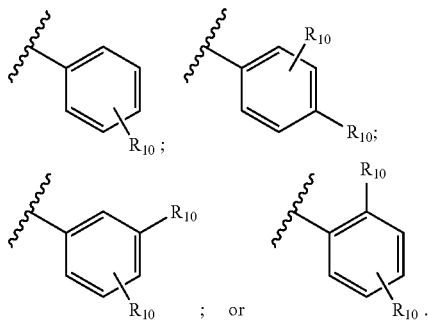

Preferably each $R_9$ is independently —H, halogen, $C_1$-$C_3$ alkyl or $C_1$-$C_3$ haloalkyl. Most preferably each $R_9$ is independently —H, halogen, methyl, or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (III), or pharmaceutically acceptable salts thereof, $R_1$ is a group of the formula:

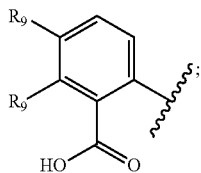

wherein each $R_9$ is independently —H, halogen, $C_1$-$C_3$ alkyl or $C_1$-$C_3$ haloalkyl, and $R_2$ is a group of the formula:

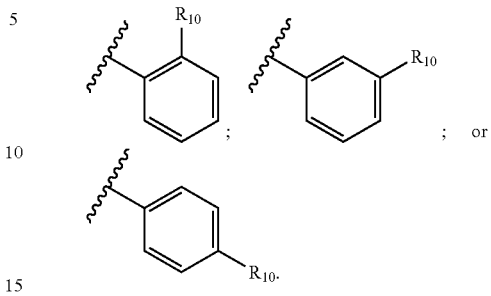

Preferably each $R_9$ is independently —H, halogen, methyl or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (III), or pharmaceutically acceptable salts thereof, $R_1$ is a group of the formula:

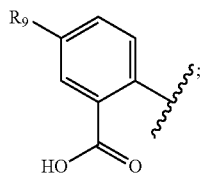

wherein $R_9$ is —H, halogen, or $C_1$-$C_3$ haloalkyl, and $R_2$ is a group of the formula:

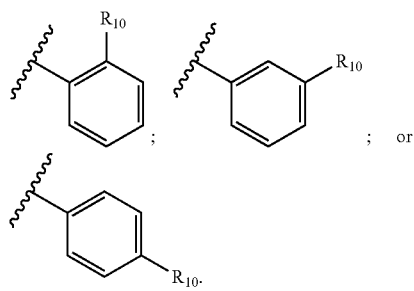

Preferably $R_9$ is —H, or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (III), or pharmaceutically acceptable salts thereof, $R_1$ is a group of the formula:

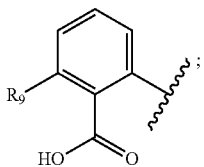

wherein $R_9$ is —H, halogen, or $C_1$-$C_3$ haloalkyl, and $R_2$ is a group of the formula:

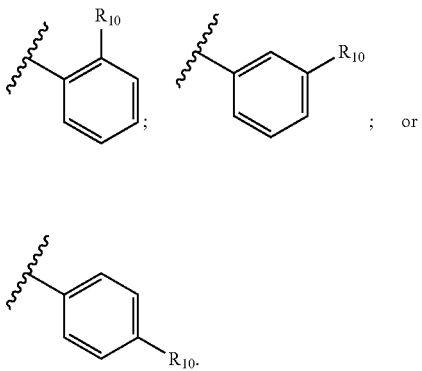

Preferably $R_9$ is —H, or halogen. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (III), or pharmaceutically acceptable salts thereof, $R_1$ is a group of the formula:

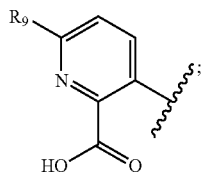

wherein $R_9$ is —H, halogen, $C_1$-$C_3$ alkyl, $C_1$-$C_3$ haloalkyl, or $C_3$-$C_5$ cycloalkyl, and $R_2$ is a group of the formula:

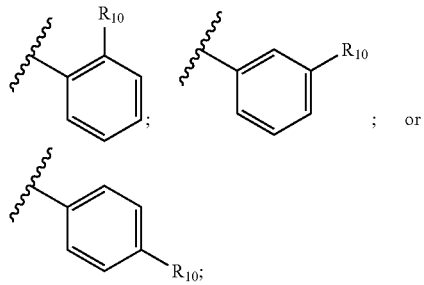

preferably $R_9$ is —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (III), or pharmaceutically acceptable salts thereof, $R_1$ is a group of the formula:

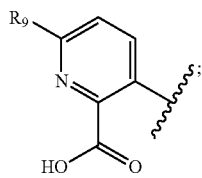

wherein $R_9$ is halogen, or $C_1$-$C_3$ haloalkyl, and $R_2$ is a group of the formula:

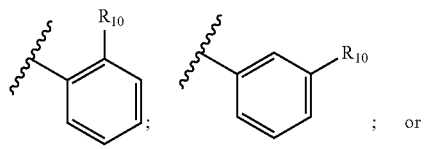

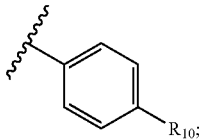

preferably $R_9$ is halogen or trifluoromethyl. More preferably $R_9$ is chloro or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

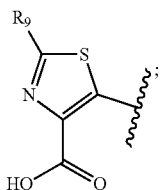

wherein $R_9$ is —H, halogen, $C_1$-$C_3$ alkyl or $C_1$-$C_3$ haloalkyl, and $R_2$ is a group of the formula:

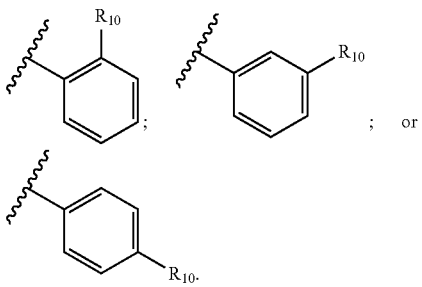

Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_1$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

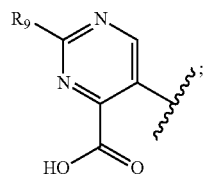

wherein $R_9$ is —H, halogen, $C_1$-$C_3$ alkyl, $C_1$-$C_3$ haloalkyl, or $C_3$-$C_5$ cycloalkyl, and $R_2$ is a group of the formula:

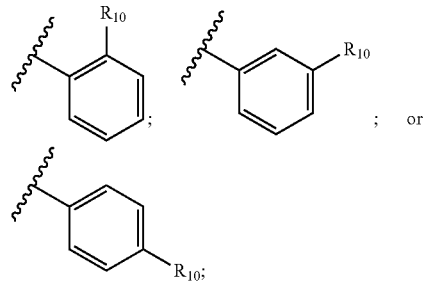

preferably $R_9$ is —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_3$ is —H, —CN, $C_1$-$C_3$ alkyl, $C_1$-$C_3$ haloalkyl (preferably $R_3$ is —H, —CN, or $C_1$-$C_3$ alkyl), $R_5$ is —H, halogen, $C_1$-$C_6$ alkyl, or $C_1$-$C_6$ haloalkyl, $R_6$ is —H or halogen, $R_7$ is —CN, methyl or trifluoromethyl, and $R_2$ is a group of the formula:

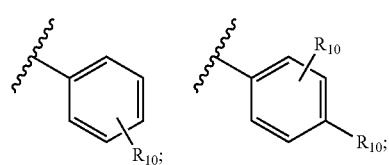

-continued

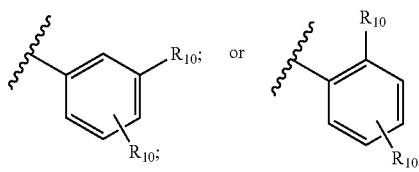

more preferably $R_3$ is —H, or methyl, $R_5$ is —H, halogen, methyl, or trifluoromethyl, $R_6$ is —H, $R_7$ is methyl, and $R_2$ is a group of the formula:

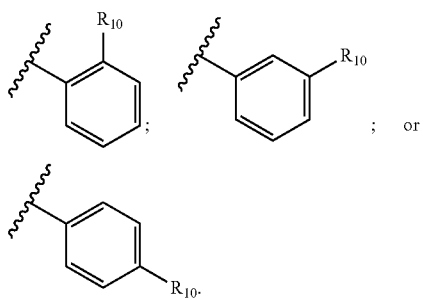

Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (III), or pharmaceutically acceptable salts thereof, $R_2$ is a group of the formula:

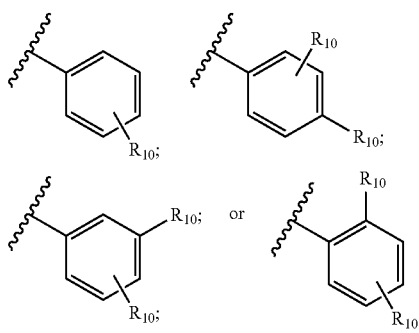

$R_3$ is —H, —CN, $C_1$-$C_3$ alkyl, or $C_1$-$C_3$ haloalkyl, $R_5$ is —H, halogen, $C_1$-$C_3$ alkyl or $C_1$-$C_3$ haloalkyl, $R_6$ is —H or halogen, and $R_1$ is a group of the formula:

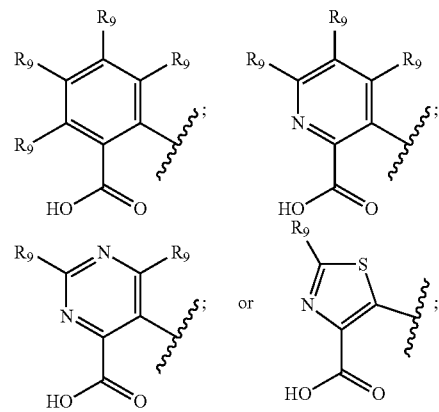

wherein each $R_9$ is independently —H, halogen, $C_1$-$C_3$ alkyl, $C_1$-$C_3$ haloalkyl, or $C_3$-$C_5$ cycloalkyl. Preferably $R_3$ is —H, methyl, or trifluoromethyl, $R_5$ is —H, halogen, methyl, or trifluoromethyl, $R_6$ is —H or halogen, and each $R_9$ is independently —H, halogen, methyl, trifluoromethyl, or cyclopropyl. Preferably, each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN.

In yet a further compound of Formula (III), or pharmaceutically acceptable salts thereof, $R_2$ is a group of the formula:

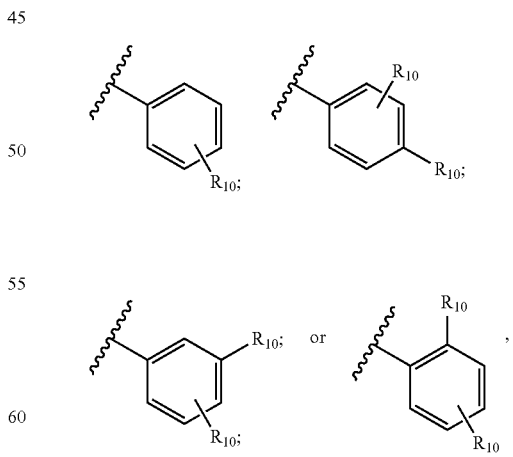

$R_3$ is —H, —CN, $C_1$-$C_3$ alkyl, or $C_1$-$C_3$ haloalkyl (preferably $R_3$ is —H, —CN, or $C_1$-$C_3$ alkyl), $R_5$ is —H, halogen, $C_1$-$C_3$ alkyl or $C_1$-$C_3$ haloalkyl, $R_6$ is —H or halogen, and $R_1$ is a group of the formula:

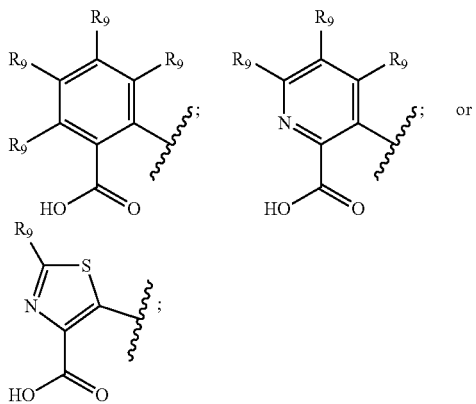

wherein each $R_9$ is independently —H, halogen, $C_1$-$C_3$ alkyl or $C_1$-$C_3$ haloalkyl. More preferably $R_3$ is —H, or methyl, $R_5$ is —H, halogen, methyl, or trifluoromethyl, $R_6$ is —H or halogen, and each $R_9$ is independently —H, halogen, methyl, or trifluoromethyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_2$ is a group of the formula:

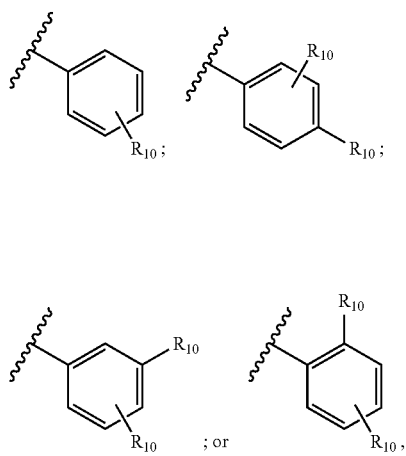

$R_3$ is —H, —CN, $C_1$-$C_3$ alkyl, or $C_1$-$C_3$ haloalkyl, $R_5$ is —H, halogen, $C_1$-$C_3$ alkyl or $C_1$-$C_3$ haloalkyl, $R_6$ is —H or halogen, $R_7$ is —CN, methyl or trifluoromethyl, and $R_1$ is a group of the formula:

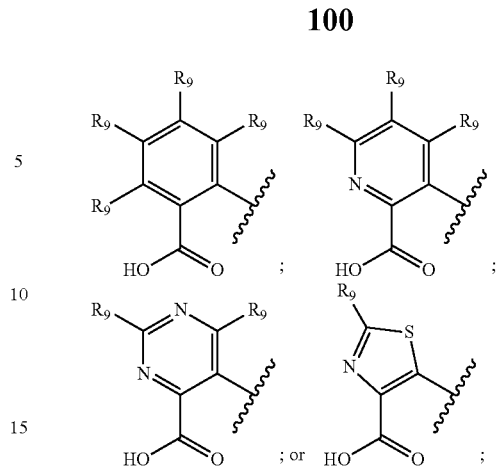

wherein each $R_9$ is independently —H, halogen, $C_1$-$C_3$ alkyl, $C_1$-$C_3$ haloalkyl, or $C_3$-$C_5$ cycloalkyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_2$ is a group of the formula:

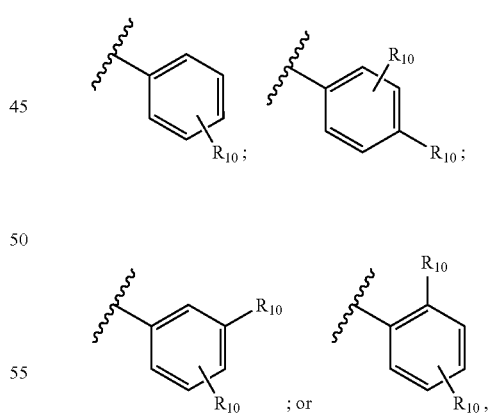

$R_3$ is —H, —CN, $C_1$-$C_3$ alkyl, or $C_1$-$C_3$ haloalkyl (preferably $R_3$ is —H, —CN, or $C_1$-$C_3$ alkyl), $R_5$ is —H, halogen, $C_1$-$C_3$ alkyl or $C_1$-$C_3$ haloalkyl, $R_6$ is —H or halogen, $R_7$ is —CN, methyl or trifluoromethyl, and $R_1$ is a group of the formula:

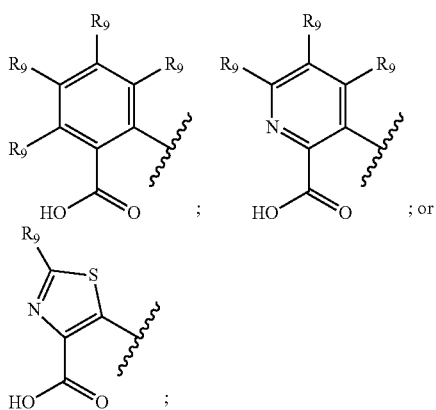

wherein each $R_9$ is independently —H, halogen, $C_1$-$C_3$ alkyl or $C_1$-$C_3$ haloalkyl. Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

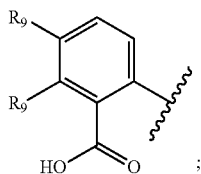

wherein each $R_9$ is independently —H, halogen, methyl or trifluoromethyl, $R_2$ is a group of the formula:

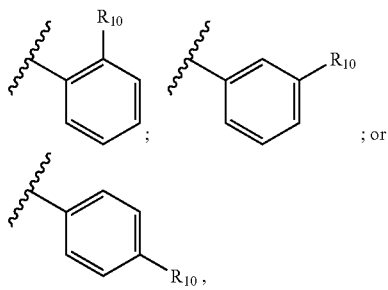

$R_3$ is —H, methyl, or trifluoromethyl, $R_5$ is —H, halogen, methyl or trifluoromethyl, $R_6$ is —H, or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

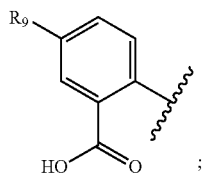

wherein $R_9$ is —H, halogen, or trifluoromethyl, (preferably $R_9$ is —H, or trifluoromethyl), $R_2$ is a group of the formula:

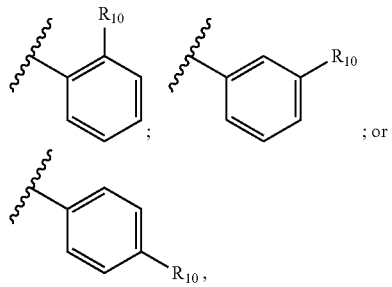

$R_3$ is —H, or methyl, $R_5$ is —H, halogen, methyl, or trifluoromethyl, $R_6$ is —H or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

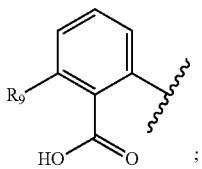

wherein R$_9$ is —H, halogen, or C$_1$-C$_3$ haloalkyl (preferably R$_9$ is —H, or halogen), R$_2$ is a group of the formula:

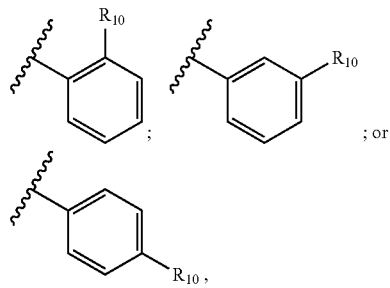

R$_3$ is —H, or methyl, R$_5$ is —H, halogen, methyl, or trifluoromethyl, R$_6$ is —H or halogen, and R$_7$ is C$_1$-C$_3$ alkyl (preferably methyl). Preferably, each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_3$-C$_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted C$_1$-C$_6$ alkyl is optionally substituted with a —CN, —OH, or C$_1$-C$_3$ alkoxy; the optionally substituted C$_3$-C$_5$ cycloalkyl, phenyl, heterocycle or heteroaryl is each optionally substituted with one to three substituents each independently selected from halogen, C$_1$-C$_3$ alkyl, C$_1$-C$_3$ haloalkyl, C$_1$-C$_3$ alkoxy, C$_1$-C$_3$ haloalkoxy, —NR$_{11}$R$_{11}$, —OH or —CN.

In yet a further compound of Formula (III), or pharmaceutically acceptable salts thereof, R$_1$ is a group of the formula:

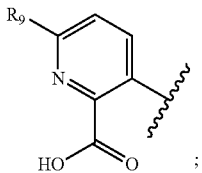

wherein R$_9$ is —H, halogen, methyl, trifluoromethyl, or cyclopropyl, R$_2$ is a group of the formula:

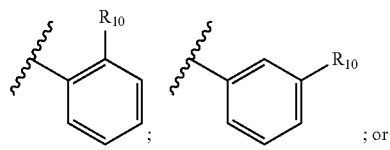

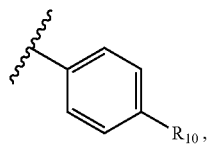

R$_3$ is —H, methyl, or trifluoromethyl, R$_5$ is —H, halogen, methyl or trifluoromethyl, R$_6$ is —H, or halogen, and R$_7$ is C$_1$-C$_3$ alkyl (preferably methyl). Preferably, each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_3$-C$_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted C$_1$-C$_6$ alkyl is optionally substituted with a —CN, —OH, or C$_1$-C$_3$ alkoxy; the optionally substituted C$_3$-C$_5$ cycloalkyl, phenyl, heterocycle or heteroaryl is each optionally substituted with one to three substituents each independently selected from halogen, C$_1$-C$_3$ alkyl, C$_1$-C$_3$ haloalkyl, C$_1$-C$_3$ alkoxy, C$_1$-C$_3$ haloalkoxy, —NR$_{11}$R$_{11}$, —OH or —CN.

In yet a further compound of Formula (III), or pharmaceutically acceptable salts thereof, R$_1$ is a group of the formula:

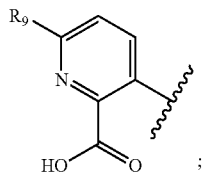

wherein R$_9$ is —H, halogen, or trifluoromethyl, (preferably R$_9$ is halogen or trifluoromethyl), R$_2$ is a group of the formula:

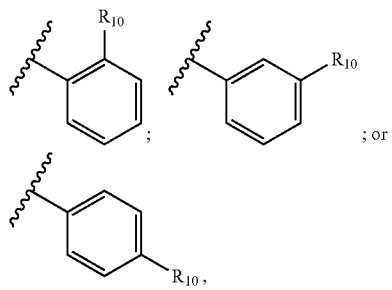

R$_3$ is —H, or methyl, R$_5$ is —H, halogen, methyl, or trifluoromethyl, R$_6$ is —H or halogen, and R$_7$ is C$_1$-C$_3$ alkyl (preferably methyl). Preferably, each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted C$_1$-C$_6$ alkyl, an optionally substituted C$_3$-C$_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

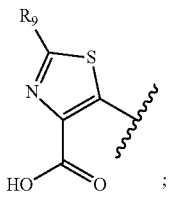

wherein $R_9$ is —H, halogen, $C_1$-$C_3$ alkyl or $C_1$-$C_3$ haloalkyl, $R_2$ is a group of the formula:

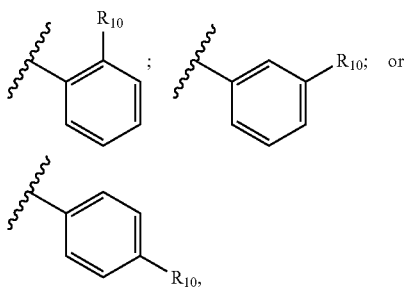

$R_3$ is —H, or methyl, $R_5$ is —H, halogen, methyl, or trifluoromethyl, $R_6$ is —H or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (III), or pharmaceutically acceptable salts thereof, $R_1$ is a group of the formula:

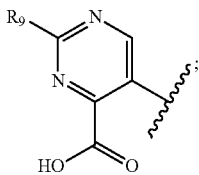

wherein $R_9$ is —H, halogen, methyl, trifluoromethyl, or cyclopropyl, $R_2$ is a group of the formula:

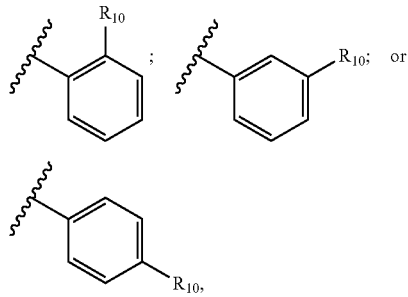

$R_3$ is —H, methyl, or trifluoromethyl, $R_5$ is —H, halogen, methyl or trifluoromethyl, $R_6$ is —H, or halogen, and $R_7$ is $C_1$-$C_3$ alkyl (preferably methyl). Preferably, each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN.

In yet a further compound of Formula (I), the compound is selected from:

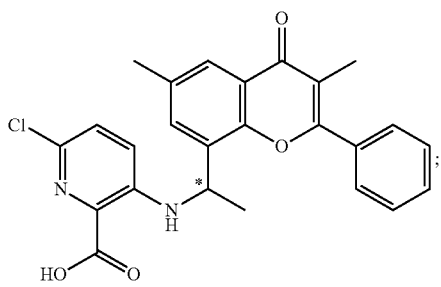

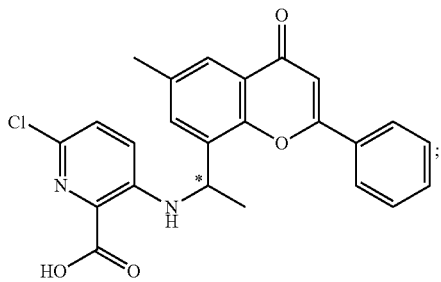

-continued
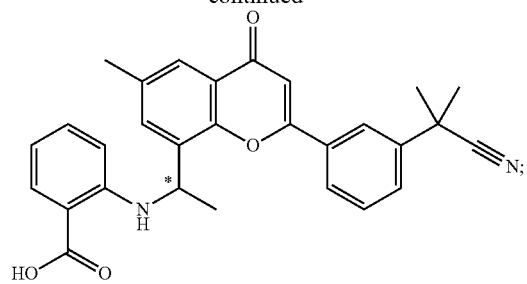
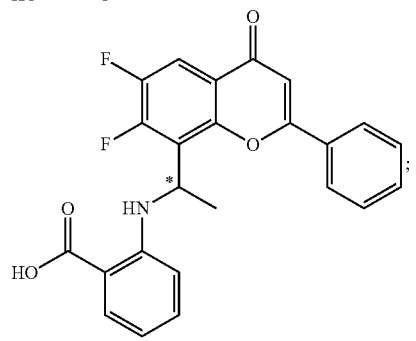
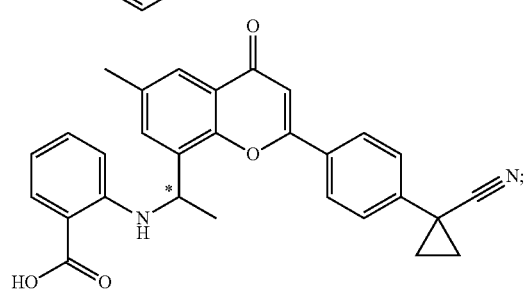
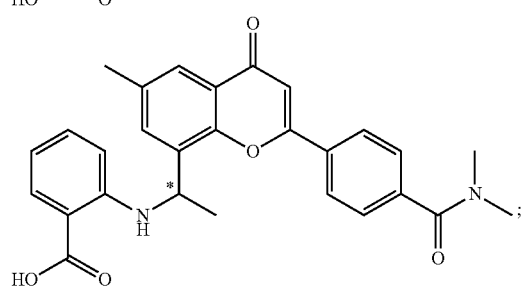
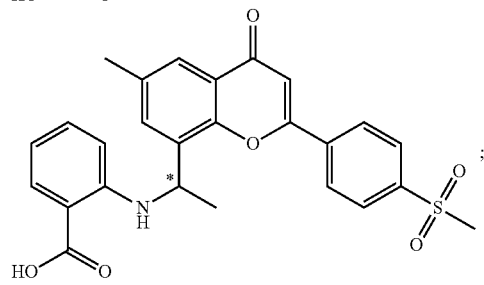
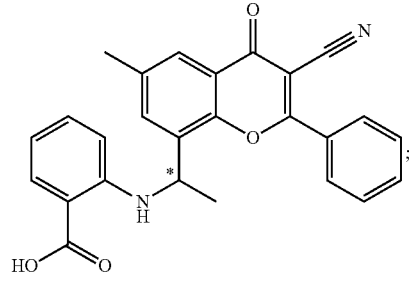
-continued
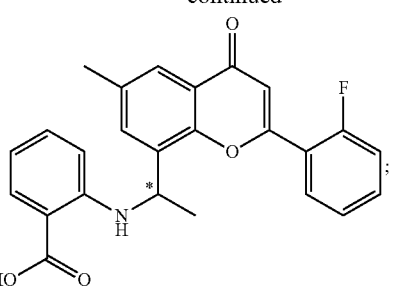
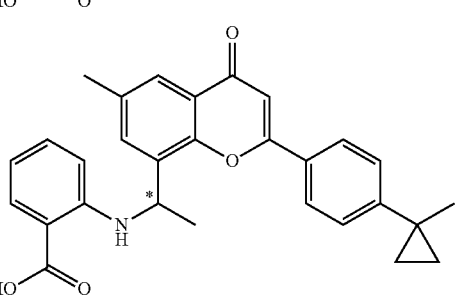
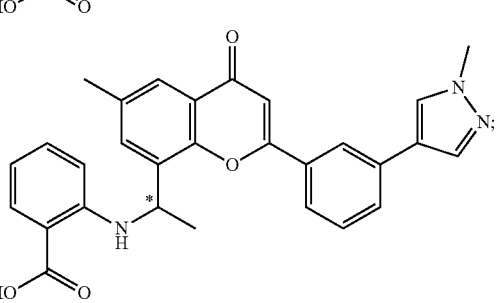
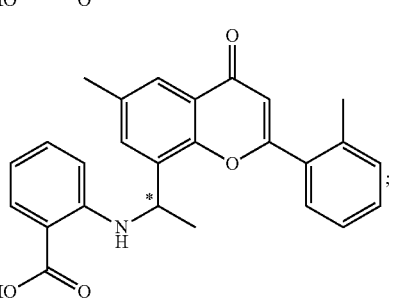
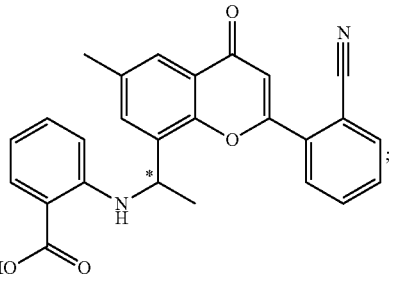
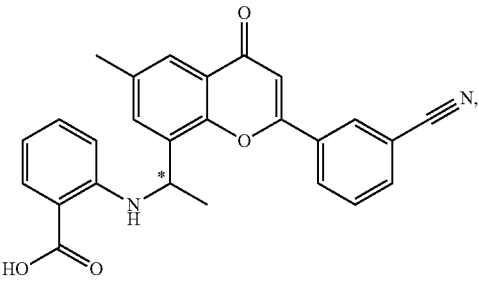

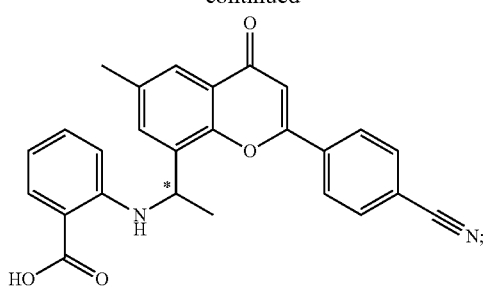
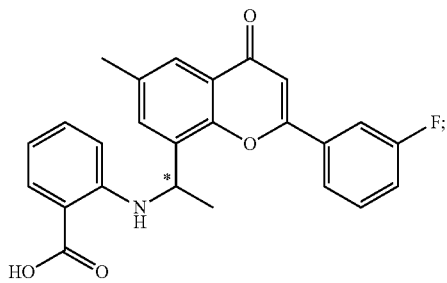
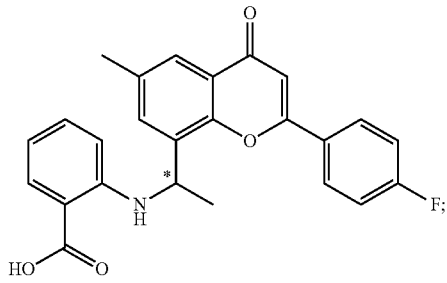
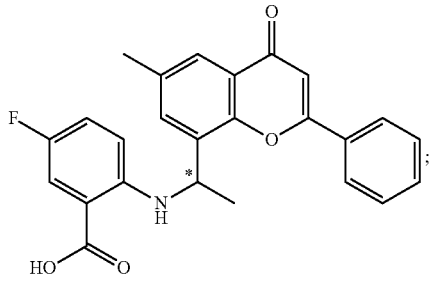
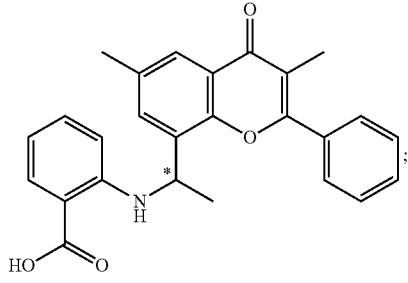
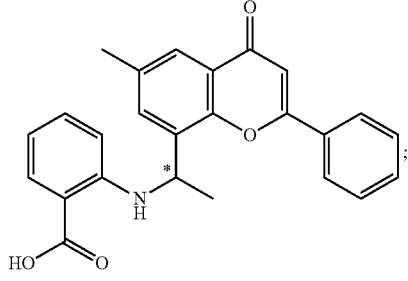
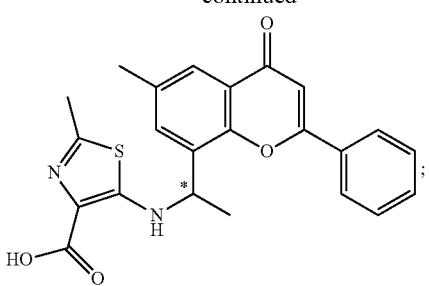
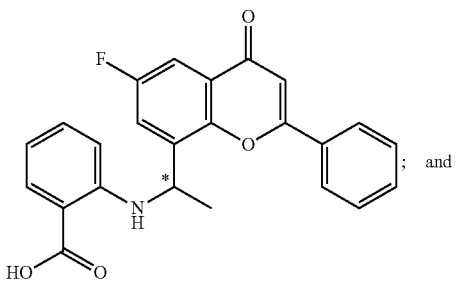
; and
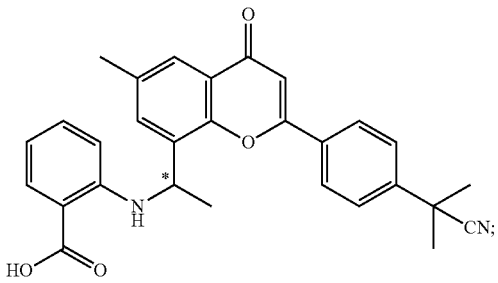
or a pharmaceutically acceptable salt of any of the foregoing,
wherein the bond at the * position is as represented,
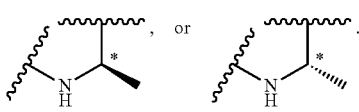
In yet a further compound of Formula (I), the compound is selected from:
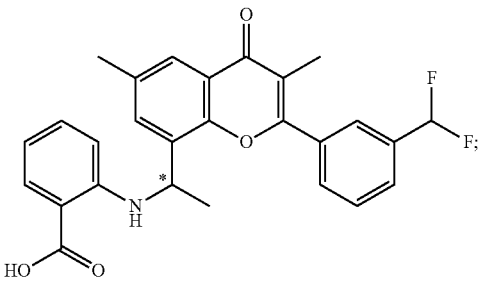

-continued
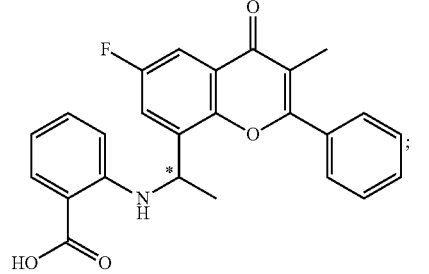 [SMILES: Cc1cc(C(C)Nc2cncnc2C(=O)O)c2oc(-c3ccccc3)c(C)c(=O)c2c1]
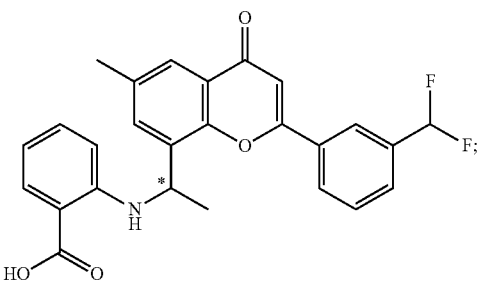
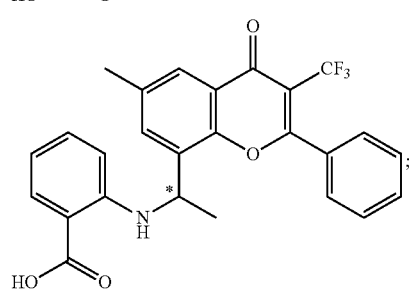
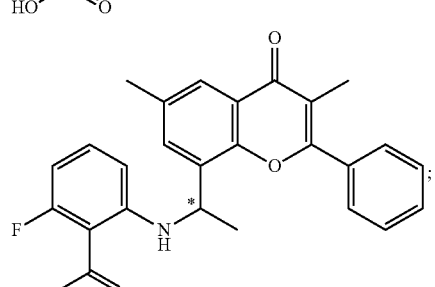
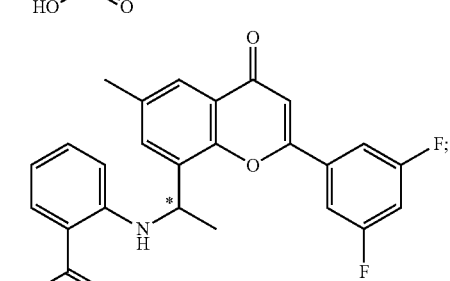
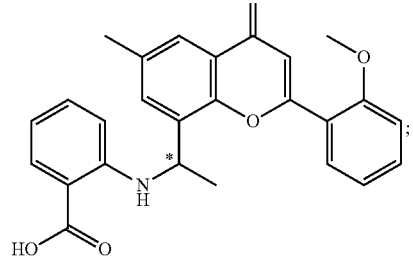
-continued
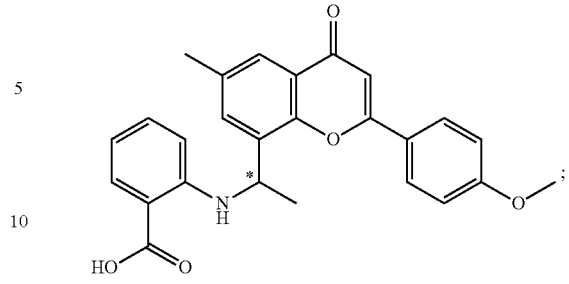
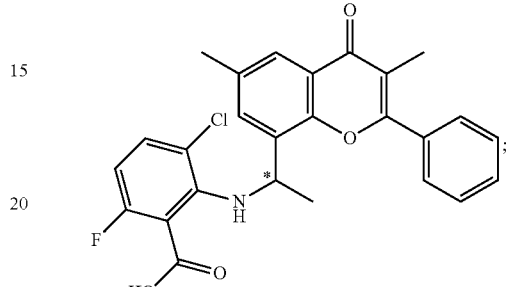
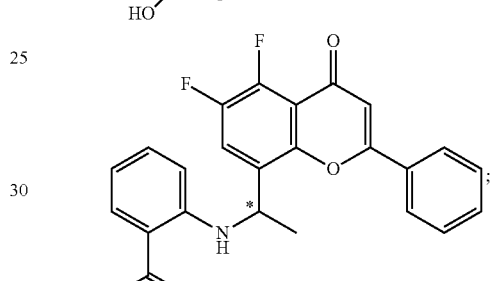
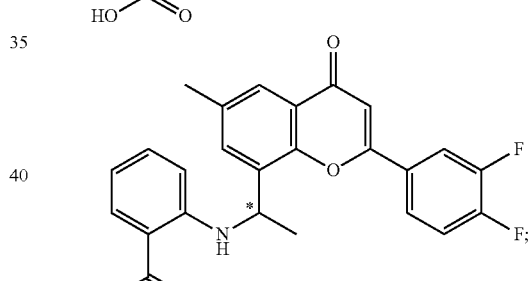
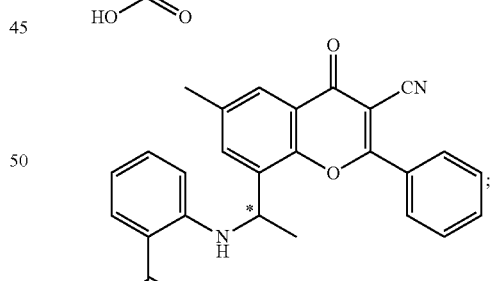
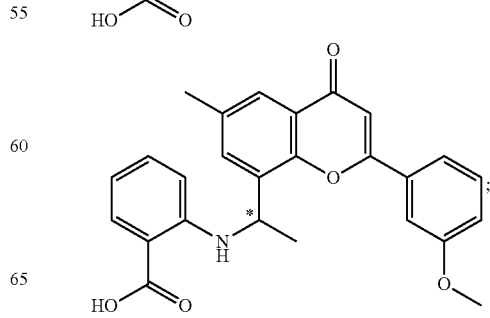

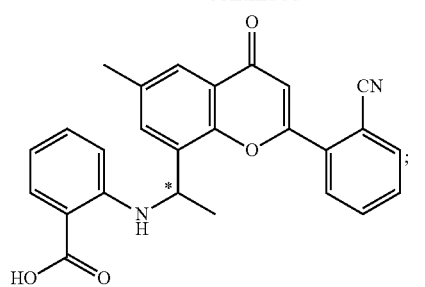
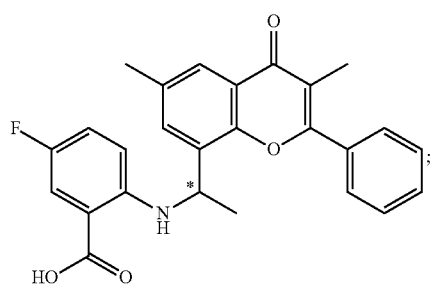
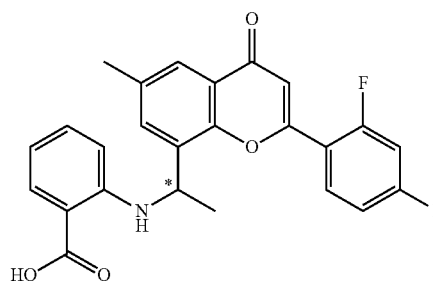
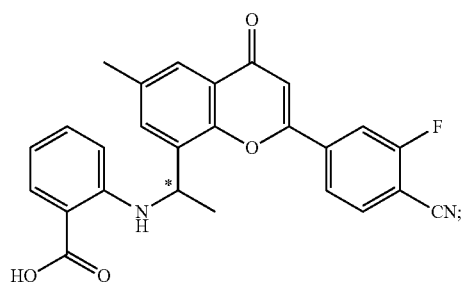
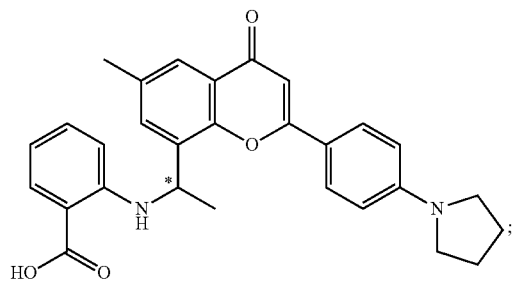
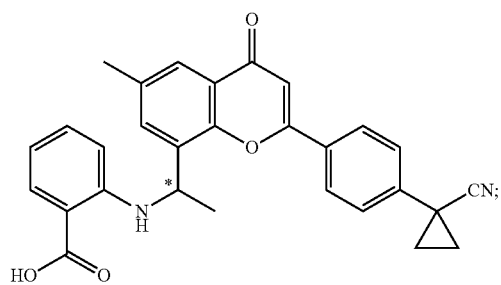
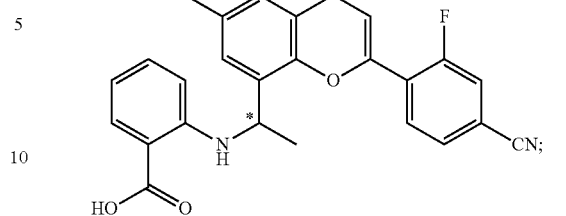
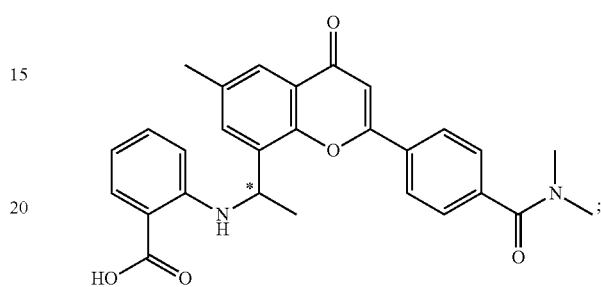
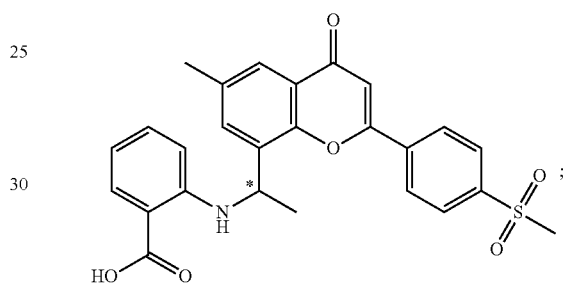
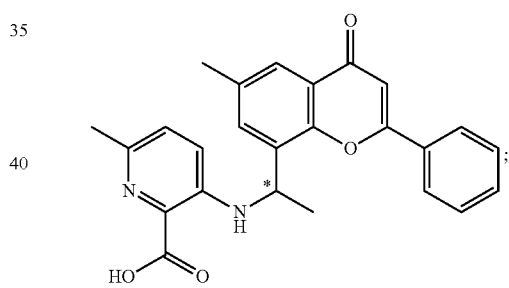
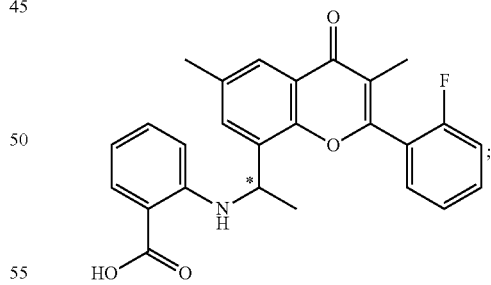
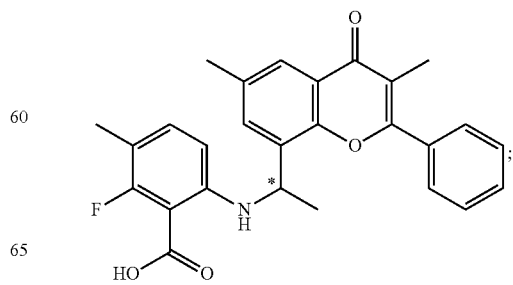

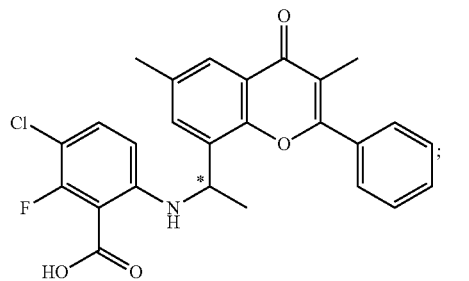
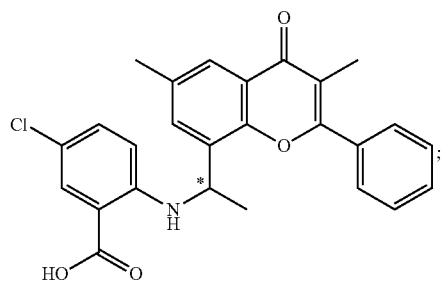
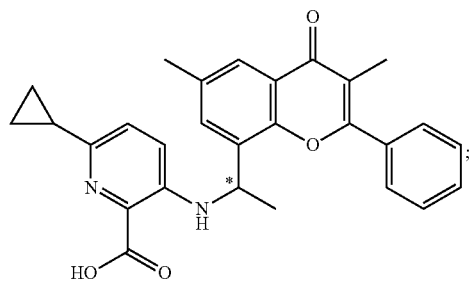
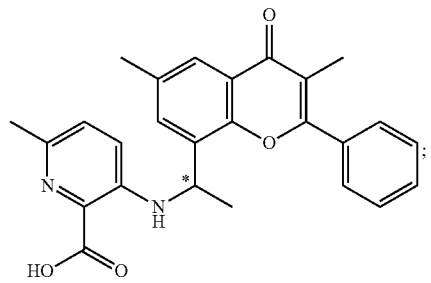
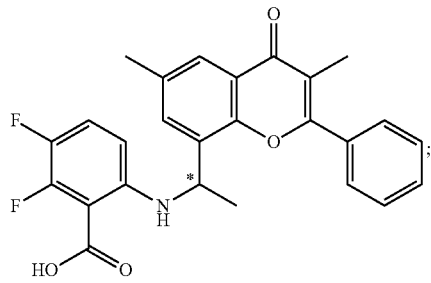
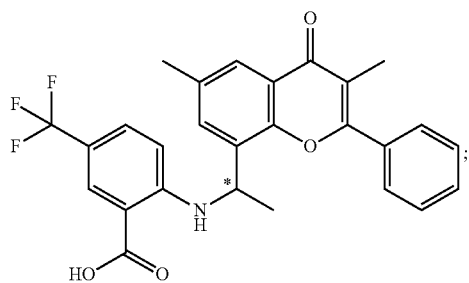
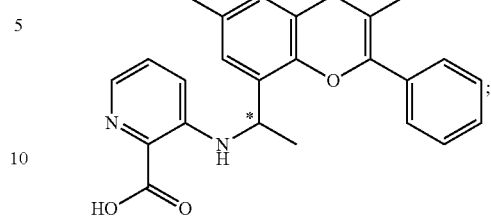
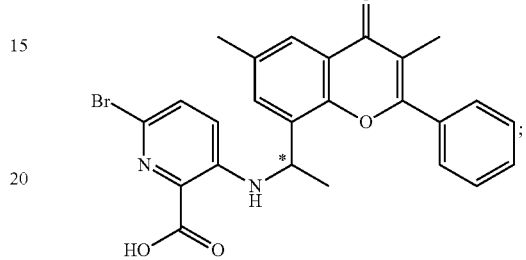
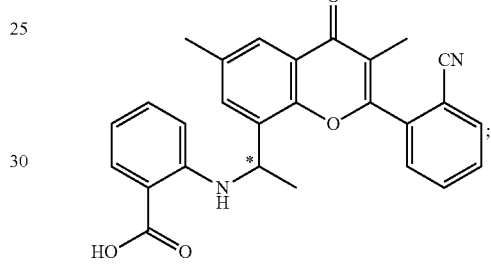
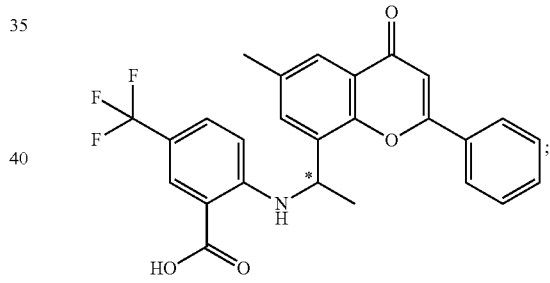
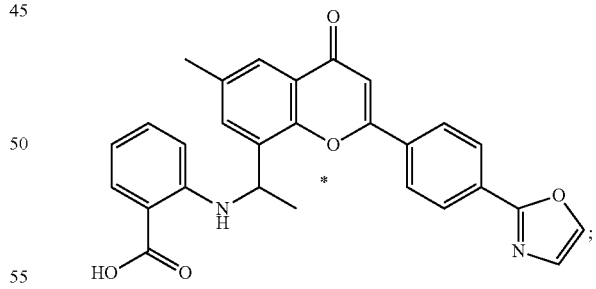
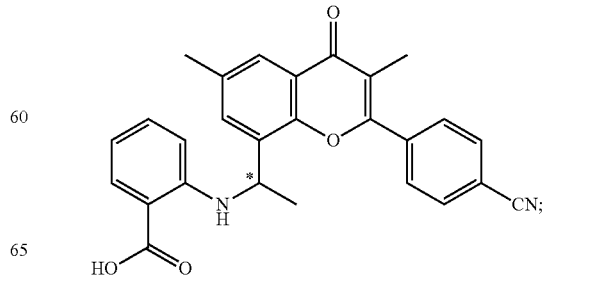

-continued
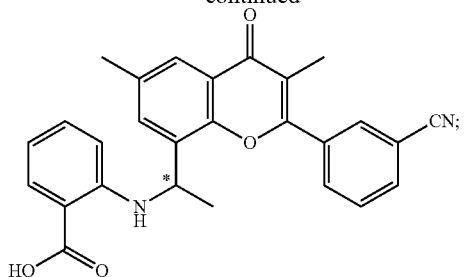
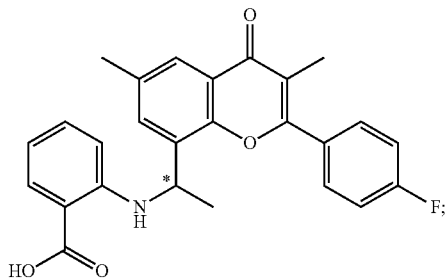
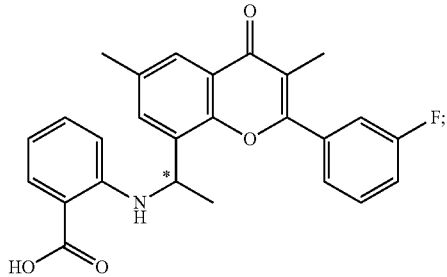
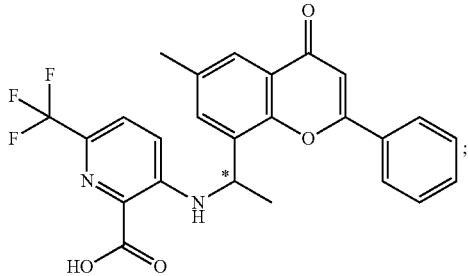
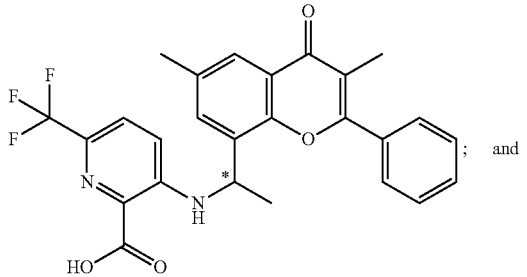
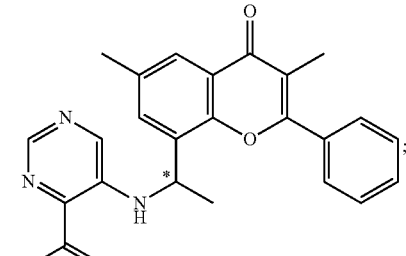
or a pharmaceutically acceptable salt of any of the foregoing;
wherein the bond at the * position is as represented,
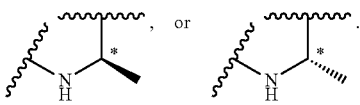
In yet a further compound of Formula (I), the compound is selected from:
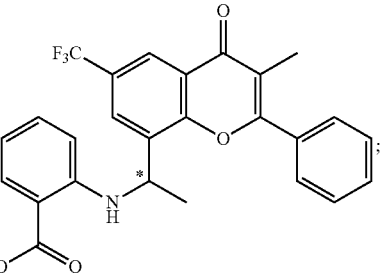
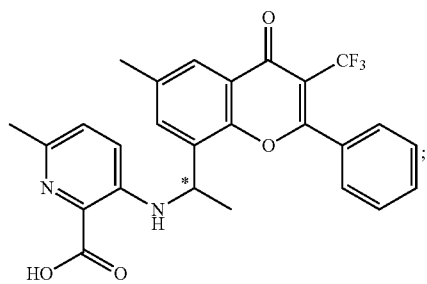
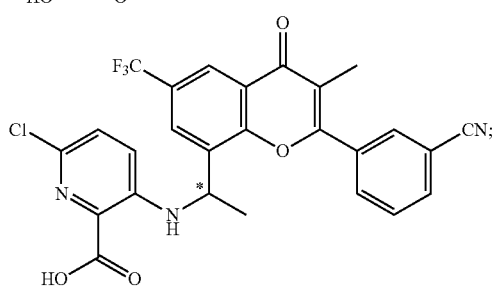
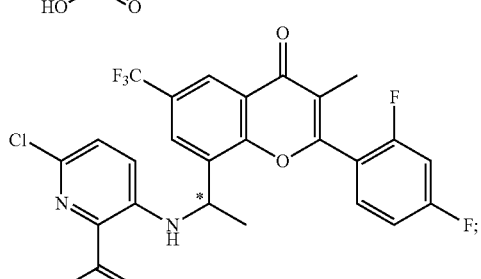
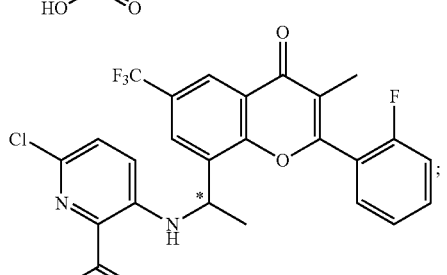

119
-continued
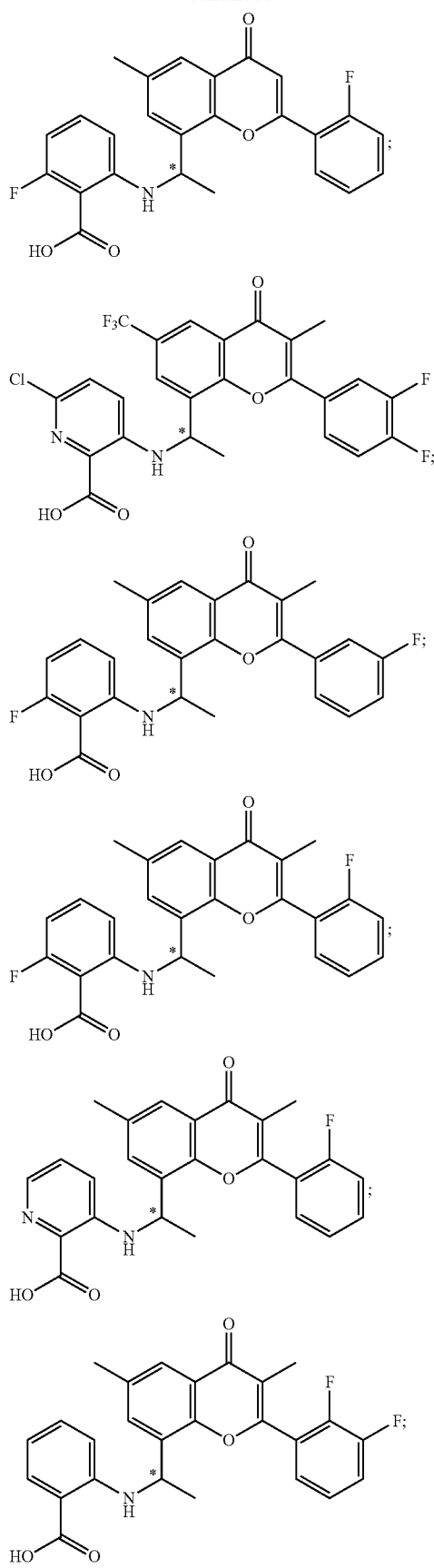
120
-continued
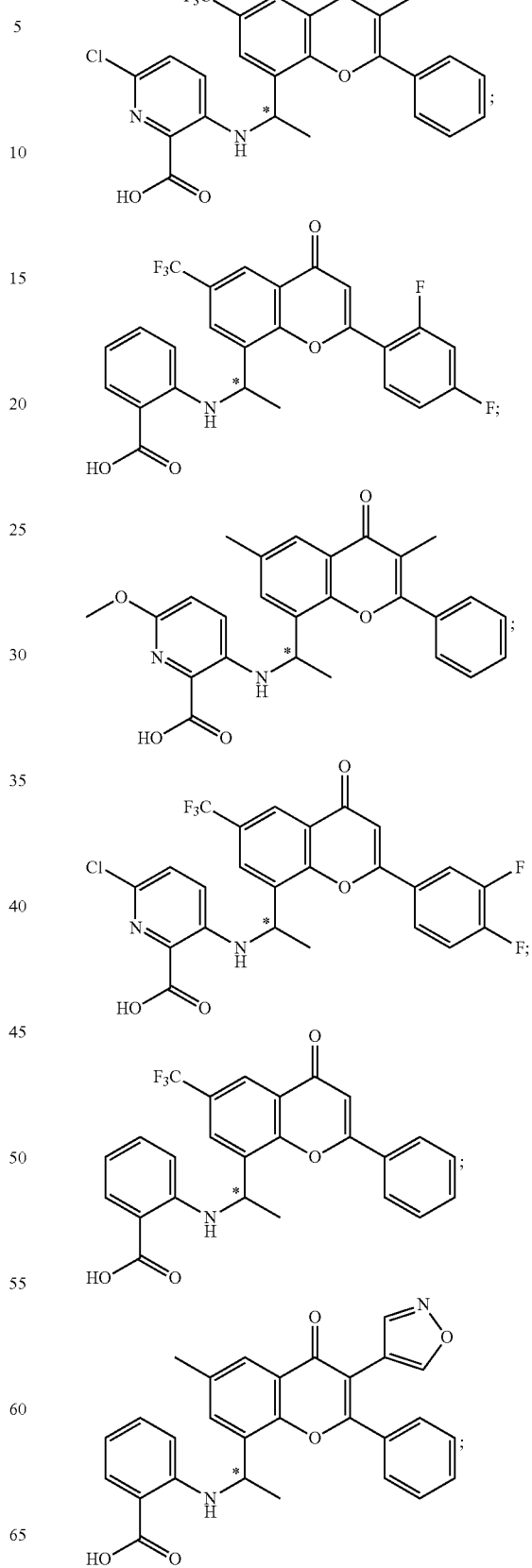

121
-continued
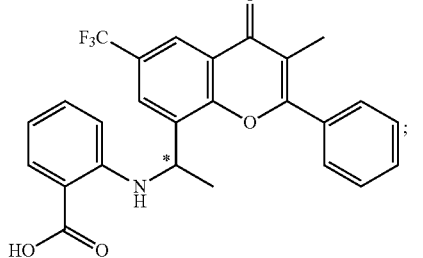
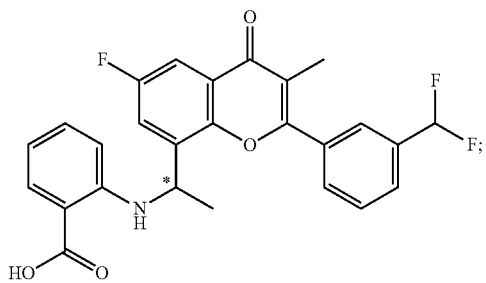
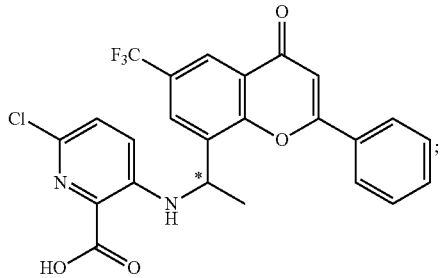
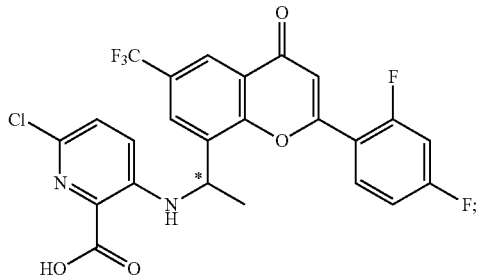
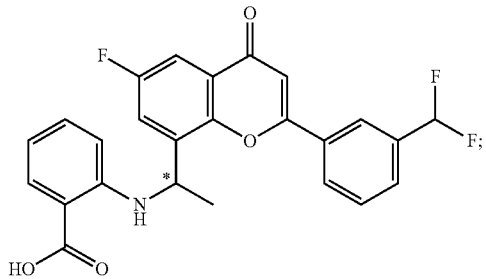
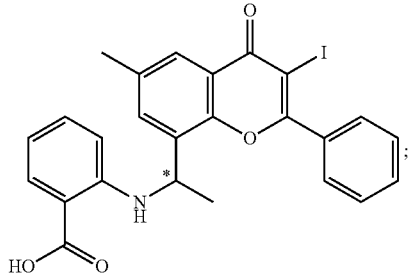
122
-continued
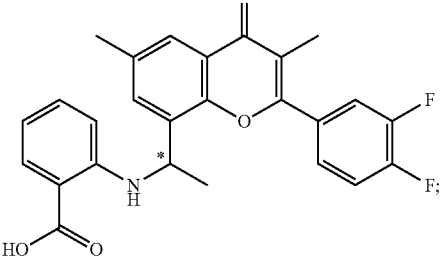
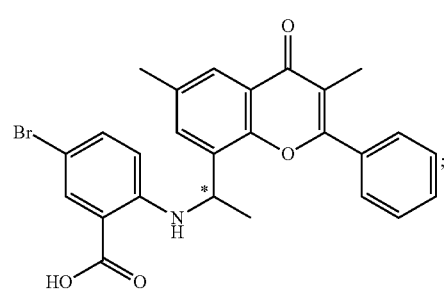
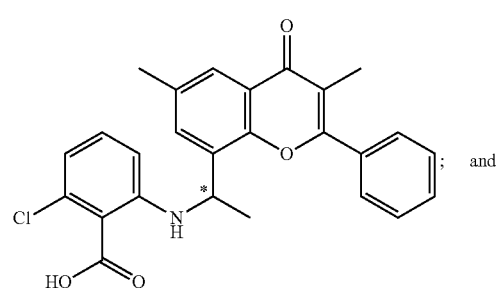; and
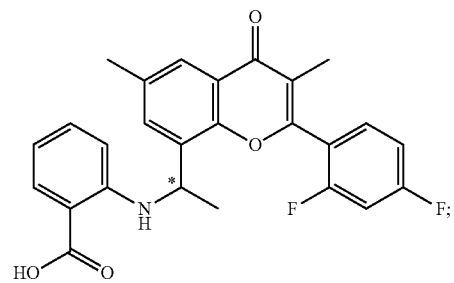
or a pharmaceutically acceptable salt of any of the foregoing;
wherein the bond at the * position is as represented,
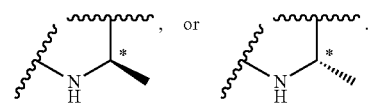
In yet a further compound of Formula (I), the compound is selected from:

123
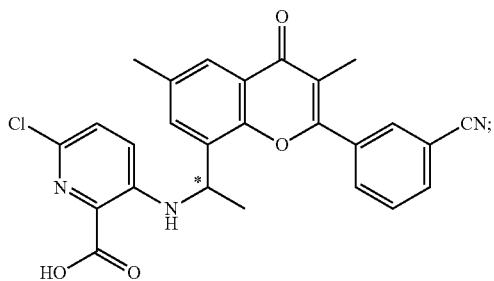
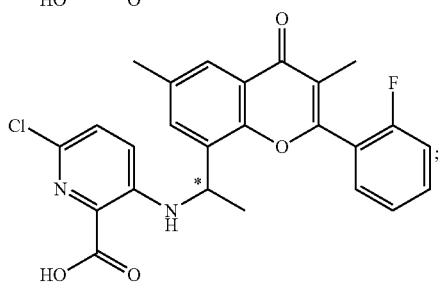
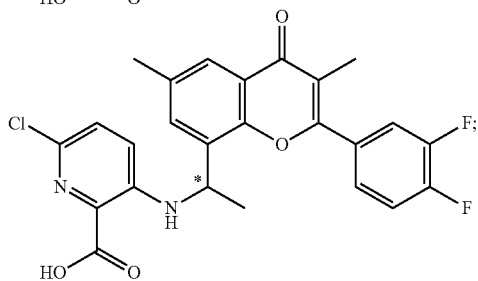
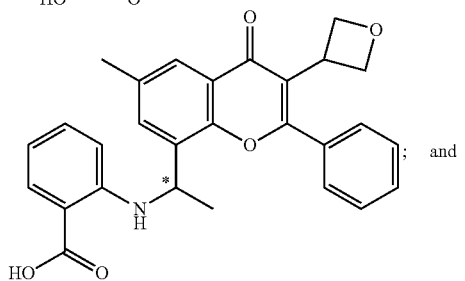
; and
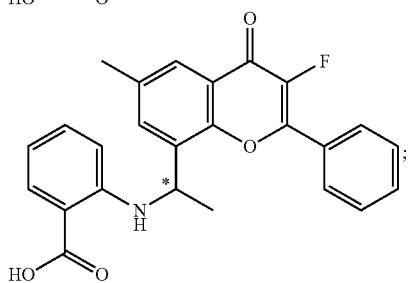
;
or a pharmaceutically acceptable salt of any of the foregoing;
wherein the bond at the * position is as represented,
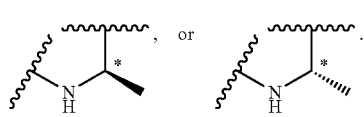
In yet a further compound of Formula (I), the compound is selected from:
124
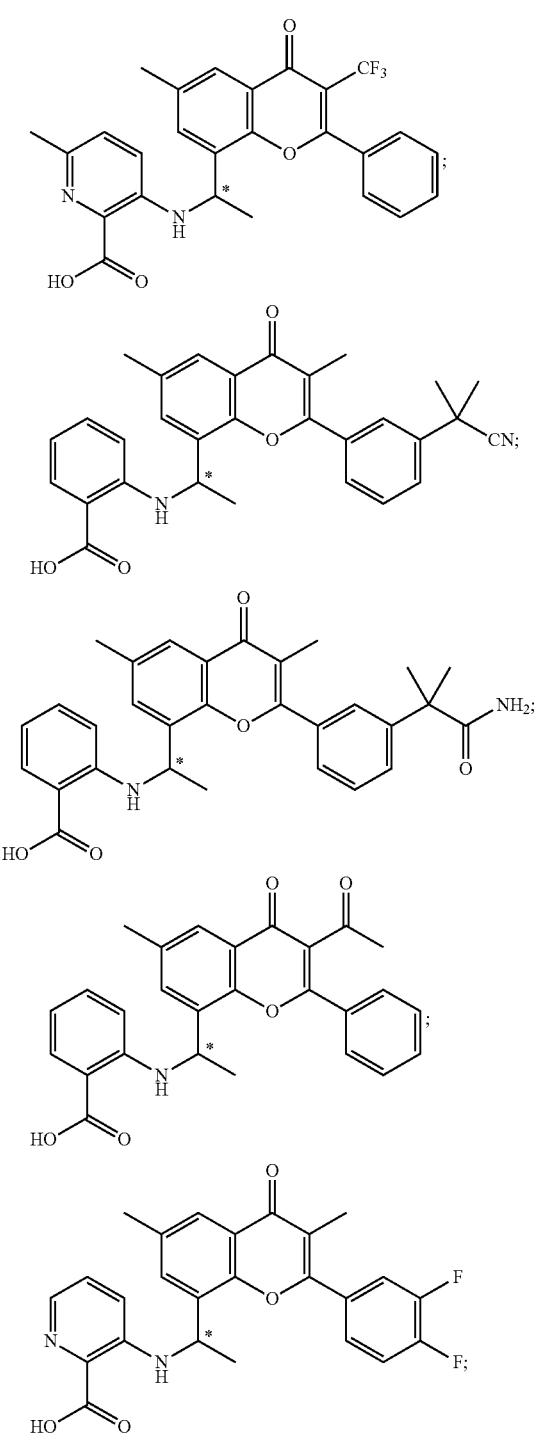
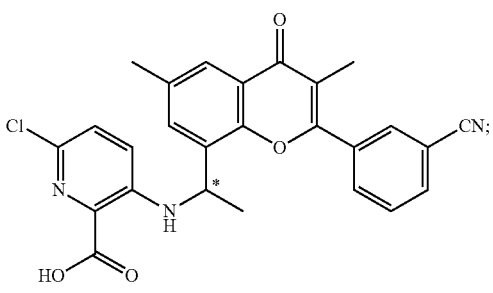

125
-continued
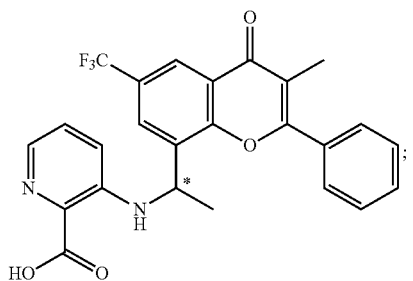
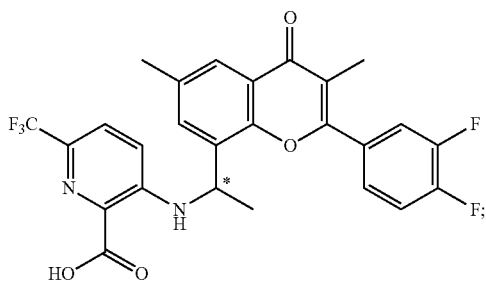
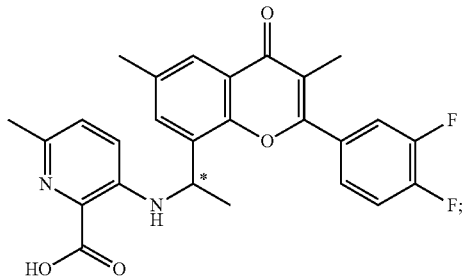
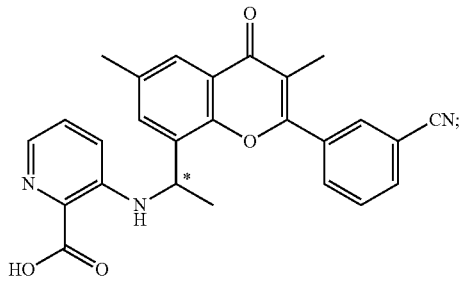
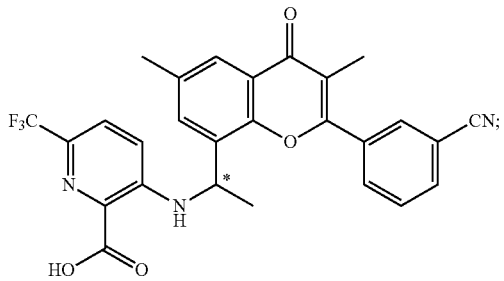
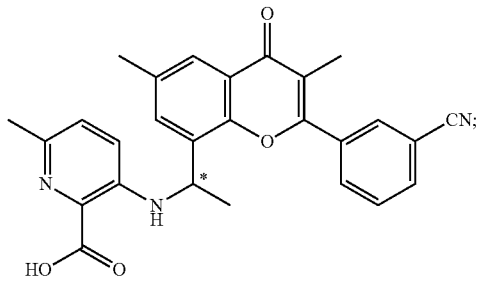
126
-continued
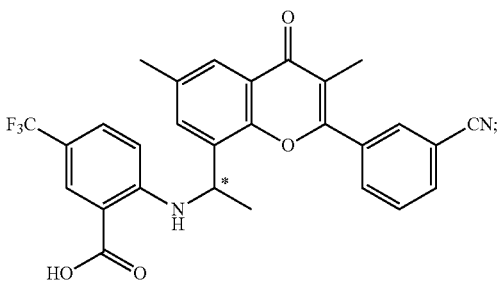
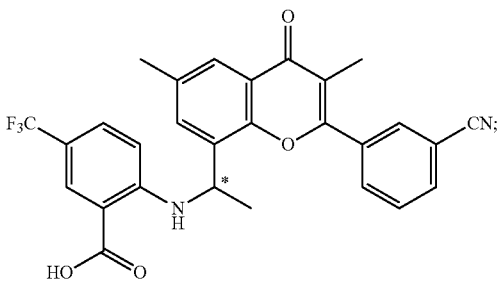
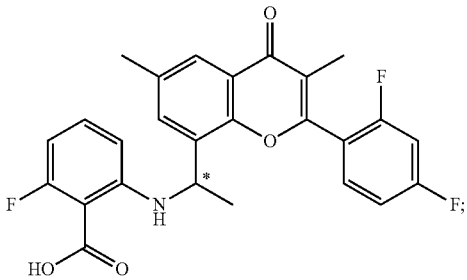
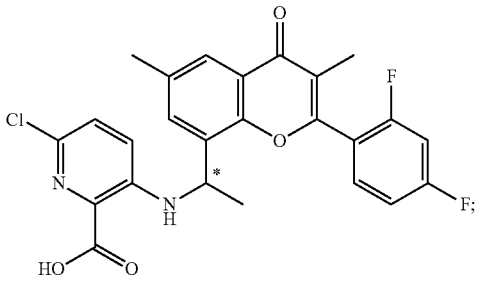
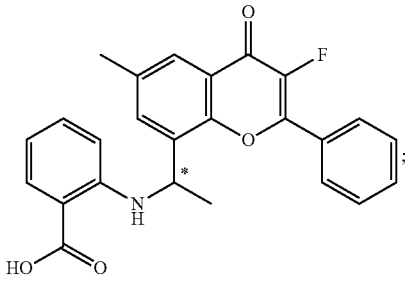
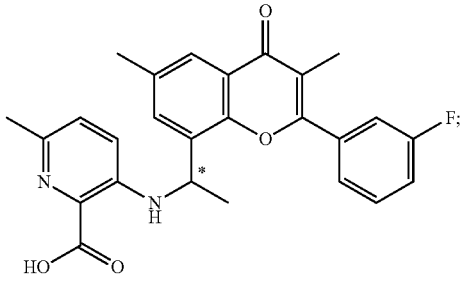

127
-continued
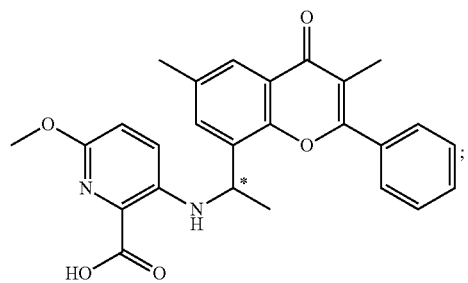
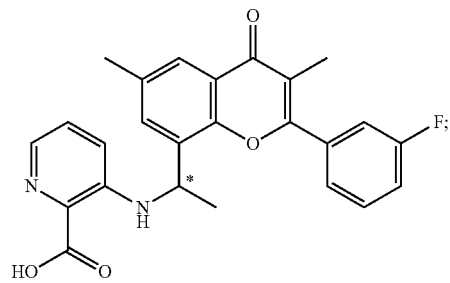
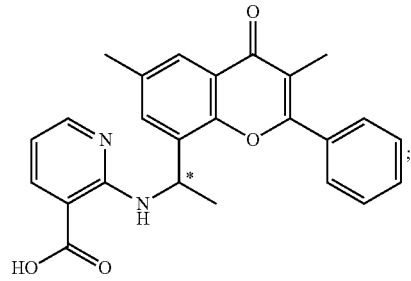
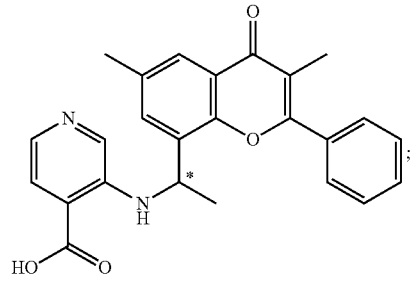
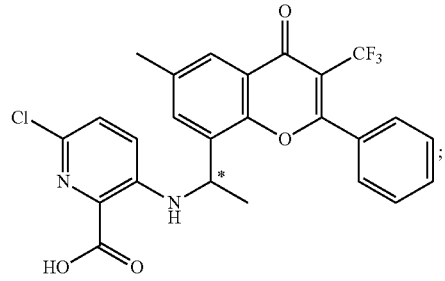
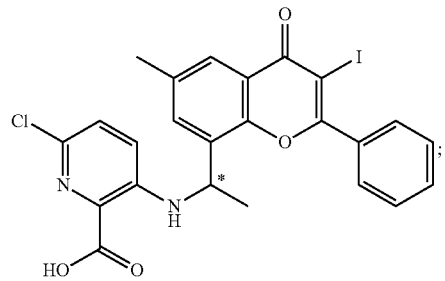
128
-continued
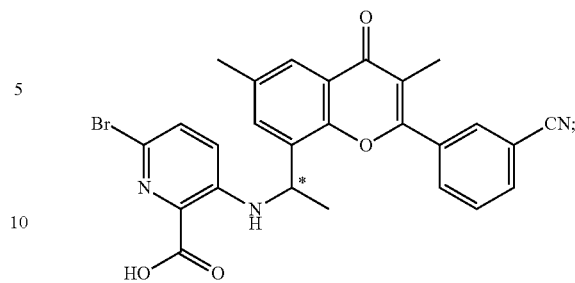
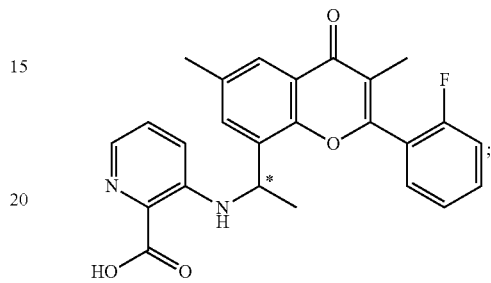
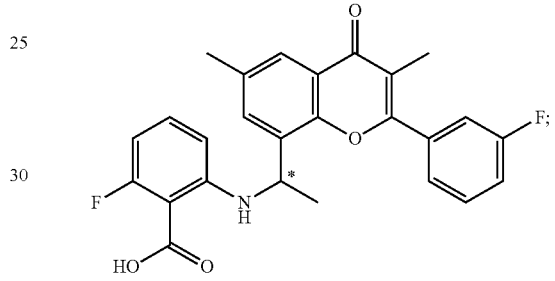
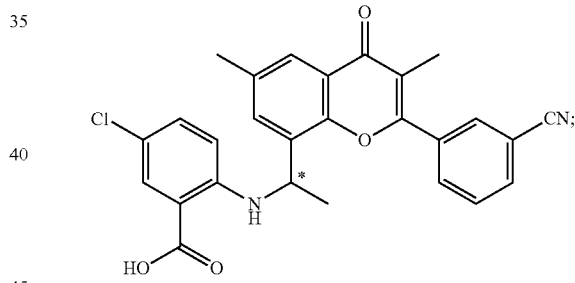
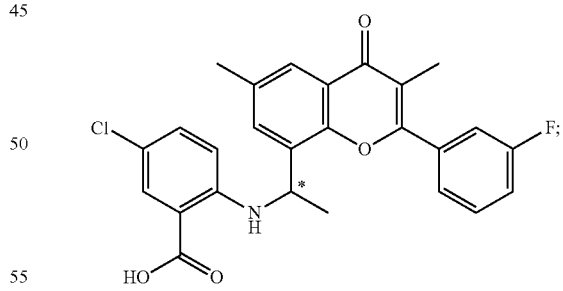
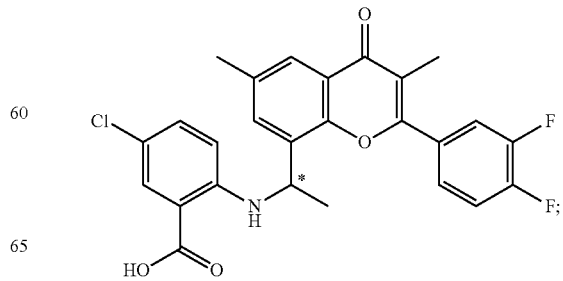

129
-continued
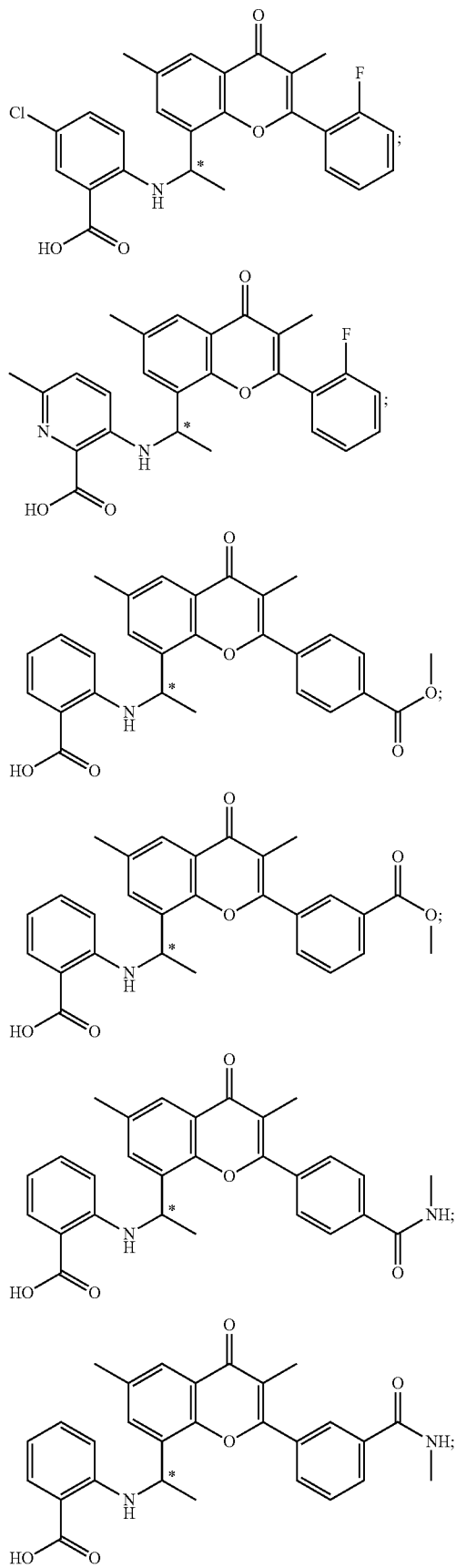
130
-continued
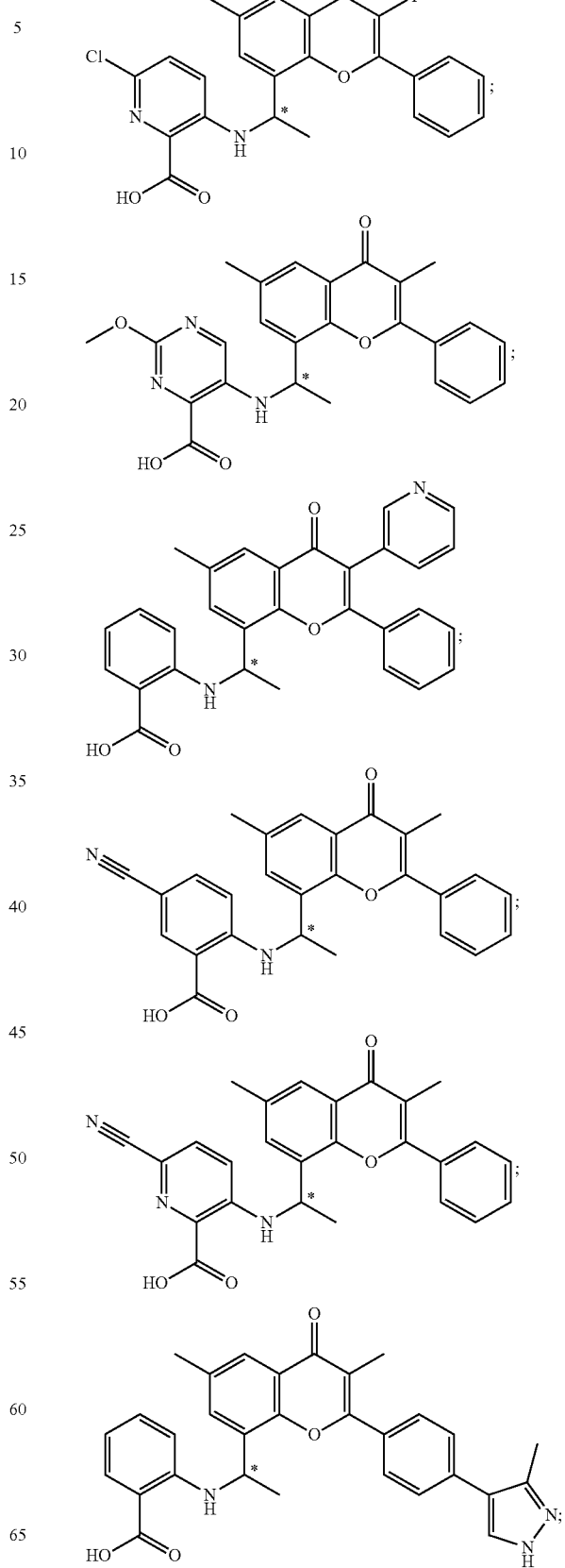

131
-continued
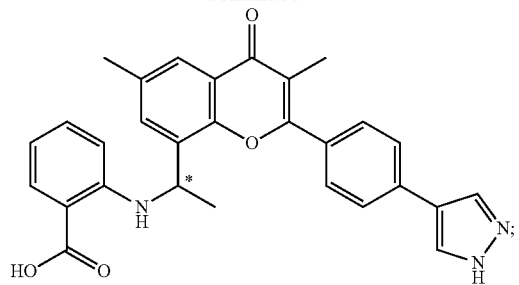
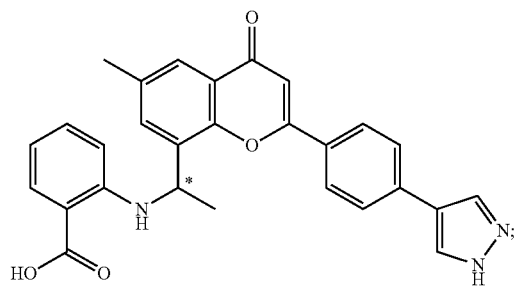
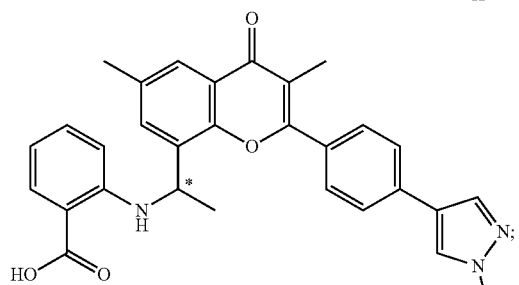
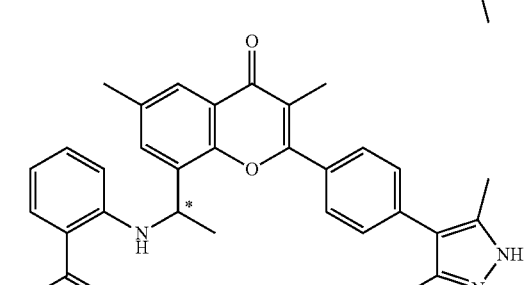
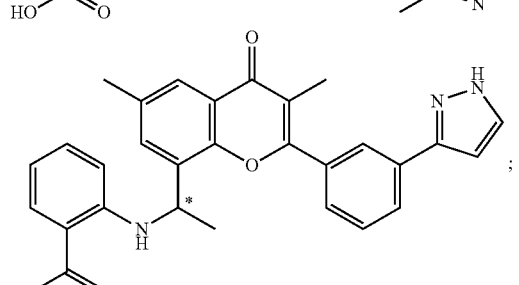
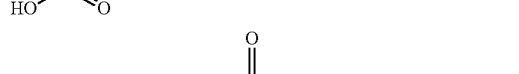
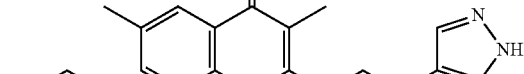
132
-continued
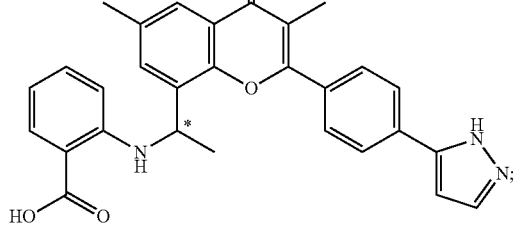
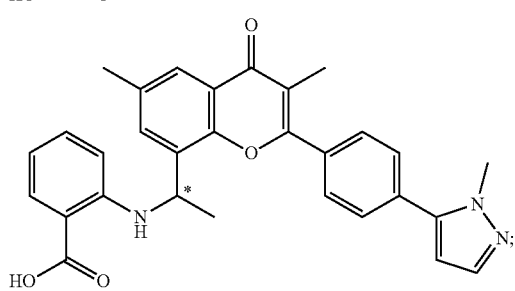
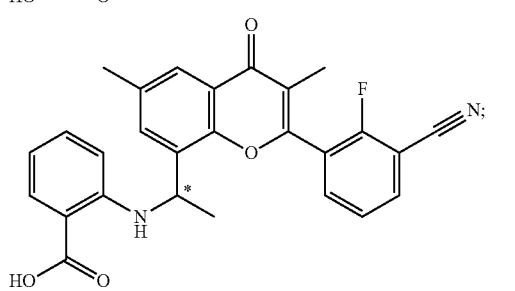
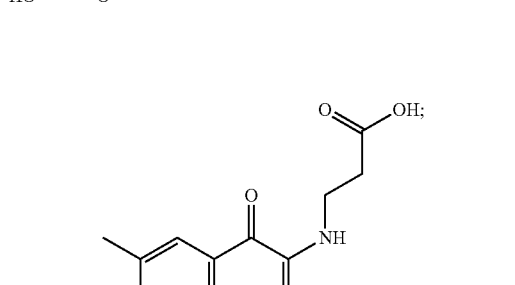
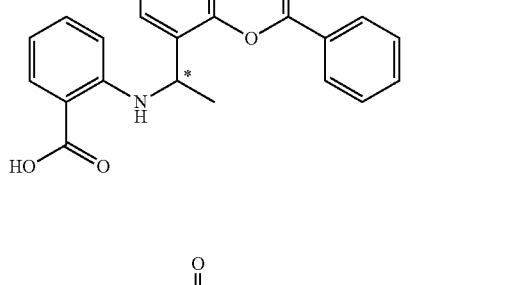
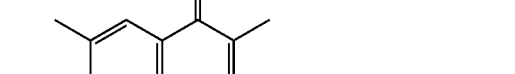
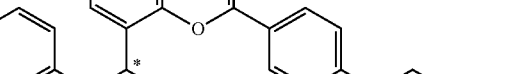

wherein the bond at the * position is as represented,

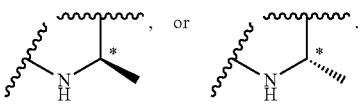

A further embodiment is a compound of Formula

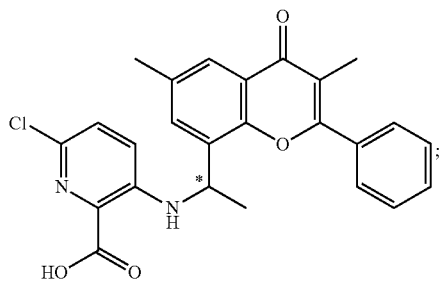 [SMILES: Cc1cc(C(C)Nc2ccc(Cl)nc2C(=O)O)c2oc(-c3ccccc3)c(C)c(=O)c2c1]

or pharmaceutically acceptable salt thereof. In yet a further embodiment, the bond at the * position is

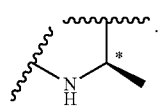

In yet a further embodiment, the bond at the * position is

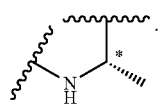

A further embodiment is a compound of Formula

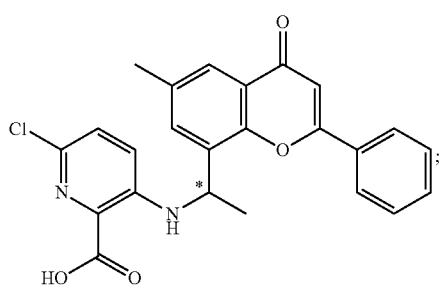 [SMILES: Cc1cc(C(C)Nc2ccc(Cl)nc2C(=O)O)c2oc(-c3ccccc3)cc(=O)c2c1]

or pharmaceutically acceptable salt thereof. In yet a further embodiment, the bond at the * position is

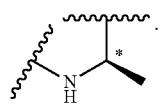

In yet a further embodiment, the bond at the * position is

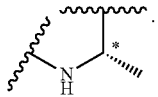

A further embodiment is a compound of Formula

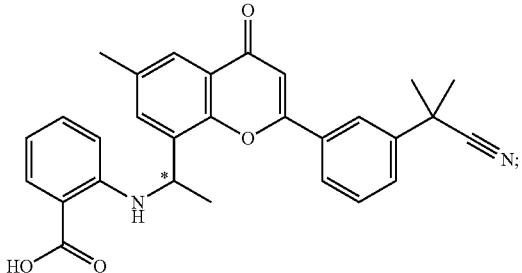 [SMILES: Cc1cc(C(C)Nc2ccccc2C(=O)O)c2oc(-c3cccc(C(C)(C)C#N)c3)cc(=O)c2c1]

or a pharmaceutically acceptable salt thereof. In yet a further embodiment, the bond at the * position is

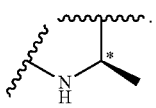

In yet a further embodiment, the bond at the * position is

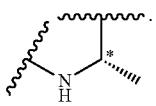

A further embodiment is a compound of Formula

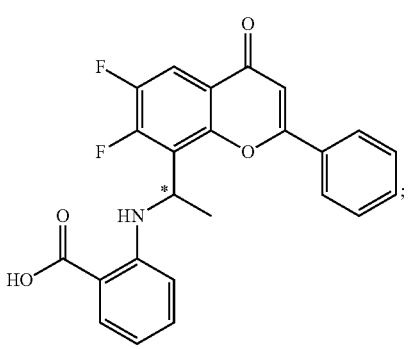 [SMILES: CC(Nc1ccccc1C(=O)O)c1c(F)c(F)cc2c(=O)cc(-c3ccccc3)oc12]

or a pharmaceutically acceptable salt thereof. In yet a further embodiment, the bond at the * position is

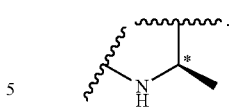

In yet a further embodiment, the bond at the * position is

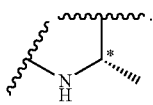 [SMILES: *N[C@H](*)C]

A further embodiment is a compound of Formula

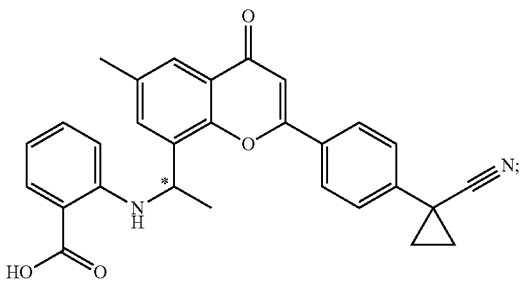 [SMILES: Cc1cc(C(C)Nc2ccccc2C(=O)O)c2oc(-c3ccc(C4(C#N)CC4)cc3)cc(=O)c2c1]

or a pharmaceutically acceptable salt thereof. In yet a further embodiment, the bond at the * position is

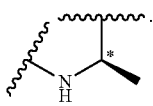 [SMILES: *N[C@@H](*)C]

In yet a further embodiment, the bond at the * position is

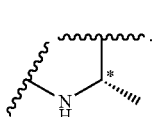

A further embodiment is a compound of Formula

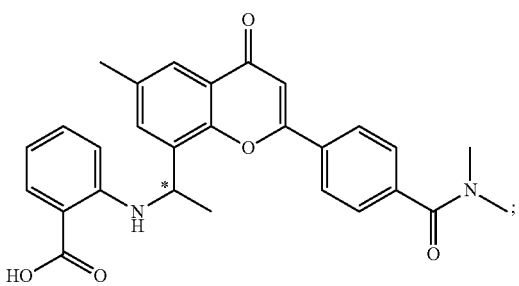 [SMILES: Cc1cc(C(C)Nc2ccccc2C(=O)O)c2oc(-c3ccc(C(=O)N(C)C)cc3)cc(=O)c2c1]

or a pharmaceutically acceptable salt thereof. In yet a further embodiment, the bond at the * position is

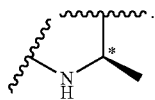 [SMILES: *N[C@@H](*)C]

In yet a further embodiment, the bond at the * position is

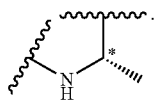

A further embodiment is a compound of Formula

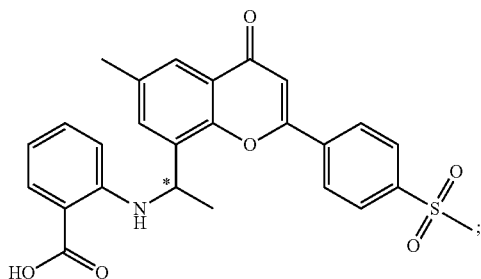 [SMILES: Cc1cc(C(C)Nc2ccccc2C(=O)O)c2oc(-c3ccc(S(C)(=O)=O)cc3)cc(=O)c2c1]

or a pharmaceutically acceptable salt thereof. In yet a further embodiment, the bond at the * position is

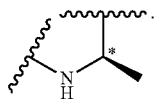

In yet a further embodiment, the bond at the * position is

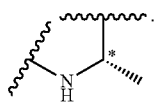

A further embodiment is a compound of Formula

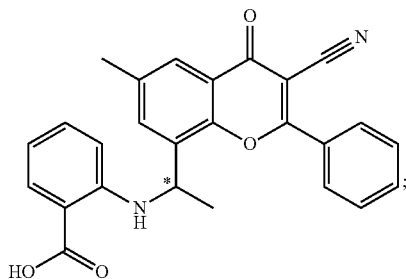 [SMILES: Cc1cc(C(C)Nc2ccccc2C(=O)O)c2oc(-c3ccccc3)c(C#N)c(=O)c2c1]

or a pharmaceutically acceptable salt thereof. In yet a further embodiment, the bond at the * position is

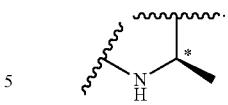

In yet a further embodiment, the bond at the * position is

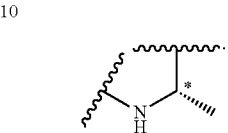

A further embodiment is a compound of Formula

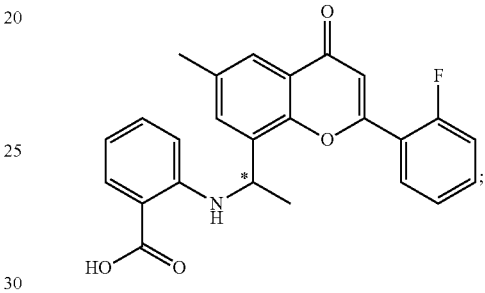

or a pharmaceutically acceptable salt thereof. In yet a further embodiment, the bond at the * position is

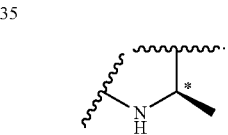

In yet a further embodiment, the bond at the * position is

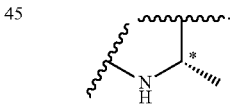

A further embodiment is a compound of Formula

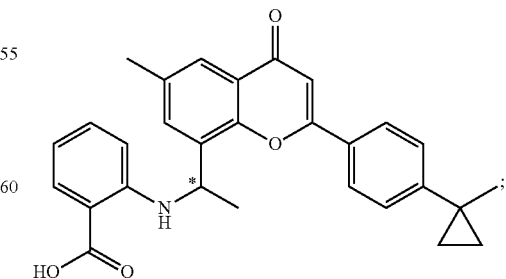

or a pharmaceutically acceptable salt thereof. In yet a further embodiment, the bond at the * position is

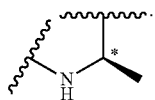

In yet a further embodiment, the bond at the * position is

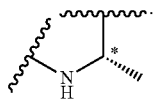

A further embodiment is a compound of Formula

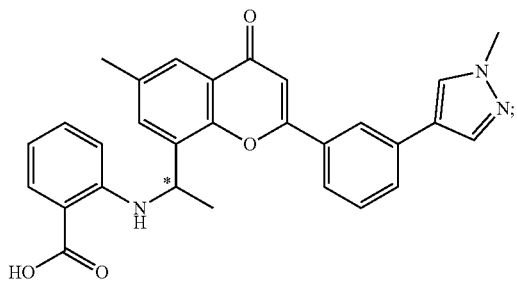 [SMILES: Cc1cc(C(C)Nc2ccccc2C(=O)O)c2oc(-c3cccc(-c4cnn(C)c4)c3)cc(=O)c2c1]

or a pharmaceutically acceptable salt thereof. In yet a further embodiment, the bond at the * position is

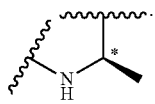

In yet a further embodiment, the bond at the * position is

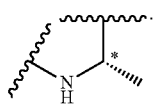

A further embodiment is a compound of Formula

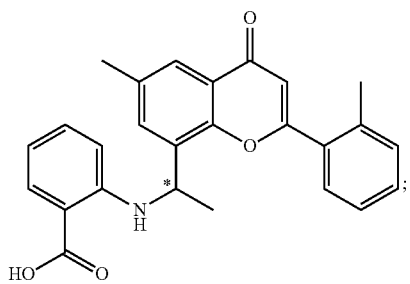 [SMILES: Cc1cc(C(C)Nc2ccccc2C(=O)O)c2oc(-c3ccccc3C)cc(=O)c2c1]

or a pharmaceutically acceptable salt thereof. In yet a further embodiment, the bond at the * position is

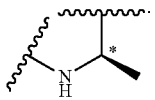 [SMILES: *N[C@@H](*)C]

In yet a further embodiment, the bond at the * position is

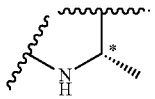

A further embodiment is a compound of Formula

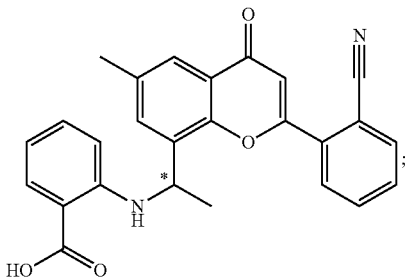 [SMILES: Cc1cc(C(C)Nc2ccccc2C(=O)O)c2oc(-c3ccccc3C#N)cc(=O)c2c1]

or a pharmaceutically acceptable salt thereof. In yet a further embodiment, the bond at the * position is

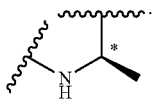

In yet a further embodiment, the bond at the * position is

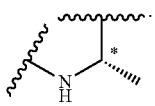

A further embodiment is a compound of Formula

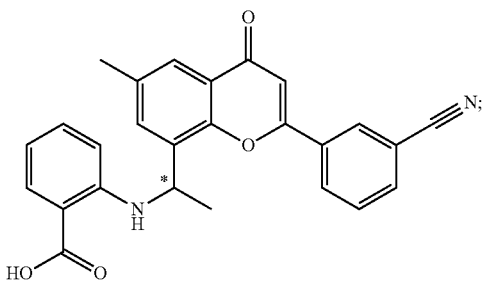 [SMILES: Cc1cc(C(C)Nc2ccccc2C(=O)O)c2oc(-c3cccc(C#N)c3)cc(=O)c2c1]

or a pharmaceutically acceptable salt thereof. In yet a further embodiment, the bond at the * position is

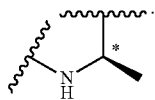

In yet a further embodiment, the bond at the * position is

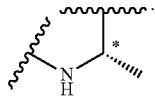

A further embodiment is a compound of Formula

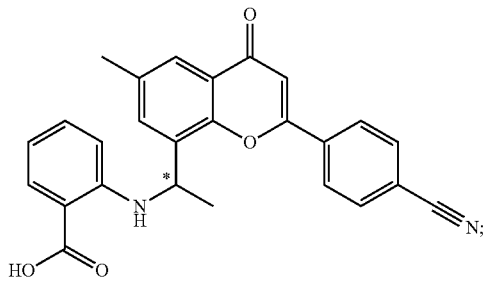 [SMILES: Cc1cc(C(C)Nc2ccccc2C(=O)O)c2oc(-c3ccc(C#N)cc3)cc(=O)c2c1]

or a pharmaceutically acceptable salt thereof. In yet a further embodiment, the bond at the * position is

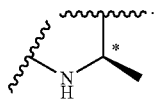

In yet a further embodiment, the bond at the * position is

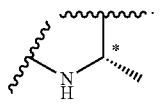

A further embodiment is a compound of Formula

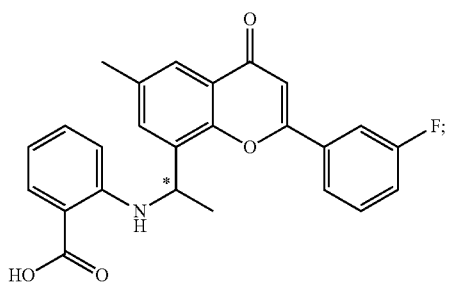

or a pharmaceutically acceptable salt thereof. In yet a further embodiment, the bond at the * position is

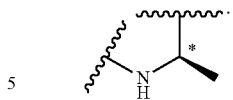

In yet a further embodiment, the bond at the * position is

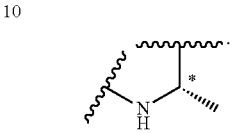

A further embodiment is a compound of Formula

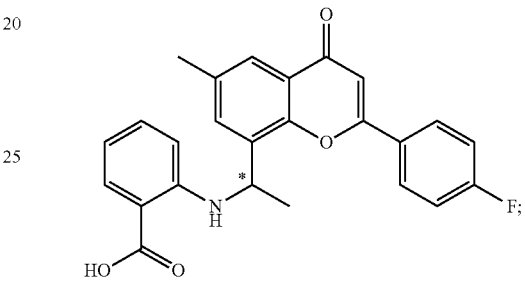

or a pharmaceutically acceptable salt thereof. In yet a further embodiment, the bond at the * position is

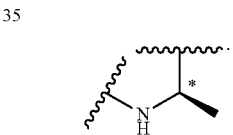

In yet a further embodiment, the bond at the * position is

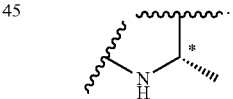

A further embodiment is a compound of Formula

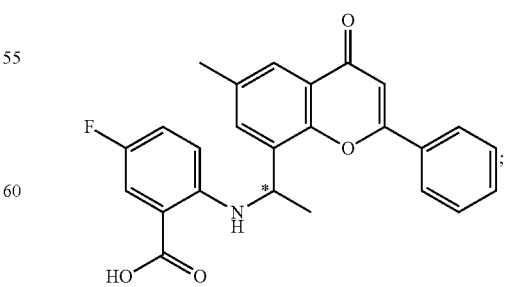

or a pharmaceutically acceptable salt thereof. In yet a further embodiment, the bond at the * position is

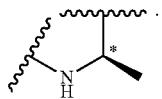

In yet a further embodiment, the bond at the * position is

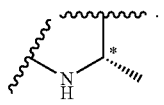 [SMILES: *N[C@H](*)C]

A further embodiment is a compound of Formula

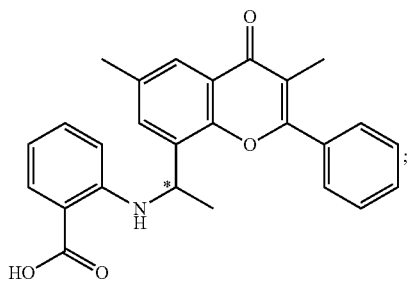 [SMILES: Cc1cc(C(C)Nc2ccccc2C(=O)O)c2oc(-c3ccccc3)c(C)c(=O)c2c1]

or a pharmaceutically acceptable salt thereof. In yet a further embodiment, the bond at the * position is

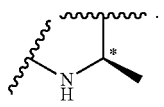

In yet a further embodiment, the bond at the * position is

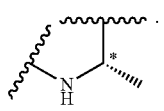

A further embodiment is a compound of Formula

or a pharmaceutically acceptable salt thereof. In yet a further embodiment, the bond at the * position is

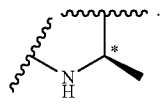

In yet a further embodiment, the bond at the * position is

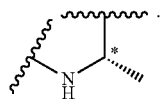

A further embodiment is a compound of Formula

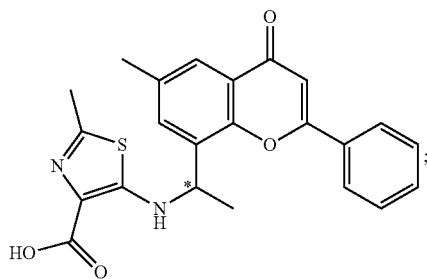 [SMILES: Cc1cc(C(C)Nc2sc(C)nc2C(=O)O)c2oc(-c3ccccc3)cc(=O)c2c1]

or a pharmaceutically acceptable salt thereof. In yet a further embodiment, the bond at the * position is

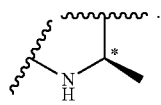

In yet a further embodiment, the bond at the * position is

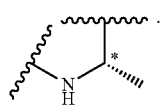

A further embodiment is a compound of Formula

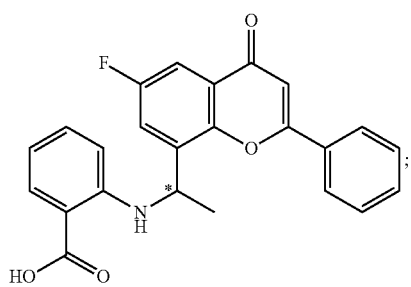

or a pharmaceutically acceptable salt thereof. In yet a further embodiment, the bond at the * position is

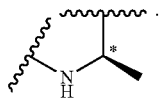

In yet a further embodiment, the bond at the * position is

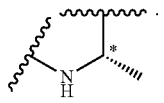 [SMILES: *N[C@H](*)C]

A further embodiment is a compound of Formula

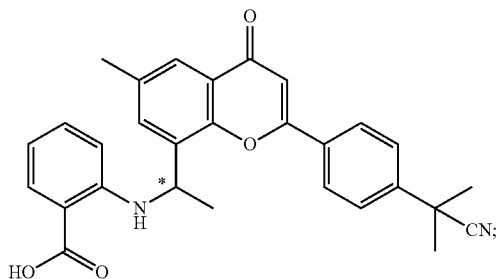

or a pharmaceutically acceptable salt thereof. In yet a further embodiment, the bond at the * position is

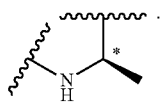

In yet a further embodiment, the bond at the * position is

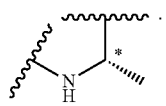

A further embodiment is a compound of Formula

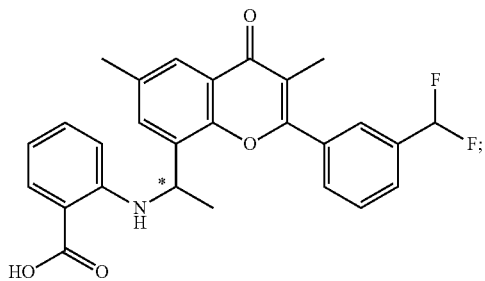

or a pharmaceutically acceptable salt thereof. In yet a further embodiment, the bond at the * position is

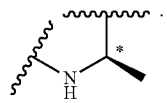

In yet a further embodiment, the bond at the * position is

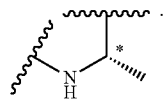

A further embodiment is a compound of Formula

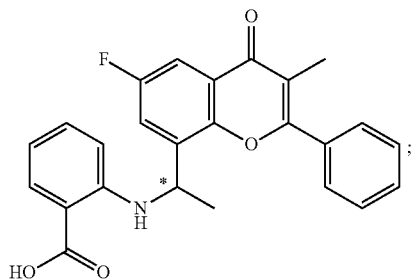

or a pharmaceutically acceptable salt thereof. In yet a further embodiment, the bond at the * position is

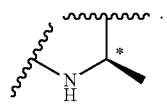

In yet a further embodiment, the bond at the * position is

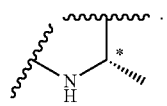

A further embodiment is a compound of Formula

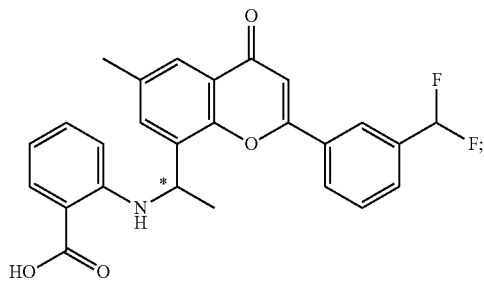 [SMILES: Cc1cc(C(C)Nc2ccccc2C(=O)O)c2oc(-c3cccc(C(F)F)c3)cc(=O)c2c1]

or a pharmaceutically acceptable salt thereof. In yet a further embodiment, the bond at the * position is

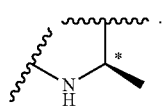

In yet a further embodiment, the bond at the * position is

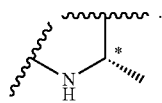

A further embodiment is a compound of Formula

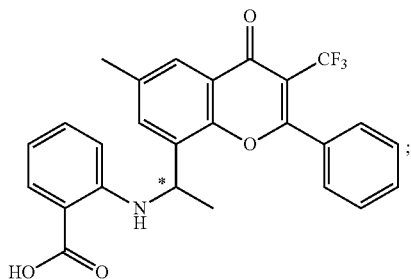

or a pharmaceutically acceptable salt thereof. In yet a further embodiment, the bond at the * position is

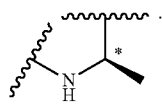 [SMILES: *N[C@@H](*)C]

In yet a further embodiment, the bond at the * position is

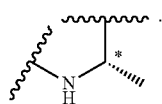

A further embodiment is a compound of Formula

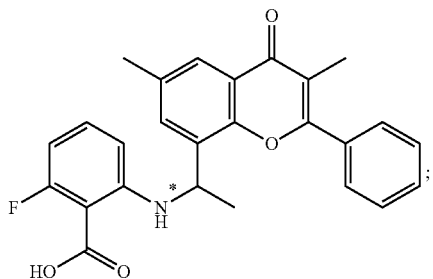 [SMILES: Cc1cc(C(C)Nc2cccc(F)c2C(=O)O)c2oc(-c3ccccc3)c(C)c(=O)c2c1]

or a pharmaceutically acceptable salt thereof. In yet a further embodiment, the bond at the * position is

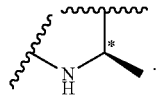

In yet a further embodiment, the bond at the * position is

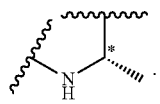

A further embodiment is a compound of Formula

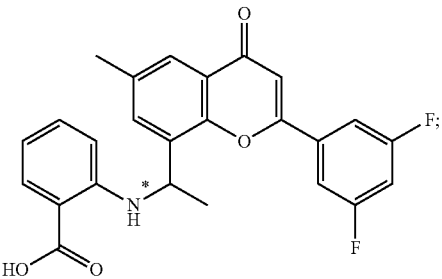 [SMILES: Cc1cc(C(C)Nc2ccccc2C(=O)O)c2oc(-c3cc(F)cc(F)c3)cc(=O)c2c1]

or a pharmaceutically acceptable salt thereof. In yet a further embodiment, the bond at the * position is

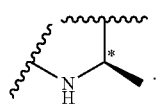

In yet a further embodiment, the bond at the * position is

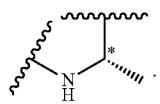

A further embodiment is a compound of Formula

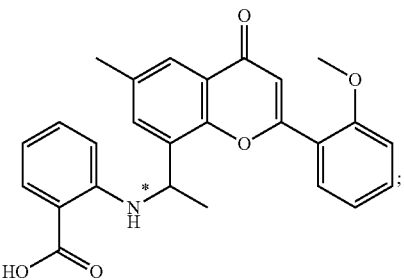 [SMILES: COc1ccccc1-c1cc(=O)c2cc(C)cc(C(C)Nc3ccccc3C(=O)O)c2o1]

or a pharmaceutically acceptable salt thereof. In yet a further embodiment, the bond at the * position is

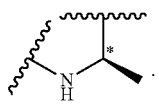 [SMILES: *N[C@@H](*)C]

In yet a further embodiment, the bond at the * position is

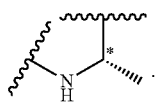

A further embodiment is a compound of Formula

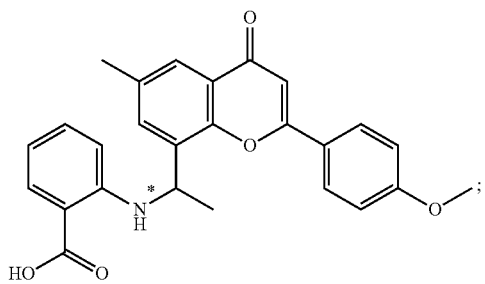 [SMILES: COc1ccc(-c2cc(=O)c3cc(C)cc(C(C)Nc4ccccc4C(=O)O)c3o2)cc1]

or a pharmaceutically acceptable salt thereof. In yet a further embodiment, the bond at the * position is

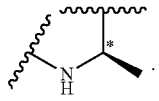

In yet a further embodiment, the bond at the * position is

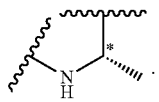

A further embodiment is a compound of Formula

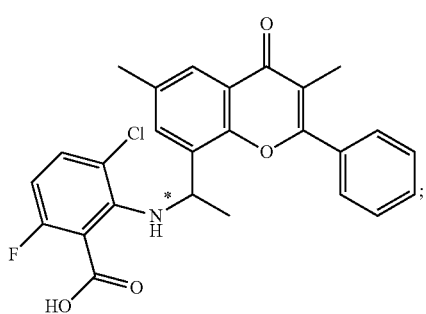 [SMILES: Cc1cc(C(C)Nc2c(Cl)ccc(F)c2C(=O)O)c2oc(-c3ccccc3)c(C)c(=O)c2c1]

or a pharmaceutically acceptable salt thereof. In yet a further embodiment, the bond at the * position is

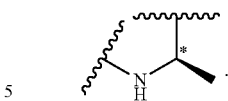

In yet a further embodiment, the bond at the * position is

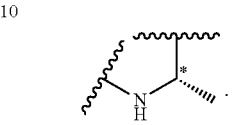

A further embodiment is a compound of Formula

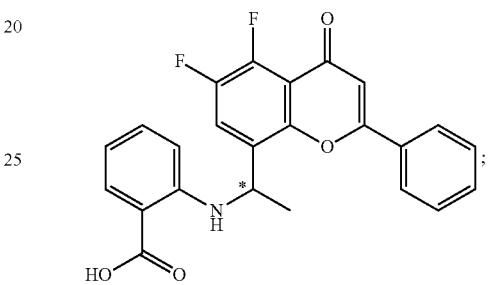

or a pharmaceutically acceptable salt thereof. In yet a further embodiment, the bond at the * position is

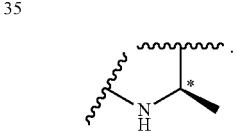

In yet a further embodiment, the bond at the * position is

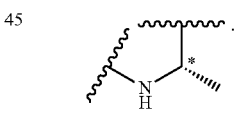

A further embodiment is a compound of Formula

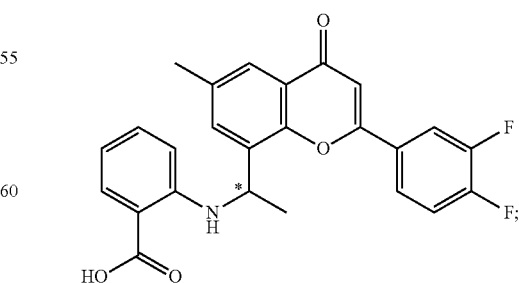

or a pharmaceutically acceptable salt thereof. In yet a further embodiment, the bond at the * position is

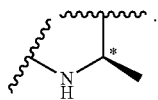

In yet a further embodiment, the bond at the * position is

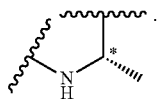

A further embodiment is a compound of Formula

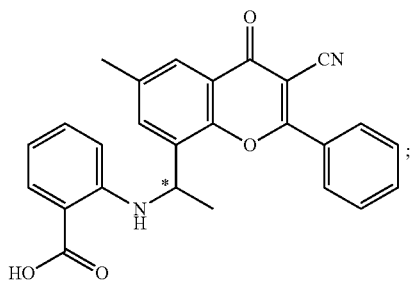 [SMILES: Cc1cc(C(C)Nc2ccccc2C(=O)O)c2oc(-c3ccccc3)c(C#N)c(=O)c2c1]

or a pharmaceutically acceptable salt thereof. In yet a further embodiment, the bond at the * position is

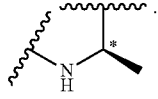 [SMILES: *N[C@@H](*)C]

In yet a further embodiment, the bond at the * position is

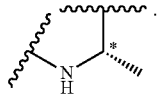

A further embodiment is a compound of Formula

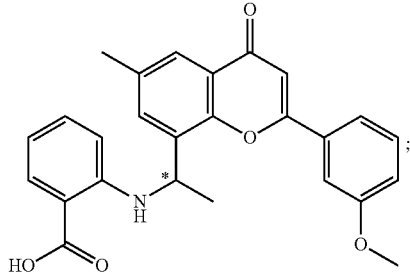 [SMILES: COc1cccc(-c2cc(=O)c3cc(C)cc(C(C)Nc4ccccc4C(=O)O)c3o2)c1]

or a pharmaceutically acceptable salt thereof. In yet a further embodiment, the bond at the position is

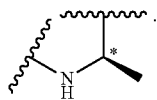

In yet a further embodiment, the bond at the * position is

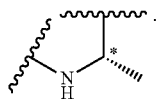

A further embodiment is a compound of Formula

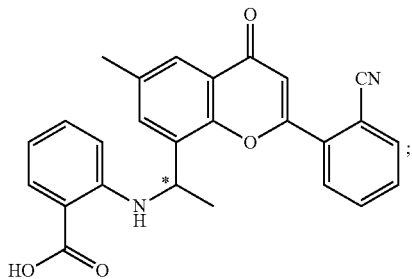 [SMILES: Cc1cc(C(C)Nc2ccccc2C(=O)O)c2oc(-c3ccccc3C#N)cc(=O)c2c1]

or a pharmaceutically acceptable salt thereof. In yet a further embodiment, the bond at the * position is

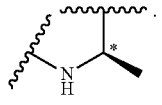

In yet a further embodiment, the bond at the * position is

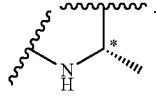

A further embodiment is a compound of Formula

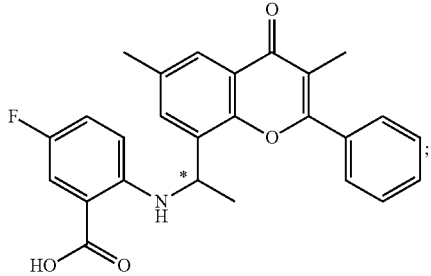 [SMILES: Cc1cc(C(C)Nc2ccc(F)cc2C(=O)O)c2oc(-c3ccccc3)c(C)c(=O)c2c1]

or a pharmaceutically acceptable salt thereof. In yet a further embodiment, the bond at the * position is

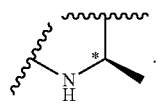

In yet a further embodiment, the bond at the * position is

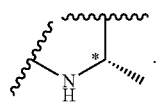

A further embodiment is a compound of Formula

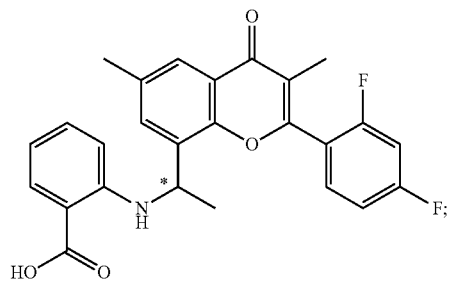 [SMILES: Cc1cc(C(C)Nc2ccccc2C(=O)O)c2oc(-c3ccc(F)cc3F)c(C)c(=O)c2c1]

or a pharmaceutically acceptable salt thereof. In yet a further embodiment, the bond at the * position is

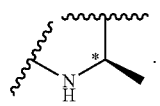

In yet a further embodiment, the bond at the * position is

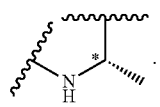

A further embodiment is a compound of Formula

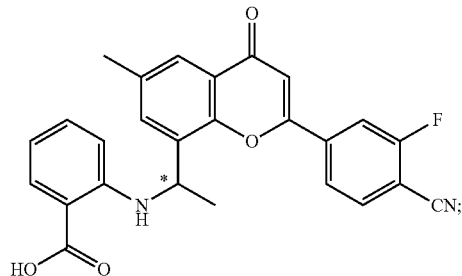 [SMILES: Cc1cc(C(C)Nc2ccccc2C(=O)O)c2oc(-c3ccc(C#N)c(F)c3)cc(=O)c2c1]

or a pharmaceutically acceptable salt thereof. In yet a further embodiment, the bond at the * position is

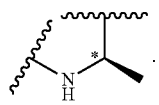

In yet a further embodiment, the bond at the * position is

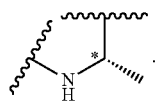

A further embodiment is a compound of Formula

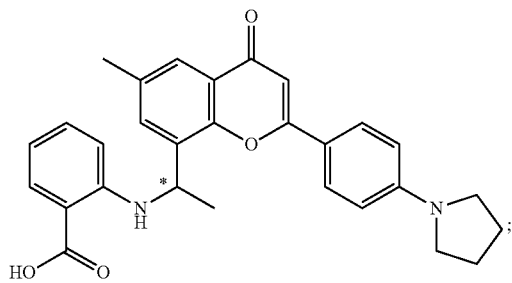 [SMILES: Cc1cc(C(C)Nc2ccccc2C(=O)O)c2oc(-c3ccc(N4CCCC4)cc3)cc(=O)c2c1]

or a pharmaceutically acceptable salt thereof. In yet a further embodiment, the bond at the * position is

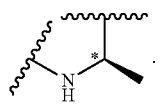

In yet a further embodiment, the bond at the * position is

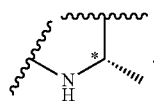

A further embodiment is a compound of Formula

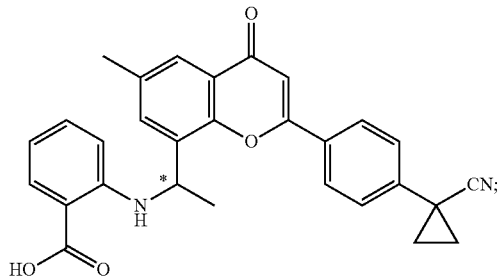 [SMILES: Cc1cc(C(C)Nc2ccccc2C(=O)O)c2oc(-c3ccc(C4(C#N)CC4)cc3)cc(=O)c2c1]

or a pharmaceutically acceptable salt thereof. In yet a further embodiment, the bond at the * position is

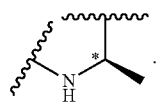

In yet a further embodiment, the bond at the * position is

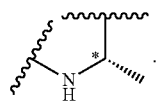

A further embodiment is a compound of Formula

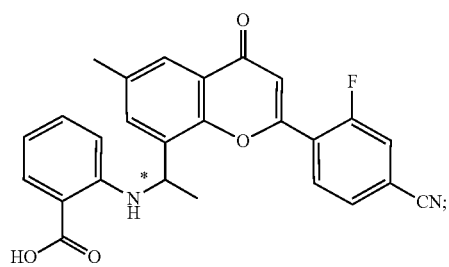 [SMILES: Cc1cc(C(C)Nc2ccccc2C(=O)O)c2oc(-c3ccc(C#N)cc3F)cc(=O)c2c1]

or a pharmaceutically acceptable salt thereof. In yet a further embodiment, the bond at the * position is

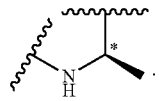

In yet a further embodiment, the bond at the * position is

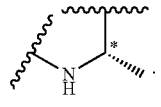

A further embodiment is a compound of Formula

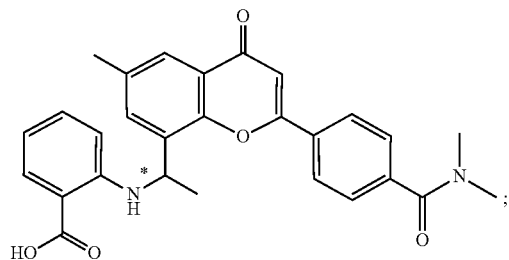 [SMILES: Cc1cc(C(C)Nc2ccccc2C(=O)O)c2oc(-c3ccc(C(=O)N(C)C)cc3)cc(=O)c2c1]

or a pharmaceutically acceptable salt thereof. In yet a further embodiment, the bond at the * position is

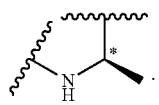

In yet a further embodiment, the bond at the * position is

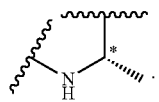

A further embodiment is a compound of Formula

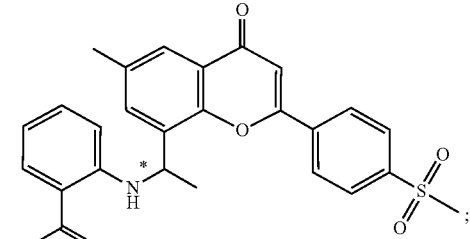

or a pharmaceutically acceptable salt thereof. In yet a further embodiment, the bond at the * position is

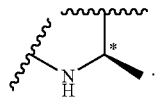

In yet a further embodiment, the bond at the * position is

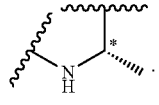

A further embodiment is a compound of Formula

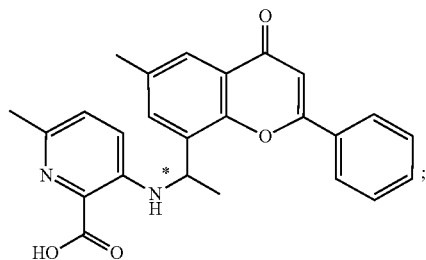 [SMILES: Cc1cc(C(C)Nc2ccc(C)nc2C(=O)O)c2oc(-c3ccccc3)cc(=O)c2c1]

or a pharmaceutically acceptable salt thereof. In yet a further embodiment, the bond at the * position is

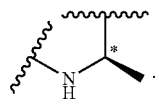 [SMILES: *N[C@@H](*)C]

In yet a further embodiment, the bond at the * position is

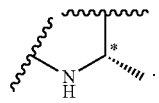

A further embodiment is a compound of Formula

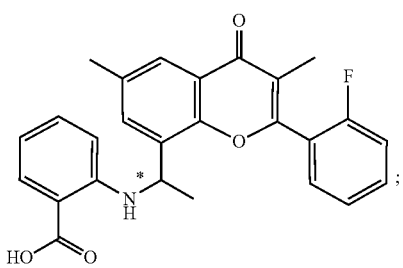 [SMILES: Cc1cc(C(C)Nc2ccccc2C(=O)O)c2oc(-c3ccccc3F)c(C)c(=O)c2c1]

or a pharmaceutically acceptable salt thereof. In yet a further embodiment, the bond at the * position is

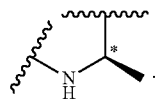

In yet a further embodiment, the bond at the * position is

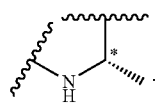

A further embodiment is a compound of Formula

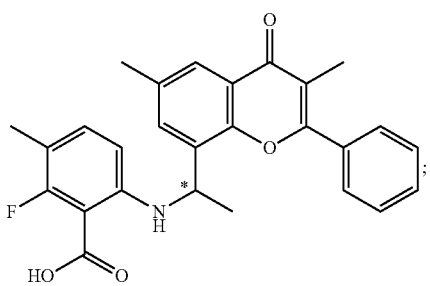 [SMILES: Cc1cc(C(C)Nc2ccc(C)c(F)c2C(=O)O)c2oc(-c3ccccc3)c(C)c(=O)c2c1]

or a pharmaceutically acceptable salt thereof. In yet a further embodiment, the bond at the * position is

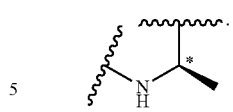

In yet a further embodiment, the bond at the * position is

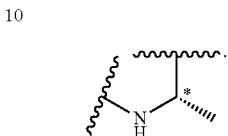

A further embodiment is a compound of Formula

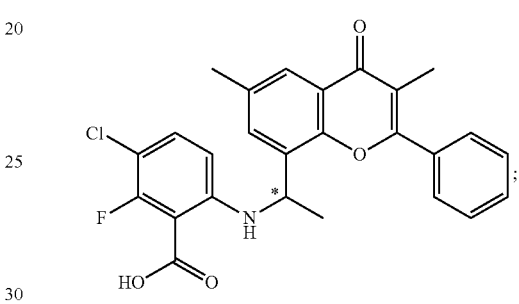

or a pharmaceutically acceptable salt thereof. In yet a further embodiment, the bond at the * position is

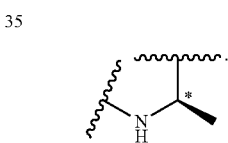

In yet a further embodiment, the bond at the * position is

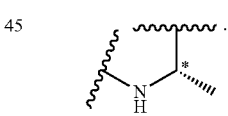

A further embodiment is a compound of Formula

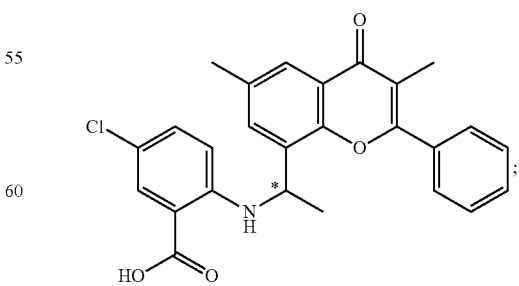

or a pharmaceutically acceptable salt thereof. In yet a further embodiment, the bond at the * position is

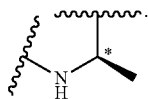

In yet a further embodiment, the bond at the * position is

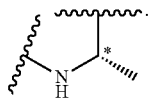

A further embodiment is a compound of Formula

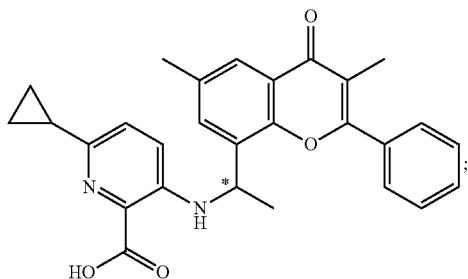

or a pharmaceutically acceptable salt thereof. In yet a further embodiment, the bond at the * position is

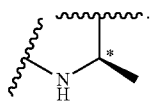

In yet a further embodiment, the bond at the * position is

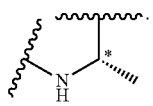

A further embodiment is a compound of Formula

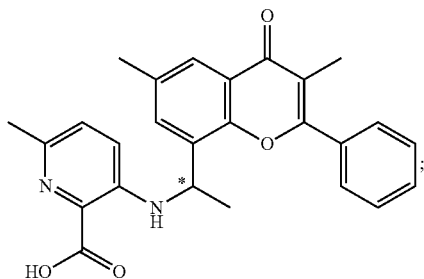 [SMILES: Cc1cc(C(C)Nc2ccc(C)nc2C(=O)O)c2oc(-c3ccccc3)c(C)c(=O)c2c1]

or a pharmaceutically acceptable salt thereof. In yet a further embodiment, the bond at the * position is

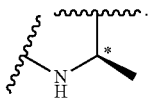

In yet a further embodiment, the bond at the * position is

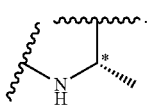

A further embodiment is a compound of Formula

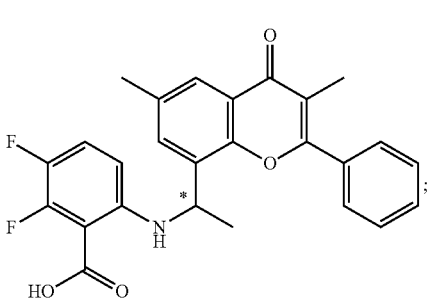

or a pharmaceutically acceptable salt thereof. In yet a further embodiment, the bond at the * position is

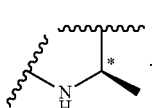

In yet a further embodiment, the bond at the * position is

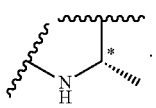

A further embodiment is a compound of Formula

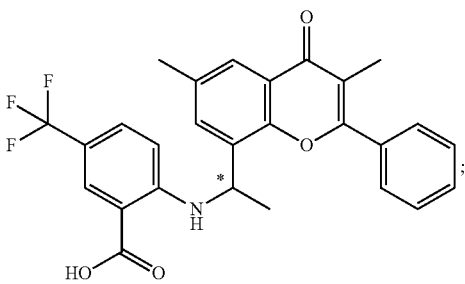

or a pharmaceutically acceptable salt thereof. In yet a further embodiment, the bond at the * position is

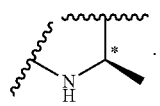

In yet a further embodiment, the bond at the * position is

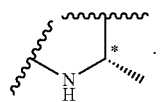

A further embodiment is a compound of Formula

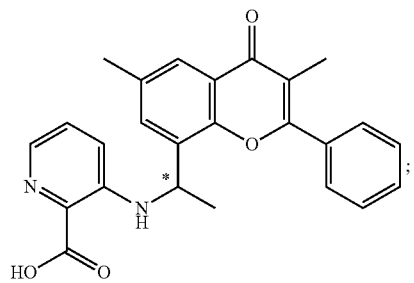 [SMILES: Cc1cc(C(C)Nc2cccnc2C(=O)O)c2oc(-c3ccccc3)c(C)c(=O)c2c1]

or a pharmaceutically acceptable salt thereof. In yet a further embodiment, the bond at the * position is

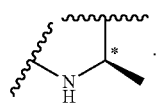

In yet a further embodiment, the bond at the * position is

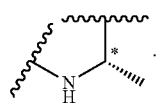

A further embodiment is a compound of Formula

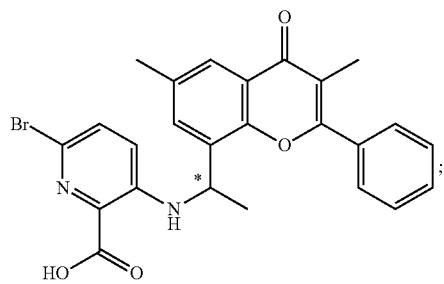

or a pharmaceutically acceptable salt thereof. In yet a further embodiment, the bond at the * position is

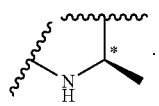

In yet a further embodiment, the bond at the * position is

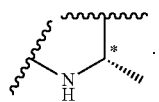

A further embodiment is a compound of Formula

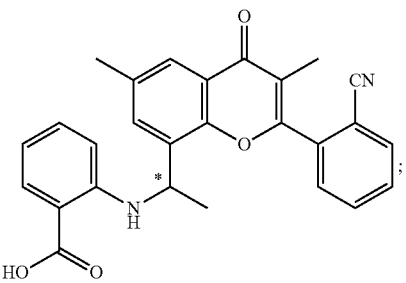 [SMILES: Cc1cc(C(C)Nc2ccccc2C(=O)O)c2oc(-c3ccccc3C#N)c(C)c(=O)c2c1]

or a pharmaceutically acceptable salt thereof. In yet a further embodiment, the bond at the * position is

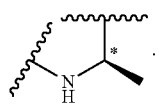

In yet a further embodiment, the bond at the * position is

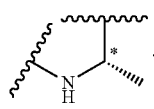

A further embodiment is a compound of Formula

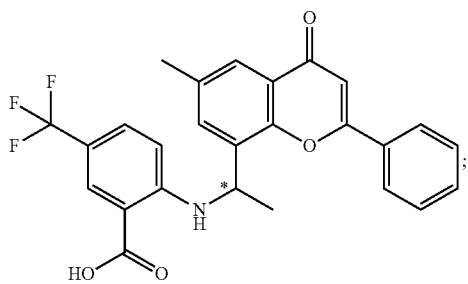 [SMILES: Cc1cc(C(C)Nc2ccc(C(F)(F)F)cc2C(=O)O)c2oc(-c3ccccc3)cc(=O)c2c1]

or a pharmaceutically acceptable salt thereof. In yet a further embodiment, the bond at the * position is

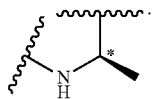 [SMILES: *N[C@@H](*)C]

In yet a further embodiment, the bond at the * position is

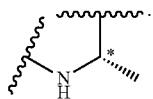

A further embodiment is a compound of Formula

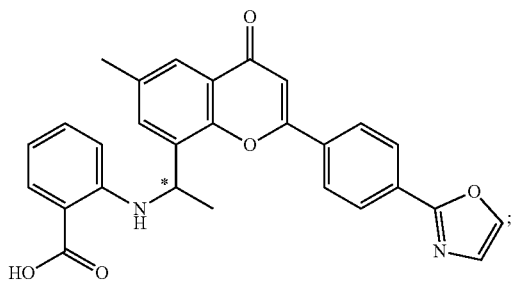 [SMILES: Cc1cc(C(C)Nc2ccccc2C(=O)O)c2oc(-c3ccc(-c4ncco4)cc3)cc(=O)c2c1]

or a pharmaceutically acceptable salt thereof. In yet a further embodiment, the bond at the * position is

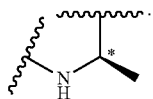 [SMILES: *N[C@@H](*)C]

In yet a further embodiment, the bond at the * position is

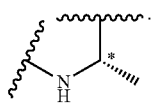

A further embodiment is a compound of Formula

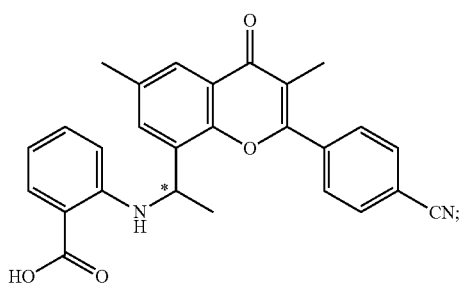 [SMILES: Cc1cc(C(C)Nc2ccccc2C(=O)O)c2oc(-c3ccc(C#N)cc3)c(C)c(=O)c2c1]

or a pharmaceutically acceptable salt thereof. In yet a further embodiment, the bond at the * position is

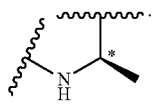

In yet a further embodiment, the bond at the * position is

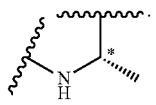

A further embodiment is a compound of Formula

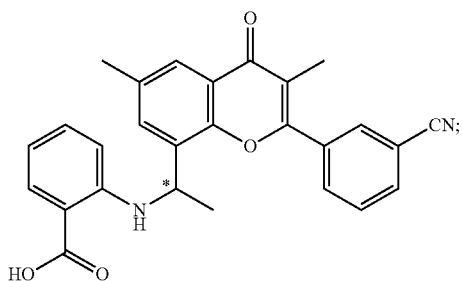 [SMILES: Cc1cc(C(C)Nc2ccccc2C(=O)O)c2oc(-c3cccc(C#N)c3)c(C)c(=O)c2c1]

or a pharmaceutically acceptable salt thereof. In yet a further embodiment, the bond at the * position is

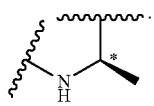

In yet a further embodiment, the bond at the * position is

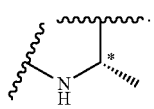

A further embodiment is a compound of Formula

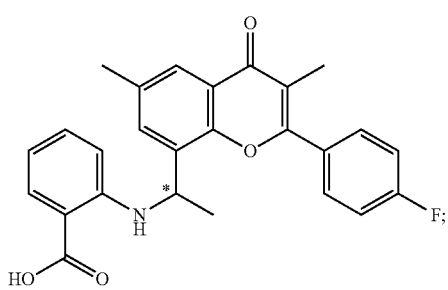 [SMILES: Cc1cc(C(C)Nc2ccccc2C(=O)O)c2oc(-c3ccc(F)cc3)c(C)c(=O)c2c1]

or a pharmaceutically acceptable salt thereof. In yet a further embodiment, the bond at the * position is

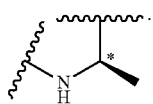 [SMILES: *N[C@@H](*)C]

In yet a further embodiment, the bond at the * position is

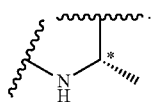

A further embodiment is a compound of Formula

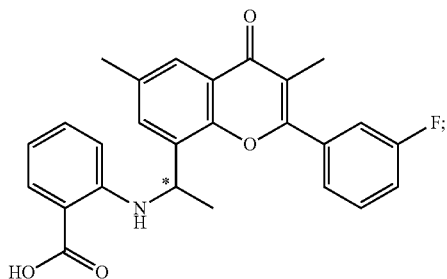 [SMILES: Cc1cc(C(C)Nc2ccccc2C(=O)O)c2oc(-c3cccc(F)c3)c(C)c(=O)c2c1]

or a pharmaceutically acceptable salt thereof. In yet a further embodiment, the bond at the * position is

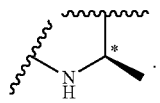

In yet a further embodiment, the bond at the * position is

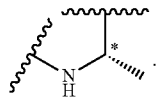

A further embodiment is a compound of Formula

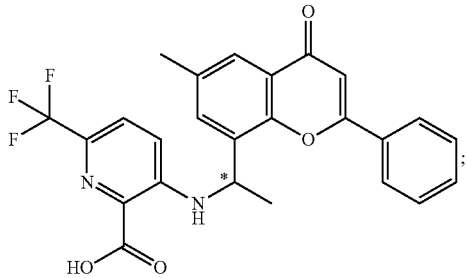 [SMILES: Cc1cc(C(C)Nc2ccc(C(F)(F)F)nc2C(=O)O)c2oc(-c3ccccc3)cc(=O)c2c1]

or a pharmaceutically acceptable salt thereof. In yet a further embodiment, the bond at the * position is

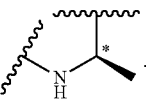 [SMILES: *N[C@@H](*)C]

In yet a further embodiment, the bond at the * position is

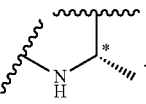

A further embodiment is a compound of Formula

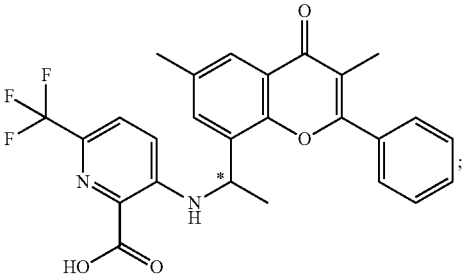 [SMILES: Cc1cc(C(C)Nc2ccc(C(F)(F)F)nc2C(=O)O)c2oc(-c3ccccc3)c(C)c(=O)c2c1]

or a pharmaceutically acceptable salt thereof. In yet a further embodiment, the bond at the * position is

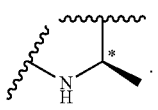 [SMILES: *N[C@@H](*)C]

In yet a further embodiment, the bond at the * position is


A further embodiment is a compound of Formula

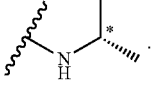

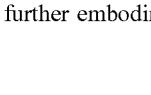

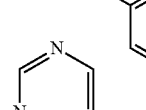

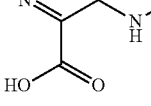

or a pharmaceutically acceptable salt thereof. In yet a further embodiment, the bond at the * position is

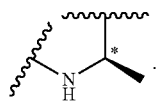

In yet a further embodiment, the bond at the * position is

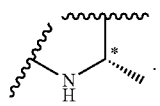

A further embodiment is a compound of Formula

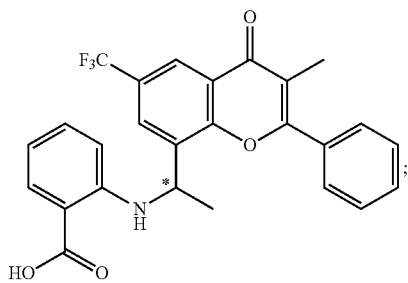 [SMILES: Cc1c(-c2ccccc2)oc2c(C(C)Nc3ccccc3C(=O)O)cc(C(F)(F)F)cc2c1=O]

or a pharmaceutically acceptable salt thereof. In yet a further embodiment, the bond at the * position is

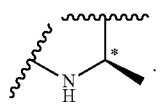

In yet a further embodiment, the bond at the * position is

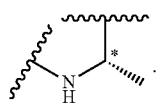

A further embodiment is a compound of Formula

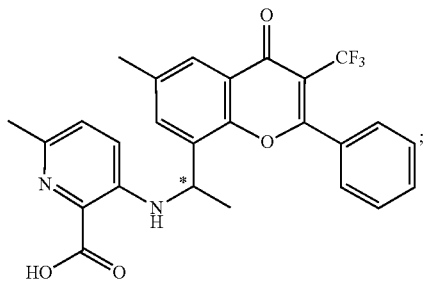 [SMILES: Cc1cc(C(C)Nc2ccc(C)nc2C(=O)O)c2oc(-c3ccccc3)c(C(F)(F)F)c(=O)c2c1]

or a pharmaceutically acceptable salt thereof. In yet a further embodiment, the bond at the * position is

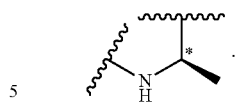

In yet a further embodiment, the bond at the * position is

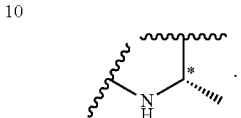

A further embodiment is a compound of Formula

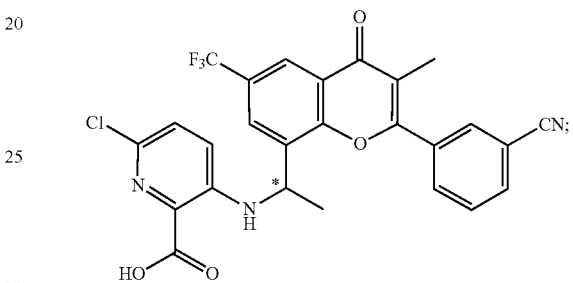

or a pharmaceutically acceptable salt thereof. In yet a further embodiment, the bond at the * position is

In yet a further embodiment, the bond at the * position is

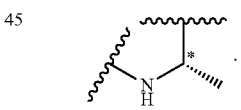

A further embodiment is a compound of Formula

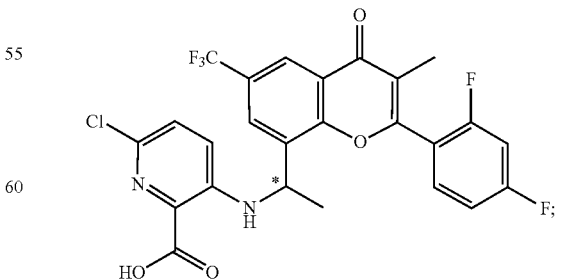

or a pharmaceutically acceptable salt thereof. In yet a further embodiment, the bond at the * position is

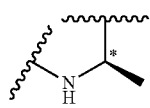

In yet a further embodiment, the bond at the * position is

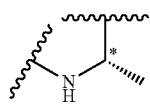

A further embodiment is a compound of Formula

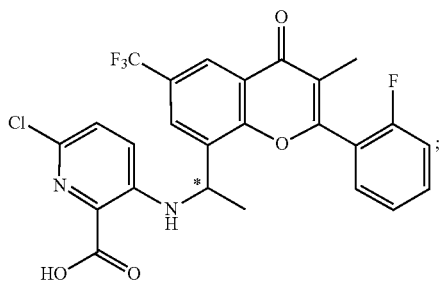 [SMILES: Cc1c(-c2ccccc2F)oc2c(C(C)Nc3ccc(Cl)nc3C(=O)O)cc(C(F)(F)F)cc2c1=O]

or a pharmaceutically acceptable salt thereof. In yet a further embodiment, the bond at the * position is

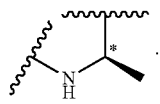

In yet a further embodiment, the bond at the * position is

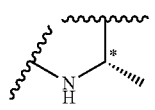

A further embodiment is a compound of Formula

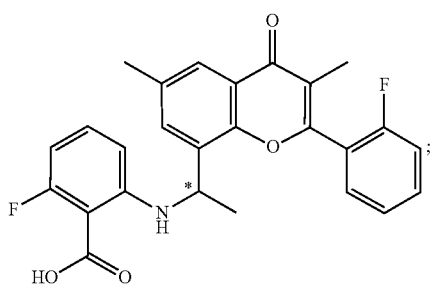 [SMILES: Cc1cc(C(C)Nc2cccc(F)c2C(=O)O)c2oc(-c3ccccc3F)c(C)c(=O)c2c1]

or a pharmaceutically acceptable salt thereof. In yet a further embodiment, the bond at the * position is

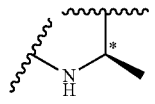

In yet a further embodiment, the bond at the * position is

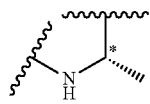

A further embodiment is a compound of Formula

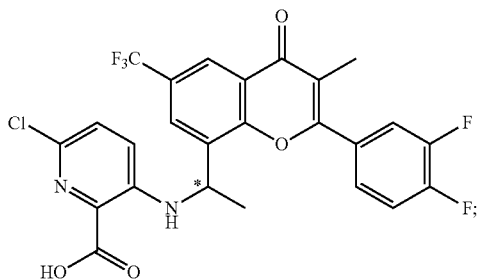 [SMILES: Cc1c(-c2ccc(F)c(F)c2)oc2c(C(C)Nc3ccc(Cl)nc3C(=O)O)cc(C(F)(F)F)cc2c1=O]

or a pharmaceutically acceptable salt thereof. In yet a further embodiment, the bond at the position is

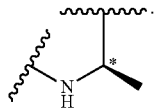

In yet a further embodiment, the bond at the * position is

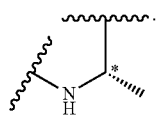

A further embodiment is a compound of Formula

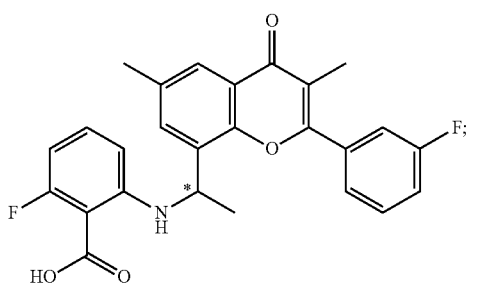 [SMILES: Cc1cc(C(C)Nc2cccc(F)c2C(=O)O)c2oc(-c3cccc(F)c3)c(C)c(=O)c2c1]

or a pharmaceutically acceptable salt thereof. In yet a further embodiment, the bond at the * position is

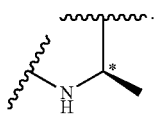

In yet a further embodiment, the bond at the * position is

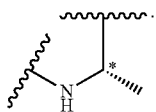

A further embodiment is a compound of Formula

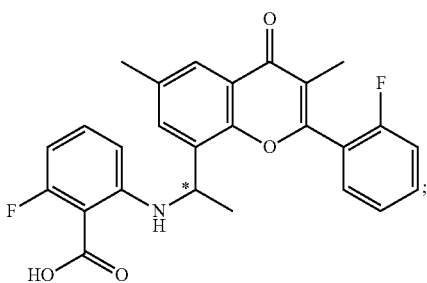 [SMILES: Cc1cc(C(C)Nc2cccc(F)c2C(=O)O)c2oc(-c3ccccc3F)c(C)c(=O)c2c1]

or a pharmaceutically acceptable salt thereof. In yet a further embodiment, the bond at the * position is

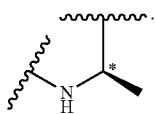

In yet a further embodiment, the bond at the * position is

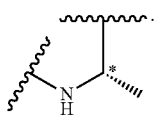

A further embodiment is a compound of Formula

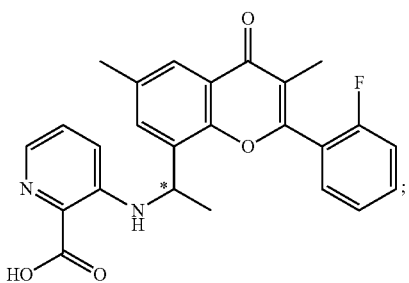 [SMILES: Cc1cc(C(C)Nc2cccnc2C(=O)O)c2oc(-c3ccccc3F)c(C)c(=O)c2c1]

or a pharmaceutically acceptable salt thereof. In yet a further embodiment, the bond at the * position is

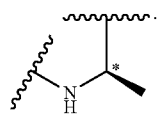 [SMILES: *N[C@@H](*)C]

In yet a further embodiment, the bond at the * position is

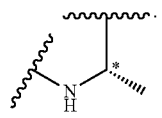

A further embodiment is a compound of Formula

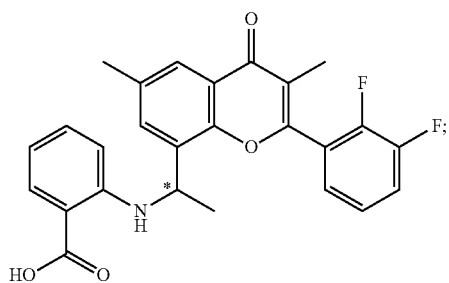 [SMILES: Cc1cc(C(C)Nc2ccccc2C(=O)O)c2oc(-c3cccc(F)c3F)c(C)c(=O)c2c1]

or a pharmaceutically acceptable salt thereof. In yet a further embodiment, the bond at the * position is

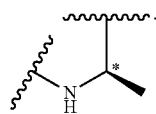 [SMILES: *N[C@@H](*)C]

In yet a further embodiment, the bond at the * position is

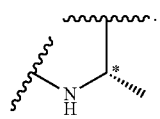

A further embodiment is a compound of Formula

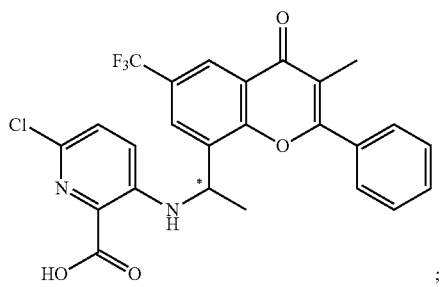

or a pharmaceutically acceptable salt thereof. In yet a further embodiment, the bond at the * position is

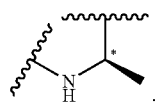

In yet a further embodiment, the bond at the * position is

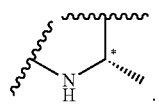

A further embodiment is a compound of Formula

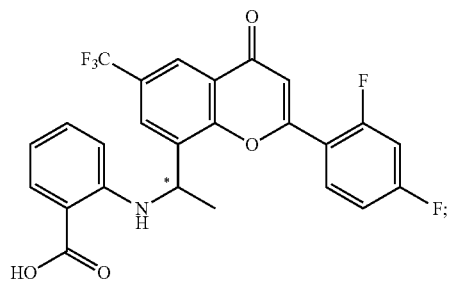 [SMILES: CC(Nc1ccccc1C(=O)O)c1cc(C(F)(F)F)cc2c(=O)cc(-c3ccc(F)cc3F)oc12]

or a pharmaceutically acceptable salt thereof. In yet a further embodiment, the bond at the * position is

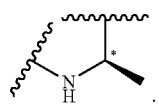

In yet a further embodiment, the bond at the * position is

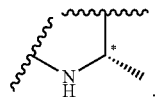

A further embodiment is a compound of Formula

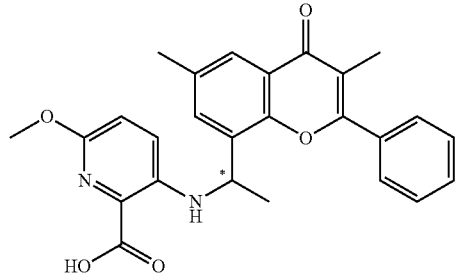

or a pharmaceutically acceptable salt thereof. In yet a further embodiment, the bond at the * position is

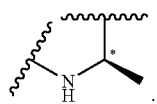 [SMILES: *N[C@@H](*)C]

In yet a further embodiment, the bond at the * position is

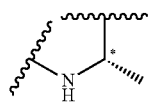

A further embodiment is a compound of Formula

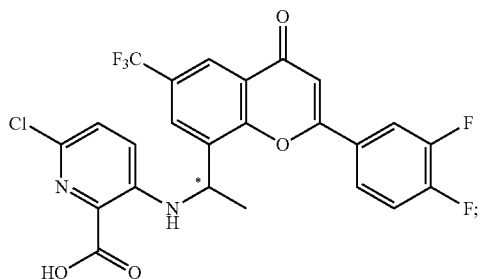 [SMILES: CC(Nc1ccc(Cl)nc1C(=O)O)c1cc(C(F)(F)F)cc2c(=O)cc(-c3ccc(F)c(F)c3)oc12]

or a pharmaceutically acceptable salt thereof. In yet a further embodiment, the bond at the * position is

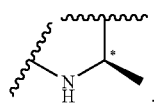 [SMILES: *N[C@@H](*)C]

In yet a further embodiment, the bond at the * position is

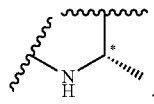 [SMILES: *N[C@H](*)C]

A further embodiment is a compound of Formula

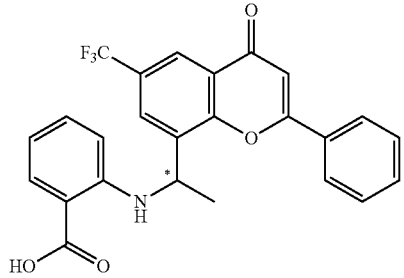

or a pharmaceutically acceptable salt thereof. In yet a further embodiment, the bond at the * position is

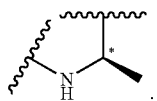

In yet a further embodiment, the bond at the * position is

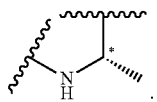

A further embodiment is a compound of Formula

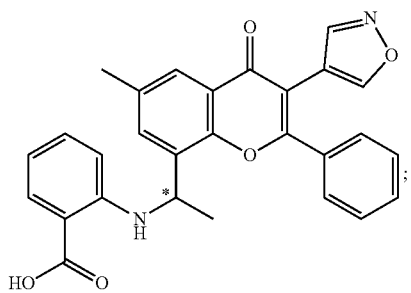 [SMILES: Cc1cc(C(C)Nc2ccccc2C(=O)O)c2oc(-c3ccccc3)c(-c3cnoc3)c(=O)c2c1]

or a pharmaceutically acceptable salt thereof. In yet a further embodiment, the bond at the * position is

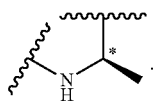

In yet a further embodiment, the bond at the * position is

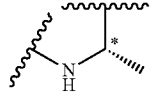

A further embodiment is a compound of Formula

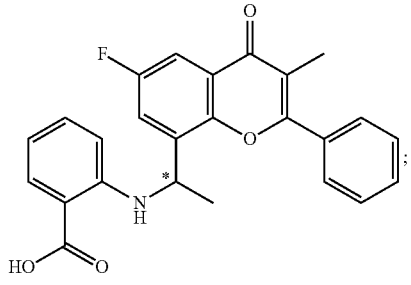 [SMILES: Cc1c(-c2ccccc2)oc2c(C(C)Nc3ccccc3C(=O)O)cc(F)cc2c1=O]

or a pharmaceutically acceptable salt thereof. In yet a further embodiment, the bond at the * position is

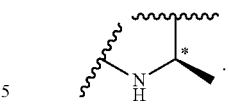

In yet a further embodiment, the bond at the * position is

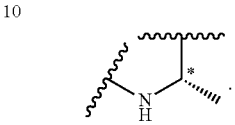

A further embodiment is a compound of Formula

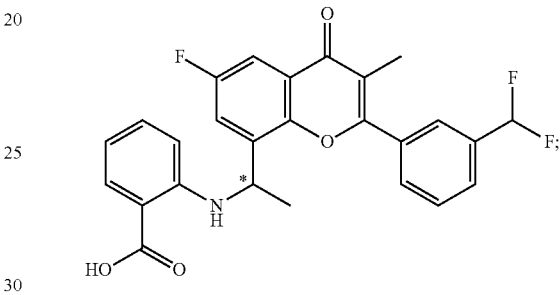

or a pharmaceutically acceptable salt thereof. In yet a further embodiment, the bond at the * position is

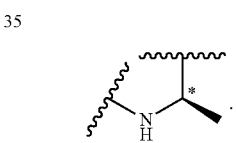

In yet a further embodiment, the bond at the * position is

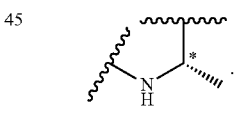

A further embodiment is a compound of Formula

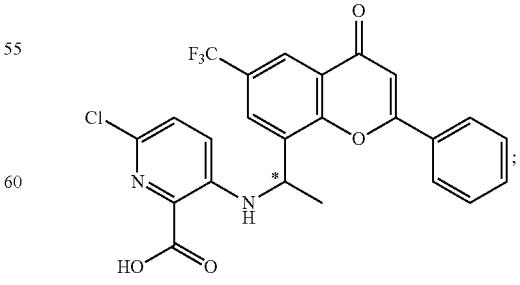

or a pharmaceutically acceptable salt thereof. In yet a further embodiment, the bond at the * position is

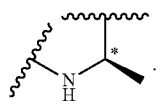

In yet a further embodiment, the bond at the * position is

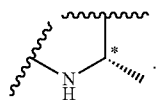

A further embodiment is a compound of Formula

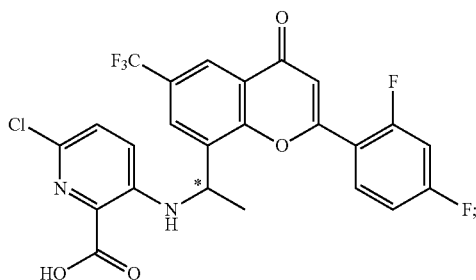 [SMILES: CC(Nc1ccc(Cl)nc1C(=O)O)c1cc(C(F)(F)F)cc2c(=O)cc(-c3ccc(F)cc3F)oc12]

or a pharmaceutically acceptable salt thereof. In yet a further embodiment, the bond at the * position is

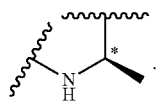

In yet a further embodiment, the bond at the * position is

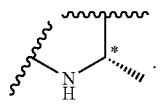

A further embodiment is a compound of Formula

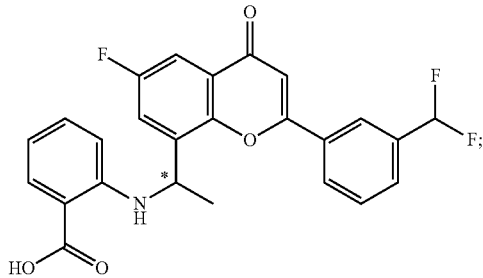 [SMILES: CC(Nc1ccccc1C(=O)O)c1cc(F)cc2c(=O)cc(-c3cccc(C(F)F)c3)oc12]

or a pharmaceutically acceptable salt thereof. In yet a further embodiment, the bond at the * position is

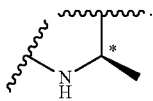

In yet a further embodiment, the bond at the * position is

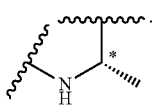

A further embodiment is a compound of Formula

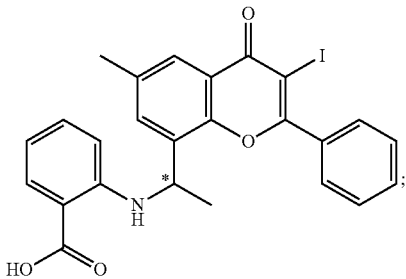

or a pharmaceutically acceptable salt thereof. In yet a further embodiment, the bond at the * position is

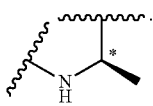

In yet a further embodiment, the bond at the * position is

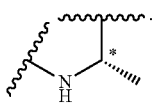

A further embodiment is a compound of Formula

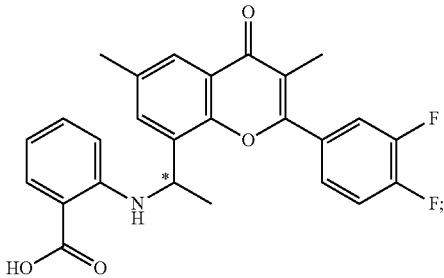 [SMILES: Cc1cc(C(C)Nc2ccccc2C(=O)O)c2oc(-c3ccc(F)c(F)c3)c(C)c(=O)c2c1]

or a pharmaceutically acceptable salt thereof. In yet a further embodiment, the bond at the * position is

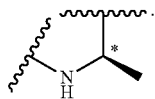

In yet a further embodiment, the bond at the * position is

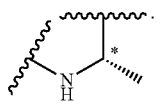

A further embodiment is a compound of Formula

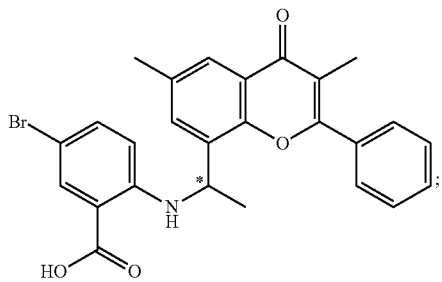

or a pharmaceutically acceptable salt thereof. In yet a further embodiment, the bond at the * position is

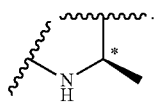

In yet a further embodiment, the bond at the * position is

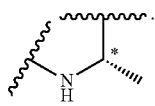

A further embodiment is a compound of Formula

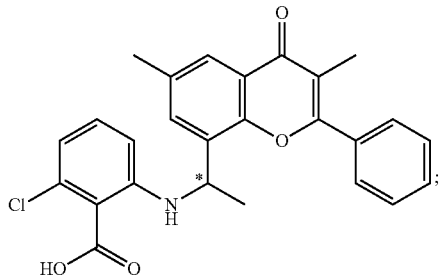 [SMILES: Cc1cc(C(C)Nc2cccc(Cl)c2C(=O)O)c2oc(-c3ccccc3)c(C)c(=O)c2c1]

or a pharmaceutically acceptable salt thereof. In yet a further embodiment, the bond at the * position is

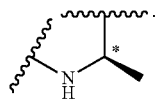

In yet a further embodiment, the bond at the * position is

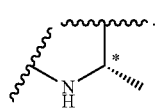

A further embodiment is a compound of Formula

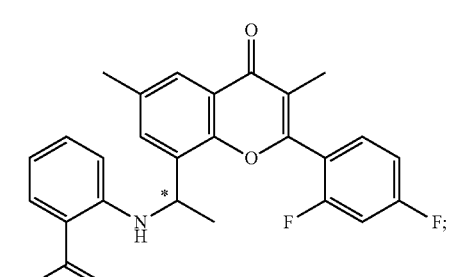

or a pharmaceutically acceptable salt thereof. In yet a further embodiment, the bond at the * position is

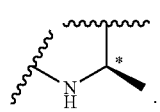 [SMILES: *N[C@@H](*)C]

In yet a further embodiment, the bond at the * position is

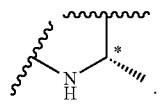

A further embodiment is a compound of Formula

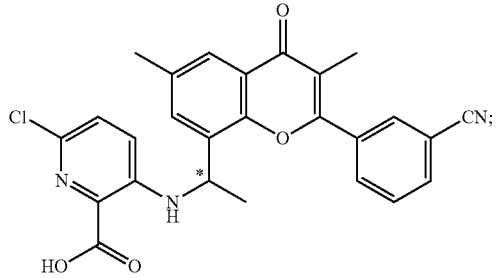 [SMILES: Cc1cc(C(C)Nc2ccc(Cl)nc2C(=O)O)c2oc(-c3cccc(C#N)c3)c(C)c(=O)c2c1]

or a pharmaceutically acceptable salt thereof. In yet a further embodiment, the bond at the * position is

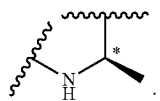

In yet a further embodiment, the bond at the * position is

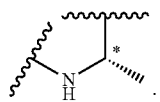

A further embodiment is a compound of Formula

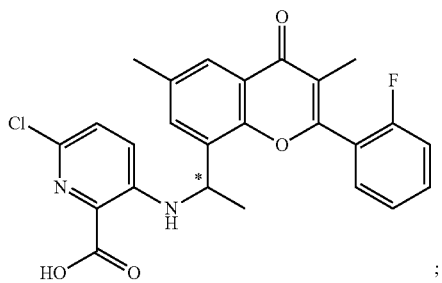 [SMILES: Cc1cc(C(C)Nc2ccc(Cl)nc2C(=O)O)c2oc(-c3ccccc3F)c(C)c(=O)c2c1]

or a pharmaceutically acceptable salt thereof. In yet a further embodiment, the bond at the * position is

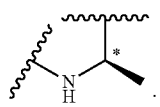

In yet a further embodiment, the bond at the * position is

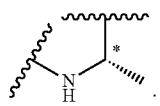

A further embodiment is a compound of Formula

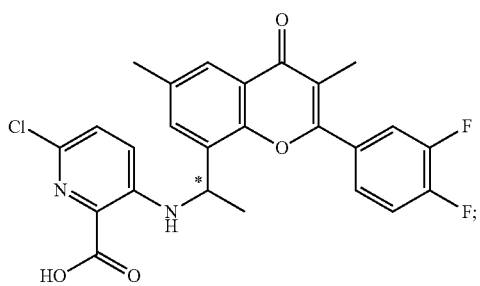 [SMILES: Cc1cc(C(C)Nc2ccc(Cl)nc2C(=O)O)c2oc(-c3ccc(F)c(F)c3)c(C)c(=O)c2c1]

or a pharmaceutically acceptable salt thereof. In yet a further embodiment, the bond at the * position is

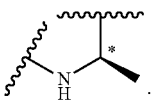

In yet a further embodiment, the bond at the * position is

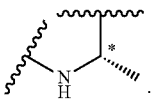

A further embodiment is a compound of Formula

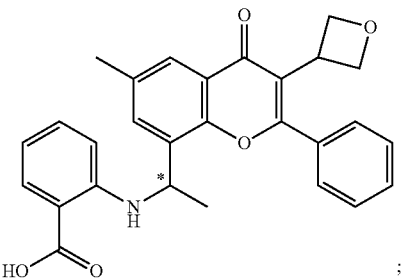 [SMILES: Cc1cc(C(C)Nc2ccccc2C(=O)O)c2oc(-c3ccccc3)c(C3COC3)c(=O)c2c1]

or a pharmaceutically acceptable salt thereof. In yet a further embodiment, the bond at the * position is

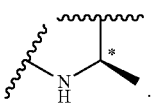

In yet a further embodiment, the bond at the * position is

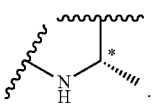

A further embodiment is a compound of Formula

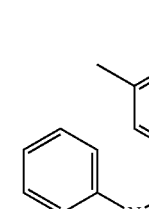

or a pharmaceutically acceptable salt thereof. In yet a further embodiment, the bond at the * position is

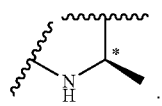

In yet a further embodiment, the bond at the * position is

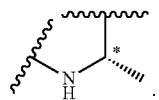

A further embodiment is a compound of Formula

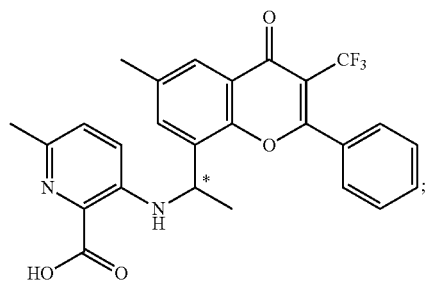 [SMILES: Cc1cc(C(C)Nc2ccc(C)nc2C(=O)O)c2oc(-c3ccccc3)c(C(F)(F)F)c(=O)c2c1]

or a pharmaceutically acceptable salt thereof. In yet a further embodiment, the bond at the * position is

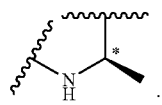

In yet a further embodiment, the bond at the * position is

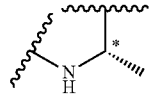

A further embodiment is a compound of Formula

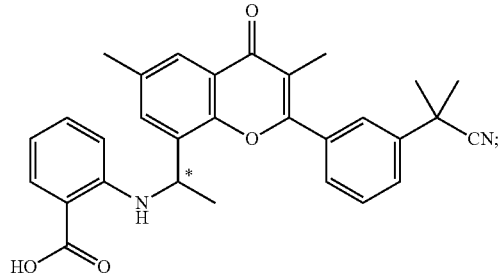 [SMILES: Cc1cc(C(C)Nc2ccccc2C(=O)O)c2oc(-c3cccc(C(C)(C)C#N)c3)c(C)c(=O)c2c1]

or a pharmaceutically acceptable salt thereof. In yet a further embodiment, the bond at the * position is

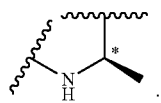

In yet a further embodiment, the bond at the * position is

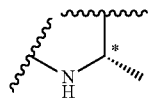

A further embodiment is a compound of Formula

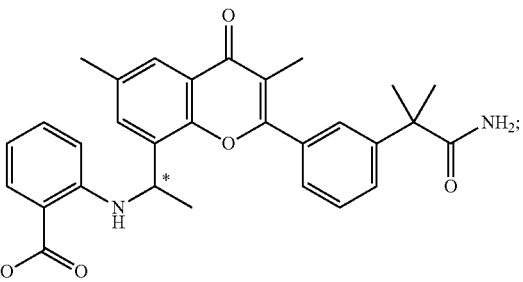

or a pharmaceutically acceptable salt thereof. In yet a further embodiment, the bond at the * position is

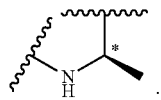

In yet a further embodiment, the bond at the * position is

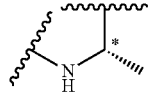

A further embodiment is a compound of Formula

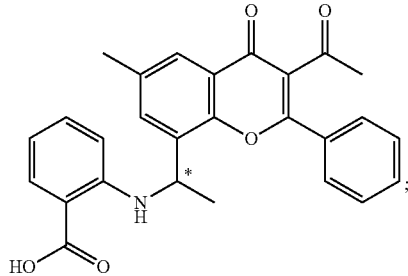 [SMILES: CC(=O)c1c(-c2ccccc2)oc2c(C(C)Nc3ccccc3C(=O)O)cc(C)cc2c1=O]

or a pharmaceutically acceptable salt thereof. In yet a further embodiment, the bond at the * position is

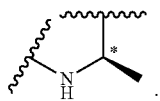

In yet a further embodiment, the bond at the * position is

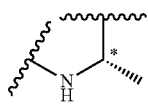

A further embodiment is a compound of Formula

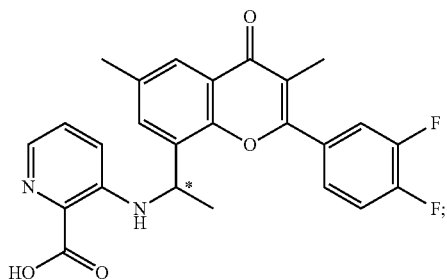 [SMILES: Cc1cc(C(C)Nc2cccnc2C(=O)O)c2oc(-c3ccc(F)c(F)c3)c(C)c(=O)c2c1]

or a pharmaceutically acceptable salt thereof. In yet a further embodiment, the bond at the * position is

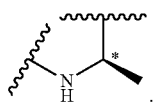 [SMILES: *N[C@@H](*)C]

In yet a further embodiment, the bond at the * position is

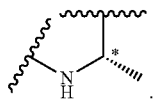

A further embodiment is a compound of Formula

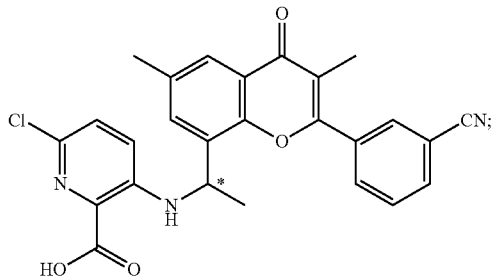 [SMILES: Cc1cc(C(C)Nc2ccc(Cl)nc2C(=O)O)c2oc(-c3cccc(C#N)c3)c(C)c(=O)c2c1]

or a pharmaceutically acceptable salt thereof. In yet a further embodiment, the bond at the * position is

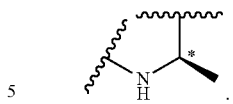

In yet a further embodiment, the bond at the * position is

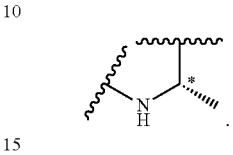

A further embodiment is a compound of Formula

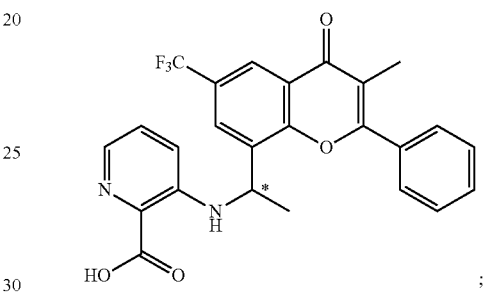

;

or a pharmaceutically acceptable salt thereof. In yet a further embodiment, the bond at the * position is

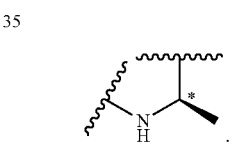

In yet a further embodiment, the bond at the * position is

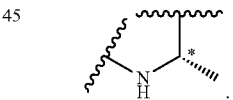

A further embodiment is a compound of Formula

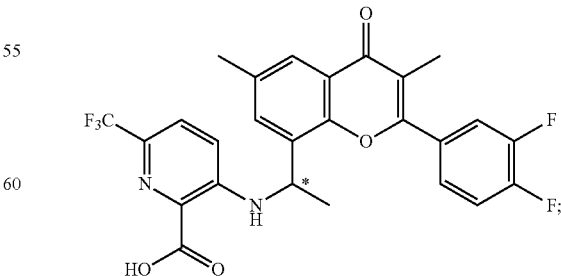

or a pharmaceutically acceptable salt thereof. In yet a further embodiment, the bond at the * position is

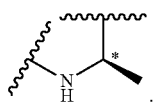 [SMILES: *N[C@@H](*)C]

In yet a further embodiment, the bond at the * position is

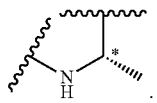 [SMILES: *N[C@H](*)C]

A further embodiment is a compound of Formula

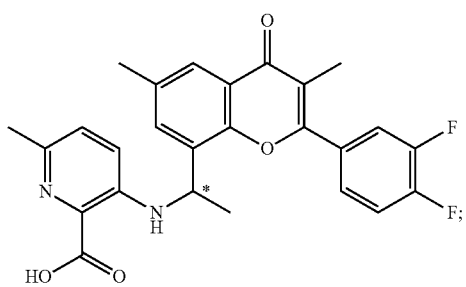 [SMILES: Cc1cc(C(C)Nc2ccc(C)nc2C(=O)O)c2oc(-c3ccc(F)c(F)c3)c(C)c(=O)c2c1]

or a pharmaceutically acceptable salt thereof. In yet a further embodiment, the bond at the * position is

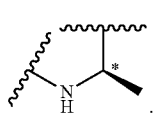 [SMILES: *N[C@@H](*)C]

In yet a further embodiment, the bond at the * position is

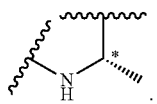

A further embodiment is a compound of Formula

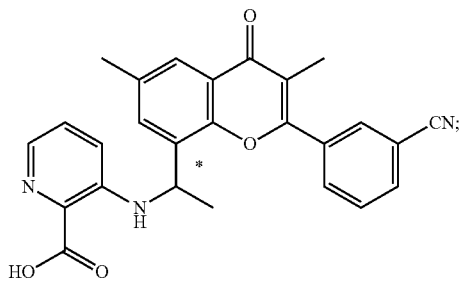 [SMILES: Cc1cc(C(C)Nc2cccnc2C(=O)O)c2oc(-c3cccc(C#N)c3)c(C)c(=O)c2c1]

or a pharmaceutically acceptable salt thereof. In yet a further embodiment, the bond at the * position is

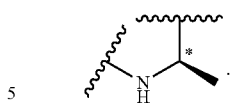

In yet a further embodiment, the bond at the * position is

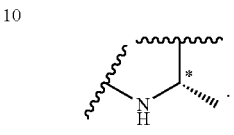

A further embodiment is a compound of Formula

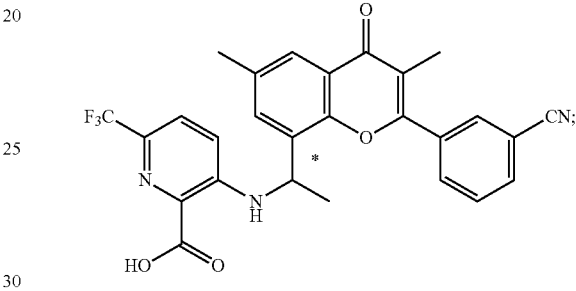

or a pharmaceutically acceptable salt thereof. In yet a further embodiment, the bond at the * position is

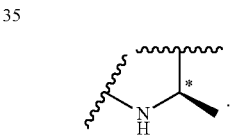

In yet a further embodiment, the bond at the * position is

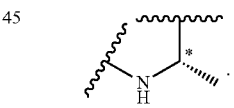

A further embodiment is a compound of Formula

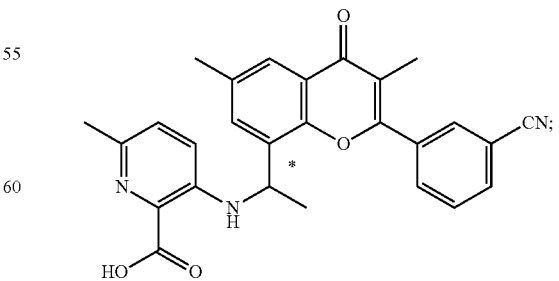

or a pharmaceutically acceptable salt thereof. In yet a further embodiment, the bond at the * position is

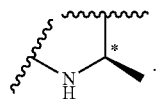

In yet a further embodiment, the bond at the * position is

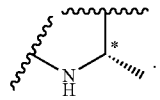

A further embodiment is a compound of Formula

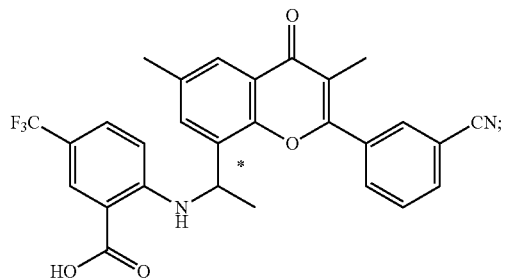 [SMILES: Cc1cc(C(C)Nc2ccc(C(F)(F)F)cc2C(=O)O)c2oc(-c3cccc(C#N)c3)c(C)c(=O)c2c1]

or a pharmaceutically acceptable salt thereof. In yet a further embodiment, the bond at the * position is

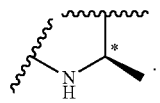

In yet a further embodiment, the bond at the * position is

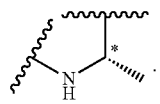

A further embodiment is a compound of Formula

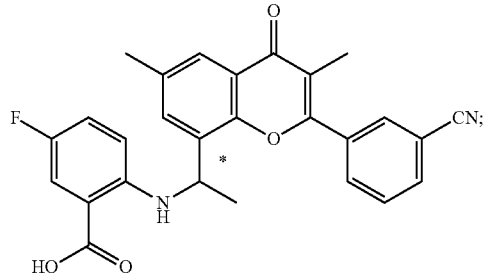 [SMILES: Cc1cc(C(C)Nc2ccc(F)cc2C(=O)O)c2oc(-c3cccc(C#N)c3)c(C)c(=O)c2c1]

or a pharmaceutically acceptable salt thereof. In yet a further embodiment, the bond at the * position is

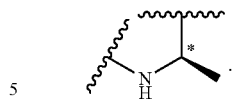

In yet a further embodiment, the bond at the * position is

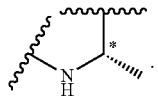

A further embodiment is a compound of Formula

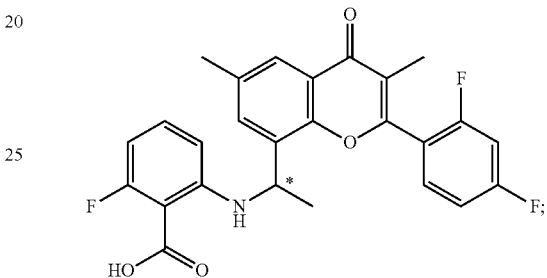

or a pharmaceutically acceptable salt thereof. In yet a further embodiment, the bond at the * position is

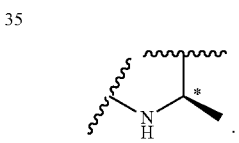

In yet a further embodiment, the bond at the * position is

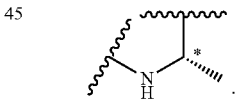

A further embodiment is a compound of Formula

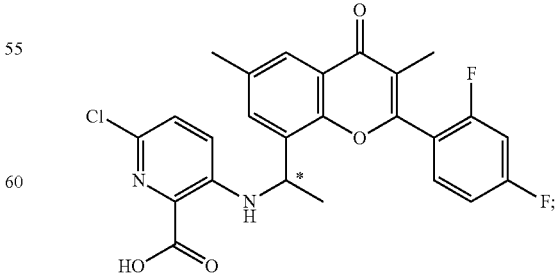

or a pharmaceutically acceptable salt thereof. In yet a further embodiment, the bond at the * position is

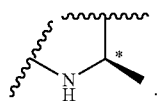

In yet a further embodiment, the bond at the * position is

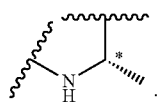

A further embodiment is a compound of Formula

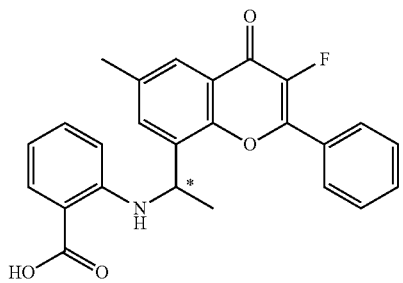

or a pharmaceutically acceptable salt thereof. In yet a further embodiment, the bond at the * position is

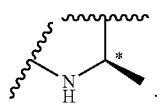

In yet a further embodiment, the bond at the * position is

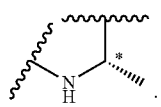

A further embodiment is a compound of Formula

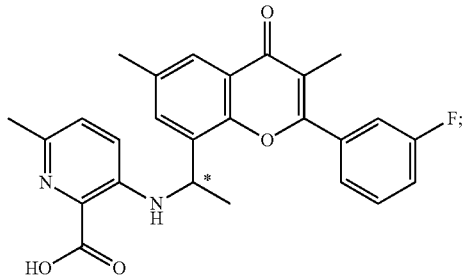 [SMILES: Cc1cc(C(C)Nc2ccc(C)nc2C(=O)O)c2oc(-c3cccc(F)c3)c(C)c(=O)c2c1]

or a pharmaceutically acceptable salt thereof. In yet a further embodiment, the bond at the * position is

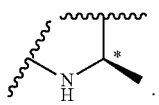

In yet a further embodiment, the bond at the * position is

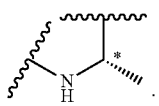

A further embodiment is a compound of Formula

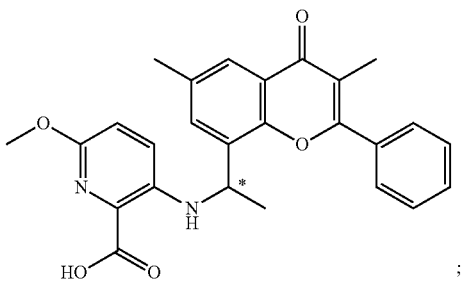 [SMILES: COc1ccc(NC(C)c2cc(C)cc3c(=O)c(C)c(-c4ccccc4)oc23)c(C(=O)O)n1]

or a pharmaceutically acceptable salt thereof. In yet a further embodiment, the bond at the * position is

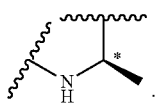

In yet a further embodiment, the bond at the * position is

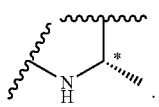

A further embodiment is a compound of Formula

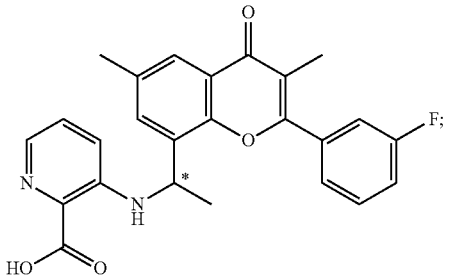 [SMILES: Cc1cc(C(C)Nc2cccnc2C(=O)O)c2oc(-c3cccc(F)c3)c(C)c(=O)c2c1]

or a pharmaceutically acceptable salt thereof. In yet a further embodiment, the bond at the * position is

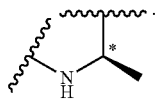 [SMILES: *N[C@@H](*)C]

In yet a further embodiment, the bond at the * position is

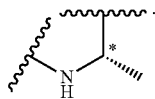

A further embodiment is a compound of Formula

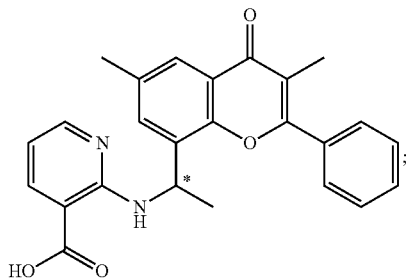 [SMILES: Cc1cc(C(C)Nc2ncccc2C(=O)O)c2oc(-c3ccccc3)c(C)c(=O)c2c1]

or a pharmaceutically acceptable salt thereof. In yet a further embodiment, the bond at the * position is

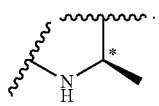

In yet a further embodiment, the bond at the * position is

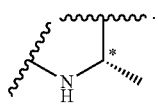

A further embodiment is a compound of Formula

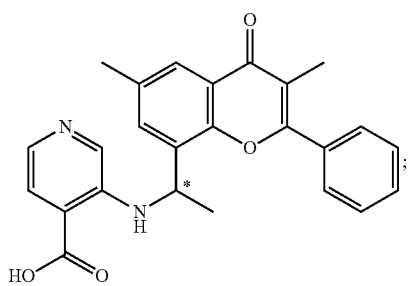

or a pharmaceutically acceptable salt thereof. In yet a further embodiment, the bond at the * position is

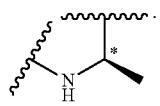 [SMILES: *N[C@@H](*)C]

In yet a further embodiment, the bond at the * position is

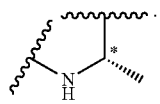

A further embodiment is a compound of Formula

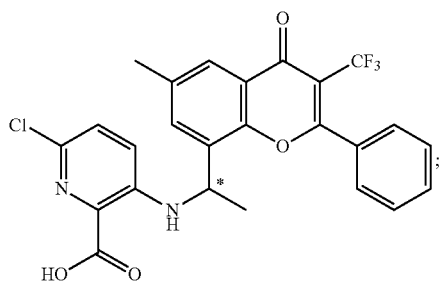 [SMILES: Cc1cc(C(C)Nc2ccc(Cl)nc2C(=O)O)c2oc(-c3ccccc3)c(C(F)(F)F)c(=O)c2c1]

or a pharmaceutically acceptable salt thereof. In yet a further embodiment, the bond at the * position is

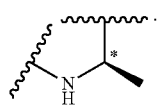

In yet a further embodiment, the bond at the * position is

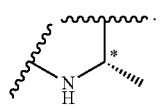

A further embodiment is a compound of Formula

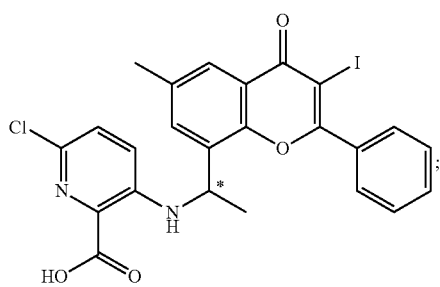

or a pharmaceutically acceptable salt thereof. In yet a further embodiment, the bond at the * position is

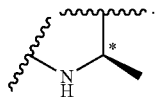 [SMILES: *N[C@@H](*)C]

In yet a further embodiment the bond at the * position is

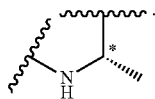

A further embodiment is a compound of Formula

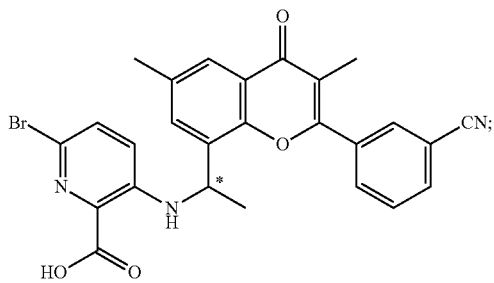

or a pharmaceutically acceptable salt thereof. In yet a further embodiment, the bond at the * position is

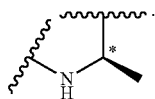 [SMILES: *N[C@@H](*)C]

In yet a further embodiment the bond at the * position is

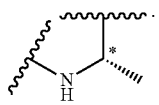

A further embodiment is a compound of Formula

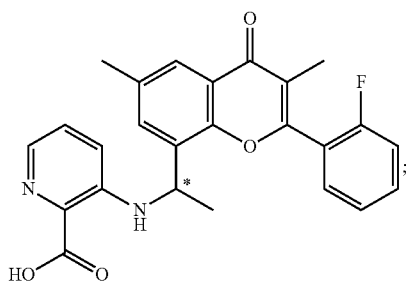 [SMILES: Cc1cc(C(C)Nc2cccnc2C(=O)O)c2oc(-c3ccccc3F)c(C)c(=O)c2c1]

or a pharmaceutically acceptable salt thereof. In yet a further embodiment, the bond at the * position is

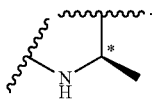 [SMILES: *N[C@@H](*)C]

In yet a further embodiment, the bond at the * position is

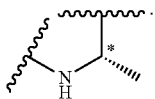

A further embodiment is a compound of Formula

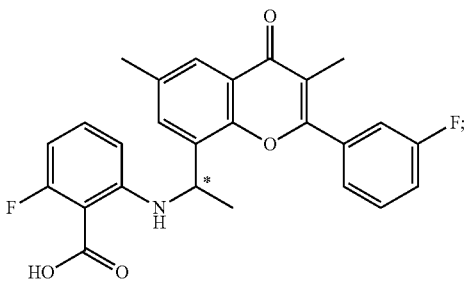 [SMILES: Cc1cc(C(C)Nc2cccc(F)c2C(=O)O)c2oc(-c3cccc(F)c3)c(C)c(=O)c2c1]

or a pharmaceutically acceptable salt thereof. In yet a further embodiment, the bond at the * position is

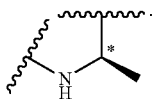 [SMILES: *N[C@@H](*)C]

In yet a further embodiment, the bond at the * position is

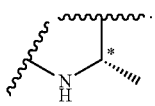 [SMILES: *N[C@H](*)C]

A further embodiment is a compound of Formula

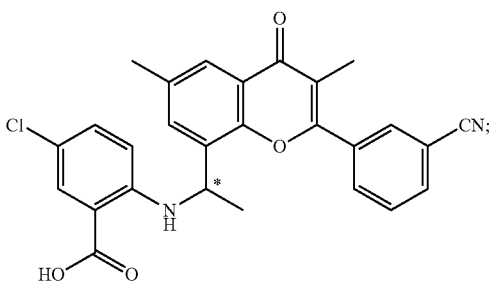

or a pharmaceutically acceptable salt thereof. In yet a further embodiment, the bond at the * position is

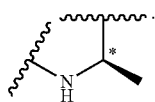

In yet a further embodiment the bond at the * position is

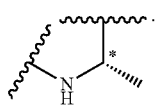

A further embodiment is a compound of Formula

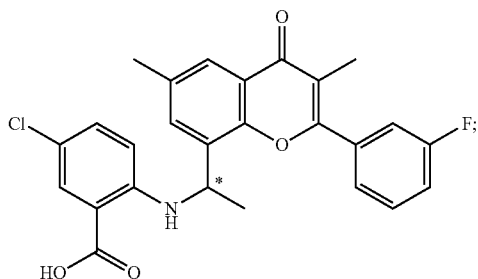 [SMILES: Cc1cc(C(C)Nc2ccc(Cl)cc2C(=O)O)c2oc(-c3cccc(F)c3)c(C)c(=O)c2c1]

or a pharmaceutically acceptable salt thereof. In yet a further embodiment, the bond at the * position is

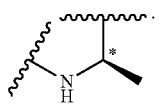

In yet a further embodiment, the bond at the * position is

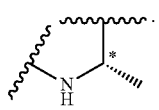

A further embodiment is a compound of Formula

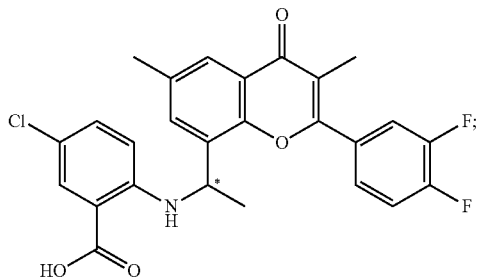 [SMILES: Cc1cc(C(C)Nc2ccc(Cl)cc2C(=O)O)c2oc(-c3ccc(F)c(F)c3)c(C)c(=O)c2c1]

or a pharmaceutically acceptable salt thereof. In yet a further embodiment, the bond at the * position is

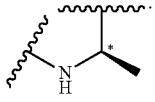

In yet a further embodiment, the bond at the * position is

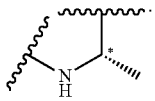

A further embodiment is a compound of Formula

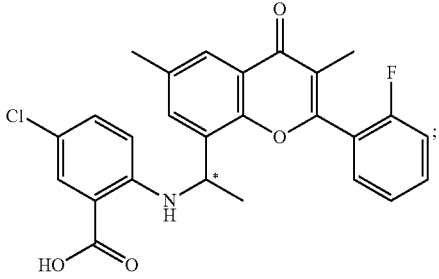 [SMILES: Cc1cc(C(C)Nc2ccc(Cl)cc2C(=O)O)c2oc(-c3ccccc3F)c(C)c(=O)c2c1]

or a pharmaceutically acceptable salt thereof. In yet a further embodiment, the bond at the * position is

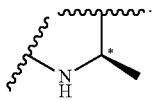

In yet a further embodiment, the bond at the * position is

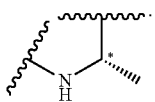

A further embodiment is a compound of Formula

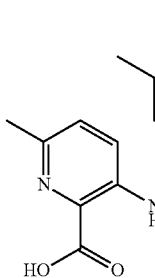

or a pharmaceutically acceptable salt thereof. In yet a further embodiment, the bond at the * position is

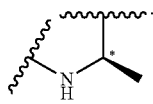

In yet a further embodiment, the bond at the * position is

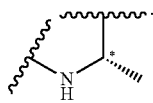

A further embodiment is a compound of Formula

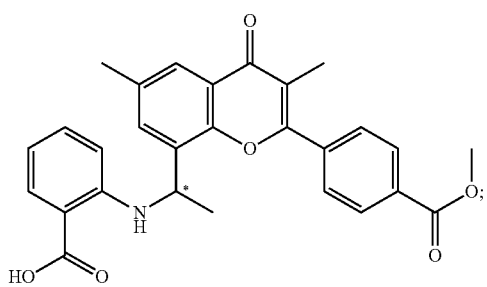 [SMILES: COC(=O)c1ccc(-c2oc3c(C(C)Nc4ccccc4C(=O)O)cc(C)cc3c(=O)c2C)cc1]

or a pharmaceutically acceptable salt thereof. In yet a further embodiment, the bond at the * position is

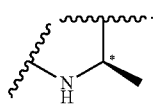

In yet a further embodiment, the bond at the * position is

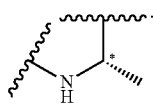

A further embodiment is a compound of Formula

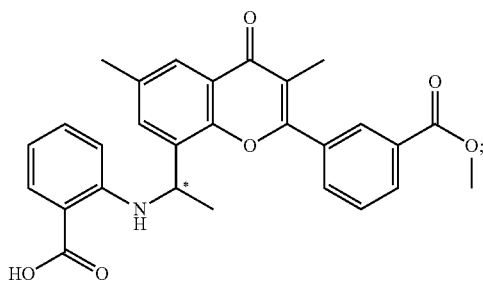 [SMILES: COC(=O)c1cccc(-c2oc3c(C(C)Nc4ccccc4C(=O)O)cc(C)cc3c(=O)c2C)c1]

or a pharmaceutically acceptable salt thereof. In yet a further embodiment, the bond at the * position is

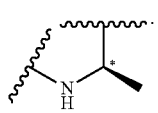

In yet a further embodiment the bond at the * position is

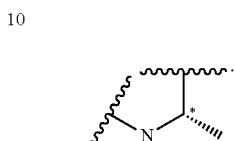

A further embodiment is a compound of Formula

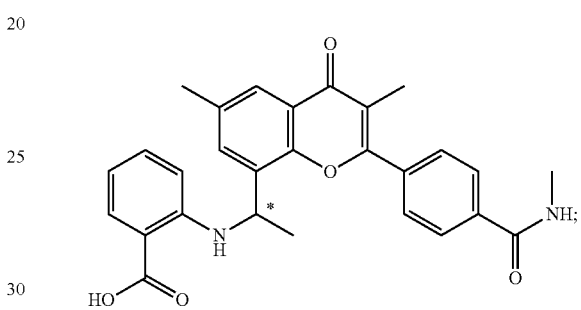

or a pharmaceutically acceptable salt thereof. In yet a further embodiment, the bond at the * position is

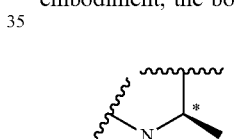

In yet a further embodiment, the bond at the * position is

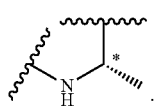 [SMILES: *N[C@H](*)C]

A further embodiment is a compound of Formula

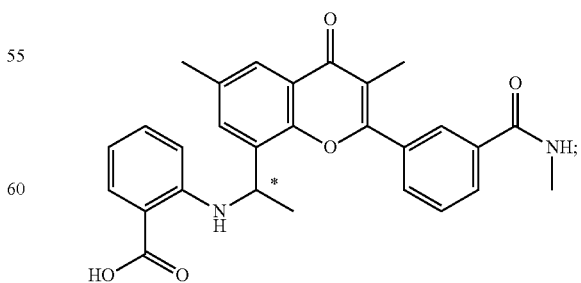

or a pharmaceutically acceptable salt thereof. In yet a further embodiment, the bond at the * position is

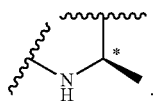

In yet a further embodiment, the bond at the * position is

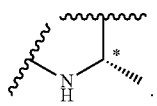

A further embodiment is a compound of Formula

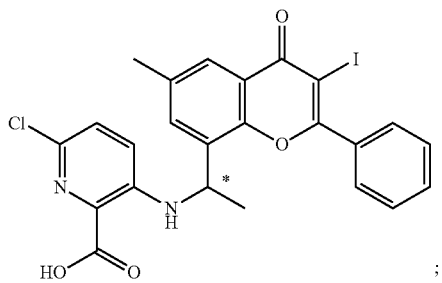 [SMILES: Cc1cc(C(C)Nc2ccc(Cl)nc2C(=O)O)c2oc(-c3ccccc3)c(I)c(=O)c2c1]

or a pharmaceutically acceptable salt thereof. In yet a further embodiment, the bond at the * position is

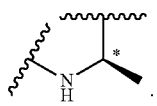

In yet a further embodiment, the bond at the * position is

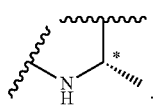

A further embodiment is a compound of Formula

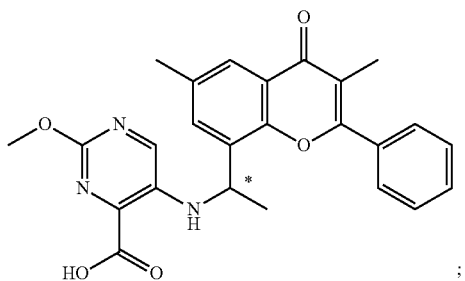

or a pharmaceutically acceptable salt thereof. In yet a further embodiment, the bond at the * position is

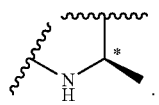

In yet a further embodiment, the bond at the * position is

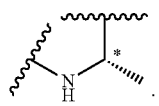

A further embodiment is a compound of Formula

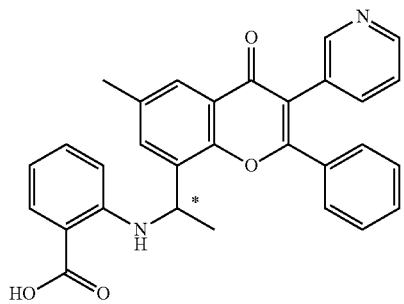

or a pharmaceutically acceptable salt thereof. In yet a further embodiment, the bond at the * position is

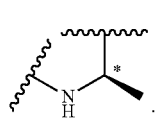 [SMILES: *N[C@@H](*)C]

In yet a further embodiment, the bond at the * position is

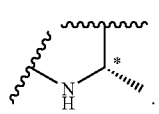

A further embodiment is a compound of Formula

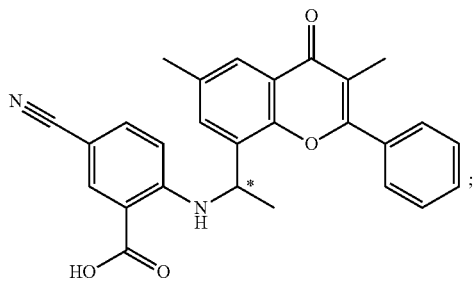 [SMILES: Cc1cc(C(C)Nc2ccc(C#N)cc2C(=O)O)c2oc(-c3ccccc3)c(C)c(=O)c2c1]

or a pharmaceutically acceptable salt thereof. In yet a further embodiment, the bond at the * position is

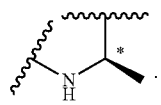

In yet a further embodiment the bond at the * position is

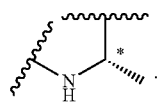

A further embodiment is a compound of Formula

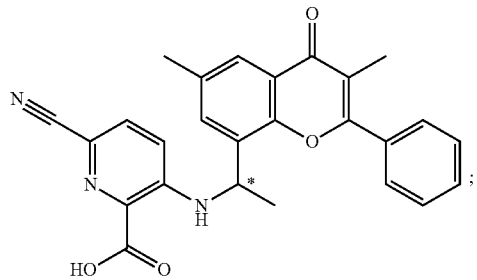 [SMILES: Cc1cc(C(C)Nc2ccc(C#N)nc2C(=O)O)c2oc(-c3ccccc3)c(C)c(=O)c2c1]

or a pharmaceutically acceptable salt thereof. In yet a further embodiment, the bond at the * position is

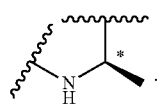

In yet a further embodiment, the bond at the * position is

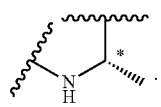

A further embodiment is a compound of Formula

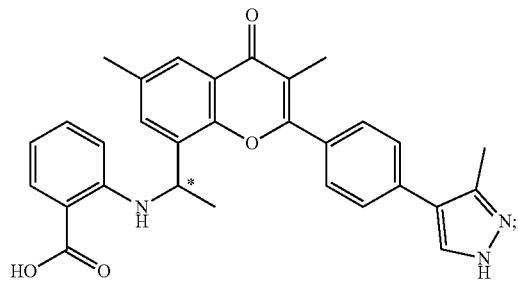 [SMILES: Cc1cc(C(C)Nc2ccccc2C(=O)O)c2oc(-c3ccc(-c4c[nH]nc4C)cc3)c(C)c(=O)c2c1]

or a pharmaceutically acceptable salt thereof. In yet a further embodiment, the bond at the * position is

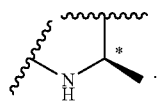

In yet a further embodiment, the bond at the * position is

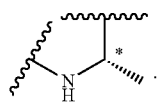

A further embodiment is a compound of Formula

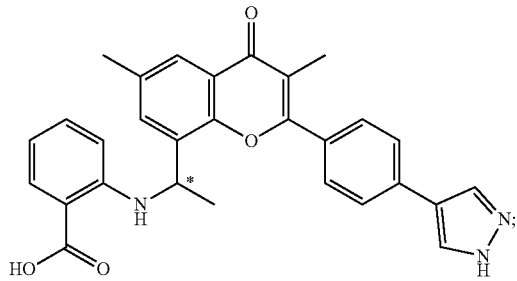 [SMILES: Cc1cc(C(C)Nc2ccccc2C(=O)O)c2oc(-c3ccc(-c4cn[nH]c4)cc3)c(C)c(=O)c2c1]

or a pharmaceutically acceptable salt thereof. In yet a further embodiment, the bond at the * position is

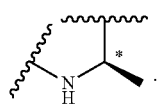

In yet a further embodiment the bond at the * position is

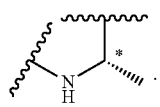

A further embodiment is a compound of Formula

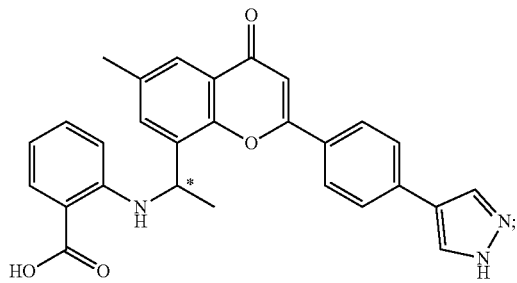 [SMILES: Cc1cc(C(C)Nc2ccccc2C(=O)O)c2oc(-c3ccc(-c4cn[nH]c4)cc3)cc(=O)c2c1]

or a pharmaceutically acceptable salt thereof. In yet a further embodiment, the bond at the * position is

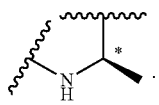

In yet a further embodiment, the bond at the * position is

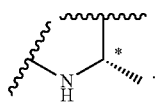

A further embodiment is a compound of Formula

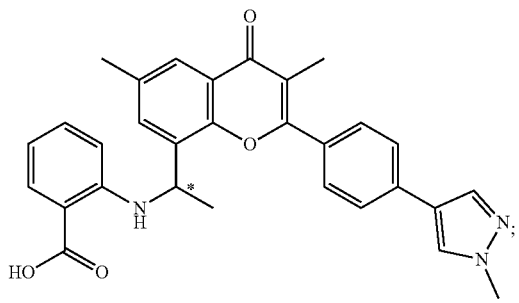 [SMILES: Cc1cc(C(C)Nc2ccccc2C(=O)O)c2oc(-c3ccc(-c4cnn(C)c4)cc3)c(C)c(=O)c2c1]

or a pharmaceutically acceptable salt thereof. In yet a further embodiment, the bond at the * position is

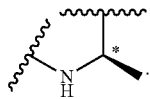

In yet a further embodiment, the bond at the * position is

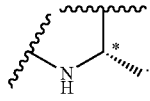

A further embodiment is a compound of Formula

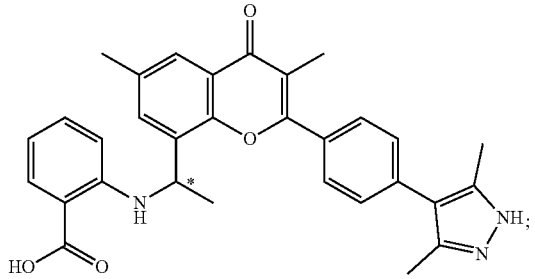 [SMILES: Cc1cc(C(C)Nc2ccccc2C(=O)O)c2oc(-c3ccc(-c4c(C)n[nH]c4C)cc3)c(C)c(=O)c2c1]

or a pharmaceutically acceptable salt thereof. In yet a further embodiment, the bond at the * position is

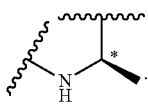 [SMILES: *N[C@@H](*)C]

In yet a further embodiment, the bond at the * position is

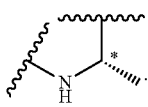

A further embodiment is a compound of Formula

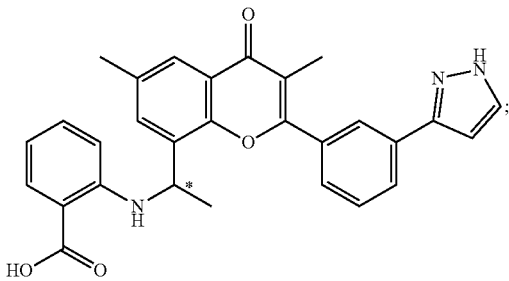 [SMILES: Cc1cc(C(C)Nc2ccccc2C(=O)O)c2oc(-c3cccc(-c4cc[nH]n4)c3)c(C)c(=O)c2c1]

or a pharmaceutically acceptable salt thereof. In yet a further embodiment, the bond at the * position is

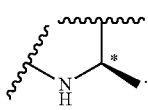 [SMILES: *N[C@@H](*)C]

In yet a further embodiment, the bond at the * position is

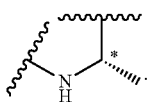

A further embodiment is a compound of Formula

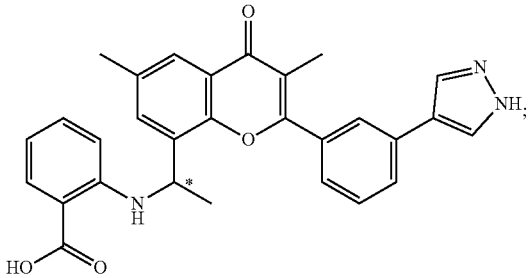 [SMILES: Cc1cc(C(C)Nc2ccccc2C(=O)O)c2oc(-c3cccc(-c4cn[nH]c4)c3)c(C)c(=O)c2c1]

or a pharmaceutically acceptable salt thereof. In yet a further embodiment, the bond at the * position is

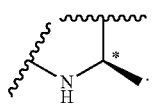

In yet a further embodiment, the bond at the * position is

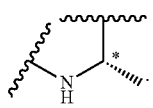

A further embodiment is a compound of Formula

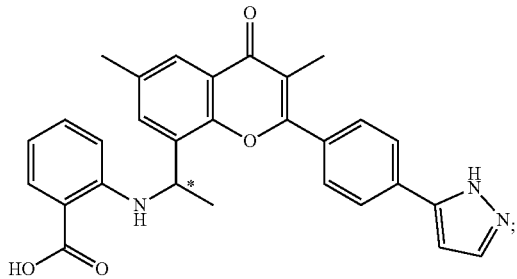 [SMILES: Cc1cc(C(C)Nc2ccccc2C(=O)O)c2oc(-c3ccc(-c4ccn[nH]4)cc3)c(C)c(=O)c2c1]

or a pharmaceutically acceptable salt thereof. In yet a further embodiment, the bond at the * position is

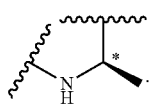

In yet a further embodiment, the bond at the * position is

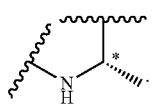

A further embodiment is a compound of Formula

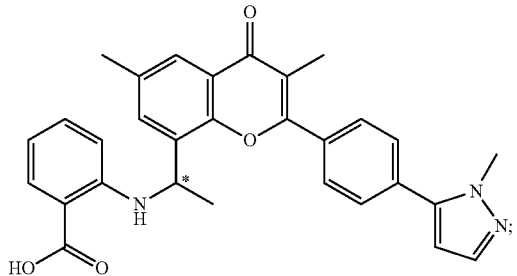 [SMILES: Cc1cc(C(C)Nc2ccccc2C(=O)O)c2oc(-c3ccc(-c4ccnn4C)cc3)c(C)c(=O)c2c1]

or a pharmaceutically acceptable salt thereof. In yet a further embodiment, the bond at the * position is

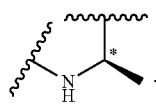

In yet a further embodiment, the bond at the * position is

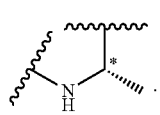

A further embodiment is a compound of Formula

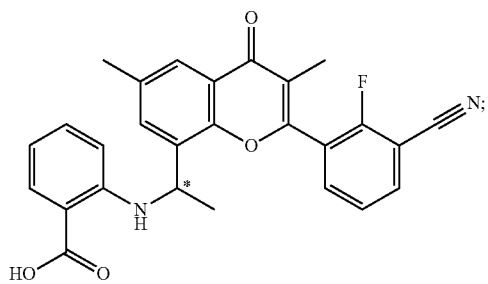 [SMILES: Cc1cc(C(C)Nc2ccccc2C(=O)O)c2oc(-c3cccc(C#N)c3F)c(C)c(=O)c2c1]

or a pharmaceutically acceptable salt thereof. In yet a further embodiment, the bond at the * position is

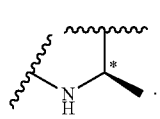

In yet a further embodiment, the bond at the * position is

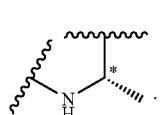

A further embodiment is a compound of Formula

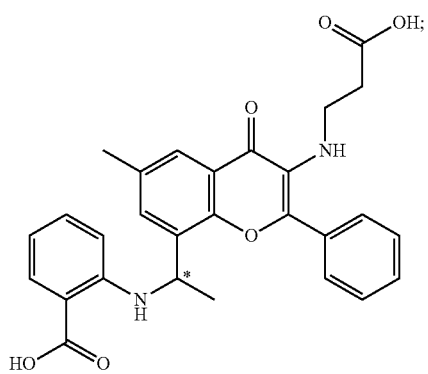 [SMILES: Cc1cc(C(C)Nc2ccccc2C(=O)O)c2oc(-c3ccccc3)c(NCCC(=O)O)c(=O)c2c1]

or a pharmaceutically acceptable salt thereof. In yet a further embodiment, the bond at the * position is

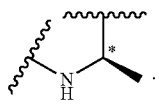

In yet a further embodiment, the bond at the * position is

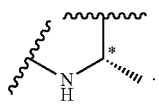

A further embodiment is a compound of Formula

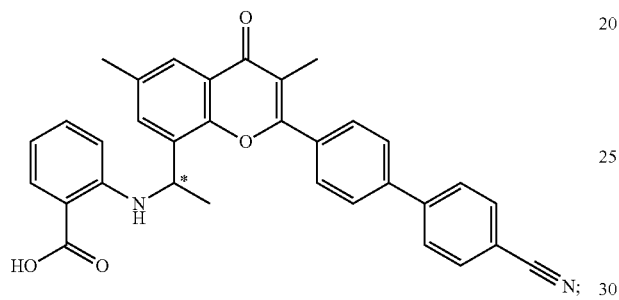

or a pharmaceutically acceptable salt thereof. In yet a further embodiment, the bond at the * position is

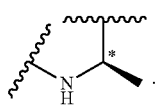

In yet a further embodiment, the bond at the * position is

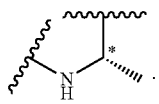

A further embodiment is a compound of Formula

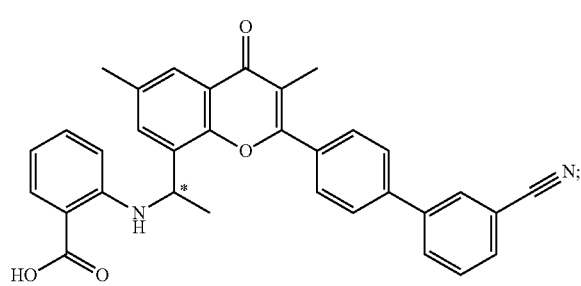 [SMILES: Cc1cc(C(C)Nc2ccccc2C(=O)O)c2oc(-c3ccc(-c4cccc(C#N)c4)cc3)c(C)c(=O)c2c1]

or a pharmaceutically acceptable salt thereof. In yet a further embodiment, the bond at the * position is

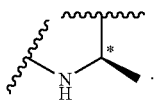

In yet a further embodiment, the bond at the * position is

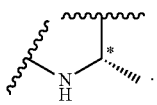

A further embodiment is a compound of Formula

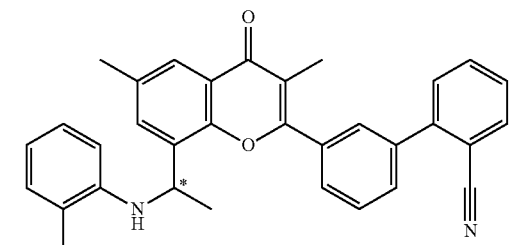

or a pharmaceutically acceptable salt thereof. In yet a further embodiment, the bond at the * position is

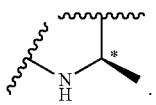 [SMILES: *N[C@@H](*)C]

In yet a further embodiment the bond at the * position is

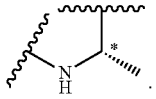

A further embodiment is a compound of Formula

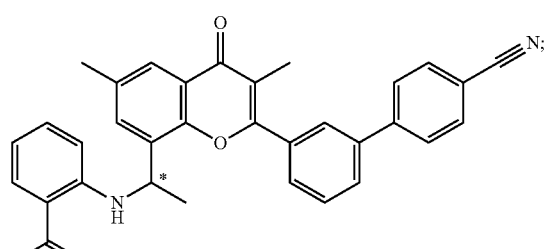

or a pharmaceutically acceptable salt thereof. In yet a further embodiment, the bond at the * position is

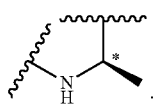

In yet a further embodiment, the bond at the * position is

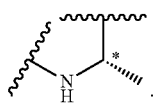

A further embodiment is a compound of Formula

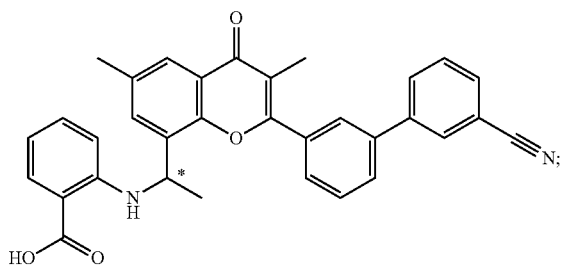 [SMILES: Cc1cc(C(C)Nc2ccccc2C(=O)O)c2oc(-c3cccc(-c4cccc(C#N)c4)c3)c(C)c(=O)c2c1]

or a pharmaceutically acceptable salt thereof. In yet a further embodiment, the bond at the * position is

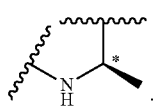

In yet a further embodiment, the bond at the * position is

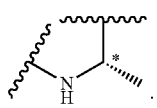

A further embodiment is a compound of Formula

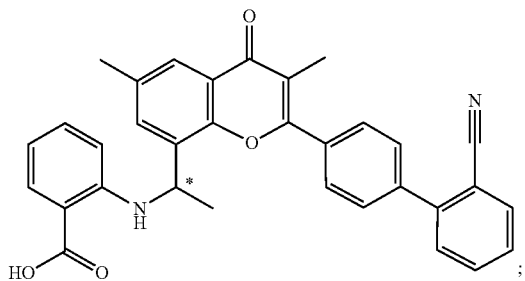 [SMILES: Cc1cc(C(C)Nc2ccccc2C(=O)O)c2oc(-c3ccc(-c4ccccc4C#N)cc3)c(C)c(=O)c2c1]

or a pharmaceutically acceptable salt thereof. In yet a further embodiment, the bond at the * position is

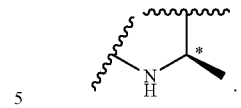

In yet a further embodiment, the bond at the * position is

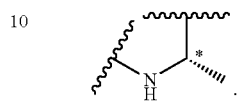

A further embodiment is a compound of Formula

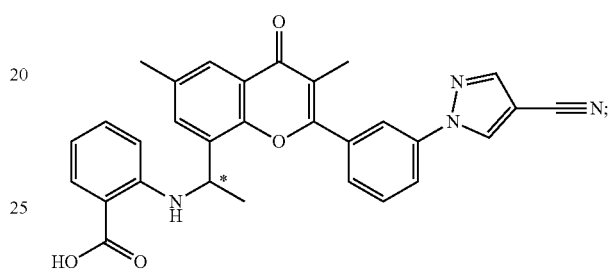

or a pharmaceutically acceptable salt thereof. In yet a further embodiment, the bond at the * position is

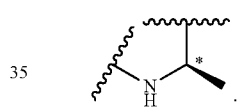

In yet a further embodiment, the bond at the * position is

A pharmaceutically acceptable salt of a compound of the present invention is, for example, an acid-addition salt of a compound of the invention, which is sufficiently basic, for example, an acid-addition salt with, for example, an inorganic or organic acid, for example hydrochloric, hydrobromic, sulfuric, phosphoric, trifluoroacetic, formic, citric, methane sulfonate or maleic acid. In addition, a pharmaceutically acceptable salt of a compound of the present invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine. Pharmaceutically acceptable salts, and common methodology for preparing them are well known in the art (see, e.g., P. Stahl, et al. *Handbook of Pharmaceutical Salts: Properties, Selection, and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977).

Further representative "pharmaceutically acceptable salts" include, e.g., water-soluble, and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulanate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, pantothenate, phosphate/diphosphate, picrate, polygalacturonate, propionate, p-toluenesulfonate, salicylate, stearate, subacetate, succinate, sulfate, sulfosalicylate, tannate, tartrate, teoclate, tosylate, triethiodide, and valerate salts.

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1, 2, 3, and 4 which comprise different sequences of assembling intermediates or compounds. Starting materials are either commercially available or made by known procedures in the reported literature or as illustrated below.

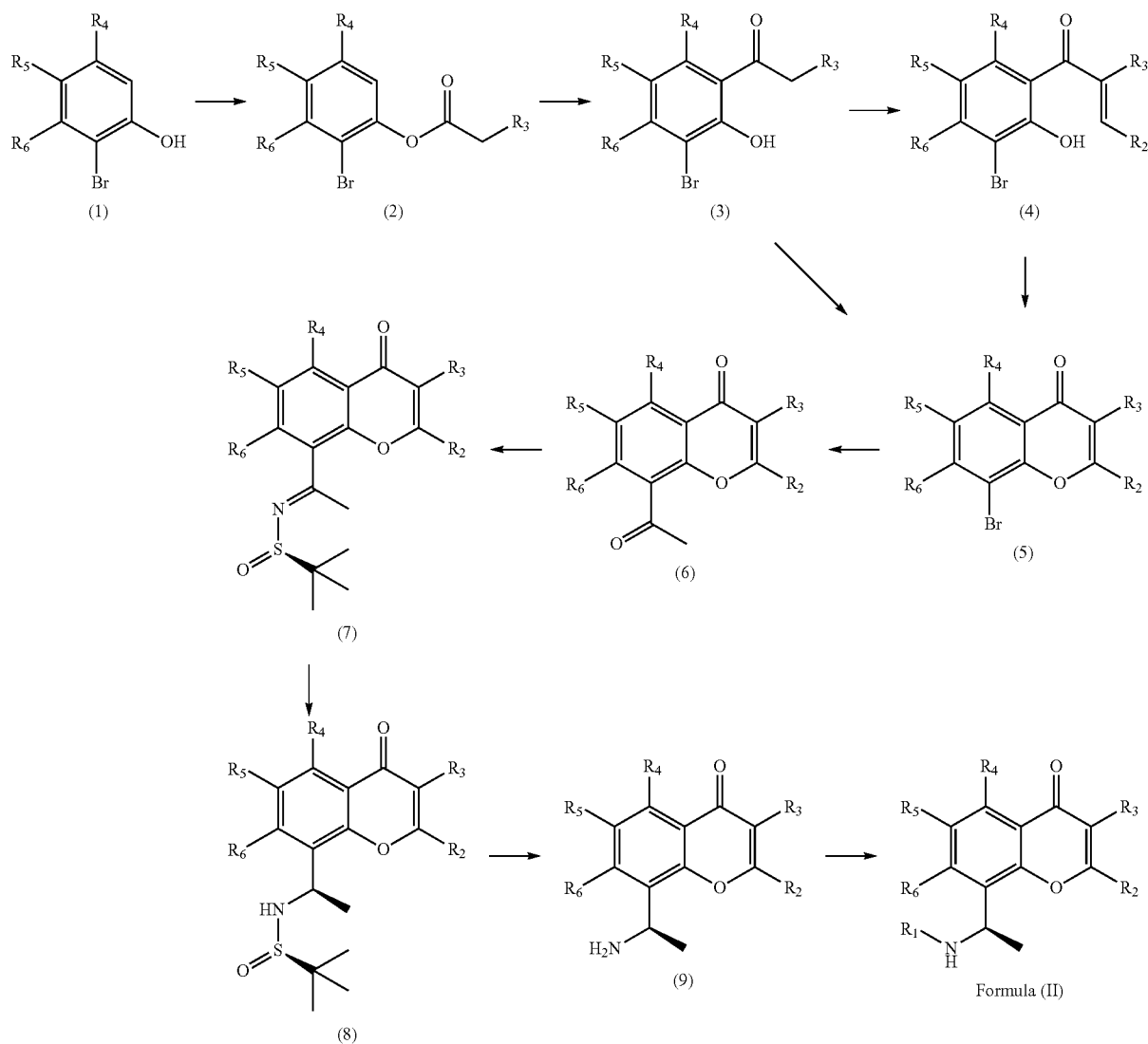

Scheme 1

Scheme 1 depicts the preparation of compounds of Formula (II), where R is H and $R_7$ is methyl. Acylation of substituted phenol (1) may provide ester (2). Ester (2) may undergo rearrangement under Lewis acid (e.g., AlCl$_3$) or Brønsted acid (e.g., triflic acid) conditions to the hydroxy aryl ketone (3). Acidic condensation of an aryl aldehyde with hydroxy aryl ketone (3) may provide keto-alkene (4) which may cyclize to the 2-substituted chromen-4-one (5). Alternatively, alkylation of hydroxy aryl ketone (3) with an aryl halide in the presence of a base (e.g., pyridine or lithium bis(trimethylsilyl)amide), followed by acidic conditions (e.g., HCl) may affect cyclization to 2-substituted chromen-4-one (5).

(III) chloride to yield chirally enriched sulfinamide (8). Removal of the sulfinyl group under acidic conditions may be used to transform sulfinamide (8) to benzylamine (9) which can be alkylated with an aryl or heteroaryl halide under Finkelstein or Ullmann-type conditions to give compounds of Formula (II) after hydrolysis of ester present on $R_1$.

Scheme 2

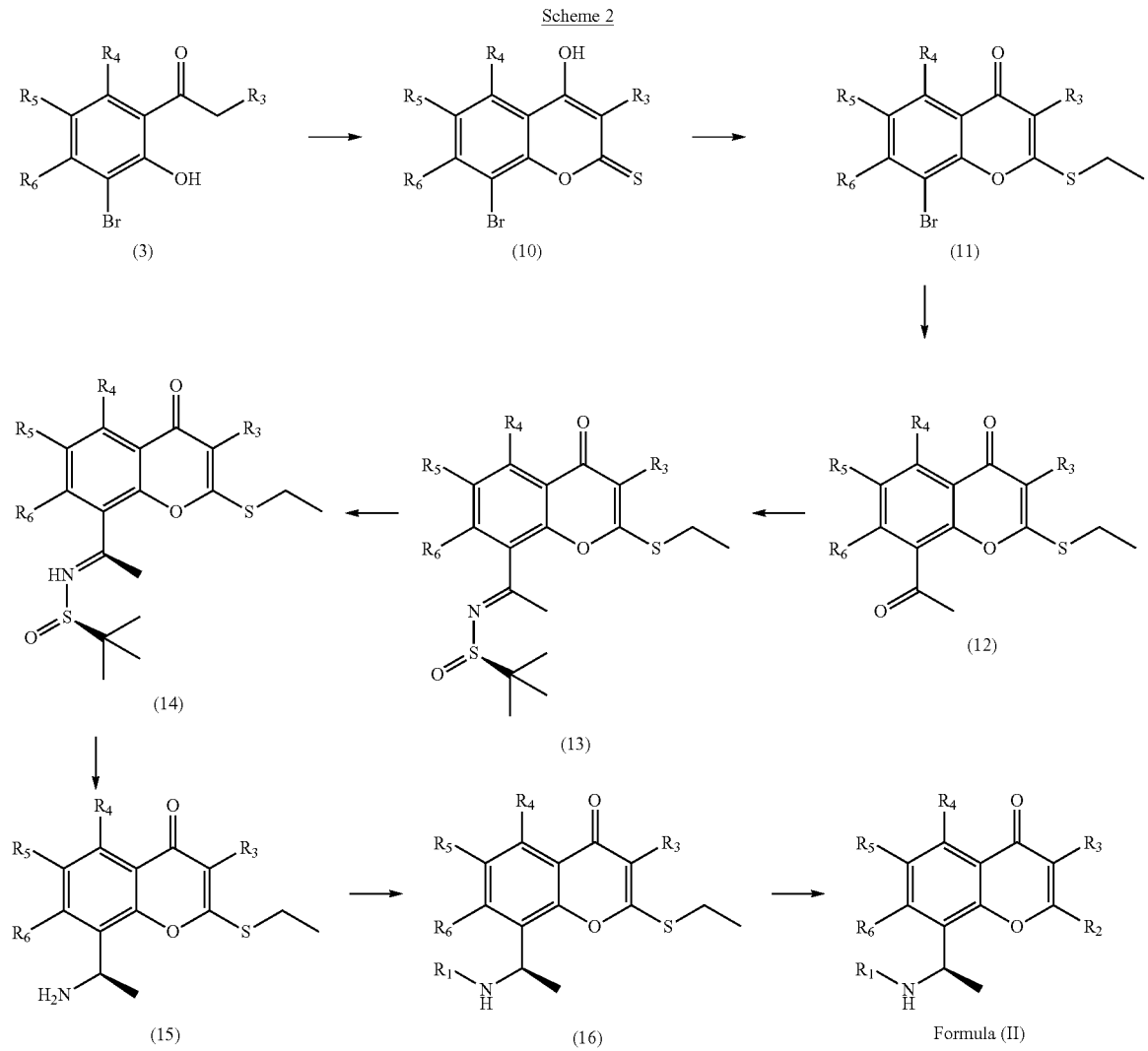

Phenyl bromide (5) can be acylated via palladium catalysis to produce acyl chromen-4-one (6). Exemplary palladium catalysis conditions may include phenyl bromide (5), about 5-10 mol % $PdCl_2(Ph_3)_2$ and about 1.2 mol % tributyl (1-ethoxyvinyl)stannane in about 30-35 equivalents dioxane at 95° C. for about 16 hours; or phenyl bromide (5), about 1 mol % $Pd(OAc)_2$, about 2 mol % 1,3-bis(diphenylphosphino)propane, about 5 equivalents butyl vinyl ether, about 3 equivalents triethylamine, and about 10 volumes of ethylene glycol at about 100° C. for about 16 hours. Condensation of ketone (6) with tert-butanesulfinamide using a Lewis acidic dehydrating agent such as a titanium(IV) alkoxide may afford ketimine (7). Asymmetric reduction of sulfinimine (7) may be affected with a borohydride reagent in the presence of a transition metal catalyst such as cerium Scheme 2 depicts additional preparation of compounds of Formula (II), where R is H and $R_7$ is methyl. Basic deprotonation of ketone (3) in the presence of carbon disulfide gives the bicyclic chromene-2-thione (10). Alkylation of thione (10) under basic conditions affords thioether (11).

Phenyl bromide (11) can be acylated via palladium catalysis to produce acyl chromen-4-one (12) which can be condensed with tert-butanesulfinamide using a Lewis acidic dehydrating agent such as a titanium(IV) alkoxide to afford ketimine (13). Asymmetric reduction of sulfinimine (13) may be affected with a borohydride reagent in the presence of a transition metal catalyst such as cerium (III) chloride to yield chirally enriched sulfinamide (14). Removal of the sulfinyl group under acidic conditions may be used to transform sulfinamide (14) to benzylamine (15) which can be alkylated with an aryl or heteroaryl halide under Finkelstein or Ullmann-type conditions to give arylamine (16).

Thiolether (16) can be converted to compounds of Formula (II) using transition metal catalysis to couple phenyl boronic acids, boronic esters, or other coupling partners, followed by hydrolysis of ester present on $R_1$.

Scheme 3

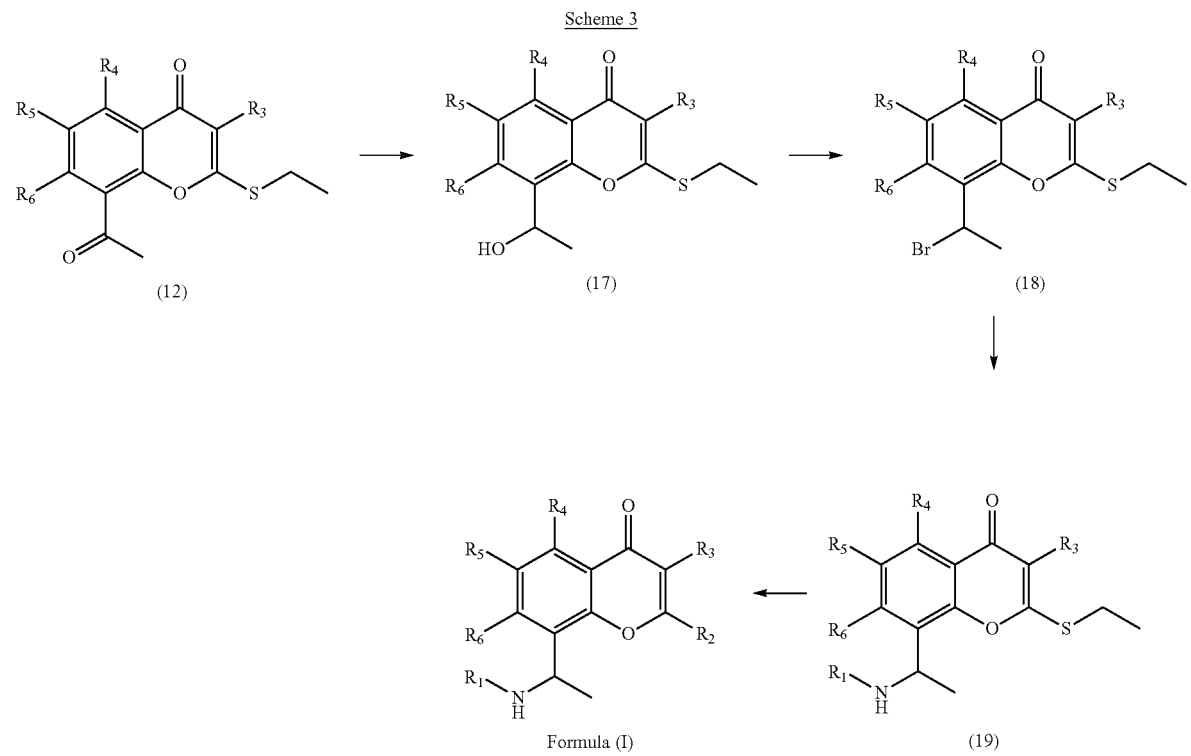

Scheme 3 depicts the preparation of compounds of Formula (I), where R is H, $R_7$ is methyl, and $R_8$ is H. Aryl ketone (12) can be reduced to hydroxy compound (17) with a reagent such as sodium borohydride. Use of a halogenating agent such as phosphorus tribromide can be used to convert hydroxy compound (17) to the halo compound (18). Halo compound (18) can be used to alkylate an arylamine or heteroarylamine to give arylamine or heteroarylamine (19). Thiolether (19) can be converted to compounds of Formula (I) using transition metal catalysis to couple phenyl boronic acids, boronic esters, or other coupling partners, followed by hydrolysis of ester present on $R_1$.

Scheme 4

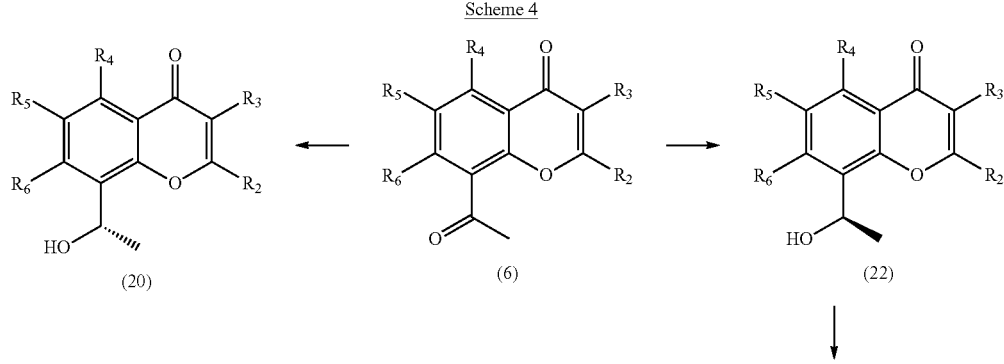

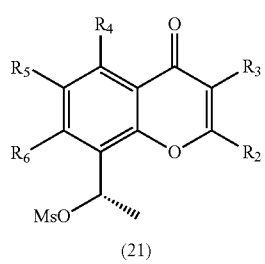
(21)

-continued

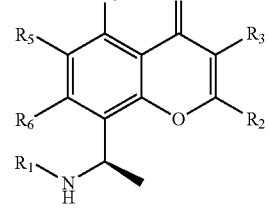
Formula (II)

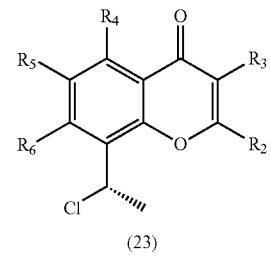
(23)

Scheme 4 depicts the preparation of compounds of Formula (II) where R is H and $R_7$ is methyl. Ketone (6) can be reduced to hydroxy compound (20) with a chiral catalyst such as the Noyori catalyst. The hydroxyl compound (20) can be converted into a leaving group with methanesulfonic anhydride or methanesulfonyl chloride to give mesylate (21). Mesylate (21) can be used to alkylate an arylamine or heteroarylamine to give compounds of Formula (II) after hydrolysis of the ester present on $R_1$.

Alternatively, ketone (6) can be reduced to hydroxy compound (22) with a chiral catalyst such as the Noyori catalyst. The hydroxyl group can be converted to chloride (23) with a chlorinating agent such as 2,4,6-trichloro-1,3,5-triazine. Chloride (23) can then be used to alkylate an arylamine or heteroarylamine to give compounds of Formula (II) after hydrolysis of the ester present on $R_1$.

Pharmaceutical Compositions

In some aspects, the present disclosure provides a pharmaceutical composition comprising a compound of Formula (I), (II), or (III) as an active ingredient. In some embodiments, the present disclosure provides a pharmaceutical composition comprising a compound of Formula (I), (II), or (III), or a pharmaceutically acceptable salt thereof, and one or more pharmaceutically acceptable carriers or excipients.

As used herein, the term "composition" is intended to encompass a product comprising the specified ingredients in the specified amounts, as well as any product which results, directly or indirectly, from combination of the specified ingredients in the specified amounts.

The compounds of Formula (I), (II), or (III) can be formulated for oral administration in forms such as tablets, capsules (each of which includes sustained release or timed release formulations), pills, powders, granules, elixirs, tinctures, suspensions, syrups and emulsions. The compounds of Formula (I), (II), or (III) can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

According to a further aspect of the disclosure there is provided a pharmaceutical composition which comprises a compound any one of the Formulae disclosed herein, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

Methods of Use

In some aspects, the present disclosure provides a method of modulating PI3K (e.g., PI3Kα) activity (e.g., in vitro or in vivo), comprising contacting a cell with a therapeutically effective amount of a compound of Formula (I), (II), or (III), or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of Formula (I), (II), or (III), or a pharmaceutically acceptable salt thereof, or a pharmaceutical composition of the present disclosure.

In some embodiments, the disease or disorder is associated with an implicated PI3K activity. In some embodiments, the disease or disorder is a disease or disorder in which PI3K activity is implicated.

In some embodiments, the disease or disorder is a cancer.

In some embodiments, the cancer is selected from acute lymphoblastic leukemia (ALL), acute myeloid leukemia (AML), adrenocortical carcinoma, aids-related cancers, aids-related lymphoma, anal cancer, astrocytoma, basal cell carcinoma, bile duct cancer, bladder cancer, bone cancer, osteosarcoma, malignant fibrous histiocytoma, brain tumors, breast cancer, bronchial tumors, Burkitt lymphoma, carcinoid tumor, cancer of unknown primary, cardiac (heart) tumors, atypical teratoid/rhabdoid tumor, primary CNS lymphoma, cervical cancer, cholangiocarcinoma, chordoma, chronic lymphocytic leukemia (CLL), chronic myelogenous leukemia (CML), colorectal cancer, craniopharyngioma, cutaneous t-cell lymphoma, mycosis fungoides, Sezary syndrome, ductal carcinoma in situ (DCIS), embryonal tumors, medulloblastoma, endometrial cancer, ependymoma, esophageal cancer, esthesioneuroblastoma, Ewing sarcoma, extracranial germ cell tumor, extragonadal germ cell tumor, fallopian tube cancer, gallbladder cancer, gastric cancer, gastrointestinal carcinoid tumor, malignant gastrointestinal stromal tumors (GIST), germ cell tumors, gestational trophoblastic disease, hairy cell leukemia, head and neck cancer, hepatocellular cancer, Langerhans cell histiocytosis, Hodgkin lymphoma, islet cell tumors, pancreatic neuroendocrine tumors, Kaposi sarcoma, kidney cancer, laryngeal cancer, leukemia, liver cancer, lung cancer, lymphoma, male breast cancer, intraocular melanoma, Merkel cell carcinoma, malignant mesothelioma, metastatic cancer, metastatic squamous neck cancer, midline tract carcinoma with nut gene changes, mouth cancer, multiple endocrine neoplasia syndromes, multiple myeloma/plasma cell neoplasms, myelodysplastic syndromes, myelodysplastic neoplasms, myeloproliferative neoplasms, chronic myeloproliferative neoplasm, nasal cavity and paranasal sinus cancer, nasopharyngeal cancer, neuroblastoma, non-Hodgkin lymphoma, non-small cell lung cancer, oral cancer, lip and oral cavity cancer, oropharyngeal cancer, malignant fibrous histiocytoma of bone, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, multiple myeloma, pleuropulmonary blastoma, primary central nervous system (CNS) lymphoma, primary peritoneal cancer, prostate cancer, rectal cancer, recurrent cancer, renal cell (kidney) cancer, retinoblastoma, rhabdomyosarcoma, salivary gland cancer, sarcoma, childhood vascular tumors, skin cancer, small cell lung cancer, small intestine cancer, soft tissue sarcoma, squamous cell carcinoma of the skin, testicular cancer, oropharyngeal cancer, hypopharyngeal cancer, thymoma, thymic carcinoma, thyroid cancer, tracheobronchial tumors, transitional cell cancer of the renal pelvis and ureter, urethral cancer, uterine sarcoma, vaginal cancer, vascular tumors, vulvar cancer, and Wilms tumor.

In some embodiments, the cancer is Endometrial cancer, Breast cancer, Oesophageal squamous-cell cancer, Cervical squamous-cell carcinoma, Cervical adenocarcinoma, Colorectal adenocarcinoma, Bladder Urothelial Carcinoma, Glioblastoma, Ovarian cancer, Non-small-cell Lung cancer, Esophagogastric cancer, Nerve-sheath tumor, Head and neck squamous-cell carcinoma, Melanoma, Esophagogastric adenocarcinoma, Soft-tissue sarcoma, Prostate cancer, Fibrolamellar carcinoma, Hepatocellular carcinoma, Diffuse glioma, Colorectal cancer, Pancreatic cancer, Cholangiocarcinoma, B-cell lymphoma, Mesothelioma, Adrenocortical carcinoma, Renal non-clear-cell carcinoma, Renal clear-cell carcinoma, Germ-cell carcinoma, Thymic tumor, Pheochromocytoma, Miscellaneous neuroepithelial tumor, thyroid cancer, leukemia, or encapsulated glioma.

In some embodiments, the cancer is a breast cancer, a prostate cancer, or a brain cancer.

In some embodiments, the cancer is a breast cancer. In some embodiments, the cancer is a prostate cancer. In some embodiments, the cancer is a brain cancer.

In some embodiments, the breast cancer is metastatic breast cancer. In some embodiments, the breast cancer is ductal carcinoma in situ (DCIS). In some embodiments, the breast cancer is invasive ductal carcinoma. In some embodiments, the breast cancer is triple negative breast cancer. In some embodiments, the breast cancer is medullary carcinoma. In some embodiments, the breast cancer is tubular carcinoma. In some embodiments, the breast cancer is mucinous carcinoma. In some embodiments, the breast cancer is Paget disease of the breast or nipple. In some embodiments, the breast cancer is inflammatory breast cancer (IBC). In some embodiments, the breast cancer is hormone receptor-positive (HR+), human epidermal growth factor receptor 2-negative (HER2−) advanced or metastatic breast cancer.

In some embodiments, the prostate cancer is an adenocarcinoma. In some embodiments, the prostate cancer is a small cell carcinoma. In some embodiments, the prostate cancer is a neuroendocrine tumor. In some embodiments, the prostate cancer is a transitional cell carcinoma. In some embodiments, the prostate cancer is a sarcoma.

In some embodiments, the brain cancer is an acoustic neuroma. In some embodiments, the brain cancer is an astrocytoma. In some embodiments, the brain cancer is a brain metastasis. In some embodiments, the brain cancer is choroid plexus carcinoma. In some embodiments, the brain cancer is craniopharyngioma. In some embodiments, the brain cancer is an embryonal tumor. In some embodiments, the brain cancer is an ependymoma. In some embodiments, the brain cancer is a glioblastoma. In some embodiments, the brain cancer is a glioma. In some embodiments, the brain cancer is a medulloblastoma. In some embodiments, the brain cancer is a meningioma. In some embodiments, the brain cancer is an oligodendroglioma. In some embodiments, the brain cancer is a pediatric brain tumor. In some embodiments, the brain cancer is a pineoblastoma. In some embodiments, the brain cancer is a pituitary tumor.

In some embodiments, the disease or disorder associated with PI3K includes, but is not limited to, CLOVES syndrome (congenital lipomatous overgrowth, vascular malformations, epidermal naevi, scoliosis/skeletal and spinal syndrome), PIK3CA-related overgrowth syndrome (PROS), breast cancer, brain cancer, prostate cancer, endometrial cancer, gastric cancer, leukemia, lymphoma, sarcoma, colorectal cancer, lung cancer, ovarian cancer, skin cancer, or head and neck cancer.

In some embodiments, the diseases or disorder associated with PI3K is CLOVES syndrome (congenital lipomatous overgrowth, vascular malformations, epidermal naevi, scoliosis/skeletal and spinal syndrome).

In some embodiments, the disease or disorder associated with PI3K is PIK3CA-related overgrowth syndrome (PROS).

In some embodiments, the disease or disorder associated with PI3K is breast cancer, brain cancer, prostate cancer, endometrial cancer, gastric cancer, leukemia, lymphoma, sarcoma, colorectal cancer, lung cancer, ovarian cancer, skin cancer, or head and neck cancer.

In some embodiments, the disease or disorder associated with PI3K is a breast neoplasm, a thyroid neoplasm, an ovarian neoplasm, non-small-cell lung carcinoma, an endometrial neoplasm, or a pancreatic neoplasm. In some embodiments, the disease or disorder associated with PI3K is a breast neoplasm. In some embodiments, the disease or disorder associated with PI3K is a thyroid neoplasm. In some embodiments, the disease or disorder associated with PI3K is an ovarian neoplasm. In some embodiments, the disease or disorder associated with PI3K is non-small-cell lung carcinoma. In some embodiments, the disease or disorder associated with PI3K is an endometrial neoplasm. In some embodiments, the disease or disorder associated with PI3K is a pancreatic neoplasm.

In some embodiments, the disease or disorder associated with PI3K is breast cancer, brain cancer, prostate cancer, endometrial cancer, gastric cancer, colorectal cancer, lung cancer, ovarian cancer, skin cancer, or head and neck cancer.

In some embodiments, the disease or disorder associated with PI3K is leukemia, lymphoma, or sarcoma.

In some embodiments, the cancer is endometrial cancer, head and neck cancer, or a sarcoma.

In some embodiments, the cancer is endometrial cancer. In some embodiments the cancer is head and neck cancer. In some embodiments, the cancer is a sarcoma.

In some embodiments, the sarcoma is soft tissue sarcoma, osteosarcoma, chondrosarcoma, Ewing sarcoma, hemangioendothelioma, angiosarcoma, fibrosarcoma, myofibrosarcoma, chordoma, adamantinoma, liposarcoma, leiomyosarcoma, malignant peripheral nerve sheath tumor, rhabdomyosarcoma, synovial sarcoma, or malignant solitary fibrous tumor.

In some embodiments, the sarcoma is soft tissue sarcoma. In some embodiments the soft tissue sarcoma is liposarcoma, atypical lipomatous tumor, dermatofibrosarcoma protuberans, malignant solitary fibrous tumor, inflammatory myofibroblastic tumor, low-grade myofibroblastic sarcoma, fibrosarcoma, myxofibrosarcoma, low-grade fibromyxoid sarcoma, giant cell tumor of soft tissues, leiomyosarcoma, malignant glomus tumor, rhabdomyosarcoma, hemangioendothelioma, angiosarcoma of soft tissue, extraskeletal osteosarcoma, gastrointestinal stromal tumor, malignant gastrointestinal stromal tumor (GIST), malignant peripheral nerve sheath tumor, malignant Triton tumor, malignant granular cell tumor, malignant ossifying fibromyxoid tumor, stromal sarcoma, myoepithelial carcinoma, malignant phosphaturic mesenchymal tumor, synovial sarcoma, epithelioid sarcoma, alveolar soft part sarcoma, clear cell sarcoma of soft tissue, extraskeletal myxoid chondrosarcoma, extraskeletal Ewing sarcoma, desmoplastic small round cell tumor, extrarenal rhabdoid tumor, perivascular epithelioid cell tumor, intimal sarcoma, undifferentiated spindle cell sarcoma, undifferentiated pleomorphic sarcoma, undifferentiated round cell sarcoma, undifferentiated epithelioid sarcoma, or undifferentiated sarcoma, not otherwise specified.

In some aspects, the present disclosure provides a method of treating or preventing a cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating or preventing a breast cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a breast cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating or preventing a prostate cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a prostate cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating or preventing a brain cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a brain cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a compound of Formula (I), (II), or (III), or a pharmaceutically acceptable salt thereof for use in therapy.

In some aspects, the present disclosure provides a compound of Formula (I), (II), or (III), or a pharmaceutically acceptable salt thereof for use in modulating PI3K (e.g., PI3Kα) activity (e.g., in vitro or in vivo).

In some aspects, the present disclosure provides a compound of Formula (I), (II), or (III), or a pharmaceutically acceptable salt thereof for use in treating or preventing a disease or disorder disclosed herein.

In some aspects, the present disclosure provides a compound of Formula (I), (II), or (III), or a pharmaceutically acceptable salt thereof for use in treating a disease or disorder disclosed herein.

In some aspects, the present disclosure provides a compound of Formula (I), (II), or (III), or a pharmaceutically acceptable salt thereof for use in treating or preventing a cancer.

In some aspects, the present disclosure provides a compound of Formula (I), (II), or (III), or a pharmaceutically acceptable salt thereof for use in treating a cancer.

In some aspects, the present disclosure provides a compound of Formula (I), (II), or (III), or a pharmaceutically acceptable salt thereof for use in treating or preventing a breast cancer.

In some aspects, the present disclosure provides a compound of Formula (I), (II), or (III), or a pharmaceutically acceptable salt thereof for use in treating a breast cancer.

In some aspects, the present disclosure provides a compound of Formula (I), (II), or (III), or a pharmaceutically acceptable salt thereof for use in treating or preventing a prostate cancer.

In some aspects, the present disclosure provides a compound of Formula (I), (II), or (III), or a pharmaceutically acceptable salt thereof for use in treating a prostate cancer.

In some aspects, the present disclosure provides a compound of Formula (I), (II), or (III), or a pharmaceutically acceptable salt thereof for use in treating or preventing a brain cancer.

In some aspects, the present disclosure provides a compound of Formula (I), (II), or (III), or a pharmaceutically acceptable salt thereof for use in treating a brain cancer.

In some aspects, the present disclosure provides use of a compound of Formula (I), (II), or (III), or a pharmaceutically acceptable salt thereof in the manufacture of a medicament for modulating PI3K (e.g., PI3Kα) activity (e.g., in vitro or in vivo).

In some aspects, the present disclosure provides use of a compound of Formula (I), (II), or (III), or a pharmaceutically acceptable salt thereof in the manufacture of a medicament for treating or preventing a disease or disorder disclosed herein.

In some aspects, the present disclosure provides use of a compound of Formula (I), (II), or (III), or a pharmaceutically acceptable salt thereof in the manufacture of a medicament for treating a disease or disorder disclosed herein.

In some aspects, the present disclosure provides use of a compound of Formula (I), (II), or (III), or a pharmaceutically acceptable salt thereof in the manufacture of a medicament for treating or preventing a cancer in a subject in need thereof.

In some aspects, the present disclosure provides use of a compound of Formula (I), (II), or (III), or a pharmaceutically acceptable salt thereof in the manufacture of a medicament for treating a cancer in a subject in need thereof.

In some aspects, the present disclosure provides use of a compound of Formula (I), (II), or (III), or a pharmaceutically acceptable salt thereof in the manufacture of a medicament for treating or preventing a breast cancer in a subject in need thereof.

In some aspects, the present disclosure provides use of a compound of Formula (I), (II), or (III), or a pharmaceutically acceptable salt thereof in the manufacture of a medicament for treating a breast cancer in a subject in need thereof.

In some aspects, the present disclosure provides use of a compound of Formula (I), (II), or (III), or a pharmaceutically acceptable salt thereof in the manufacture of a medicament for treating or preventing a prostate cancer in a subject in need thereof.

In some aspects, the present disclosure provides use of a compound of Formula (I), (II), or (III), or a pharmaceutically acceptable salt thereof in the manufacture of a medicament for treating a prostate cancer in a subject in need thereof.

In some aspects, the present disclosure provides use of a compound of Formula (I), (II), or (III), or a pharmaceutically acceptable salt thereof in the manufacture of a medicament for treating or preventing a brain cancer in a subject in need thereof.

In some aspects, the present disclosure provides use of a compound of Formula (I), (II), or (III), or a pharmaceutically acceptable salt thereof in the manufacture of a medicament for treating a brain cancer in a subject in need thereof.

The present disclosure provides compounds that function as modulators of PI3K activity. The present disclosure therefore provides a method of modulating PI3K activity in vitro or in vivo, said method comprising contacting a cell with a therapeutically effective amount of a compound, or a pharmaceutically acceptable salt thereof, as defined herein.

In some embodiments, PI3K modulation is inhibition of PI3K.

In some embodiments, the PI3K inhibitor is a PI3Kα inhibitor. In some embodiments, the PI3K inhibitor is a PI3Kα H1047R mutant inhibitor.

Effectiveness of compounds of the disclosure can be determined by industry-accepted assays/disease models according to standard practices of elucidating the same as described in the art and are found in the current general knowledge.

The present disclosure also provides a method of treating a disease or disorder in which PI3K activity is implicated in a patient in need of such treatment, said method comprising administering to said patient a therapeutically effective amount of a compound, or a pharmaceutically acceptable salt thereof, or a pharmaceutical composition as defined herein.

Routes of Administration

The compounds of Formula (I), (II), or (III), or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

Exemplary compounds of Formula (I), (II), and (III) are synthesized and tested in the examples. It is understood that compounds of Formula (I), (II), and (III) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz or 300 MHz as stated and at 300.3 K unless otherwise stated; the chemical shifts (δ) are reported in parts per million (ppm). Spectra were recorded using a Bruker or Varian instrument with 8, 16 or 32 scans.

LC-MS chromatograms and spectra were recorded using an Agilent 1200 or Shimadzu LC-20 AD&MS 2020 instrument using a C-18 column such as a Luna-C18 2.0×30 mm or Xbridge Shield RPC18 2.1×50 mm. Injection volumes were 0.7-8.0 μl and the flow rates were typically 0.8 or 1.2 ml/min. Detection methods were diode array (DAD) or evaporative light scattering (ELSD) as well as positive ion electrospray ionization. MS range was 100-1000 Da. Solvents were gradients of water and acetonitrile both containing a modifier (typically 0.01-0.04%) such as trifluoroacetic acid or ammonium carbonate.

Abbreviations

AcOH/HOAc Acetic Acid
ADP Adenosine diphosphate
ATP Adenosine triphosphate
$CDCl_3$ Chloroform-d
DCM Dichloromethane
DIEA N,N-diisopropylethylamine DMF N,N-dimethylformamide
DMSO dimethylsulfoxide
DMSO-$d_6$ Hexadeuterodimethylsulfoxide
eq. equivalents
EtI Ethyl iodide
EtOAc ethyl acetate
h hour(s)
HEPES 4-(2-hydroxyethyl)-1-piperazineethanesulfonic acid
$^1$H NMR Proton nuclear magnetic resonance spectroscopy
LC-MS Liquid chromatography-mass spectrometry
MeOH Methanol
min minute(s)
NaHMDS Sodium bis(trimethylsilyl)amide
PIP2 Phosphatidylinositol 4,5-bisphosphate
PPh$_3$ triphenylphosphine
ppm parts per million
rt room temperature
TFA trifluoroacetic acid
THF Tetrahydrofuran
Ti(i-PrO)$_4$ Titanium(IV) isopropoxide Intermediate 1: (2-Bromo-4-methyl-phenyl) propanoate

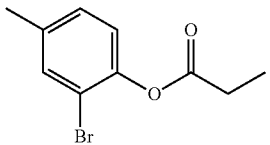

A mixture of 2-bromo-4-methyl-phenol (10.0 g, 53.5 mmol) and pyridine (6.34 g, 80.2 mmol) in DCM (100 mL) was treated with propanoyl chloride (5.44 g, 58.8 mmol) at 0° C. and stirred at 25° C. for 16 h. The mixture was diluted with water (100 mL), the pH adjusted to 5 with HCl (2 M), and extracted with DCM (2×100 mL). The combined organic extracts were washed with brine (2×150 mL), dried over anhydrous Na$_2$SO$_4$, filtered, and concentrated to give the product as an oil (13 g, crude). $^1$H NMR (400 MHz, DMSO-d6) δ ppm 1.17 (t, J=7.6 Hz, 3H), 2.30 (s, 3H), 2.62 (q, J=7.6 Hz, 2H), 7.11-7.18 (m, 1H), 7.19-7.26 (m, 1H), 7.50-7.55 (m, 1H).

Intermediate 2: 1-(3-Bromo-2-hydroxy-5-methyl-phenyl)propan-1-one

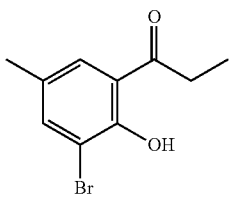

A mixture of (2-bromo-4-methyl-phenyl) propanoate (12.5 g, 51.4 mmol) and AlCl$_3$ (24.0 g, 180 mmol) was stirred at 140° C. for 1 h. When cooled to rt, the mixture was quenched with water (80 mL) dropwise and stirred for 30 min. The mixture was extracted with EtOAc (3×100 mL). The combined organic extracts were washed with brine (2×200 mL), dried over anhydrous Na$_2$SO$_4$, and filtered. The filtrate was concentrated and triturated with petroleum ether (20 mL) to give the product as a solid (9.82 g, 79%). $^1$H NMR (400 MHz, DMSO-d6) δ ppm 1.10 (t, J=7.2 Hz, 3H), 2.28 (s, 3H), 3.15 (q, J=7.2 Hz, 2H), 7.66-7.73 (m, 1H), 7.77-7.83 (m, 1H), 12.66 (s, 1H).

Intermediate 3: (E)-1-(3-Bromo-2-hydroxy-5-methyl-phenyl)-2-methyl-3-phenyl-prop-2-en-1-one

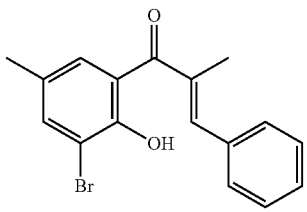 [SMILES: C/C(=C\c1ccccc1)C(=O)c1cc(C)cc(Br)c1O]

A mixture of 1-(3-bromo-2-hydroxy-5-methyl-phenyl) propan-1-one (200 g, 822.72 mmol), benzaldehyde (96.04 g, 904.99 mmol), AcOH (105.23 g, 1.75 mol), and piperidine (172.33 g, 2.02 mol) in EtOH (1600 mL) was stirred at 70° C. for 16 h. The resulting dark solution was poured into water (3 L), filtered, and the solid dissolved in 6 L of DCM. The organic solution was dried over anhydrous Na$_2$SO$_4$, filtered, and concentrated to give the product as a dark gum. MS ES+m/z 331, 333 [M+H]$^+$.

Intermediate 4: 8-Bromo-3,6-dimethyl-2-phenyl-chromen-4-one

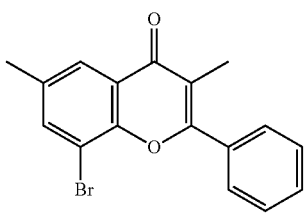 [SMILES: Cc1cc(Br)c2oc(-c3ccccc3)c(C)c(=O)c2c1]

A mixture of (E)-1-(3-bromo-2-hydroxy-5-methyl-phenyl)-2-methyl-3-phenyl-prop-2-en-1-one (284 g, 857.48 mmol) and I2 (21.76 g, 85.75 mmol, 17.27 mL, 0.1 eq) in DMSO (1200 mL) was stirred at 140° C. for 2 h to give a black-brown solution. Cooled to rt, poured the reaction into 3 L of water, filtered, dissolved the solid product in DCM (4 L), dried over anhydrous Na$_2$SO$_4$, filtered, and concentrated to give a residue. The residue was triturated with petroleum ether/EtOAc (1:1, 1 L) to give the product as a light yellow solid (195 g, 69%). MS ES+ m/z 329, 331 [M+H]$^+$.

Intermediate 5:
8-Acetyl-3,6-dimethyl-2-phenyl-chromen-4-one

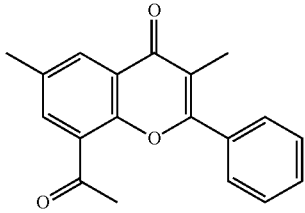 [SMILES: CC(=O)c1cc(C)cc2c(=O)c(C)c(-c3ccccc3)oc12]

A mixture of 8-bromo-3,6-dimethyl-2-phenyl-chromen-4-one (195 g, 592.37 mmol), bis(triphenylphosphine)palladium(II) dichloride (20.79 g, 29.62 mmol), and tributyl(1-ethoxyvinyl)stannane (256.72 g, 710.84 mmol, 239.92 mL) in dioxane (1600 mL) was stirred under $N_2$ at 95° C. for 16 h to give a black-brown solution. After cooling to rt, treated the reaction with 1M aqueous HCl (100 mL) and stirred at 20° C. for 30 min. The mixture was quenched with saturated aqueous KF (2000 mL), stirred for 30 min, and filtered. The filter cake was washed with 10% MeOH in DCM (5×5000 mL). The combined extracts were dried over anhydrous $Na_2SO_4$, filtered, and concentrated to give a residue. The residue was triturated with petroleum ether/EtOAc (5/1, 1000 mL) to give a crude product which was triturated with DCM/MeOH (10/1, 500 mL) to give the product as a light yellow solid (180 g, 96%, 92% purity). MS ES+ m/z 293 $[M+H]^+$.

Intermediate 6: (NE,R)—N-[1-(3,6-Dimethyl-4-oxo-2-phenyl-chromen-8-yl)ethylidene]-2-methyl-propane-2-sulfinamide

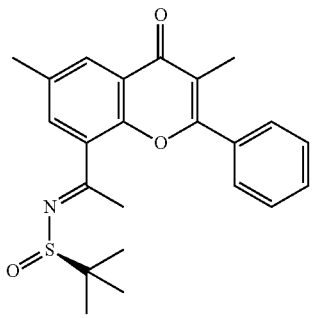 [SMILES: C/C(=N\[S@](=O)C(C)(C)C)c1cc(C)cc2c(=O)c(C)c(-c3ccccc3)oc12]

To a mixture of 8-acetyl-3,6-dimethyl-2-phenyl-chromen-4-one (180 g, 615.75 mmol) and (R)-2-methylpropane-2-sulfinamide (149.26 g, 1.23 mol) in THF (1500 mL) was added tetraisopropoxytitanium (700.01 g, 2.46 mol, 726.90 mL). The mixture was stirred at 80° C. for 56 h to give a black-brown solution. After cooling to rt, quenched the reaction with brine (2000 mL) and stirred for 30 min and filtered. The filter cake was washed with EtOAc (4000 mL). After separating the organic layer, the aqueous layer was extracted with EtOAc (1000 mL). The combined organic extracts were dried over anhydrous $Na_2SO_4$, filtered, and concentrated to give a residue. The residue was triturated with petroleum ether/EtOAc (1/1, 600 mL) to give the product as a white solid (186 g, 76%). MS ES+ m/z 396 $[M+H]^+$.

Intermediate 7: (R)—N-[(1R)-1-(3,6-Dimethyl-4-oxo-2-phenyl-chromen-8-yl)ethyl]-2-methyl-propane-2-sulfinamide To a mixture of (NE,R)—N-[1-(3,6-dimethyl-4-oxo-2-phenyl-chromen-8-yl)ethylidene]-2-methyl-propane-2-sulfinamide (186 g, 470.27 mmol) and $CeCl_3.7H_2O$ (87.61 g, 235.14 mmol, 22.35 mL) in MeOH (1600 mL) was added $NaBH_4$ (26.69 g, 705.41 mmol) at 15° C. The mixture was stirred at 15° C. for 1 h to give a dark suspension. The reaction was quenched with saturated aqueous $NH_4Cl$ (1500 mL) at 15° C. Extracted with DCM (2×1500 mL), washed the combined organic phases with brine (1500 mL), dried the organic phase over anhydrous $Na_2SO_4$, filtered, and concentrated to give the product as a yellow solid (180 g, 96%). MS ES+ m/z 398 $[M+H]^+$.

Intermediate 8: 8-[(1R)-1-Aminoethyl]-3,6-dimethyl-2-phenyl-chromen-4-one

A mixture of (R)—N-[(1R)-1-(3,6-dimethyl-4-oxo-2-phenyl-chromen-8-yl)ethyl]-2-methyl-propane-2-sulfinamide (180 g, 452.80 mmol) in MeOH (1500 mL) was treated with HCl/MeOH (4 M, 300 mL) and the mixture was stirred at 15° C. for 1 h to give a white suspension. Concentrated the reaction, poured the residue into water (1000 mL) and DCM (2000 mL), adjusted the pH to 12 with $NH_3$ in $H_2O$ (25%), and extracted with DCM (2×1000 mL). The combined organic phases were washed with brine (1000 mL), dried over anhydrous $Na_2SO_4$, filtered, and concentrated to give a residue. The residue was triturated with DCM (200 mL) to give the product as a white solid (122 g, 89%). MS ES+ m/z 294 $[M+H]^+$.

Intermediate 9: Methyl 6-chloro-3-[[(1R)-1-(3,6-dimethyl-4-oxo-2-phenyl-chromen-8-yl)ethyl]amino]pyridine-2-carboxylate

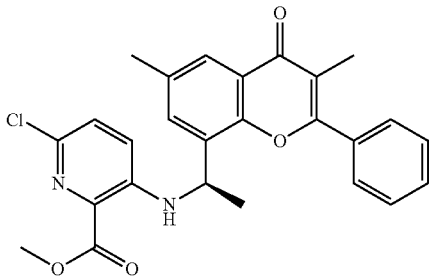 [SMILES: COC(=O)c1nc(Cl)ccc1N[C@H](C)c1cc(C)cc2c(=O)c(C)c(-c3ccccc3)oc12]

A mixture of 8-[(1R)-1-aminoethyl]-3,6-dimethyl-2-phenyl-chromen-4-one (10 g, 34.09 mmol), methyl 6-chloro-3-fluoro-pyridine-2-carboxylate (7.75 g, 40.91 mmol) and DIEA (22.03 g, 170.44 mmol, 29.69 mL) in DMSO (100 mL) was stirred at 100° C. for 16 h to give a dark solution. After cooling to rt, quenched the reaction with water (150 mL), extracted with EtOAc (2×300 mL), dried over anhydrous $Na_2SO_4$, filtered, and concentrated to give a residue. Purified via silica gel using a gradient of EtOAc in petroleum ether (0 to 30%) to give the product as a yellow oil (15 g, 95%). MS ES+ m/z 463 [M+H]+.

Intermediate 10: (2-Bromo-4-methyl-phenyl) acetate

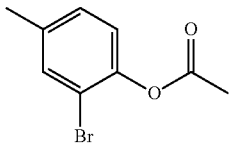

A DCM (2.4 L) mixture of 2-bromo-4-methyl-phenol (300 g, 1.6 mol) and pyridine (152 g, 1.92 mol) at 0° C. was treated with acetyl chloride and stirred at 25° C. for 16 h. The mixture was diluted with water (1500 mL), the pH adjusted to 5 with HCl (2 M aqueous), and extracted with DCM (3×500 mL). The combined organic extracts were washed with brine (2×250 mL), dried over $Na_2SO_4$, filtered, and concentrated to give the product as an oil (400 g, crude). $^1$H NMR (400 MHz, $CDCl_3$) δ ppm 2.24 (s, 3H), 2.25 (s, 3H), 6.91 (d, J=8.4 Hz, 2H), 7.01-7.02 (m, 2H), 7.33 (s, 1H).

Intermediate 11: 1-(3-Bromo-2-hydroxy-5-methyl-phenyl)ethanone

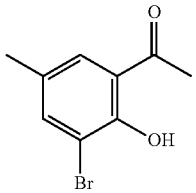

A mixture of (2-bromo-4-methyl-phenyl) acetate (50 g, 218 mmol) and $AlCl_3$ (102 g, 764 mmol) was degassed and purged with $N_2$ three times and stirred at 140° C. for 1 h. After cooling to rt, the reaction was diluted with DCM (30 mL) and dropped into 150 mL of water at 0° C. The mixture was filtered and the aqueous phase extracted with DCM (2×150 mL). The combined organic extracts were washed with brine, dried over anhydrous $Na_2SO_4$, filtered, and concentrated. The residue was triturated with petroleum ether (2×150 mL) to give the product as a solid (30 g, 52%). $^1$H NMR (400 MHz, $CDCl_3$) δ ppm 2.30 (s, 3H), 2.68 (s, 3H), 7.73 (s, 1H), 7.33 (s, 1H), 12.64 (s, 1H).

Intermediate 12: 8-Bromo-4-hydroxy-6-methyl-chromene-2-thione

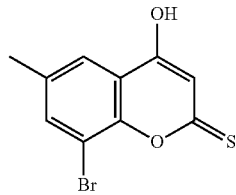

A solution of 1-(3-bromo-2-hydroxy-5-methyl-phenyl)ethanone (65 g, 284 mmol) in THF (800 mL) was treated with NaHMDS (851 mL, 1 M) at −50° C. over 30 min, allowed to warm to between −5° C. and 0° C., and stirred for 1 h. The reaction was cooled to −20° C. and treated with $CS_2$ (64.8 g, 851 mmol) dropwise over 1 h, allowed to warm to 25° C., and stirred for another 16 h. The reaction was quenched with $H_2SO_4$ (800 mL, 15%) at −50° C. over 1 h, allowed to warm to rt, and extracted with EtOAc (2×1 L). The combined organic extracts were washed with brine (1 L), dried over anhydrous $Na_2SO_4$, filtered, and concentrated. The residue was triturated with EtOAc (0.5 L) to give the product as a solid (210 g crude, 64%, purity ~76%).

Intermediate 13: 8-Bromo-2-ethylsulfanyl-6-methyl-chromen-4-one

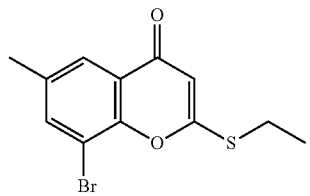 [SMILES: CCSc1cc(=O)c2cc(C)cc(Br)c2o1]

A mixture of 8-bromo-4-hydroxy-6-methyl-chromene-2-thione (20.0 g, 73.8 mmol), EtI (46 g, 295 mmol), and $K_2CO_3$ (12.2 g, 88.5 mmol) in acetone (200 mL) was stirred at 60° C. for 3 h. When the reaction had cooled to rt, the mixture was diluted with water (200 mL) and extracted with DCM (2×200 mL). The combined organic extracts were concentrated and purified via silica gel chromatography eluted with 20%-40% EtOAc in petroleum ether to give the product as a gum. $^1$H NMR (400 MHz, $CDCl_3$) δ ppm 1.51 (t, J=7.2 Hz, 3H), 2.45 (s, 3H), 3.22 (q, J=7.2 Hz, 2H), 6.32 (s, 1H), 7.70 (s, 1H), 7.93 (s, 1H).

Intermediate 14: 8-Acetyl-2-ethylsulfanyl-6-methyl-chromen-4-one

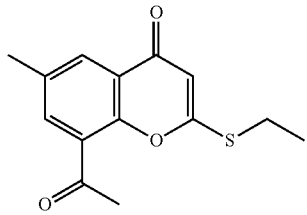 [SMILES: CCSc1cc(=O)c2cc(C)cc(C(C)=O)c2o1]

A mixture of 8-bromo-2-ethylsulfanyl-6-methyl-chromen-4-one (9.00 g, 30.0 mmol), tributyl(1-ethoxyvinyl) tin (13.3 g, 36.8 mmol) and Pd(PPh$_3$)$_2$Cl$_2$ (2.11 g, 3.01 mmol) in dioxane (90 mL) was stirred at 95° C. for 16 h. HCl (30 mL, 1 M) was added to the mixture and stirred at 50° C. for 0.5 h. When cooled to rt, the mixture was treated with saturated aqueous KF (100 mL) and stirred for 0.5 h, then filtered. The filter cake was washed with EtOAc (3×40 mL). The filtrate was extracted with EtOAc (2×80 mL). The combined organic extracts were concentrated and purified on a silica gel column eluted with 0-60% EtOAc in petroleum ether to give the product as a solid (5.8 g, 60%). MS ES+ m/z 263 [M+H]$^+$.

Intermediate 15: (NE,R)—N-[1-(2-Ethylsulfanyl-6-methyl-4-oxo-chromen-8-yl)ethylidene]-2-methyl-propane-2-sulfinamide

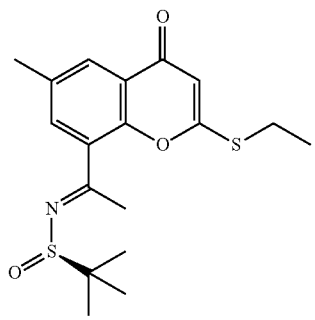 [SMILES: CCSc1cc(=O)c2cc(C)cc(/C(C)=N/[S@](=O)C(C)(C)C)c2o1]

A mixture of 8-acetyl-2-ethylsulfanyl-6-methyl-chromen-4-one (9.49 g, 36.2 mmol) and (R)-2-methylpropane-2-sulfinamide (8.77 g, 72.4 mmol) in THF (100 mL) was treated with Ti(i-PrO)$_4$ (41.1 g, 145 mmol) and stirred at 75° C. for 16 h. The reaction was treated with additional (R)-2-methylpropane-2-sulfinamide (6.58 g, 54.3 mmol) and Ti(i-PrO)$_4$ (30.9 g, 109 mmol) and stirred at 75° C. for another 16 h. The mixture was quenched with brine (200 mL), stirred for 0.5 h, and filtered. The filter cake was washed with EtOAc (300 mL). The aqueous layer was extracted with EtOAc (2×300 mL). The combined organic extracts were washed with brine (2×200 mL), dried over anhydrous Na$_2$SO$_4$, filtered, and concentrated to give the product as a solid (13 g, crude). MS ES+ m/z 366 [M+H]$^+$.

Intermediate 16: (R)—N-[(1R)-1-(2-Ethylsulfanyl-6-methyl-4-oxo-chromen-8-yl)ethyl]-2-methyl-propane-2-sulfinamide

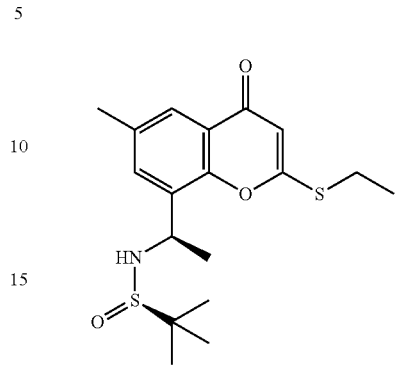

A mixture of (NE,R)—N-[1-(2-ethylsulfanyl-6-methyl-4-oxo-chromen-8-yl)ethylidene]-2-methyl-propane-2-sulfinamide (12.0 g, 32.8 mmol) in DCM (100 mL) and MeOH (100 mL) was treated with AcOH (15.8 g, 262 mmol) and NaBH$_3$CN (6.19 g, 98.5 mmol) at −10° C., and stirred at 25° C. for 16 h. The mixture was quenched with NH$_3$·H$_2$O (250 mL) and extracted with DCM (3×200 mL). The combined organic extracts were washed with brine (300 mL), dried over anhydrous Na$_2$SO$_4$, filtered, and concentrated to give the product as a solid (11 g, isomer ratio: 3/2, crude). MS ES+ m/z 368 [M+H]$^+$.

Intermediate 17: 8-[(1R)-1-Aminoethyl]-2-ethylsulfanyl-6-methyl-chromen-4-one

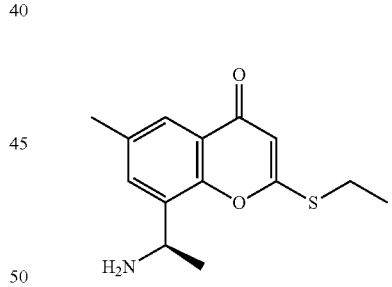

A mixture of (R)—N-[(1R)-1-(2-ethylsulfanyl-3,6-dimethyl-4-oxo-chromen-8-yl)ethyl]-2-methyl-propane-2-sulfinamide (6.00 g, 16.3 mmol) in EtOAc (40 mL) was treated with HCl (82 mL, 4 M in EtOAc) and stirred at 25° C. for 16 h. The mixture was concentrated, diluted with water (100 mL), and washed with EtOAc (100 mL). The pH of the aqueous phase was adjusted to 8 with NH$_3$·H$_2$O (25%) and extracted with DCM (3×100 mL). The combined organic phases were washed with brine (100 mL), dried over anhydrous Na$_2$SO$_4$, filtered, and concentrated to give the product as an oil (2.4 g, crude). MS ES+ m/z 264 [M+H]$^+$.

Intermediate 18: Methyl 6-chloro-3-[[(1R)-1-(2-ethylsulfanyl-6-methyl-4-oxo-chromen-8-yl)ethyl]amino]pyridine-2-carboxylate

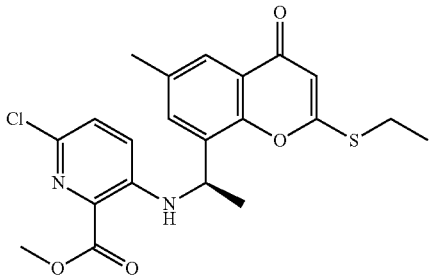 [SMILES: CCSc1cc(=O)c2cc(C)cc([C@@H](C)Nc3ccc(Cl)nc3C(=O)OC)c2o1]

A mixture of 8-[(1R)-1-aminoethyl]-2-ethylsulfanyl-6-methyl-chromen-4-one (880 mg, 3.34 mmol), methyl 6-chloro-3-fluoro-pyridine-2-carboxylate (950 mg, 5.01 mmol) and DIEA (2.16 g, 16.7 mmol) in DMF (10 mL) was stirred at 100° C. for 21 h. The mixture was diluted with water (30 mL) and extracted with EtOAc (2×30 mL). The combined organic extracts were washed with brine (10 mL), dried over anhydrous $Na_2SO_4$, filtered, and concentrated. The residue was purified by silica gel chromatography eluted with 0%-35% EtOAc in petroleum ether to give the product as a solid (1.08 g, yield: 75%). MS ES+ m/z 433 $[M+H]^+$.

Intermediate 19: Methyl 6-chloro-3-[[(1R)-1-(6-methyl-4-oxo-2-phenyl-chromen-8-yl)ethyl]amino]pyridine-2-carboxylate

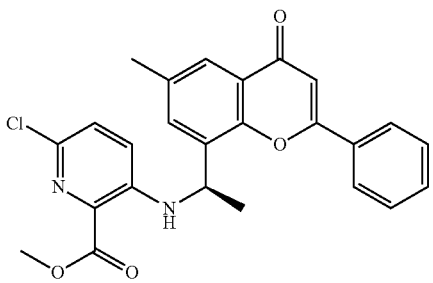 [SMILES: COC(=O)c1nc(Cl)ccc1N[C@H](C)c1cc(C)cc2c(=O)cc(-c3ccccc3)oc12]

A mixture of methyl 6-chloro-3-[[(1R)-1-(2-ethylsulfanyl-6-methyl-4-oxo-chromen-8-yl)ethyl]amino]pyridine-2-carboxylate (150 mg, 346.48 umol), phenylboronic acid (168.99 mg, 1.39 mmol), thiophene-2-carbonyloxycopper (132.14 mg, 692.97 umol), Pd(PPh$_3$)$_4$ (40.04 mg, 34.65 umol), and Cs$_2$CO$_3$ (338.67 mg, 1.04 mmol) in 2-MeTHF (2 mL) was stirred at 90° C. for 24 h to give a black suspension. After cooling to rt, filtered the reaction and concentrated to a residue which was purified via flash silica gel chromatography using a gradient of EtOAc (0-30%) in petroleum ether to give the product as a yellow oil (88 mg, 54%). MS ES+ m/z 449 $[M+H]^+$.

Intermediate 20: 2-Ethylsulfanyl-8-(1-hydroxyethyl)-6-methyl-chromen-4-one

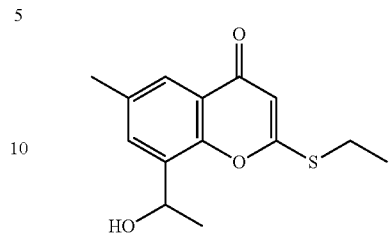

A solution of 8-acetyl-2-ethylsulfanyl-6-methyl-chromen-4-one (8.30 g, 31.6 mmol) in DCM (30 mL) and MeOH (30 mL) was treated with NaBH$_4$ (1.32 g, 34.8 mmol) in portions at 0° C., and stirred at 15° C. for 1 h. The mixture was diluted with water (50 mL) and extracted with DCM (2×100 mL). The combined organic extracts were washed with brine (80 mL), dried over anhydrous Na$_2$SO$_4$, filtered, and concentrated. The residue was purified on a silica gel column eluted with 04% MeOH in DCM to give the product as a solid (6.0 g, 60%). MS ES+ m/z 265 $[M+H]^+$.

Intermediate 21: 8-(1-Bromoethyl)-2-ethylsulfanyl-6-methyl-chromen-4-one

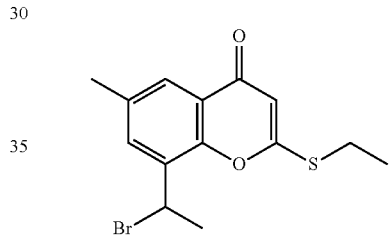

A mixture of 2-ethylsulfanyl-8-(1-hydroxyethyl)-6-methyl-chromen-4-one (5.50 g, 20.8 mmol) in DCM (50 mL) was treated dropwise with PBr$_3$ (16.9 g, 62.4 mmol) at 0° C., then stirred at 30° C. for 4 h. The reaction was quenched with water (20 mL) at 0° C. and the pH adjusted to 8 with saturated aqueous NaHCO$_3$. The mixture was extracted with DCM (2×80 mL). The combined organic extracts were washed with brine, dried over anhydrous Na$_2$SO$_4$, filtered, and concentrated to give the product as an oil (4.7 g, 61%). MS ES+ m/z 329 $[M+2+H]^+$.

Intermediate 22: tert-Butyl 2-[1-(2-ethylsulfanyl-6-methyl-4-oxo-chromen-8-yl)ethylamino]benzoate

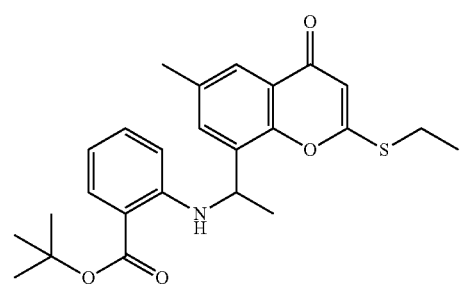 [SMILES: CCSc1cc(=O)c2cc(C)cc(C(C)Nc3ccccc3C(=O)OC(C)(C)C)c2o1]

8-(1-Bromoethyl)-2-ethylsulfanyl-6-methyl-chromen-4-one (25.0 g, 76.4 mmol), tert-butyl 2-aminobenzoate (29.5 g, 153 mmol) and DIEA (14.8 g, 20.0 mL, 115 mmol) were combined with DMF (150 mL) in a 500 mL round bottom flask and heated at 80° C. After cooling to rt, the reaction was partially concentrated to ~100 mL, poured into 1.1 L of water, and extracted with EtOAc (2×350 mL). The combined organic layers were washed with brine (400 mL). The combined aqueous layers were re-extracted with fresh EtOAc. The organic layers were combined, dried over anhydrous $Na_2SO_4$, filtered, and concentrated to give a thick oil. Purified the residue via silica gel chromatography using EtOAc in DCM (0% to 10%) to provide an off-white foam. Triturated with heptanes/DCM and washed with heptanes to give the product as a white solid (27.1 g, 81%). MS ES+ m/z 440 [M+H]+.

Intermediate 23: tert-Butyl 2-[1-[2-[3-(1-cyano-1-methyl-ethyl)phenyl]-6-methyl-4-oxo-chromen-8-yl]ethylamino]benzoate

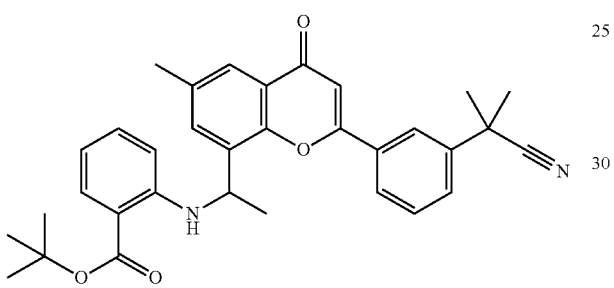

Combined tert-butyl 2-[1-(2-ethylsulfanyl-6-methyl-4-oxo-chromen-8-yl)ethylamino]benzoate (150 mg, 341 μmol), (3-(2-cyanopropan-2-yl)phenyl)boronic acid (96.8 mg, 512 μmol), tris(dibenzylideneacetone)dipalladium(0) (31.2 mg, 34.1 μmol), copper(I) thiophene-2-carboxylate (97.6 mg, 512 μmol), cesium carbonate (334 mg, 1.02 mmol), and tri(2-furyl)phosphine (7.92 mg, 34.1 μmol) in 1,4-dioxane (5 mL) and heated at 85° C. for 12 h. The crude product mixture was filtered, concentrated, and purified using silica column (10-80% ethyl acetate in heptane) to afford the product (110.0 mg, 62%). MS ESI+ m/z 523 [M+H]+.

Intermediate 24: Methyl 3-bromo-2-hydroxy-5-methyl-benzoate

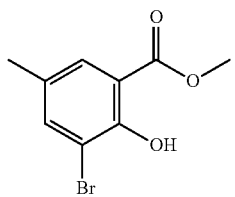

Bromine (1.0 g, 6.3 mmol) was added to a stirred mixture of methyl 2-hydroxy-5-methylbenzoate (1.0 g, 0.87 mL, 6.0 mmol) and sodium acetate (0.74 g, 9.0 mmol) in AcOH (5 mL) at rt. After 15 min, added water (20 mL) and filtered. The solids were washed with water (5 mL) and assumed quantitative yield. MS ES+ m/z 245,247 [M+H]+.

Intermediate 25: 3-(3-Bromo-2-hydroxy-5-methyl-phenyl)-3-oxo-propanenitrile

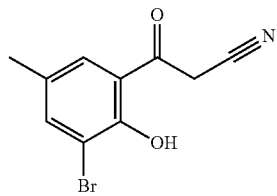

Sodium hydride (408 mg, 60% wt, 10.2 mmol) was added to a solution of methyl 3-bromo-2-hydroxy-5-methylbenzoate (1.00 g, 4.08 mmol) in THF (5 mL) at rt. After ~65 minutes, acetonitrile (234 μL, 4.49 mmol) was added to the above mixture and the reaction allowed to stir at rt for ~2 h. Concentrated the reaction and added EtOAc and AcOH to the residue and diluted with heptanes. The resulting solids were removed by filtration and washed with heptanes to give the product as an orange solid (0.95 g, 92%). MS ES+ m/z 254,256 [M+H]+.

Intermediate 26: 8-Bromo-6-methyl-4-oxo-2-phenyl-chromene-3-carbonitrile

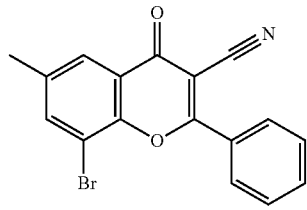 [SMILES: Cc1cc(Br)c2oc(-c3ccccc3)c(C#N)c(=O)c2c1]

Benzoyl chloride (74.1 mg, 61.3 μL, 527 μmol) was added to 3-(3-bromo-2-hydroxy-5-methylphenyl)-3-oxopropanenitrile (134 mg, 527 μmol) in pyridine (4 mL) at rt. After 90 min, toluene (2 mL) was added and the reaction mixture was concentrated. The crude product was purified by column chromatography, eluting with DCM, to give the product (115 mg, 64%). MS ES+ m/z 340,342 [M+H]+.

Intermediate 27 and Intermediate 28: tert-Butyl 2-[1-(2-ethylsulfanyl-6-methyl-4-oxo-chromen-8-yl)ethylamino]benzoate, Isomer 1 and Isomer 2

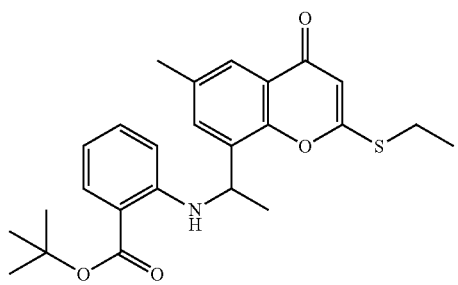 [SMILES: CCSc1cc(=O)c2cc(C)cc(C(C)Nc3ccccc3C(=O)OC(C)(C)C)c2o1]

tert-Butyl 2-[1-(2-ethylsulfanyl-6-methyl-4-oxo-chromen-8-yl)ethylamino]benzoate (22.04 g, 50.14 mmol) was separated into component isomers using a Chiralcel OJ column (8×34 cm; 20 micron) eluted with 100% MeOH with 0.2% DMEA to give isomer 1 (wet 11.3 g) and isomer 2 (wet 12.9 g). MS ES+ m/z 440 [M+H]+.

Intermediate 29: tert-Butyl 2-[1-(6-methyl-4-oxo-2-phenyl-chromen-8-yl)ethylamino]benzoate, Isomer 2

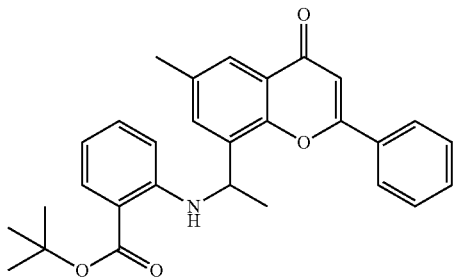 [SMILES: Cc1cc(C(C)Nc2ccccc2C(=O)OC(C)(C)C)c2oc(-c3ccccc3)cc(=O)c2c1]

Combined tert-butyl 2-[1-(2-ethylsulfanyl-6-methyl-4-oxo-chromen-8-yl)ethylamino]benzoate, Isomer 2 (1.00 g, 2.27 mmol), phenylboronic acid (0.56 g, 4.55 mmol), tris(dibenzylideneacetone)dipalladium(0) (0.21 g, 0.23 mmol), copper(I) thiophene-2-carboxylate (0.87 g, 4.55 mmol), zinc (II) acetate (0.84 g, 4.55 mmol), and tri(2-furyl)phosphine (0.26 g, 1.14 mmol) in 1,4-dioxane (20 mL) and heated at 85° C. for 12 h. The crude product mixture was purified using silica column (10-60% ethyl acetate in heptane), then reversed phase chromatography (0-100% acetonitrile in water, with 0.1% TFA) to afford the product (0.53 g, 48%). MS ES+ m/z 456 [M+H]+.

Intermediate 30: tert-Butyl 2-[1-(3-iodo-6-methyl-4-oxo-2-phenyl-chromen-8-yl)ethylamino]benzoate, Isomer 2

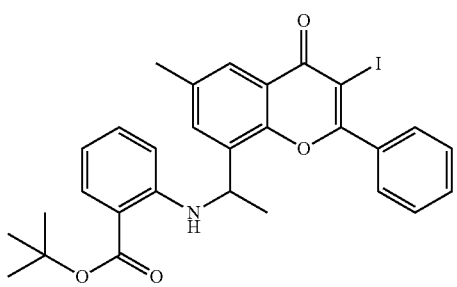 [SMILES: Cc1cc(C(C)Nc2ccccc2C(=O)OC(C)(C)C)c2oc(-c3ccccc3)c(I)c(=O)c2c1]

A dry flask equipped with a stir bar and septum was flushed with argon gas and then charged with tert-butyl 2-[1-(6-methyl-4-oxo-2-phenyl-chromen-8-yl)ethylamino]benzoate, Isomer 2 (0.53 g, 1.16 mmol) and 3 mL of dry THF. The reaction was cooled in an ice bath. When cold, 2,2,6,6-tetramethylpiperidinylzinc chloride lithium chloride complex (1M in THF, 3.5 mL, 3.50 mmol) was added dropwise via addition funnel over 30 min. After addition was complete, allowed the reaction to stir at rt for 7 h. The reaction was cooled in an ice bath and iodine in dry THF (1M, 1.39 mL, 1.39 mmol) was added dropwise via addition funnel. After addition was complete, the reaction was stirred at 0° C. for 1 h and rt for 12 h. The reaction was cooled to −40° C. and quenched with methanol (10 mL). Added 50 mL of an ammonium chloride/ammonia solution (aqueous 2M solution; 50 mL) and stirred the reaction at rt for 2 h. Extracted three times with 300 mL of dichloromethane. The organics were combined, washed with aqueous sodium carbonate, collected, dried over Na2SO4, filtered, and concentrated. The residue was purified by reversed phase chromatography (0-100% acetonitrile in water, with 0.1% TFA), then using silica column (0-40% ethyl acetate in heptane) to give the product (0.43 g, 61%). MS ES+ m/z 582 [M+H]+.

Intermediate 31: tert-Butyl 2-[1-(3-isoxazol-4-yl-6-methyl-4-oxo-2-phenyl-chromen-8-yl)ethylamino]benzoate, Isomer 2

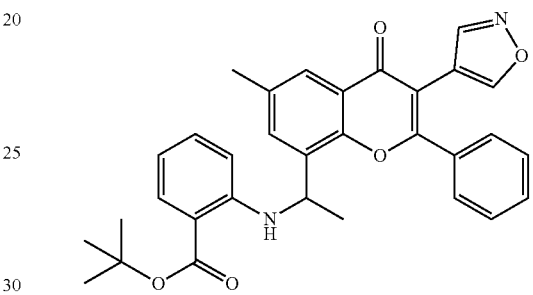

Combined tert-butyl 2-[1-(3-iodo-6-methyl-4-oxo-2-phenyl-chromen-8-yl)ethylamino]benzoate, Isomer 2 (0.34 g, 0.58 mmol), 1,2-oxazol-4-ylboronic acid (0.098 g, 0.87 mmol), potassium phosphate (0.25 g, 1.16 mmol), and 1,1'-bis(diphenylphosphino)ferrocene-palladium(II) dichloride (0.043 g, 0.058 mmol) in THF:water (4:1, 20 mL) and heated at 80° C. for 16 h. The crude product mixture was purified using silica column (0-10% ethyl acetate in DCM) to afford the product (0.052 g, 16%). MS ES+ m/z 523 [M+H]+.

Intermediate 32: tert-Butyl 2-[1-[6-methyl-4-oxo-2-phenyl-3-(trifluoromethyl)chromen-8-yl]ethylamino]benzoate, Isomer 2

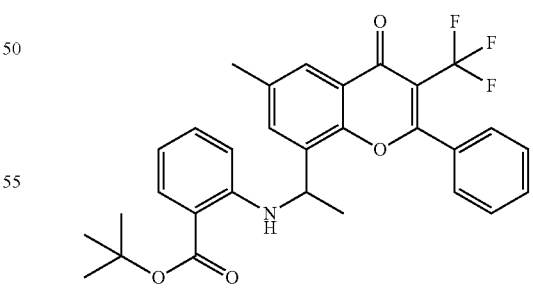

Combined tert-butyl 2-[1-(3-iodo-6-methyl-4-oxo-2-phenyl-chromen-8-yl)ethylamino]benzoate, Isomer 2 (0.086 g, 0.15 mmol), copper(I) iodide (0.034 g, 0.18 mmol), and methyl difluoro(fluorosulfonyl)acetate (0.14 g, 0.74 mmol) in DMF (2 mL) and stirred for 18 h. The reaction mixture was cooled to rt and quenched with saturated aqueous ammonium chloride (1 mL). Extracted two times with 1 mL of dichloromethane. The organics were combined, dried over Na$_2$SO$_4$, filtered, and concentrated. The residue was purified by silica column (0-20% ethyl acetate in DCM) to give the product (0.053 g, 68%). MS ES+ m/z 524 [M+H]$^+$.

Intermediate 33: 1-[3-Bromo-2-hydroxy-5-(trifluoromethyl)phenyl]ethanone

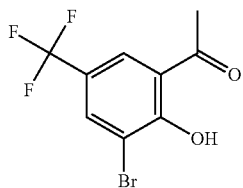

To a mixture of 2-bromo-4-(trifluoromethyl)phenol (50.0 g, 207 mmol) in 1,4-dioxane (400 mL) was added Pd(PPh$_3$)$_2$Cl$_2$ (7.28 g, 10.37 mmol) and tributyl(1-ethoxyvinyl)stannane (90.0 g, 249 mmol) under N$_2$ atmosphere, and stirred at 95° C. for 16 h. To the reaction was added HCl (1 M, 207 mL) and stirred at 50° C. for 1 h. When cooled to rt, to the mixture was added saturated aqueous potassium fluoride (200 mL), stirred for 0.5 h and filtered. The aqueous layer was extracted with DCM (100 mL×2). The combined organic layer was washed with brine (150 mL×2), dried over anhydrous Na$_2$SO$_4$, filtered and concentrated to give 1-[2-hydroxy-5-(trifluoromethyl)phenyl]ethanone (31 g, crude).

A mixture of bromine (29.0 g, 182 mmol) in AcOH (50 mL) was added to a mixture of 1-[2-hydroxy-5-(trifluoromethyl)phenyl]ethanone (31.0 g, 152 mmol) and sodium acetate (15.0 g, 182 mmol) in AcOH (250 mL) dropwise at 0° C., and stirred at 20° C. for 16 h. The reaction mixture was poured into ice and water (500 mL) and filtered. The filter cake was dried in vacuum to give the product (31 g, yield: 72%).

Intermediate 34: (E)-1-(3-Bromo-2-hydroxy-5-methyl-phenyl)-3-(dimethylamino)prop-2-en-1-one

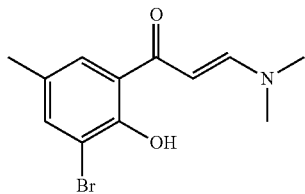

Combined 1-(3-bromo-2-hydroxy-5-methyl-phenyl)ethenone (13.06 g, 57.01 mmol) and N,N-dimethylformamide dimethyl acetal (7.57 mL, 57.01 mmol) in toluene (45 mL) and stirred at 80° C. for 1 h. The reaction mixture was concentrated to dryness, taken up in hot ethyl acetate/heptane, and filtered to remove solids that were discarded. The filtrate was concentrated until material crystallized, then filtered. The solids were washed with heptane and dried to give product (9.92 g, 61%) that was used in the next reaction.

Intermediate 35: 8-Bromo-3-fluoro-6-methyl-chromen-4-one

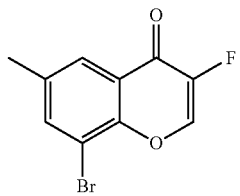

To a stirred solution of (E)-1-(3-bromo-2-hydroxy-5-methyl-phenyl)-3-(dimethylamino)prop-2-en-1-one (9.92 g, 34.91 mmol) in THF (140 mL) was added N-chloromethyl-N-fluorotriethylenediammonium bis(tetrafluoroborate) (12.37 g, 34.91 mmol). After 4 h, the reaction mixture was concentrated to dryness. The residue was purified by silica column (0-10% ethyl acetate in heptane) to give the product (4.14 g, 44%). MS ES+ m/z 257 [M+H]$^+$.

Intermediate 36: tert-Butyl 2-[1-(3-fluoro-6-methyl-4-oxo-chromen-8-yl)ethylamino]benzoate

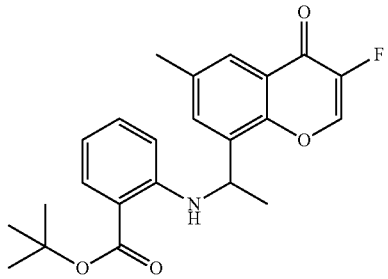 [SMILES: Cc1cc(C(C)Nc2ccccc2C(=O)OC(C)(C)C)c2occ(F)c(=O)c2c1]

Intermediate 36 can be made according to the foregoing Intermediates. MS ES+ m/z 398 [M+H]$^+$.

Intermediate 37: tert-Butyl 2-[1-(3-fluoro-6-methyl-4-oxo-2-phenyl-chromen-8-yl)ethylamino]benzoate

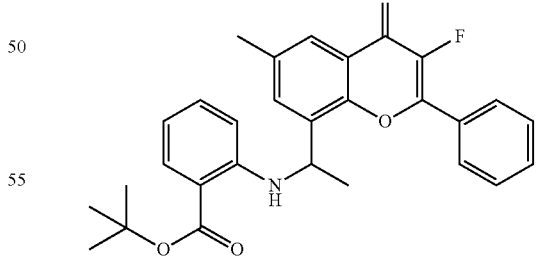

A dry flask equipped with a stir bar and septum was flushed with argon gas and then charged with tert-butyl 2-[1-(3-fluoro-6-methyl-4-oxo-chromen-8-yl)ethylamino]benzoate (0.23 g, 0.57 mmol) and magnesium chloride (0.4 M in dry THF, 5.24 mL, 2.09 mmol). The reaction was cooled to −5° C. When cold, 2,2,6,6-tetramethylpiperidinylzinc chloride lithium chloride complex (1M in THF, 2.26 mL, 2.26 mmol) was added dropwise via addition funnel.

After addition was complete, allowed the reaction to stir at 0° C. for 30 min. Added iodine (1M in dry THF, 1.13 mL, 1.13 mmol) dropwise via addition funnel over 30 min. Diluted with dichloromethane and washed with aqueous sodium thiosulfate. The organics were dried over $Na_2SO_4$, filtered, and concentrated. The residue was purified by silica column (0-100% ethyl acetate in heptane) to give tert-butyl 2-[1-(3-fluoro-2-iodo-6-methyl-4-oxo-chromen-8-yl)ethylamino]benzoate (0.14 g, 45%). MS ES+ m/z 524 [M+H]+.

Combined tert-butyl 2-[1-(3-fluoro-2-iodo-6-methyl-4-oxo-chromen-8-yl)ethylamino]benzoate (0.13 g, 0.25 mmol), phenylboronic acid (0.045 g, 0.37 mmol), potassium phosphate (0.11 g, 0.50 mmol), and 1,1'-bis(diphenylphosphino)ferrocene-palladium(II) dichloride (0.018 g, 0.025 mmol) in THF:water (4:1, 20 mL) and heated at 80° C. for 15 min. The crude product mixture was concentrated, then purified using silica column (0-30% ethyl acetate in heptane) to afford the product (0.060 g, 51%). MS ES+ m/z 474 [M+H]+.

Intermediate 38: 8-Acetyl-6-methyl-2-phenyl-chromen-4-one

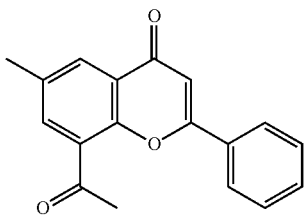 [SMILES: CC(=O)c1cc(C)cc2c(=O)cc(-c3ccccc3)oc12]

Intermediate 38 can be made according to the foregoing Intermediates. MS ES+ m/z 279 [M+H]+.

Intermediate 39: 8-[(1S)-1-Hydroxyethyl]-6-methyl-2-phenyl-chromen-4-one

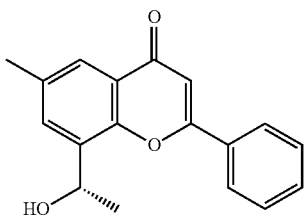 [SMILES: Cc1cc([C@H](C)O)c2oc(-c3ccccc3)cc(=O)c2c1]

A solution of 8-acetyl-6-methyl-2-phenyl-chromen-4-one (30 g, 108 mmol), formic acid (14.9 g, 324 mmol), and RuCl(p-cymene)[(S,S)-Ts-DPEN] (CAS 192139-90-5, 2.04 g, 3.24 mmol) in DCM (300 mL) was stirred at 0-5° C. 1,8-Diazabicyclo[5.4.0]undec-7-ene (4.93 g, 324 mmol) was added dropwise, maintaining the temperature below 10° C. The reaction was stirred at room temperature for 14 h. Diluted with DCM (300 mL) and washed with saturated aqueous sodium bicarbonate and brine. The organics were concentrated, slurried in acetonitrile (150 mL) for 30 min, and filtered to afford the product (27.8 g, 91%). MS ES+ m/z 281 [M+H]+.

Intermediate 40: [(1S)-1-(6-Methyl-4-oxo-2-phenyl-chromen-8-yl)ethyl] methanesulfonate

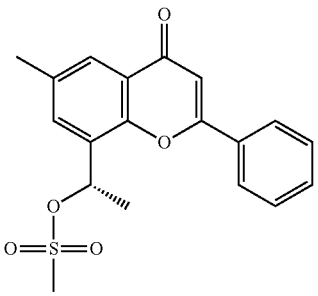 [SMILES: Cc1cc([C@H](C)OS(C)(=O)=O)c2oc(-c3ccccc3)cc(=O)c2c1]

A solution of 8-[(1S)-1-hydroxyethyl]-6-methyl-2-phenyl-chromen-4-one (30 g, 107 mmol) in DCM (300 mL) was stirred at 0-5° C. Methanesulfonic anhydride (54.7 g, 314 mmol) was added, followed by dropwise addition of diisopropylethylamine (41.5 g, 321 mmol), maintaining the temperature below 15° C. The reaction was stirred at room temperature for 2 h. Diluted with DCM (150 mL) and washed with saturated aqueous sodium bicarbonate and brine. The organics were dried over magnesium sulfate, filtered, and concentrated to afford the product (48.6 g, 100%). $^1$H NMR (400 MHz, DMSO-d6) δ ppm 1.84 (d, J=6.5 Hz, 3H), 2.40 (s, 6H), 6.33 (q, J=6.3 Hz, 1H), 7.10 (s, 1H), 7.59-7.67 (m, 3H), 7.81 (d, J=2.3 Hz, 1H), 7.90-7.94 (m, 1H), 8.12-8.20 (m, 2H).

Intermediate 41: 8-[(1R)-1-Hydroxyethyl]-3,6-dimethyl-2-phenyl-chromen-4-one

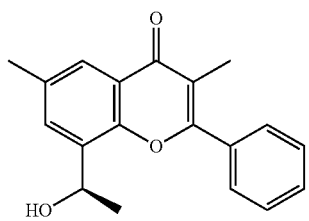 [SMILES: Cc1cc([C@@H](C)O)c2oc(-c3ccccc3)c(C)c(=O)c2c1]

Intermediate 41 can be made according to the foregoing Intermediates. MS ES+ m/z 295 [M+H]+.

Intermediate 42: 8-[(1S)-1-Chloroethyl]-3,6-dimethyl-2-phenyl-chromen-4-one

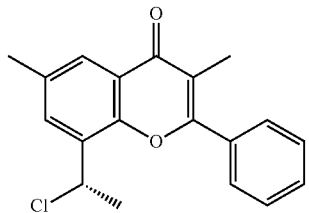 [SMILES: Cc1cc([C@H](C)Cl)c2oc(-c3ccccc3)c(C)c(=O)c2c1]

A solution of 8-[(1R)-1-hydroxyethyl]-3,6-dimethyl-2-phenyl-chromen-4-one (20 g, 68.0 mmol) in cyclopentyl methyl ether (200 mL) was stirred at room temperature.

2,4,6-Trichloro[1,3,5]triazine (12.5 g, 68.0 mmol) was added, followed by DMF (7.9 mL, 102 mmol). The reaction was stirred at room temperature for 14 h. Diluted with 2M aqueous sodium hydroxide (100 mL) and separated the layers. The organics were washed with water (100 mL)/saturated aqueous sodium bicarbonate (100 mL) and 5% aqueous lithium chloride (100 mL). The organics were concentrated and diluted with isopropanol (120 mL). The slurry was heated at 45° C. for 2 h and cooled to room temperature. Water (80 mL) was slowly added. Filtered to afford the product (18.4 g, 87%, 94% ee). MS ES+ m/z 313 [M+H]+.

Intermediate 43: Methyl 3-[[(1R)-1-(3,6-dimethyl-4-oxo-2-phenyl-chromen-8-yl)ethyl]amino]pyridine-2-carboxylate

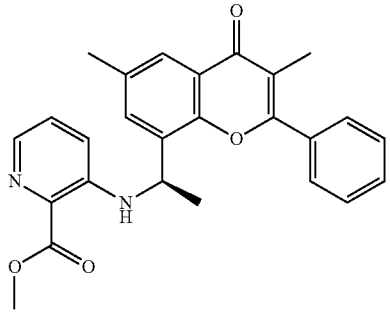 [SMILES: COC(=O)c1ncccc1N[C@H](C)c1cc(C)cc2c(=O)c(C)c(-c3ccccc3)oc12]

A solution of 8-[(1S)-1-chloroethyl]-3,6-dimethyl-2-phenyl-chromen-4-one (5.0 g, 16 mmol) and methyl 3-aminopicolinate (15 g, 96 mmol) in tert-amyl alcohol (25 mL) was stirred at room temperature. Triethylamine (8.9 mL, 64 mmol) was added. The reaction was stirred at 100° C. for 24 h, cooled to room temperature, and concentrated. Diluted with methyl tert-butyl ether (25 mL) and 1M aqueous hydrochloric acid (25 mL). Filtered to afford the product (4.7 g, 68%). MS ES+ m/z 429 [M+H]+.

Example 1: 6-Chloro-3-[[(1R)-1-(3,6-dimethyl-4-oxo-2-phenyl-chromen-8-yl)ethyl]amino]pyridine-2-carboxylic acid

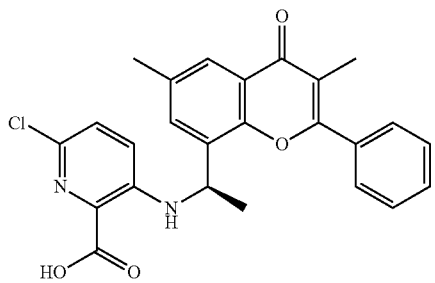 [SMILES: Cc1cc([C@@H](C)Nc2ccc(Cl)nc2C(=O)O)c2oc(-c3ccccc3)c(C)c(=O)c2c1]

A mixture of methyl 6-chloro-3-[[(1R)-1-(3,6-dimethyl-4-oxo-2-phenyl-chromen-8-yl)ethyl]amino]pyridine-2-carboxylate (1 g, 2.16 mmol) and NaOH (2 M, 7.35 mL) in MeOH (20 mL) was stirred at 45° C. for 2 h to give a white suspension. Added 10 mL of water, adjusted the pH to 3 with 2M aqueous HCl, and extracted with EtOAc (2×10 mL). The combined organic phases were washed with brine (20 mL), dried over anhydrous Na2SO4, filtered, and concentrated to give a residue. The residue was triturated with acetonitrile (5 mL) to give the product as a white solid (418 mg, 42%). MS ES+ m/z 449 [M+H]+.

Example 2: 6-Chloro-3-[[(1R)-1-(6-methyl-4-oxo-2-phenyl-chromen-8-yl)ethyl]amino]pyridine-2-carboxylic acid

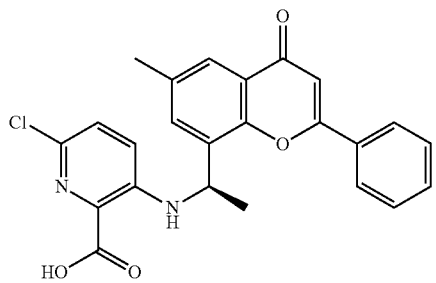 [SMILES: Cc1cc([C@@H](C)Nc2ccc(Cl)nc2C(=O)O)c2oc(-c3ccccc3)cc(=O)c2c1]

Solid NaOH (124.74 mg, 3.12 mmol) was dissolved in water (0.7 mL) and added to the mixture of methyl 6-chloro-3-[[(1R)-1-(6-methyl-4-oxo-2-phenyl-chromen-8-yl)ethyl]amino]pyridine-2-carboxylate (700.00 mg, 1.56 mmol) in MeOH (7 mL). The mixture was stirred at 50° C. for 1 hour to give a yellow suspension. The reaction was poured into water (100 mL), the pH adjusted to 2 with aqueous HCl (2 M), and the mixture extracted with DCM (3×50 mL). The combined organic layers were washed with brine (50 mL), dried over Na2SO4, filtered, and concentrated to a residue. The residue was triturated with refluxing acetonitrile (2×5 mL) to give the product as a light yellow solid (293 mg, 43%). MS ES+ m/z 435 [M+H]+.

Example 3: 2-[1-[2-[3-(1-Cyano-1-methyl-ethyl)phenyl]-6-methyl-4-oxo-chromen-8-yl]ethylamino]benzoic acid 2,2,2-trifluoroacetic acid

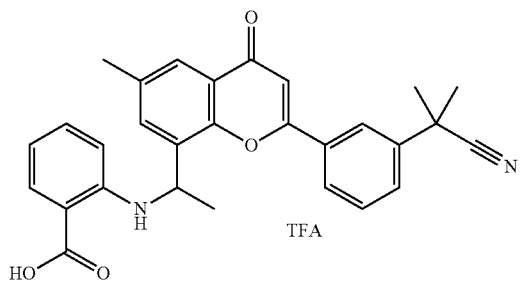 [SMILES: Cc1cc(C(C)Nc2ccccc2C(=O)O)c2oc(-c3cccc(C(C)(C)C#N)c3)cc(=O)c2c1]

Combined tert-butyl 2-[1-[2-[3-(1-cyano-1-methyl-ethyl)phenyl]-6-methyl-4-oxo-chromen-8-yl]ethylamino]benzoate (110.0 mg, 210.5 μmol) and TFA (3.0 g, 2.0 mL, 26 mmol) in DCM (2 mL) and heated at 40° C. for 3 hours. Concentrated the reaction and purified using a C-18 column, eluted with 10-90% acetonitrile in water (0.1% TFA additive), to give the product (45.0 mg, 46%). MS ES+ m/z 467 [M+H]+.

Example 4 and Example 5: 2-[1-[2-[3-(1-Cyano-1-methyl-ethyl)phenyl]-6-methyl-4-oxo-chromen-8-yl]ethylamino]benzoic acid, Isomer 1 and Isomer 2

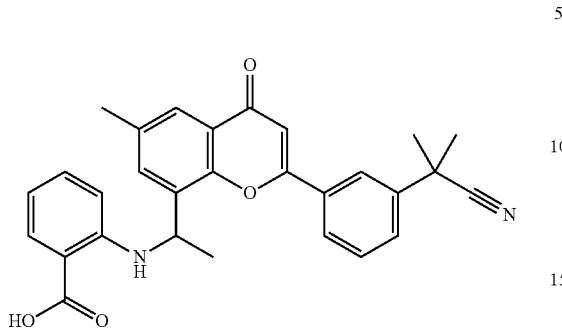

Dissolved 2-[1-[2-[3-(1-cyano-1-methyl-ethyl)phenyl]-6-methyl-4-oxo-chromen-8-yl]ethylamino]benzoic acid 2,2,2-trifluoroacetic acid (40 mg) in MeOH (2.25 mL) and DCM (2.25 mL). Separated via supercritical fluid chromatography (Chiralpak AS-H, 250 mm×21 mm; 20% MeOH w/0.5% DMEA: 80% CO$_2$) to obtain the product isomers (20 mg, 19 mg). MS ES+ m/z 467 [M+H]$^+$, for both.

Example 22: 2-[[(1R)-1-(6-Methyl-4-oxo-2-phenyl-chromen-8-yl)ethyl]amino]benzoic acid

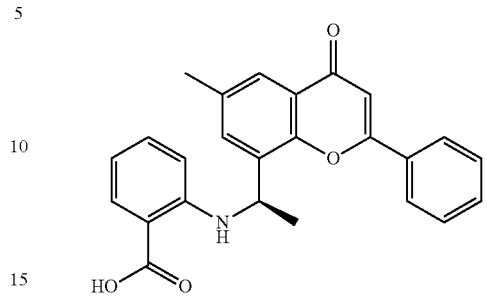

A solution of [(1S)-1-(6-methyl-4-oxo-2-phenyl-chromen-8-yl)ethyl] methanesulfonate (48.6 g, 107 mmol) in DCM (480 mL) was stirred at room temperature. Anthranilic acid (44.0 g, 321 mmol), followed slowly by 2,6-lutidine (22.9 g, 214 mmol) was added. The reaction was stirred at room temperature for 14 h. Diluted with DCM (240 mL) and washed with 1M aqueous hydrochloric acid (3×240 mL) and brine. The organics were dried over magnesium sulfate, filtered, and concentrated. Slurried in acetonitrile (200 mL) for 30 min and filtered to afford the product as a yellow solid (24.2 g, 57%). MS ES− m/z 398 [M−H]$^−$.

The following compounds in Table 1 can be made according to Schemes 1-4 or the foregoing Examples.

TABLE 1

| Example # | Chemical Name | Structure | MS ES+ m/z |
|---|---|---|---|
| 6 | 2-[1-(6,7-Difluoro-4-oxo-2-phenyl-chromen-8-yl)ethylamino]benzoic acid 2,2,2-trifluoroacetic acid | 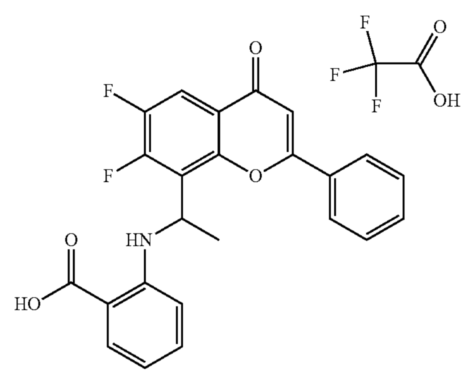 | 422 [M + H]$^+$ |
| 7 | 2-[1-[2-[4-(1-Cyanocyclopropyl)-phenyl]-6-methyl-4-oxo-chromen-8-yl]ethylamino]benzoic acid | 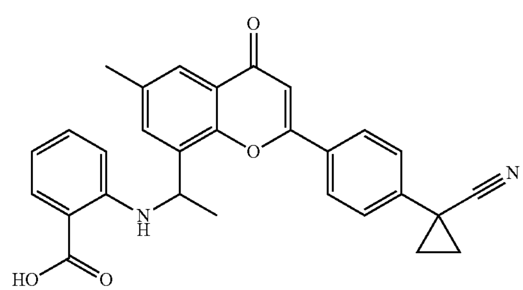 [SMILES: Cc1cc(C(C)Nc2ccccc2C(=O)O)c2oc(-c3ccc(C4(C#N)CC4)cc3)cc(=O)c2c1] | 465 [M + H]$^+$ |

TABLE 1-continued

| Example # | Chemical Name | Structure | MS ES+ m/z |
|---|---|---|---|
| 8 | 2-[1-[2-[4-(Dimethylcarbamoyl)-phenyl]-6-methyl-4-oxo-chromen-8-yl]ethylamino]benzoic acid 2,2,2-trifluoroacetic acid | 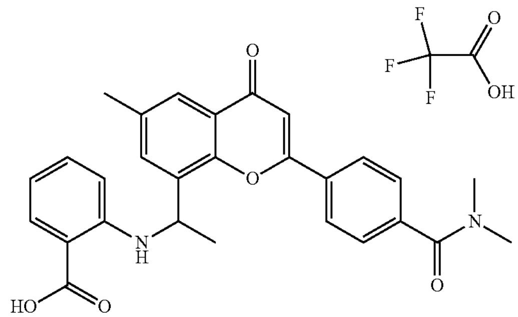 [SMILES: Cc1cc(C(C)Nc2ccccc2C(=O)O)c2oc(-c3ccc(C(=O)N(C)C)cc3)cc(=O)c2c1 ; O=C(O)C(F)(F)F] | 471 [M + H]+ |
| 9 | 2-[1-[6-Methyl-2-(4-methylsulfonylphenyl)-4-oxo-chromen-8-yl]ethylamino]benzoic acid 2,2,2-trifluoroacetic acid | 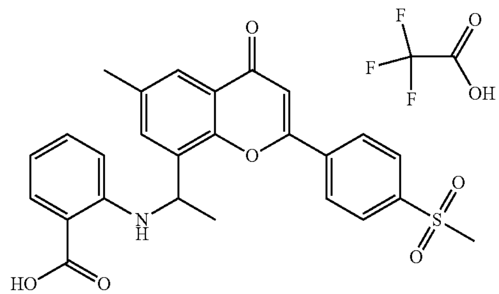 | 478 [M + H]+ |
| 10 | 2-[1-(3-Cyano-6-methyl-4-oxo-2-phenyl-chromen-8-yl)ethylamino]benzoic acid 2,2,2-trifluoroacetic acid | 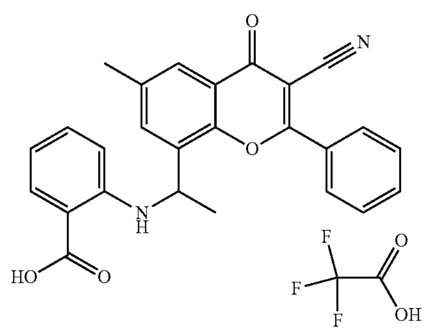 | 425 [M + H]+ |
| 11 | 2-[[(1R)-1-[2-(2-Fluorophenyl)-6-methyl-4-oxo-chromen-8-yl]ethyl]amino]benzoic acid | 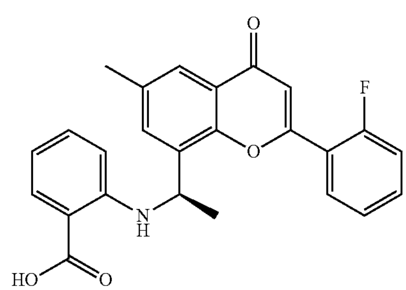 [SMILES: Cc1cc([C@@H](C)Nc2ccccc2C(=O)O)c2oc(-c3ccccc3F)cc(=O)c2c1] | 418 [M + H]+ |
| 12 | 2-[1-[6-Methyl-2-[4-(1-methylcyclopropyl)-phenyl]-4-oxo-chromen-8-yl]ethylamino]benzoic acid 2,2,2-trifluoroacetic acid | 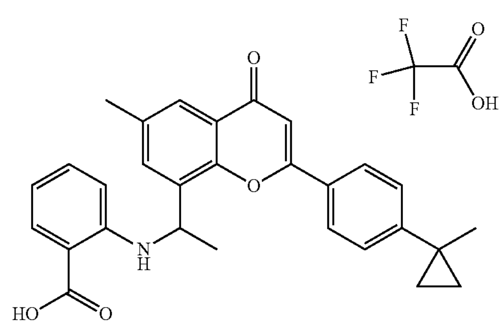 [SMILES: Cc1cc(C(C)Nc2ccccc2C(=O)O)c2oc(-c3ccc(C4(C)CC4)cc3)cc(=O)c2c1 ; O=C(O)C(F)(F)F] | 454 [M + H]+ |

TABLE 1-continued

| Example # | Chemical Name | Structure | MS ES+ m/z |
|---|---|---|---|
| 13 | 2-[1-[6-Methyl-2-[3-(1-methylpyrazol-4-yl)phenyl]-4-oxo-chromen-8-yl]ethylamino]benzoic acid 2,2,2-trifluoroacetic acid | 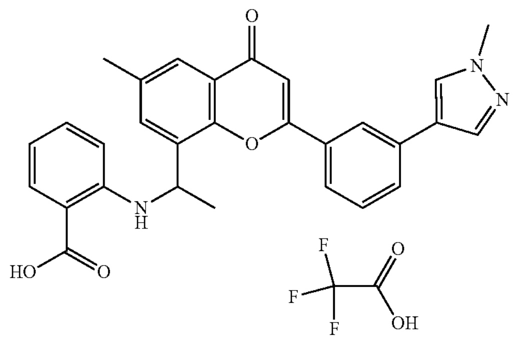 | 480 [M + H]+ |
| 14 | 2-[[(1R)-1-[6-Methyl-2-(o-tolyl)-4-oxo-chromen-8-yl]ethyl]amino]benzoic acid | 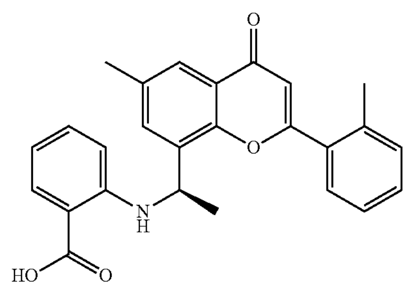 [SMILES: Cc1cc([C@@H](C)Nc2ccccc2C(=O)O)c2oc(-c3ccccc3C)cc(=O)c2c1] | 414 [M + H]+ |
| 15 | 2-[[(1R)-1-[2-(2-Cyanophenyl)-6-methyl-4-oxo-chromen-8-yl]ethyl]amino]benzoic acid | 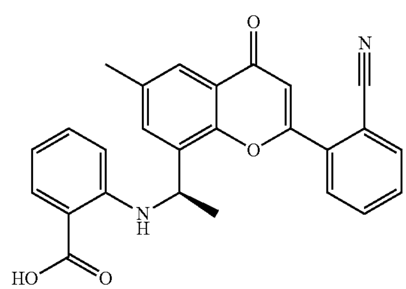 [SMILES: Cc1cc([C@@H](C)Nc2ccccc2C(=O)O)c2oc(-c3ccccc3C#N)cc(=O)c2c1] | 425 [M + H]+ 447 [M + Na]+ |
| 16 | 2-[[(1R)-1-[2-(3-Cyanophenyl)-6-methyl-4-oxo-chromen-8-yl]ethyl]amino]benzoic acid | 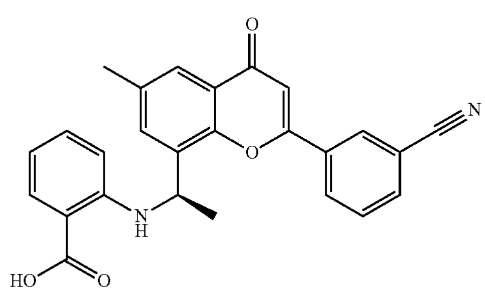 [SMILES: Cc1cc([C@@H](C)Nc2ccccc2C(=O)O)c2oc(-c3cccc(C#N)c3)cc(=O)c2c1] | 425 [M + H]+ |
| 17 | 2-[[(1R)-1-[2-(4-Cyanophenyl)-6-methyl-4-oxo-chromen-8-yl]ethyl]amino]benzoic acid | 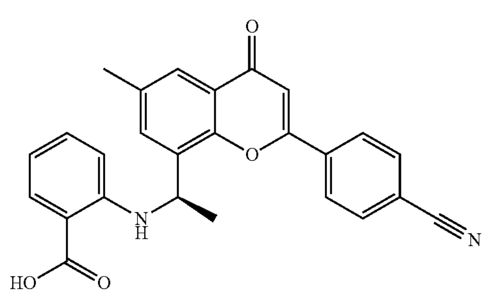 [SMILES: Cc1cc([C@@H](C)Nc2ccccc2C(=O)O)c2oc(-c3ccc(C#N)cc3)cc(=O)c2c1] | 425 [M + H]+ |

TABLE 1-continued

| Example # | Chemical Name | Structure | MS ES+ m/z |
|---|---|---|---|
| 18 | 2-[[(1R)-1-[2-(3-Fluorophenyl)-6-methyl-4-oxo-chromen-8-yl]ethyl]amino]benzoic acid | 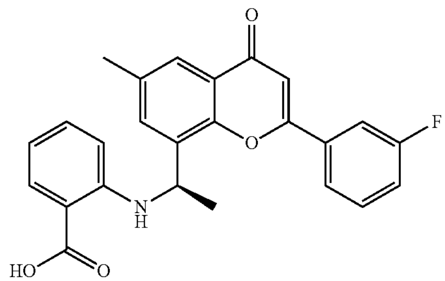 [SMILES: Cc1cc([C@@H](C)Nc2ccccc2C(=O)O)c2oc(-c3cccc(F)c3)cc(=O)c2c1] | 418 [M + H]+ |
| 19 | 2-[[(1R)-1-[2-(4-Fluorophenyl)-6-methyl-4-oxo-chromen-8-yl]ethyl]amino]benzoic acid | 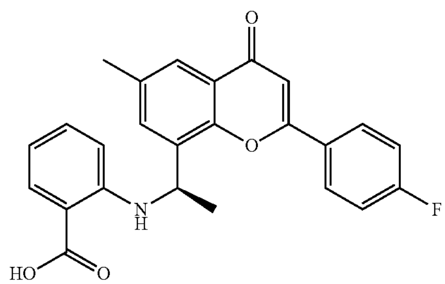 [SMILES: Cc1cc([C@@H](C)Nc2ccccc2C(=O)O)c2oc(-c3ccc(F)cc3)cc(=O)c2c1] | 418 [M + H]+ |
| 20 | 5-Fluoro-2-[[(1R)-1-(6-methyl-4-oxo-2-plienyl-chromen-8-yl)ethyl]amino]benzoic acid | 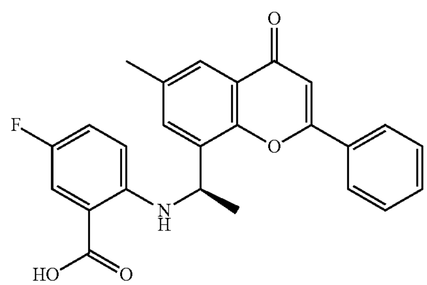 [SMILES: Cc1cc([C@@H](C)Nc2ccc(F)cc2C(=O)O)c2oc(-c3ccccc3)cc(=O)c2c1] | 418 [M + H]+ |
| 21 | 2-[[(1R)-1-(3,6-Dimethyl-4-oxo-2-phenyl-chromen-8-yl)ethyl]amino]benzoic acid | 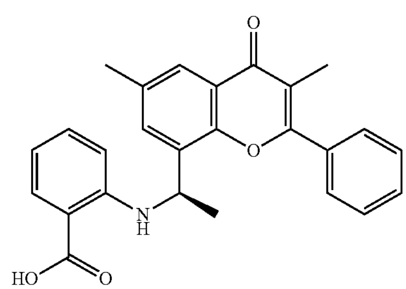 [SMILES: Cc1cc([C@@H](C)Nc2ccccc2C(=O)O)c2oc(-c3ccccc3)c(C)c(=O)c2c1] | 414 [M + H]+ |
| 22 | 2-[[(1R)-1-(6-Methyl-4-oxo-2-phenyl-chromen-8-yl)ethyl]amino]benzoic acid | 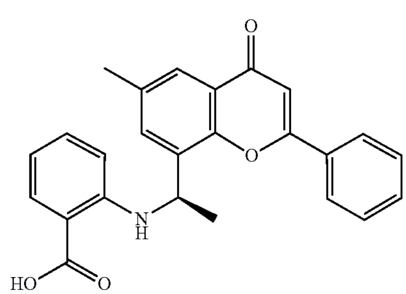 [SMILES: Cc1cc([C@@H](C)Nc2ccccc2C(=O)O)c2oc(-c3ccccc3)cc(=O)c2c1] | 400 [M + H]+ |

TABLE 1-continued

| Example # | Chemical Name | Structure | MS ES+ m/z |
|---|---|---|---|
| 23 | 2-Methyl-5-[1-(6-methyl-4-oxo-2-phenyl-chromen-8-yl)ethylamino]-thiazole-4-carboxylic acid 2,2,2-trifluoroacetic acid | 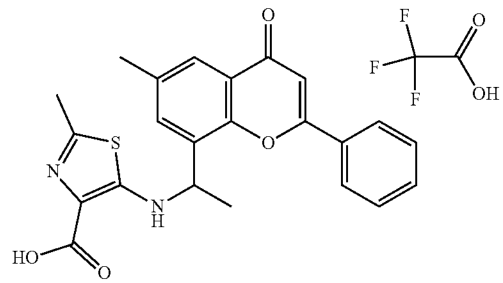 | 421 [M + H]+ |
| 24 | 2-[[(1R)-1-(6-Fluoro-4-oxo-2-phenyl-chromen-8-yl)ethyl]amino]benzoic acid | 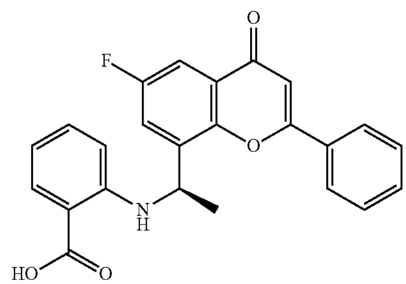 [SMILES: C[C@@H](Nc1ccccc1C(=O)O)c1cc(F)cc2c(=O)cc(-c3ccccc3)oc12] | 404 [M + H]+ |
| 25 | 2-[[(1R)-1-[2-[4-(1-Cyano-1-methyl-ethylphenyl]-6-methyl-4-oxo-chromen-8-yl]ethyl]amino]benzoic acid 2,2,2-trifluoroacetic acid | 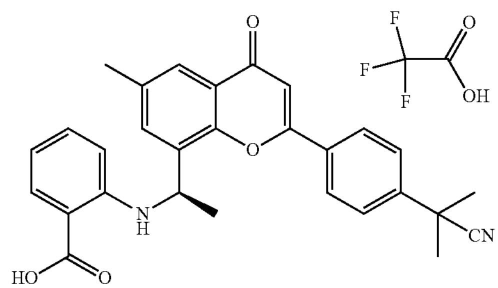 | 467 [M + H]+ |
| 26 | 3-[[(1R)-1-(3,6-Dimethyl-4-oxo-2-phenyl-chromen-8-yl)ethyl]amino]-6-(trifluoromethyl)-pyridine-2-carboxylic acid | 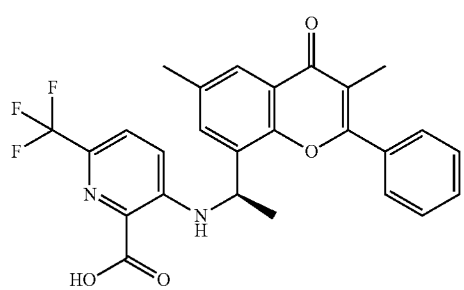 [SMILES: Cc1cc([C@@H](C)Nc2ccc(C(F)(F)F)nc2C(=O)O)c2oc(-c3ccccc3)c(C)c(=O)c2c1] | 483 [M + H]+ |
| 27 | 3-[[(1R)-1-(6-Methyl-4-oxo-2-phenyl-chromen-8-yl)ethyl]amino]-6-(trifluoromethyl)-pyridine-2-carboxylic acid | 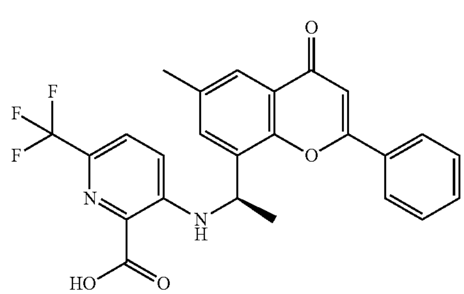 | 469 [M + H]+ |

TABLE 1-continued

| Example # | Chemical Name | Structure | MS ES+ m/z |
|---|---|---|---|
| 28 | 2-[[(1R)-1-[2-(3-Fluorophenyl)-3,6-dimethyl-4-oxo-chromen-8-yl]ethyl]amino]benzoic acid | 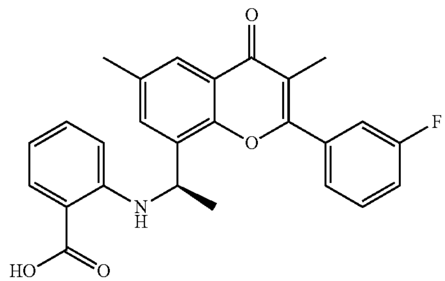 [SMILES: Cc1cc([C@@H](C)Nc2ccccc2C(=O)O)c2oc(-c3cccc(F)c3)c(C)c(=O)c2c1] | 432 [M + H]+ |
| 29 | 2-[[(1R)-1-[2-(4-Fluorophenyl)-3,6-dimethyl-4-oxo-chromen-8-yl]ethyl]amino]benzoic acid | 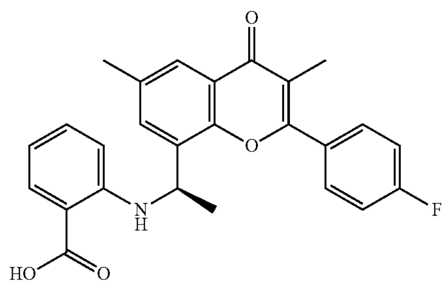 [SMILES: Cc1cc([C@@H](C)Nc2ccccc2C(=O)O)c2oc(-c3ccc(F)cc3)c(C)c(=O)c2c1] | 432 [M + H]+ |
| 30 | 2-[[(1R)-1-[2-(3-Cyanophenyl)-3,6-dimethyl-4-oxo-chromen-8-yl]ethyl]amino]benzoic acid | 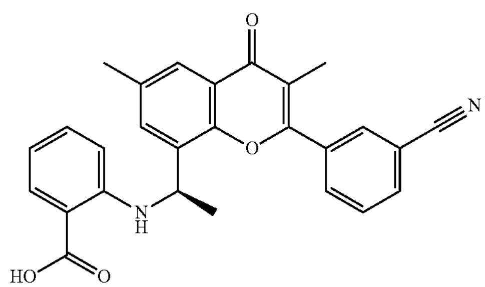 [SMILES: Cc1cc([C@@H](C)Nc2ccccc2C(=O)O)c2oc(-c3cccc(C#N)c3)c(C)c(=O)c2c1] | 439 [M + H]+ |
| 31 | 2-[[(1R)-1-[2-(4-Cyanophenyl)-3,6-dimethyl-4-oxo-chromen-8-yl]ethyl]amino]benzoic acid | 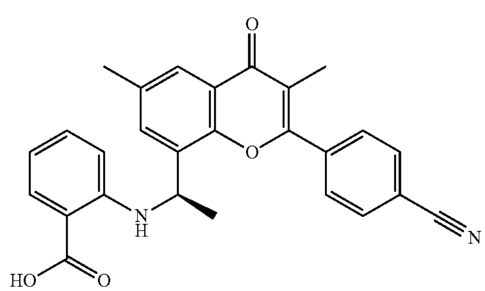 [SMILES: Cc1cc([C@@H](C)Nc2ccccc2C(=O)O)c2oc(-c3ccc(C#N)cc3)c(C)c(=O)c2c1] | 439 [M + H]+ |
| 32 | 2-[[(1R)-1-[6-Methyl-2-(4-oxazol-2-ylphenyl)-4-oxo-chromen-8-yl]ethyl]amino]benzoic acid | 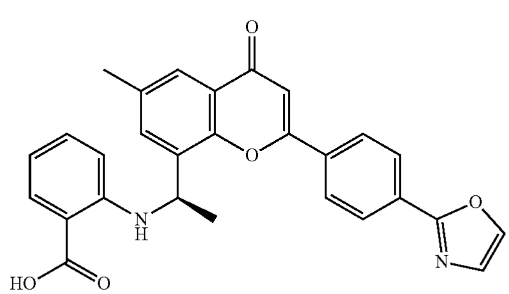 [SMILES: Cc1cc([C@@H](C)Nc2ccccc2C(=O)O)c2oc(-c3ccc(-c4ncco4)cc3)cc(=O)c2c1] | 467 [M + H]+ |

TABLE 1-continued

| Example # | Chemical Name | Structure | MS ES+ m/z |
|---|---|---|---|
| 33 | 2-[[(1R)-1-(6-Methyl-4-oxo-2-phenyl-chromen-8-yl)ethyl]amino]-5-(trifluoromethyl)benzoic acid | 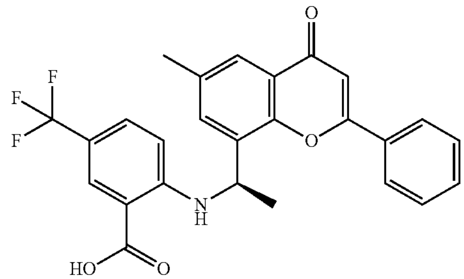 [SMILES: Cc1cc([C@@H](C)Nc2ccc(C(F)(F)F)cc2C(=O)O)c2oc(-c3ccccc3)cc(=O)c2c1] | 468 [M + H]+ |
| 34 | 2-[[(1R)-1-[2-(2-Cyanophenyl)-3,6-dimethyl-4-oxo-chromen-8-yl]ethyl]amino]benzoic acid | 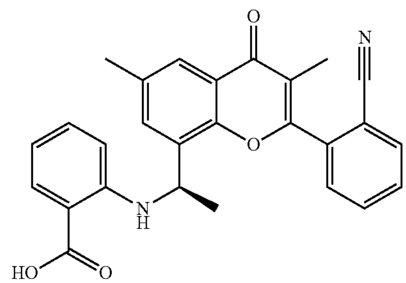 [SMILES: Cc1cc([C@@H](C)Nc2ccccc2C(=O)O)c2oc(-c3ccccc3C#N)c(C)c(=O)c2c1] | 439 [M + H]+ |
| 35 | 6-Bromo-3-[[(1R)-1-(3,6-dimethyl-4-oxo-2-phenyl-chromen-8-yl)ethyl]amino]-pyridine-2-carboxylic acid | 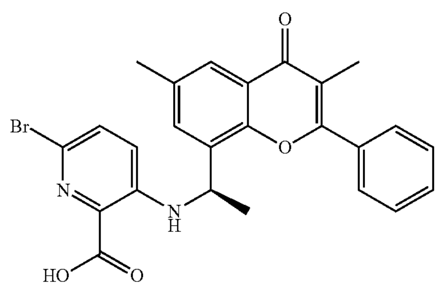 [SMILES: Cc1cc([C@@H](C)Nc2ccc(Br)nc2C(=O)O)c2oc(-c3ccccc3)c(C)c(=O)c2c1] | 494 [M + H]+ |
| 36 | 3-[[(1R)-1-(3,6-Dimethyl-4-oxo-2-phenyl-chromen-8-yl)ethyl]amino]-pyridine-2-carboxylic acid | 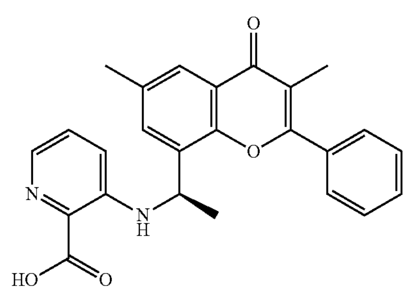 [SMILES: Cc1cc([C@@H](C)Nc2cccnc2C(=O)O)c2oc(-c3ccccc3)c(C)c(=O)c2c1] | 415 [M + H]+ |
| 37 | 2-[[(1R)-1-(3,6-Dimethyl-4-oxo-2-phenyl-chromen-8-yl)ethyl]amino]-5-(trifluoromethyl)benzoic acid | 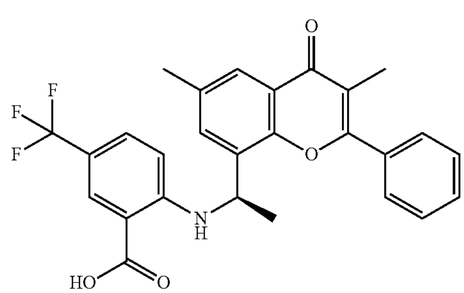 [SMILES: Cc1cc([C@@H](C)Nc2ccc(C(F)(F)F)cc2C(=O)O)c2oc(-c3ccccc3)c(C)c(=O)c2c1] | 482 [M + H]+ |

TABLE 1-continued

| Example # | Chemical Name | Structure | MS ES+ m/z |
|---|---|---|---|
| 38 | 6-[[(1R)-1-(3,6-Dimethyl-4-oxo-2-phenyl-chromen-8-yl)ethyl]amino]-2,3-difluoro-benzoic acid | 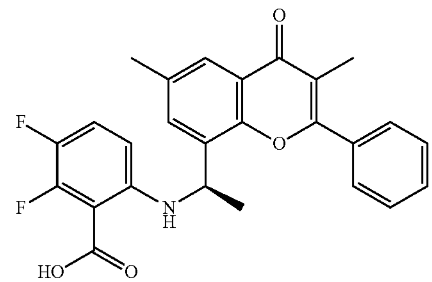 [SMILES: Cc1cc([C@@H](C)Nc2ccc(F)c(F)c2C(=O)O)c2oc(-c3ccccc3)c(C)c(=O)c2c1] | 450 [M + H]+ |
| 39 | 3-[[(1R)-1-(3,6-Dimethyl-4-oxo-2-phenyl-chromen-8-yl)ethyl]amino]-6-methyl-pyridine-2-carboxylic acid | 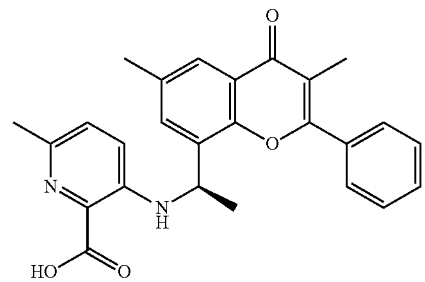 [SMILES: Cc1cc([C@@H](C)Nc2ccc(C)nc2C(=O)O)c2oc(-c3ccccc3)c(C)c(=O)c2c1] | 429 [M + H]+ |
| 40 | 6-Cyclopropyl-3-[[(1R)-1-(3,6-dimethyl-4-oxo-2-phenyl-chromen-8-yl)ethyl]amino]-pyridine-2-carboxylic acid | 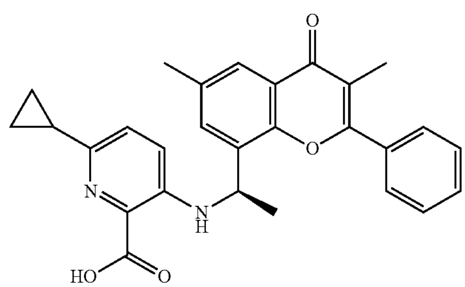 [SMILES: Cc1cc([C@@H](C)Nc2ccc(C3CC3)nc2C(=O)O)c2oc(-c3ccccc3)c(C)c(=O)c2c1] | 455 [M + H]+ |
| 41 | 5-Chloro-2-[[(1R)-1-(3,6-dimethyl-4-oxo-2-phenyl-chromen-8-yl)ethyl]amino]benzoic acid | 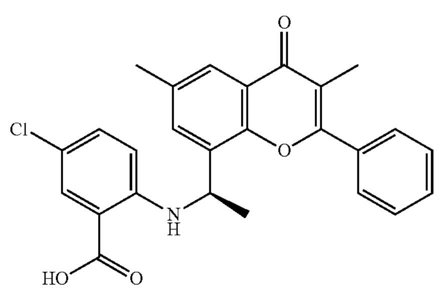 [SMILES: Cc1cc([C@@H](C)Nc2ccc(Cl)cc2C(=O)O)c2oc(-c3ccccc3)c(C)c(=O)c2c1] | 448 [M + H]+ |
| 42 | 3-Chloro-6-[[(1R)-1-(3,6-dimethyl-4-oxo-2-phenyl-chromen-8-yl)ethyl]amino]-2-fluoro-benzoic acid | 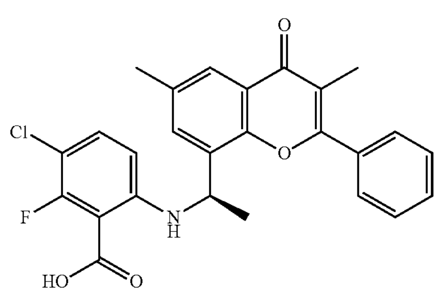 [SMILES: Cc1cc([C@@H](C)Nc2ccc(Cl)c(F)c2C(=O)O)c2oc(-c3ccccc3)c(C)c(=O)c2c1] | 466 [M + H]+ |

TABLE 1-continued

| Example # | Chemical Name | Structure | MS ES+ m/z |
|---|---|---|---|
| 43 | 6-[[(1R)-1-(3,6-Dimethyl-4-oxo-2-phenyl-chromen-8-yl)ethyl]amino]-2-fluoro-3-methyl-benzoic acid | 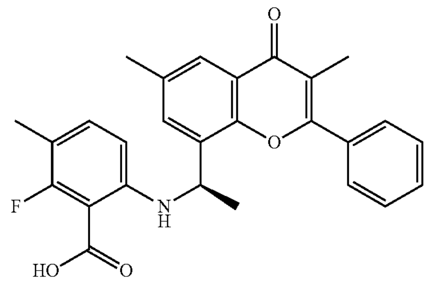 [SMILES: Cc1cc([C@@H](C)Nc2ccc(C)c(F)c2C(=O)O)c2oc(-c3ccccc3)c(C)c(=O)c2c1] | 446 [M + H]+ |
| 44 | 2-[[(1R)-1-[2-(2-Fluorophenyl)-3,6-dimethyl-4-oxo-chromen-8-yl]ethyl]amino]benzoic acid | 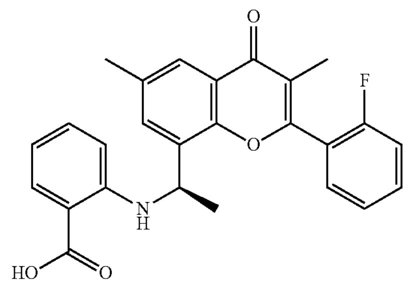 [SMILES: Cc1cc([C@@H](C)Nc2ccccc2C(=O)O)c2oc(-c3ccccc3F)c(C)c(=O)c2c1] | 432 [M + H]+ |
| 45 | 2-[1-[6-Methyl-4-oxo-2-(4-pyrrolidin-1-ylphenyl)chromen-8-yl]ethylamino]benzoic acid 2,2,2-trifluoroacetic acid | 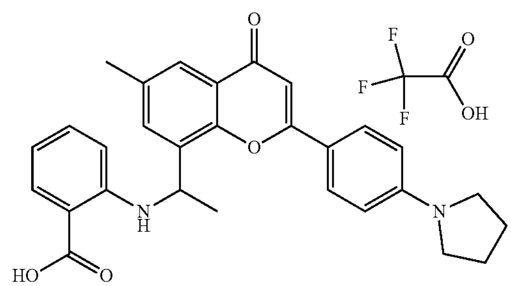 | 469 [M + H]+ |
| 46 | 6-Methyl-3-[[(1R)-1-(6-methyl-4-oxo-2-phenyl-chromen-8-yl)ethyl]amino]-pyridine-2-carboxylic acid | 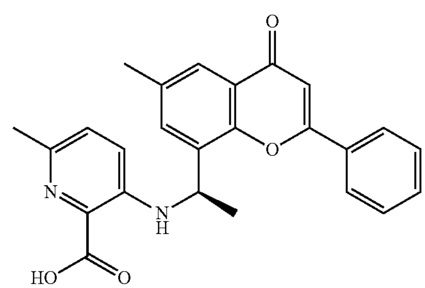 [SMILES: Cc1cc([C@@H](C)Nc2ccc(C)nc2C(=O)O)c2oc(-c3ccccc3)cc(=O)c2c1] | 415 [M + H]+ |
| 47 | 2-[1-[6-Methyl-2-(4-methylsulfonylphenyl)-4-oxo-chromen-8-yl]ethylamino]benzoic acid, Isomer 1 | 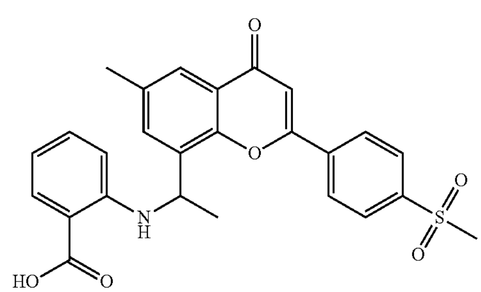 [SMILES: Cc1cc(C(C)Nc2ccccc2C(=O)O)c2oc(-c3ccc(S(C)(=O)=O)cc3)cc(=O)c2c1] | 478 [M + H]+ |

TABLE 1-continued

| Example # | Chemical Name | Structure | MS ES+ m/z |
|---|---|---|---|
| 48 | 2-[1-[6-Methyl-2-(4-methylsulfonylphenyl)-4-oxo-chromen-8-yl]ethylamino]benzoic acid, Isomer 2 | 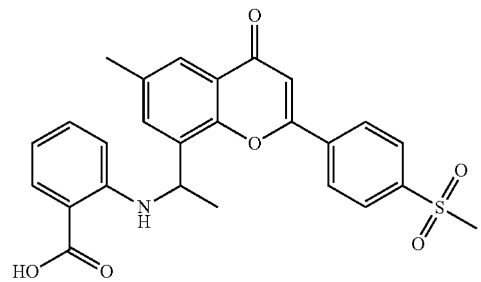 [SMILES: Cc1cc(C(C)Nc2ccccc2C(=O)O)c2oc(-c3ccc(S(C)(=O)=O)cc3)cc(=O)c2c1] | 478 [M + H]+ |
| 49 | 2-[1-[2-[4-(Dimethylcarbamoyl)-phenyl]-6-methyl-4-oxo-chromen-8-yl]ethylamino]benzoic acid, Isomer 1 | 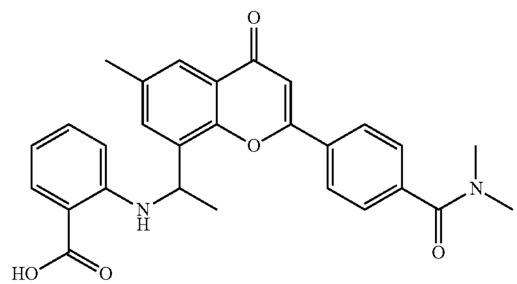 [SMILES: Cc1cc(C(C)Nc2ccccc2C(=O)O)c2oc(-c3ccc(C(=O)N(C)C)cc3)cc(=O)c2c1] | 471 [M + H]+ |
| 50 | 2-[1-[2-[4-(Dimethylcarbamoyl)-phenyl]-6-methyl-4-oxo-chromen-8-yl]ethylamino]benzoic acid, Isomer 2 | 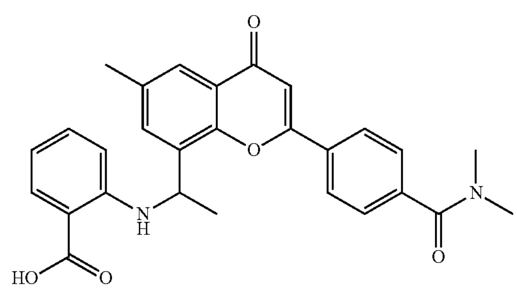 [SMILES: Cc1cc(C(C)Nc2ccccc2C(=O)O)c2oc(-c3ccc(C(=O)N(C)C)cc3)cc(=O)c2c1] | 471 [M + H]+ |
| 51 | 2-[[(1R)-1-[2-(4-Cyano-2-fluoro-phenyl)-6-methyl-4-oxo-chromen-8-yl]ethyl]amino]benzoic acid 2,2,2-trifluoroacetic acid | 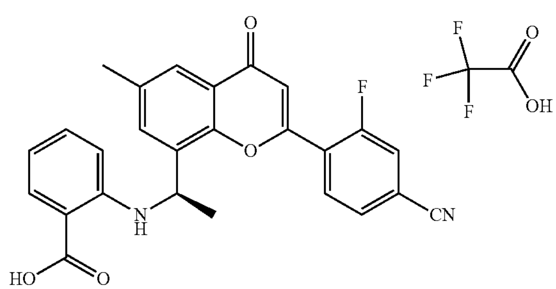 [SMILES: Cc1cc([C@@H](C)Nc2ccccc2C(=O)O)c2oc(-c3ccc(C#N)cc3F)cc(=O)c2c1 ; O=C(O)C(F)(F)F] | 443 [M + H]+ |
| 52 | 2-[1-[2-[4-(1-Cyanocyclopropyl)phenyl]-6-methyl-4-oxo-chromen-8-yl]ethylamino]benzoic acid, Isomer 1 | 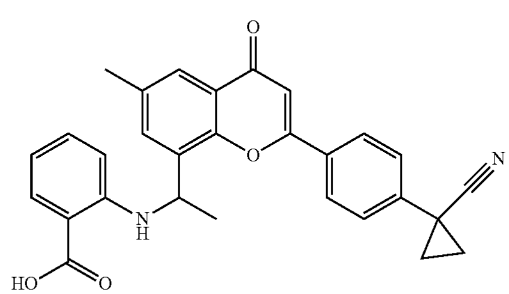 [SMILES: Cc1cc(C(C)Nc2ccccc2C(=O)O)c2oc(-c3ccc(C4(C#N)CC4)cc3)cc(=O)c2c1] | 465 [M + H]+ |

TABLE 1-continued

| Example # | Chemical Name | Structure | MS ES+ m/z |
|---|---|---|---|
| 53 | 2-[1-[2-[4-(1-Cyanocyclopropyl)-phenyl]-6-methyl-4-oxo-chromen-8-yl]ethylamino]benzoic acid, Isomer 2 | 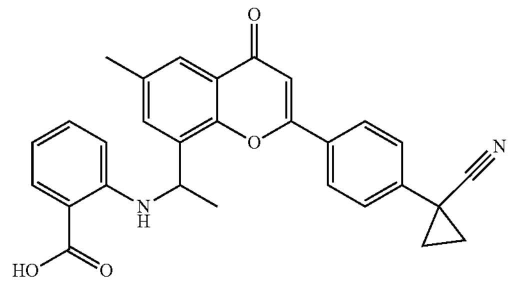 [SMILES: Cc1cc(C(C)Nc2ccccc2C(=O)O)c2oc(-c3ccc(C4(C#N)CC4)cc3)cc(=O)c2c1] | 465 [M + H]+ |
| 54 | 2-[1-[6-Methyl-4-oxo-2-(4-pyrrolidin-1-ylphenyl)chromen-8-yl]ethylamino]benzoic acid, Isomer 1 | 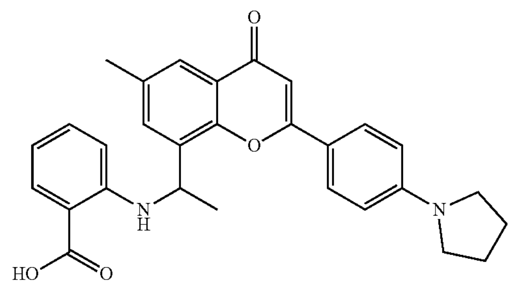 [SMILES: Cc1cc(C(C)Nc2ccccc2C(=O)O)c2oc(-c3ccc(N4CCCC4)cc3)cc(=O)c2c1] | 469 [M + H]+ |
| 55 | 2-[1-[6-Methyl-4-oxo-2-(4-pyrrolidin-1-ylphenyl)chromen-8-yl]ethylamino]benzoic acid, Isomer 2 | 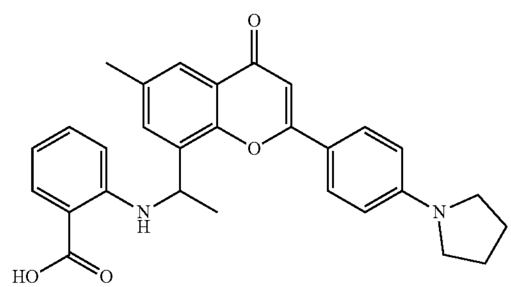 [SMILES: Cc1cc(C(C)Nc2ccccc2C(=O)O)c2oc(-c3ccc(N4CCCC4)cc3)cc(=O)c2c1] | 469 [M + H]+ |
| 56 | 2-[[(1R)-1-[2-(4-Cyano-3-fluoro-phenyl)-6-methyl-4-oxo-chromen-8-yl]ethyl]amino]benzoic acid 2,2,2-trifluoroacetic acid | 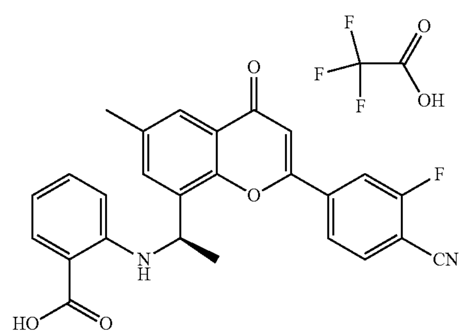 [SMILES: Cc1cc([C@@H](C)Nc2ccccc2C(=O)O)c2oc(-c3ccc(C#N)c(F)c3)cc(=O)c2c1 ; O=C(O)C(F)(F)F] | 443 [M + H]+ |
| 57 | 2-[[(1R)-1-[2-(2,4-Difluorophenyl)-6-methyl-4-oxo-chromen-8-yl]ethyl]amino]benzoic acid 2,2,2-trifluoroacetic acid | 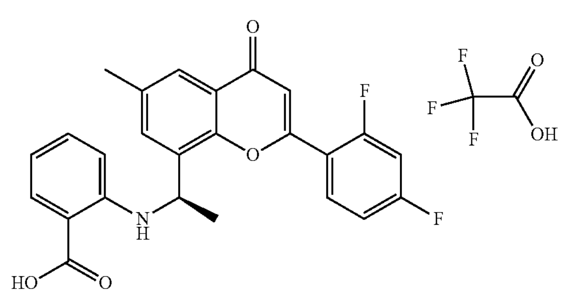 | 436 [M + H]+ |

TABLE 1-continued

| Example # | Chemical Name | Structure | MS ES+ m/z |
|---|---|---|---|
| 58 | 2-[[(1R)-1-(3,6-Dimethyl-4-oxo-2-phenyl-chromen-8-yl)ethyl]amino]-5-fluoro-benzoic acid | 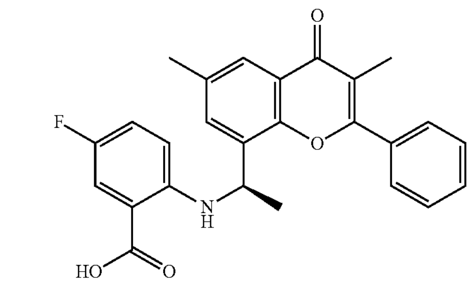 [SMILES: Cc1cc([C@@H](C)Nc2ccc(F)cc2C(=O)O)c2oc(-c3ccccc3)c(C)c(=O)c2c1] | 432 [M + H]+ |
| 59 | 2-[[(1R)-1-[2-(2-Cyanophenyl)-6-methyl-4-oxo-chromen-8-yl]ethyl]amino]benzoic acid 2,2,2-trifluoroacetic acid | 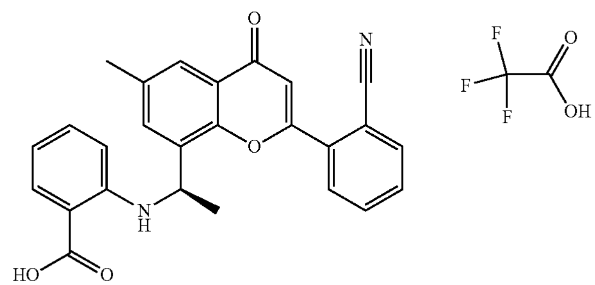 [SMILES: Cc1cc([C@@H](C)Nc2ccccc2C(=O)O)c2oc(-c3ccccc3C#N)cc(=O)c2c1 ; O=C(O)C(F)(F)F] | 425 [M + H]+ |
| 60 | 2-[[(1R)-1-[2-(3-Methoxyphenyl)-6-methyl-4-oxo-chromen-8-yl]ethyl]amino]benzoic acid 2,2,2-trifluoroacetic acid | 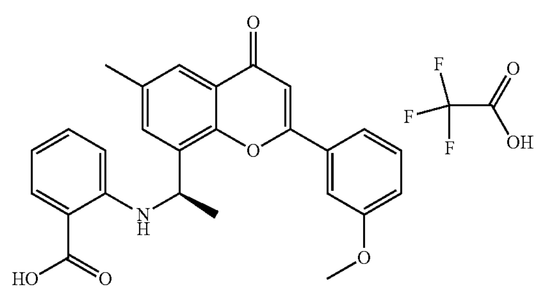 | 430 [M + H]+ |
| 61 | 2-[1-(3-Cyano-6-methyl-4-oxo-2-phenyl-chromen-8-yl)ethylamino]benzoic acid, Isomer 1 | 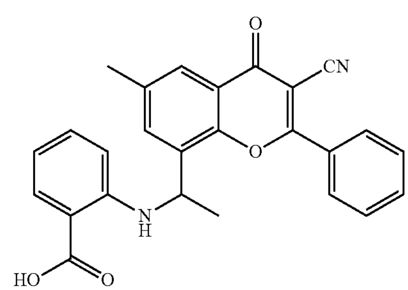 [SMILES: Cc1cc(C(C)Nc2ccccc2C(=O)O)c2oc(-c3ccccc3)c(C#N)c(=O)c2c1] | 425 [M + H]+ |
| 62 | 2-[1-(3-Cyano-6-methyl-4-oxo-2-phenyl-chromen-8-yl)ethylamino]benzoic acid, Isomer 2 | 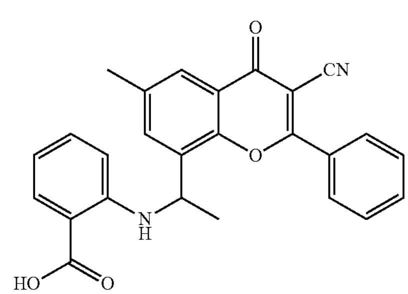 [SMILES: Cc1cc(C(C)Nc2ccccc2C(=O)O)c2oc(-c3ccccc3)c(C#N)c(=O)c2c1] | 425 [M + H]+ |

TABLE 1-continued

| Example # | Chemical Name | Structure | MS ES+ m/z |
|---|---|---|---|
| 63 | 2-[[(1R)-1-[2-(3,4-Difluorophenyl)-6-methyl-4-oxo-chromen-8-yl]ethyl]amino]benzoic acid 2,2,2-trifluoroacetic acid | 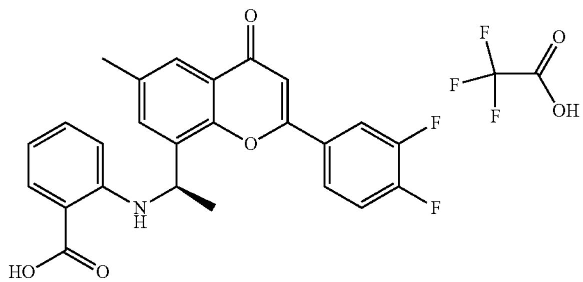 | 436 [M + H]+ |
| 64 | 2-[1-(5,6-Difluoro-4-oxo-2-phenyl-chromen-8-yl)ethylamino]benzoic acid 2,2,2-trifluoroacetic acid | 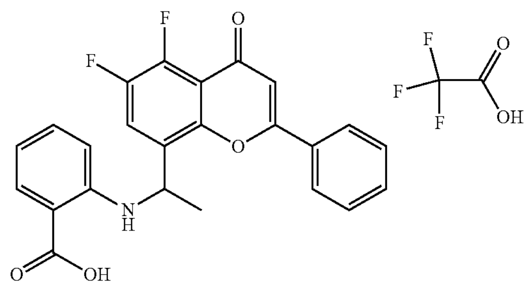 | 422 [M + H]+ |
| 65 | 3-Chloro-2-[[(1R)-1-(3,6-dimethyl-4-oxo-2-phenyl-chromen-8-yl)ethyl]amino]-6-fluoro-benzoic acid | 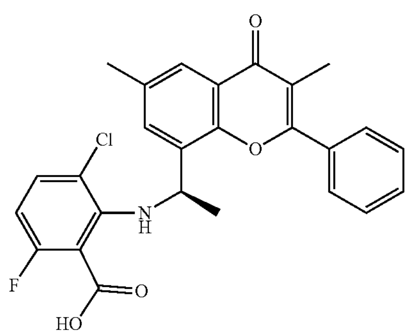 [SMILES: Cc1cc([C@@H](C)Nc2c(Cl)ccc(F)c2C(=O)O)c2oc(-c3ccccc3)c(C)c(=O)c2c1] | 466 [M + H]+ |
| 66 | 2-[[(1R)-1-[2-(4-Methoxyphenyl)-6-methyl-4-oxo-chromen-8-yl]ethyl]amino]benzoic acid 2,2,2-trifluoroacetic acid | 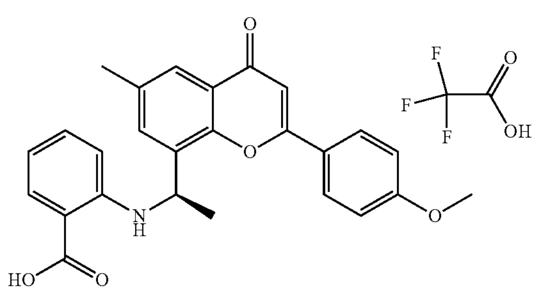 | 430 [M + H]+ |
| 67 | 2-[[(1R)-1-[2-(2-Methoxyphenyl)-6-methyl-4-oxo-chromen-8-yl]ethyl]amino]benzoic acid 2,2,2-trifluoroacetic acid | 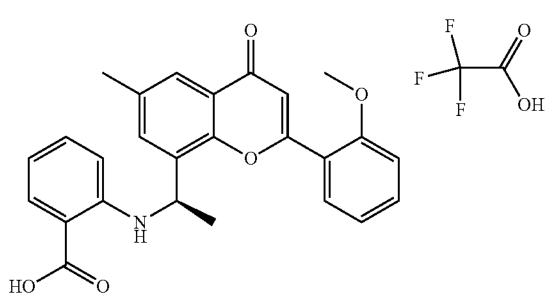 | 430 [M + H]+ |

TABLE 1-continued

| Example # | Chemical Name | Structure | MS ES+ m/z |
|---|---|---|---|
| 68 | 2-[[(1R)-1-[2-(3,5-Difluorophenyl)-6-methyl-4-oxo-chromen-8-yl]ethyl]amino]benzoic acid 2,2,2-trifluoroacetic acid | 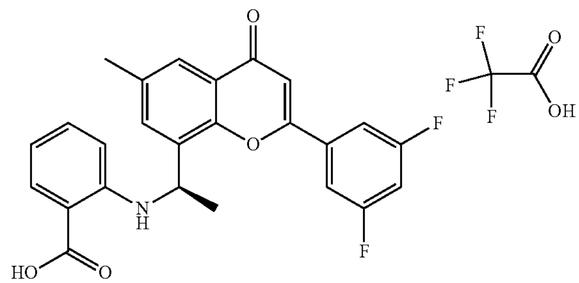 | 436 [M + H]+ |
| 69 | 2-[[(1R)-1-(3,6-Dimethyl-4-oxo-2-phenyl-chromen-8-yl)ethyl]amino]-6-fluoro-benzoic acid | 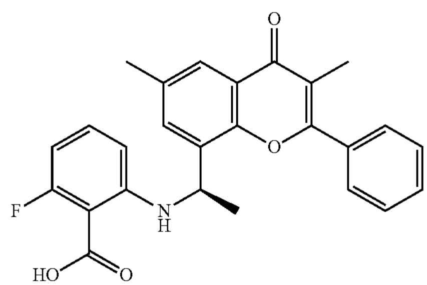 [SMILES: Cc1cc([C@@H](C)Nc2cccc(F)c2C(=O)O)c2oc(-c3ccccc3)c(C)c(=O)c2c1] | 432 [M + H]+ |
| 70 | 2-[[(1R)-1-[6-Methyl-4-oxo-2-phenyl-3-(trifluoromethyl)-chromen-8-yl]ethyl]amino]benzoic acid 2,2,2-trifluoroacetic acid | 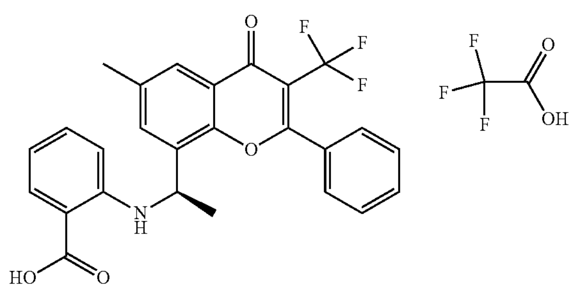 [SMILES: Cc1cc([C@@H](C)Nc2ccccc2C(=O)O)c2oc(-c3ccccc3)c(C(F)(F)F)c(=O)c2c1 ; O=C(O)C(F)(F)F] | 468 [M + H]+ |
| 71 | 2-[[(1R)-1-[2-[3-(Difluoromethyl)phenyl]-6-methyl-4-oxo-chromen-8-yl]ethyl]amino]benzoic acid | 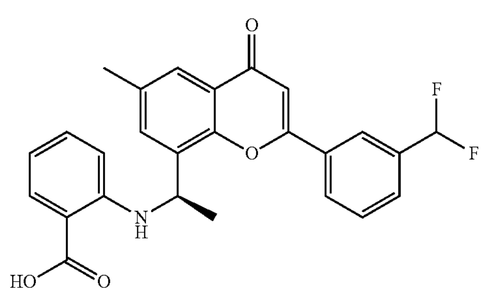 [SMILES: Cc1cc([C@@H](C)Nc2ccccc2C(=O)O)c2oc(-c3cccc(C(F)F)c3)cc(=O)c2c1] | 450 [M + H]+ |
| 72 | 2-[[(1R)-1-(6-Fluoro-3-methyl-4-oxo-2-phenyl-chromen-8-yl)ethyl]amino]benzoic acid 2,2,2-trifluoroacetic acid | 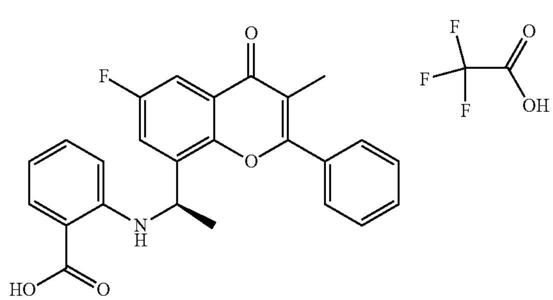 [SMILES: Cc1c(-c2ccccc2)oc2c([C@@H](C)Nc3ccccc3C(=O)O)cc(F)cc2c1=O ; O=C(O)C(F)(F)F] | 418 [M + H]+ |

TABLE 1-continued

| Example # | Chemical Name | Structure | MS ES+ m/z |
|---|---|---|---|
| 73 | 2-[[(1R)-1-[2-[3-(Difluoromethyl)phenyl]-3,6-dimethyl-4-oxo-chromen-8-yl]ethyl]amino]benzoic acid 2,2,2-trifluoroacetic acid | 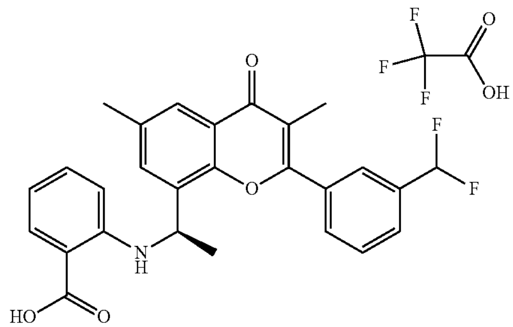 | 464 [M + H]+ |
| 74 | 5-[[(1R)-1-(3,6-Dimethyl-4-oxo-2-phenyl-chromen-8-yl)ethyl]amino]pyrimidine-4-carboxylic acid | 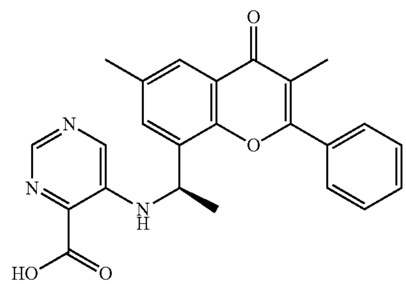 | 416 [M + H]+ |
| 75 | 2-[[(1R)-1-[2-(2,4-Difluorophenyl)-3,6-dimethyl-4-oxo-chromen-8-yl]ethyl]amino]benzoic acid | 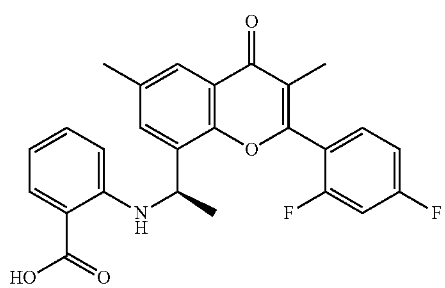 | 450 [M + H]+ |
| 76 | 2-Chloro-6-[[(1R)-1-(3,6-dimethyl-4-oxo-2-phenyl-chromen-8-yl)ethyl]amino]benzoic acid | 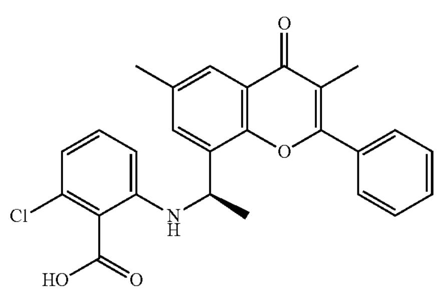 | 4448 [M + H]+ |
| 77 | 5-Bromo-2-[[(1R)-1-(3,6-dimethyl-4-oxo-2-phenyl-chromen-8-yl)ethyl]amino]benzoic acid | 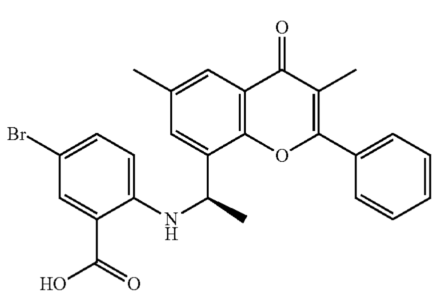 [SMILES: Cc1cc([C@@H](C)Nc2ccc(Br)cc2C(=O)O)c2oc(-c3ccccc3)c(C)c(=O)c2c1] | 494 [M + H]+ |

TABLE 1-continued

| Example # | Chemical Name | Structure | MS ES+ m/z |
|---|---|---|---|
| 78 | 2-[[(1R)-1-[2-(3,4-Difluorophenyl)-3,6-dimethyl-4-oxo-chromen-8-yl]ethyl]amino]benzoic acid 2,2,2-trifluoroacetic acid | 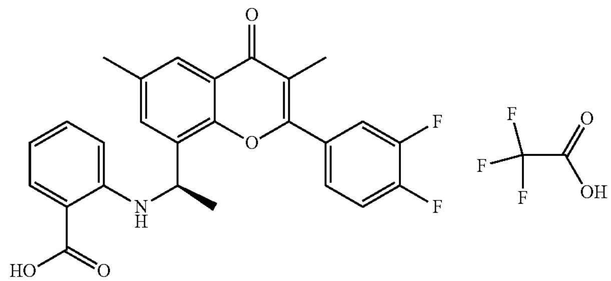 [SMILES: Cc1cc([C@@H](C)Nc2ccccc2C(=O)O)c2oc(-c3ccc(F)c(F)c3)c(C)c(=O)c2c1 ; O=C(O)C(F)(F)F] | 450 [M + H]+ |
| 79 | 2-[[(1R)-1-(3-Iodo-6-methyl-4-oxo-2-phenyl-chromen-8-yl)ethyl]amino]benzoic acid 2,2,2-trifluoroacetic acid | 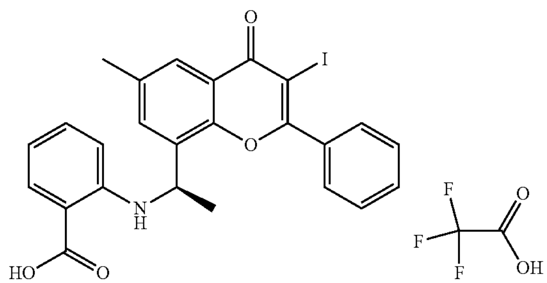 | 526 [M + H]+ |
| 80 | 2-[[(1R)-1-[2-[3-(Difluoromethyl)phenyl]-6-fluoro-4-oxo-chromen-8-yl]ethyl]amino]benzoic acid 2,2,2-trifluoroacetic acid | 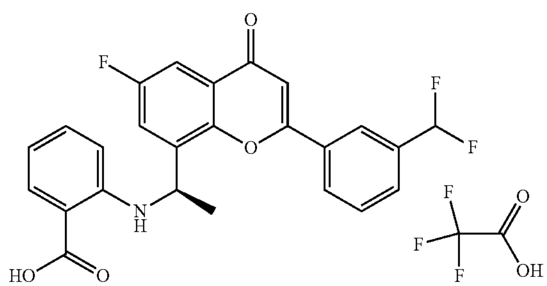 | 454 [M + H]+ |
| 81 | 6-Chloro-3-[[(1R)-1-[2-(2,4-difluorophenyl)-4-oxo-6-(trifluoromethyl)-chromen-8-yl]ethyl]amino]pyridine-2-carboxylic acid | 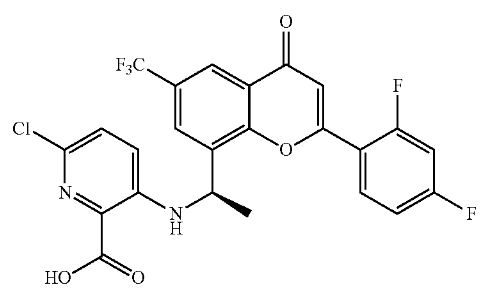 [SMILES: C[C@@H](Nc1ccc(Cl)nc1C(=O)O)c1cc(C(F)(F)F)cc2c(=O)cc(-c3ccc(F)cc3F)oc12] | 525 [M + H]+ |
| 82 | 6-Chloro-3-[[(1R)-1-[4-oxo-2-phenyl-6-(trifluoromethyl)-chromen-8-yl]ethyl]amino]pyridine-2-carboxylic acid | 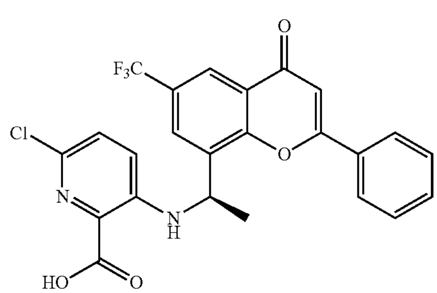 [SMILES: C[C@@H](Nc1ccc(Cl)nc1C(=O)O)c1cc(C(F)(F)F)cc2c(=O)cc(-c3ccccc3)oc12] | 489 [M + H]+ |

TABLE 1-continued

| Example # | Chemical Name | Structure | MS ES+ m/z |
|---|---|---|---|
| 83 | 2-[[(1R)-1-[2-[3-(Difluoromethyl)phenyl]-6-fluoro-3-methyl-4-oxo-chromen-8-yl]ethyl]amino]benzoic acid 2,2,2-trifluoroacetic acid | 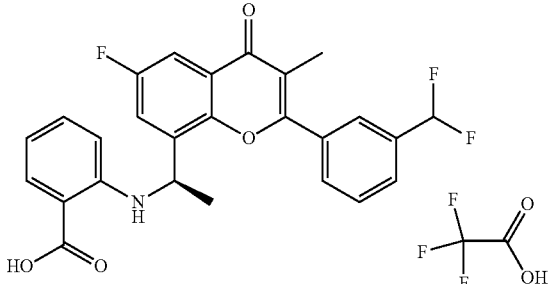 | 468 [M + H]+ |
| 84 | 2-[[(1R)-1-(6-Fluoro-3-methyl-4-oxo-2-phenyl-chromen-8-yl)ethyl]amino]benzoic acid 2,2,2-trifluoroacetic acid | 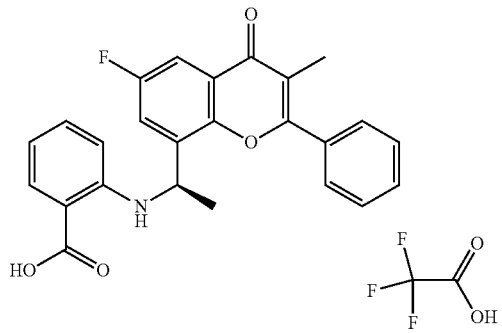 | 418 [M + H]+ |
| 85 | 2-[[(1R)-1-(3-Isoxazol-4-yl-6-methyl-4-oxo-2-phenyl-chromen-8-yl)ethyl]amino]benzoic acid 2,2,2-trifluoroacetic acid | 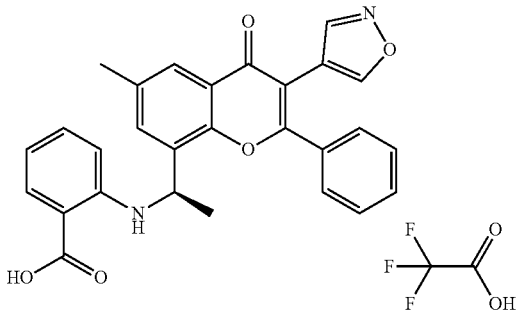 | 467 [M + H]+ |
| 86 | 2-[1-[4-Oxo-2-phenyl-6-(trifluoromethyl)-chromen-8-yl]ethylamino]benzoic acid, Isomer 1 | 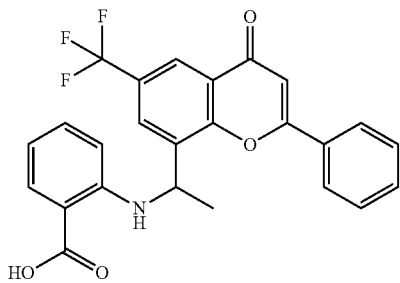 [SMILES: CC(Nc1ccccc1C(=O)O)c1cc(C(F)(F)F)cc2c(=O)cc(-c3ccccc3)oc12] | 454 [M + H]+ |
| 87 | 2-[1-[4-Oxo-2-phenyl-6-(trifluoromethyl)-chromen-8-yl]ethylamino]benzoic acid, Isomer 2 | 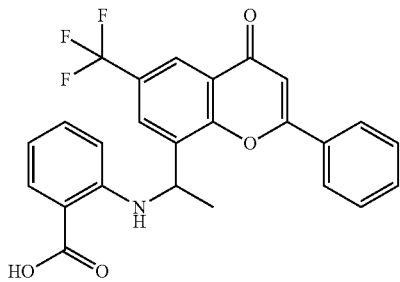 [SMILES: CC(Nc1ccccc1C(=O)O)c1cc(C(F)(F)F)cc2c(=O)cc(-c3ccccc3)oc12] | 454 [M + H]+ |

TABLE 1-continued

| Example # | Chemical Name | Structure | MS ES+ m/z |
|---|---|---|---|
| 88 | 6-Chloro-3-[[(1R)-1-[2-(3,4-difluorophenyl)-4-oxo-6-(trifluoromethyl)-chromen-8-yl]ethyl]amino]pyridine-2-carboxylic acid | 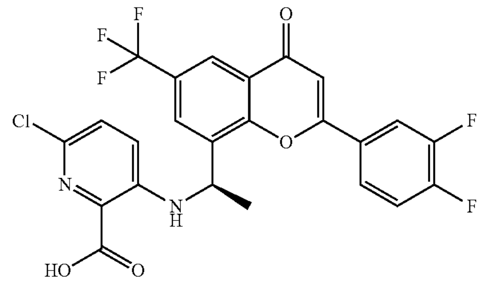 [SMILES: C[C@@H](Nc1ccc(Cl)nc1C(=O)O)c1cc(C(F)(F)F)cc2c(=O)cc(-c3ccc(F)c(F)c3)oc12] | 525 [M + H]+ |
| 89 | 3-[1-(3,6-Dimethyl-4-oxo-2-phenyl-chromen-8-yl)ethylamino]-6-methoxy-pyridine-2-carboxylic acid 2,2,2-trifluoroacetic acid | 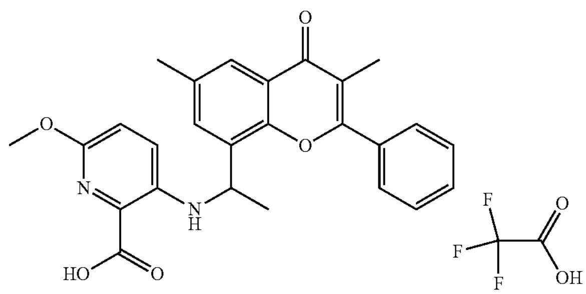 | 445 [M + H]+ |
| 90 | 2-[[(1R)-1-[2-(2,4-Difluorophenyl)-4-oxo-6-(trifluoromethyl)-chromen-8-yl]ethyl]amino]benzoic acid | 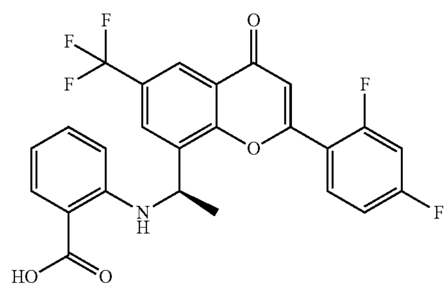 [SMILES: C[C@@H](Nc1ccccc1C(=O)O)c1cc(C(F)(F)F)cc2c(=O)cc(-c3ccc(F)cc3F)oc12] | 490 [M + H]+ |
| 91 | 6-Chloro-3-[[(1R)-1-[3-methyl-4-oxo-2-phenyl-6-(trifluoromethyl)-chromen-8-yl]ethyl]amino]pyridine-2-carboxylic acid | 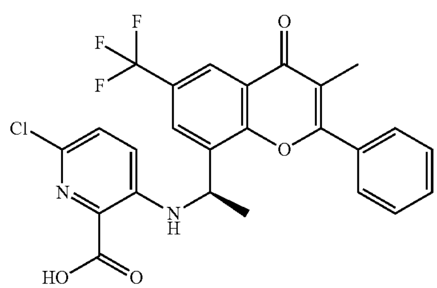 [SMILES: Cc1c(-c2ccccc2)oc2c([C@@H](C)Nc3ccc(Cl)nc3C(=O)O)cc(C(F)(F)F)cc2c1=O] | 503 [M + H]+ |
| 92 | 2-[[(1R)-1-[2-(2,3-Difluorophenyl)-3,6-dimethyl-4-oxo-chromen-8-yl]ethyl]amino]benzoic acid 2,2,2-trifluoroacetic acid | 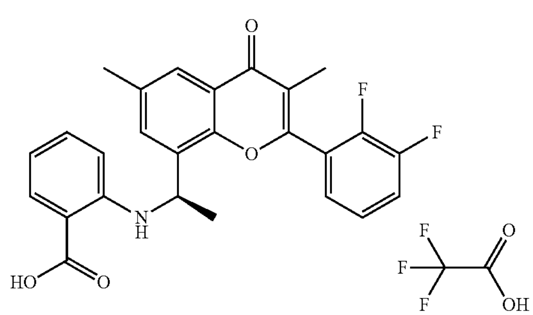 | 450 [M + H]+ |

TABLE 1-continued

| Example # | Chemical Name | Structure | MS ES+ m/z |
|---|---|---|---|
| 93 | 3-[1-[2-(2-Fluorophenyl)-3,6-dimethyl-4-oxo-chromen-8-yl]ethylamino]pyridine-2-carboxylic acid 2,2,2-trifluoroacetic acid | 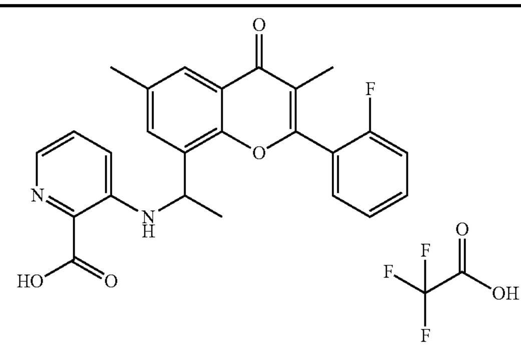 | 433 [M + H]+ |
| 94 | 2-Fluoro-6-[1-[2-(2-fluorophenyl)-3,6-dimethyl-4-oxo-chromen-8-yl]ethylamino]benzoic acid 2,2,2-trifluoroacetic acid | 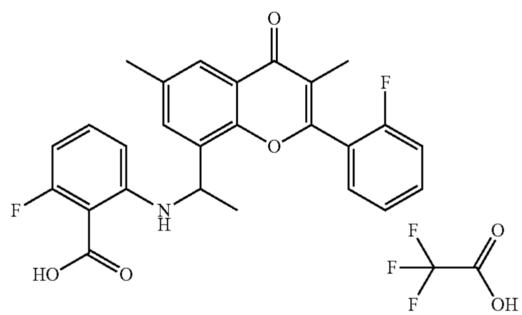 | 450 [M + H]+ |
| 95 | 2-Fluoro-6-[1-[2-(3-fluorophenyl)-3,6-dimethyl-4-oxo-chromen-8-yl]ethylamino]benzoic acid 2,2,2-trifluoroacetic acid | 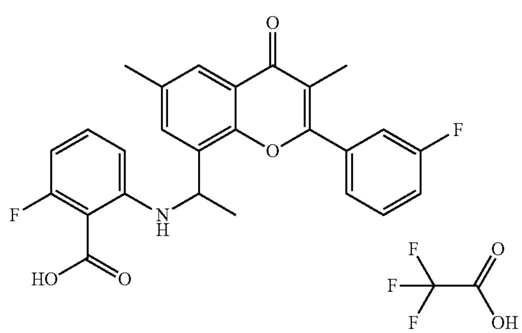 | 450 [M + H]+ |
| 96 | 6-Chloro-3-[[(1R)-1-[2-(3,4-difluorophenyl)-3-methyl-4-oxo-6-(trifluoromethyl)-chromen-8-yl]ethyl]amino]pyridine-2-carboxylic acid | 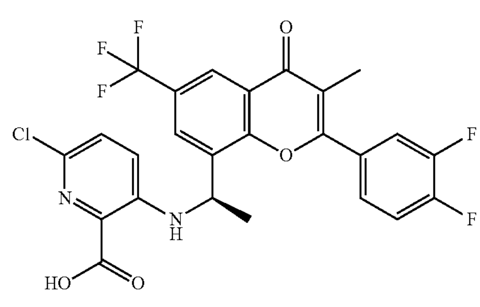 [SMILES: Cc1c(-c2ccc(F)c(F)c2)oc2c([C@@H](C)Nc3ccc(Cl)nc3C(=O)O)cc(C(F)(F)F)cc2c1=O] | 539 [M + H]+ |
| 97 | 2-Fluoro-6-[1-[2-(2-fluorophenyl)-6-methyl-4-oxo-chromen-8-yl]ethylamino]benzoic acid 2,2,2-trifluoroacetic acid | 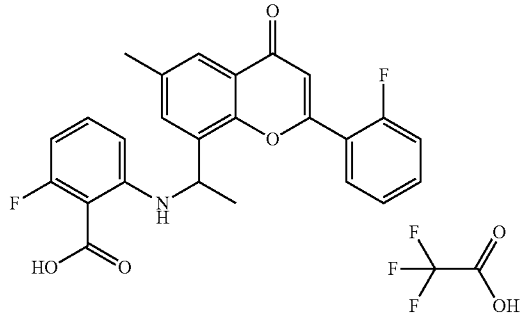 | 436 [M + H]+ |

TABLE 1-continued

| Example # | Chemical Name | Structure | MS ES+ m/z |
|---|---|---|---|
| 98 | 6-Chloro-3-[[(1R)-1-[2-(2-fluorophenyl)-3-methyl-4-oxo-6-(trifluoromethyl)-chromen-8-yl]ethyl]amino]pyridine-2-carboxylic acid | 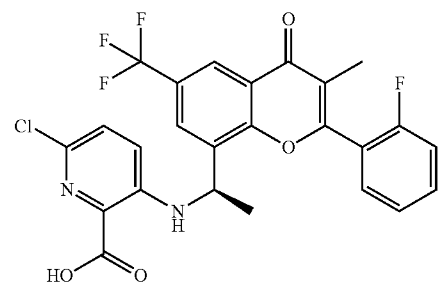 [SMILES: Cc1c(-c2ccccc2F)oc2c([C@@H](C)Nc3ccc(Cl)nc3C(=O)O)cc(C(F)(F)F)cc2c1=O] | 521 [M + H]+ |
| 99 | 6-Chloro-3-[[(1R)-1-[2-(2,4-difluorophenyl)-3-methyl-4-oxo-6-(trifluoromethyl)-chromen-8-yl]ethyl]amino]pyridine-2-carboxylic acid | 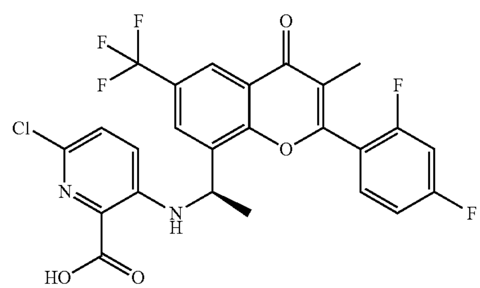 [SMILES: Cc1c(-c2ccc(F)cc2F)oc2c([C@@H](C)Nc3ccc(Cl)nc3C(=O)O)cc(C(F)(F)F)cc2c1=O] | 539 [M + H]+ |
| 100 | 6-Chloro-3-[[(1R)-1-[2-(3-cyanophenyl)-3-methyl-4-oxo-6-(trifluoromethyl)-chromen-8-yl]ethyl]amino]pyridine-2-carboxylic acid | 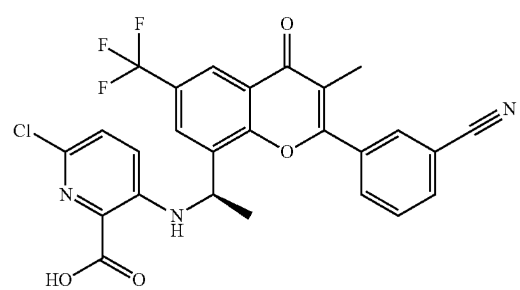 [SMILES: Cc1c(-c2cccc(C#N)c2)oc2c([C@@H](C)Nc3ccc(Cl)nc3C(=O)O)cc(C(F)(F)F)cc2c1=O] | 528 [M + H]+ |
| 101 | 6-Methyl-3-[1-[6-methyl-4-oxo-2-phenyl-3-(trifluoromethyl)-chromen-8-yl]ethylamino]pyridine-2-carboxylic acid 2,2,2-trifluoroacetic acid | 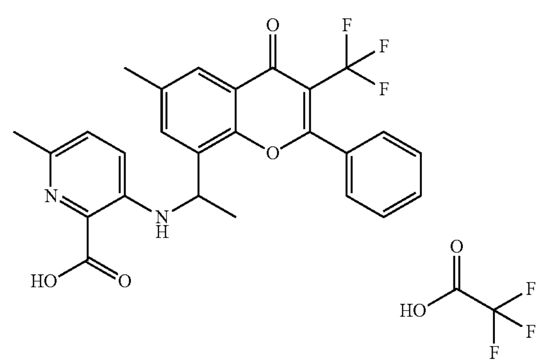 [SMILES: Cc1cc(C(C)Nc2ccc(C)nc2C(=O)O)c2oc(-c3ccccc3)c(C(F)(F)F)c(=O)c2c1 ; O=C(O)C(F)(F)F] | 483 [M + H]+ |
| 102 | 2-[[(1R)-1-[3-Methyl-4-oxo-2-phenyl-6-(trifluoromethyl)-chromen-8-yl]ethyl]amino]benzoic acid | 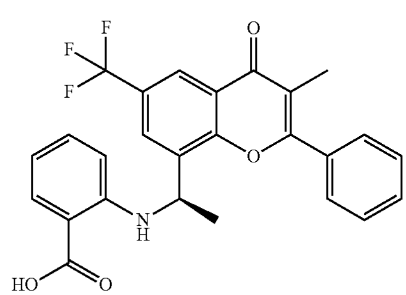 [SMILES: Cc1c(-c2ccccc2)oc2c([C@@H](C)Nc3ccccc3C(=O)O)cc(C(F)(F)F)cc2c1=O] | 468 [M + H]+ |

TABLE 1-continued

| Example # | Chemical Name | Structure | MS ES+ m/z |
|---|---|---|---|
| 103 | 2-Fluoro-6-[1-[2-(2-fluorophenyl)-3,6-dimethyl-4-oxo-chromen-8-yl]ethylamino]benzoic acid, Isomer 1 | 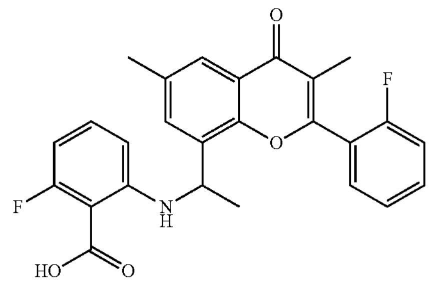 [SMILES: Cc1cc(C(C)Nc2cccc(F)c2C(=O)O)c2oc(-c3ccccc3F)c(C)c(=O)c2c1] | 450 [M + H]+ |
| 104 | 2-Fluoro-6-[1-[2-(2-fluorophenyl)-3,6-dimethyl-4-oxo-chromen-8-yl]ethylamino]benzoic acid, Isomer 2 | 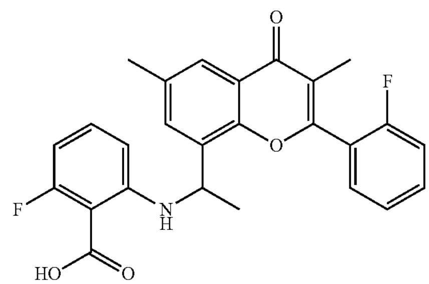 [SMILES: Cc1cc(C(C)Nc2cccc(F)c2C(=O)O)c2oc(-c3ccccc3F)c(C)c(=O)c2c1] | 450 [M + H]+ |
| 105 | 2-Fluoro-6-[1-[2-(3-fluorophenyl)-3,6-dimethyl-4-oxo-chromen-8-yl]ethylamino]benzoic acid, Isomer 1 | 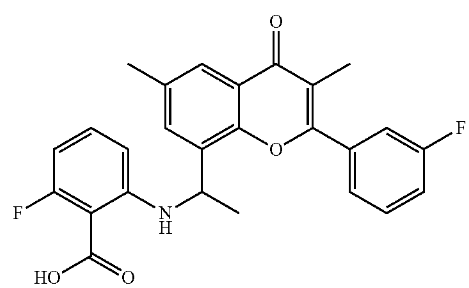 [SMILES: Cc1cc(C(C)Nc2cccc(F)c2C(=O)O)c2oc(-c3cccc(F)c3)c(C)c(=O)c2c1] | 450 [M + H]+ |
| 106 | 2-Fluoro-6-[1-[2-(3-fluorophenyl)-3,6-dimethyl-4-oxo-chromen-8-yl]ethylamino]benzoic acid, Isomer 2 | 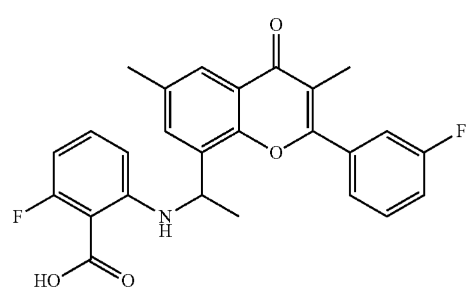 [SMILES: Cc1cc(C(C)Nc2cccc(F)c2C(=O)O)c2oc(-c3cccc(F)c3)c(C)c(=O)c2c1] | 450 [M + H]+ |
| 107 | 2-Fluoro-6-[1-[2-(2-fluorophenyl)-6-methyl-4-oxo-chromen-8-yl]ethylamino]benzoic acid, Isomer 1 | 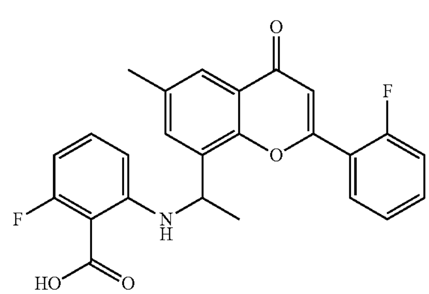 [SMILES: Cc1cc(C(C)Nc2cccc(F)c2C(=O)O)c2oc(-c3ccccc3F)cc(=O)c2c1] | 436 [M + H]+ |

TABLE 1-continued

| Example # | Chemical Name | Structure | MS ES+ m/z |
|---|---|---|---|
| 108 | 2-Fluoro-6-[1-[2-(2-fluorophenyl)-6-methyl-4-oxo-chromen-8-yl]ethylamino]benzoic acid, Isomer 2 | 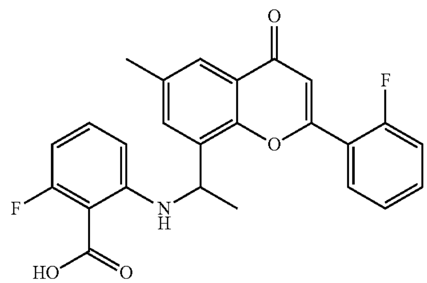 [SMILES: Cc1cc(C(C)Nc2cccc(F)c2C(=O)O)c2oc(-c3ccccc3F)cc(=O)c2c1] | 436 [M + H]+ |
| 109 | 3-[1-(3,6-Dimethyl-4-oxo-2-phenyl-chromen-8-yl)ethylamino]-6-methoxy-pyridine-2-carboxylic acid, Isomer 1 | 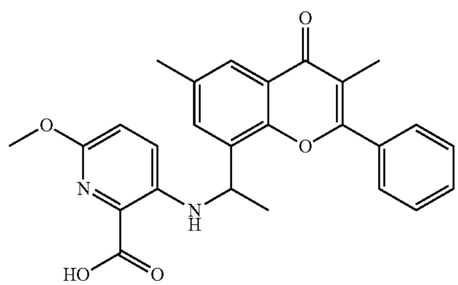 [SMILES: COc1ccc(NC(C)c2cc(C)cc3c(=O)c(C)c(-c4ccccc4)oc23)c(C(=O)O)n1] | 445 [M + H]+ |
| 110 | 3-[1-(3,6-Dimethyl-4-oxo-2-phenyl-chromen-8-yl)ethylamino]-6-methoxy-pyridine-2-carboxylic acid, Isomer 2 | 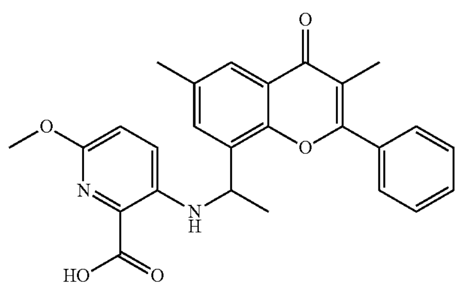 [SMILES: COc1ccc(NC(C)c2cc(C)cc3c(=O)c(C)c(-c4ccccc4)oc23)c(C(=O)O)n1] | 445 [M + H]+ |
| 111 | 2-[1-(3-Fluoro-6-methyl-4-oxo-2-phenyl-chromen-8-yl)ethylamino]benzoic acid 2,2,2-trifluoroacetic acid | 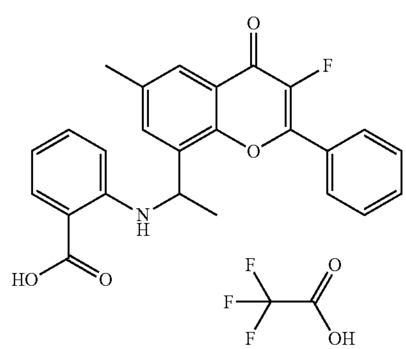 | 418 [M + H]+ |
| 112 | 2-[[(1R)-1-[6-methyl-3-(oxetan-3-yl)-4-oxo-2-phenyl-chromen-8-yl]ethyl]amino]benzoic acid 2,2,2-trifluoroacetic acid | 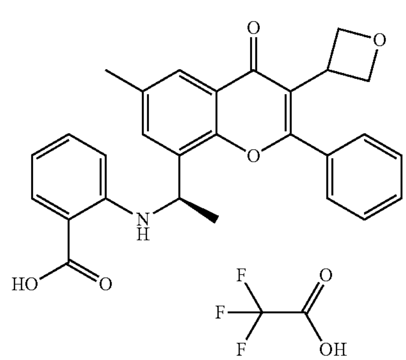 [SMILES: Cc1cc([C@@H](C)Nc2ccccc2C(=O)O)c2oc(-c3ccccc3)c(C3COC3)c(=O)c2c1 ; O=C(O)C(F)(F)F] | 456 [M + H]+ |

TABLE 1-continued

| Example # | Chemical Name | Structure | MS ES+ m/z |
|---|---|---|---|
| 113 | 6-Chloro-3-[[(1R)-1-[2-(3,4-difluorophenyl)-3,6-dimethyl-4-oxo-chromen-8-yl]ethyl]amino]pyridine-2-carboxylic acid | 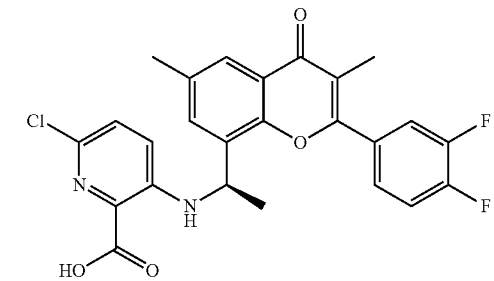 [SMILES: Cc1cc([C@@H](C)Nc2ccc(Cl)nc2C(=O)O)c2oc(-c3ccc(F)c(F)c3)c(C)c(=O)c2c1] | |
| 114 | 6-Chloro-3-[[(1R)-1-[2-(2-fluorophenyl)-3,6-dimethyl-4-oxo-chromen-8-yl]ethyl]amino]pyridine-2-carboxylic acid 2,2,2-trifluoroacetic acid | 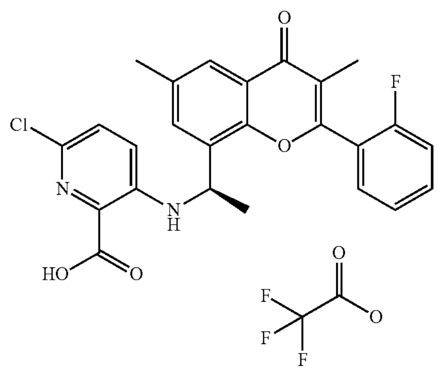 | 467 [M + H]+ |
| 115 | 6-Chloro-3-[[(1R)-1-[2-(3-cyanophenyl)-3,6-dimethyl-4-oxo-chromen-8-yl]ethyl]amino]pyridine-2-carboxylic acid 2,2,2-trifluoroacetic acid | 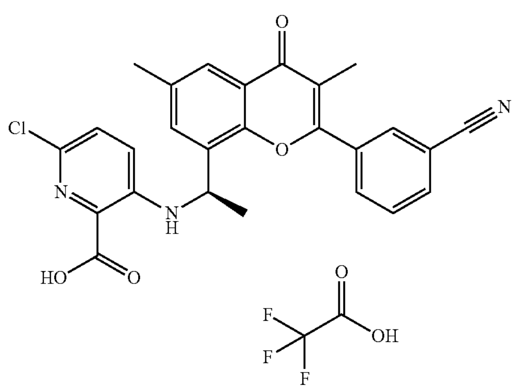 [SMILES: Cc1cc([C@@H](C)Nc2ccc(Cl)nc2C(=O)O)c2oc(-c3cccc(C#N)c3)c(C)c(=O)c2c1 ; O=C(O)C(F)(F)F] | 474 [M + H]+ |
| 116 | 6-Methyl-3-[[(1R)-1-[6-methyl-4-oxo-2-phenyl-3-(trifluoromethyl)-chromen-8-yl]ethyl]amino]pyridine-2-carboxylic acid | 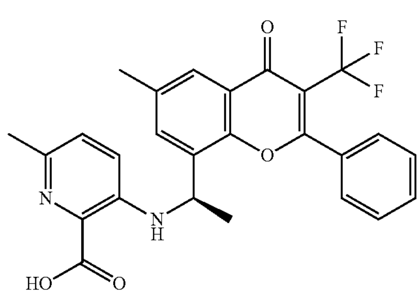 [SMILES: Cc1cc([C@@H](C)Nc2ccc(C)nc2C(=O)O)c2oc(-c3ccccc3)c(C(F)(F)F)c(=O)c2c1] | 483 [M + H]+ |

TABLE 1-continued

| Example # | Chemical Name | Structure | MS ES+ m/z |
|---|---|---|---|
| 117 | 2-[[(1R)-1-[2-[3-(1-Cyano-1-methyl-ethyl)phenyl]-3,6-dimethyl-4-oxo-chromen-8-yl]ethyl]amino]benzoic acid 2,2,2-trifluoroacetic acid | 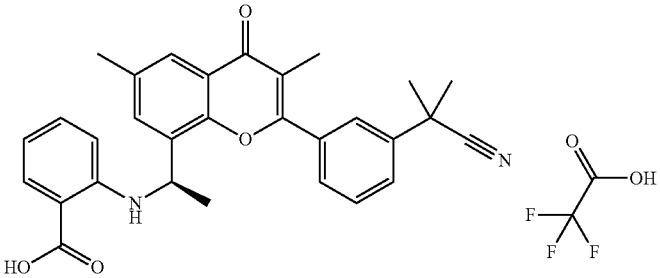 [SMILES: Cc1cc([C@@H](C)Nc2ccccc2C(=O)O)c2oc(-c3cccc(C(C)(C)C#N)c3)c(C)c(=O)c2c1 ; O=C(O)C(F)(F)F] | 481 [M + H]+ |
| 118 | 2-[[(1R)-1-[2-[3-(2-Amino-1,1-dimethyl-2-oxo-ethyl)phenyl]-3,6-dimethyl-4-oxo-chromen-8-yl]ethyl]amino]benzoic acid 2,2,2-trifluoroacetic acid | 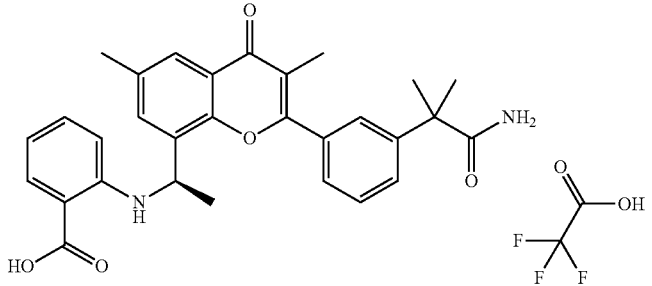 [SMILES: Cc1cc([C@@H](C)Nc2ccccc2C(=O)O)c2oc(-c3cccc(C(C)(C)C(N)=O)c3)c(C)c(=O)c2c1 ; O=C(O)C(F)(F)F] | 499 [M + H]+ |
| 119 | 2-[[(1R)-1-(3-Acetyl-6-methyl-4-oxo-2-phenyl-chromen-8-yl)ethyl]amino]benzoic acid 2,2,2-trifluoroacetic acid | 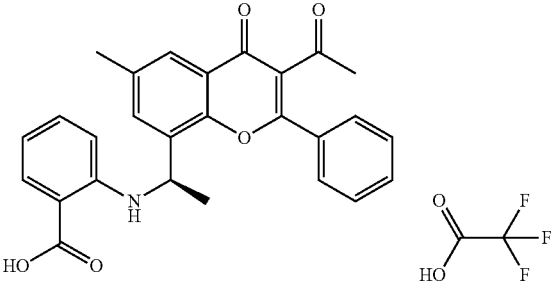 | 442 [M + H]+ |
| 120 | 3-[[(1R)-1-[2-(3,4-Difluorophenyl)-3,6-dimethyl-4-oxo-chromen-8-yl]ethyl]amino]pyridine-2-carboxylic acid | 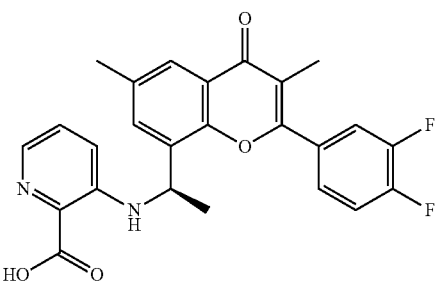 [SMILES: Cc1cc([C@@H](C)Nc2cccnc2C(=O)O)c2oc(-c3ccc(F)c(F)c3)c(C)c(=O)c2c1] | 451 [M + H]+ |
| 121 | 6-Chloro-3-[[(1R)-1-[2-(3-cyanophenyl)-3,6-dimethyl-4-oxo-chromen-8-yl]ethyl]amino]pyridine-2-carboxylic acid | 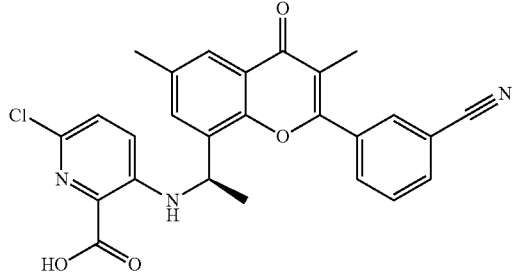 [SMILES: Cc1cc([C@@H](C)Nc2ccc(Cl)nc2C(=O)O)c2oc(-c3cccc(C#N)c3)c(C)c(=O)c2c1] | 474 [M + H]+ |

TABLE 1-continued

| Example # | Chemical Name | Structure | MS ES+ m/z |
|---|---|---|---|
| 122 | 3-[[(1R)-1-[3-Methyl-4-oxo-2-phenyl-6-(trifluoromethyl)-chromen-8-yl]ethyl]amino]pyridine-2-carboxylic acid | 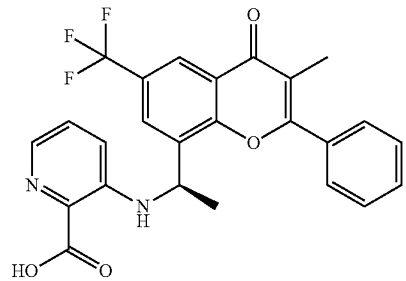 [SMILES: Cc1c(-c2ccccc2)oc2c([C@@H](C)Nc3cccnc3C(=O)O)cc(C(F)(F)F)cc2c1=O] | 469 [M + H]+ |
| 123 | 3-[[(1R)-1-[2-(3,4-Difluorophenyl)-3,6-dimethyl-4-oxo-chromen-8-yl]ethyl]amino]-6-(trifluoromethyl)pyridine-2-carboxylic acid | 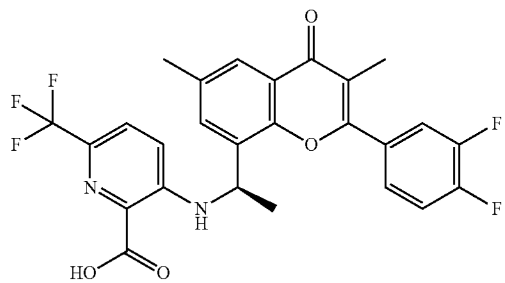 [SMILES: Cc1cc([C@@H](C)Nc2ccc(C(F)(F)F)nc2C(=O)O)c2oc(-c3ccc(F)c(F)c3)c(C)c(=O)c2c1] | 519 [M + H]+ |
| 124 | 3-[[(1R)-1-[2-(3,4-Difluorophenyl)-3,6-dimethyl-4-oxo-chromen-8-yl]ethyl]amino]-6-methyl-pyridine-2-carboxylic acid | 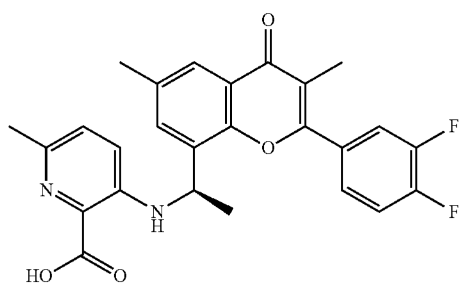 [SMILES: Cc1cc([C@@H](C)Nc2ccc(C)nc2C(=O)O)c2oc(-c3ccc(F)c(F)c3)c(C)c(=O)c2c1] | 465 [M + H]+ |
| 125 | 3-[[(1R)-1-[2-(3-Cyanophenyl)-3,6-dimethyl-4-oxo-chromen-8-yl]ethyl]amino]pyridine-2-carboxylic acid | 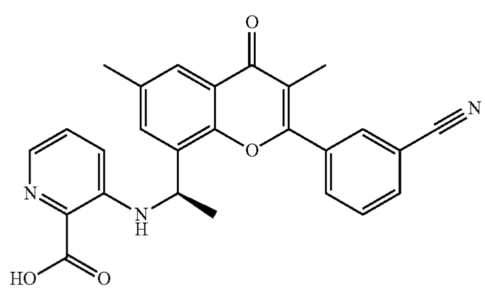 [SMILES: Cc1cc([C@@H](C)Nc2cccnc2C(=O)O)c2oc(-c3cccc(C#N)c3)c(C)c(=O)c2c1] | 440 [M + H]+ |
| 126 | 3-[[(1R)-1-[2-(3-Cyanophenyl)-3,6-dimethyl-4-oxo-chromen-8-yl]ethyl]amino]-6-(trifluoromethyl)pyridine-2-carboxylic acid | 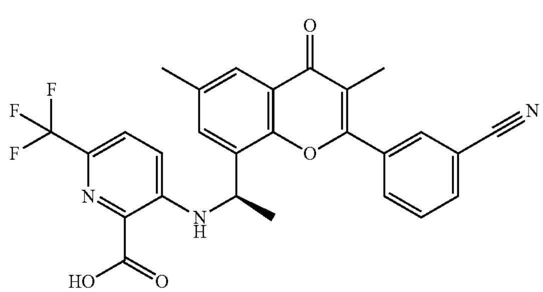 [SMILES: Cc1cc([C@@H](C)Nc2ccc(C(F)(F)F)nc2C(=O)O)c2oc(-c3cccc(C#N)c3)c(C)c(=O)c2c1] | 508 [M + H]+ |

TABLE 1-continued

| Example # | Chemical Name | Structure | MS ES+ m/z |
|---|---|---|---|
| 127 | 3-[[(1R)-1-[2-(3-Cyanophenyl)-3,6-dimethyl-4-oxo-chromen-8-yl]ethyl]amino]-6-methyl-pyridine-2-carboxylic acid | 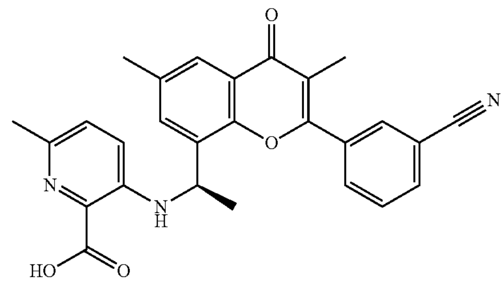 [SMILES: Cc1cc([C@@H](C)Nc2ccc(C)nc2C(=O)O)c2oc(-c3cccc(C#N)c3)c(C)c(=O)c2c1] | 454 [M + H]+ |
| 128 | 2-[[(1R)-1-[2-(3-Cyanophenyl)-3,6-dimethyl-4-oxo-chromen-8-yl]ethyl]amino]-5-(trifluoromethyl)benzoic acid | 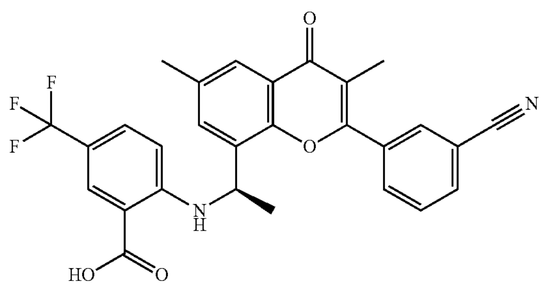 [SMILES: Cc1cc([C@@H](C)Nc2ccc(C(F)(F)F)cc2C(=O)O)c2oc(-c3cccc(C#N)c3)c(C)c(=O)c2c1] | 507 [M + H]+ |
| 129 | 2-[[(1R)-1-[2-(3-Cyanophenyl)-3,6-dimethyl-4-oxo-chromen-8-yl]ethyl]amino]-5-fluoro-benzoic acid | 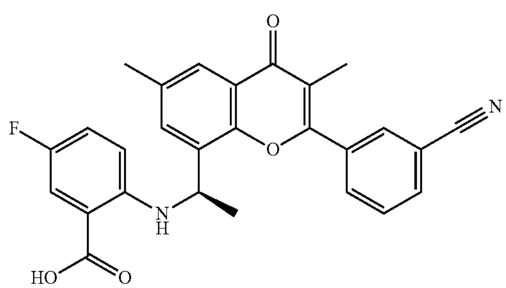 [SMILES: Cc1cc([C@@H](C)Nc2ccc(F)cc2C(=O)O)c2oc(-c3cccc(C#N)c3)c(C)c(=O)c2c1] | 457 [M + H]+ |
| 130 | 2-[[(1R)-1-[2-(2,4-Difluorophenyl)-3,6-dimethyl-4-oxo-chromen-8-yl]ethyl]amino]-6-fluoro-benzoic acid 2,2,2-trifluoroacetic acid | 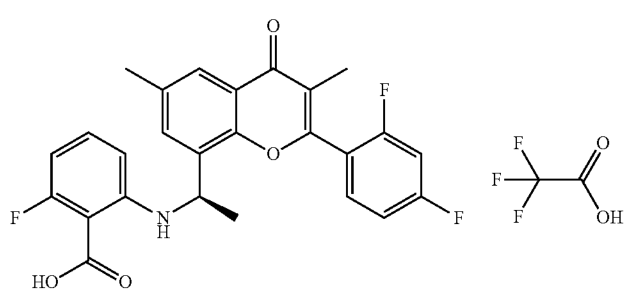 | 468 [M + H]+ |
| 131 | 6-Chloro-3-[[(1R)-1-[2-(2,4-difluorophenyl)-3,6-dimethyl-4-oxo-chromen-8-yl]ethyl]amino]pyridine-2-carboxylic acid 2,2,2-trifluoroacetic acid | 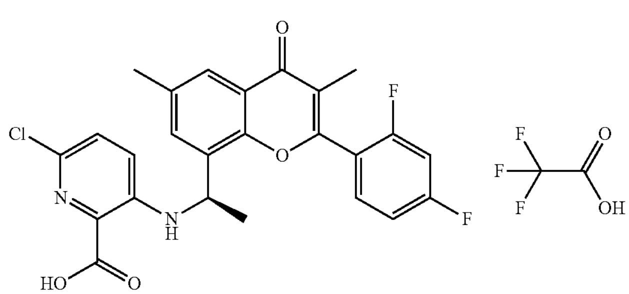 | 485 [M + H]+ |

TABLE 1-continued

| Example # | Chemical Name | Structure | MS ES+ m/z |
|---|---|---|---|
| 132 | 2-[1-(3-Fluoro-6-methyl-4-oxo-2-phenyl-chromen-8-yl)ethylamino]benzoic acid, Isomer 1 | 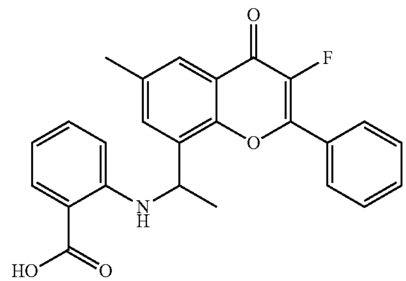 [SMILES: Cc1cc(C(C)Nc2ccccc2C(=O)O)c2oc(-c3ccccc3)c(F)c(=O)c2c1] | 418 [M + H]+ |
| 133 | 2-[1-(3-Fluoro-6-methyl-4-oxo-2-phenyl-chromen-8-yl)ethylamino]benzoic acid, Isomer 2 | 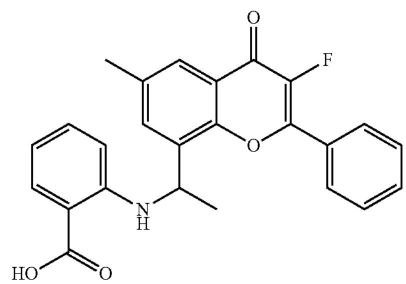 [SMILES: Cc1cc(C(C)Nc2ccccc2C(=O)O)c2oc(-c3ccccc3)c(F)c(=O)c2c1] | 418 [M + H]+ |
| 134 | 3-[[(1R)-1-[2-(3-Fluorophenyl)-3,6-dimethyl-4-oxo-chromen-8-yl]ethyl]amino]-6-methyl-pyridine-2-carboxylic acid | 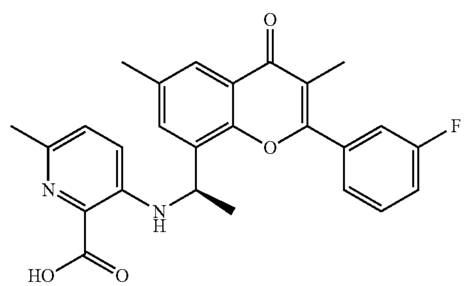 [SMILES: Cc1cc([C@@H](C)Nc2ccc(C)nc2C(=O)O)c2oc(-c3cccc(F)c3)c(C)c(=O)c2c1] | 447 [M + H]+ |
| 135 | 6-Methoxy-3-[[(1R)-1-(3,6-dimethyl-4-oxo-2-phenyl-chromen-8-yl)ethyl]amino]pyridine-2-carboxylic acid 2,2,2-trifluoroacetic acid | 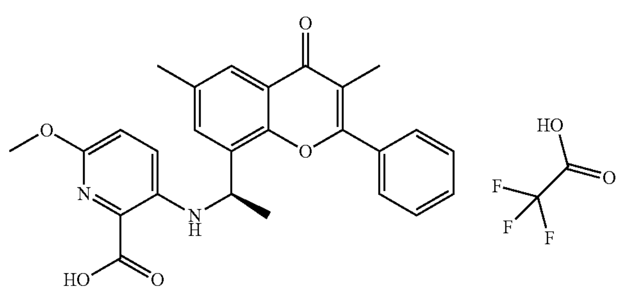 | 445 [M + H]+ |
| 136 | 3-[[(1R)-1-[2-(3-Fluorophenyl)-3,6-dimethyl-4-oxo-chromen-8-yl]ethyl]amino]pyridine-2-carboxylic acid | 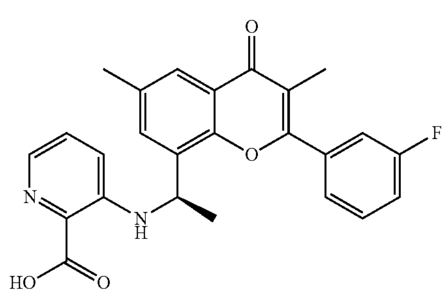 [SMILES: Cc1cc([C@@H](C)Nc2cccnc2C(=O)O)c2oc(-c3cccc(F)c3)c(C)c(=O)c2c1] | 433 [M + H]+ |

TABLE 1-continued

| Example # | Chemical Name | Structure | MS ES+ m/z |
|---|---|---|---|
| 137 | 2-[[(1R)-1-(3,6-Dimethyl-4-oxo-2-phenyl-chromen-8-yl)ethyl]amino]pyridine-3-carboxylic acid | 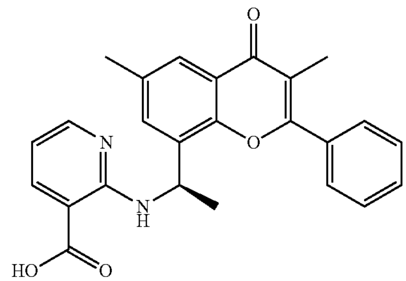 [SMILES: Cc1cc([C@@H](C)Nc2ncccc2C(=O)O)c2oc(-c3ccccc3)c(C)c(=O)c2c1] | 415 [M + H]+ |
| 138 | 3-[[(1R)-1-(3,6-Dimethyl-4-oxo-2-phenyl-chromen-8-yl)ethyl]amino]pyridine-4-carboxylic acid | 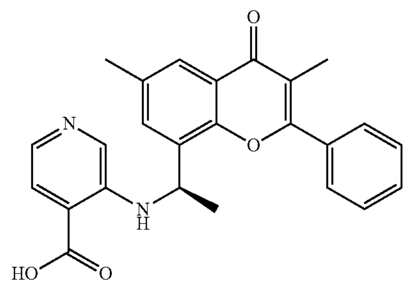 [SMILES: Cc1cc([C@@H](C)Nc2cnccc2C(=O)O)c2oc(-c3ccccc3)c(C)c(=O)c2c1] | 415 [M + H]+ |
| 139 | 6-Chloro-3-[[(1R)-1-[6-methyl-4-oxo-2-phenyl-3-(trifluoromethyl)-chromen-8-yl]ethyl]amino]pyridine-2-carboxylic acid 2,2,2-trifluoroacetic acid | 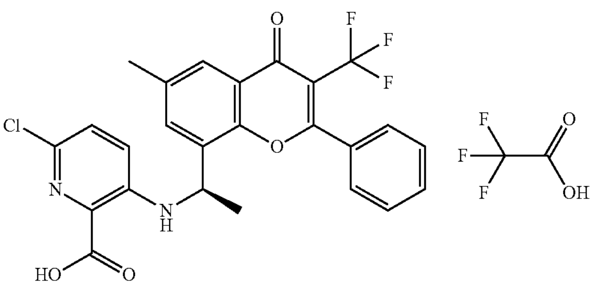 | 503 [M + H]+ |
| 140 | 6-Chloro-3-[1-(3-iodo-6-methyl-4-oxo-2-phenyl-chromen-8-yl)ethylamino]pyridine-2-carboxylic acid 2,2,2-trifluoroacetic acid | 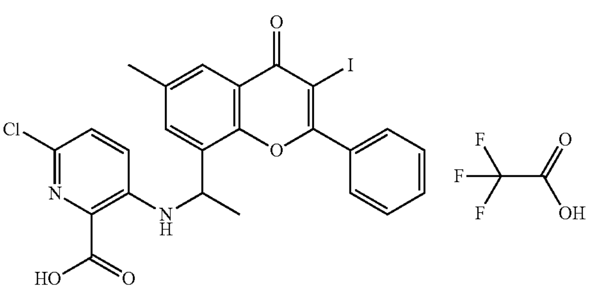 | 561 [M + H]+ |
| 141 | 6-Bromo-3-[[(1R)-1-[2-(3-cyanophenyl)-3,6-dimethyl-4-oxo-chromen-8-yl]ethyl]amino]pyridine-2-carboxylic acid | 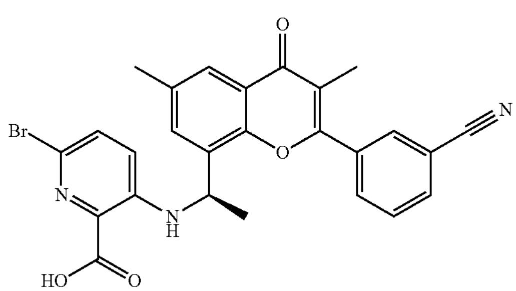 [SMILES: Cc1cc([C@@H](C)Nc2ccc(Br)nc2C(=O)O)c2oc(-c3cccc(C#N)c3)c(C)c(=O)c2c1] | 520 [M + H]+ |

TABLE 1-continued

| Example # | Chemical Name | Structure | MS ES+ m/z |
|---|---|---|---|
| 142 | 3-[[(1R)-1-[2-(2-Fluorophenyl)-3,6-dimethyl-4-oxo-chromen-8-yl]ethyl]amino]pyridine-2-carboxylic acid | 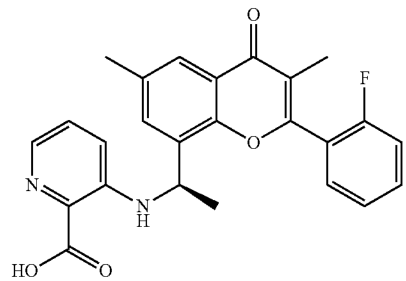 [SMILES: Cc1cc([C@@H](C)Nc2cccnc2C(=O)O)c2oc(-c3ccccc3F)c(C)c(=O)c2c1] | 433 [M + H]+ |
| 143 | 2-Fluoro-6-[[(1R)-1-[2-(3-fluorophenyl)-3,6-dimethyl-4-oxo-chromen-8-yl]ethyl]amino]benzoic acid 2,2,2-trifluoroacetic acid | 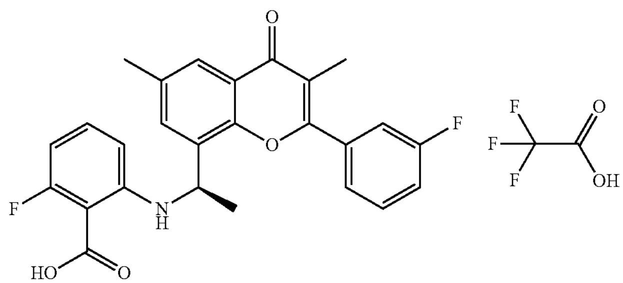 | 450 [M + H]+ |
| 144 | 5-Chloro-2-[[(1R)-1-[2-(3-cyanophenyl)-3,6-dimethyl-4-oxo-chromen-8-yl]ethyl]amino]benzoic acid | 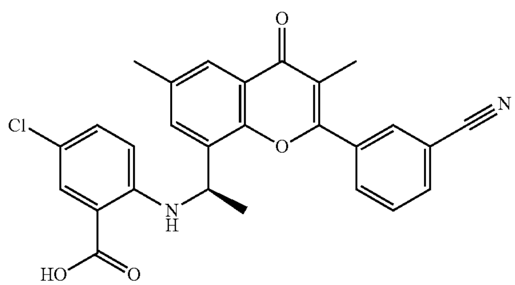 [SMILES: Cc1cc([C@@H](C)Nc2ccc(Cl)cc2C(=O)O)c2oc(-c3cccc(C#N)c3)c(C)c(=O)c2c1] | 473 [M + H]+ |
| 145 | 5-Chloro-2-[[(1R)-1-[2-(3-fluorophenyl)-3,6-dimethyl-4-oxo-chromen-8-yl]ethyl]amino]benzoic acid | 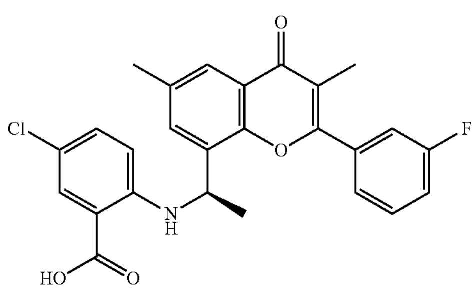 [SMILES: Cc1cc([C@@H](C)Nc2ccc(Cl)cc2C(=O)O)c2oc(-c3cccc(F)c3)c(C)c(=O)c2c1] | 466 [M + H]+ |
| 146 | 5-Chloro-2-[[(1R)-1-[2-(3,4-difluorophenyl)-3,6-dimethyl-4-oxo-chromen-8-yl]ethyl]amino]benzoic acid | 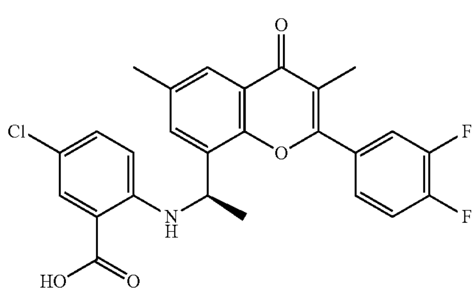 [SMILES: Cc1cc([C@@H](C)Nc2ccc(Cl)cc2C(=O)O)c2oc(-c3ccc(F)c(F)c3)c(C)c(=O)c2c1] | 484 [M + H]+ |

TABLE 1-continued

| Example # | Chemical Name | Structure | MS ES+ m/z |
|---|---|---|---|
| 147 | 5-Chloro-2-[[(1R)-1-[2-(2-fluorophenyl)-3,6-dimethyl-4-oxo-chromen-8-yl]ethyl]amino]benzoic acid | 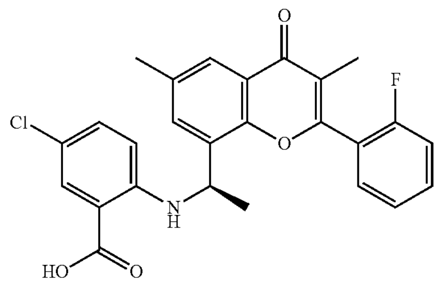 [SMILES: Cc1cc([C@@H](C)Nc2ccc(Cl)cc2C(=O)O)c2oc(-c3ccccc3F)c(C)c(=O)c2c1] | 466 [M + H]+ |
| 148 | 3-[[(1R)-1-[2-(2-Fluorophenyl)-3,6-dimethyl-4-oxo-chromen-8-yl]ethyl]amino]-6-methyl-pyridine-2-carboxylic acid | 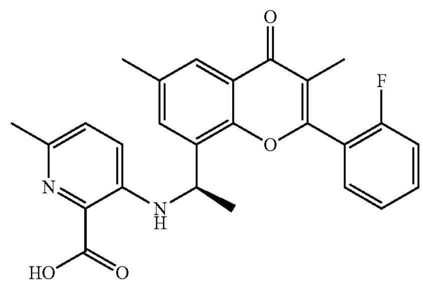 [SMILES: Cc1cc([C@@H](C)Nc2ccc(C)nc2C(=O)O)c2oc(-c3ccccc3F)c(C)c(=O)c2c1] | 447 [M + H]+ |
| 149 | 2-[[(1R)-1-[2-(4-Methoxycarbonylphenyl)-3,6-dimethyl-4-oxo-chromen-8-yl]ethyl]amino]benzoic acid | 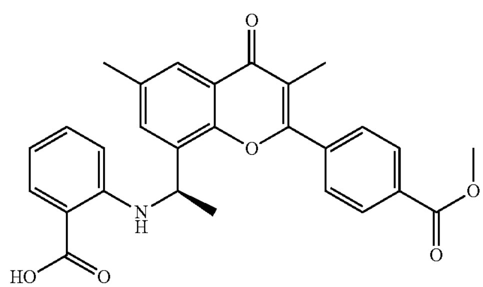 [SMILES: COC(=O)c1ccc(-c2oc3c([C@@H](C)Nc4ccccc4C(=O)O)cc(C)cc3c(=O)c2C)cc1] | 472 [M + H]+ |
| 150 | 2-[[(1R)-1-[2-(3-Methoxycarbonylphenyl)-3,6-dimethyl-4-oxo-chromen-8-yl]ethyl]amino]benzoic acid | 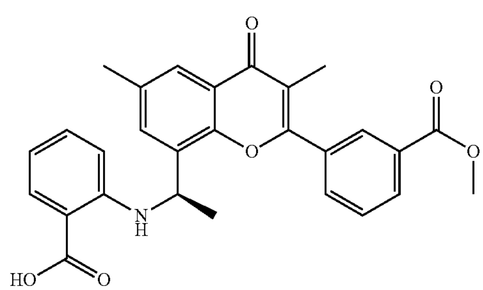 [SMILES: COC(=O)c1cccc(-c2oc3c([C@@H](C)Nc4ccccc4C(=O)O)cc(C)cc3c(=O)c2C)c1] | 472 [M + H]+ |
| 151 | 2-[[(1R)-1-[3,6-Dimethyl-2-[4-(methylcarbamoyl)phenyl]-4-oxo-chromen-8-yl]ethyl]amino]benzoic acid | 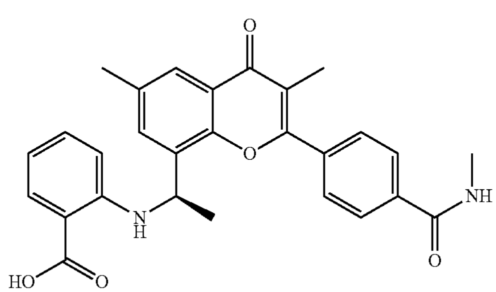 [SMILES: CNC(=O)c1ccc(-c2oc3c([C@@H](C)Nc4ccccc4C(=O)O)cc(C)cc3c(=O)c2C)cc1] | 471 [M + H]+ |

TABLE 1-continued

| Example # | Chemical Name | Structure | MS ES+ m/z |
|---|---|---|---|
| 152 | 2-[[(1R)-1-[3,6-Dimethyl-2-[3-(methylcarbamoyl)phenyl]-4-oxo-chromen-8-yl]ethyl]amino]benzoic acid | 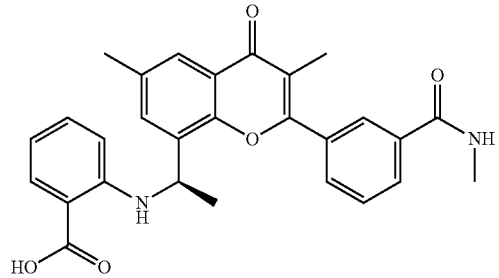 [SMILES: CNC(=O)c1cccc(-c2oc3c([C@@H](C)Nc4ccccc4C(=O)O)cc(C)cc3c(=O)c2C)c1] | 471 [M + H]+ |
| 153 | 6-Chloro-3-[1-(3-iodo-6-methyl-4-oxo-2-phenyl-chromen-8-yl)ethylamino]pyridine-2-carboxylic acid, Isomer 1 | 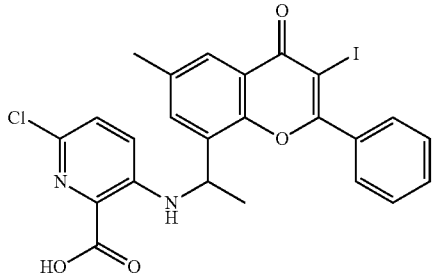 [SMILES: Cc1cc(C(C)Nc2ccc(Cl)nc2C(=O)O)c2oc(-c3ccccc3)c(I)c(=O)c2c1] | 561 [M + H]+ |
| 154 | 6-Chloro-3-[1-(3-iodo-6-methyl-4-oxo-2-phenyl-chromen-8-yl)ethylamino]pyridine-2-carboxylic acid, Isomer 2 | 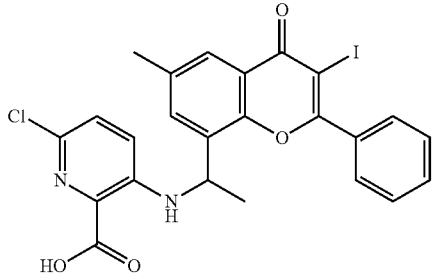 [SMILES: Cc1cc(C(C)Nc2ccc(Cl)nc2C(=O)O)c2oc(-c3ccccc3)c(I)c(=O)c2c1] | 561 [M + H]+ |
| 155 | 2-Methoxy-5-[[(1R)-1-(3,6-dimethyl-4-oxo-2-phenyl-chromen-8-yl)ethyl]amino]pyrimidine-4-carboxylic acid 2,2,2-trifluoroacetic acid | 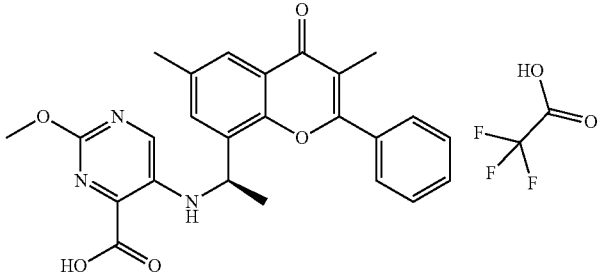 | 446 [M + H]+ |
| 156 | 2-[[(1R)-1-[6-Methyl-4-oxo-2-phenyl-3-(3-pyridyl)chromen-8-yl]ethyl]amino]benzoic acid 2,2,2-trifluoroacetic acid | 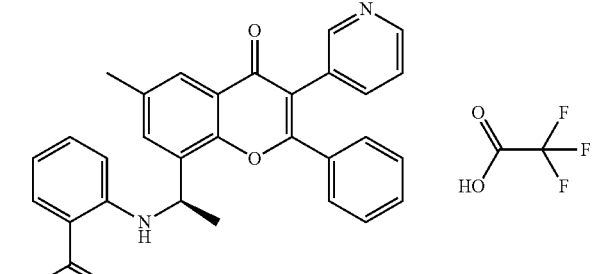 | 477 [M + H]+ |

TABLE 1-continued

| Example # | Chemical Name | Structure | MS ES+ m/z |
|---|---|---|---|
| 157 | 5-Cyano-2-[[(1R)-1-(3,6-dimethyl-4-oxo-2-phenyl-chromen-8-yl)ethyl]amino]benzoic acid, Isomer 1 | 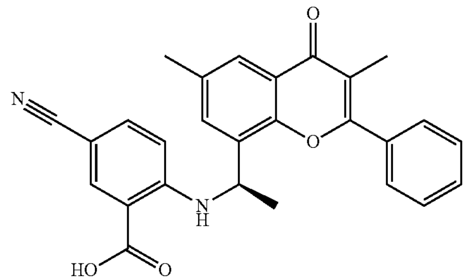 [SMILES: Cc1cc([C@@H](C)Nc2ccc(C#N)cc2C(=O)O)c2oc(-c3ccccc3)c(C)c(=O)c2c1] | 439 [M + H]+ |
| 158 | 5-Cyano-2-[[(1R)-1-(3,6-dimethyl-4-oxo-2-phenyl-chromen-8-yl)ethyl]amino]benzoic acid, Isomer 2 | 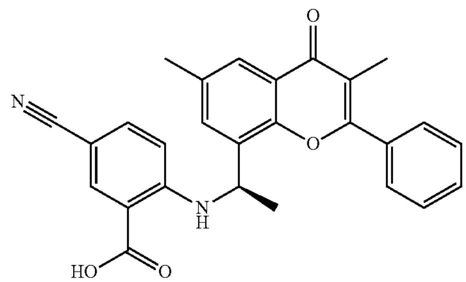 | 439 [M + H]+ |
| 159 | 6-Cyano-3-[[(1R)-1-(3,6-dimethyl-4-oxo-2-phenyl-chromen-8-yl)ethyl]amino]pyridine-2-carboxylic acid, Isomer 1 | 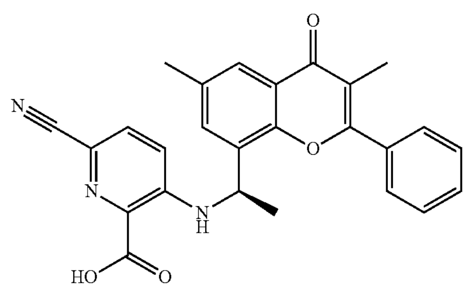 [SMILES: Cc1cc([C@@H](C)Nc2ccc(C#N)nc2C(=O)O)c2oc(-c3ccccc3)c(C)c(=O)c2c1] | 440 [M + H]+ |
| 160 | 6-Cyano-3-[[(1R)-1-(3,6-dimethyl-4-oxo-2-phenyl-chromen-8-yl)ethyl]amino]pyridine-2-carboxylic acid, Isomer 2 | 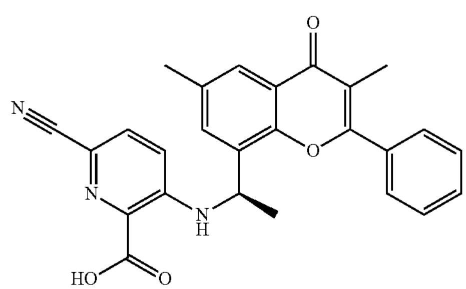 [SMILES: Cc1cc([C@@H](C)Nc2ccc(C#N)nc2C(=O)O)c2oc(-c3ccccc3)c(C)c(=O)c2c1] | 440 [M + H]+ |
| 161 | 2-[[(1R)-1-[3,6-Dimethyl-2-[4-(3-methyl-1H-pyrazol-4-yl)phenyl]-4-oxo-chromen-8-yl]ethyl]amino]benzoic acid | 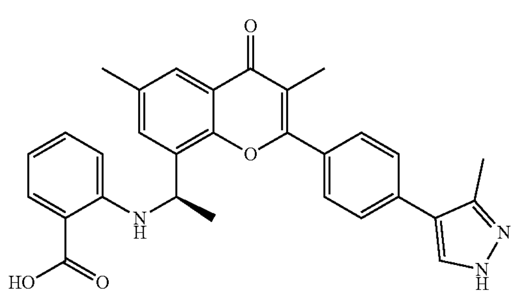 [SMILES: Cc1cc([C@@H](C)Nc2ccccc2C(=O)O)c2oc(-c3ccc(-c4c[nH]nc4C)cc3)c(C)c(=O)c2c1] | 494 [M + H]+ |

TABLE 1-continued

| Example # | Chemical Name | Structure | MS ES+ m/z |
|---|---|---|---|
| 162 | 2-[[(1R)-1-[3,6-Dimethyl-4-oxo-2-[4-(1H-pyrazol-4-yl)phenyl]chromen-8-yl]ethyl]amino]benzoic acid | 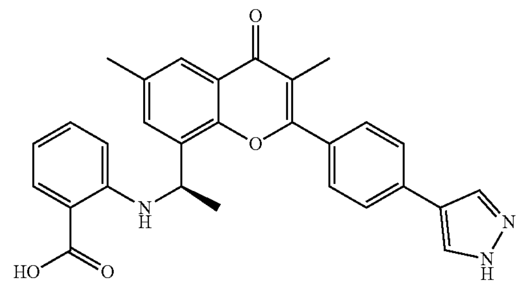 [SMILES: Cc1cc([C@@H](C)Nc2ccccc2C(=O)O)c2oc(-c3ccc(-c4cn[nH]c4)cc3)c(C)c(=O)c2c1] | 480 [M + H]+ |
| 163 | 2-[[(1R)-1-[6-Methyl-4-oxo-2-[4-(1H-pyrazol-4-yl)phenyl]chromen-8-yl]ethyl]amino]benzoic acid | 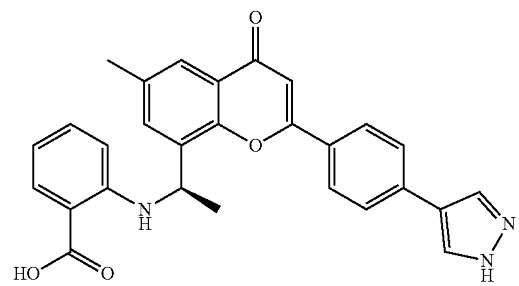 [SMILES: Cc1cc([C@@H](C)Nc2ccccc2C(=O)O)c2oc(-c3ccc(-c4cn[nH]c4)cc3)cc(=O)c2c1] | 466 [M + H]+ |
| 164 | 2-[[(1R)-1-[3,6-Dimethyl-2-[4-(1-methylpyrazol-4-yl)phenyl]-4-oxo-chromen-8-yl]ethyl]amino]benzoic acid | 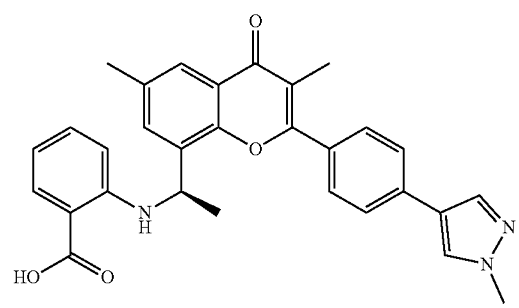 [SMILES: Cc1cc([C@@H](C)Nc2ccccc2C(=O)O)c2oc(-c3ccc(-c4cnn(C)c4)cc3)c(C)c(=O)c2c1] | 494 [M + H]+ |
| 165 | 2-[[(1R)-1-[2-[4-(3,5-Dimethyl-1H-pyrazol-4-yl)phenyl]-3,6-dimethyl-4-oxo-chromen-8-yl]ethyl]amino]benzoic acid | 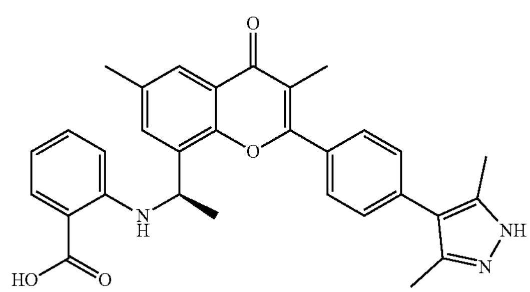 [SMILES: Cc1cc([C@@H](C)Nc2ccccc2C(=O)O)c2oc(-c3ccc(-c4c(C)n[nH]c4C)cc3)c(C)c(=O)c2c1] | 508 [M + H]+ |
| 166 | 2-[[(1R)-1-[3,6-Dimethyl-4-oxo-2-[3-(1H-pyrazol-3-yl)phenyl]chromen-8-yl]ethyl]amino]benzoic acid | 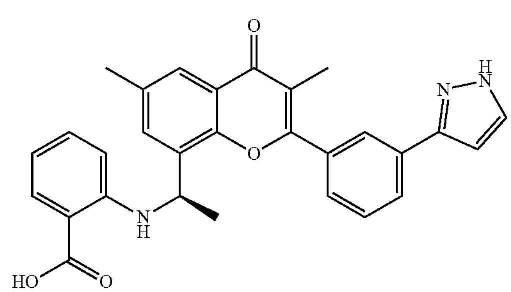 [SMILES: Cc1cc([C@@H](C)Nc2ccccc2C(=O)O)c2oc(-c3cccc(-c4cc[nH]n4)c3)c(C)c(=O)c2c1] | 480 [M + H]+ |

TABLE 1-continued

| Example # | Chemical Name | Structure | MS ES+ m/z |
|---|---|---|---|
| 167 | 2-[[(1R)-1-[3,6-Dimethyl-4-oxo-2-[3-(1H-pyrazol-4-yl)phenyl]chromen-8-yl]ethyl]amino]benzoic acid | 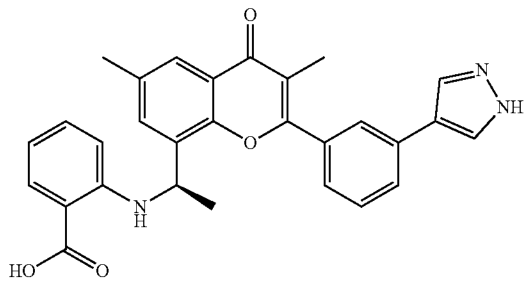 [SMILES: Cc1cc([C@@H](C)Nc2ccccc2C(=O)O)c2oc(-c3cccc(-c4cn[nH]c4)c3)c(C)c(=O)c2c1] | 480 [M + H]+ |
| 168 | 2-[[(1R)-1-[3,6-Dimethyl-4-oxo-2-[4-(1H-pyrazol-5-yl)phenyl]chromen-8-yl]ethyl]amino]benzoic acid | 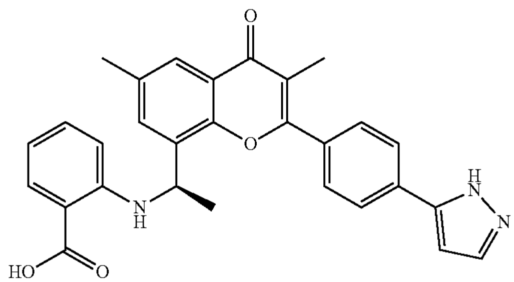 [SMILES: Cc1cc([C@@H](C)Nc2ccccc2C(=O)O)c2oc(-c3ccc(-c4ccn[nH]4)cc3)c(C)c(=O)c2c1] | 480 [M + H]+ |
| 169 | 2-[[(1R)-1-[3,6-Dimethyl-4-oxo-2-[4-(1H-pyrazol-5-yl)phenyl]chromen-8-yl]ethyl]amino]benzoic acid | 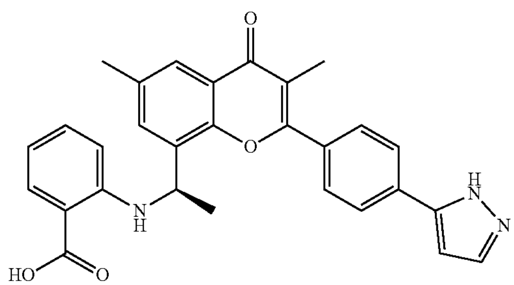 | 494 [M + H]+ |
| 170 | 2-[[(1R)-1-[2-(3-Cyano-2-fluoro-phenyl)-3,6-dimethyl-4-oxo-chromen-8-yl]ethyl]amino]benzoic acid | 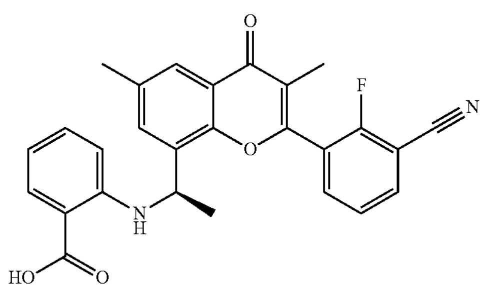 [SMILES: Cc1cc([C@@H](C)Nc2ccccc2C(=O)O)c2oc(-c3cccc(C#N)c3F)c(C)c(=O)c2c1] | 457 [M + H]+ |
| 171 | 2-[[(1R)-1-[3-(2-Carboxyethylamino)-6-methyl-4-oxo-2-phenyl-chromen-8-yl]ethyl]amino]benzoic acid 2,2,2-trifluoroacetic acid | 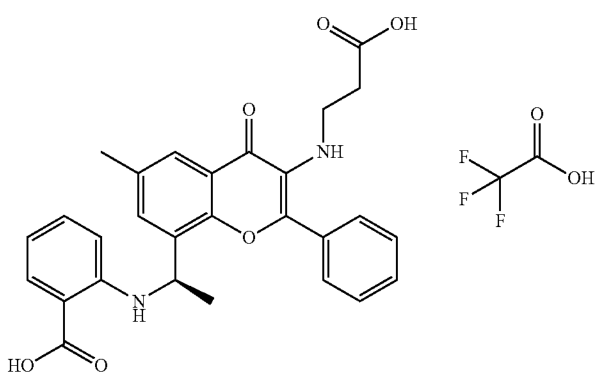 [SMILES: Cc1cc([C@@H](C)Nc2ccccc2C(=O)O)c2oc(-c3ccccc3)c(NCCC(=O)O)c(=O)c2c1 ; O=C(O)C(F)(F)F] | 487 [M + H]+ |

TABLE 1-continued

| Example # | Chemical Name | Structure | MS ES+ m/z |
|---|---|---|---|
| 172 | 2-[[(1R)-1-[2-[4-(4-Cyanophenyl)phenyl]-3,6-dimethyl-4-oxo-chromen-8-yl]ethyl]amino]benzoic acid | 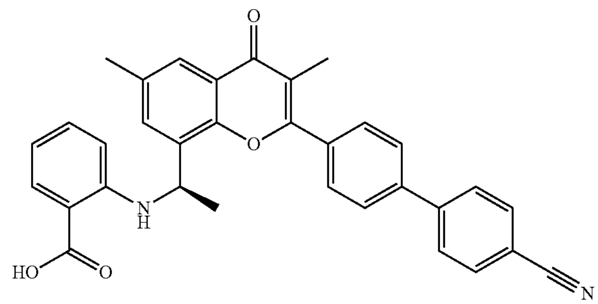 [SMILES: Cc1cc([C@@H](C)Nc2ccccc2C(=O)O)c2oc(-c3ccc(-c4ccc(C#N)cc4)cc3)c(C)c(=O)c2c1] | 515 [M + H]⁺ |
| 173 | 2-[[(1R)-1-[2-[4-(3-Cyanophenyl)phenyl]-3,6-dimethyl-4-oxo-chromen-8-yl]ethyl]amino]benzoic acid | 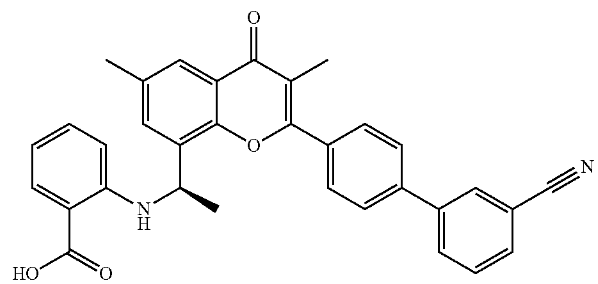 [SMILES: Cc1cc([C@@H](C)Nc2ccccc2C(=O)O)c2oc(-c3ccc(-c4cccc(C#N)c4)cc3)c(C)c(=O)c2c1] | 515 [M + H]⁺ |
| 174 | 2-[[(1R)-1-[2-[3-(2-Cyanophenyl)phenyl]-3,6-dimethyl-4-oxo-chromen-8-yl]ethyl]amino]benzoic acid | 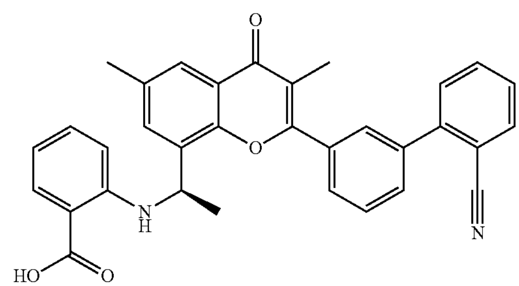 [SMILES: Cc1cc([C@@H](C)Nc2ccccc2C(=O)O)c2oc(-c3cccc(-c4ccccc4C#N)c3)c(C)c(=O)c2c1] | 515 [M + H]⁺ |
| 175 | 2-[[(1R)-1-[2-[3-(4-Cyanophenyl)phenyl]-3,6-dimethyl-4-oxo-chromen-8-yl]ethyl]amino]benzoic acid | 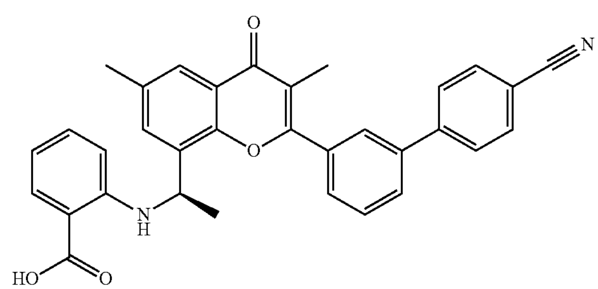 [SMILES: Cc1cc([C@@H](C)Nc2ccccc2C(=O)O)c2oc(-c3cccc(-c4ccc(C#N)cc4)c3)c(C)c(=O)c2c1] | 515 [M + H]⁺ |
| 176 | 2-[[(1R)-1-[2-[3-(3-Cyanophenyl)phenyl]-3,6-dimethyl-4-oxo-chromen-8-yl]ethyl]amino]benzoic acid | 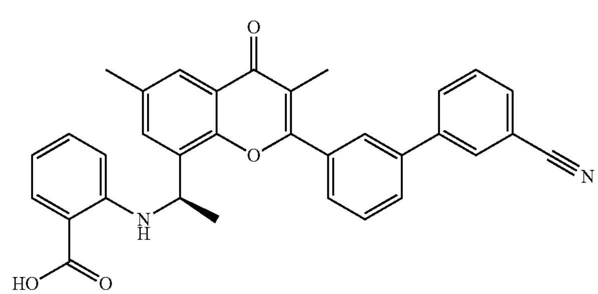 [SMILES: Cc1cc([C@@H](C)Nc2ccccc2C(=O)O)c2oc(-c3cccc(-c4cccc(C#N)c4)c3)c(C)c(=O)c2c1] | 515 [M + H]⁺ |

TABLE 1-continued

| Example # | Chemical Name | Structure | MS ES+ m/z |
|---|---|---|---|
| 177 | 2-[[(1R)-1-[2-[4-(2-Cyanophenyl)phenyl]-3,6-dimethyl-4-oxo-chromen-8-yl]ethyl]amino]benzoic acid | 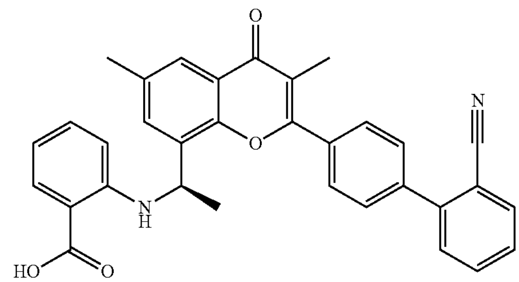 [SMILES: Cc1cc([C@@H](C)Nc2ccccc2C(=O)O)c2oc(-c3ccc(-c4ccccc4C#N)cc3)c(C)c(=O)c2c1] | 515 [M + H]+ |
| 178 | 2-[[(1R)-1-[2-[3-(4-Cyanopyrazol-1-yl)phenyl]-3,6-dimethyl-4-oxo-chromen-8-yl]ethyl]amino]benzoic acid 2,2,2-trifluoroacetic acid | 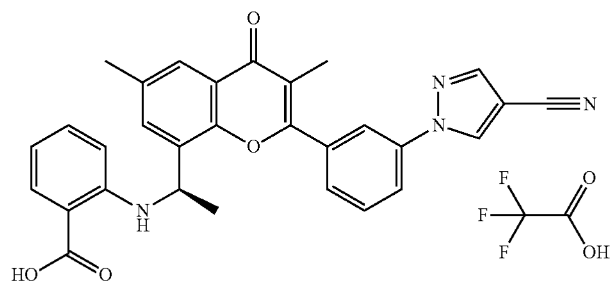 | 505 [M + H]+ |

TABLE 2

| Ex # | NMR Line Listing |
|---|---|
| 1 | $^1$H NMR (400 MHz, DMSO-d6) δ ppm 1.58 (d, J = 6.8 Hz, 3H), 2.07 (s, 3H), 2.36 (s, 3H), 5.09-5.11 (m, 1H), 6.95 (d, J = 8.2 Hz, 1H), 7.19 (d, J = 8.8 Hz, 1H), 7.51 (d, J = 2.0 Hz, 1H), 7.58-7.59 (m, 3H), 7.78-7.81 (m, 3H), 8.72 (s, 1H) |
| 2 | $^1$H NMR (400 MHz, DMSO-d6) δ ppm 1.62 (d, J = 6.4 Hz, 3H), 2.34 (s, 3H), 5.20-5.23 (m, 1H), 6.74 (d, J = 8.4 Hz, 1H), 6.98 (d, J = 8.4 Hz, 1H), 7.07 (s, 1H), 7.51 (d, J = 2.0 Hz, 1H), 7.57-7.62 (m, 3H), 7.73 (s, 1H), 8.13 (dd, J = 8.0, 2.0 Hz, 2H), 9.88 (s, 1H) |
| 3 | $^1$H NMR (400 MHz, DMSO-d6) δ ppm 1.66-1.74 (m, 3H), 1.77 (br s, 6H), 2.37 (br s, 3H), 5.26-5.44 (m, 1H), 6.47-6.62 (m, 2H), 7.18-7.28 (m, 2H), 7.55 (br s, 1H), 7.63-7.71 (m, 1H), 7.74-7.86 (m, 3H), 8.09-8.18 (m, 1H), 8.25 (br s, 1H), 8.41-8.50 (m, 1H), 12.65-12.99 (m, 1H) |
| 5 | $^1$H NMR (400 MHz, DMSO-d6) δ ppm 1.71 (br d, J = 5.26 Hz, 3H), 1.77 (br s, 6H), 2.29-2.44 (m, 4H), 5.34 (br s, 1H), 6.49-6.57 (m, 2H), 7.22 (br s, 2H), 7.55 (br s, 1H), 7.64-7.69 (m, 1H), 7.77 (br s, 1H), 7.82 (br d, J = 8.56 Hz, 1H), 8.13 (br d, J = 7.46 Hz, 1H), 8.25 (br s, 1H), 8.45 (br s, 1H), 12.61-12.94 (m, 1H) |
| 6 | $^1$H NMR (400 MHz, METHANOL-d4) δ ppm 1.90 (br d, J = 5.4 Hz, 3H), 5.56 (br d, J = 4.8 Hz, 1H), 6.52-6.65 (m, 1H), 6.66-6.78 (m, 1H), 7.05 (s, 1H), 7.20-7.33 (m, 1H), 7.55-7.72 (m, 3H), 7.85-7.98 (m, 2H), 8.11-8.22 (m, 2H) |
| 7 | $^1$H NMR (400 MHz, DMSO-d6) δ ppm 1.61-1.72 (m, 5H), 1.88 (br s, 2H), 2.37 (br s, 3H), 5.33 (br s, 1H), 6.52 (br d, J = 8.68 Hz, 1H), 6.57 (br s, 1H), 7.11 (br s, 1H), 7.19-7.26 (m, 1H), 7.52 (br d, J = 7.95 Hz, 2H), 7.56 (br s, 1H), 7.76 (br s, 1H), 7.83 (br d, J = 7.58 Hz, 1H), 8.16 (br d, J = 7.46 Hz, 2H), 8.44 (br s, 1H), 12.79 (br s, 1H) |
| 8 | $^1$H NMR (400 MHz, DMSO-d6) δ ppm 1.63-1.74 (m, 3H), 2.37 (s, 3H), 2.93 (s, 3H), 3.02 (s, 3H), 5.35 (s, 1H), 6.51-6.57 (m, 2H), 7.15 (s, 1H), 7.20-7.26 (m, 1H), 7.56-7.62 (m, 3H), 7.77 (s, 1H), 7.82 (d, J = 7.7 Hz, 1H), 8.19 (d, J = 7.5 Hz, 2H), 8.45 (s, 1H), 12.81 (s, 1H) |
| 9 | $^1$H NMR (400 MHz, DMSO-d6) δ ppm 1.64-1.72 (m, 3H), 2.38 (s, 3H), 3.32-3.40 (m, 4H), 5.35 (s, 1H), 6.51-6.58 (m, 2H), 7.21-7.29 (m, 2H), 7.60 (s, 1H), 7.77 (s, 1H), 7.83 (d, J = 7.4 Hz, 1H), 8.11 (d, J = 7.8 Hz, 2H), 8.41 (d, J = 7.7 Hz, 2H), 12.83 (s, 1H) |
| 10 | $^1$H NMR (400 MHz, DMSO-d6) δ ppm 1.63 (bs, 3H), 2.40 (bs, 3H), 5.19 (bs, 1H), 6.50 (d, J = 7.70 Hz, 1H), 6.56-6.59 (m, 1H), 7.19-7.23 (m, 1H), 7.64 (bs, 1H), 7.69-7.73 (m, 2H), 7.76 (d, J = 4.4 Hz, 1H), 7.83 (m, 2H), 8.14 (bd, J = 6.9 Hz, 2H), 8.38 (bs, 1H), 12.75 (bs, 1H) |
| 11 | $^1$H NMR (400 MHz, DMSO-d6) δ ppm 1.62 (d, J = 6.8 Hz, 3H), 2.36 (s, 3H), 5.23-5.25 (m, 1H), 6.44 (d, J = 8.4 Hz, 1H), 6.53 (t, J = 7.6 Hz, 1H), 6.84 (s, 1H), 7.15-7.20 (m, 1H), 7.44-7.55 (m, 2H), 7.56 (d, J = 2.0 Hz, 1H), 7.65-7.69 (m, 1H), 7.75 (s, 1H), 7.81 (d, J = 8.0 Hz, 1H), 8.04-8.05 (m, 1H), 8.57 (s, 1H) |
| 12 | $^1$H NMR (400 MHz, DMSO-d6) δ ppm 0.87 (br s, 2H) 0.91-1.01 (m, 2H) 1.44 (br s, 3H) 1.63-1.74 (m, 3H) 2.37 (br s, 3H) 5.27-5.37 (m, 1H) 6.49-6.60 (m, 2H) 7.02-7.09 (m, 1H) 7.18-7.28 (m, 1H) 7.36-7.46 (m, 2H) 7.53-7.61 (m, 1H) 7.73-7.78 (m, 1H) 7.79-7.86 (m, 1H) 8.00-8.09 (m, 2H) 8.40-8.49 (m, 1H) 12.68-12.96 (m, 1H) |

TABLE 2-continued

| Ex # | NMR Line Listing |
|---|---|
| 13 | $^1$H NMR (400 MHz, DMSO-d6) δ ppm 1.72 (br d, J = 3.6 Hz, 3H), 2.38 (br s, 3H), 3.83-3.94 (m, 3H), 5.42 (s, 1H), 6.51-6.63 (m, 2H), 7.18-7.31 (m, 2H), 7.53-7.63 (m, 2H), 7.75-7.89 (m, 3H), 7.90-8.00 (m, 1H), 8.00-8.10 (m, 1H), 8.24-8.38 (m, 2H), 8.41-8.55 (m, 1H), 12.65-12.96 (m, 1H) |
| 14 | $^1$H NMR (400 MHz, DMSO-d6) δ ppm 1.56 (d, J = 6.4 Hz, 3H), 2.36 (s, 3H), 2.50 (s, 3H), 5.13-5.15 (m, 1H), 6.38 (d, J = 8.4 Hz, 1H), 6.52-6.56 (m, 2H), 7.16-7.18 (m, 1H), 7.40-7.41 (m, 2H), 7.46-7.49 (m, 1H), 7.55 (s, 1H), 7.67 (d, J = 7.2 Hz, 1H), 7.78-7.82 (m, 2H), 8.37 (d, J = 4.0 Hz, 1H) |
| 15 | $^1$H NMR (400 MHz, DMSO-d6) δ ppm 1.53 (d, J = 5.6 Hz, 3H), 2.34 (s, 3H), 5.27-5.29 (m, 1H), 6.34-6.38 (m, 3H), 6.87 (t, J = 7.2 Hz, 1H), 6.92 (s, 1H), 7.59 (s, 1H), 7.75 (s, 1H), 7.82 (t, J = 7.6 Hz, 1H), 7.94 (t, J = 7.6 Hz, 1H), 8.11-8.14 (m, 2H), 9.84 (s, 1H) |
| 16 | $^1$H NMR (400 MHz, DMSO-d6) δ ppm 1.65 (d, J = 6.8 Hz, 3H), 2.36 (s, 3H), 5.38-5.39 (m, 1H), 6.50-6.55 (m, 2H), 7.16-7.20 (m, 1H), 7.24 (s, 1H), 7.57 (d, J = 2.0 Hz, 1H), 7.75 (s, 1H), 7.77-7.81 (m, 2H), 8.07-8.08 (m, 2H), 8.45 (d, J = 8.4 Hz, 1H), 8.61 (s, 1H) |
| 17 | $^1$H NMR (400 MHz, DMSO-d6) δ ppm 1.66 (d, J = 6.8 Hz, 3H), 2.37 (s, 3H), 5.32-5.35 (m, 1H), 6.51-6.57 (m, 2H), 7.22-7.25 (m, 2H), 7.58 (d, J = 2.0 Hz, 1H), 7.76 (s, 1H), 7.81 (d, J = 8.0 Hz, 1H), 8.04-8.06 (m, 2H), 8.31-8.33 (m, 2H), 8.45 (s, 1H), 12.79 (s, 1H) |
| 18 | $^1$H NMR (400 MHz, DMSO-d6) δ ppm 1.67 (d, J = 6.8 Hz, 3H), 2.37 (s, 3H), 5.34-5.35 (m, 1H), 6.50-6.57 (m, 2H), 7.18-7.22 (m, 2H), 7.43-7.48 (m, 1H), 7.57 (d, J = 2.0 Hz, 1H), 7.62-7.64 (m, 1H), 7.75 (s, 1H), 7.82 (d, J = 8.0 Hz, 1H), 7.97-8.01 (m, 2H), 8.55 (s, 1H), 12.84 (br s, 1H) |
| 19 | $^1$H NMR (400 MHz, DMSO-d6) δ ppm 1.66 (d, J = 6.0 Hz, 3H), 2.36 (s, 3H), 5.32-5.33 (m, 1H), 6.50-6.57 (m, 2H), 7.08 (s, 1H), 7.21 (t, J = 7.6 Hz, 1H), 7.42 (t, J = 8.8 Hz, 2H), 7.56 (s, 1H), 7.74 (s, 1H), 7.82 (d, J = 8.0 Hz, 1H), 8.19-8.22 (m, 2H), 8.47 (s, 1H), 12.83 (br s, 1H) |
| 20 | $^1$H NMR (400 MHz, DMSO-d6) δ ppm 1.67 (d, J = 6.4 Hz, 3H), 2.36 (s, 3H), 5.31-5.32 (m, 1H), 6.51-6.52 (m, 1H), 7.09 (s, 1H), 7.11-7.14 (m, 1H), 7.52-7.54 (m, 2H), 7.57-7.62 (m, 3H), 7.75 (s, 1H), 8.13-8.14 (m, 2H), 8.29 (s, 1H), 13.15 (br s, 1H) |
| 21 | $^1$H NMR (400 MHz, DMSO-d6) δ ppm 1.58 (d, J = 6.8 Hz, 3H), 2.09 (s, 3H), 2.36 (s, 3H), 5.10-5.13 (m, 1H), 6.44 (d, J = 8.8 Hz, 1H), 6.54 (t, J = 7.6 Hz, 1H), 7.19-7.21 (m, 1H), 7.52 (d, J = 2.0 Hz, 1H), 7.58-7.60 (m, 3H), 7.79-7.82 (m, 4H), 8.39 (s, 1H), 12.74 (br s, 1H) |
| 22 | $^1$H NMR (400 MHz, DMSO-d6) δ ppm 1.68 (d, J = 6.8 Hz, 3H), 2.36 (s, 3H), 5.32-5.35 (m, 1H), 6.51-6.57 (m, 2H), 7.08 (s, 1H), 7.19-7.24 (m, 1H), 7.56-7.60 (m, 4H), 7.75 (s, 1H), 7.82 (d, J = 7.6 Hz, 1H), 8.13 (d, J = 7.6 Hz, 2H), 8.45 (d, J = 5.2 Hz, 1H), 12.88 (br s, 1H) |
| 23 | $^1$H NMR (400 MHz, DMSO-d6) δ ppm 1.72 (d, J = 6.72 Hz, 3H), 2.33 (s, 3H), 2.41 (s, 3H), 5.07-5.16 (m, 1H), 7.08 (s, 1H), 7.57-7.64 (m, 3H), 7.66 (d, J = 2.08 Hz, 1H), 7.80 (d, J = 1.34 Hz, 1H), 7.95 (d, J = 6.72 Hz, 1H), 8.12 (dd, J = 7.95, 1.59 Hz, 2H), 12.17 (br s, 1H) |
| 24 | $^1$H NMR (400 MHz, DMSO-d6) δ ppm 1.70 (d, J = 6.8 Hz, 3H), 5.36-5.39 (m, 1H), 6.51 (d, J = 8.4 Hz, 1H), 6.58 (t, J = 7.6 Hz, 1H), 7.15 (s, 1H), 7.20-7.24 (m, 1H), 7.53 (dd, J = 8.8, 3.2 Hz, 1H), 7.60-7.64 (m, 4H), 7.83 (d, J = 8.0 Hz, 1H), 8.14-8.16 (m, 2H), 8.44 (s, 1H), 12.73 (s, 1H) |
| 25 | $^1$H NMR (400 MHz, DMSO-d6) δ ppm 1.68 (br d, J = 6.60 Hz, 3H), 1.75 (s, 6H), 2.37 (s, 3H), 5.30-5.39 (m, 1H), 6.50-6.60 (m, 2H), 7.13 (s, 1H), 7.23 (t, J = 7.04 Hz, 1H), 7.52-7.61 (m, 1H), 7.71-7.79 (m, 3H), 7.83 (d, J = 7.24 Hz, 1H), 8.21 (d, J = 8.44 Hz, 2H), 8.45 (br d, J = 5.99 Hz, 1H), 12.80 (br s, 1H) |
| 26 | $^1$H NMR (400 MHz, DMSO-d6) δ ppm 1.63 (d, J = 6.8 Hz, 3H), 2.07 (s, 3H), 2.37 (s, 3H), 5.17-5.24 (m, 1H), 7.02-7.07 (m, 1H), 7.56-7.58 (m, 4H), 7.63 (d, J = 8.8 Hz, 1H), 7.78-7.80 (m, 3H), 8.63 (d, J = 6.4 Hz, 1H), 13.32 (s, 1H) |
| 27 | $^1$H NMR (400 MHz, DMSO-d6) δ ppm 1.72 (d, J = 6.4 Hz, 3H), 2.36 (s, 3H), 5.39-5.46 (m, 1H), 7.09 (s, 1H), 7.16 (d, J = 9.2 Hz, 1H), 7.56-7.62 (m, 4H), 7.66 (d, J = 9.2 Hz, 1H), 7.77 (s, 1H), 8.13 (d, J = 6.8 Hz, 2H), 8.75 (d, J = 6.0 Hz, 1H) |
| 28 | $^1$H NMR (400 MHz, DMSO-d6) δ ppm 1.58 (d, J = 6.4 Hz, 3H), 2.08 (s, 3H), 2.37 (s, 3H), 5.11-5.14 (m, 1H), 6.46 (d, J = 8.4 Hz, 1H), 6.54 (t, J = 7.6 Hz, 1H), 7.20 (t, J = 7.2 Hz, 1H), 7.42-7.48 (m, 1H), 7.53 (s, 1H), 7.66-7.69 (m, 3H), 7.78-7.82 (m, 2H), 8.36-8.37 (m, 1H) |
| 29 | $^1$H NMR (400 MHz, DMSO-d6) δ ppm 1.58 (d, J = 6.8 Hz, 3H), 2.06 (s, 3H), 2.37 (s, 3H), 5.10-5.13 (m, 1H), 6.46 (d, J = 8.0 Hz, 1H), 6.55 (t, J = 7.2 Hz, 1H), 7.20 (t, J = 6.8 Hz, 1H), 7.41-7.46 (m, 2H), 7.53 (d, J = 2.0 Hz, 1H), 7.78-7.80 (m, 2H), 7.86-7.90 (m, 2H), 8.37-8.38 (m, 1H) |
| 30 | $^1$H NMR (400 MHz, DMSO-d6) δ ppm 1.58 (d, J = 6.0 Hz, 3H), 2.06 (s, 3H), 2.37 (s, 3H), 5.13-5.15 (m, 1H), 6.47 (d, J = 8.4 Hz, 1H), 6.53 (t, J = 7.6 Hz, 1H), 7.18 (t, J = 7.6 Hz, 1H), 7.54 (s, 1H), 7.79-7.83 (m, 3H), 8.07 (d, J = 7.6 Hz, 1H), 8.13 (d, J = 7.6 Hz, 1H), 8.30 (s, 1H), 8.39 (s, 1H) |
| 31 | $^1$H NMR (400 MHz, DMSO-d6) δ ppm 1.56 (d, J = 6.8 Hz, 3H), 2.06 (s, 3H), 2.36 (s, 3H), 5.08-5.10 (m, 1H), 6.45 (d, J = 8.4 Hz, 1H), 6.53 (t, J = 7.6 Hz, 1H), 7.18 (t, J = 7.2 Hz, 1H), 7.54 (d, J = 2.0 Hz, 1H), 7.77-7.80 (m, 2H), 7.98-8.00 (m, 2H), 8.05-8.07 (m, 2H), 8.38 (s, 1H) |
| 32 | $^1$H NMR (400 MHz, DMSO-d6) δ ppm 1.69 (d, J = 6.4 Hz, 3H), 2.37 (s, 3H), 5.34-5.37 (m, 1H), 6.54-6.58 (m, 2H), 7.16 (s, 1H), 7.24 (t, J = 7.6 Hz, 1H), 7.59 (s, 1H), 7.76 (s, 1H), 7.82 (d, J = 7.6 Hz, 1H), 8.15 (d, J = 8.4 Hz, 2H), 8.28-8.31 (m, 3H), 8.43 (d, J = 6.0 Hz, 1H), 12.79 (s, 1H) |
| 33 | $^1$H NMR (400 MHz, DMSO-d6) δ ppm 1.71 (d, J = 6.8 Hz, 3H), 2.37 (s, 3H), 5.41-5.46 (m, 1H), 6.72 (d, J = 9.2 Hz, 1H), 7.09 (s, 1H), 7.53-7.60 (m, 5H), 7.72 (s, 1H) 8.06 (s, 1H), 8.11-8.13 (m, 2H), 8.82 (d, J = 6.4 Hz, 1H), 13.43 (s, 1H) |

TABLE 2-continued

| Ex # | NMR Line Listing |
|---|---|
| 34 | $^1$H NMR (400 MHz, DMSO-d6) δ ppm 1.54 (d, J = 6.8 Hz, 3H), 1.92 (s, 3H), 2.37 (s, 3H), 5.07-5.10 (m, 1H), 6.42 (d, J = 8.4 Hz, 1H), 6.51 (t, J = 7.6 Hz, 1H), 7.13 (t, J = 6.8 Hz, 1H), 7.54 (s, 1H), 7.77-7.84 (m, 3H), 7.94-7.95 (m, 2H), 8.13 (d, J = 7.6 Hz, 1H), 8.37 (s, 1H) |
| 35 | $^1$H NMR (400 MHz, DMSO-d6) δ ppm 1.60 (d, J = 6.8 Hz, 3H), 2.07 (s, 3H), 2.37 (s, 3H), 5.10-5.17 (m, 1H), 6.95 (d, J = 8.8 Hz, 1H), 7.38 (d, J = 9.2 Hz, 1H), 7.52 (d, J = 2.0 Hz, 1H), 7.58-7.59 (m, 3H), 7.77-7.79 (m, 3H), 8.30 (d, J = 6.4 Hz, 1H), 13.08 (s, 1H) |
| 36 | $^1$H NMR (400 MHz, DMSO-d6) δ ppm 1.61 (d, J = 6.8 Hz, 3H), 2.08 (s, 3H), 2.37 (s, 3H), 5.14-5.17 (m, 1H), 7.08 (d, J = 8.4 Hz, 1H), 7.30-7.34 (m, 1H), 7.54 (s, 1H), 7.58-7.60 (m, 3H), 7.79-7.84 (m, 4H), 8.64 (d, J = 6.4 Hz, 1H) |
| 37 | $^1$H NMR (400 MHz, CHLOROFORM-d) δ ppm 1.70 (d, J = 6.8 Hz, 3H), 2.22 (s, 3H), 2.42 (s, 3H), 5.19-5.23 (m, 1H), 6.46 (d, J = 8.8 Hz, 1H), 7.40-7.44 (m, 2H), 7.54-7.56 (m, 3H), 7.66-7.68 (m, 2H), 7.98 (s, 1H), 8.26 (s, 1H), 8.44 (d, J = 6.0 Hz, 1H) |
| 38 | $^1$H NMR (400 MHz, DMSO-d6) δ ppm 1.56 (d, J = 6.4 Hz, 3H), 2.08 (s, 3H), 2.37 (s, 3H), 5.04-5.06 (m, 1H), 6.18-6.21 (m, 1H), 7.22-7.26 (m, 1H), 7.51 (d, J = 2.0 Hz, 1H), 7.58-7.60 (m, 3H), 7.78-7.80 (m, 3H), 7.86 (s, 1H) |
| 39 | $^1$H NMR (400 MHz, DMSO-d6) δ ppm 1.56 (d, J = 6.4 Hz, 3H), 2.08 (s, 3H), 2.35-2.37 (m, 6H), 5.04-5.06 (m, 1H), 6.18-6.21 (m, 1H), 7.22-7.26 (m, 1H), 7.51 (d, J = 2.0 Hz, 1H), 7.58-7.60 (m, 3H), 7.78-7.80 (m, 3H), 7.86 (s, 1H) |
| 40 | $^1$H NMR (400 MHz, DMSO-d6) δ ppm 0.82-0.84 (m, 4H), 1.58 (d, J = 6.8 Hz, 3H), 1.94-2.00 (m, 1H), 2.07 (s, 3H), 2.36 (s, 3H), 5.11-5.15 (m, 1H), 6.93 (d, J = 8.8 Hz, 1H), 7.12 (d, J = 8.8 Hz, 1H), 7.52 (d, J = 2.0 Hz, 1H), 7.58-7.59 (m, 3H), 7.78-7.81 (m, 3H), 8.10 (d, J = 6.4 Hz, 1H) |
| 41 | $^1$H NMR (400 MHz, DMSO-d6) δ ppm 1.58 (d, J = 6.4 Hz, 3H), 2.08 (s, 3H), 2.37 (s, 3H), 5.09-5.12 (m, 1H), 6.48 (d, J = 9.2 Hz, 1H), 7.23 (dd, J = 8.8, 2.4 Hz, 1H), 7.51 (s, 1H), 7.58-7.60 (m, 3H), 7.74 (d, J = 2.8 Hz, 1H), 7.79-7.80 (m, 3H), 8.34 (s, 1H), 13.17 (s, 1H) |
| 42 | $^1$H NMR (400 MHz, DMSO-d6) δ ppm 1.55 (d, J = 6.4 Hz, 3H), 2.08 (s, 3H), 2.37 (s, 3H), 5.05-5.07 (m, 1H), 6.23 (d, J = 9.2 Hz, 1H), 7.22 (t, J = 8.8 Hz, 1H), 7.51 (d, J = 2.4 Hz, 1H), 7.58-7.60 (m, 3H), 7.78-7.80 (m, 3H), 8.10 (s, 1H) |
| 43 | $^1$H NMR (400 MHz, DMSO-d6) δ ppm 1.54 (d, J = 6.8 Hz, 3H), 2.01 (s, 3H), 2.08 (s, 3H), 2.36 (s, 3H), 5.04-5.05 (m, 1H), 6.15 (d, J = 8.4 Hz, 1H), 7.01 (t, J = 8.4 Hz, 1H), 7.05-7.06 (m, 1H), 7.58-7.60 (m, 3H), 7.77-7.80 (m, 4H) |
| 44 | $^1$H NMR (400 MHz, DMSO-d6) δ ppm 1.55 (d, J = 6.4 Hz, 3H), 1.92 (s, 3H), 2.36 (s, 3H), 5.02-5.05 (m, 1H), 6.40 (d, J = 8.4 Hz, 1H), 6.53 (t, J = 7.6 Hz, 1H), 7.18 (t, J = 8.0 Hz, 1H), 7.42-7.50 (m, 2H), 7.53 (s, 1H), 7.62-7.73 (m, 1H), 7.78-7.80 (m, 3H), 8.36 (s, 1H) |
| 45 | $^1$H NMR (400 MHz, METHANOL-d4) δ ppm 1.65 (d, J = 5.6 Hz, 3H), 1.98 (s, 4H), 2.29 (s, 3H), 4.02 (s, 4H), 5.23 (d, J = 5.9 Hz, 1H), 6.29 (d, J = 8.5 Hz, 1H), 6.47-6.52 (m, 1H), 6.55 (d, J = 8.3 Hz, 2H), 6.65 (s, 1H), 7.10 (t, J = 7.5 Hz, 1H), 7.31 (s, 1H), 7.43 (s, 1H), 7.72-7.80 (m, 3H), 7.90 (d, J = 7.8 Hz, 1H) |
| 46 | $^1$H NMR (400 MHz, DMSO-d6) δ ppm 1.69 (d, J = 6.8 Hz, 3H), 2.36 (s, 6H), 5.35-5.38 (m, 1H), 7.08-7.10 (m, 2H), 7.23 (d, J = 8.8 Hz, 1H), 7.54 (d, J = 2.0 Hz, 1H), 7.58-7.63 (m, 3H), 7.76 (s, 1H), 8.13-8.15 (m, 2H), 8.52 (d, J = 6.8 Hz, 1H) |
| 48 | $^1$H NMR (400 MHz, DMSO-d6) δ ppm 1.64-1.72 (m, 3H), 2.38 (s, 3H), 3.32-3.40 (m, 4H), 5.35 (s, 1H), 6.51-6.58 (m, 2H), 7.21-7.29 (m, 2H), 7.60 (s, 1H), 7.77 (s, 1H), 7.83 (d, J = 7.4 Hz, 1H), 8.11 (d, J = 7.8 Hz, 2H), 8.41 (d, J = 7.7 Hz, 2H), 12.83 (s, 1H) |
| 50 | $^1$H NMR (400 MHz, DMSO-d6) δ ppm 1.63-1.74 (m, 3H), 2.37 (s, 3H), 2.93 (s, 3H), 3.02 (s, 3H), 5.35 (s, 1H), 6.51-6.57 (m, 2H), 7.15 (s, 1H), 7.20-7.26 (m, 1H), 7.56-7.62 (m, 3H), 7.77 (s, 1H), 7.82 (d, J = 7.7 Hz, 1H), 8.19 (d, J = 7.5 Hz, 2H), 8.45 (s, 1H), 12.81 (s, 1H) |
| 51 | $^1$H NMR (400 MHz, DMSO-d6) δ ppm 1.63 (d, J = 6.60 Hz, 3H), 2.38 (s, 3H), 5.20-5.28 (m, 1H), 6.48 (d, J = 8.56 Hz, 1H), 6.56 (t, J = 7.40 Hz, 1H), 6.94 (s, 1H), 7.21 (t, J = 7.53 Hz, 1H), 7.59 (d, J = 1.96 Hz, 1H), 7.77 (d, J = 1.10 Hz, 1H), 7.79-7.83 (m, 1H), 7.91-7.96 (m, 1H), 8.15-8.20 (m, 1H), 8.24 (t, J = 7.82 Hz, 1H), 8.40 (br d, J = 5.99 Hz, 1H), 12.76 (br s, 1 H) |
| 52 | $^1$H NMR (400 MHz, DMSO-d6) δ ppm 1.61-1.72 (m, 5H), 1.88 (br s, 2H), 2.37 (br s, 3H), 5.33 (br s, 1H), 6.52 (br d, J = 8.68 Hz, 1H), 6.57 (br s, 1H), 7.11 (br s, 1H), 7.19-7.26 (m, 1H), 7.52 (br d, J = 7.95 Hz, 2H), 7.56 (br s, 1H), 7.76 (br s, 1H), 7.83 (br d, J = 7.58 Hz, 1H), 8.16 (br d, J = 7.46 Hz, 2H), 8.44 (br s, 1H), 12.79 (br s, 1H) |
| 53 | $^1$H NMR (400 MHz, DMSO-d6) δ ppm 1.61-1.72 (m, 5H), 1.88 (br s, 2H), 2.37 (br s, 3H), 5.33 (br s, 1H), 6.52 (br d, J = 8.68 Hz, 1H), 6.57 (br s, 1H), 7.11 (br s, 1H), 7.19-7.26 (m, 1H), 7.52 (br d, J = 7.95 Hz, 2H), 7.56 (br s, 1H), 7.76 (br s, 1H), 7.83 (br d, J = 7.58 Hz, 1H), 8.16 (br d, J = 7.46 Hz, 2H), 8.44 (br s, 1H), 12.79 (br s, 1H) |
| 55 | $^1$H NMR (400 MHz, METHANOL-d4) δ ppm 1.65 (d, J = 5.6 Hz, 3H), 1.98 (s, 4H), 2.29 (s, 3H), 4.02 (s, 4H), 5.23 (d, J = 5.9 Hz, 1H), 6.29 (d, J = 8.5 Hz, 1H), 6.47-6.52 (m, 1H), 6.55 (d, J = 8.3 Hz, 2H), 6.65 (s, 1H), 7.10 (t, J = 7.5 Hz, 1H), 7.31 (s, 1H), 7.43 (s, 1H), 7.72-7.80 (m, 3H), 7.90 (d, J = 7.8 Hz, 1H) |
| 56 | $^1$H NMR (400 MHz, DMSO-d6) δ ppm 1.59 (d, J = 6.60 Hz, 3H), 2.30 (s, 3H), 5.27-5.35 (m, 1H), 6.44-6.52 (m, 2H), 7.15 (t, J = 6.91 Hz, 1H), 7.26 (s, 1H), 7.51 (d, J = 1.96 Hz, 1H), 7.69 (s, 1H), 7.74 (d, J = 7.37 Hz, 1H), 8.06-8.12 (m, 2H), 8.22 (d, J = 10.51 Hz, 1H), 8.34 (br d, J = 5.99 Hz, 1H), 12.69 (br s, 1H) |
| 57 | $^1$H NMR (400 MHz, DMSO-d6) δ ppm 1.63 (d, J = 6.60 Hz, 3H), 2.37 (s, 3H), 5.21-5.29 (m, 1H), 6.48 (d, J = 8.44 Hz, 1H), 6.56 (t, J = 7.27 Hz, 1H), 6.82 (s, 1H), 7.19-7.25 (m, 1H), 7.32-7.38 (m, 1H), 7.55-7.62 (m, 2H), 7.76 (d, J = 1.34 Hz, 1H), 7.79-7.83 (m, 1H), 8.10-8.17 (m, 1H), 8.40 (d, J = 6.24 Hz, 1H), 12.75 (br s, 1H) |

TABLE 2-continued

| Ex # | NMR Line Listing |
|---|---|
| 58 | $^1$H NMR (400 MHz, DMSO-d6) δ ppm 1.57 (d, J = 6.8 Hz, 3H), 2.08 (s, 3H), 2.36 (s, 3H), 5.01-5.15 (m, 1H), 6.45 (dd, J = 7.2, 4.4 Hz, 1H), 7.12-7.12 (m, 1H), 7.51-7.52 (m, 2H), 7.59-7.60 (m, 3H), 7.78-7.81 (m, 3H), 8.17 (s, 1H) |
| 59 | $^1$H NMR (400 MHz, DMSO-d6) δ ppm 1.60 (d, J = 6.60 Hz, 3H), 2.37 (s, 3H), 5.17-5.38 (m, 1H), 6.47-6.57 (m, 2H), 6.93 (s, 1H), 7.12-7.20 (m, 1H), 7.56 (d, J = 2.08 Hz, 1H), 7.77-7.87 (m, 3H), 7.94 (td, J = 7.76, 1.22 Hz, 1H), 8.06-8.16 (m, 2H), 8.29-8.41 (m, 1H), 12.76 (br s, 1H) |
| 60 | $^1$H NMR (400 MHz, DMSO-d6) δ ppm 1.67-1.73 (m, 3H) 2.37 (s, 3H) 3.87 (s, 3H) 5.28-5.39 (m, 1H) 6.50-6.59 (m, 2H) 7.13-7.16 (m, 1H) 7.17-7.27 (m, 2H) 7.49-7.54 (m, 1H) 7.54-7.58 (m, 1H) 7.62-7.66 (m, 1H) 7.70-7.78 (m, 2H) 7.80-7.85 (m, 1H) 8.41-8.47 (m, 1H) 12.68-12.96 (m, 1H) |
| 61 | $^1$H NMR (400.13 MHz, DMSO-d6) δ ppm 1.62 (d, J = 6.7 Hz, 3H), 2.40 (s, 3H), 5.15-5.21 (m, 1H), 6.51-6.58 (m, 2H), 7.20-7.23 (m, 1H), 7.64-7.83 (m, 7H), 8.13-8.16 (m, 2H), 12.97-13.03 (m, 1H) |
| 62 | $^1$H NMR (400.13 MHz, DMSO-d6) δ ppm 1.60-1.78 (m, 3H), 2.40 (s, 3H), 5.14-5.19 (m, 1H), 6.41-6.48 (m, 1H), 6.50-6.55 (m, 1H), 7.15-7.19 (m, 1H), 7.77-7.82 (m, 7H), 8.14-8.16 (m, 2H) |
| 63 | $^1$H NMR (400 MHz, METHANOL-d4) δ ppm 1.65 (d, J = 6.7 Hz, 3H), 2.31 (s, 3H), 5.25 (q, J = 6.6 Hz, 1H), 6.41 (d, J = 8.4 Hz, 1H), 6.47 (t, J = 7.5 Hz, 1H), 6.84 (s, 1H), 7.10 (t, J = 7.8 Hz, 1H), 7.35-7.43 (m, 1H), 7.55 (d, J = 2.0 Hz, 1H), 7.72-7.77 (m, 1H), 7.78-7.86 (m, 2H), 7.89 (ddd, J = 11.3, 7.5, 2.2 Hz, 1H) |
| 64 | $^1$H NMR (400 MHz, DMSO-d6) δ ppm 1.69 (d, J = 6.60 Hz, 3H), 5.27-5.36 (m, 1H), 6.50 (d, J = 8.31 Hz, 1H), 6.60 (t, J = 7.40 Hz, 1H), 7.11 (s, 1H), 7.23 (t, J = 7.19 Hz, 1H), 7.57-7.67 (m, 3H), 7.70-7.76 (m, 1H), 7.82-7.86 (m, 1H), 8.10-8.18 (m, 2H), 8.39 (br d, J = 5.62 Hz, 1H), 12.81 (br s, 1H) |
| 65 | $^1$H NMR (400 MHz, DMSO-d6) δ ppm 1.47 (d, J = 6.8 Hz, 3H), 2.04 (s, 3H), 2.38 (s, 3H), 5.46-5.47 (m, 1H), 6.53 (t, J = 8.8 Hz, 1H), 7.12-7.14 (m, 1H), 7.18 (s, 1H), 7.58-7.60 (m, 3H), 7.62 (d, J = 2.0 Hz, 1H), 7.72-7.74 (m, 3H) |
| 66 | $^1$H NMR (400 MHz, DMSO-d6) δ ppm 1.68 (d, J = 6.72 Hz, 3H), 2.33-2.40 (m, 3H), 3.87 (s, 3H), 5.28-5.38 (m, 1H), 6.50-6.59 (m, 2H), 6.98-7.00 (m, 1H), 7.11-7.16 (m, 2H), 7.21-7.26 (m, 1H), 7.54-7.56 (m, 1H), 7.73-7.76 (m, 1H), 7.81-7.85 (m, 1H), 8.10 (d, J = 9.05 Hz, 2H), 8.44 (d, J = 6.60 Hz, 1H), 12.77 (br s, 1H) |
| 67 | $^1$HNMR (400 MHz, DMSO-d6) δ ppm 1.64 (d, J = 6.60 Hz, 3H), 2.37 (s, 3H), 3.95 (s, 3H), 5.20-5.28 (m, 1H), 6.47 (d, J = 8.56 Hz, 1H), 6.56 (t, J = 7.52 Hz, 1H), 6.93 (s, 1H), 7.13-7.30 (m, 3H), 7.52-7.62 (m, 2H), 7.73-7.77 (m, 1H), 7.82 (dd, J = 8.07, 1.59 Hz, 1H), 7.92 (dd, J = 7.76, 1.65 Hz, 1H), 8.39 (br d, J = 6.60 Hz, 1H), 12.71-12.86 (m, 1H) |
| 68 | $^1$H NMR (400 MHz, DMSO-d6) δ ppm 1.67 (d, J = 6.60 Hz, 3H), 2.37 (s, 3H), 5.35-5.44 (m, 1H), 6.52-6.60 (m, 2H), 7.20-7.27 (m, 2H), 7.52-7.60 (m, 2H), 7.76 (s, 1H), 7.82 (d, J = 7.58 Hz, 1H), 7.85-7.91 (m, 2H), 8.40 (br d, J = 6.11 Hz, 1H), 12.75 (br s, 1H) |
| 69 | $^1$H NMR (400 MHz, DMSO-d6) δ ppm 1.57 (d, J = 6.8 Hz, 3H), 2.08 (s, 3H), 2.37 (s, 3H), 5.07-5.11 (m, 1H), 6.26 (d, J = 8.4 Hz, 1H), 6.32 (dd, J = 11.6, 8.0 Hz, 1H), 7.14-7.16 (m, 1H), 7.52 (d, J = 2.0 Hz, 1H), 7.58-7.60 (m, 3H), 7.78-7.81 (m, 3H), 8.08 (d, J = 6.0 Hz, 1H) |
| 70 | $^1$H NMR (400 MHz, DMSO-d6) δ ppm 1.55 (d, J = 6.7 Hz, 3H), 2.38 (s, 3H), 5.00 (m, 1H), 6.43 (d, J = 8.4 Hz, 1H), 6.56 (t, J = 7.5 Hz, 1H), 7.20 (t, J = 7.7 Hz, 1H), 7.58-7.68 (m, 4H), 7.76-7.82 (m, 4H), 8.33 (bd, J = 6.0 Hz, 1H), 12.80 (bs, 1H) |
| 71 | 1H NMR (400 MHz, DMSO-d6) δ ppm 1.69 (d, J = 6.6 Hz, 3H), 2.37 (s, 3H), 5.36 (br t, J = 6.4 Hz, 1H), 6.51-6.59 (m, 2H), 7.15-7.20 (m, 2H), 7.23 (t, J = 7.8 Hz, 1H), 7.57 (s, 1H), 7.77 (br s, 2H), 7.83 (br d, J = 7.9 Hz, 2H), 8.29-8.35 (m, 2H), 8.44 (br d, J = 6.0 Hz, 1H), 12.80 (br s, 1H) |
| 72 | $^1$H NMR (400 MHz, DMSO-d6) δ ppm 1.58-1.66 (m, 3H) 2.06-2.16 (m, 3H) 5.10-5.19 (m, 1H) 6.42-6.50 (m, 1H) 6.52-6.62 (m, 1H) 7.14-7.27 (m, 1H) 7.48-7.56 (m, 1H) 7.59-7.72 (m, 4H) 7.82-7.87 (m, 3H) 8.33-8.39 (m, 1H) 12.77-12.94 (m, 1H) |
| 73 | $^1$H NMR (400 MHz, DMSO-d6) δ ppm 1.59 (d, J = 6.6 Hz, 3H), 2.09 (s, 3H), 2.37 (s, 3H), 3.17 (s, 1H), 5.12 (br d, J = 5.4 Hz, 1H), 6.46 (d, J = 8.6 Hz, 1H), 6.55 (t, J = 7.5 Hz, 1H), 7.15-7.23 (m, 1H), 7.54 (s, 1H), 7.74-7.83 (m, 3H), 8.00 (d, J = 7.1 Hz, 2H), 8.01 (s, 1H), 8.36 (br d, J = 5.3 Hz, 1H), 12.79 (br s, 1H) |
| 74 | $^1$H NMR (400 MHz, DMSO-d6) δ ppm 1.62 (d, J = 6.4 Hz, 3H), 2.07 (s, 3H), 2.37 (s, 3H), 5.27-5.33 (m, 1H), 7.57-7.60 (m, 4H), 7.79-7.80 (m, 3H), 7.81 (d, J = 2.4 Hz, 1H), 8.30 (s, 1H), 8.48 (s, 1H) |
| 75 | $^1$H NMR (400 MHz, DMSO-d6) δ ppm 1.55 (d, J = 6.8 Hz, 3H), 1.90 (s, 3H), 2.36 (s, 3H), 5.01-5.05 (m, 1H), 6.40 (d, J = 8.8 Hz, 1H), 6.52 (t, J = 7.2 Hz, 1H), 7.15-7.17 (m, 1H), 7.33-7.34 (m, 1H), 7.52-7.54 (m, 2H), 7.78-7.80 (m, 2H), 7.84-7.88 (m, 1H), 8.38 (s, 1H) |
| 76 | $^1$H NMR (400 MHz, DMSO-d6) δ ppm 1.55 (d, J = 6.8 Hz, 3H), 2.09 (s, 3H), 2.38 (s, 3H), 5.05-5.08 (m, 1H), 6.34-6.41 (m, 2H), 6.66 (d, J = 7.6 Hz, 1H), 7.06 (t, J = 8.0 Hz, 1H), 7.56-7.61 (m, 4H), 7.78-7.81 (m, 3H) |
| 77 | $^1$H NMR (400 MHz, DMSO-d6) δ ppm 1.58 (d, J = 6.8 Hz, 3H), 2.08 (s, 3H), 2.37 (s, 3H), 5.07-5.13 (m, 1H), 6.42 (d, J = 9.2 Hz, 1H), 7.32 (q, J = 7.2 Hz, 1H), 7.50 (d, J = 2 Hz, 1H), 7.58-7.60 (m, 3H), 7.78-7.80 (m, 3H), 7.85-7.86 (m, 1H), 8.33-8.36 (m, 1H), 13.17 (s, 1H) |
| 78 | $^1$H NMR (400 MHz, METHANOL-d4) δ ppm 1.66 (d, J = 6.7 Hz, 3H), 2.16 (s, 3H), 2.41 (s, 3H), 5.14-5.21 (m, 1H), 6.45 (d, J = 8.4 Hz, 1H), 6.55 (t, J = 7.5 Hz, 1H), 7.18 (t, J = 7.7 Hz, 1H), 7.44-7.57 (m, 1H), 7.61 (s, 2H), 7.74 (t, J = 9.3 Hz, 1H), 7.87 (s, 1H), 7.91 (d, J = 7.9 Hz, 1H) |

TABLE 2-continued

| Ex # | NMR Line Listing |
|---|---|
| 79 | $^1$H NMR (400 MHz, DMSO-d6) δ ppm 1.56 (br d, J = 6.60 Hz, 3H) 2.38 (s, 3H) 5.04 (br s, 1H) 6.43 (d, J = 8.56 Hz, 1H) 6.55 (t, J = 7.46 Hz, 1H) 7.20 (t, J = 7.76 Hz, 1H) 7.55-7.58 (m, 1H) 7.58-7.63 (m, 3H) 7.78-7.83 (m, 2H) 7.87-7.94 (m, 2H) 8.34 (br d, J = 4.77 Hz, 1H) 12.70-12.93 (m, 1H) |
| 80 | $^1$H NMR (400 MHz, METHANOL-d4) δ ppm 1.77 (d, J = 6.6 Hz, 3H), 5.40 (q, J = 6.7 Hz, 1H), 6.48 (d, J = 8.5 Hz, 1H), 6.60 (t, J = 7.5 Hz, 1H), 6.93 (t, J = 56.0 Hz, 1H), 7.06 (s, 1H), 7.21 (t, J = 7.8 Hz, 1H), 7.50-7.56 (m, 1H), 7.67-7.82 (m, 3H), 7.94 (d, J = 7.9 Hz, 1H), 8.22-8.26 (m, 2H) |
| 81 | $^1$H NMR (400.21 MHz, DMSO-d6) δ ppm 1.66 (d, J = 6.6 Hz, 3H), 5.27 (s, 1H), 6.92-6.96 (m, 2H), 7.12 (d, J = 8.8 Hz, 1H), 7.39 (td, J = 8.4, 2.3 Hz, 1H), 7.58-7.64 (m, 1H), 7.96 (d, J = 2.2 Hz, 1H), 8.17-8.23 (m, 2H), 9.34-9.39 (m, 1H) |
| 82 | $^1$H NMR (500 MHz, DMSO-d6) δ ppm 1.76 (d, J = 6.7 Hz, 3H), 5.46 (quintet, J = 6.6 Hz, 1H), 7.17 (d, J = 8.9 Hz, 1H), 7.26 (s, 1H), 7.32 (d, J = 8.9 Hz, 1H), 7.61-7.68 (m, 3H), 7.99 (d, J = 1.8 Hz, 1H), 8.19 (d, J = 7.3 Hz, 2H), 8.24 (s, 1H), 8.42 (d, J = 6.3 Hz, 1H), 13.22-13.23 (m, 1H) |
| 83 | $^1$H NMR (400 MHz, DMSO-d6) δ ppm 1.61 (br d, J = 6.4 Hz, 3H), 2.09 (s, 3H), 5.14 (br d, J = 5.2 Hz, 1H), 6.45 (d, J = 8.4 Hz, 1H), 6.57 (t, J = 7.4 Hz, 1H), 7.04-7.31 (m, 2H), 7.45-7.59 (m, 1H), 7.66 (dd, J = 7.8, 2.3 Hz, 1H), 7.74-7.85 (m, 3H), 7.97-8.04 (m, 2H), 8.35 (br s, 1H), 12.82 (br s, 1H) |
| 85 | $^1$H NMR (400 MHz, DMSO-d6) δ ppm 1.62 (br d, J = 6.36 Hz, 3H) 2.40 (s, 3H) 5.16 (br s, 1H) 6.49 (br d, J = 8.56 Hz, 1H) 6.57 (br t, J = 7.46 Hz, 1H) 6.23 (br t, J = 7.70 Hz, 1H) 7.49-7.62 (m, 4H) 7.66 (br d, J = 7.58 Hz, 2H) 7.79-7.87 (m, 2H) 8.13 (s, 1H) 8.38 (br d, J = 5.50 Hz, 1H) 9.01 (s, 1H) 12.82 (br s, 1H) |
| 86 | $^1$H NMR (500 MHz, DMSO-d6) δ ppm 1.73 (d, J = 6.7 Hz, 3H), 5.42 (quintet, J = 6.4 Hz, 1H), 6.54 (d, J = 8.5 Hz, 1H), 6.58-6.61 (m, 1H), 7.20-7.24 (m, 1H), 7.25 (s, 1H), 7.60-7.67 (m, 3H), 7.84 (dd, J = 1.5, 7.9 Hz, 1H), 7.95 (d, J = 2.0 Hz, 1H), 8.18-8.22 (m, 3H), 8.46 (d, J = 6.1 Hz, 1H), 12.82-12.89 (m, 1H) |
| 87 | $^1$H NMR (500 MHz, DMSO-d6) δ ppm 1.73 (d, J = 6.7 Hz, 3H), 5.42 (quintet, J = 6.4 Hz, 1H), 6.54 (d, J = 8.5 Hz, 1H), 6.58-6.61 (m, 1H), 7.20-7.24 (m, 1H), 7.25 (s, 1H), 7.60-7.67 (m, 3H), 7.84 (dd, J = 1.5, 7.9 Hz, 1H), 7.95 (d, J = 2.0 Hz, 1H), 8.18-8.22 (m, 3H), 8.46 (d, J = 6.1 Hz, 1H), 12.82-12.89 (m, 1H) |
| 88 | $^1$H NMR (500 MHz, DMSO-d6) δ ppm 1.74 (d, J = 6.7 Hz, 3H), 5.48-5.54 (m, 1H), 7.17 (d, J = 9.1 Hz, 1H), 7.32-7.34 (m, 2H), 7.68-7.73 (m, 1H), 7.99 (d, J = 1.9 Hz, 1H), 8.08-8.10 (m, 1H), 8.23 (d, J = 1.3 Hz, 1H), 8.28-8.33 (m, 1H), 8.39 (d, J = 6.4 Hz, 1H), 13.20-13.23 (m, 1H) |
| 89 | $^1$H NMR (400 MHz, DMSO-d6) δ ppm 1.59 (br d, J = 6.6 Hz, 3H), 2.08 (s, 3H), 2.37 (s, 3H), 3.79 (s, 3H), 5.07-5.24 (m, 1H), 6.78-6.89 (m, 1H), 7.04-7.14 (m, 1H), 7.48-7.55 (m, 1H), 7.57-7.67 (m, 3H), 7.76-7.89 (m, 3H), 7.93-8.07 (m, 1H), 12.06-12.42 (m, 1H) |
| 90 | $^1$H NMR (500.11 MHz, DMSO-d6) δ ppm 1.68 (d, J = 6.6 Hz, 3H), 5.32 (dd, J = 1.7, 2.5 Hz, 1H), 6.47-6.59 (m, 2H), 6.97 (s, 1H), 7.18-7.21 (m, 1H), 7.38 (td, J = 8.4, 1.9 Hz, 1H), 7.59-7.64 (m, 1H), 7.82-7.84 (m, 1H), 7.97 (d, J = 1.8 Hz, 1H), 8.16-8.22 (m, 2H), 8.63-8.65 (m, 1H) |
| 91 | $^1$H NMR (500.11 MHz, DMSO-d6) δ ppm 1.64 (d, J = 6.1 Hz, 3H), 2.12 (s, 3H), 5.18-5.23 (m, 1H), 6.74 (s, 1H), 7.17-7.23 (m, 2H), 7.63 (s, 3H), 7.85 (s, 2H), 7.92-7.97 (m, 1H), 8.26 (s, 1H), 8.97-9.01 (m, 1H) |
| 92 | $^1$H NMR (400 MHz, DMSO-d6) δ ppm 1.55 (d, J = 6.4 Hz, 3H), 1.94 (s, 3H), 2.38 (s, 3H), 5.05 (m, 1H), 6.42 (d, J = 8.31 Hz, 1H), 6.54 (m, 1H), 7.19 (m, 1H), 7.46 (m, 1H), 7.55 (d, J = 2.2 Hz, 1H), 7.62 (m, 1H), 7.73 (m, 1H), 7.79 (m, 2H), 8.34 (d, J = 6.4 Hz, 1H), 12.74 (br s, 1H) |
| 93 | $^1$H NMR (400 MHz, DMSO-d6) δ ppm 1.47-1.58 (m, 3H), 1.84 (d, J = 1.6 Hz, 3H), 2.26-2.35 (m, 3H), 5.02 (quin, J = 6.5 Hz, 1H), 7.01 (d, J = 8.1 Hz, 1H), 7.23-7.32 (m, 1H), 7.32-7.43 (m, 2H), 7.47-7.53 (m, 1H), 7.56-7.66 (m, 1H), 7.67-7.81 (m, 3H), 8.54 (br d, J = 6.6 Hz, 1H) |
| 94 | $^1$H NMR (400 MHz, DMSO-d6) δ ppm 1.54 (d, J = 6.7 Hz, 3H), 1.91 (d, J = 1.4 Hz, 3H), 2.37 (s, 3H), 4.96-5.05 (m, 1H), 6.21 (d, J = 8.5 Hz, 1H), 6.34 (dd, J = 11.4, 8.0 Hz, 1H), 7.14 (td, J = 8.2, 6.3 Hz, 1H), 7.41-7.54 (m, 1H), 7.64-7.72 (m, 1H), 7.76-7.81 (m, 2H), 8.09 (d, J = 6.2 Hz, 1H), 13.19 (br s, 1H) |
| 95 | $^1$H NMR (400 MHz, DMSO-d6) δ ppm 1.57 (d, J = 6.7 Hz, 3H), 2.07 (s, 3H), 2.37 (s, 3H), 5.02-5.16 (m, 1H), 6.27 (d, J = 8.6 Hz, 1H), 6.35 (dd, J = 11.4, 8.0 Hz, 1H), 7.16 (td, J = 8.3, 6.3 Hz, 1H), 7.41-7.54 (m, 2H), 7.58-7.72 (m, 3H), 7.78 (d, J = 1.2 Hz, 1H), 7.95-8.22 (m, 1H), 13.19 (br s, 1H) |
| 96 | $^1$H NMR (500 MHz, DMSO-d6) δ ppm 1.65-1.67 (m, J = 6.8 Hz, 3H), 2.10 (s, 3H), 5.24-5.29 (m, 1H), 7.14-7.16 (m, 1H), 7.29-7.31 (m, 1H), 7.69-7.74 (m, 2H), 7.95-7.99 (m, 1H), 8.00 (d, J = 1.9 Hz, 1H), 8.27 (d, J = 1.3 Hz, 1H), 8.33-8.35 (m, 1H), 13.12-13.15 (m, 1H) |
| 97 | $^1$H NMR (400 MHz, DMSO-d6) δ ppm 1.59 (d, J = 6.8 Hz, 3H), 2.37 (s, 3H), 5.15-5.19 (m, 1H), 6.16 (d, J = 7.6 Hz, 1H), 6.27 (dd, J = 10.0, 8.4 Hz, 1H), 6.84 (s, 1H), 6.98-7.02 (m, 1H), 7.44-7.71 (m, 2H), 8.58 (d, J = 2.0 Hz, 1H), 7.62-7.72 (m, 1H), 7.75-7.76 (m, 1H), 8.06 (td, J = 7.6, 1.6 Hz, 1H), 8.32 (br s, 1H), 13.19 (br s, 1H) |
| 98 | $^1$H NMR (500 MHz, DMSO-d6) δ ppm 1.64 (d, J = 6.8 Hz, 3H), 1.95 (d, J = 1.3 Hz, 3H), 5.14-5.19 (m, 1H), 7.09 (d, J = 8.9 Hz, 1H), 7.27 (d, J = 8.9 Hz, 1H), 7.45-7.51 (m, 2H), 7.69-7.74 (m, 1H), 7.81 (td, J = 7.5, 1.4 Hz, 1H), 8.02 (d, J = 1.9 Hz, 1H), 8.28-8.31 (m, 2H), 13.14-13.16 (m, 1H) |
| 99 | $^1$H NMR (500 MHz, DMSO-d6) δ ppm 1.68-1.69 (m, 3H), 1.94 (s, 3H), 5.23-5.24 (m, 1H), 7.16-7.17 (m, 1H), 7.38-7.41 (m, 2H), 7.58-7.61 (m, 1H), 7.91-7.93 (m, 1H), 8.03-8.07 (m, 1H), 8.35-8.36 (m, 2H), 13.20-13.27 (m, 1H) |

TABLE 2-continued

| Ex # | NMR Line Listing |
|---|---|
| 100 | ¹H NMR (500 MHz, DMSO-d6) δ ppm 1.66 (d, J = 6.7 Hz, 3H), 2.10 (s, 3H), 5.27-5.31 (m, 1H), 7.13-7.15 (m, 1H), 7.28-7.29 (m, 1H), 7.84 (t, J = 7.8 Hz, 1H), 8.00 (d, J = 2.0 Hz, 1H), 8.11 (d, J = 7.9 Hz, 1H), 8.17 (d, J = 7.9 Hz, 1H), 8.30-8.33 (m, 3H), 13.14-13.15 (m, 1H) |
| 101 | ¹H NMR (400 MHz, DMSO-d6) δ ppm 1.57 (br d, J = 6.5 Hz, 3H), 2.37-2.42 (m, 6H), 5.05 (br s, 1H), 7.11 (br d, J = 8.8 Hz, 1H), 7.24 (br d, J = 8.7 Hz, 1H), 7.57-7.64 (m, 4H), 7.76 (br d, J = 7.3 Hz, 2H), 7.82 (s, 1H), 8.36 (br s, 1H) |
| 102 | ¹H NMR (500.11 MHz, DMSO-d6) d ppm 1.64 (d, J = 6.6 Hz, 3H), 2.13 (s, 3H), 5.18-5.23 (m, 1H), 6.48 (d, J = 8.5 Hz, 1H), 6.59 (t, J = 7.5 Hz, 1H), 7.21 (t, J = 7.4 Hz, 1H), 7.63-7.64 (m, 3H), 7.82-7.86 (m, 3H), 7.93 (d, J = 1.0 Hz, 1H), 8.26 (s, 1H), 8.38 (d, J = 6.1 Hz, 1H), 12.79-12.87 (m, 1H) |
| 103 | ¹H NMR (400 MHz, DMSO-d6) δ ppm 1.54 (d, J = 6.7 Hz, 3H), 1.91 (d, J = 1.4 Hz, 3H), 2.37 (s, 3H), 4.96-5.05 (m, 1H), 6.21 (d, J = 8.5 Hz, 1H), 6.34 (dd, J = 11.4, 8.0 Hz, 1H), 7.14 (td, J = 8.2, 6.3 Hz, 1H), 7.41-7.54 (m, 3H), 7.64-7.72 (m, 1H), 7.76-7.81 (m, 2H), 8.09 (d, J = 6.2 Hz, 1H), 13.19 (br s, 1H) |
| 104 | ¹H NMR (400 MHz, DMSO-d6) δ ppm 1.54 (d, J = 6.7 Hz, 3H), 1.91 (d, J = 1.4 Hz, 3H), 2.37 (s, 3H), 4.96-5.05 (m, 1H), 6.21 (d, J = 8.5 Hz, 1H), 6.34 (dd, J = 11.4, 8.0 Hz, 1H), 7.14 (td, J = 8.2, 6.3 Hz, 1H), 7.41-7.54 (m, 3H), 7.64-7.72 (m, 1H), 7.76-7.81 (m, 2H), 8.09 (d, J = 6.2 Hz, 1H), 13.19 (br s, 1H) |
| 105 | ¹H NMR (400 MHz, DMSO-d6) δ ppm 1.57 (d, J = 6.7 Hz, 3H), 2.07 (s, 3H), 2.37 (s, 3H), 5.02-5.16 (m, 1H), 6.27 (d, J = 8.6 Hz, 1H), 6.35 (dd, J = 11.4, 8.0 Hz, 1H), 7.16 (td, J = 8.3, 6.3 Hz, 1H), 7.41-7.54 (m, 2H), 7.58-7.72 (m, 3H), 7.78 (d, J = 1.2 Hz, 1H), 7.95-8.22 (m, 1H), 13.19 (br s, 1H) |
| 106 | ¹H NMR (400 MHz, DMSO-d6) δ ppm 1.57 (d, J = 6.7 Hz, 3H), 2.07 (s, 3H), 2.37 (s, 3H), 5.02-5.16 (m, 1H), 6.27 (d, J = 8.6 Hz, 1H), 6.35 (dd, J = 11.4, 8.0 Hz, 1H), 7.16 (td, J = 8.3, 6.3 Hz, 1H), 7.41-7.54 (m, 2H), 7.58-7.72 (m, 3H), 7.78 (d, J = 1.2 Hz, 1H), 7.95-8.22 (m, 1H), 13.19 (br s, 1H) |
| 107 | ¹H NMR (400 MHz, DMSO-d6) δ ppm 1.59 (d, J = 6.8 Hz, 3H), 2.37 (s, 3H), 5.15-5.19 (m, 1H), 6.16 (d, J = 7.6 Hz, 1H), 6.27 (dd, J = 10.0, 8.4 Hz, 1H), 6.84 (s, 1H), 6.98-7.02 (m, 1H), 7.44-7.71 (m, 2H), 8.58 (d, J = 2.0 Hz, 1H), 7.62-7.72 (m, 1H), 7.75-7.76 (m, 1H), 8.06 (td, J = 7.6, 1.6 Hz, 1H), 8.32 (br s, 1H), 13.19 (br s, 1H) |
| 108 | ¹H NMR (400 MHz, DMSO-d6) δ ppm 1.59 (d, J = 6.8 Hz, 3H), 2.37 (s, 3H), 5.15-5.19 (m, 1H), 6.16 (d, J = 7.6 Hz, 1H), 6.27 (dd, J = 10.0, 8.4 Hz, 1H), 6.84 (s, 1H), 6.98-7.02 (m, 1H), 7.44-7.71 (m, 2H), 8.58 (d, J = 2.0 Hz, 1H), 7.62-7.72 (m, 1H), 7.75-7.76 (m, 1H), 8.06 (td, J = 7.6, 1.6 Hz, 1H), 8.32 (br s, 1 H), 13.19 (br s, 1H) |
| 109 | ¹H NMR (400 MHz, DMSO-d6) δ ppm 1.59 (br d, J = 6.6 Hz, 3H), 2.08 (s, 3H), 2.37 (s, 3H), 3.79 (s, 3H), 5.07-5.24 (m, 1H), 6.78-6.89 (m, 1H), 7.04-7.14 (m, 1H), 7.48-7.55 (m, 1H), 7.57-7.67 (m, 3H), 7.76-7.89 (m, 3H), 7.93-8.07 (m, 1H), 12.06-12.42 (m, 1H) |
| 110 | ¹H NMR (400 MHz, DMSO-d6) δ ppm 1.59 (br d, J = 6.6 Hz, 3H), 2.08 (s, 3H), 2.37 (s, 3H), 3.79 (s, 3H), 5.07-5.24 (m, 1H), 6.78-6.89 (m, 1H), 7.04-7.14 (m, 1H), 7.48-7.55 (m, 1H), 7.57-7.67 (m, 3H), 7.76-7.89 (m, 3H), 7.93-8.07 (m, 1H), 12.06-12.42 (m, 1H) |
| 111 | ¹H NMR (400 MHz, DMSO-d6) δ ppm 1.59 (d, J = 6.72 Hz, 3H) 2.32 (s, 3H) 5.22 (br t, J = 6.54 Hz, 1H) 6.43 (d, J = 8.31 Hz, 1H) 6.50 (t, J = 7.58 Hz, 1H) 7.12-7.17 (m, 1H) 7.53 (d, J = 2.20 Hz, 1H) 7.55-7.61 (m, 3H) 7.73-7.79 (m, 2H) 7.99 (dd, J = 6.54, 2.87 Hz, 2H) 8.33 (br d, J = 5.75 Hz, 1H) 12.57-12.85 (m, 1H) |
| 112 | ¹H NMR (400 MHz, DMSO-d6) δ ppm 0.87-1.10 (m, 1H) 1.60 (d, J = 6.60 Hz, 3H) 2.37 (s, 3H) 4.19 (s, 2H) 4.87 (s, 1H) 5.14-5.24 (m, 1H) 5.36 (d, J = 1.59 Hz, 1H) 6.48 (d, J = 8.44 Hz, 1H) 6.50-6.61 (m, 1H) 7.16-7.27 (m, 1H) 7.46-7.59 (m, 4H) 7.76-7.85 (m, 2H) 7.87-7.95 (m, 2H) 8.36 (br s, 1H) 12.77 (br s, 1H) |
| 113 | ¹H NMR (400 MHz, DMSO-d6) δ ppm 1.60 (d, J = 17 Hz, 3H), 2.06 (s, 3H), 2.38 (s, 3H), 5.16-5.19 (m, 1H), 7.08-7.11 (d, J = 9.2 Hz, 1H), 7.29-7.31 (d, J = 8.8 Hz, 1H), 7.55 (s, 1H), 7.64-7.68 (m, 2H), 7.79 (s, 1H), 7.90-8.30 (m, 1H), 8.31 (s, 1H) |
| 114 | ¹H NMR (400 MHz, CHLOROFORM-d) δ ppm 1.59 (d, J = 6.7 Hz, 3H), 2.00 (d, J = 1.1 Hz, 3H), 2.34 (s, 3H), 5.01 (br d, J = 3.8 Hz, 1H), 6.74 (d, J = 9.0 Hz, 1H), 7.05-7.09 (m, 1H), 7.24-7.30 (m, 1H), 7.37 (d, J = 2.1 Hz, 1H), 7.41-7.59 (m, 3H), 7.90 (s, 1H), 8.11 (br s, 1H) |
| 115 | ¹H NMR (400 MHz, CHLOROFORM-d) d ppm 1.59 (d, J = 6.7 Hz, 3H), 2.00 (d, J = 1.1 Hz, 3H), 2.34 (s, 3H), 5.01 (br d, J = 3.8 Hz, 1H), 6.74 (d, J = 9.0 Hz, 1H), 7.04-7.09 (m, 1H), 7.24-7.29 (m, 1H), 7.37 (d, J = 2.1 Hz, 1H), 7.42-7.58 (m, 3H), 7.89-7.92 (m, 1H), 8.11 (br s, 1H) |
| 116 | ¹H NMR (400 MHz, DMSO-d6) δ ppm 1.53 (d, J = 6.63 Hz, 3H), 2.30 (s, 3H), 2.37 (s, 3H), 4.97 (m, 1H), 6.87 (m, 1H), 7.00-7.09 (m, 1H), 7.55-7.70 (m, 5H), 7.73-7.83 (m, 3H), 8.62-8.89 (br s, 1H) |
| 117 | ¹H NMR (400 MHz, DMSO-d6) δ ppm 1.61 (d, J = 6.6 Hz, 3H), 1.76 (s, 6H), 2.12 (s, 3H), 2.37 (s, 3H), 5.14 (br t, J = 6.1 Hz, 1H), 6.44 (d, J = 8.3 Hz, 1H), 6.55 (t, J = 7.3 Hz, 1H), 7.20 (t, J = 7.8 Hz, 1H), 7.52 (d, J = 2.0 Hz, 1H), 7.64-7.70 (m, 1H), 7.74-7.83 (m, 4H), 7.97 (s, 1H), 8.36 (br d, J = 5.7 Hz, 1H), 12.74 (br s, 1H) |
| 118 | ¹H NMR (400 MHz, DMSO-d6) δ ppm 1.50 (s, 6H), 1.62 (d, J = 6.6 Hz, 3H), 2.08-2.15 (m, 3H), 2.37 (s, 3H), 5.14 (br s, 1H), 6.42 (d, J = 8.4 Hz, 1H), 6.55 (t, J = 7.5 Hz, 1H), 6.99 (s, 1H), 7.05 (s, 1H), 7.21 (t, J = 7.8 Hz, 1H), 7.51 (d, J = 2.0 Hz, 1H), 7.56 (d, J = 5.0 Hz, 2H), 7.65-7.72 (m, 1H), 7.77-7.83 (m, 3H), 8.37 (br s, 1H), 12.61-12.98 (m, 1H) |
| 119 | ¹H NMR (400 MHz, CHLOROFORM-d) δ ppm 1.72 (d, J = 6.8 Hz, 3H), 2.44 (s, 3H), 2.51 (s, 3H), 5.22 (q, J = 6.6 Hz, 1H), 6.39 (d, J = 8.5 Hz, 1H), 6.67 (t, J = 7.5 Hz, 1H), 7.50-7.65 (m, 4H), 7.65-7.72 (m, 2H), 7.93-8.00 (m, 1H), 8.03 (dd, J = 8.1, 1.4 Hz, 1H) |

TABLE 2-continued

| Ex # | NMR Line Listing |
|---|---|
| 120 | $^1$H NMR (400 MHz, DMSO-d6) δ ppm 1.60 (d, J = 6.8 Hz, 3H), 2.06 (s, 3H), 2.37 (s, 3H), 5.12-5.19 (m, 1H), 7.11 (d, J = 9.4 Hz, 1H), 7.32-7.33 (m, 1H), 7.55 (s, 1H), 7.64-7.68 (m, 2H), 7.79-7.83 (m, 2H), 7.89-7.98 (m, 1H), 8.63-8.69 (m, 1H) |
| 121 | $^1$H NMR (500 MHz, CDCl$_3$) δ ppm 1.70 (d, J = 6.5 Hz, 3H), 2.17 (s, 3H) 2.42 (s, 3H), 5.03-5.06 (m, 1H), 6.79 (d, J = 9.0 Hz, 1H), 7.17 (d, J = 9.0 Hz, 1H), 7.45 (s, 1 H), 7.71 (t, J = 8.0 Hz, 1 H), 7.87 (dd, J = 16.5, 7.5 Hz, 2H), 7.92 (s, 1H), 7.98 (s, 1H), 8.24 (s, 1H), 10.83 (br s, 1H) |
| 122 | $^1$H NMR (500.11 MHz, DMSO-d6) d ppm 1.67 (d, J = 6.7 Hz, 3H), 2.13 (s, 3H), 5.21-5.27 (m, 1H), 7.13 (d, J = 8.5 Hz, 1H), 7.32 (dd, J = 4.4, 8.6 Hz, 1H), 7.62-7.64 (m, 3H), 7.85-7.87 (m, 3H), 7.97 (d, J = 2.1 Hz, 1H), 8.27 (d, J = 1.7 Hz, 1H), 8.64 (d, J = 6.7 Hz, 1H) |
| 123 | $^1$H NMR (400 MHz, DMSO-d6) δ ppm 1.60 (d, J = 6.4 Hz, 3H), 2.05 (s, 3H), 2.37 (s, 3H), 5.16-5.19 (m, 1H), 7.02 (d, J = 8.8 Hz, 1H), 7.52 (d, J = 9.2 Hz, 1H), 7.57 (d, J = 2.0 Hz, 1H), 7.66-7.68 (m, 2H), 7.78 (s, 1H), 7.91-7.93 (m, 1H), 9.15 (br s, 1H) |
| 124 | $^1$H NMR (400 MHz, DMSO-d6) δ ppm 1.59 (d, J = 6.8 Hz, 3 H), 2.06 (s, 3H), 2.34-2.37 (m, 6H), 5.14-5.17 (m, 1H), 7.07 (d, J = 8.8 Hz, 1H), 7.20 (d, J = 8.8 Hz, 1H), 7.53 (d, J = 2.0 Hz, 1H), 7.64-7.69 (m, 2H), 7.78-7.79 (m, 1H), 7.91-7.95 (m, 1H), 8.42 (d, J = 6.8 Hz, 1H) |
| 125 | $^1$H NMR (400 MHz, DMSO-d6) δ ppm 1.54-1.60 (m, 3H), 2.04-2.07 (m, 3H), 2.29-2.36 (m, 3H), 5.08-5.18 (m, 1H), 6.93-7.21 (m, 2H), 7.24-7.31 (m, 1H), 7.37-7.48 (m, 1H), 7.50-7.58 (m, 1H), 7.75-7.82 (m, 2H), 8.03-8.07 (m, 1H), 8.11-8.16 (m, 1H), 8.31 (s, 1H) |
| 126 | $^1$H NMR (400 MHz, DMSO-d6) δ ppm 1.63 (d, J = 6.8 Hz, 3H), 2.05 (s, 3H), 2.38 (s, 3H), 5.23-5.27 (m, 1H), 7.14 (d, J = 8.8 Hz, 1H), 7.60-7.66 (m, 2H), 7.79-7.81 (m, 2H), 8.05 (d, J = 8.0 Hz, 1H), 8.12 (d, J = 8.0 Hz, 1H), 8.29 (s, 1H), 8.60 (br s, 1H) |
| 127 | $^1$H NMR (400 MHz, DMSO-d6) δ ppm 1.57 (d, J = 6.4 Hz, 3H), 2.06 (s, 3H), 2.35 (s, 3H), 2.37 (s, 3H), 5.15-5.19 (m, 1H), 7.04 (d, J = 4.4 Hz, 1H), 7.16 (d, J = 8.8 Hz, 1H) 7.54 (s, 1H), 7.78-7.83 (m, 2H), 8.06 (d, J = 8.0 Hz, 1H), 8.13 (d, J = 8.0 Hz, 1H), 8.29 (s, 1H), 8.46 (s, 1H) |
| 128 | $^1$H NMR (400 MHz, DMSO-d6) δ ppm 1.62 (d, J = 6.8 Hz, 3H), 2.06 (s, 3H), 2.39 (s, 3H), 5.20-5.29 (m, 1H), 6.68 (d, J = 9.2 Hz, 1H), 7.48 (s, 1H) 7.57 (s, 1H), 7.78-7.82 (m, 2H), 8.02-8.07 (m, 1H), 8.12 (d, J = 8.0 Hz, 1H), 8.29 (s, 1H), 8.73 (d, J = 6.4 Hz, 1H) |
| 129 | $^1$H NMR (400 MHz, DMSO-d6) δ ppm 1.57 (d, J = 6.4 Hz, 3H), 2.06 (s, 3H), 2.37 (s, 3H), 5.10-5.13 (m, 1H), 6.48 (dd, J = 9.6, 4.8 Hz, 1H), 7.11-7.14 (m, 1H), 7.48-7.49 (m, 1H), 7.50-7.52 (m, 1H), 7.78-7.79 (m, 1H), 7.80-7.82 (m, 1H), 8.06 (d, J = 7.6 Hz, 1H), 8.13 (d, J = 8.0 Hz, 2H), 8.28 (s, 1H), 13.07 (br s, 1H) |
| 130 | $^1$H NMR (400 MHz, DMSO-d6) δ ppm 1.55 (d, J = 6.72 Hz, 3H), 1.91 (d, J = 1.34 Hz, 3H), 2.38 (s, 3H), 5.01 (br t, J = 6.48 Hz, 1H), 6.23 (d, J = 8.56 Hz, 1H), 6.34 (dd, J = 11.43, 7.89 Hz, 1H), 7.15 (td, J = 8.28, 6.30 Hz, 1H), 7.35 (td, J = 8.38, 2.32 Hz, 1H), 7.52-7.58 (m, 2H), 7.78-7.90 (m, 2H), 8.07 (br d, J = 6.36 Hz, 1H), 13.12 (br s, 1H) |
| 131 | $^1$H NMR (400 MHz, DMSO-d6) δ ppm 1.59 (d, J = 6.72 Hz, 3H), 1.90 (d, J = 1.34 Hz, 3H), 2.39 (s, 3H), 5.07 (quin, J = 6.69 Hz, 1H), 7.04 (d, J = 9.17 Hz, 1H), 7.19-7.39 (m, 2H), 7.49-7.61 (m, 2H), 7.79-7.89 (m, 2H), 8.27 (d, J = 6.85 Hz, 1H), 12.48-13.32 (m, 1H) |
| 132 | $^1$H NMR (400 MHz, DMSO-d6) δ ppm 1.59 (d, J = 6.72 Hz, 3H) 2.32 (s, 3H) 5.22 (br t, J = 6.54 Hz, 1H) 6.43 (d, J = 8.31 Hz, 1H) 6.50 (t, J = 7.58 Hz, 1H) 7.12-7.17 (m, 1H) 7.53 (d, J = 2.20 Hz, 1H) 7.55-7.61 (m, 3H) 7.73-7.79 (m, 2H) 7.99 (dd, J = 6.54, 2.87 Hz, 2H) 8.33 (br d, J = 5.75 Hz, 1H) 12.57-12.85 (m, 1H) |
| 133 | $^1$H NMR (400 MHz, DMSO-d6) δ ppm 1.59 (d, J = 6.72 Hz, 3H) 2.32 (s, 3H) 5.22 (br t, J = 6.54 Hz, 1H) 6.43 (d, J = 8.31 Hz, 1H) 6.50 (t, J = 7.58 Hz, 1H) 7.12-7.17 (m, 1H) 7.53 (d, J = 2.20 Hz, 1H) 7.55-7.61 (m, 3H) 7.73-7.79 (m, 2H) 7.99 (dd, J = 6.54, 2.87 Hz, 2H) 8.33 (br d, J = 5.75 Hz, 1H) 12.57-12.85 (m, 1H) |
| 134 | $^1$H NMR (500.11 MHz, DMSO-d6) d ppm 1.60 (d, J = 6.7 Hz, 3H), 2.08 (s, 3H), 2.37 (d, J = 2.4 Hz, 6H), 5.13-5.18 (m, 1H), 7.06 (d, J = 8.8 Hz, 1H), 7.20 (d, J = 8.8 Hz, 1H), 7.20 (d, J = 8.8 Hz, 1H), 7.45-7.48 (m, 1H), 7.53 (d, J = 2.0 Hz, 1H), 7.63-7.68 (m, 3H), 7.79 (d, J = 1.2 Hz, 1H), 8.41 (d, J = 6.8 Hz, 1H) |
| 135 | $^1$H NMR (400 MHz, DMSO-d6) d ppm 1.59 (d, J = 6.7 Hz, 3H), 2.03-2.13 (m, 3H), 2.32-2.42 (m, 3H), 3.80 (s, 3H), 5.07-5.24 (m, 1H), 6.69-6.90 (m, 1H), 7.01-7.19 (m, 1H), 7.44-7.55 (m, 1H), 7.55-7.65 (m, 3H), 7.76-7.86 (m, 3H), 7.91-8.07 (m, 1H), 11.99-12.64 (m, 1H) |
| 136 | $^1$H NMR (500.11 MHz, DMSO-d6) d ppm 1.62 (d, J = 6.7 Hz, 3H), 2.08 (s, 3H), 2.38 (s, 3H), 5.18 (quintet, J = 6.5 Hz, 1H), 7.13 (d, J = 8.3 Hz, 1H), 7.35 (dd, J = 4.5, 8.6 Hz, 1H), 7.43-7.47 (m, 1H), 7.56 (d, J = 1.8 Hz, 1H), 7.63-7.70 (m, 3H), 7.80 (d, J = 1.1 Hz, 1H), 7.84 (dd, J = 1.0, 4.4 Hz, 1H), 8.63 (d, J = 6.6 Hz, 1H) |
| 137 | $^1$H NMR (500.11 MHz, DMSO-d6) d ppm 1.59 (d, J = 6.8 Hz, 3H), 2.09 (s, 3H), 2.40 (s, 3H), 5.79-5.85 (m, 1H), 6.58-6.61 (m, 1H), 7.57-7.59 (m, 4H), 7.77-7.79 (m, 3H), 8.07-8.10 (m, 1H), 8.15 (dd, J = 1.8, 4.7 Hz, 1H), 8.56 (d, J = 7.3 Hz, 1H), 13.11-13.21 (m, 1H) |
| 138 | $^1$H NMR (500.11 MHz, DMSO-d6) d ppm 1.64 (d, J = 6.4 Hz, 3H), 2.08 (s, 3H), 2.39 (s, 3H), 5.30 (t, J = 6.0 Hz, 1H), 7.60 (d, J = 12.3 Hz, 4H), 7.80-7.84 (m, 4H), 7.92 (d, J = 5.2 Hz, 1H), 8.06 (s, 1H), 8.18 (d, J = 5.5 Hz, 1H) |
| 139 | $^1$H NMR (400 MHz, DMSO-d6) δ ppm 1.50 (d, J = 6 Hz, 3H), 2.32 (s, 3H), 4.97 (m, 1H), 6.97 (d, J = 8 Hz, 1H), 7.18 (d, J = 8 Hz, 1H), 7.54 (m, 4H), 7.67 (m, 2H), 7.75 (m, 1H), 8.19 (d, J = 8 Hz, 1H), 13.0 (br s, 1H) |
| 140 | $^1$H NMR (400 MHz, DMSO-d6) δ ppm 1.51 (d, J = 6.6 Hz, 3H), 2.31 (s, 3H), 4.99 (m, 1H), 6.98 (d, J = 12 Hz, 1H), 7.19 (d, J = 8.93 Hz, 1H), 7.52 (m, 4H), 7.74 (m, 1H), 7.81 (m, 2H), 8.22 (d, J = 8 Hz, 1H), 12.97 (br s, 1H) |

TABLE 2-continued

| Ex # | NMR Line Listing |
|---|---|
| 141 | $^1$H NMR (400 MHz, DMSO-d6) δ ppm 1.62 (d, J = 6.8 Hz, 3H), 2.03 (s, 3H), 2.38 (s, 3H), 3.81 (s, 3H), 5.15-5.22 (m, 1H), 7.07 (d, J = 8.8 Hz, 1H), 7.40 (d, J = 8.8 Hz, 1H), 7.60 (d, J = 2.0 Hz, 1H), 7.78-7.82 (m, 2H), 8.07 (d, J = 8.0 Hz, 1H), 8.11 (d, J = 7.6 Hz, 2H), 8.29 (s, 1H) |
| 142 | $^1$H NMR (500.11 MHz, DMSO-d6) d ppm 1.60 (d, J = 6.7 Hz, 3H), 1.92 (d, J = 1.3 Hz, 3H), 2.38 (s, 3H), 5.09 (quintet, J = 6.7 Hz, 1H), 7.03 (d, J = 8.1 Hz, 1H), 7.31 (dd, J = 4.5, 8.6 Hz, 1H), 7.42-7.49 (m, 2H), 7.57 (d, J = 2.0 Hz, 1H), 7.67-7.71 (m, 1H), 7.78-7.83 (m, 3H), 8.60 (d, J = 6.8 Hz, 1H) |
| 143 | $^1$H NMR (400 MHz, DMSO-d6) δ ppm 1.58 (d, J = 6.63 Hz, 3H), 2.08 (s, 3H), 2.38 (s, 3H), 5.10 (br t, J = 6.19 Hz, 1H), 6.28 (d, J = 8.63 Hz, 1H), 6.35 (dd, J = 10.94, 8.57 Hz, 1H), 7.16 (q, J = 7.63 Hz, 1H), 7.41-7.50 (m, 1H), 7.54 (s, 1H), 7.62-7.69 (m, 3H), 7.79 (s, 1H), 8.07 (br d, J = 5.75 Hz, 1H), 13.17 (br s, 1H) |
| 144 | $^1$H NMR (400 MHz, DMSO-d6) δ ppm 1.54 (d, J = 6.8 Hz, 3H), 2.07 (s, 3H), 2.36 (s, 3H), 5.05-5.07 (m, 1H), 7.32 (d, J = 8.8 Hz, 1H), 7.00 (d, J = 8.8 Hz, 1H), 7.50 (s, 1H), 7.77-7.83 (m, 3H), 8.07 (d, J = 7.6 Hz, 1H), 8.16 (d, J = 8.0 Hz, 1H), 8.31 (s, 1H), 9.47 (br s, 1H) |
| 145 | $^1$H NMR (400 MHz, DMSO-d6) δ ppm 1.57 (d, J = 6.4 Hz, 3H), 2.08 (s, 3H), 2.37 (s, 3H), 5.09-5.11 (m, 1H), 6.44 (d, J = 8.8 Hz, 1H), 7.15-7.17 (m, 1H), 7.40-7.47 (m, 1H), 7.51 (s, 1H), 7.64-7.68 (m, 3H), 7.74-7.76 (m, 1H), 7.77-7.78 (m, 1H), 8.69 (br s, 1H) |
| 146 | $^1$H NMR (400 MHz, DMSO-d6) δ ppm 1.58 (d, J = 6.8 Hz, 3H), 2.06 (s, 3H), 2.37 (s, 3 H), 5.10-5.13 (m, 1H), 6.51 (d, J = 9.2 Hz, 1H), 7.23 (dd, J = 8.8, 2.4 Hz, 1H), 7.51 (d, J = 2.0 Hz, 1H), 7.61-7.69 (m, 2H), 7.72 (d, J = 2.8 Hz, 1H), 7.78 (s, 1H), 7.90-7.94 (m, 1H), 8.33 (d, J = 5.6 Hz, 1H), 13.18 (br s, 1H) |
| 147 | $^1$H NMR (400 MHz, DMSO-d6) δ ppm 1.55 (d, J = 6.8 Hz, 3H), 1.91 (s, 3H), 2.37 (s, 3H), 5.01-5.04 (m, 1H), 6.43 (d, J = 9.2 Hz, 1H), 7.20 (dd, J = 9.2, 2.8 Hz, 1H), 7.41-7.49 (m, 2H), 7.52 (d, J = 2.0 Hz, 1H), 7.65-7.72 (m, 2H), 7.75-7.79 (m, 2H), 8.32 (d, J = 6.0 Hz, 1H), 13.16 (br s, 1H) |
| 148 | $^1$H NMR (500.11 MHz, DMSO-d6) d ppm 1.58 (d, J = 6.7 Hz, 3H), 1.91 (d, J = 1.1 Hz, 3H), 2.35 (s, 3H), 2.37 (s, 3H), 5.07 (quintet, J = 6.7 Hz, 1H), 6.98 (d, J = 8.8 Hz, 1H), 7.17 (d, J = 8.7 Hz, 1H), 7.42-7.49 (m, 2H), 7.54 (d, J = 1.9 Hz, 1H), 7.66-7.71 (m, 1H), 7.77-7.80 (m, 2H), 8.38 (d, J = 6.9 Hz, 1H) |
| 149 | $^1$H NMR (500.11 MHz, DMSO-d6) d ppm 1.59 (d, J = 6.3 Hz, 3H), 2.08 (s, 3H), 2.37 (s, 3H), 3.91 (s, 3H), 5.12 (t, J = 5.9 Hz, 1H), 6.48 (d, J = 8.3 Hz, 1H), 6.55 (t, J = 7.3 Hz, 1H), 7.21 (t, J = 7.5 Hz, 1H), 7.56 (s, 1H), 7.79-7.82 (m, 2H), 7.95 (d, J = 7.9 Hz, 2H), 8.14 (d, J = 8.0 Hz, 2H), 8.35 (d, J = 5.4 Hz, 1H), 12.68-12.83 (m, 1H) |
| 150 | $^1$H NMR (500.11 MHz, DMSO-d6) d ppm 1.60 (d, J = 6.7 Hz, 3H), 2.08 (s, 3H), 2.38 (s, 3H), 3.89 (s, 3H), 5.12 (quintet, J = 6.3 Hz, 1H), 6.47 (d, J = 8.5 Hz, 1H), 6.55 (t, J = 7.5 Hz, 1H), 7.19-7.23 (m, 1H), 7.54 (d, J = 1.8 Hz, 1H), 7.75-7.81 (m, 3H), 8.10 (d, J = 8.0 Hz, 1H), 8.16 (d, J = 7.9 Hz, 1H), 8.35-8.37 (m, 2H), 12.81-12.83 (m, 1H) |
| 151 | $^1$H NMR (500.11 MHz, DMSO-d6) d ppm 1.60 (d, J = 6.7 Hz, 3H), 2.10 (s, 3H), 2.37 (s, 3H), 2.84 (d, J = 4.5 Hz, 3H), 5.13 (quintet, J = 6.4 Hz, 1H), 6.47 (d, J = 8.5 Hz, 1H), 6.55 (t, J = 7.5 Hz, 1H), 7.20-7.23 (m, 1H), 7.54 (d, J = 1.8 Hz, 1H), 7.79-7.82 (m, 2H), 7.90 (d, J = 8.3 Hz, 2H), 8.01 (d, J = 8.3 Hz, 2H), 8.36 (d, J = 6.3 Hz, 1H), 8.62 (q, J = 4.2 Hz, 1H), 12.76 (s, 1H) |
| 152 | $^1$H NMR (500.11 MHz, DMSO-d6) d ppm 1.59 (d, J = 6.7 Hz, 3H), 2.09 (s, 3H), 2.38 (s, 3H), 2.83 (d, J = 4.4 Hz, 3H), 5.12-5.16 (m, 1H), 6.45-6.47 (m, 1H), 6.55 (t, J = 7.5 Hz, 1H), 7.19-7.22 (m, 1H), 7.54 (d, J = 1.8 Hz, 1H), 7.70 (t, J = 7.7 Hz, 1H), 7.80-7.82 (m, 2H), 7.96 (d, J = 7.7 Hz, 1H), 8.04 (d, J = 7.9 Hz, 1H), 8.23 (s, 1H), 8.36 (d, J = 6.0 Hz, 1H), 8.60 (d, J = 4.3 Hz, 1H), 12.70-12.79 (m, 1H) |
| 155 | 1H NMR (400 MHz, DMSO-d6) δ ppm 1.53 (d, J = 6.6 Hz, 3H), 1.96-2.03 (m, 3H), 2.28-2.33 (m, 3H), 3.73 (s, 3H), 5.06-5.29 (m, 1H), 7.19-7.44 (m, 1H), 7.44-7.64 (m, 4H), 7.65-7.90 (m, 3H), 7.96-8.25 (m, 1H), 13.02-13.71 (m, 1H) |
| 156 | $^1$H NMR (400 MHz, DMSO-d6) δ ppm 1.65 (d, J = 6.6 Hz, 3H), 2.41 (s, 3H), 5.21 (br s, 1H), 6.49-6.55 (m, 1H), 6.58 (t, J = 7.5 Hz, 1H), 7.17-7.31 (m, 1H), 7.38-7.44 (m, 2H), 7.44-7.53 (m, 3H), 7.64 (d, J = 2.0 Hz, 1H), 7.67-7.75 (m, 1H), 7.82-7.86 (m, 2H), 7.97 (br d, J = 7.8 Hz, 1H), 8.39 (br s, 1H), 8.70 (br s, 1H), 12.79 (br s, 1H) |
| 157 | $^1$H NMR (400 MHz, DMSO-d6) δ ppm 1.55 (d, J = 6.6 Hz, 3H), 1.97-2.04 (m, 3H), 2.28-2.34 (m, 3H), 5.15 (quin, J = 6.4 Hz, 1H), 6.40-6.72 (m, 1H), 7.39-7.61 (m, 5H), 7.61-7.89 (m, 3H), 7.90-8.20 (m, 1H), 8.67-8.95 (m, 1H), 13.18-13.47 (m, 1H) |
| 158 | $^1$H NMR (400 MHz, DMSO-d6) δ ppm 1.55 (d, J = 6.6 Hz, 3H), 1.97-2.04 (m, 3H), 2.28-2.34 (m, 3H), 5.15 (quin, J = 6.4 Hz, 1H), 6.40-6.72 (m, 1H), 7.39-7.61 (m, 5H), 7.61-7.89 (m, 3H), 7.90-8.20 (m, 1H), 8.67-8.95 (m, 1H), 13.18-13.47 (m, 1H) |
| 159 | $^1$H NMR (400 MHz, DMSO-d6) δ ppm 1.64 (d, J = 6.7 Hz, 3H), 2.08 (s, 3H), 2.39 (s, 3H), 5.14-5.30 (m, 1H), 7.09 (d, J = 9.2 Hz, 1H), 7.53-7.66 (m, 4H), 7.68-7.90 (m, 4H), 8.69-8.87 (m, 1H), 13.33-13.63 (m, 1H) |
| 160 | $^1$H NMR (400 MHz, DMSO-d6) δ ppm 1.64 (d, J = 6.7 Hz, 3H), 2.08 (s, 3H), 2.39 (s, 3H), 5.14-5.30 (m, 1H), 7.09 (d, J = 9.2 Hz, 1H), 7.53-7.66 (m, 4H), 7.68-7.90 (m, 4H), 8.69-8.87 (m, 1H), 13.33-13.63 (m, 1H) |
| 161 | $^1$H NMR (500.11 MHz, DMSO-d6) d ppm 1.61 (d, J = 6.6 Hz, 3H), 2.15 (s, 3H), 2.38 (s, 3H), 2.45 (s, 3H), 5.19-5.14 (m, 1H), 6.48 (d, J = 8.5 Hz, 1H), 6.56 (t, J = 7.5 Hz, 1H), 7.24-7.21 (m, 1H), 7.54 (d, J = 1.8 Hz, 1H), 7.68 (d, J = 8.3 Hz, 2H), 7.84-7.79 (m, 4H), 7.97-7.91 (m, 1H), 8.37 (d, J = 5.7 Hz, 1H), 12.94-12.93 (m, 2H) |
| 162 | $^1$H NMR (500.11 MHz, DMSO-d6) d ppm 1.61 (d, J = 6.7 Hz, 3H), 2.14 (s, 3H), 2.37 (s, 3H), 5.14-5.19 (m, 1H), 6.46-6.49 (m, 1H), 6.54-6.57 (m, 1H), 7.20-7.24 (m, 1H), 7.53 (d, J = 1.9 Hz, 1H), 7.78-7.85 (m, 6H), 8.41-8.43 (m, 3H), 13.16-13.20 (m, 2H) |

TABLE 2-continued

| Ex # | NMR Line Listing |
|---|---|
| 163 | $^1$H NMR (500.11 MHz, DMSO-d6) d ppm 1.70 (d, J = 6.7 Hz, 3H), 2.37 (s, 3H), 5.33-5.37 (m, 1H), 6.53-6.57 (m, 2H), 7.10 (s, 1H), 7.26-7.28 (m, 1H), 7.54-7.56 (m, 1H), 7.76 (d, J = 1.3 Hz, 1H), 7.84 (d, J = 8.6 Hz, 3H), 8.13 (d, J = 8.6 Hz, 2H), 8.17-8.63 (br, 3H), 13.16-13.18 (br, 2H) |
| 164 | $^1$H NMR (500.11 MHz, DMSO-d6) d ppm 1.61 (d, J = 6.7 Hz, 3H), 2.14 (s, 3H), 2.37 (s, 3H), 3.91 (s, 3H), 5.13-5.18 (m, 1H), 6.47 (d, J = 8.5 Hz, 1H), 6.56 (t, J = 7.5 Hz, 1H), 7.20-7.24 (m, 1H), 7.53 (d, J = 1.9 Hz, 1H), 7.77-7.83 (m, 6H), 8.00 (s, 1H), 8.28 (s, 1H), 8.35-8.41 (m, 1H), 13.05-13.11 (m, 1H) |
| 165 | $^1$H NMR (500.11 MHz, DMSO-d6) d ppm 1.62 (d, J = 6.7 Hz, 3H), 2.16 (s, 3H), 2.29 (s, 6H), 2.38 (s, 3H), 5.16-5.21 (m, 1H), 6.48 (d, J = 8.5 Hz, 1H), 6.56 (t, J = 7.6 Hz, 1H), 7.21-7.24 (m, 1H), 7.51-7.54 (m, 3H), 7.79-7.86 (m, 4H), 8.33-8.36 (m, 1H) |
| 166 | $^1$H NMR (500.11 MHz, DMSO-d6) d ppm 1.61 (d, J = 6.7 Hz, 3H), 2.13 (s, 3H), 2.38 (s, 3H), 5.14-5.18 (m, 1H), 6.45-6.48 (m, 1H), 6.52-6.56 (m, 1H), 6.82 (d, J = 2.3 Hz, 1H), 7.19-7.22 (m, 1H), 7.51-7.53 (m, 1H), 7.62-7.67 (m, 1H), 7.71-7.75 (m, 1H), 7.76-7.82 (m, 4H), 8.01-8.04 (m, 1H), 8.23 (s, 1H), 8.40-8.41 (m, 1H), 13.09-13.12 (m, 1H) |
| 167 | $^1$H NMR (500.11 MHz, DMSO-d6) d ppm 1.60 (d, J = 6.7 Hz, 3H), 2.13 (s, 3H), 2.38 (s, 3H), 5.12-5.17 (m, 1H), 6.48 (d, J = 8.5 Hz, 1H), 6.55 (t, J = 7.6 Hz, 1H), 7.20-7.23 (m, 1H), 7.54 (d, J = 1.9 Hz, 1H), 7.56-7.62 (m, 2H), 7.80-7.84 (m, 3H), 8.03 (s, 1H), 8.22-8.24 (m, 2H), 8.34-8.41 (m, 1H), 13.08-13.10 (m, 2H) |
| 168 | $^1$H NMR (500.11 MHz, DMSO-d6) d ppm 1.62 (d, J = 6.7 Hz, 3H), 2.15 (s, 3H), 2.38 (s, 3H), 5.14-5.19 (m, 1H), 6.47-6.50 (m, 1H), 6.54-6.57 (m, 1H), 6.86 (d, J = 2.3 Hz, 1H), 7.21-7.24 (m, 1H), 7.54 (d, J = 2.0 Hz, 1H), 7.80-7.87 (m, 5H), 8.00-8.03 (m, 2H), 8.35-8.40 (m, 1H), 13.16-13.18 (m, 2H) |
| 169 | $^1$H NMR (500.11 MHz, DMSO-d6) d ppm 1.59-1.62 (m, 3H), 2.15 (s, 3H), 2.38 (s, 3H), 3.96 (s, 3H), 5.15-5.19 (m, 1H), 6.46-6.51 (m, 1H), 6.54-6.57 (m, 2H), 7.21-7.24 (m, 1H), 7.51-7.57 (m, 2H), 7.77-7.83 (m, 4H), 7.94 (d, J = 8.2 Hz, 2H), 8.41-8.34 (m, 1H), 12.96-12.91 (m, 1H) |
| 170 | $^1$H NMR (500.11 MHz, DMSO-d6) d ppm 1.57 (d, J = 6.7 Hz, 3H), 1.92 (d, J = 1.1 Hz, 3H), 2.39 (s, 3H), 5.04-5.09 (m, 1H), 6.43-6.45 (m, 1H), 6.53 (t, J = 7.5 Hz, 1H), 7.17-7.20 (m, 1H), 7.57 (d, J = 2.0 Hz, 1H), 7.65 (t, J = 7.8 Hz, 1H), 7.78 (dd, J = 1.6, 7.9 Hz, 1H), 7.80 (d, J = 1.2 Hz, 1H), 8.15-8.18 (m, 1H), 8.19-8.22 (m, 1H), 8.32-8.34 (m, 1H), 12.77-12.80 (m, 1H) |
| 171 | $^1$H NMR (400 MHz, DMSO-d6) δ ppm 1.62 (d, J = 6.6 Hz, 3H), 2.31-2.38 (m, 5H), 2.84-2.89 (m, 2H), 5.22 (br t, J = 6.1 Hz, 1H), 6.48 (d, J = 8.4 Hz, 1H), 6.56 (t, J = 7.6 Hz, 1H), 7.19-7.24 (m, 1H), 7.49-7.53 (m, 2H), 7.56-7.60 (m, 2H), 7.79-7.83 (m, 2H), 8.04 (d, J = 7.2 Hz, 2H), 8.37 (br d, J = 6.1 Hz, 1H), 11.83 (s, 1H), 12.48-13.10 (m, 1H) |
| 172 | $^1$H NMR (500.11 MHz, DMSO-d6) d ppm 1.61 (d, J = 6.7 Hz, 3H), 2.14 (s, 3H), 2.38 (s, 3H), 5.13-5.18 (m, 1H), 6.49 (d, J = 8.5 Hz, 1H), 6.56 (t, J = 7.4 Hz, 1H), 7.21-7.24 (m, 1H), 7.55 (d, J = 1.7 Hz, 1H), 7.80-7.83 (m, 2H), 7.94-8.02 (m, 8H), 8.37 (d, J = 6.2 Hz, 1H), 12.73-12.76 (m, 1H) |
| 173 | $^1$H NMR (500.11 MHz, DMSO-d6) d ppm 1.61 (d, J = 6.6 Hz, 3H), 2.14 (s, 3H), 2.38 (s, 3H), 5.15 (t, J = 6.1 Hz, 1H), 6.49 (d, J = 8.5 Hz, 1H), 6.56 (t, J = 7.5 Hz, 1H), 7.23 (t, J = 7.6 Hz, 1H), 7.55 (s, 1H), 7.73 (t, J = 7.8 Hz, 1H), 7.79-7.83 (m, 2H), 7.89-7.99 (m, 5H), 8.14 (d, J = 7.9 Hz, 1H), 8.28 (s, 1H), 8.38 (d, J = 5.5 Hz, 1H), 12.77-12.83 (m, 1H) |
| 174 | $^1$H NMR (500.11 MHz, DMSO-d6) d ppm 1.59 (d, J = 6.6 Hz, 3H), 2.16 (s, 3H), 2.37 (s, 3H), 5.21-5.26 (m, 1H), 6.45 (d, J = 8.5 Hz, 1H), 6.53 (t, J = 7.5 Hz, 1H), 7.16-7.19 (m, 1H), 7.53 (d, J = 1.8 Hz, 1H), 7.61-7.65 (m, 1H), 7.73 (d, J = 7.6 Hz, 1H), 7.80-7.85 (m, 5H), 7.95 (d, J = 7.2 Hz, 1H), 8.00-8.03 (m, 2H), 8.35 (d, J = 6.1 Hz, 1H), 12.80-12.81 (m, 1H) |
| 175 | $^1$H NMR (500.11 MHz, DMSO-d6) d ppm 1.61 (d, J = 6.6 Hz, 3H), 2.13 (s, 3H), 2.38 (s, 3H), 5.15 (quintet, J = 6.3 Hz, 1H), 6.48 (d, J = 8.5 Hz, 1H), 6.54 (t, J = 7.5 Hz, 1H), 7.18-7.21 (m, 1H), 7.55 (d, J = 1.5 Hz, 1H), 7.74 (t, J = 7.7 Hz, 1H), 7.80-7.81 (m, 2H), 7.89 (d, J = 7.7 Hz, 1H), 7.96-7.98 (m, 5H), 8.17 (s, 1H), 8.36 (d, J = 6.2 Hz, 1H), 12.66-12.79 (m, 1H) |
| 176 | $^1$H NMR (500.11 MHz, DMSO-d6) d ppm 1.61 (d, J = 6.7 Hz, 3H), 2.14 (s, 3H), 2.38 (s, 3H), 5.16 (t, J = 6.1 Hz, 1H), 6.48 (d, J = 8.5 Hz, 1H), 6.53 (t, J = 7.5 Hz, 1H), 7.19-7.22 (m, 1H), 7.55 (d, J = 1.7 Hz, 1H), 7.69-7.75 (m, 2H), 7.79-7.81 (m, 2H), 7.87 (t, J = 6.7 Hz, 2H), 7.98 (d, J = 7.9 Hz, 1H), 8.11 (d, J = 8.0 Hz, 1H), 8.18 (s, 1H), 8.27 (s, 1H), 8.37 (d, J = 5.7 Hz, 1H), 12.83-12.84 (m, 1H) |
| 177 | $^1$H NMR (500.11 MHz, DMSO-d6) d ppm 1.62 (d, J = 6.7 Hz, 3H), 2.16 (s, 3H), 2.38 (s, 3H), 5.18 (quintet, J = 6.2 Hz, 1H), 6.49 (d, J = 8.6 Hz, 1H), 6.55 (t, J = 7.5 Hz, 1H), 7.21-7.24 (m, 1H), 7.55 (d, J = 2.0 Hz, 1H), 7.66 (td, J = 7.6, 1.0 Hz, 1H), 7.76 (d, J = 7.4 Hz, 1H), 7.83-7.88 (m, 5H), 7.99-8.03 (m, 3H), 8.36-8.43 (m, 1H), 12.87-12.89 (m, 1H) |

PI3K-Alpha Kinase (PIK3CA) Activity, Wild-Type and H1047R Mutant and Determining IC50 Values for Inhibitors Recombinant, catalytically active human full length PIK3KA Wild-type and H1047R mutant were purchased as 1:1 complex of N-terminal 6× his tagged p110α (catalytic) and untagged p85α (regulatory subunit) from EMD Millipore Sigma (cat. no. 14-602M and 14-792M, respectively). PIP2diC8 (Avanti Polar Lipids Inc., cat. no. 850185) or Soy PI (Avanti Polar Lipids Inc., cat. No. 840044P) was used as lipid substrate. PIP2diC8 or PI lyophilized powder was dissolved in milliQ water to a concentration of 1 mM just before use. 10 mM stock compounds in DMSO were serially diluted 1:3 to generate a 10-point curve and plated using an acoustic liquid handler system (Echo 550 series instrument, Labcyte). A 10× intermediate compound plate (200 uM starting compound concentration and 10% DMSO) was prepared before starting the reaction. A typical reaction mixture (50 uL) comprised 40 mM HEPES buffer, pH 7.4, 25 mM MgCl$_2$, 0.01% v/v triton-X-100, 1% v/v DMSO, 20 mM NaCl, 1-5 nM WT or H1047R PI3K protein, 20 uM ATP, and 50 uM PIP2diC8 or Soy PI. 1% DMSO buffer alone without test compound was employed as MAX control (full activity in the absence of any inhibitor), and no enzyme control was used to determine the level of background Adenosine 5'-diphosphate (ADP) (MIN control). First, Wild-type (WT) and H1047R mutant protein in kinase buffer with all components except ATP were incubated with or without compound at 27° C. for 1 h. After the pre-incubation, the reaction was initiated by the addition of 20 uL of 50 uM ATP (20 uM final concentration). The reaction was allowed to proceed until about 10% conversion of ATP (2 uM ADP) at 27° C. After that time, 5 uL of reaction was mixed with 5 uL of ADP-Kinase Glo Reagent (ADP-Glo Kinase assay kit, Promega cat. no. V9102) supplemented with MgCl$_2$ 10 mM to stop the reaction and deplete the remaining ATP for 40 min at room temperature. Then, 10 uL of Kinase Detection Reagent (ADP-Glo Kinase assay kit, Promega cat. no. V9102) was added to simultaneously convert ADP to ATP and allow the newly synthesized ATP to be measured using a luciferase/luciferin reaction. After 30 min at room temperature the light generated was measured using a luminometer (EnVision plate reader, Perkin Elmer). Process data through Genedata-Screener tool. Relative IC$_{50}$ values are determined using luminescence units by calculating percent inhibition with respect to on-plate "MIN" and "MAX" controls. Data was analyzed using a 4-parameter nonlinear logistic equation (four-parameter logistic concentration-response curve):

$$Y=bot+[(top-bot)/1+(x/IC50)slope]$$

where Y=% inhibition, X=concentration yielding y % inhibition, Bottom=minimum value of y attained by curve, Top=maximum value of y attained by curve and Slope=steepness of curve at IC50.

$$\% \text{ Inh}=[(\text{median Max}-x/\text{median Max}-\text{median Min})]\cdot 100$$

IC50: concentration of compound that reduces a given response (ligand binding, enzyme response) by 50%. IC50 relative: concentration giving half the compound's maximum response.

For IC$_{50}$ values shown in Table A, "A" means IC$_{50}$<0.5 μM; "B" means IC$_{50}$ ranging between 0.5 μM and 1.0 μM; "C" means IC$_{50}$ ranging between 1 μM and 5 μM; "D" means IC$_{50}$ ranging between 5 μM and 10 μM; "E" means IC$_{50}$>10 μM.

TABLE A

PI3K-α (PIK3CA) Biochemical IC$_{50}$ of PI3K wild-type (WT) and H1047R mutant, using Soy PI lipid substrate

| Example # | IC$_{50}$ H1047R | IC$_{50}$ WT |
|---|---|---|
| 1 | A | B |
| 2 | A | A |
| 3 | A | D |
| 4 | E | E |
| 5 | A | E |
| 6[1] | A | C |
| 7[1] | A | B |
| 8 | A | E |
| 9 | A | E |
| 10 | A | C |
| 11 | A | C |
| 12 | B | D |
| 13 | A | C |
| 14 | A | E |
| 15 | A | D |
| 16[1] | A | B |
| 17[1] | A | A |
| 18[1] | A | A |
| 19[1] | A | C |
| 20[1] | A | A |
| 21 | A | C |
| 22[1] | A | A |
| 23 | A | D |
| 24 | A | C |
| 25 | A | C |
| 26 | A | B |
| 27 | A | C |
| 28 | A | C |
| 29 | A | B |
| 30 | A | B |
| 31 | A | C |
| 32 | A | D |
| 33 | A | D |
| 34 | A | E |
| 35 | A | C |
| 36 | B | D |
| 37 | B | C |
| 38 | A | A |
| 39 | A | C |
| 40 | A | D |
| 41 | A | C |
| 42 | A | B |
| 43 | A | C |
| 44 | A | C |
| 45 | A | E |
| 46 | A | D |
| 47 | E | E |
| 48 | A | E |
| 49 | A | D |
| 50 | D | E |
| 51 | A | C |
| 52 | D | D |
| 53 | A | C |
| 54 | B | E |
| 55 | A | C |
| 56 | A | C |
| 57 | A | C |
| 58 | A | A |
| 59 | A | D |
| 60 | A | B |
| 61 | E | E |
| 62 | A | A |
| 63 | A | C |
| 64 | A | E |
| 65 | E | E |
| 66 | A | C |
| 67 | A | E |
| 68 | A | C |
| 69 | A | B |
| 70 | A | C |
| 71 | A | C |
| 72 | C | C |
| 73 | A | E |
| 74 | A | E |
| 75 | A | C |
| 76 | A | D |
| 77 | A | C |
| 78 | A | C |
| 79 | A | B |
| 80 | A | D |
| 81 | A | C |
| 82 | A | C |
| 83 | A | D |
| 84 | A | D |
| 85 | A | C |

TABLE A-continued

PI3K-α (PIK3CA) Biochemical IC$_{50}$ of PI3K wild-type (WT) and H1047R mutant, using Soy PI lipid substrate

| Example # | IC$_{50}$ H1047R | IC$_{50}$ WT |
|---|---|---|
| 86 | E | D |
| 87 | A | D |
| 88 | A | C |
| 89 | A | C |
| 90 | A | D |
| 91 | A | C |
| 92 | A | D |
| 93 | C | E |
| 94 | A | C |
| 95 | A | C |
| 96 | A | C |
| 97 | A | C |
| 98 | A | C |
| 99 | A | B |
| 100 | A | B |
| 101 | A | A |
| 102 | A | C |
| 103 | A | A |
| 104 | B | E |
| 105 | A | C |
| 106 | C | C |
| 107 | A | C |
| 108 | D | E |
| 109 | A | B |
| 110 | C | C |
| 111 | A | C |
| 112 | A | C |
| 113 | A | C |
| 114 | A | C |
| 115 | A | A |
| 117 | A | C |
| 118 | A | C |
| 119 | A | B |
| 120 | C | E |
| 121 | A | B |
| 122 | C | E |
| 123 | A | C |
| 124 | A | C |
| 125 | B | D |
| 126 | A | C |
| 127 | A | C |
| 128 | A | C |
| 129 | A | A |
| 130 | A | C |
| 131 | A | C |
| 132 | A | C |
| 133 | A | C |
| 134 | A | D |
| 135 | A | B |
| 136 | B | D |
| 137 | A | C |
| 138 | A | E |
| 139 | A | A |
| 140 | A | C |
| 141 | A | A |
| 142 | C | E |
| 144 | A | B |
| 145 | A | C |
| 146 | C | C |
| 147 | B | C |
| 148 | B | D |
| 149 | A | C |
| 150 | A | C |
| 151 | A | C |
| 152 | A | E |
| 153 | C | C |
| 154 | A | B |
| 155 | A | C |
| 156 | B | C |
| 157 | D | D |
| 158 | A | C |
| 159 | A | B |
| 160 | A | C |
| 161 | A | B |
| 162 | A | B |
| 163 | B | C |
| 164 | A | A |
| 165 | A | C |
| 166 | B | C |
| 167 | A | B |
| 168 | A | B |
| 169 | A | A |
| 171 | B | E |

[1] PIP2diC8 lipid substrate
*For Example 13, IC$_{50}$ WT/IC$_{50}$ H1047R = 7.7

PI3K-Alpha Kinase (PIK3CA) Activity In Vitro Cell Based Assay and Determining IC50 Values for Inhibitors The MDA-MB-453 (ATCC-HTB-131) cell line was obtained from the American Type Culture Collection (Manassas, VA). Cells were maintained in Dulbecco's Modified Eagle Media (DMEM, Gibco 11965-092) supplemented with 10% Fetal Bovine Serum, heat inactivated (FBS HI, Gibco 10082-147), 1× non-essential amino acids (NEAA, Gibco 11140-050), and 1 mM sodium pyruvate (Gibco 11360-070). Cultures were maintained in a humidified incubator at 37° C. under 5% CO$_2$/95% air.

For compound testing in 0% FBS, MDA-MB-453 cells were seeded at a density of $1.5 \times 10^4$ cells per well in white 384-well plates in 20 µl of Minimum Essential Media (MEM) assay media with 1×NEAA, 1 mM sodium pyruvate, and 1 µg/mL human insulin (Sigma I9278). Compounds dissolved in 10 mM stock solutions in DMSO were serially diluted 1:3 in DMSO to generate a 10-point dilution series and plated using an acoustic liquid handler system (Echo 550 Series Liquid Handler, Labcyte). A 5× intermediate compound dilution plate in MEM with 1×NEAA and 1 mM sodium pyruvate (150 µM starting compound concentration in 1.5% DMSO) was then prepared. Five µl of the intermediate serially diluted compounds were added to the cell plate to final concentrations ranging from 30 mM to 0.0015 mM in 0.3% DMSO. 0.3% DMSO alone was used to establish the maximum (MAX) signal and GDC-0032 at a final concentration of 1 µM was used as a reference compound for the minimum (MIN) signal. After 3 hours treatment, the medium was removed, and the cells lysed in 10 µL of 1× SureFire Lysis buffer with shaking for 10 minutes at room temperature. The Acceptor Mix (Reaction Buffer 1+Reaction Buffer 2+Activation Buffer+SureFire Ultra Acceptor Beads) was prepared by diluting Activation buffer 25-fold in combined Reaction Buffer 1 and Reaction Buffer 2. The Acceptor beads were diluted 50-fold in the combined Reaction Buffers. Five µL of Acceptor Mix was added to each well, the plate was sealed and covered with foil and incubated for 1 hour at room temperature. The Donor Mix (dilution buffer+SureFire Ultra Donor Beads) was prepared by diluting Donor Beads 50-fold in dilution buffer. Five µL of the Donor Mix was added to each well and the plate sealed and covered with foil and incubated for 1 hour at room temperature in the dark. The plates were read on a Neo2 plate reader instrument from Biotek using standard AlphaLisa settings. Compounds were tested in duplicate and the average % inhibition at each compound concentration was used to generate a single dose response curve. The data were processed using the Genedata-Screener tool. Relative IC$_{50}$ values were determined using luminescence units by calculating percent inhibition with respect to the in-plate "MIN" (GDC-0032 reference control) and "MAX" (DMSO) controls. The data was analyzed using a 4-parameter non-linear logistic equation (four-parameter logistic concentration-response curve):

$$Y = \text{bottom} + [(\text{top} - \text{bottom})/1 + (X/IC50)\text{slope}]$$

where Y=% inhibition, X=concentration of inhibitor, bottom=minimum value of y attained by curve-fit, top=maximum value of y attained by curve-fit and slope=steepness of curve at the $IC_{50}$.

% Inhibition=[(signal at X−median Min)/(median Max−median Min)]×100

$IC_{50}$: concentration of compound that reduces a given response (ligand binding, enzyme response) by 50%. Relative $IC_{50}$: concentration giving half the compound's maximum response.

For $IC_{50}$ values shown in Table B, "A" means $IC_{50}$<50 nM; "B" means $IC_{50}$ ranging between 50 nM and 100 nM; "C" means $IC_{50}$ ranging between 100 nM and 500 nM; "D" means $IC_{50}$>500 nM.

TABLE B

PI3K-α (PIK3CA) in vitro cell based assay $IC_{50}$

| Example # | $IC_{50}$ |
| --- | --- |
| 1 | A |
| 4 | D |
| 14 | A |
| 15 | A |
| 21 | A |
| 25 | B |
| 26 | B |
| 28 | A |
| 29 | A |
| 30 | A |
| 31 | A |
| 32 | A |
| 33 | C |
| 35 | A |
| 36 | B |
| 37 | C |
| 38 | A |
| 39 | A |
| 40 | B |
| 41 | A |
| 42 | A |
| 43 | B |
| 44 | A |
| 50 | D |
| 52 | D |
| 55 | C |
| 58 | A |
| 60 | A |
| 62 | A |
| 63 | A |
| 66 | A |
| 67 | B |
| 68 | A |
| 69 | A |
| 70 | A |
| 73 | A |
| 75 | A |
| 76 | A |
| 78 | A |
| 81 | A |
| 84 | D |
| 85 | A |
| 88 | A |
| 91 | A |
| 92 | A |
| 93 | C |
| 94 | A |
| 95 | A |
| 96 | A |
| 98 | A |
| 99 | A |
| 101 | A |
| 102 | A |
| 104 | C |
| 105 | A |
| 106 | D |
| 108 | D |
| 109 | A |
| 110 | D |
| 111 | A |
| 112 | B |
| 113 | A |
| 114 | A |
| 115 | A |
| 116 | A |
| 117 | A |
| 118 | C |
| 119 | A |
| 120 | B |
| 121 | A |
| 122 | B |
| 123 | A |
| 124 | A |
| 125 | B |
| 126 | A |
| 127 | B |
| 128 | B |
| 129 | A |
| 130 | A |
| 131 | A |
| 132 | A |
| 133 | B |
| 134 | A |
| 135 | A |
| 136 | B |
| 137 | A |
| 138 | C |
| 140 | A |
| 141 | A |
| 142 | B |
| 143 | A |
| 144 | A |
| 145 | A |
| 146 | A |
| 147 | A |
| 148 | A |
| 149 | A |
| 150 | A |
| 151 | A |
| 152 | A |
| 155 | C |
| 156 | C |
| 157 | D |
| 158 | A |
| 159 | A |
| 160 | C |
| 161 | A |
| 162 | A |
| 163 | B |
| 164 | A |
| 165 | A |
| 166 | A |
| 167 | A |
| 168 | A |
| 169 | A |
| 170 | A |
| 171 | D |
| 172 | B |
| 173 | B |
| 174 | A |
| 175 | B |

TABLE B-continued

PI3K-α (PIK3CA) in vitro cell based assay IC$_{50}$

| Example # | IC$_{50}$ |
|---|---|
| 176 | B |
| 177 | A |
| 178 | A |

The invention claimed is:

1. A compound of the Formula:

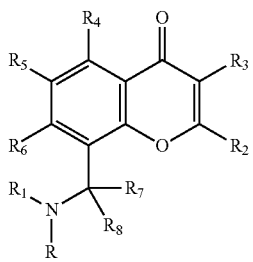

or pharmaceutically acceptable salt thereof, wherein:
R is —H or C$_1$-C$_3$ alkyl;
R$_1$ is a group of the formula:

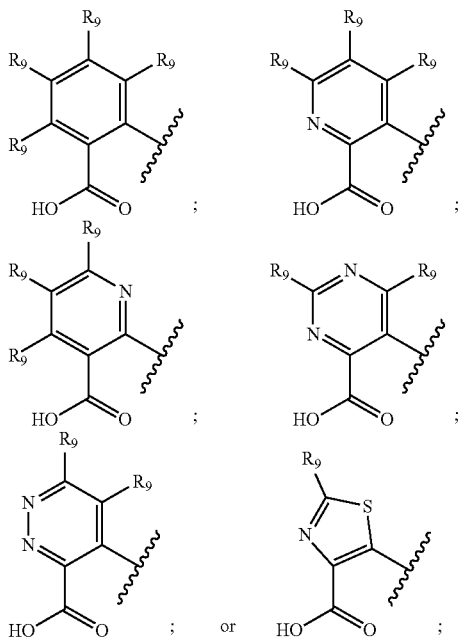

R$_2$ is a group of the formula:

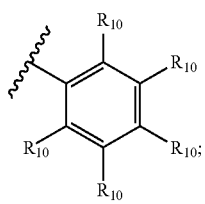

R$_3$ is —H, halogen, —CN, C$_1$-C$_6$ alkyl, C$_1$-C$_6$ haloalkyl, C$_3$-C$_5$ cycloalkyl, a heterocycle of 3 to 5 ring atoms containing 1, 2, or 3 ring heteroatoms independently selected from N, O, or S, or a heteroaryl of 5 ring atoms containing 1, 2, or 3 ring heteroatoms independently selected from N, O, or S;
each of R$_4$, R$_5$ and R$_6$ is independently —H, halogen, C$_1$-C$_6$ alkyl or C$_1$-C$_6$ haloalkyl;
R$_7$ is —CN, C$_1$-C$_6$ alkyl or C$_1$-C$_6$ haloalkyl;
R$_8$ is —H or C$_1$-C$_6$ alkyl;
each R$_9$ is independently —H, halogen, C$_1$-C$_6$ alkyl, C$_1$-C$_6$ haloalkyl, C$_1$-C$_6$ alkoxy, or C$_3$-C$_5$ cycloalkyl;
each R$_{10}$ is independently —H, —CN, halogen, C$_1$-C$_6$ haloalkyl, C$_1$-C$_6$ alkoxy, C$_1$-C$_6$ haloalkoxy, —SO$_2$R$_{11}$, CONR$_{11}$R$_{11}$, NR$_{11}$R$_{11}$, NR$_{11}$CO$_2$R$_{11}$, an optionally substituted C$_1$-C$_6$ alkyl, an optionally substituted C$_2$-C$_6$ alkenyl, an optionally substituted C$_2$-C$_6$ alkynyl, an optionally substituted C$_3$-C$_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyrazole, isoxazole, isothiazole, imidazole, oxazole, or thiazole; wherein the optionally substituted C$_1$-C$_6$ alkyl, C$_2$-C$_6$ alkenyl, or C$_2$-C$_6$ alkynyl is each optionally substituted with a —CN, —OH, oxetanyl, or C$_1$-C$_3$ alkoxy; the optionally substituted C$_3$-C$_5$ cycloalkyl, phenyl, 1,3-benzodioxole, 2,3-dihydro-1,4-benzodioxine, heterocycle or heteroaryl is each optionally substituted with one to three substituents each independently selected from halogen, C$_1$-C$_3$ alkyl, C$_1$-C$_3$ haloalkyl, C$_1$-C$_3$ alkoxy, C$_1$-C$_3$ haloalkoxy, —SO$_2$R$_{11}$, —NR$_{11}$R$_{11}$, —OH or —CN; and
each R$_{11}$ is independently —H or C$_1$-C$_3$ alkyl.

2. The compound of claim 1, or pharmaceutically acceptable salt thereof, having the Formula:

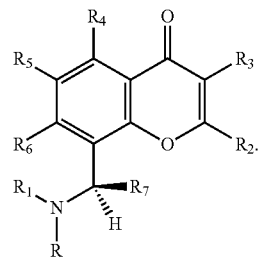

3. The compound of claim 1, or pharmaceutically acceptable salt thereof, having the Formula:

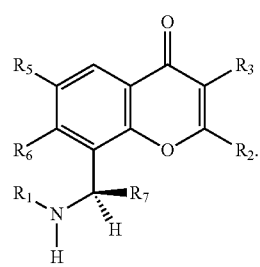

4. The compound of claim 1, or pharmaceutically acceptable salt thereof, wherein R is —H.

5. The compound of claim 1, or pharmaceutically acceptable salt thereof, wherein $R_1$ is a group of the formula:

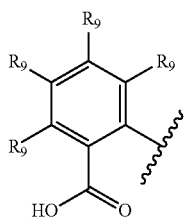 ; 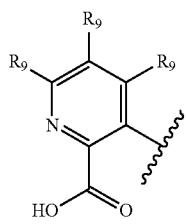 ;

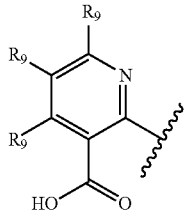 ; 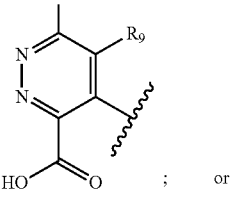 ; or

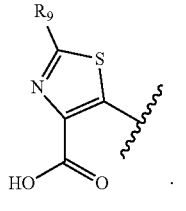 .

6. The compound of claim 1, or pharmaceutically acceptable salt thereof, wherein $R_1$ is a group of the formula:

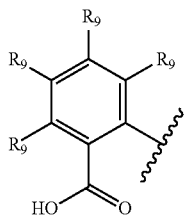 ; 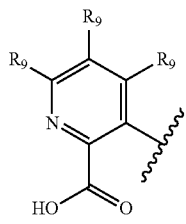 ;

 or 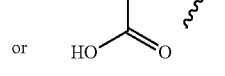 .

7. The compound of claim 1, or pharmaceutically acceptable salt thereof, wherein $R_1$ is a group of the formula:

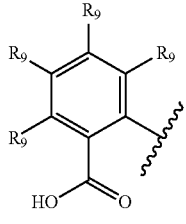 ; 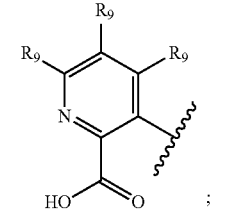 or

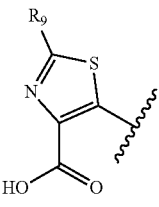 .

8. The compound of claim 1, or pharmaceutically acceptable salt thereof, wherein $R_1$ is a group of the formula:

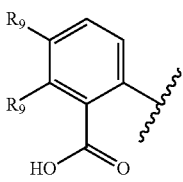 ; 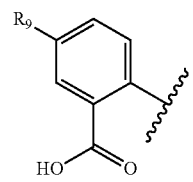 ;

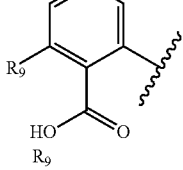 ; 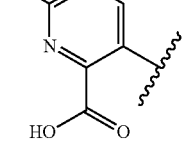 ;

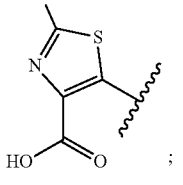 ; or 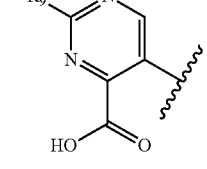 .

9. The compound of claim 1, or pharmaceutically acceptable salt thereof, wherein each $R_9$ is independently —H, halogen, $C_1$-$C_3$ alkyl, $C_1$-$C_3$ haloalkyl, $C_1$-$C_3$ alkoxy, or $C_3$-$C_5$ cycloalkyl.

10. The compound of claim 1, or pharmaceutically acceptable salt thereof, wherein each $R_9$ is independently —H, halogen, $C_1$-$C_3$ alkyl, $C_1$-$C_3$ haloalkyl, or $C_3$-$C_5$ cycloalkyl.

11. The compound of claim 1, or pharmaceutically acceptable salt thereof, wherein each $R_9$ is independently —H, halogen, $C_1$-$C_3$ alkyl or $C_1$-$C_3$ haloalkyl.

12. The compound of claim 1, or pharmaceutically acceptable salt thereof, wherein $R_1$ is a group of the formula:

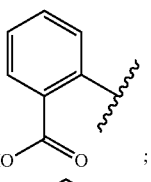 ; 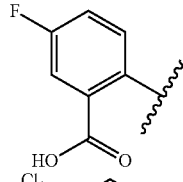 ;

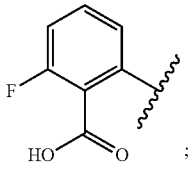 ; 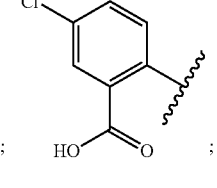 ;

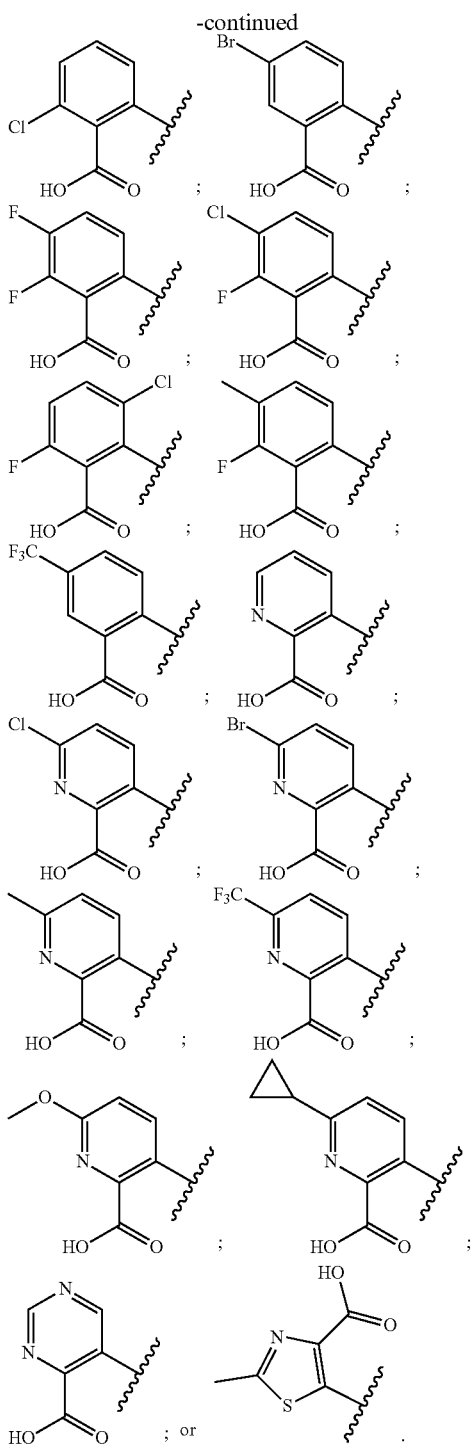

13. The compound of claim 1, or pharmaceutically acceptable salt thereof, wherein R₂ is a group of the formula:

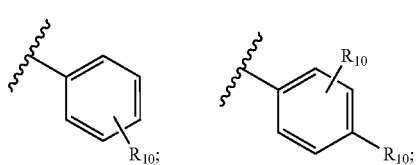

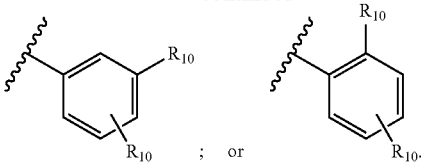

14. The compound of claim 1, or pharmaceutically acceptable salt thereof, wherein R₂ is a group of the formula:

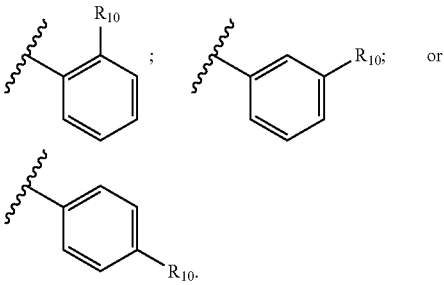

15. The compound of claim 1, or pharmaceutically acceptable salt thereof, wherein each $R_{10}$ is independently —H, —CN, halogen, $C_1$-$C_6$ haloalkyl, $C_1$-$C_6$ alkoxy, $C_1$-$C_6$ haloalkoxy, —SO₂$R_{11}$, —CONR₁₁$R_{11}$, —NR₁₁$R_{11}$, —NR₁₁—CO₂$R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR₁₁$R_{11}$, —OH or —CN.

16. The compound of claim 1, or pharmaceutically acceptable salt thereof, wherein each $R_{10}$ is independently —H, —CN, halogen, $C_1$-$C_6$ haloalkyl, $C_1$-$C_6$ alkoxy, —SO₂$R_{11}$, —CONR₁₁$R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, or an optionally substituted heteroaryl selected from selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; and the optionally substituted $C_3$-$C_5$ cycloalkyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR₁₁$R_{11}$, —OH or —CN.

17. The compound of claim 1, or pharmaceutically acceptable salt thereof, wherein each $R_{10}$ is independently —H, —CN, halogen, $C_1$-$C_6$ haloalkyl, $C_1$-$C_6$ alkoxy, —SO₂$R_{11}$, —CONR₁₁$R_{11}$, a $C_1$-$C_6$ alkyl optionally substituted with —CN, a $C_3$ cycloalkyl optionally substituted with $C_1$-$C_3$ alkyl or —CN, an optionally substituted heterocycle selected from pyrrolidine, or an optionally substituted heteroaryl selected from pyrazole or oxazole.

18. The compound of claim 1, or pharmaceutically acceptable salt thereof, wherein each $R_{10}$ is independently
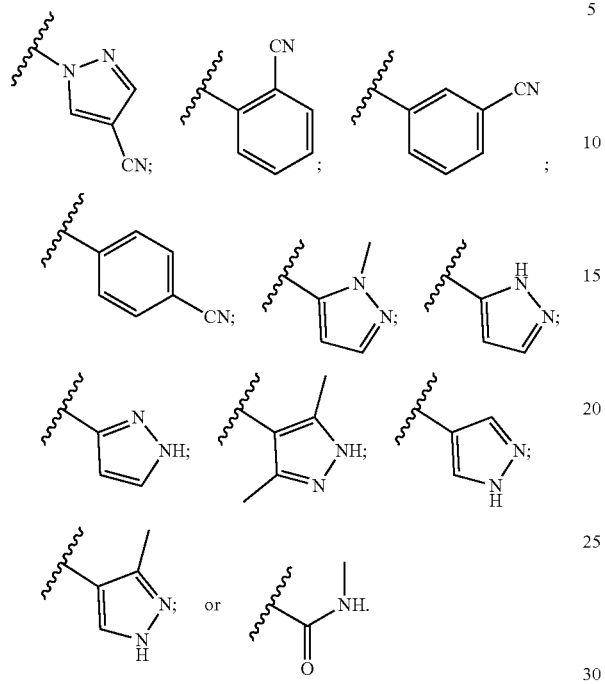
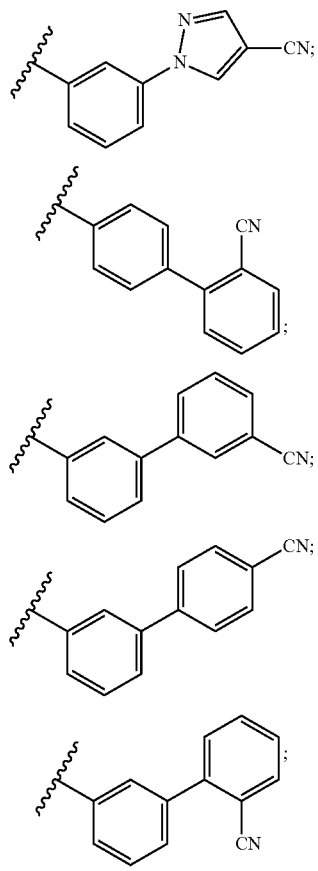
19. The compound of claim 1, or pharmaceutically acceptable salt thereof, wherein each $R_{10}$ is independently
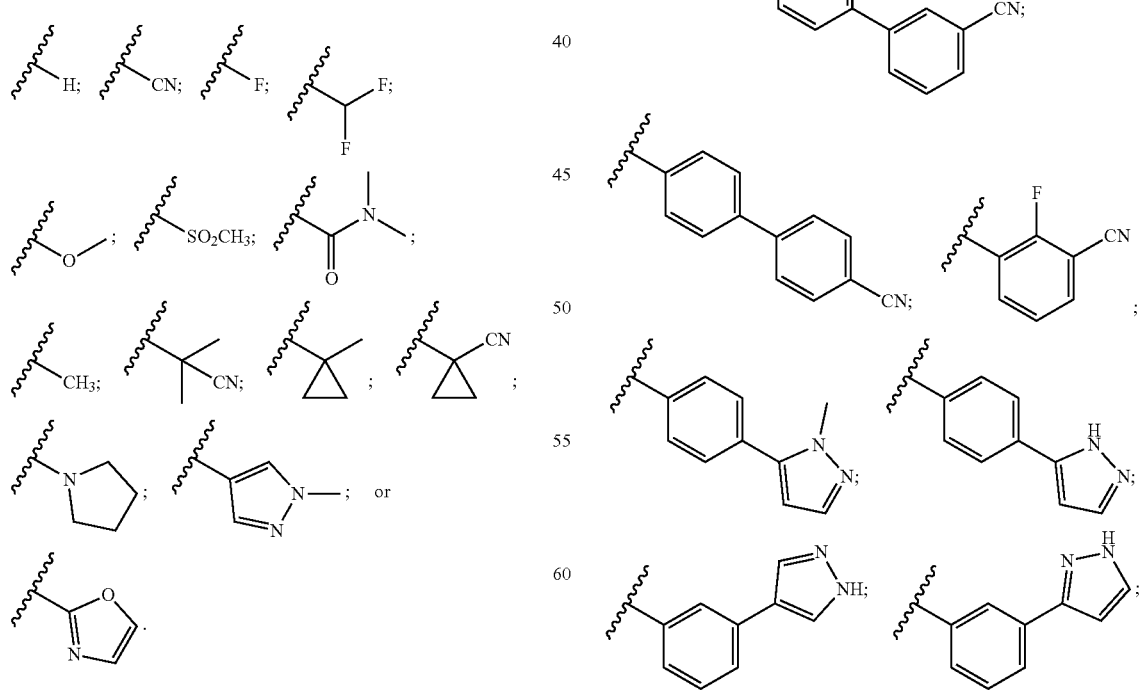
20. The compound of claim 1, or pharmaceutically acceptable salt thereof, wherein $R_2$ is a group of the formula:

21. The compound of claim 1, or pharmaceutically acceptable salt thereof, wherein $R_2$ is a group of the formula:

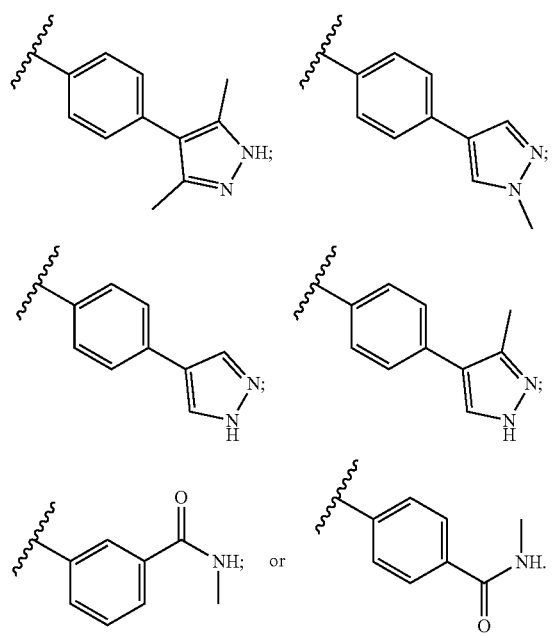

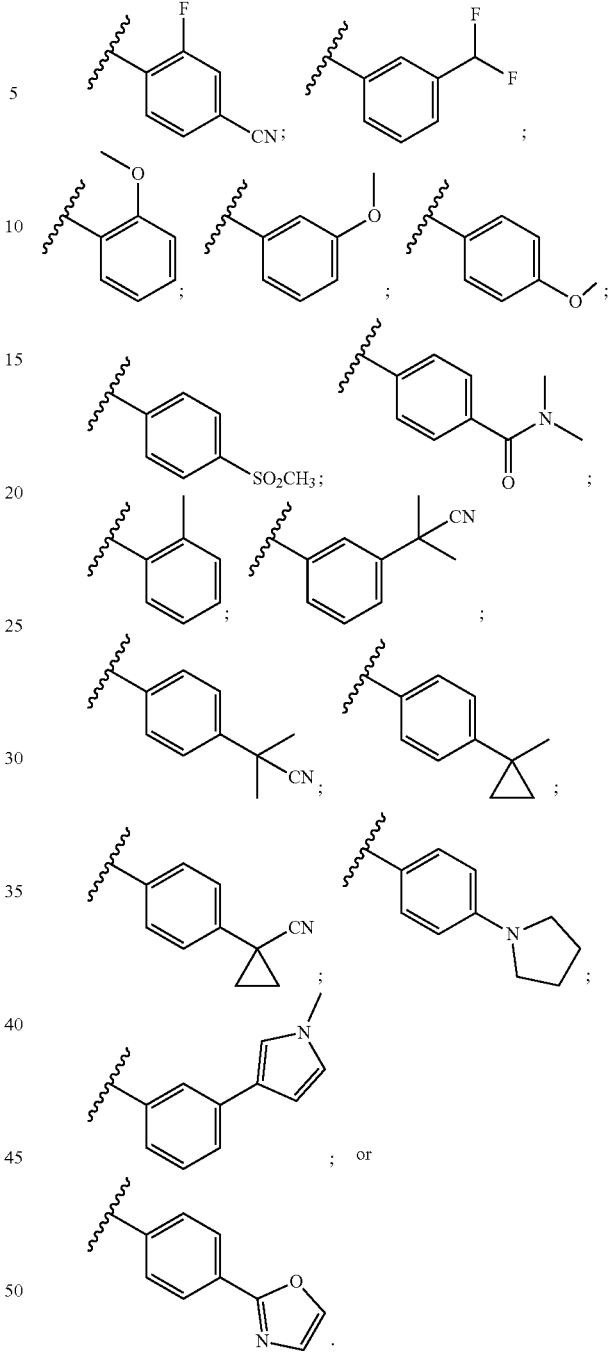

22. The compound of claim 1, or pharmaceutically acceptable salt thereof, wherein $R_3$ is —H, —CN, $C_1$-$C_6$ alkyl, or $C_1$-$C_6$ haloalkyl.

23. The compound of claim 1, or pharmaceutically acceptable salt thereof, wherein $R_3$ is —H, —CN, $C_1$-$C_3$ alkyl, or $C_1$-$C_3$ haloalkyl.

24. The compound of claim 1, or pharmaceutically acceptable salt thereof, wherein $R_3$ is —H, —CN or $C_1$-$C_3$ alkyl.

25. The compound of claim 1, or pharmaceutically acceptable salt thereof, wherein $R_3$ is H, methyl, or trifluoromethyl.

26. The compound of claim 1, or pharmaceutically acceptable salt thereof, wherein $R_3$ is —H or methyl.

27. The compound of claim 1, or pharmaceutically acceptable salt thereof, wherein $R_4$ is —H or halogen.

28. The compound of claim 1, or pharmaceutically acceptable salt thereof, wherein $R_4$ is —H.

29. The compound of claim 1, or pharmaceutically acceptable salt thereof, wherein $R_5$ is —H, halogen, $C_1$-$C_3$ alkyl or $C_1$-$C_3$ haloalkyl.

30. The compound of claim 1, or pharmaceutically acceptable salt thereof, wherein $R_6$ is —H or halogen.

31. The compound of claim 1, or pharmaceutically acceptable salt thereof, wherein $R_7$ is —CN, $C_1$-$C_3$ alkyl or $C_1$-$C_3$ haloalkyl.

32. The compound of claim 1, or pharmaceutically acceptable salt thereof, wherein $R_7$ is —CN, methyl or trifluoromethyl.

33. The compound of claim 1, or pharmaceutically acceptable salt thereof, wherein $R_7$ is methyl.

34. The compound of claim 1, or pharmaceutically acceptable salt thereof, wherein $R_8$ is H.

35. The compound of claim 1 selected from:

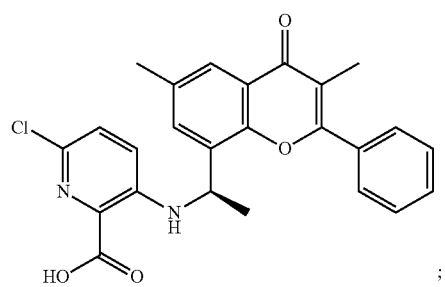

;

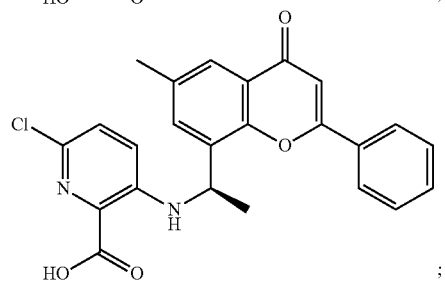

;

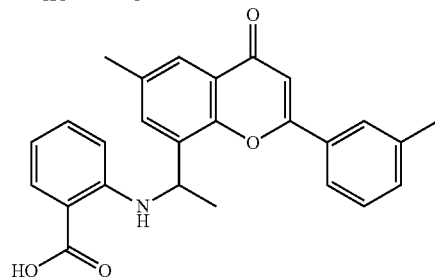

;

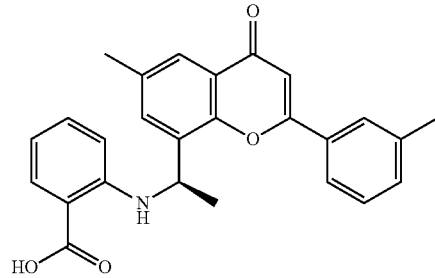

;

-continued

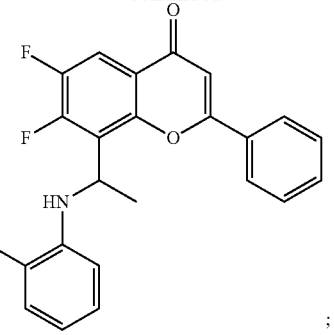

;

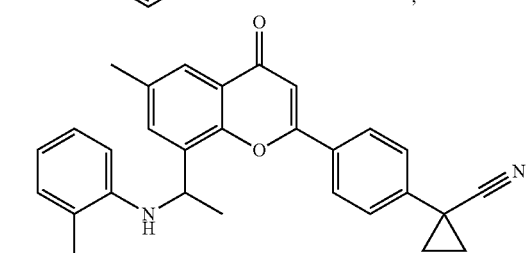

;

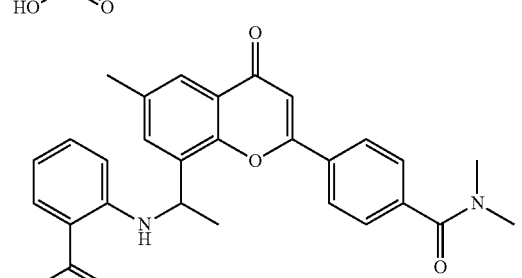

;

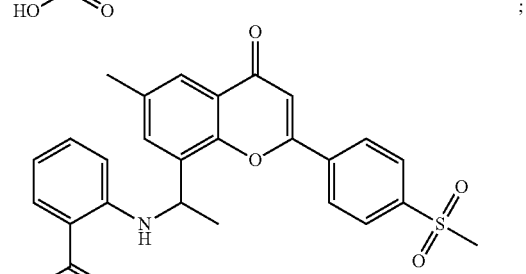

;

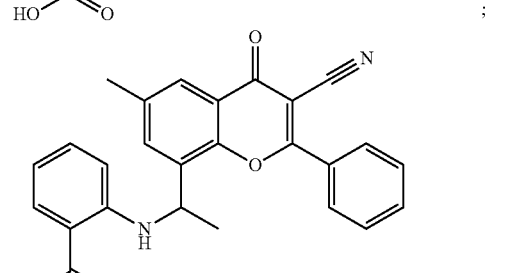

;

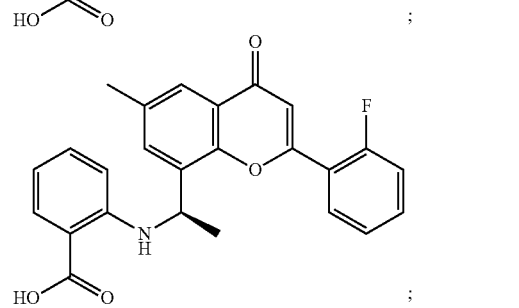

;

353
-continued
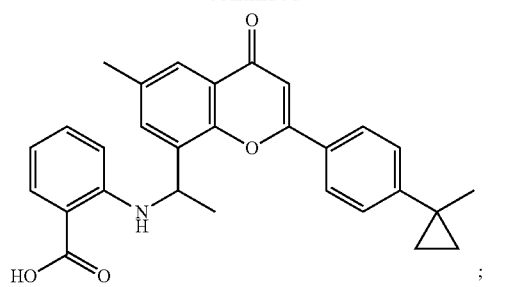
354
-continued
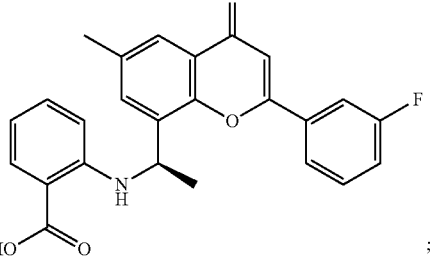
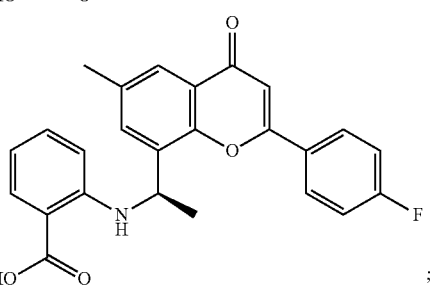
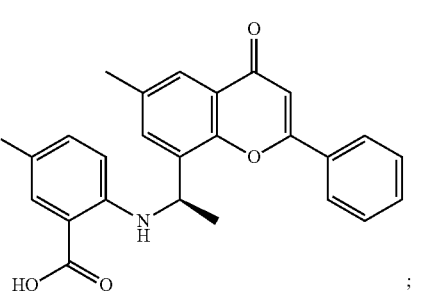
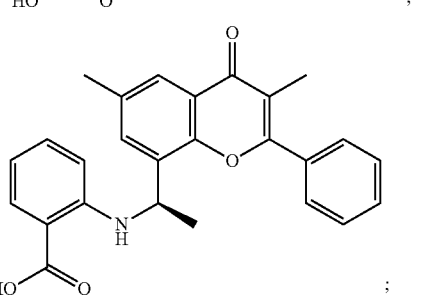
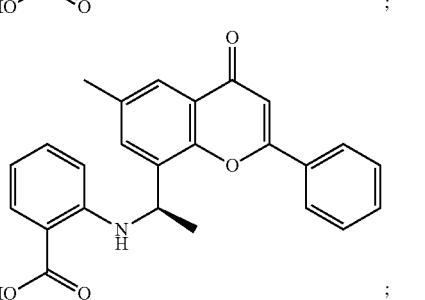
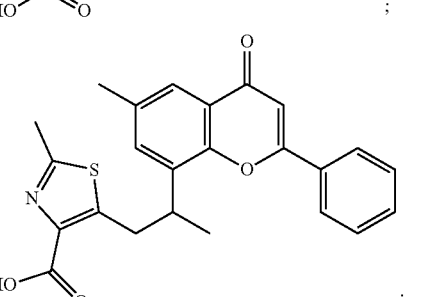

355
-continued
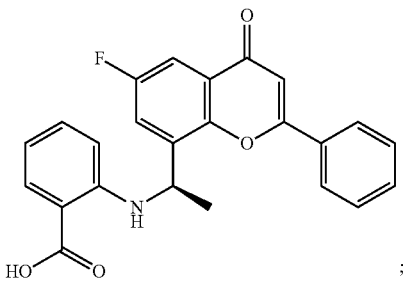
; and
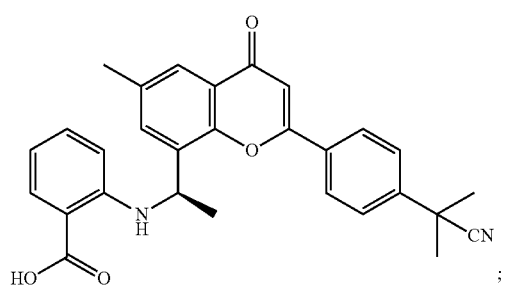
or a pharmaceutically acceptable salt thereof.
36. The compound of claim 1 selected from:
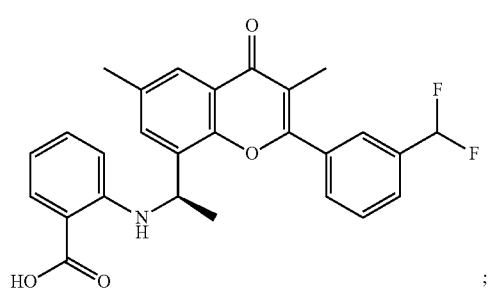
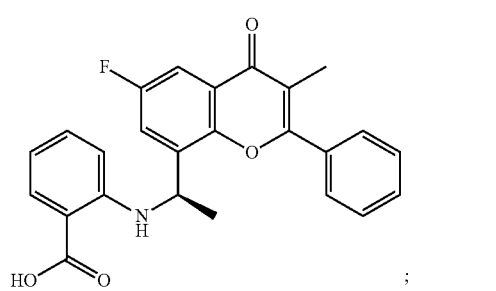
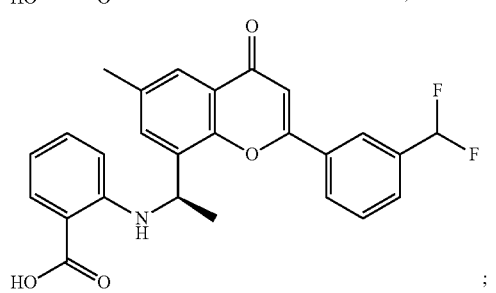
356
-continued
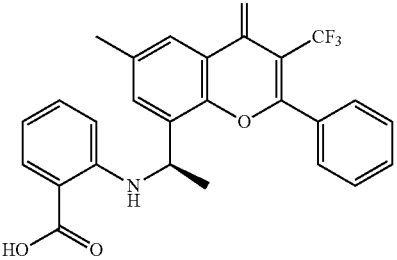
;
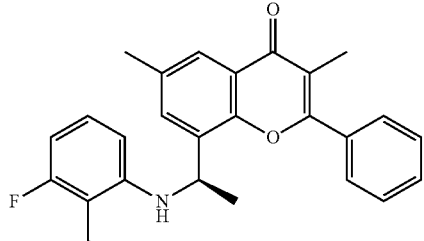
;
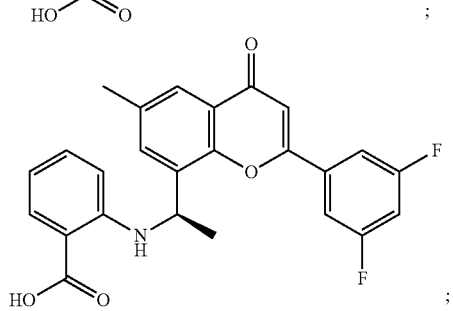
;
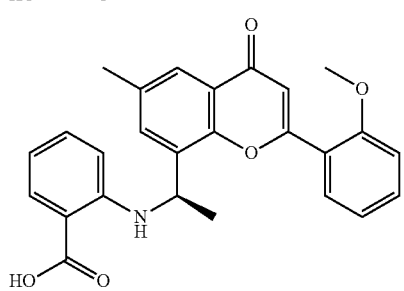
;
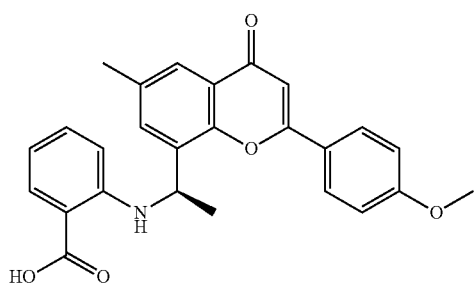
;
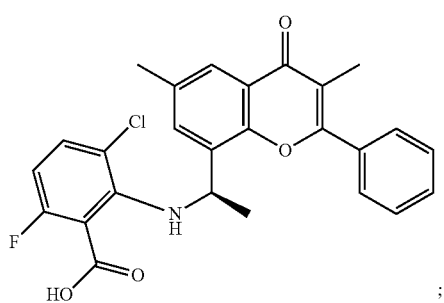
;

357
-continued
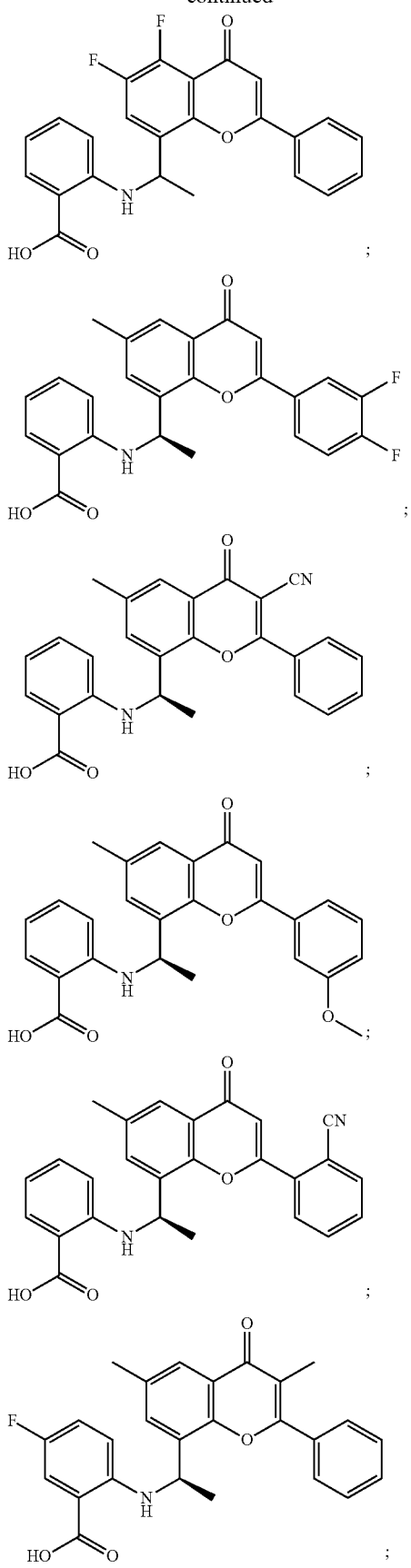
358
-continued
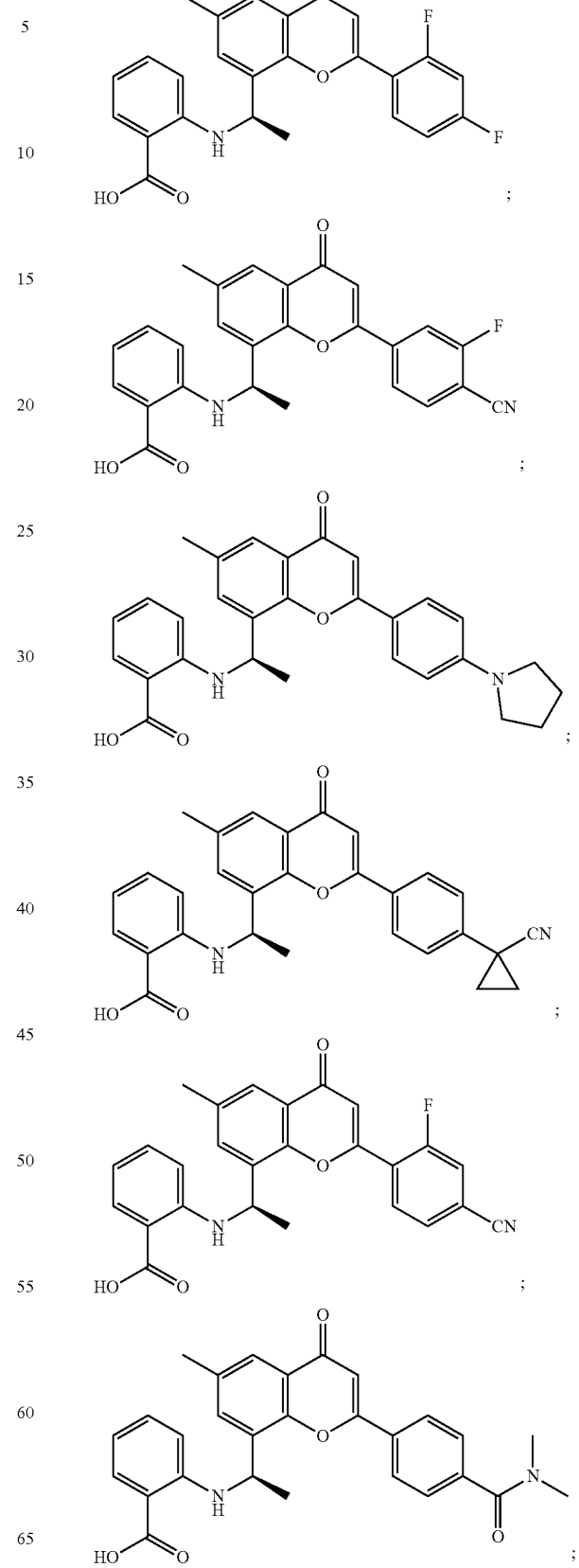

359
-continued
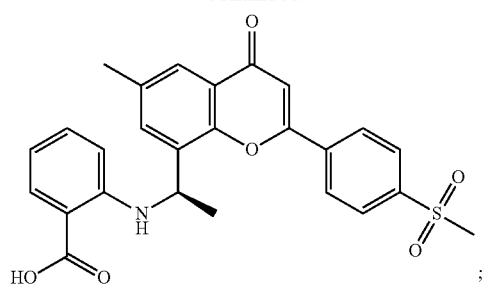
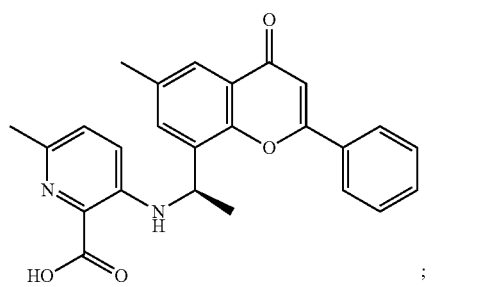
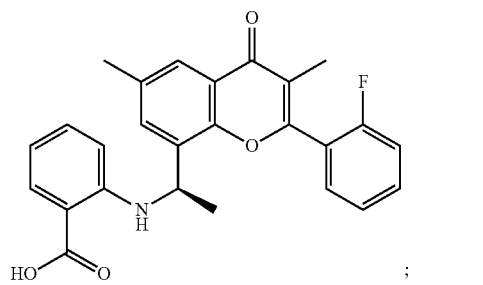 [SMILES: Cc1cc([C@@H](C)Nc2cncnc2C(=O)O)c2oc(-c3ccccc3)c(C)c(=O)c2c1]
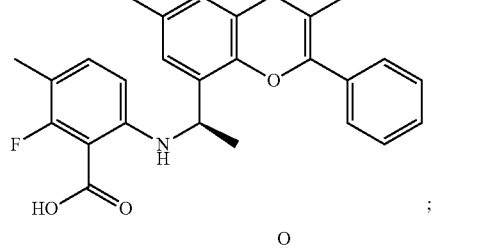
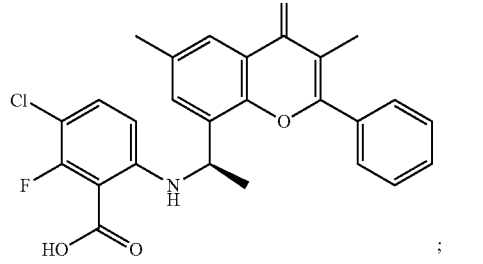
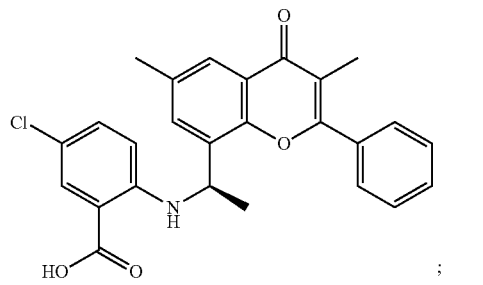
360
-continued
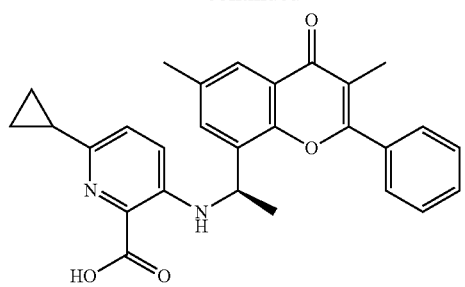
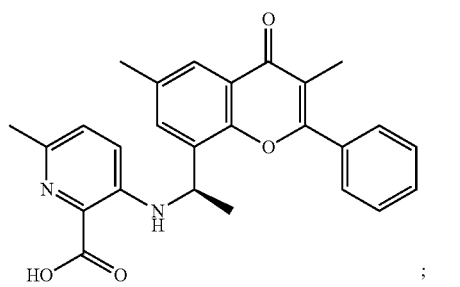
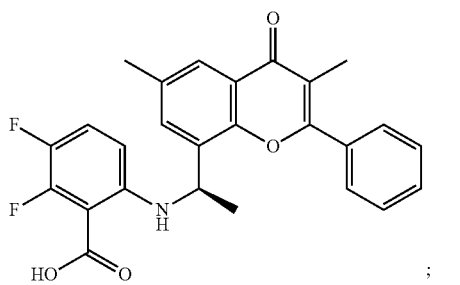
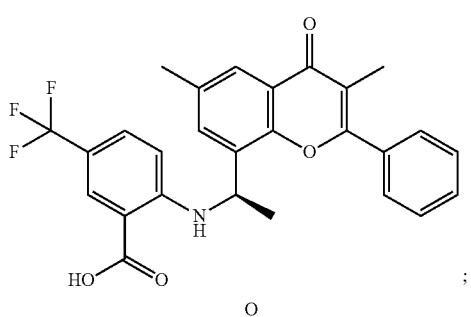
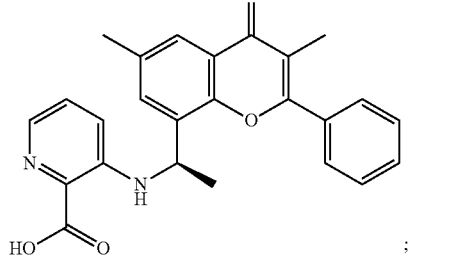
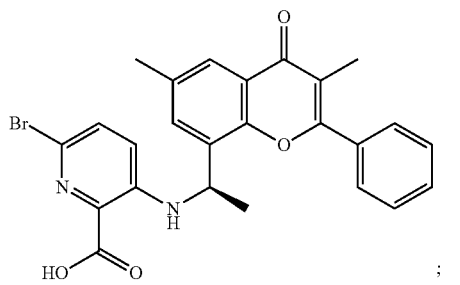

361
-continued
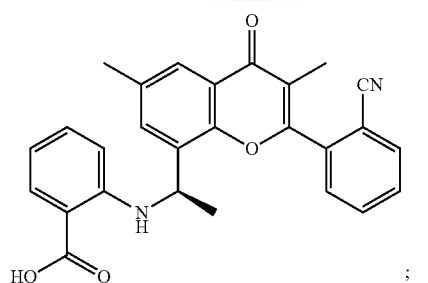
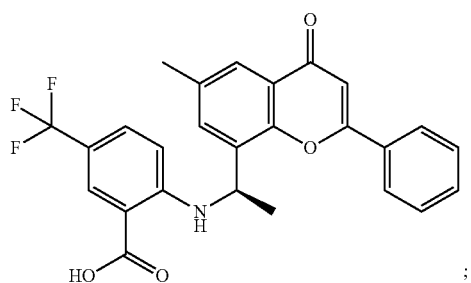
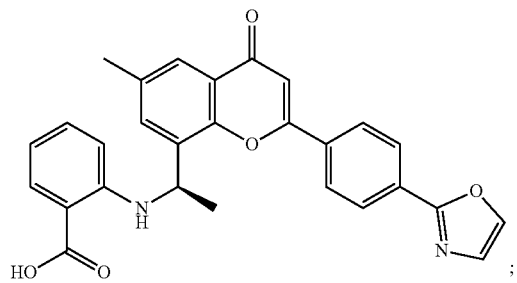
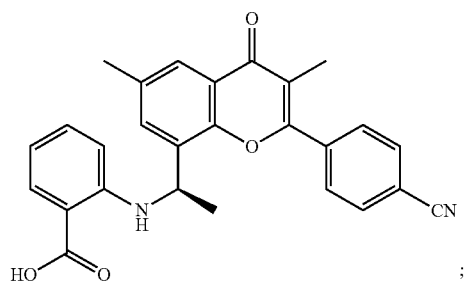
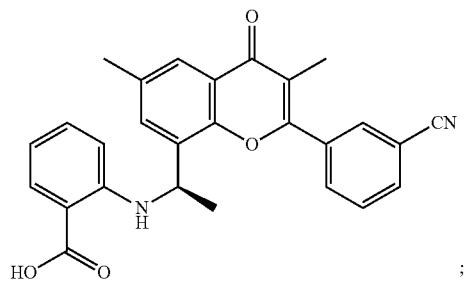
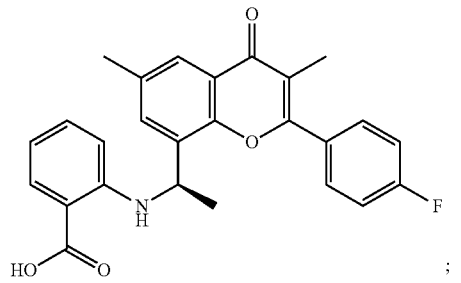
362
-continued
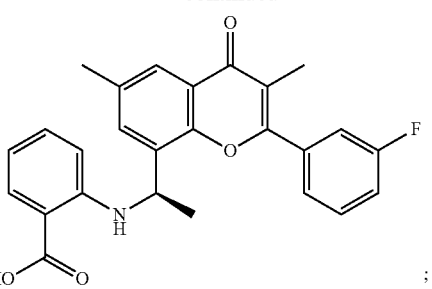
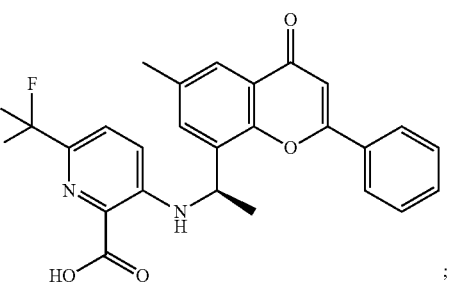
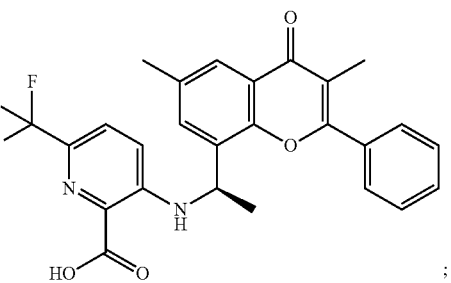
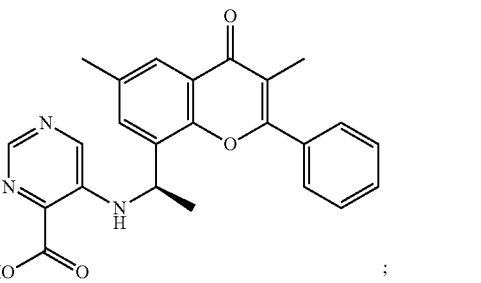
; and
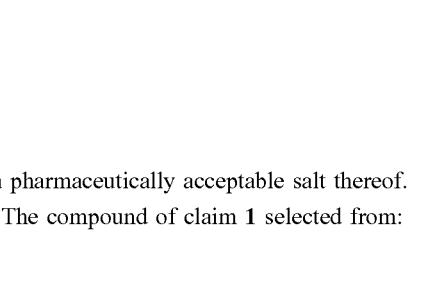
or a pharmaceutically acceptable salt thereof.
37. The compound of claim 1 selected from:
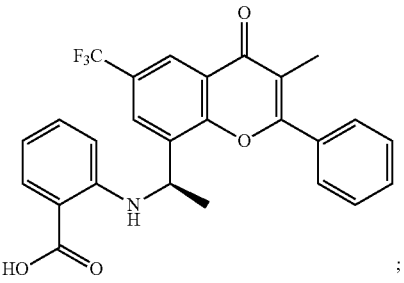

363
-continued
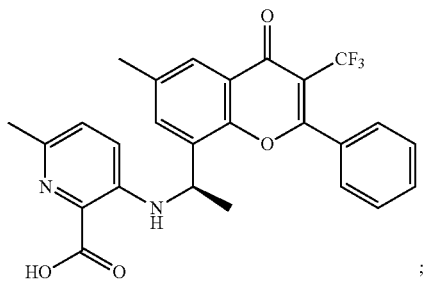
;
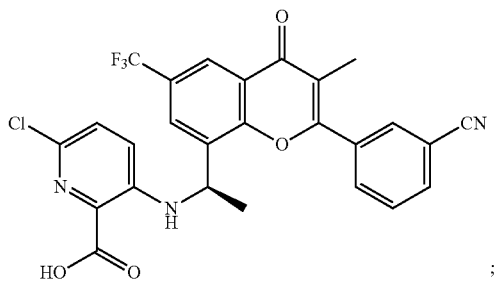
;
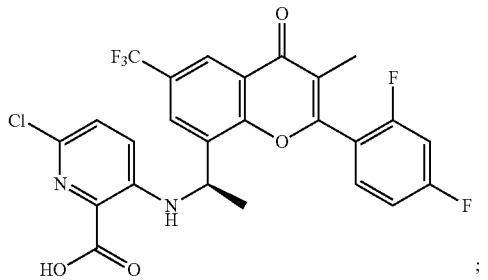
;
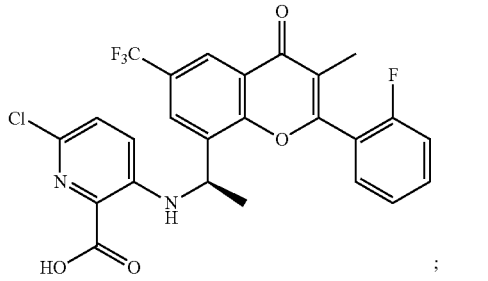
;
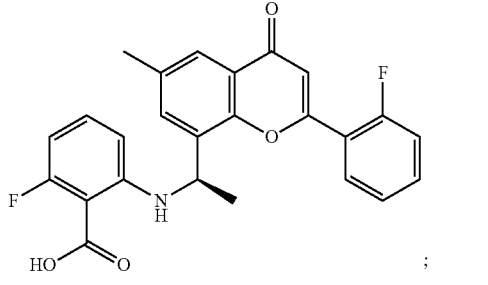
;
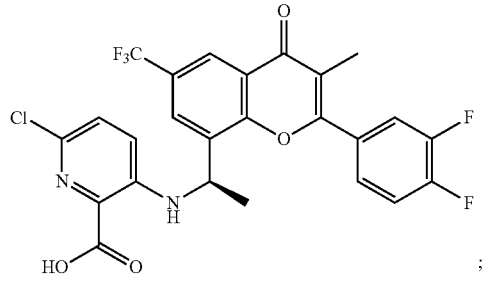
;
364
-continued
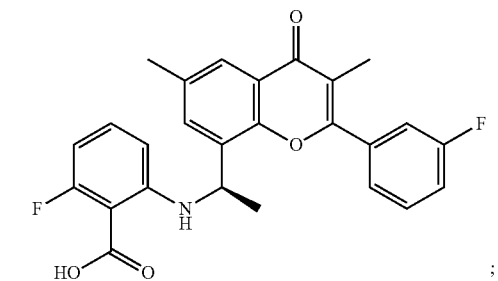
;
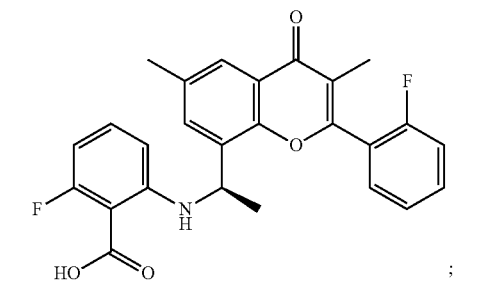
;
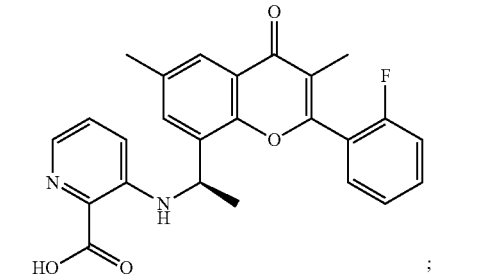
;
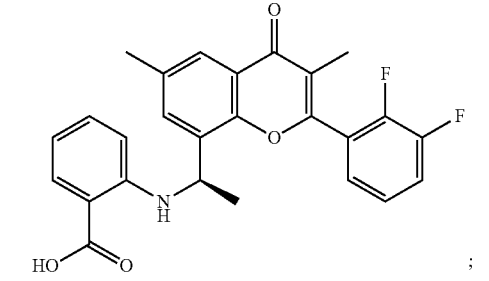
;
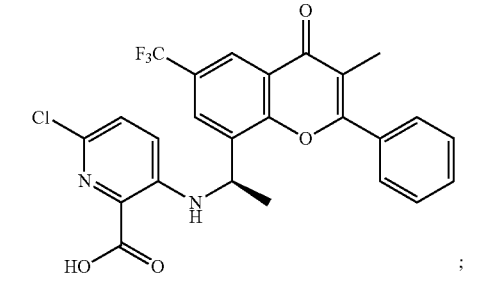
;
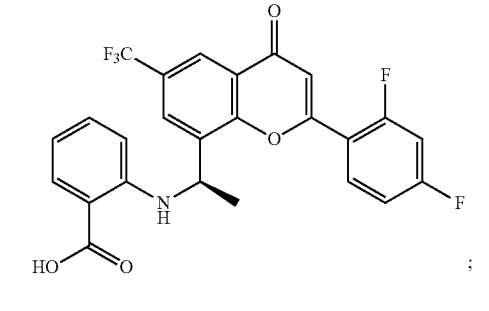
;

365
-continued
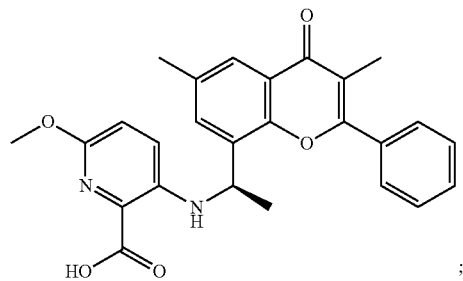
;
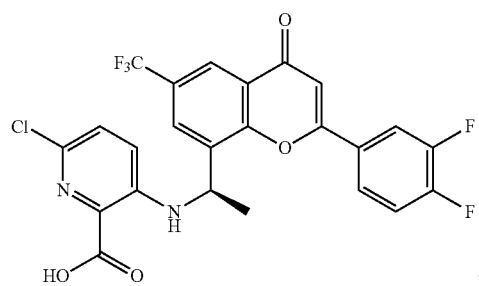
;
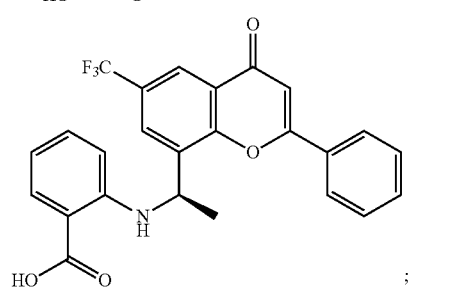
;
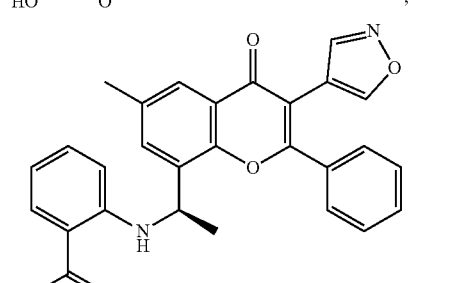
;
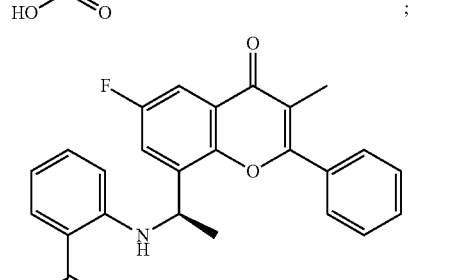
;
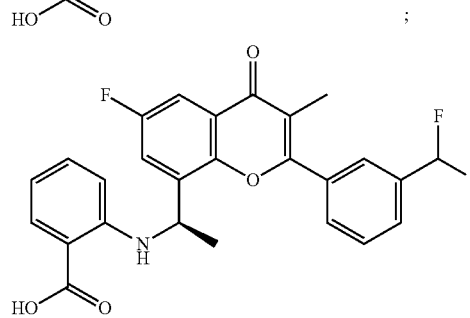
;
366
-continued
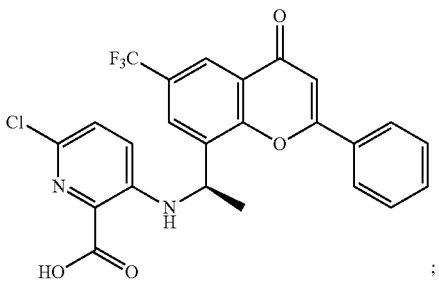
;
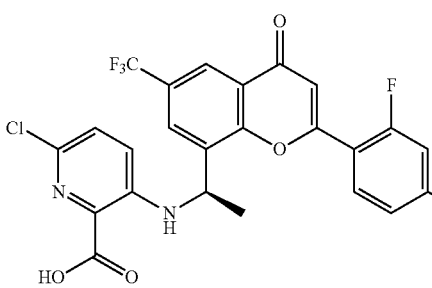
;
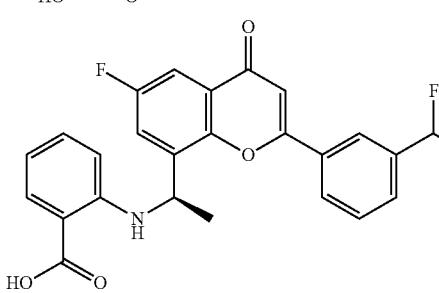
;
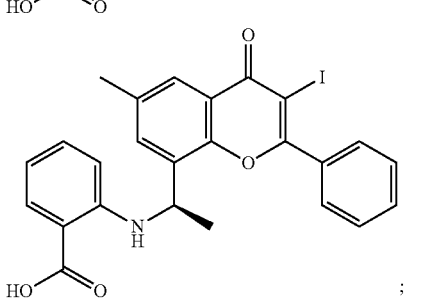
;
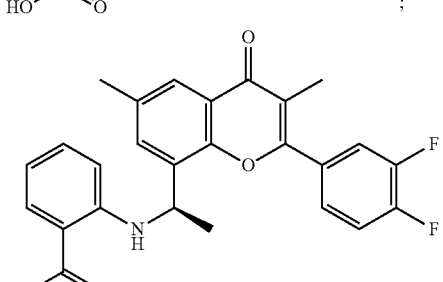
;
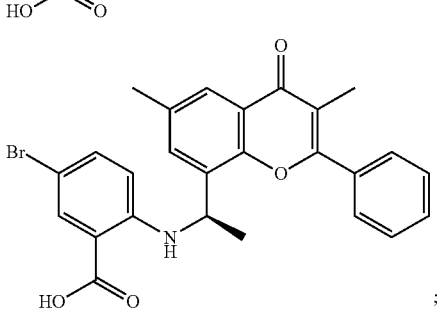
;

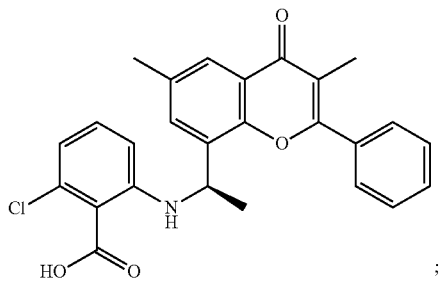
; and
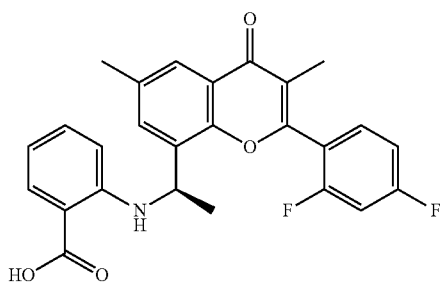
;
or a pharmaceutically acceptable salt thereof.
38. The compound of claim 1 selected from:
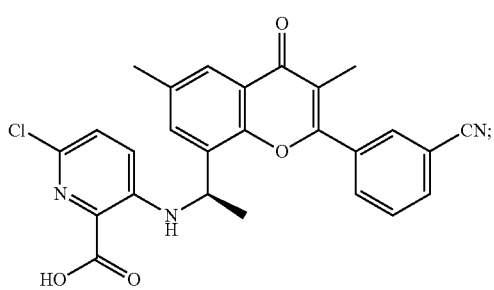
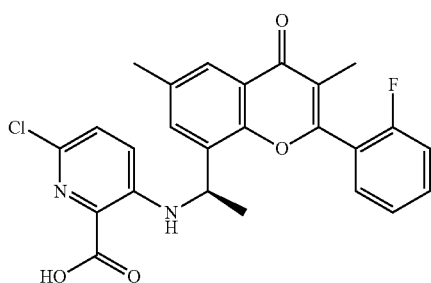
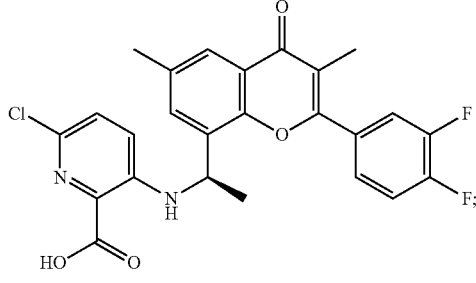
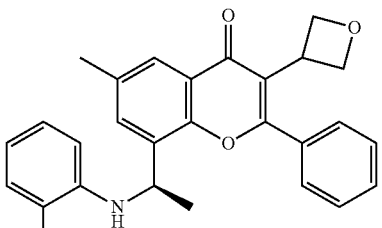
; and
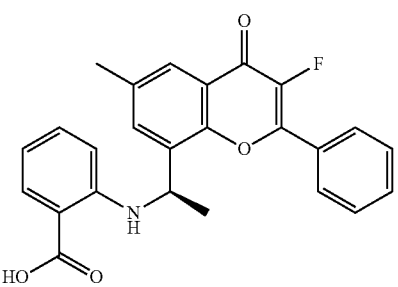
;
or a pharmaceutically acceptable salt thereof.
39. The compound of claim 1 selected from:
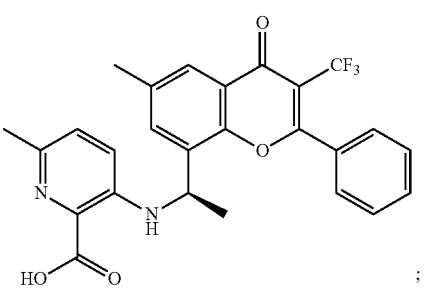
;
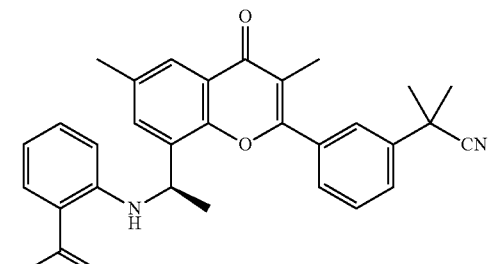
;
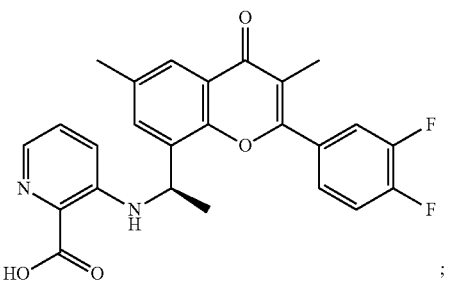
;

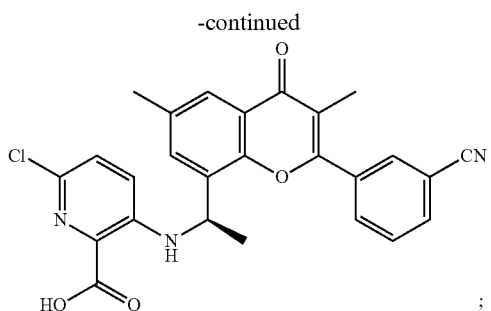
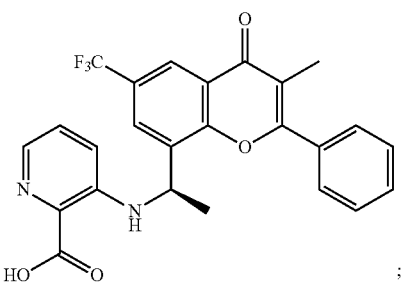
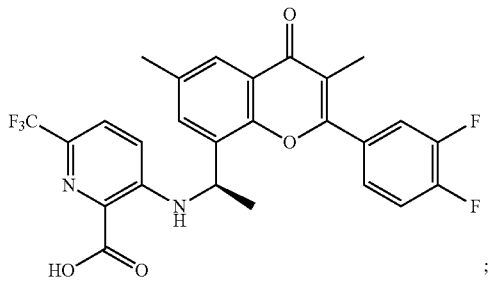
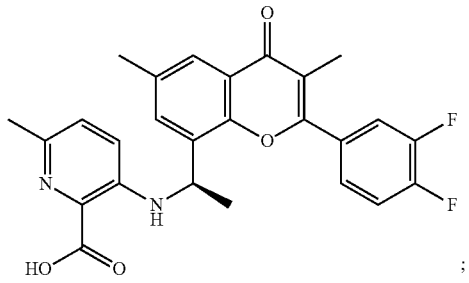
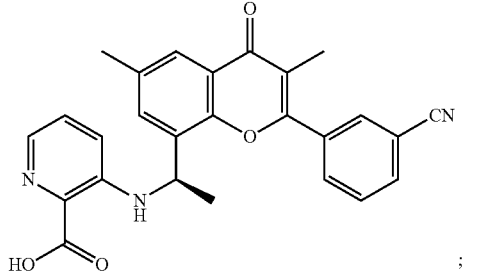
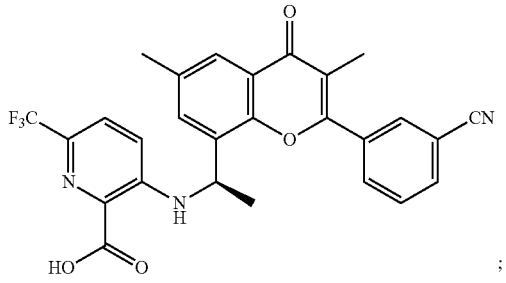
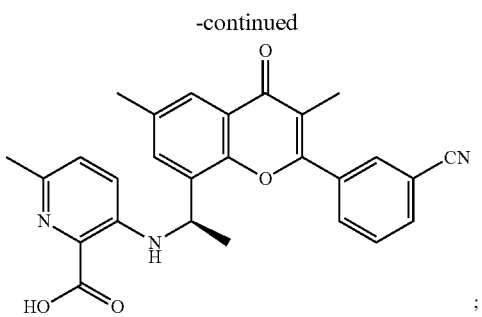
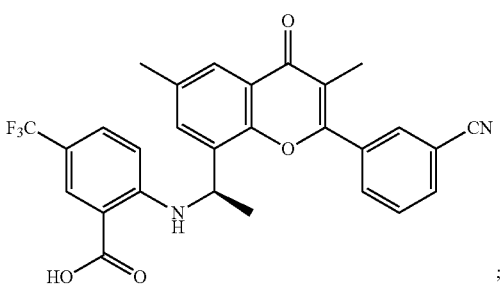
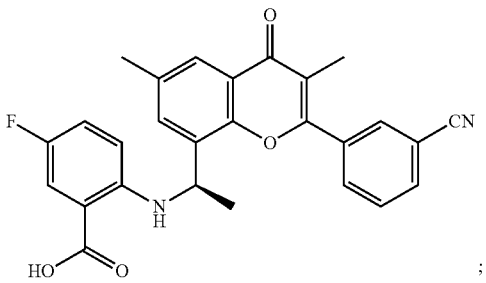
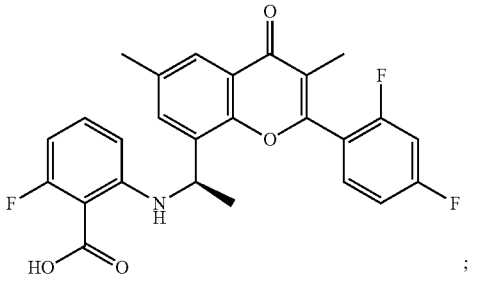
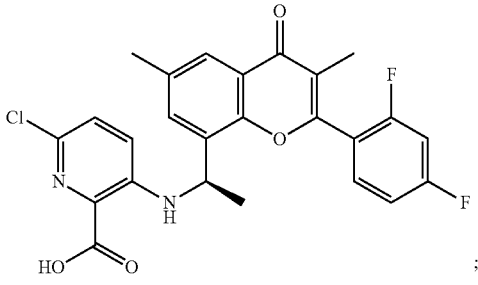
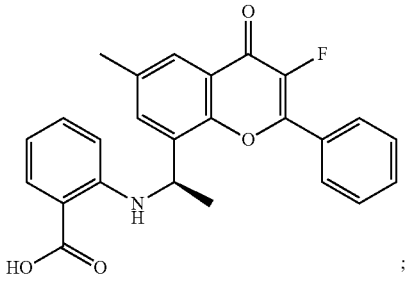

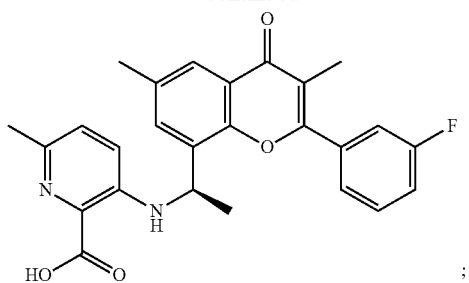;
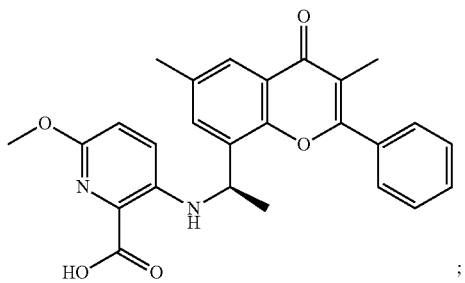;
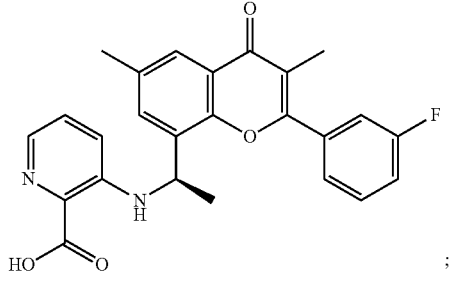;
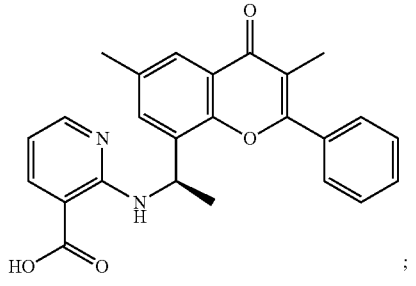;
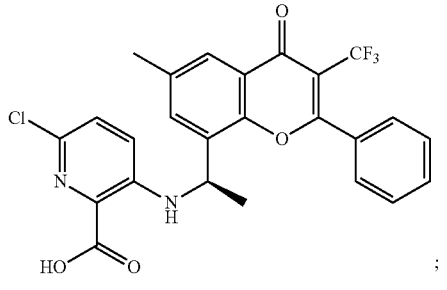;
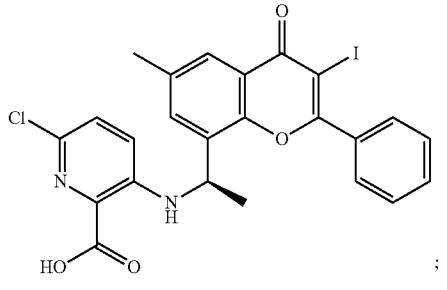;
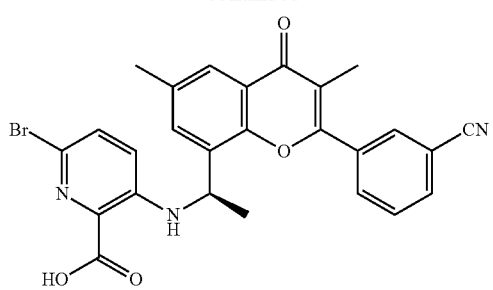;
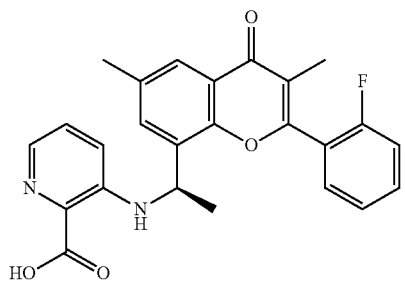;
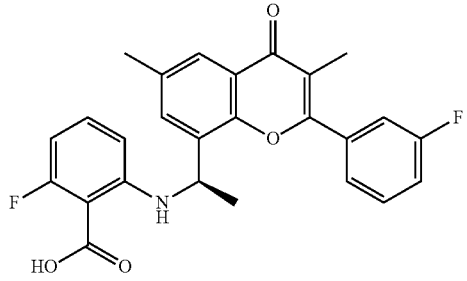;
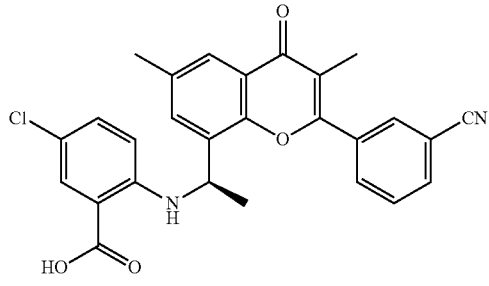;
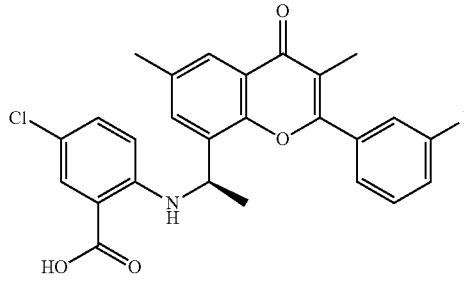;
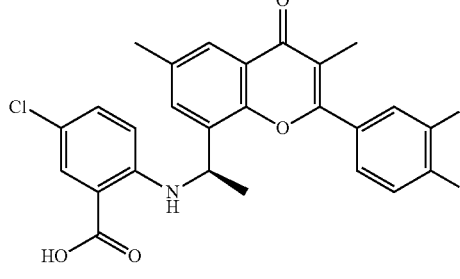;

373
-continued
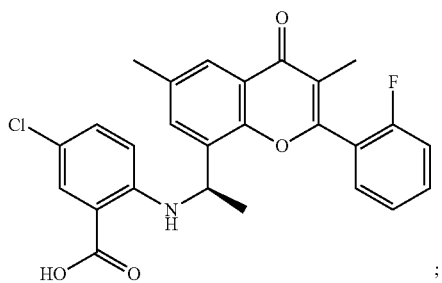
;
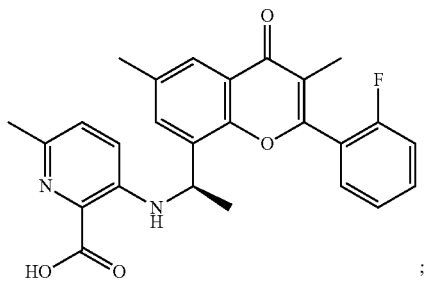
;
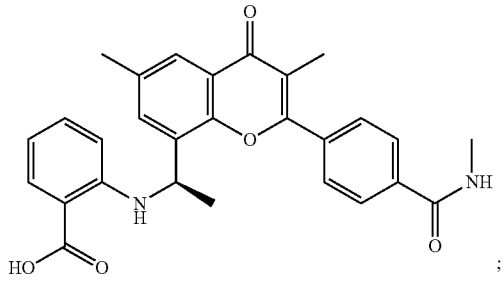
;
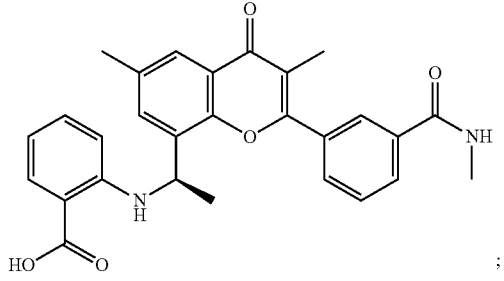
;
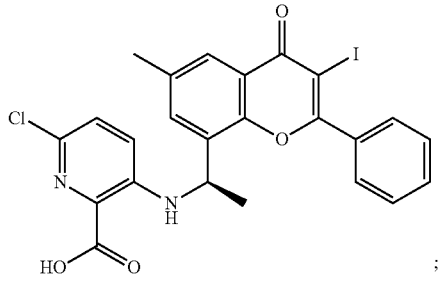
;
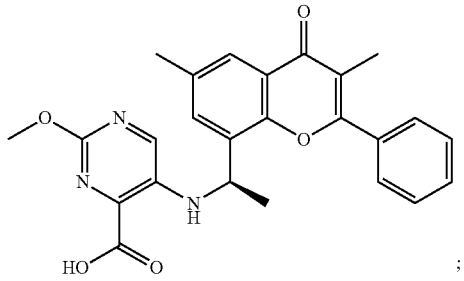
;
374
-continued
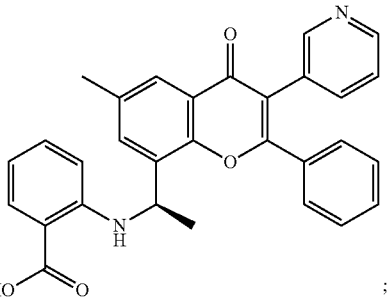
;
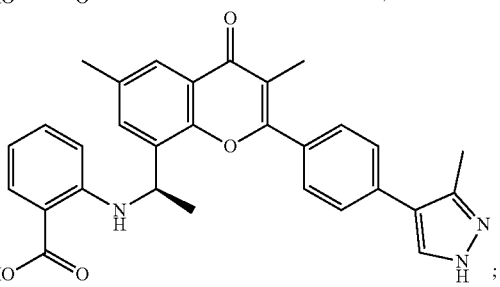
;
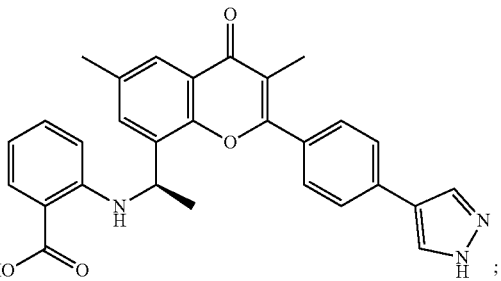
;
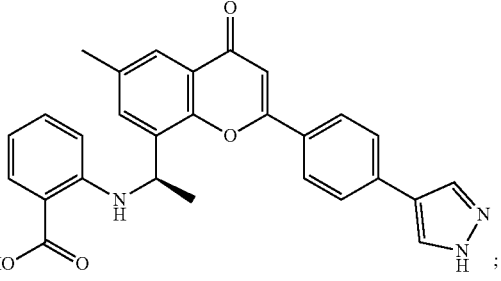
;
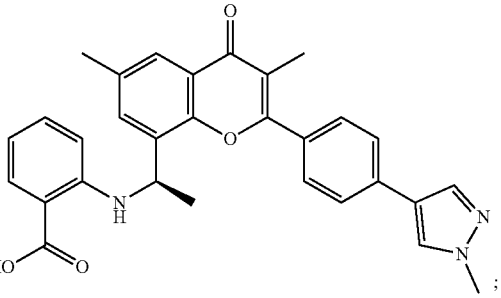
;
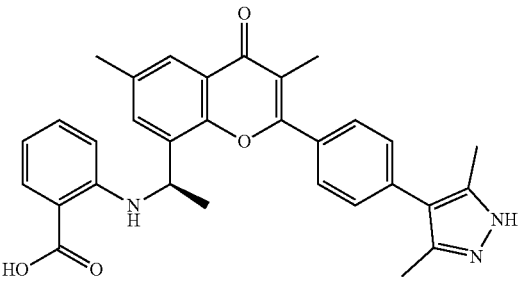
;

-continued
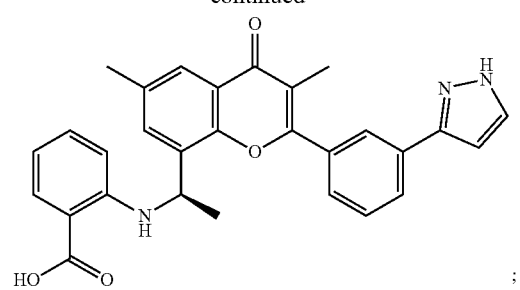
;
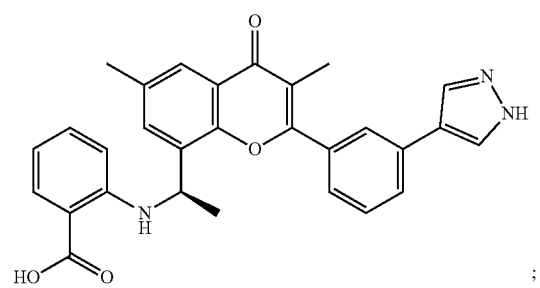
;
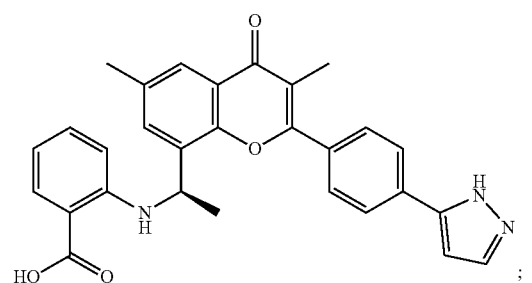
;
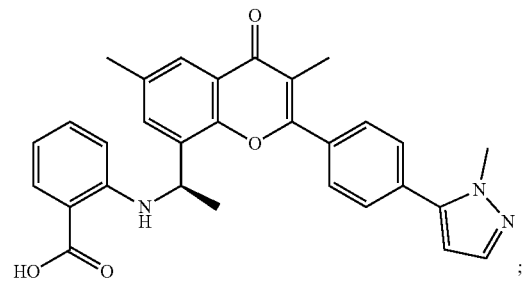
;
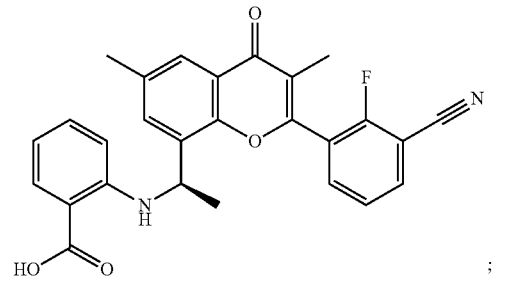
;
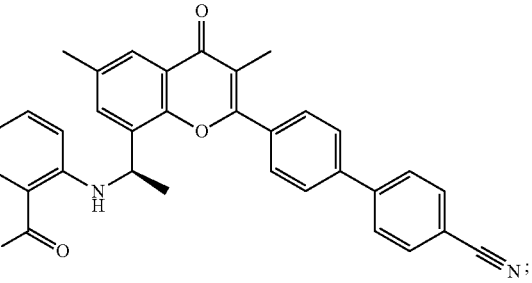
-continued
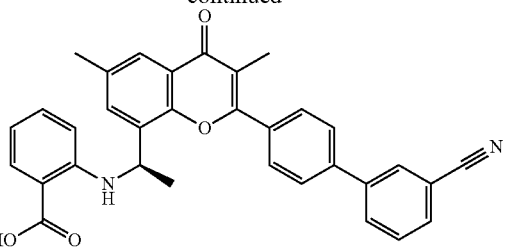
;
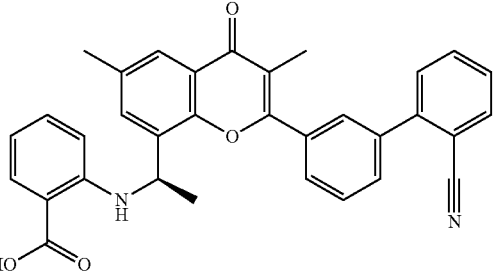
;
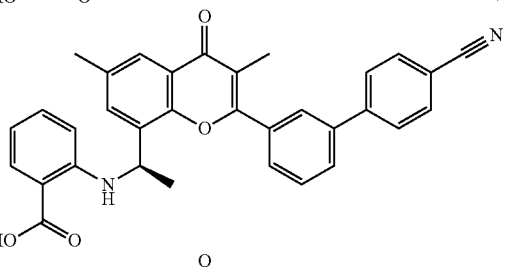
;
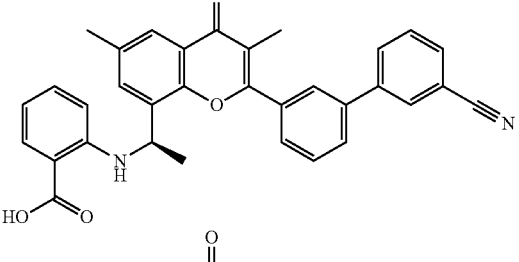
;
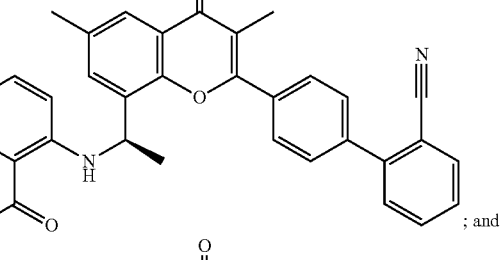
; and
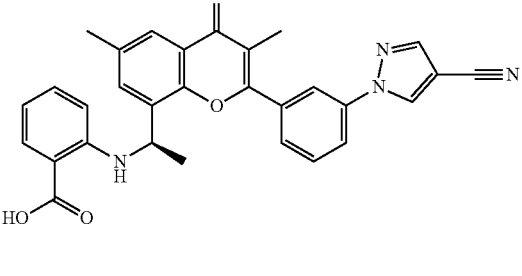
;
or a pharmaceutically acceptable salt thereof.
40. A pharmaceutical composition comprising a compound of claim 1, or a pharmaceutically acceptable salt thereof, and a pharmaceutically acceptable carrier.
41. A method of inhibiting phosphoinositide 3-kinase (PI3K), comprising administering to a patient in need thereof a therapeutically effective amount of a compound of claim 1, or a pharmaceutically acceptable salt thereof.

42. The compound of claim 1, or pharmaceutically acceptable salt thereof, wherein R is —H or $C_1$-$C_3$ alkyl;

$R_1$ is a group of the formula:

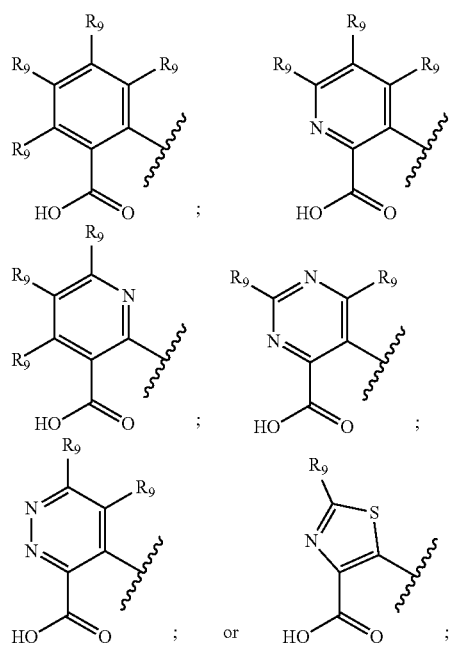

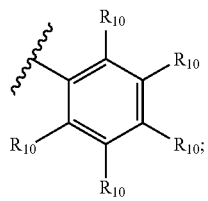

$R_2$ is a group of the formula:

$R_3$ is —H, —CN, $C_1$-$C_6$ alkyl or $C_1$-$C_6$ haloalkyl;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl;

each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and each $R_{11}$ is independently —H or $C_1$-$C_3$ alkyl.

43. The compound of claim 42, or pharmaceutically acceptable salt thereof, having the Formula:

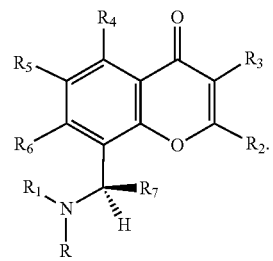

44. The compound of claim 43, or pharmaceutically acceptable salt thereof, wherein $R_1$ is a group of the formula:

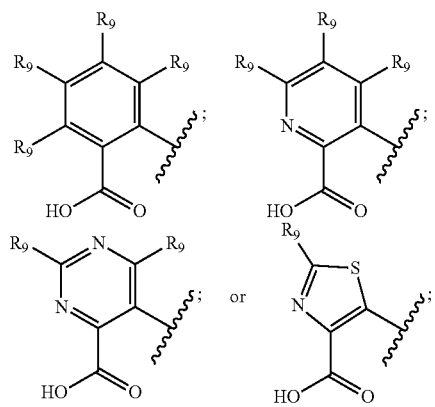

$R_2$ is a group of the formula:

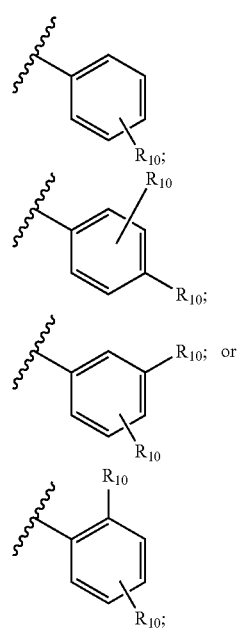

$R_3$ is —H, —CN, $C_1$-$C_3$ alkyl, or $C_1$-$C_3$ haloalkyl;
$R_4$ is —H, or halogen;
$R_5$ is —H, halogen, $C_1$-$C_3$ alkyl or $C_1$-$C_3$ haloalkyl;
$R_6$ is H, or halogen;
$R_7$ is —CN, methyl or trifluoromethyl;
R is —H;
each $R_9$ is independently —H, halogen, methyl, $C_1$-$C_3$ haloalkyl, or cyclopropyl;
each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN; and
each $R_{11}$ is independently —H or $C_1$-$C_3$ alkyl.

45. The compound of claim 1, or pharmaceutically acceptable salt thereof, wherein
R is —H or $C_1$-$C_3$ alkyl;
$R_1$ is a group of the formula:

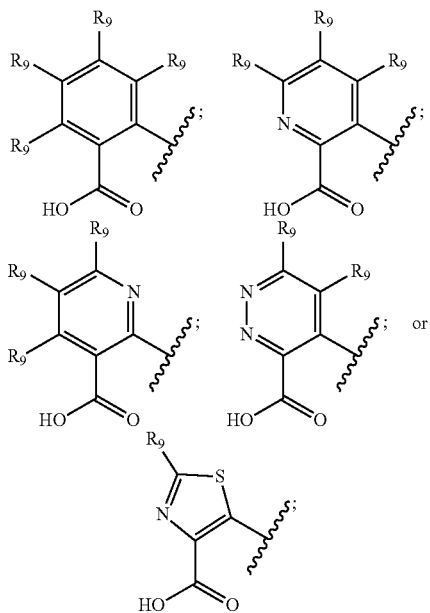

$R_2$ is a group of the formula:

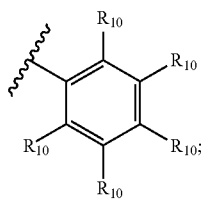

$R_3$ is —H, —CN, $C_1$-$C_6$ alkyl or $C_1$-$C_6$ haloalkyl;
each of $R_4$, $R_5$ and $R_6$ is independently —H, halogen, $C_1$-$C_6$ alkyl or $C_1$-$C_6$ haloalkyl;
$R_7$ is —CN, $C_1$-$C_6$ alkyl or $C_1$-$C_6$ haloalkyl;
$R_8$ is —H or $C_1$-$C_6$ alkyl;
each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl;
each $R_{10}$ is independently —H, —CN, halogen, $C_1$-$C_6$ haloalkyl, $C_1$-$C_6$ alkoxy, $C_1$-$C_6$ haloalkoxy, —SO$_2$R$_{11}$, —CONR$_{11}$R$_{11}$, —NR$_{11}$R$_{11}$, —NR$_{11}$—CO$_2$R$_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —NR$_{11}$R$_{11}$, —OH or —CN; and
each $R_{11}$ is independently —H or $C_1$-$C_3$ alkyl.

46. The compound of claim 45, or pharmaceutically acceptable salt thereof, having the Formula:

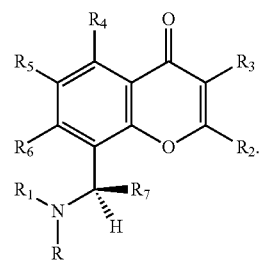

47. The compound of claim 46, or pharmaceutically acceptable salt thereof, wherein $R_1$ is a group of the formula:

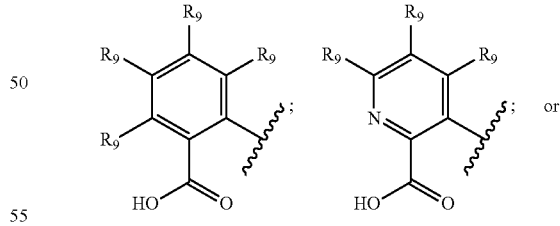

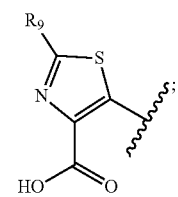

$R_2$ is a group of the formula:

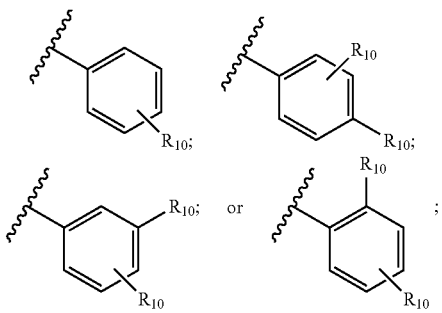

$R_3$ is —H, —CN, or $C_1$-$C_3$ alkyl;
$R_4$, and R are each —H;
$R_5$ is —H, halogen, $C_1$-$C_3$ alkyl or $C_1$-$C_3$ haloalkyl;
$R_6$ is —H or halogen;
$R_7$ is —CN, methyl or trifluoromethyl;
each $R_9$ is independently —H, halogen, methyl, or $C_1$-$C_3$ haloalkyl;
each $R_{10}$ is independently —H, —CN, halogen, $C_1$-$C_6$ haloalkyl, $C_1$-$C_6$ alkoxy, $C_1$-$C_6$ haloalkoxy, —$SO_2R_{11}$, —$CONR_{11}R_{11}$, —$NR_{11}R_{11}$, —$NR_{11}$—$CO_2R_{11}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{11}R_{11}$, —OH or —CN; and
each $R_{11}$ is independently —H or $C_1$-$C_3$ alkyl.

48. The compound of claim 46, or pharmaceutically acceptable salt thereof, wherein R is —H.

49. The compound of claim 48, or pharmaceutically acceptable salt thereof, wherein $R_1$ is a group of the formula

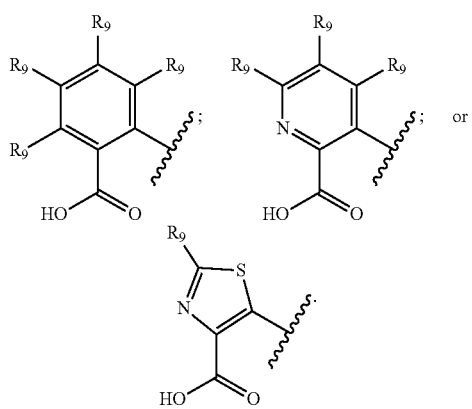

50. The compound of claim 49, or pharmaceutically acceptable salt thereof, wherein $R_9$ is —H, halogen, $C_1$-$C_3$ alkyl or $C_1$-$C_3$ haloalkyl.

51. The compound of claim 50, or pharmaceutically acceptable salt thereof, wherein $R_2$ is a group of the formula:

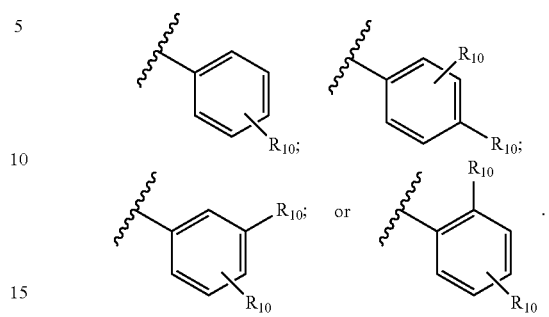

52. The compound of claim 51, or pharmaceutically acceptable salt thereof, wherein $R_3$ is —H, —CN or $C_1$-$C_3$ alkyl.

53. The compound of claim 52, or pharmaceutically acceptable salt thereof, wherein $R_3$ is —H or methyl.

54. The compound of claim 53, or pharmaceutically acceptable salt thereof, wherein $R_4$ is —H.

55. The compound of claim 54, or pharmaceutically acceptable salt thereof, wherein $R_5$ is —H, halogen, $C_1$-$C_3$ alkyl or $C_1$-$C_3$ haloalkyl.

56. The compound of claim 55, or pharmaceutically acceptable salt thereof, wherein $R_6$ is —H or halogen.

57. The compound of claim 56, or pharmaceutically acceptable salt thereof, wherein $R_7$ is —CN, methyl or trifluoromethyl.

58. The compound of claim 57, or pharmaceutically acceptable salt thereof, wherein $R_7$ is methyl.

59. The compound of claim 1 that is

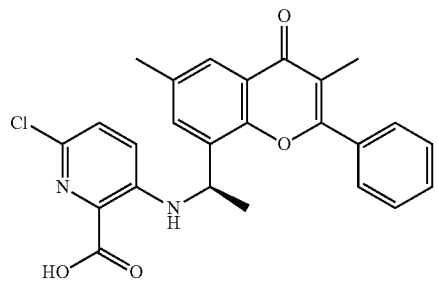 [SMILES: Cc1cc([C@@H](C)Nc2ccc(Cl)nc2C(=O)O)c2oc(-c3ccccc3)c(C)c(=O)c2c1]

or a pharmaceutically acceptable salt thereof.

60. The compound of claim 1 that is

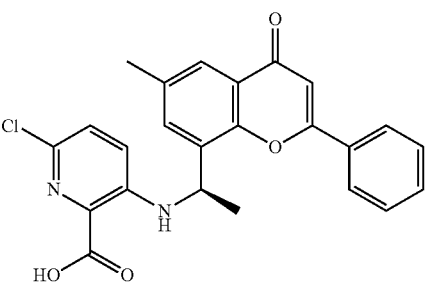 [SMILES: Cc1cc([C@@H](C)Nc2ccc(Cl)nc2C(=O)O)c2oc(-c3ccccc3)cc(=O)c2c1]

or a pharmaceutically acceptable salt thereof.

61. The compound of claim 1 that is

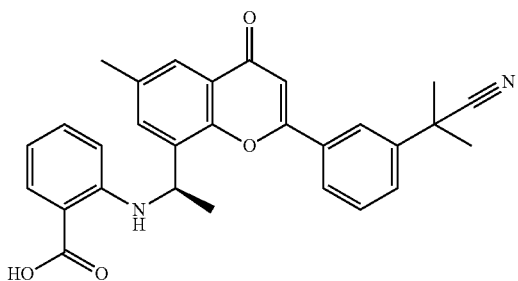 [SMILES: Cc1cc([C@@H](C)Nc2ccccc2C(=O)O)c2oc(-c3cccc(C(C)(C)C#N)c3)cc(=O)c2c1]

or a pharmaceutically acceptable salt thereof.

62. The compound of claim 1 that is

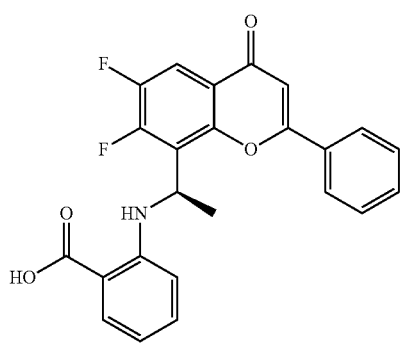 [SMILES: C[C@@H](Nc1ccccc1C(=O)O)c1c(F)c(F)cc2c(=O)cc(-c3ccccc3)oc12]

or a pharmaceutically acceptable salt thereof.

63. The compound of claim 1 that is

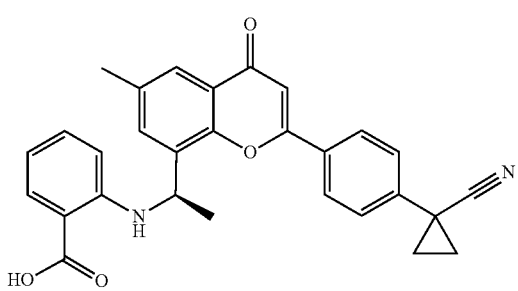 [SMILES: Cc1cc([C@@H](C)Nc2ccccc2C(=O)O)c2oc(-c3ccc(C4(C#N)CC4)cc3)cc(=O)c2c1]

or a pharmaceutically acceptable salt thereof.

64. The compound of claim 1 that is

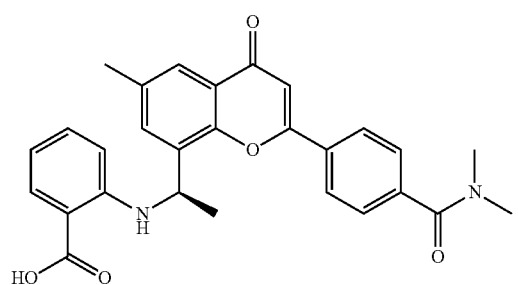

or a pharmaceutically acceptable salt thereof.

65. The compound of claim 1 that is

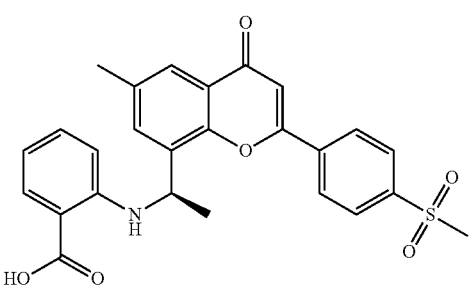 [SMILES: Cc1cc([C@@H](C)Nc2ccccc2C(=O)O)c2oc(-c3ccc(S(C)(=O)=O)cc3)cc(=O)c2c1]

or a pharmaceutically acceptable salt thereof.

66. The compound of claim 1 that is

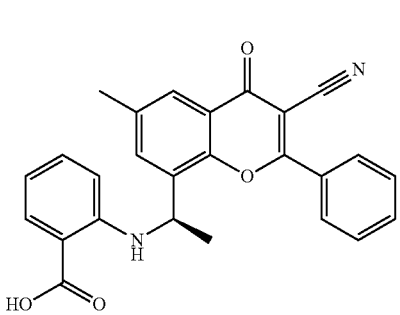 [SMILES: Cc1cc([C@@H](C)Nc2ccccc2C(=O)O)c2oc(-c3ccccc3)c(C#N)c(=O)c2c1]

or a pharmaceutically acceptable salt thereof.

67. The compound of claim 1 that is

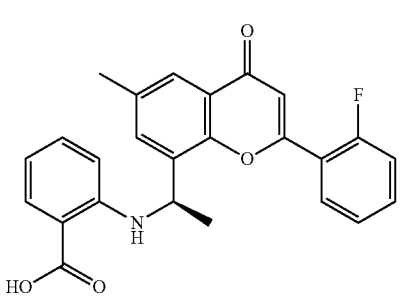

or a pharmaceutically acceptable salt thereof.

68. The compound of claim 1 that is

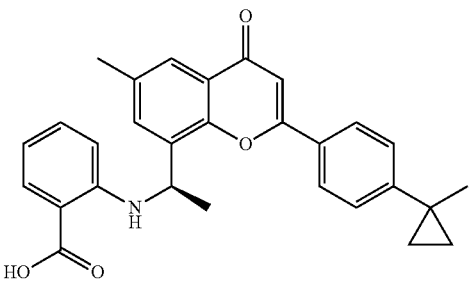 [SMILES: Cc1cc([C@@H](C)Nc2ccccc2C(=O)O)c2oc(-c3ccc(C4(C)CC4)cc3)cc(=O)c2c1]

or a pharmaceutically acceptable salt thereof.

69. The compound of claim 1 that is

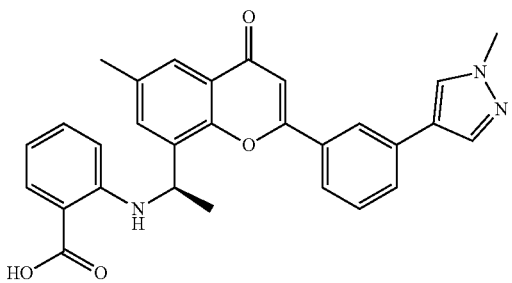 [SMILES: Cc1cc([C@@H](C)Nc2ccccc2C(=O)O)c2oc(-c3cccc(-c4cnn(C)c4)c3)cc(=O)c2c1]

or a pharmaceutically acceptable salt thereof.

70. The compound of claim 1 that is

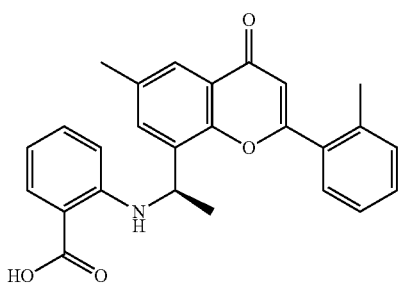 [SMILES: Cc1cc([C@@H](C)Nc2ccccc2C(=O)O)c2oc(-c3ccccc3C)cc(=O)c2c1]

or a pharmaceutically acceptable salt thereof.

71. The compound of claim 1 that is

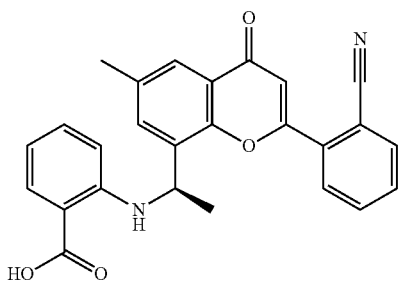 [SMILES: Cc1cc([C@@H](C)Nc2ccccc2C(=O)O)c2oc(-c3ccccc3C#N)cc(=O)c2c1]

or a pharmaceutically acceptable salt thereof.

72. The compound of claim 1 that is

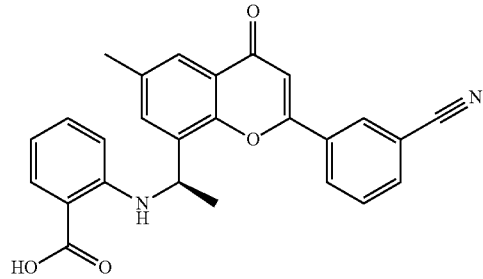 [SMILES: Cc1cc([C@@H](C)Nc2ccccc2C(=O)O)c2oc(-c3cccc(C#N)c3)cc(=O)c2c1]

or a pharmaceutically acceptable salt thereof.

73. The compound of claim 1 that is

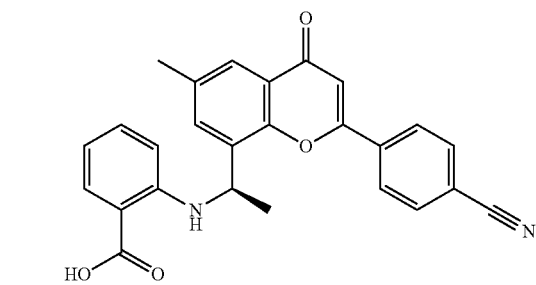 [SMILES: Cc1cc([C@@H](C)Nc2ccccc2C(=O)O)c2oc(-c3ccc(C#N)cc3)cc(=O)c2c1]

or a pharmaceutically acceptable salt thereof.

74. The compound of claim 1 that is

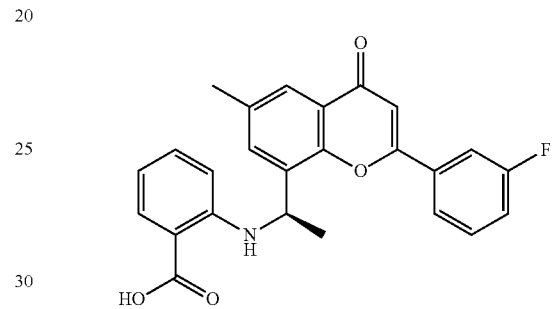

or a pharmaceutically acceptable salt thereof.

75. The compound of claim 1 that is

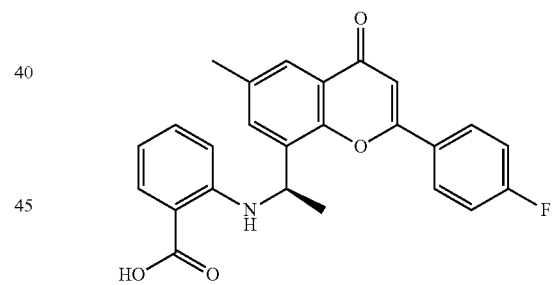

or a pharmaceutically acceptable salt thereof.

76. The compound of claim 1 that is

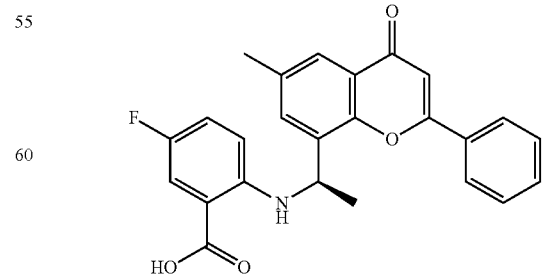

or a pharmaceutically acceptable salt thereof.

77. The compound of claim 1 that is

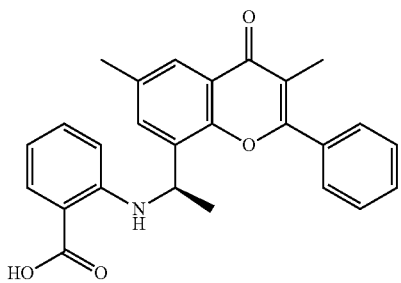 [SMILES: Cc1cc([C@@H](C)Nc2ccccc2C(=O)O)c2oc(-c3ccccc3)c(C)c(=O)c2c1]

or a pharmaceutically acceptable salt thereof.

78. The compound of claim 1 that is

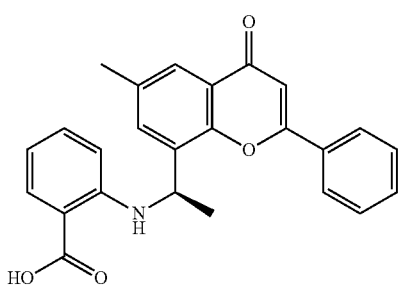 [SMILES: Cc1cc([C@@H](C)Nc2ccccc2C(=O)O)c2oc(-c3ccccc3)cc(=O)c2c1]

or a pharmaceutically acceptable salt thereof.

79. The compound of claim 1 that is

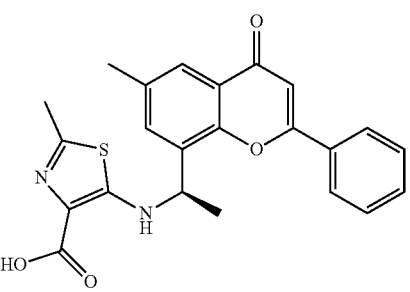 [SMILES: Cc1cc([C@@H](C)Nc2sc(C)nc2C(=O)O)c2oc(-c3ccccc3)cc(=O)c2c1]

or a pharmaceutically acceptable salt thereof.

80. The compound of claim 1 that is

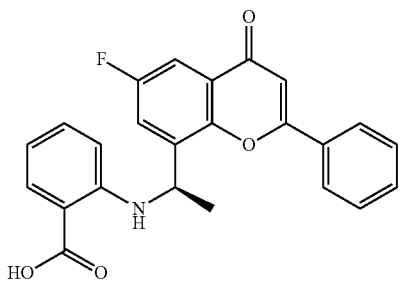 [SMILES: C[C@@H](Nc1ccccc1C(=O)O)c1cc(F)cc2c(=O)cc(-c3ccccc3)oc12]

or a pharmaceutically acceptable salt thereof.

81. The compound of claim 1 that is

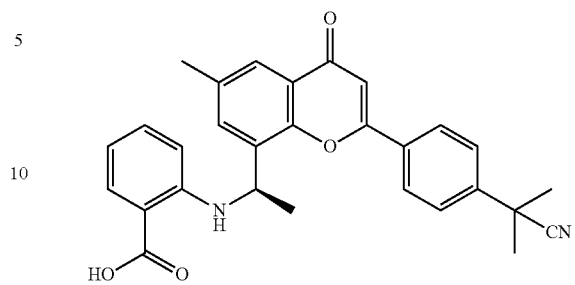

or a pharmaceutically acceptable salt thereof.

82. The compound of claim 1 that is

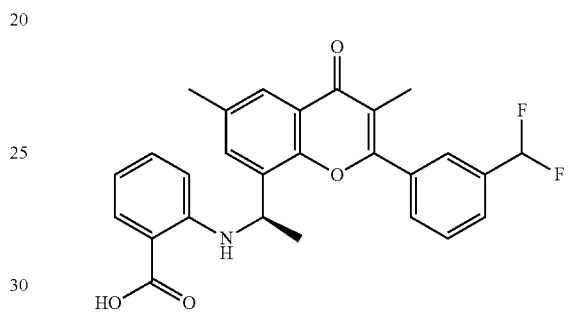

or a pharmaceutically acceptable salt thereof.

83. The compound of claim 1 that is

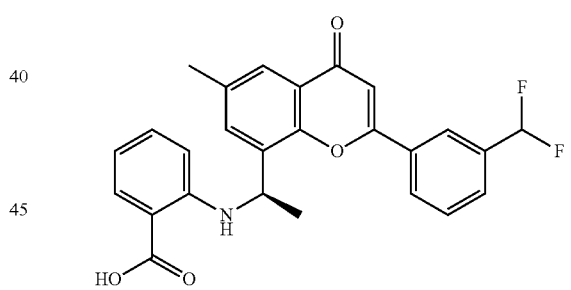

or a pharmaceutically acceptable salt thereof.

84. The compound of claim 1 that is

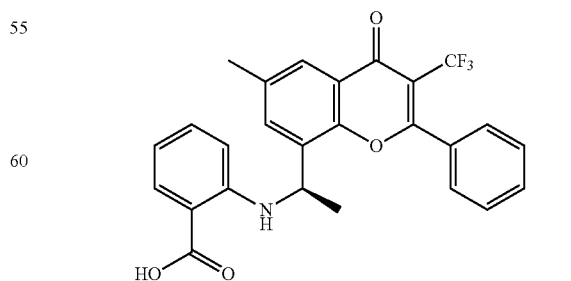

or a pharmaceutically acceptable salt thereof.

85. The compound of claim 1 that is

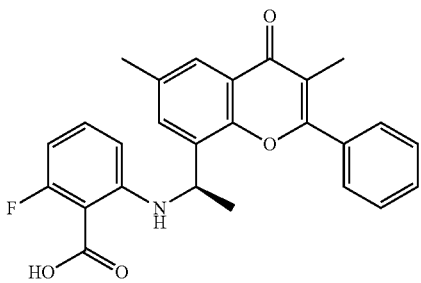

or a pharmaceutically acceptable salt thereof.

86. The compound of claim 1 that is

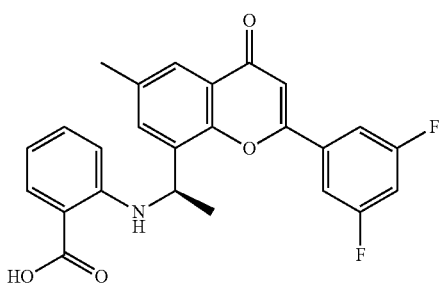 [SMILES: Cc1cc([C@@H](C)Nc2ccccc2C(=O)O)c2oc(-c3cc(F)cc(F)c3)cc(=O)c2c1]

or a pharmaceutically acceptable salt thereof.

87. The compound of claim 1 that is

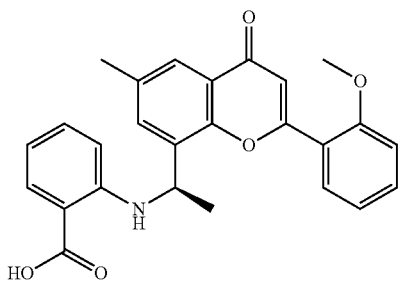 [SMILES: COc1ccccc1-c1cc(=O)c2cc(C)cc([C@@H](C)Nc3ccccc3C(=O)O)c2o1]

or a pharmaceutically acceptable salt thereof.

88. The compound of claim 1 that is

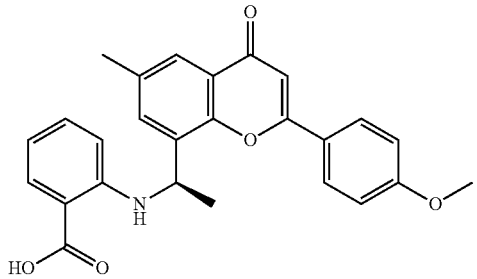 [SMILES: COc1ccc(-c2cc(=O)c3cc(C)cc([C@@H](C)Nc4ccccc4C(=O)O)c3o2)cc1]

or a pharmaceutically acceptable salt thereof.

89. The compound of claim 1 that is

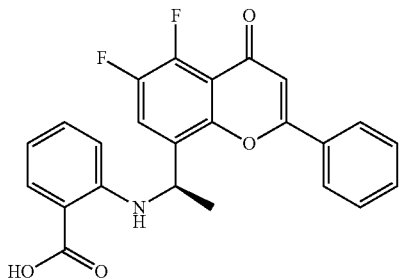

or a pharmaceutically acceptable salt thereof.

90. The compound of claim 1 that is

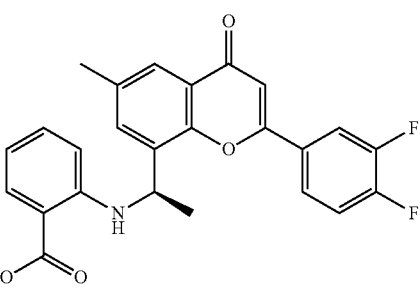

or a pharmaceutically acceptable salt thereof.

91. The compound of claim 1 that is

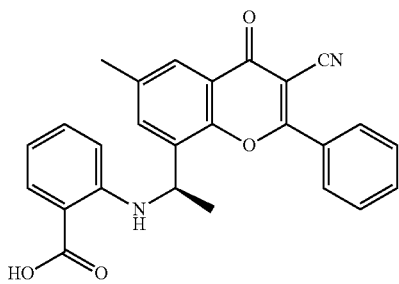 [SMILES: Cc1cc([C@@H](C)Nc2ccccc2C(=O)O)c2oc(-c3ccccc3)c(C#N)c(=O)c2c1]

or a pharmaceutically acceptable salt thereof.

92. The compound of claim 1 that is

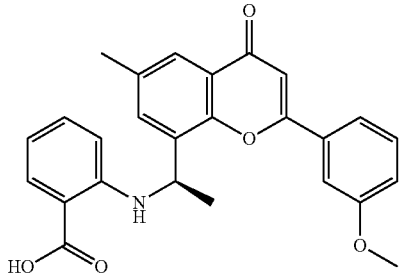 [SMILES: COc1cccc(-c2cc(=O)c3cc(C)cc([C@@H](C)Nc4ccccc4C(=O)O)c3o2)c1]

or a pharmaceutically acceptable salt thereof.

93. The compound of claim 1 that is

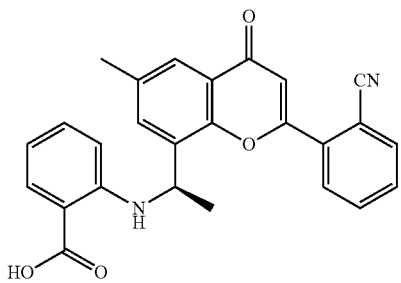 [SMILES: Cc1cc([C@@H](C)Nc2ccccc2C(=O)O)c2oc(-c3ccccc3C#N)cc(=O)c2c1]

or a pharmaceutically acceptable salt thereof.

94. The compound of claim 1 that is

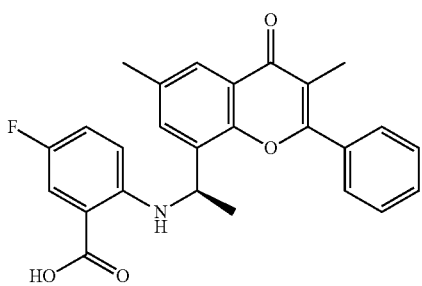 [SMILES: Cc1cc([C@@H](C)Nc2ccc(F)cc2C(=O)O)c2oc(-c3ccccc3)c(C)c(=O)c2c1]

or a pharmaceutically acceptable salt thereof.

95. The compound of claim 1 that is

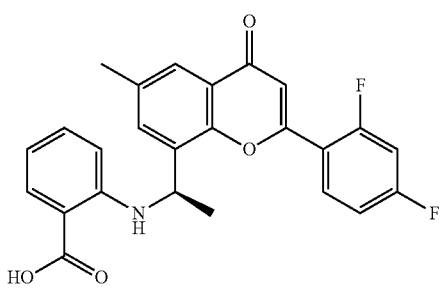 [SMILES: Cc1cc([C@@H](C)Nc2ccccc2C(=O)O)c2oc(-c3ccc(F)cc3F)cc(=O)c2c1]

or a pharmaceutically acceptable salt thereof.

96. The compound of claim 1 that is

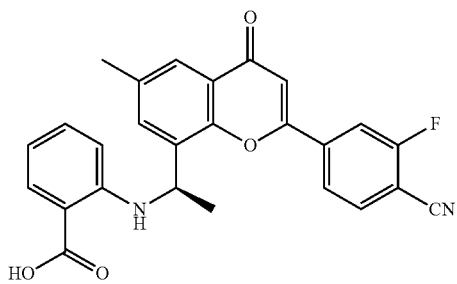 [SMILES: Cc1cc([C@@H](C)Nc2ccccc2C(=O)O)c2oc(-c3ccc(C#N)c(F)c3)cc(=O)c2c1]

or a pharmaceutically acceptable salt thereof.

97. The compound of claim 1 that is

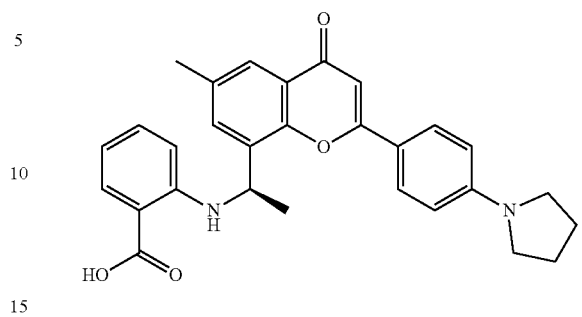

or a pharmaceutically acceptable salt thereof.

98. The compound of claim 1 that is

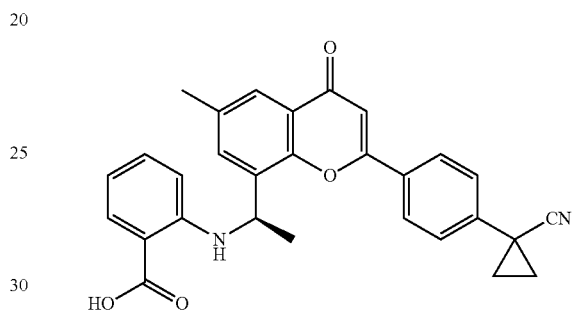

or a pharmaceutically acceptable salt thereof.

99. The compound of claim 1 that is

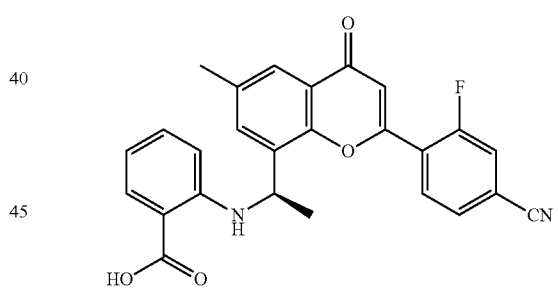

or a pharmaceutically acceptable salt thereof.

100. The compound of claim 1 that is

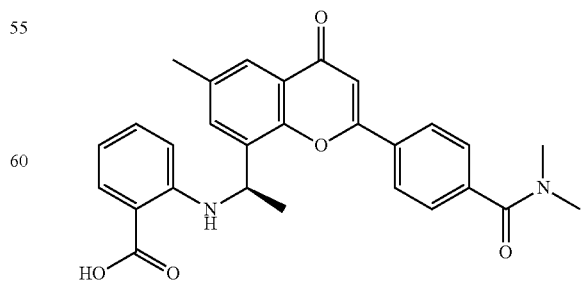

or a pharmaceutically acceptable salt thereof.

101. The compound of claim 1 that is

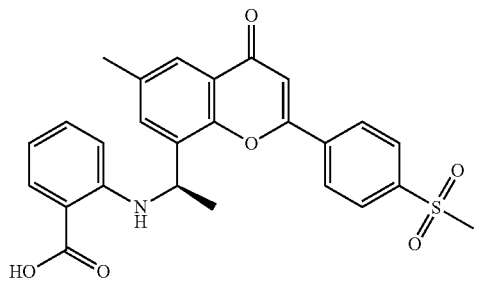 [SMILES: Cc1cc([C@@H](C)Nc2ccccc2C(=O)O)c2oc(-c3ccc(S(C)(=O)=O)cc3)cc(=O)c2c1]

or a pharmaceutically acceptable salt thereof.

102. The compound of claim 1 that is

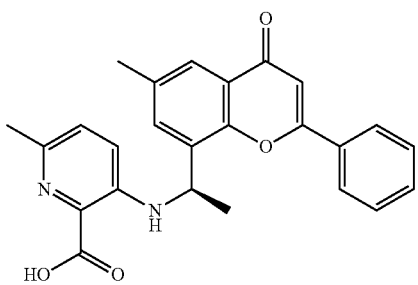 [SMILES: Cc1cc([C@@H](C)Nc2ccc(C)nc2C(=O)O)c2oc(-c3ccccc3)cc(=O)c2c1]

or a pharmaceutically acceptable salt thereof.

103. The compound of claim 1 that is

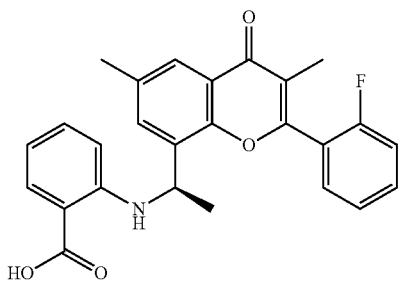 [SMILES: Cc1cc([C@@H](C)Nc2ccccc2C(=O)O)c2oc(-c3ccccc3F)c(C)c(=O)c2c1]

or a pharmaceutically acceptable salt thereof.

104. The compound of claim 1 that is

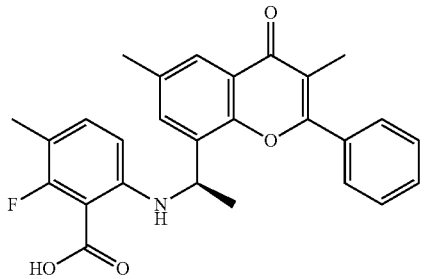 [SMILES: Cc1cc([C@@H](C)Nc2ccc(C)c(F)c2C(=O)O)c2oc(-c3ccccc3)c(C)c(=O)c2c1]

or a pharmaceutically acceptable salt thereof.

105. The compound of claim 1 that is

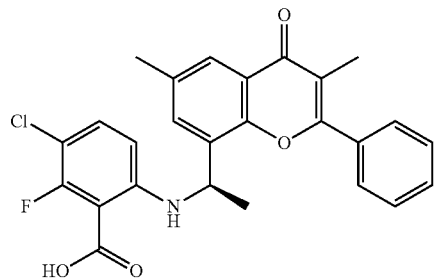 [SMILES: Cc1cc([C@@H](C)Nc2ccc(Cl)c(F)c2C(=O)O)c2oc(-c3ccccc3)c(C)c(=O)c2c1]

or a pharmaceutically acceptable salt thereof.

106. The compound of claim 1 that is

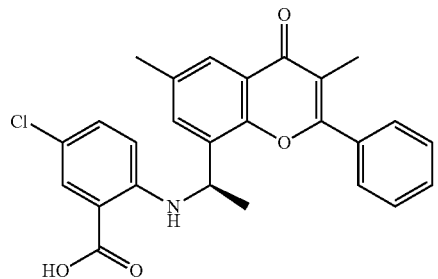 [SMILES: Cc1cc([C@@H](C)Nc2ccc(Cl)cc2C(=O)O)c2oc(-c3ccccc3)c(C)c(=O)c2c1]

or a pharmaceutically acceptable salt thereof.

107. The compound of claim 1 that is

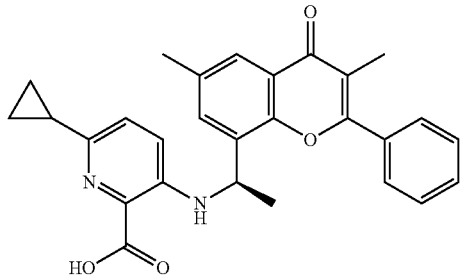 [SMILES: Cc1cc([C@@H](C)Nc2ccc(C3CC3)nc2C(=O)O)c2oc(-c3ccccc3)c(C)c(=O)c2c1]

or a pharmaceutically acceptable salt thereof.

108. The compound of claim 1 that is

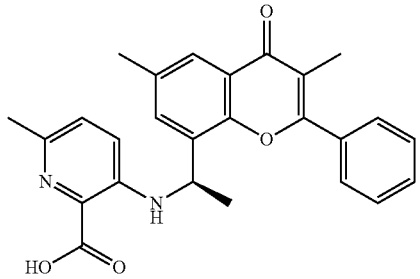 [SMILES: Cc1cc([C@@H](C)Nc2ccc(C)nc2C(=O)O)c2oc(-c3ccccc3)c(C)c(=O)c2c1]

or a pharmaceutically acceptable salt thereof.

109. The compound of claim 1 that is

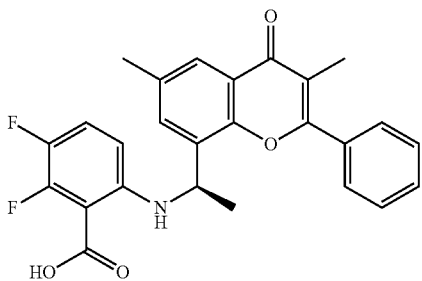

or a pharmaceutically acceptable salt thereof.

110. The compound of claim 1 that is

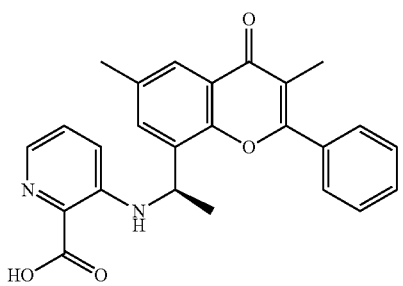

or a pharmaceutically acceptable salt thereof.

111. The compound of claim 1 that is

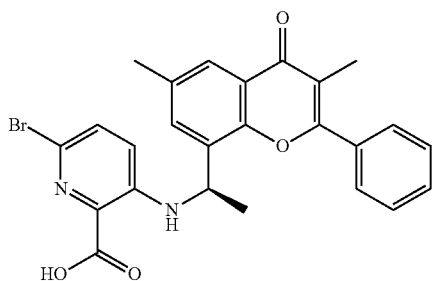

or a pharmaceutically acceptable salt thereof.

112. The compound of claim 1 that is

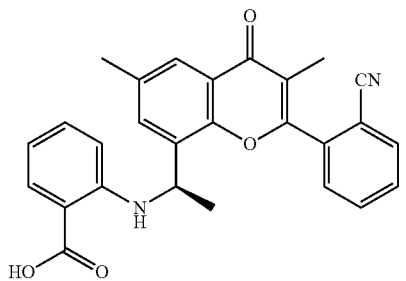 [SMILES: Cc1cc([C@@H](C)Nc2ccccc2C(=O)O)c2oc(-c3ccccc3C#N)c(C)c(=O)c2c1]

or a pharmaceutically acceptable salt thereof.

113. The compound of claim 1 that is

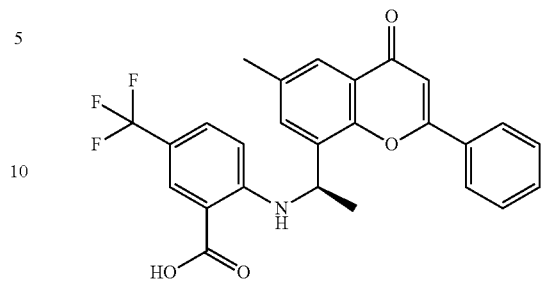

or a pharmaceutically acceptable salt thereof.

114. The compound of claim 1 that is

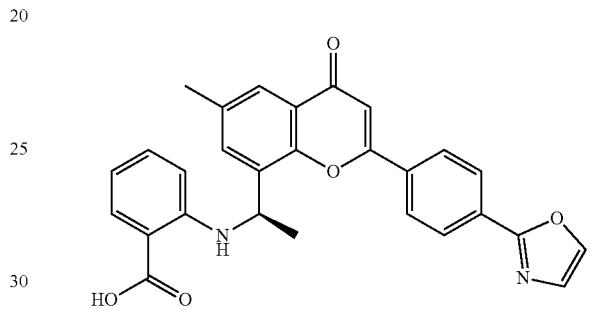

or a pharmaceutically acceptable salt thereof.

115. The compound of claim 1 that is

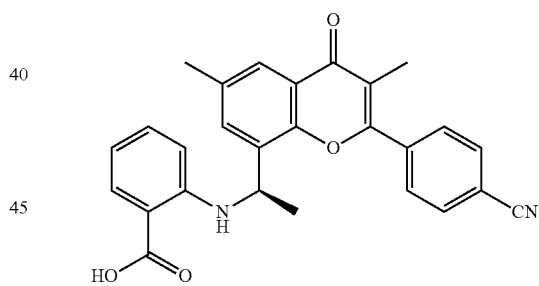

or a pharmaceutically acceptable salt thereof.

116. The compound of claim 1 that is

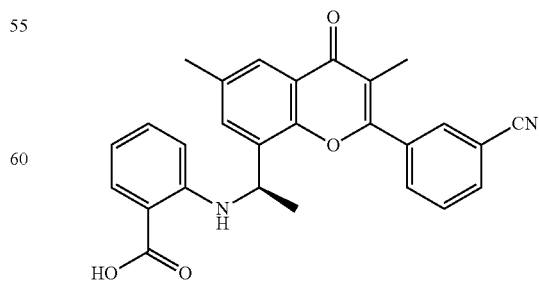

or a pharmaceutically acceptable salt thereof.

117. The compound of claim 1 that is

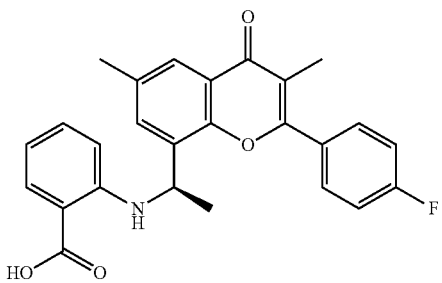

or a pharmaceutically acceptable salt thereof.

118. The compound of claim 1 that is

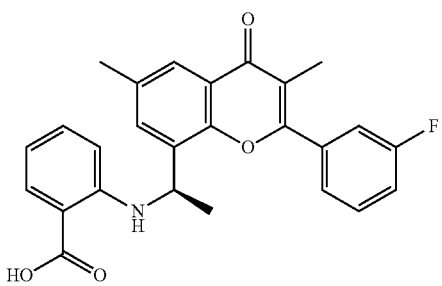 [SMILES: Cc1cc([C@@H](C)Nc2ccccc2C(=O)O)c2oc(-c3cccc(F)c3)c(C)c(=O)c2c1]

or a pharmaceutically acceptable salt thereof.

119. The compound of claim 1 that is

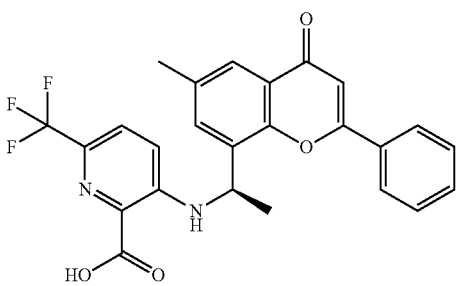 [SMILES: Cc1cc([C@@H](C)Nc2ccc(C(F)(F)F)nc2C(=O)O)c2oc(-c3ccccc3)cc(=O)c2c1]

or a pharmaceutically acceptable salt thereof.

120. The compound of claim 1 that is

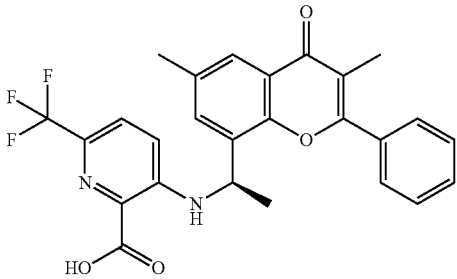 [SMILES: Cc1cc([C@@H](C)Nc2ccc(C(F)(F)F)nc2C(=O)O)c2oc(-c3ccccc3)c(C)c(=O)c2c1]

or a pharmaceutically acceptable salt thereof.

121. The compound of claim 1 that is

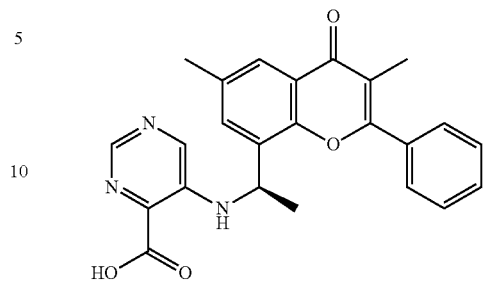

or a pharmaceutically acceptable salt thereof.

122. A compound of the Formula:

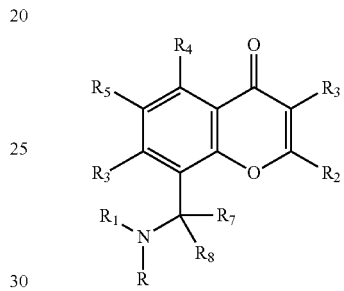

or pharmaceutically acceptable salt thereof, wherein:

R is —H or $C_1$-$C_3$ alkyl;

$R_1$ is a group of the formula:

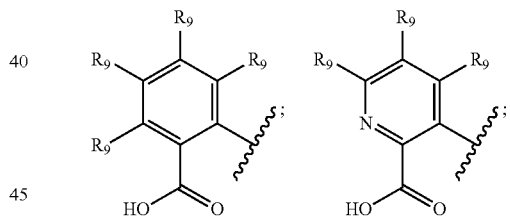

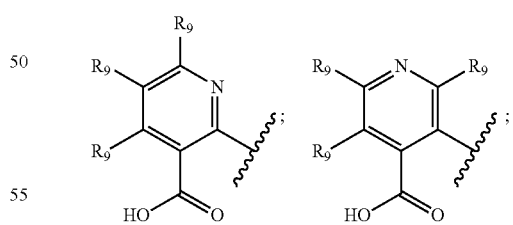

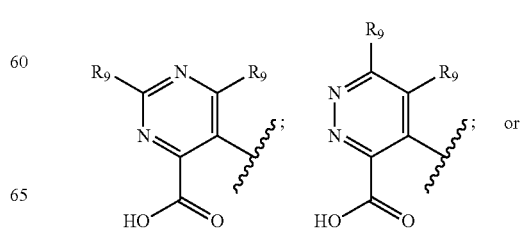 or

-continued

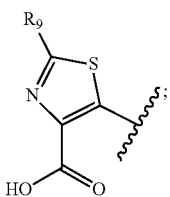

R₂ is a group of the formula:

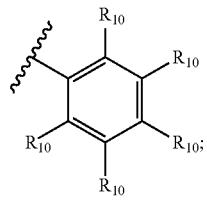

R₃ is halogen, —CN, —N(H)(C₁-C₃ alkyl), —N(C₁-C₃ alkyl)₂, —N(H)(CH₂CH₂CO₂H), —C(O) C₁-C₃ alkyl, C₁-C₆ alkyl, C₁-C₆ haloalkyl, C₁-C₆ hydroxyalkyl, C₃-C₅ cycloalkyl, an optionally substituted heterocycle of 3 to 5 ring atoms containing 1, 2, or 3 ring heteroatoms independently selected from N, O, or S, or an optionally substituted heteroaryl of 5 or 6 ring atoms containing 1, 2, or 3 ring heteroatoms independently selected from N, O, or S; wherein the optionally substituted heterocycle or heteroaryl is each optionally substituted with one to three substituents each independently selected from halogen, C₁-C₃ alkyl, or C₁-C₃ haloalkyl;

each of R₄, R₅ and R₆ is independently —H, halogen, C₁-C₆ alkyl or C₁-C₆ haloalkyl;

R₇ is —CN, C₁-C₆ alkyl or C₁-C₆ haloalkyl;

R₈ is —H or C₁-C₆ alkyl;

each R₉ is independently —H, halogen, —CN, C₁-C₆ alkyl, C₁-C₆ haloalkyl, C₁-C₆ alkoxy, or C₃-C₅ cycloalkyl;

each R₁₀ is independently —H, —CN, halogen, C₁-C₆ haloalkyl, C₁-C₆ alkoxy, C₁-C₆ haloalkoxy, —SO₂R₁₁, —C(O)OC₁-C₃ alkyl, —CONR₁₁R₁₁, —NR₁₁R₁₁, —NR₁₁—CO₂R₁₁, —OH, an optionally substituted C₁-C₆ alkyl, an optionally substituted C₂-C₆ alkenyl, an optionally substituted C₂-C₆ alkynyl, an optionally substituted C₃-C₅ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyrazole, isoxazole, isothiazole, imidazole, oxazole, or thiazole; wherein the optionally substituted C₁-C₆ alkyl, C₂-C₆ alkenyl, or C₂-C₆ alkynyl is each optionally substituted with a —CN, —OH, oxetanyl, C₁-C₃ alkoxy, or —CONR₁₁R₁₁; the optionally substituted C₃-C₅ cycloalkyl, phenyl, 1,3-benzodioxole, 2,3-dihydro-1,4-benzodioxine, heterocycle or heteroaryl is each optionally substituted with one to three substituents each independently selected from halogen, C₁-C₃ alkyl, C₁-C₃ haloalkyl, C₁-C₃ alkoxy, C₁-C₃ haloalkoxy, —SO₂R₁₁, —NR₁₁R₁₁, —OH or —CN; and each R₁₁ is independently —H or C₁-C₃ alkyl.

123. The compound of claim 122, selected from:

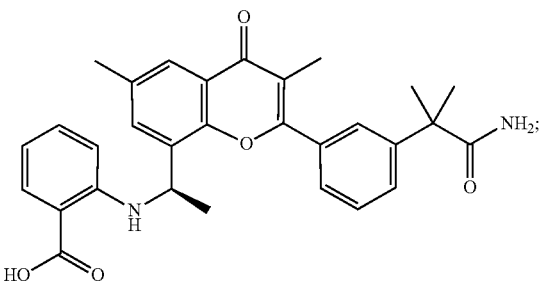

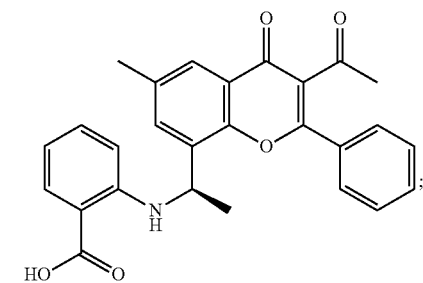

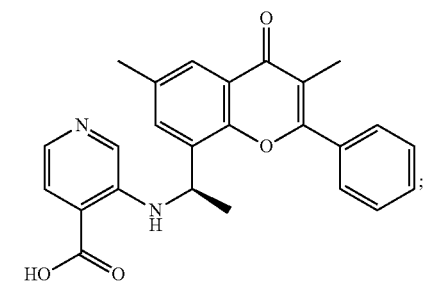

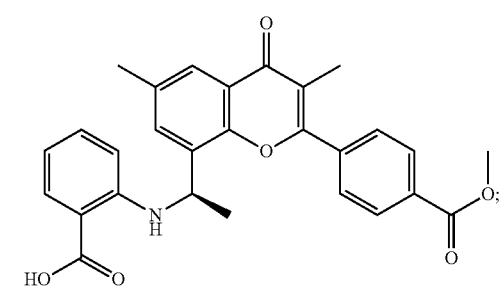

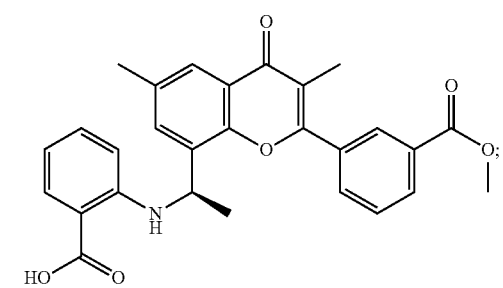

401
-continued

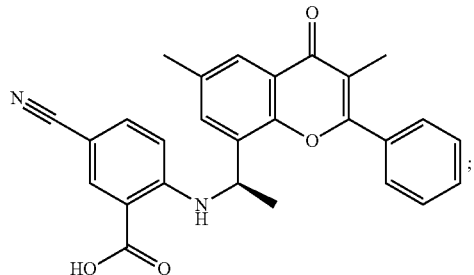

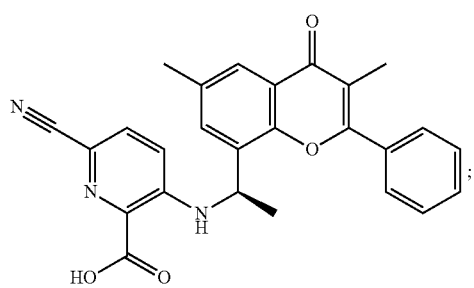
; and

402
-continued

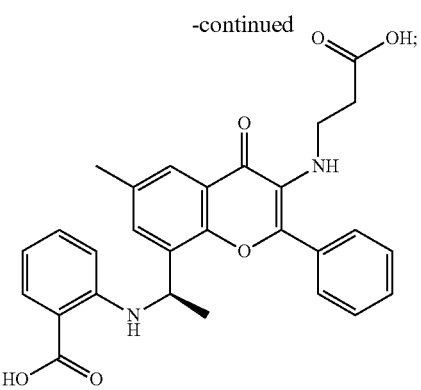

or a pharmaceutically acceptable salt thereof.

124. A pharmaceutical composition comprising a compound of claim 122, or a pharmaceutically acceptable salt thereof, and a pharmaceutically acceptable carrier.

125. A method of inhibiting phosphoinositide 3-kinase (PI3K), comprising administering to a patient in need thereof a therapeutically effective amount of a compound of claim 122, or a pharmaceutically acceptable salt thereof.

* * * * *